US010189894B2

(12) United States Patent
Vasquez et al.

(10) Patent No.: US 10,189,894 B2
(45) Date of Patent: Jan. 29, 2019

(54) RATIONALLY DESIGNED, SYNTHETIC ANTIBODY LIBRARIES AND USES THEREFOR

(71) Applicant: ADIMAB, LLC, Lebanon, NH (US)

(72) Inventors: Maximiliano Vasquez, Palo Alto, CA (US); Michael Feldhaus, Grantham, NH (US); Tillman U. Gerngross, Hanover, NH (US); K. Dane Wittrup, Chestnut Hill, MA (US)

(73) Assignee: Adimab, LLC, Lebanon, NH (US)

( * ) Notice: Subject to any disclaimer, the term of this patent is extended or adjusted under 35 U.S.C. 154(b) by 698 days.

(21) Appl. No.: 14/150,129

(22) Filed: Jan. 8, 2014

(65) Prior Publication Data

US 2014/0364340 A1 Dec. 11, 2014

Related U.S. Application Data

(62) Division of application No. 12/210,072, filed on Sep. 12, 2008, now Pat. No. 8,691,730.

(60) Provisional application No. 60/993,785, filed on Sep. 14, 2007.

(51) Int. Cl.
| | | |
|---|---|---|
| *C40B 40/10* | (2006.01) | |
| *C07K 16/18* | (2006.01) | |
| *C07K 16/00* | (2006.01) | |
| *C07K 16/40* | (2006.01) | |

(52) U.S. Cl.
CPC ............ *C07K 16/18* (2013.01); *C07K 16/005* (2013.01); *C07K 16/40* (2013.01); *C07K 2317/21* (2013.01); *C07K 2317/565* (2013.01); *C07K 2317/567* (2013.01); *C40B 40/10* (2013.01)

(58) Field of Classification Search
None
See application file for complete search history.

(56) References Cited

U.S. PATENT DOCUMENTS

| | | | |
|---|---|---|---|
| 4,230,685 A | 10/1980 | Senyei et al. | |
| 4,452,773 A | 6/1984 | Molday | |
| 4,661,454 A | 4/1987 | Botstein et al. | |
| 4,770,183 A | 9/1988 | Groman et al. | |

(Continued)

FOREIGN PATENT DOCUMENTS

| | | |
|---|---|---|
| DE | 19624562 A1 | 1/1998 |
| EP | 0404097 A2 | 12/1990 |

(Continued)

OTHER PUBLICATIONS

Dohmen et al. (Mar. 27, 2006) Clinical and Experimental Immunology vol. 144 pp. 223 to 232.*

(Continued)

*Primary Examiner* — Christian C Boesen
(74) *Attorney, Agent, or Firm* — Brenda Herschbach Jarrell; Robert N. Sahr; Choate, Hall & Stewart LLP

(57) ABSTRACT

The present invention overcomes the inadequacies inherent in the known methods for generating libraries of antibody-encoding polynucleotides by specifically designing the libraries with directed sequence and length diversity. The libraries are designed to reflect the preimmune repertoire naturally created by the human immune system and are based on rational design informed by examination of publicly available databases of human antibody sequences.

7 Claims, 26 Drawing Sheets

Specification includes a Sequence Listing.

(56) References Cited

U.S. PATENT DOCUMENTS

| | | |
|---|---|---|
| 4,816,567 A | 3/1989 | Cabilly et al. |
| 4,946,778 A | 8/1990 | Ladner et al. |
| 4,959,317 A | 9/1990 | Sauer |
| 5,118,605 A | 6/1992 | Urdea |
| 5,223,409 A | 6/1993 | Ladner et al. |
| 5,283,173 A | 2/1994 | Fields et al. |
| 5,380,833 A | 1/1995 | Urdea |
| 5,506,121 A | 4/1996 | Skerra et al. |
| 5,525,490 A | 6/1996 | Erickson et al. |
| 5,530,101 A | 6/1996 | Queen et al. |
| 5,565,332 A | 10/1996 | Hoogenboom et al. |
| 5,571,698 A | 11/1996 | Ladner et al. |
| 5,618,920 A | 4/1997 | Robinson et al. |
| 5,658,727 A | 8/1997 | Barbas et al. |
| 5,688,666 A | 11/1997 | Bass et al. |
| 5,695,941 A | 12/1997 | Brent et al. |
| 5,712,120 A | 1/1998 | Rodriguez et al. |
| 5,723,323 A | 3/1998 | Kauffman et al. |
| 5,723,584 A | 3/1998 | Schatz |
| 5,733,743 A | 3/1998 | Johnson et al. |
| 5,739,281 A | 4/1998 | Thogersen et al. |
| 5,750,373 A | 5/1998 | Garrard et al. |
| 5,767,260 A | 6/1998 | Whitlow et al. |
| 5,780,279 A | 7/1998 | Matthews et al. |
| 5,798,208 A | 8/1998 | Crea |
| 5,811,238 A | 9/1998 | Stemmer et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,830,663 A | 11/1998 | Embleton et al. |
| 5,837,242 A | 11/1998 | Holliger et al. |
| 5,837,500 A | 11/1998 | Ladner et al. |
| 5,840,479 A | 11/1998 | Little et al. |
| 5,846,765 A | 12/1998 | Matthews et al. |
| 5,858,657 A | 1/1999 | Winter et al. |
| 5,858,671 A | 1/1999 | Jones |
| 5,863,765 A | 1/1999 | Berry et al. |
| 5,866,344 A | 2/1999 | Georgiou |
| 5,869,250 A | 2/1999 | Cheng et al. |
| 5,871,907 A | 2/1999 | Winter et al. |
| 5,872,215 A | 2/1999 | Osbourne et al. |
| 5,874,239 A | 2/1999 | Schatz |
| 5,885,793 A | 3/1999 | Griffiths et al. |
| 5,888,773 A | 3/1999 | Jost et al. |
| 5,917,018 A | 6/1999 | Thogersen et al. |
| 5,922,545 A | 7/1999 | Mattheakis et al. |
| 5,928,868 A | 7/1999 | Liu et al. |
| 5,932,433 A | 8/1999 | Schatz |
| 5,935,831 A | 8/1999 | Quax et al. |
| 5,948,620 A | 9/1999 | Hurd et al. |
| 5,955,275 A | 9/1999 | Kamb |
| 5,962,255 A | 10/1999 | Griffiths et al. |
| 5,965,368 A | 10/1999 | Vidal et al. |
| 5,969,108 A | 10/1999 | McCafferty et al. |
| 5,976,862 A | 11/1999 | Kauffman et al. |
| 5,994,515 A | 11/1999 | Hoxie |
| 5,994,519 A | 11/1999 | Osbourn et al. |
| 6,010,884 A | 1/2000 | Griffiths et al. |
| 6,017,732 A | 1/2000 | Jespers et al. |
| 6,022,729 A | 2/2000 | Steinbuchel et al. |
| 6,027,910 A | 2/2000 | Klis et al. |
| 6,040,136 A | 3/2000 | Garrard et al. |
| 6,057,098 A | 5/2000 | Buechler et al. |
| 6,057,101 A | 5/2000 | Nandabalan et al. |
| 6,072,036 A | 6/2000 | Marasco et al. |
| 6,072,039 A | 6/2000 | Haase et al. |
| 6,083,693 A | 7/2000 | Nandabalan et al. |
| 6,103,493 A | 8/2000 | Skerra et al. |
| 6,114,147 A | 9/2000 | Frenken et al. |
| 6,132,963 A | 10/2000 | Brent et al. |
| 6,140,471 A | 10/2000 | Johnson et al. |
| 6,159,705 A | 12/2000 | Trueheart et al. |
| 6,171,795 B1 | 1/2001 | Korman et al. |
| 6,172,197 B1 | 1/2001 | McCafferty et al. |
| 6,180,336 B1 | 1/2001 | Osbourn et al. |
| 6,187,535 B1 | 2/2001 | LeGrain et al. |
| 6,200,759 B1 | 3/2001 | Dove et al. |
| 6,225,447 B1 | 5/2001 | Winter et al. |
| 6,248,516 B1 | 6/2001 | Winter et al. |
| 6,265,552 B1 | 7/2001 | Schatz |
| 6,291,158 B1 | 9/2001 | Winter et al. |
| 6,291,159 B1 | 9/2001 | Winter et al. |
| 6,291,160 B1 | 9/2001 | Lerner et al. |
| 6,291,161 B1 | 9/2001 | Lerner et al. |
| 6,291,650 B1 | 9/2001 | Winter et al. |
| 6,300,064 B1 | 10/2001 | Knappik et al. |
| 6,300,065 B1 | 10/2001 | Kieke et al. |
| 6,312,916 B1 | 11/2001 | Kopetzki et al. |
| 6,319,690 B1 | 11/2001 | Little et al. |
| 6,342,588 B1 | 1/2002 | Osbourn et al. |
| 6,358,733 B1 | 3/2002 | Motwani et al. |
| 6,368,813 B1 | 4/2002 | Reznik et al. |
| 6,406,863 B1 | 6/2002 | Zhu et al. |
| 6,410,246 B1 | 6/2002 | Zhu et al. |
| 6,410,271 B1 | 6/2002 | Zhu et al. |
| 6,420,113 B1 | 7/2002 | Buechler et al. |
| 6,423,538 B1 | 7/2002 | Wittrup et al. |
| 6,489,123 B2 | 12/2002 | Osbourn et al. |
| 6,492,107 B1 | 12/2002 | Kauffman et al. |
| 6,492,123 B1 | 12/2002 | Holliger et al. |
| 6,492,160 B1 | 12/2002 | Griffiths et al. |
| 6,521,404 B1 | 2/2003 | Griffiths et al. |
| 6,531,580 B1 | 3/2003 | Huse et al. |
| 6,544,731 B1 | 4/2003 | Griffiths et al. |
| 6,545,142 B1 | 4/2003 | Winter et al. |
| 6,555,313 B1 | 4/2003 | Griffiths et al. |
| 6,569,641 B1 | 5/2003 | Kauffman et al. |
| 6,582,915 B1 | 6/2003 | Griffiths et al. |
| 6,589,527 B1 | 7/2003 | Winter et al. |
| 6,589,741 B2 | 7/2003 | Pluckthun et al. |
| 6,593,081 B1 | 7/2003 | Griffiths et al. |
| 6,610,472 B1 | 8/2003 | Zhu et al. |
| 6,653,443 B2 | 11/2003 | Zhang et al. |
| 6,664,048 B1 | 12/2003 | Wanker et al. |
| 6,680,192 B1 | 1/2004 | Lerner et al. |
| 6,696,245 B2 | 2/2004 | Winter et al. |
| 6,696,248 B1 | 2/2004 | Knappik et al. |
| 6,696,251 B1 | 2/2004 | Wittrup et al. |
| 6,699,658 B1 | 3/2004 | Wittrup et al. |
| 6,706,484 B1 | 3/2004 | Knappik et al. |
| 6,750,042 B2 | 6/2004 | Summers et al. |
| 6,753,136 B2 | 6/2004 | Lohning |
| 6,806,079 B1 | 10/2004 | McCafferty et al. |
| 6,828,422 B1 | 12/2004 | Achim et al. |
| 6,833,441 B2 | 12/2004 | Wang et al. |
| 6,841,359 B2 | 1/2005 | Szostak et al. |
| 6,846,634 B1 | 1/2005 | Tomlinson et al. |
| 6,916,605 B1 | 7/2005 | McCafferty et al. |
| 6,919,183 B2 | 7/2005 | Fandl et al. |
| 6,969,586 B1 | 11/2005 | Lerner et al. |
| 7,005,503 B2 | 2/2006 | Hua et al. |
| 7,037,706 B1 | 5/2006 | Barrett et al. |
| 7,063,943 B1 | 6/2006 | McCafferty et al. |
| 7,083,945 B1 | 8/2006 | Chen et al. |
| 7,094,571 B2 | 8/2006 | Harvey et al. |
| 7,112,439 B2 | 9/2006 | Johnson et al. |
| 7,118,915 B2 | 10/2006 | Vogt et al. |
| 7,138,253 B2 | 11/2006 | Szostak et al. |
| 7,166,423 B1 | 1/2007 | Miltenyi et al. |
| 7,172,877 B2 | 2/2007 | Ting |
| 7,189,841 B2 | 3/2007 | Lerner et al. |
| 7,208,293 B2 | 4/2007 | Ladner et al. |
| 7,229,757 B2 | 6/2007 | Barrett et al. |
| 7,252,998 B2 | 8/2007 | Skerra et al. |
| 7,282,475 B2 | 10/2007 | Porter et al. |
| 7,302,146 B2 | 11/2007 | Turner et al. |
| 7,315,019 B2 | 1/2008 | Turner et al. |
| 7,335,019 B2 | 2/2008 | Suzuki et al. |
| 7,355,008 B2 | 4/2008 | Stavenhagen et al. |
| 7,371,849 B2 | 5/2008 | Honda et al. |
| 7,435,553 B2 | 10/2008 | Fandl et al. |
| 7,465,787 B2 | 12/2008 | Wittrup et al. |
| 7,569,357 B2 | 8/2009 | Kranz et al. |

(56) References Cited

U.S. PATENT DOCUMENTS

| | | |
|---|---|---|
| 7,700,302 B2 | 4/2010 | Hua et al. |
| 8,691,225 B2 | 4/2014 | Schoeberl et al. |
| 8,691,730 B2 | 4/2014 | Vasquez et al. |
| 8,877,688 B2 | 11/2014 | Vasquez et al. |
| 8,927,694 B2 | 1/2015 | McDonagh et al. |
| 8,961,966 B2 | 2/2015 | Schoeberl et al. |
| 9,464,286 B2 | 10/2016 | Zhu et al. |
| 2002/0004215 A1 | 1/2002 | Osbourn et al. |
| 2002/0069421 A1 | 6/2002 | Hale et al. |
| 2002/0155157 A1 | 10/2002 | Luo et al. |
| 2002/0169284 A1 | 11/2002 | Ashkenazi et al. |
| 2002/0197691 A1 | 12/2002 | Sugiyama |
| 2003/0083474 A1 | 5/2003 | Schmidt |
| 2003/0092073 A1 | 5/2003 | Ambrosius et al. |
| 2003/0104524 A1 | 6/2003 | Summers et al. |
| 2003/0114659 A1 | 6/2003 | Winter et al. |
| 2003/0130496 A1 | 7/2003 | Winter et al. |
| 2003/0148372 A1 | 8/2003 | Tomlinson et al. |
| 2003/0165988 A1 | 9/2003 | Hua et al. |
| 2003/0190674 A1 | 10/2003 | Griffiths et al. |
| 2003/0228302 A1 | 12/2003 | Crea |
| 2003/0232333 A1 | 12/2003 | Ladner et al. |
| 2003/0232395 A1 | 12/2003 | Hufton |
| 2004/0038921 A1 | 2/2004 | Kreutzer et al. |
| 2004/0082012 A1 | 4/2004 | Busch et al. |
| 2004/0110941 A2 | 6/2004 | Winter et al. |
| 2004/0146976 A1 | 7/2004 | Wittrup et al. |
| 2004/0157214 A1 | 8/2004 | McCafferty et al. |
| 2004/0157215 A1 | 8/2004 | McCafferty et al. |
| 2004/0175756 A1 | 9/2004 | Kolkman et al. |
| 2004/0190333 A1 | 9/2004 | Yuan et al. |
| 2004/0197347 A1 | 10/2004 | Sykes et al. |
| 2004/0197866 A1 | 10/2004 | Johnson et al. |
| 2004/0209317 A1 | 10/2004 | Ting |
| 2004/0219611 A1 | 11/2004 | Racher |
| 2004/0248298 A1 | 12/2004 | Schutz et al. |
| 2004/0259162 A1 | 12/2004 | Kappel et al. |
| 2005/0009028 A1 | 1/2005 | Heintz et al. |
| 2005/0019827 A1 | 1/2005 | Diller et al. |
| 2005/0048512 A1 | 3/2005 | Kolkman et al. |
| 2005/0048545 A1 | 3/2005 | Cull et al. |
| 2005/0053591 A1 | 3/2005 | Pun |
| 2005/0053973 A1 | 3/2005 | Kolkman et al. |
| 2005/0058661 A1 | 3/2005 | Sykes et al. |
| 2005/0089932 A1 | 4/2005 | Kolkman et al. |
| 2005/0164301 A1 | 7/2005 | Kolkman et al. |
| 2005/0176070 A1 | 8/2005 | Auton |
| 2005/0191710 A1 | 9/2005 | Hanrahan et al. |
| 2005/0202512 A1 | 9/2005 | Tomlinson et al. |
| 2005/0221384 A1 | 10/2005 | Kolkman et al. |
| 2005/0233389 A1 | 10/2005 | Ting et al. |
| 2005/0255462 A1 | 11/2005 | Barrett et al. |
| 2006/0003334 A1 | 1/2006 | Achim et al. |
| 2006/0008883 A1 | 1/2006 | Lazar et al. |
| 2006/0019260 A1 | 1/2006 | Lerner et al. |
| 2006/0024676 A1 | 2/2006 | Uhlmann et al. |
| 2006/0046261 A1 | 3/2006 | Porter et al. |
| 2006/0046285 A1 | 3/2006 | Watzele et al. |
| 2006/0052294 A1 | 3/2006 | Otto |
| 2006/0061754 A1 | 3/2006 | Turner et al. |
| 2006/0061755 A1 | 3/2006 | Turner et al. |
| 2006/0062531 A1 | 3/2006 | Turner et al. |
| 2006/0063264 A1 | 3/2006 | Turner et al. |
| 2006/0106199 A1 | 5/2006 | Erdmann et al. |
| 2006/0166252 A1 | 7/2006 | Ladner et al. |
| 2006/0172281 A1 | 8/2006 | Schutz et al. |
| 2006/0177440 A1 | 8/2006 | Siegel |
| 2006/0211087 A1 | 9/2006 | Roosild et al. |
| 2006/0234302 A1 | 10/2006 | Hoet et al. |
| 2006/0257937 A1 | 11/2006 | Ladner |
| 2007/0031879 A1 | 2/2007 | Ley et al. |
| 2007/0037216 A1 | 2/2007 | Johnson et al. |
| 2007/0082330 A1 | 4/2007 | Barrett et al. |
| 2007/0099267 A1 | 5/2007 | Harvey et al. |
| 2007/0141548 A1 | 6/2007 | Kohl et al. |
| 2007/0258954 A1 | 11/2007 | Iverson et al. |
| 2007/0275416 A1 | 11/2007 | Gloeckner et al. |
| 2008/0053543 A1 | 3/2008 | Baier et al. |
| 2008/0053901 A1 | 3/2008 | Mierendorf et al. |
| 2008/0053917 A1 | 3/2008 | Larson et al. |
| 2008/0064093 A1 | 3/2008 | Porter et al. |
| 2008/0153712 A1 | 6/2008 | Crea |
| 2008/0171059 A1 | 7/2008 | Howland et al. |
| 2008/0206239 A1 | 8/2008 | Jones et al. |
| 2009/0082213 A1 | 3/2009 | Horowitz et al. |
| 2009/0280560 A1 | 11/2009 | Wittrup et al. |
| 2010/0009866 A1 | 1/2010 | Prinz et al. |
| 2010/0292103 A1 | 11/2010 | Ladner |
| 2011/0009280 A1 | 1/2011 | Hufton et al. |
| 2011/0082054 A1 | 4/2011 | Ladner |
| 2011/0136695 A1 | 6/2011 | Crea |
| 2011/0189183 A1 | 8/2011 | Williamson et al. |
| 2013/0046056 A1 | 2/2013 | Spector et al. |
| 2014/0031292 A1 | 1/2014 | Wittrup et al. |
| 2014/0031522 A1 | 1/2014 | Li et al. |
| 2014/0080766 A1 | 3/2014 | Pirie et al. |
| 2014/0296434 A1 | 10/2014 | Spector et al. |
| 2015/0080558 A1 | 3/2015 | Spector et al. |
| 2016/0237424 A1 | 8/2016 | Zhu et al. |

FOREIGN PATENT DOCUMENTS

| | | |
|---|---|---|
| WO | WO-85/04330 A1 | 10/1985 |
| WO | WO-88/01649 A1 | 3/1988 |
| WO | WO-88/06630 A1 | 9/1988 |
| WO | WO-1990/007380 A2 | 7/1990 |
| WO | WO-93/11161 A1 | 6/1993 |
| WO | WO-94/07922 A1 | 4/1994 |
| WO | WO-95/26400 A1 | 10/1995 |
| WO | WO-96/07754 A1 | 3/1996 |
| WO | WO-97/08320 A1 | 3/1997 |
| WO | WO-97/20923 A1 | 6/1997 |
| WO | WO-97/49809 A1 | 12/1997 |
| WO | WO-98/49198 A1 | 11/1998 |
| WO | WO-199852976 A1 | 11/1998 |
| WO | WO-99/06834 A2 | 2/1999 |
| WO | WO-99/28502 A1 | 6/1999 |
| WO | WO-99/36569 A1 | 7/1999 |
| WO | WO-99/50461 A1 | 10/1999 |
| WO | WO-99/53049 A1 | 10/1999 |
| WO | WO-99/55367 A1 | 11/1999 |
| WO | WO-00/18905 A1 | 4/2000 |
| WO | WO-00/54057 A1 | 9/2000 |
| WO | WO-01/79229 A2 | 10/2001 |
| WO | WO-01/79481 A2 | 10/2001 |
| WO | WO-2004/101790 A1 | 11/2004 |
| WO | WO-2005/007121 A2 | 1/2005 |
| WO | WO-2005023993 A2 | 3/2005 |
| WO | WO-2006/138700 A2 | 12/2006 |
| WO | WO-2007/056441 A2 | 5/2007 |
| WO | WO-2008/019366 A2 | 2/2008 |
| WO | WO-2008/053275 A2 | 5/2008 |
| WO | WO-2008067547 A2 | 6/2008 |
| WO | WO-09/36379 A2 | 3/2009 |
| WO | WO-2010/005863 A1 | 1/2010 |

OTHER PUBLICATIONS

Boder, E. and Wittrup, K., Yeast Surface Display for Directed Evolution of Protein Expression, Affinity, and Stability, Methods in Enzymology, 328:430-444 (2000).

Cardoso, D. et al., Neutralizing Human Anti Crotoxin scFv Isolated from a Nonimmunized Phage Library, Scand. J. Immunol., 51:337-344 (2000).

Vaughan, T. et al., Human Antibodies with Sub-nanomolar Affinities Isolated from a Large Non-immunized Phage Display Library, Nature Biotechnology, 14:309-214 (1996).

Abbas, A.K. et al., Cellular and Molecular Immunology 4th Ed. W.B. Saunders Company, p. 133 (2000).

Adams, G.P. and Schier, R., Generating Improved Single-Chain Fv Molecules for Tumor Targeting, Journal of Immunological Methods, 231:249-260 (1999).

(56) References Cited

OTHER PUBLICATIONS

Adams, G.P. and Weiner, L. M., "Monoclonal antibody therapy of cancer" Nature Biotechnology, 23(9) 1147-1157 (2005).
Adimab Clean Copy of Claims, Filed in Interference No. 105,809, Filed May 19, 2011, pp. 1-5.
Adimab Current List of Exhibits, Filed in Interference No. 105,809, Filed Jan. 20, 2012, pp. 1-8.
Adimab Current List of Exhibits, Filed in Interference No. 105,809, Filed Sep. 30, 2011, pp. 1-5.
Adimab Designation of Lead and Backup Counsel, Filed in Interference No. 105,809, Filed May 19, 2011, pp. 1-6.
Adimab Exhibit 2001, Filed in Interference No. 105,809, Filed Aug. 19, 2011—U.S. Pat. No. 7,700,302 Issued May 19, 1992, pp. 1-69.
Adimab Exhibit 2002, Filed in Interference No. 105,809, Filed Aug. 19, 2011—Boder and Wittrup—Boder et al "Yeast surface display for screening combinatorial polypeptide libraries" Nature Biotechnology 15:553-557 (1997).
Adimab Exhibit 2003, Filed in Interference No. 105,809, Filed Aug. 19, 2011—Boder and Wittrup "Yeast Surface Display for Directed Evolution of Protein Expression, Affinity, and Stability" Methods Enzymol 328:430-444 (2000).
Adimab Exhibit 2004, Filed in Interference No. 105,809, Filed Aug. 19, 2011—Schreuder et al., "Immobilizing proteins on the surface of yeast cells" Trends Biotechnol. 14(4)115-120 (1996).
Adimab Exhibit 2005, Filed in Interference No. 105,809, Filed Aug. 19, 2011—Liu et al. "Rapid Construction of Recombinant DNA by the Univector Plasmid-Fusion System" Methods Enzymol. 328:530-549 (2000).
Adimab Exhibit 2006, Filed in Interference No. 105,809, Filed Aug. 19, 2011—Walhout et al., "Gateway Recombinational Cloning: Application to the Cloning of Large Number of Open Reading Frames or ORFeomes" Methods Enzymol. 328:575-592 (2000).
Adimab Exhibit 2007, Filed in Interference No. 105,809, Filed Aug. 19, 2011—Smith, G. "Homologous Recombination Near and Far from DNA Breaks: Alternative Roles and Contrasting Views" Annu Rev Genet 35:243-274 (2001).
Adimab Exhibit 2008, Filed in Interference No. 105,809, Filed Aug. 19, 2011—Declaration of David M. Kranz, Ph.D, pp. 1-8.
Adimab Exhibit 2009, Filed in Interference No. 105,809, Filed Aug. 19, 2011—Sauer, B. "Inducible Gene Targeting in Mice Using the Crd / Iox System" Methods 14(4)381-392 (1998).
Adimab Exhibit 2010, Filed in Interference No. 105,809, Filed Aug. 19, 2011—WO 03/02956 Published Apr. 10, 2003, pp. 1-138.
Adimab Exhibit 2011, Filed in Interference No. 105,809, Filed Aug. 19, 2011—EP 02766425 Amendment before Examination filed Jun. 16, 2004, pp. 1-18.
Adimab Exhibit 2012, Filed in Interference No. 105,809, Filed Aug. 19, 2011—EP Publication No. EP1438400 Published Jun. 17, 2009, pp. 1-85.
Adimab Exhibit 2013, Filed in Interference No. 105,809, Filed Aug. 19, 2011—U.S. Appl. No. 10/26264: Non-Final Rejection dated Dec. 13, 2007, pp. 1-12.
Adimab Exhibit 2014, Filed in Interference No. 105,809, Filed Aug. 19, 2011—Pogue and Goodnow—"Gene Dose-dependent Maturation and Receptor Editing of B Cells Expressing Immumoglobulin (Ig)G1 or IgM/IgG1 Tail Antigen Receptors" J. Exp. Med 191(6) 1031-1043 (2000).
Adimab Exhibit 2015, Filed in Interference No. 105,809, Filed Aug. 19, 2011—U.S. Appl. No. 10/262,646: Amendment in Reply to Action dated Sep. 7, 2006, pp. 1-26.
Adimab Exhibit 2016, Filed in Interference No. 105,809, Filed Aug. 19, 2011—U.S. Appl. No. 10/262,646: Amendment in Reply to Action dated Dec. 13, 2007, pp. 1-26.
Adimab Exhibit 2017, Filed in Interference No. 105,809, Filed Aug. 19, 2011—Swers et al., "Shuffled antibody libraries created by in vivo homologous recombination and yeast surface display" Nucleic Acids Research 32(3) e36 pp. 1-8 (2004).
Adimab Exhibit 2018, Filed in Interference No. 105,809, Filed Aug. 19, 2011—U.S. Appl. No. 12/625,337: Dyax's Third Preliminary Amendment and Suggestion of Interference under 37 C.F.R. § 41.202(a) filed Jan. 24, 2011, pp. 1-33.
Adimab Exhibit 2019, Filed in Interference No. 105,809, Filed Aug. 19, 2011—*Agilent Technologies, Inc.* v. *Affymetrix, Inc.* Decided Jun. 4, 2009, pp. 1-12.
Adimab Exhibit 2020, Filed in Interference No. 105,809, Filed Aug. 19, 2011—*Jones J. Robertson and Robert M. Currie* v. *Jos Timmermans and Jean C. Raymond* Decided May 5, 2010, pp. 1-6.
Adimab Exhibit 2021, Filed in Interference No. 105,809, Filed Aug. 19, 2011—U.S. Appl. No. 10/818,920: Ex parte Donald V. Smart—Appeal 2009-015036, pp. 1-13.
Adimab Exhibit 2022, Filed in Interference No. 105,809, Filed Aug. 19, 2011—Dyax Motions List filed Jun. 28, 2011, pp. 1-10.
Adimab Exhibit 2023, Filed in Interference No. 105,809, Filed Aug. 19, 2011—U.S. Appl. No. 10/262,646: Final Rejection dated Oct. 3, 2008, pp. 1-14.
Adimab Exhibit 2024, Filed in Interference No. 105,809, Filed Aug. 19, 2011—U.S. Appl. No. 10/262,646: Amendment in Reply to Action of Oct. 3, 2008 filed Apr. 3, 2009, pp. 1-13.
Adimab Exhibit 2025, Filed in Interference No. 105,809, Filed Aug. 19, 2011—U.S. Appl. No. 12/625,337: Amendment and Response to Notice to File Missing Parts filed Aug. 17, 2010, pp. 1-36.
Adimab Exhibit 2026, Filed in Interference No. 105,809, Filed Aug. 19, 2011—U.S. Appl. No. 09/703,399, filed Oct. 31, 2000, pp. 1-190.
Adimab Exhibit 2027, Filed in Interference No. 105,809, Filed Aug. 19, 2011—USSN 2011/0009280 Published Jan. 13, 2011, pp. 1-58.
Adimab Exhibit 2028, Filed in Interference No. 105,809, Filed Aug. 19, 2011—Adimab's Reissue U.S. Appl. No. 13/213,302, filed Aug. 19, 2011, pp. 1-90.
Adimab Exhibit 2029, Filed in Interference No. 105,809, Filed Aug. 19, 2011—U.S. Pat. No. 7,700,302: Amendment in Accordance with 37 C.F.R. §1.73(b) filed Aug. 19, 2011, pp. 1-17.
Adimab Exhibit 2030, Filed in Interference No. 105,809, Filed Aug. 19, 2011—Dyax's U.S. Appl. No. 10/262,646, filed Sep. 30, 2002, pp. 1-138.
Adimab Exhibit 2031, Filed in Interference No. 105,809, Filed Aug. 19, 2011—Dyax's U.S. Appl. No. 60/326,320, filed Oct. 1, 2001, pp. 1-90.
Adimab Exhibit 2032, Filed in Interference No. 105,809, Filed Aug. 19, 2011—Adimab's U.S. Appl. No. 11/593,957, filed Nov. 6, 2006, pp. 1-125.
Adimab Exhibit 2033, Filed in Interference No. 105,809, Filed Aug. 19, 2011—Adimab's U.S. Appl. No. 10/360,828, filed Feb. 7, 2003, pp. 1-135.
Adimab Exhibit 2034, Filed in Interference No. 105,809, Filed Aug. 19, 2011—Adimab's U.S. Appl. No. 10/133,978, filed Apr. 25, 2002, pp. 138.
Adimab Exhibit 2035, Filed in Interference No. 105,809, Filed Aug. 19, 2011—Adimab's U.S. Appl. No. 10/072,301, filed Feb. 8, 2002, pp. 1-123.
Adimab Exhibit 2036, Filed in Interference No. 105,809, Filed Aug. 19, 2011—Adimab's U.S. Appl. No. 10/071,866, filed Feb. 8, 2002, pp. 1-132.
Adimab Exhibit 2037, Filed in Interference No. 105,809, Filed Aug. 19, 2011—U.S. Appl. No. 12/625,337, filed Nov. 24, 2009, pp. 1-164.
Adimab Exhibit 2038, Filed in Interference No. 105,809, Filed Aug. 19, 2011—Assignment for U.S. Pat. No. 7,700,302 filed Nov. 6, 2006, pp. 1.
Adimab Exhibit 2039, Filed in Interference No. 105,809, Filed Aug. 19, 2011—Filing Receipt for U.S. Appl. No. 11/593,957 dated Dec. 4, 2006, pp. 1-3.
Adimab Exhibit 2040, Filed in Interference No. 105,809, Filed Aug. 19, 2011—Hua et al., "Minimum Length of Sequence Homology Required for in Vivo Cloning by Homologous Recombination in Yeast" Plasmid 38:91-96 (1997).
Adimab Exhibit 2041, Filed in Interference No. 105,809, Filed Aug. 19, 2011—U.S. Appl. No. 10/262,646: Notice of Abandonment dated Dec. 10, 2009, pp. 1-2.
Adimab Exhibit 2042, Filed in Interference No. 105,809, Filed Aug. 19, 2011—U.S. Appl. No. 10/133,978: Office Action Restricting Claims dated Oct. 5, 2004, pp. 1-19.

(56) References Cited

OTHER PUBLICATIONS

Adimab Exhibit 2043, Filed in Interference No. 105,809, Filed Aug. 19, 2011—U.S. Appl. No. 09/703,399 Complete File History, pp. 1-758.
Adimab Exhibit 2044, Filed in Interference No. 105,809, Filed Aug. 19, 2011—U.S. Appl. No. 13/213,302 Second Amendment to Introduce Missing Drawing Sheets filed on Aug. 19, 2011, pp. 1-9.
Adimab Exhibit 2045, Filed in Interference No. 105,809, Filed Sep. 30, 2011—U.S. Pat. No. 7,138,496 Issued Nov. 21, 2006, pp. 1-70.
Adimab Exhibit 2046, Filed in Interference No. 105,809, Filed Sep. 30, 2011—U.S. Pat. No. 7,005,503 Issued Feb. 28, 2006, pp. 1-63.
Adimab Exhibit 2047, Filed in Interference No. 105,809, Filed Sep. 30, 2011—U.S. Appl. No. 13/249,581: Complete File History of the CON of Reissue, pp. 1-113.
Adimab Exhibit 2048, Filed in Interference No. 105,809, Filed Sep. 30, 2011—U.S. Appl. No. 13/213,302: Fourth Preliminary Amendment filed Aug. 19, 2011, pp. 1-78.
Adimab Exhibit 2049, Filed in Interference No. 105,809, Filed Sep. 30, 2011—U.S. Pat. No. 6,610,472 Issued Aug. 26, 2003, pp. 1-72.
Adimab Exhibit 2050, Filed in Interference No. 105,809, Filed Sep. 30, 2011—U.S. Appl. No. 13/213,302: Third Preliminary Amendment filed Aug. 19, 2011, pp. 1-9.
Adimab Exhibit 2051, Filed in Interference No. 105,809, Filed Nov. 21, 2011—Horwitz et al., "Secretion of functional antibody and Fab fragment from yeast cells" Proc. Natl. Acad. Sci. 85:8678-8682 (1988).
Adimab Exhibit 2052, Filed in Interference No. 105,809, Filed Nov. 21, 2011—US Publication No. 2003/0232395 Published Dec. 18, 2003, pp. 1-39.
Adimab Exhibit 2053, Filed in Interference No. 105,809, Filed Nov. 21, 2011—Website of Nathalie Scholler, MD., Ph.D, pp. 1-3.
Adimab Exhibit 2054, Filed in Interference No. 105,809, Filed Nov. 21, 2011—Raymond et al., "General Method for Plasmid Construction Using Homologous Recombination" BioTechniques 26:pp. 1-6 (1999).
Adimab Exhibit 2055, Filed in Interference No. 105,809, Filed Nov. 21, 2011—U.S. Pat. No. 6,300,065 Issued Oct. 9, 2001, pp. 1-67.
Adimab Exhibit 2056, Filed in Interference No. 105,809, Filed Nov. 21, 2011—U.S. Pat. No. 6,027,910 Issued Feb. 22, 2000, pp. 1-58.
Adimab Exhibit 2057, Filed in Interference No. 105,809, Filed Nov. 21, 2011—U.S. Pat. No. 6,696,251 Issued Feb. 24, 2004, pp. 1-57.
Adimab Exhibit 2058, Filed in Interference No. 105,809, Filed Nov. 21, 2011—International Publication No. WO 94/18330 Published Aug. 18, 1994, pp. 1-69.
Adimab Exhibit 2059, Filed in Interference No. 105,809, Filed Nov. 21, 2011—U.S. Pat. No. 6,114,147 Issued Sep. 5, 2000, pp. 1-40.
Adimab Exhibit 2060, Filed in Interference No. 105,809, Filed Nov. 21, 2011—Schreuder et al., "Targeting of a Heterologous Protein to the Cell Wall of *Saccharamyces cerevisiae*" Yeast 9:399-409 (1993).
Adimab Exhibit 2061, Filed in Interference No. 105,809, Filed Nov. 21, 2011—Imai and Yamamoto "The fission yeast mating pheromone P-factor: its molecular structure, gene structure, and ability to induce gene expression and $G_1$ arrest in the mating partner" Genes & Development 8:328-338 (1993).
Adimab Exhibit 2062, Filed in Interference No. 105,809, Filed Nov. 21, 2011—Cappellaro et al "Mating type-specific cell-cell recognition of *Saccharomyces cerevisiae*: cell wall attachment and active sites of a- and α-agglutinin".
Adimab Exhibit 2063, Filed in Interference No. 105,809, Filed Nov. 21, 2011—Van der vaart et al., "Comparison of Cell Wall Proteins of *Saccharomyces cerevisiae* as Anchors for Cell Surface Expression of Heterologous Proteins" Applied and Environmental Microbiology 63(2):615-620 (1997).
Adimab Exhibit 2064, Filed in Interference No. 105,809, Filed Nov. 21, 2011—Murai et al., "Construction of a Starch-Utilizing Yeast by Cell Surface Engineering" Applied and Environmental Microbiology 63(4):1362-1366 (1997).
Adimab Exhibit 2065, Filed in Interference No. 105,809, Filed Nov. 21, 2011—Ueda and Tanaka "Cell Surface Engineering of Yeast: Construction of Arming Yeast with Biocatalyst" Journal of Bioscience and Bioengineering 90(2):125:136 (2000).
Adimab Exhibit 2066, Filed in Interference No. 105,809, Filed Nov. 21, 2011—Shibasaki et al., "Construction of an engineered yeast with glucose-inducible emission of green fluorescence from the cell surface" Applied Microbiol. Biotechnol. 54:90-96 (2000).
Adimab Exhibit 2067, Filed in Interference No. 105,809, Filed Nov. 21, 2011—Boder and Wittrup "Yeast surface display system for antibody engineeirng" pp. 283 (1996).
Adimab Exhibit 2068, Filed in Interference No. 105,809, Filed Nov. 21, 2011—Deposition of David M. Kranz, Ph.D. dated Oct. 14, 2011, pp. 1-167.
Adimab Exhibit 2069, Filed in Interference No. 105,809, Filed Nov. 21, 2011—Depostion of Nathalie Scholler, M.D., Ph. D. dated Oct. 24, 2011, pp. 1-193.
Adimab Exhibit 2070, Filed in Interference No. 105,809, Filed Nov. 21, 2011—U.S. Pat. No. 6,699,658 Issued Mar. 2, 2004, pp. 1-61.
Adimab Exhibit 2071, Filed in Interference No. 105,809, Filed Nov. 21, 2011—U.S. Pat. No. 7,208,293 Issued Apr. 24, 2007, pp. 1-282.
Adimab Exhibit 2072, Filed in Interference No. 105,809, Filed Nov. 21, 2011—International Publication No. WO 94/01567 Published Jan. 20, 1994, pp. 1-101.
Adimab Exhibit 2073, Filed in Interference No. 105,809, Filed Nov. 21, 2011—U.S. Pat. No. 6,423,538 Issued Jul. 23, 2002, pp. 1-60.
Adimab Exhibit 2074, Filed in Interference No. 105,809, Filed Nov. 21, 2011—Hendershot and Sitia "Immunoglobulin Assembly and Secretion" Molecular Biology of B Cells, Chapter 17 pp. 261-273 (2004).
Adimab Exhibit 2075, Filed in Interference No. 105,809, Filed Nov. 21, 2011—Hoogenboom and Chames "Natural and designer binding sites made by phage display technology" Immunology Today 21(8):371-378 (2000).
Adimab Exhibit 2076, Filed in Interference No. 105,809, Filed Nov. 21, 2011—U.S. Appl. No. 11/593,957 Notice of Allowance dated Nov. 19, 2009, pp. 1-7.
Adimab Exhibit 2077, Filed in Interference No. 105,809, Filed Nov. 21, 2011—Declaration of Eric T. Boder, Ph.D. filed Nov. 21, 2011, pp. 1-12.
Adimab Exhibit 2078, Filed in Interference No. 105,809, Filed Nov. 21, 2011—Second Declaration of David M. Kranz, Ph.D. filed Nov. 21, 2011, pp. 1-27.
Adimab Exhibit 2079, Filed in Interference No. 105,809, Filed Nov. 21, 2011—U.S. Appl. No. 13/300,340: Reissue Application filed Nov. 18, 2011, pp. 1-86.
Adimab Exhibit 2080 [corrected], Filed in Interference 105,809, Filed Nov. 21, 2011—U.S. Appl. No. 13/300,308: [corrected] Reissue Application filed Nov. 18, 2011. pp. 1-95.
Adimab Exhibit 2081, Filed in Interference No. 105,809, Filed Nov. 21, 2011—Declaration of James Sheridan, Ph.D. filed Nov. 21, 2011, pp. 1-4.
Adimab Exhibit 2082, Filed in Interference No. 105,809, Filed Nov. 21, 2011—*Curriculum Vitae* for Eric T. Boder, Ph.D, pp. 1-9.
Adimab Exhibit 2083, Filed in Interference No. 105,809, Filed Nov. 21, 2011—*Curriculum Vitae* for David M. Kranz, Ph.D, pp. 1-22.
Adimab Exhibit 2084, Filed in Interference No. 105,809, Filed Nov. 21, 2011—U.S. Pat. No. 5,223,409 Issued Jun. 29, 1993, pp. 1-217.
Adimab Exhibit 2085, Filed in Interference No. 105,809, Filed Nov. 21, 2011—Patel et al., "Parallel selection of antibody libraries on phage and yeast surfaces via a cross-species display" Protein Engineering, Design & Selection, pp. 1-9 (2011).
Adimab Exhibit 2086, Filed in Interference No. 105,809, Filed Nov. 21, 2011—Struhl et al., "High-frequency transformation of yeast: Autonomous replication of hybrid DNA molecules" Proc. Natl. Acad. Sci. 76(3):1035-1039 (1979).
Adimab Exhibit 2087, Filed in Interference No. 105,809, Filed Jan. 20, 2012—Ueda and Tanaka "Genetic immobilization of proteins on the yeast cell surface" Biotechnology Advances 18:121-140 (2000).
Adimab Exhibit 2088, Filed in Interference No. 105,809, Filed Jan. 20, 2012—Deposition of Eric T. Boder, Ph.D. dated Dec. 20, 2011, pp. 1-121.

(56) References Cited

OTHER PUBLICATIONS

Adimab Exhibit 2089, Filed in Interference No. 105,809, Filed Jan. 20, 2012—Second Deposition of David M. Kranz, Ph.D. dated Jan. 3, 2012, pp. 1-150.
Adimab Exhibit 2090, Filed in Interference No. 105,809, Filed Jan. 20, 2012—Schöndorf et al., "Characterization of the Complete Genome of the Tupaia (Tree Shrew) Adenovirus" Journal of Virology 77(7):4345-4356 (2002/2003).
Adimab Exhibit 2091, Filed in Interference No. 105,809, Filed Jan. 20, 2012—Availability emails for Dr. Sheridan, Dr. Boder, Dr. Kranz, Dr. Zhu and Dr. Scholler, between Wolf, Greenfield & Sacks, P.C. and Choate Hall & Stewart LLP, pp. 1-9.
Adimab Exhibit 2092, Filed in Interference No. 105,809, Filed Jan. 20, 2012—Second Deposition of Nathalie Scholler, M.D., Ph.D. dated Jan. 12, 2012, pp. 1-107.
Adimab Exhibit 2093, Filed in Interference No. 105,809, Filed Jan. 20, 2012—U.S. Pat. No. 7,700,302: Application for Reissue of Utility Patent filed on Sep. 30, 2011, pp. 1-113.
Adimab Exhibit 2094, Filed in Interference No. 105,809, Filed Jan. 20, 2012—Davison et al., "Genetic content and evolution of adenoviruses" Journal of General Virology 84:2895-2908 (2003).
Adimab Exhibit 2095, Filed in Interference No. 105,809, Filed Jan. 20, 2012—U.S. Appl. No. 13/213,302 Filing Receipt for Reissue of U.S. Pat. No. 7,700,302 dated Oct. 11, 2011, pp. 1-3.
Adimab Exhibit 2096, Filed in Interference No. 105,809, Filed Jan. 20, 2012—U.S. Appl. No. 13/300,308 Filing Receipt for Reissue of U.S. Pat. No. 7,138,496 dated Dec. 26, 2011, pp. 1-3.
Adimab Exhibit 2097, Filed in Interference No. 105,809, Filed Jan. 20, 2012—U.S. Appl. No. 13/213,302: Petition to Accept an Unintentionally Delayed Priority Claim under 37 C.F.R. § 1.78(a)(3) filed Jan. 18, 2012, pp. 1-10.
Adimab Exhibit 2098, Filed in Interference No. 105,809, Filed Jan. 20, 2012—U.S. Appl. No. 13/300,340: Petition to Accept an Unintentionally Delayed Priority Claim under 37 C.F.R. § 1.78(a)(3) filed Jan. 18, 2012, pp. 1-6.
Adimab Exhibit 2099, Filed in Interference No. 105,809, Filed Jan. 20, 2012—U.S. Appl. No. 13/300,308: Petition to Accept an Unintentionally Delayed Priority Claim under 37 C.F.R. § 1.78(a)(3) filed Jan. 19, 2012, pp. 1-7.
Adimab Exhibit 2100, Filed in Interference No. 105,809, Filed Feb. 3, 2012—Adimab's Objections to ¶¶ 26, 44-47 & 48-51 of Dyax Exhibit 1112 filed Jan. 27, 2012, pp. 1-3.
Adimab List of Exhibits, Filed in Interference No. 105,809, Filed Feb. 3, 2012, pp. 1-9.
Adimab List of Proposed Motions, Filed in Interference No. 105,809, Filed Jun. 28, 2011, pp. 1-4.
Adimab Misc. Motion 7—Approved, Filed in Interference No. 105,809, Filed Nov. 23, 2011, pp. 1.
Adimab Miscellaneous Motion 7, Filed in Interference No. 105,809, Filed Nov. 23, 2011, pp. 1-3.
Adimab Miscellaneous Motion 8, Filed in Interference No. 105,809, Filed Feb. 3, 2012, pp. 1-16.
Adimab Miscellaneous Motion 9, Filed in Interference No. 105,809, Filed Feb. 3, 2012, pp. 1-14.
Adimab Notice Designating Additional Backup Counsel, Filed in Interference No. 105,809, Filed Dec. 12, 2011, pp. 1-3.
Adimab Notice of Exhibit List Filed, Filed in Interference No. 105,809, Filed Jan. 20, 2012, pp. 1-3.
Adimab Notice of Exhibit List Filed, Filed in Interference No. 105,809, Filed Feb. 3, 2012, pp. 1-3.
Adimab Notice of Exhibits filed, Filed in Interference No. 105,809, Filed Aug. 19, 2011, pp. 1-3.
Adimab Notice of Exhibits Filed, Filed in Interference No. 105,809, Filed Sep. 30, 2011, pp. 1-3.
Adimab Notice of Real Party in Interest, Filed in Interference No. 105,809, Filed May 19, 2011, pp. 1-8.
Adimab Notice of Related Proceedings, Filed in Interference No. 105,809, Filed May 19, 2011, pp. 1-3.
Adimab Notice of Service of Priority Statement, Filed in Interference No. 105,809, Filed Aug. 26, 2011, pp. 1-2.
Adimab Opposition 1, Filed in Interference No. 105,809, Filed Nov. 21, 2011, pp. 1-36.
Adimab Opposition 2, Filed in Interference No. 105,809, Filed Nov. 21, 2011, pp. 1-39.
Adimab Opposition 3, Filed in Interference No. 105,809, Filed Nov. 21, 2011, pp. 1-33.
Adimab Opposition 4, Filed in Interference No. 105,809, Filed Nov. 21, 2011, pp. 1-52.
Adimab Priority Statement, Filed in Interference No. 105,809, Filed Aug. 19, 2011, pp. 1-3.
Adimab Reply 1, Filed in Interference No. 105,809, Filed Jan. 20, 2012, pp. 1-31.
Adimab Reply 2, Filed in Interference No. 105,809, Filed Jan. 20, 2012, pp. 1-26.
Adimab Reply 3, Filed in Interference No. 105,809, Filed Jan. 20, 2012, pp. 1-25.
Adimab Reply 4, Filed in Interference No. 105,809, Filed Jan. 20, 2012, pp. 1-33.
Adimab Reply 5, Filed in Interference No. 105,809, Filed Jan. 20, 2012, pp. 1-40.
Adimab Reply 6, Filed in Interference No. 105,809, Filed Jan. 20, 2012, pp. 1-26.
Adimab Request for File Copies, Filed in Interference No. 105,809, Filed May 19, 2011, pp. 1-5.
Adimab Request for Oral Argument, Filed in Interference No. 105,809, Filed Feb. 3, 2012, pp. 1-4.
Adimab Responsive Motion 6, Filed in Interference No. 105,809, Filed Sep. 30, 2011, pp. 1-14.
Adimab Substantive Motion 1, Filed in Interference No. 105,809, Filed Aug. 19, 2011, pp. 1-25.
Adimab Substantive Motion 2, Filed in Interference No. 105,809, Filed Aug. 19, 2011, pp. 1-25.
Adimab Substantive Motion 3, Filed in Interference No. 105,809, Filed Aug. 19, 2011, pp. 1-20.
Adimab Substantive Motion 4—request to substitute count, Filed in Interference No. 105,809, Filed Aug. 19, 2011, pp. 1-27.
Adimab Substantive Motion 5, Filed in Interference No. 105,809, Filed Aug. 19, 2011, pp. 1-25.
Adimab's Notice of Filing Preliminary Amendment, Filed in Interference No. 105,809, Filed Sep. 8, 2011, pp. 1-3.
Akamatsu, Y. et al., Construction of a human Ig combinatorial library from genomic V segments and synthetic CDR3 fragments, J. Immunol., 51(9):4651-4659 (1993).
Allen, J.B. et al., Finding prospective partners in the library: the two-hybrid system and phage display find a match, TIBS, 20:(12):511-516 (1995).
Alt, F.W. and Baltimore, D., Joining of Immunoglobulin Heavy Chain Gene Segments: Implications from a Chromosome with Evidence of Three D-JH Fusions, PNAS, 79:4118-4122 (1982).
Alves, J. et al., Accuracy of the EcoRV restriction endonuclease: binding and cleavage studies with oligodeoxynucleotide substrates containing degenerate recognition sequences, Biochemistry, 34(35): 11191-11197 (1995).
Arden, B., Conserved motifs in T-cell receptor CDR1 and CDR2: implications for ligand and CDS co-receptor binding, Current Opinion in Immunology, Current Biology LTD., 10(1):74-81 (1998).
Aronheim, Ami et al., Isolation of an AP-1 Repressor by a Novel Method for Detecting Protein-Protein Interactions, Molecular and Cellular Biology, 17(6):3094-3102 (1997).
Aujame, L. et al., High affinity human antibodies by phage display, Human Antibodies, 8(4):155-168 (1997).
Ayala, M. et al., Variable region sequence modulates periplasmic export of a single-chain Fv antibody fragment in *Escherichia coli*, BioTechniques, 18(5):832-838, 840-2 (1995).
Bahler et al., "Clonal Salivary Gland Infiltrates Assciated with Myoepithelial Sialadenitis (Sjögren's Syndrome) Begin as Nonmalignant Antigen-Selected Expansions", Blood, 91(6):1864-1872 (1998).
Bakkus et al., "Evidence that Multiple Myeloma Ig Heavy Chain VDJ Genes Contain Somatic Mutations but Show no Intraclonal Variation", Blood, 80(9):2326-2335 (1992).
Balint, R.F. and Larrick, J.W., Antibody engineering by parsimonious mutagenesis, Gene, 137:109-118 (1993).

(56) References Cited

OTHER PUBLICATIONS

Barbas et al., "Molecular Profile of an Antibody Response to HIV-1 as Probed by Combinatorial Libraries", J. Mol. Biol., 230:812-823 (1993).
Barbas, C.F. 3rd et al., "Semisynthetic combinatorial antibody libraries: a chemical solution to the diversity problem" Proceedings of the National Academy of Sciences of USA, 89:4457-4461 (1992).
Barbas, C.F. 3rd et al., Human autoantibody recognition of DNA, Proc. Natl. Acad. Sci., 92:2529-2533 (1995).
Barbas, C.F. 3rd, et al., "Assembly of combinatorial antibody libraries on phage surfaces: The gene III site" Proc. Natl. Acad. Sci., 88:7978-7982 (1991).
Basu, M. et al., "Synthesis of compositionally unique DNA by terminal deoxynucleotidyl transferase" Biochem. Biophys. Res. Comm., 111(3):1105-1112 (1983).
Bengten, E. et al., Channel Catfish Immunoglobulins: Repertoire and Expression, Dev. Camp. Immunol., 30:77-92 (2006).
Bhatia, S.K. et al., "Rolling adhesion kinematics of yeast engineered to express selectins" Biotech. Prog., 19:1033-1037 (2003).
Binz, H.K. et al., "Engineering novel binding proteins from nonimmunoglobulin domains" Nat. Biotechnol., 23(10):1257-1268 (2005).
Bird, R.E. et al., "Single-chain antigen-binding proteins" Science, 242(4877):423-426 (1988).
Blakesley, et al., "Duplex Regions in "Single-stranded" øX174 DNA Are Cleaved by a Restriction Endonuclease from Haemophilus aegyptius*" The Journal of Bilogical Chemistry, 252:7300-7306 (1977).
Boder, E.T. and Jiang, W., "Engineering Antibodies for Cancer Therapy" Annu. Rev. Chem. Biomol. Eng. 2:53-75 (2011).
Boder, E.T. and Wittrup, K.D., "Optimal screening of surface-displayed polypeptide libraries" Biotechnol Prog.,14(1):55-62 (1998).
Boder, E.T. and Wittrup, K.D., "Yeast surface display for screening combinatorial polypeptide libraries" Nat Biotechnol.,15(6):553-7 (1997).
Boder, E.T. et al., "Directed evolution of antibody fragments with monovalent femtomolar antigen-binding affinity" Proc Natl Acad Sci USA, 97(20):10701-5 (2000).
Borth, N. et al., "Efficient selection of high-producing subclones during gene amplification of recombinant Chinese hamster ovary cells by flow cytometry and cell sorting" Biotechnol. and Bioengin., 71(4):266-273 (2000-2001).
Brachmann, Rainer K. and Boeke, J.D., "Tag games in yeast: the two-hybrid system and beyond" Curr. Opin. Biotechnol., 8(5):561-568 (1997).
Bradbury, A., "Display Technologies Expand Their Horizons" TIBTECH 17:137-138 (1999).
Bradbury, A., "Molecular Library Technologies at the Millenium", TIBTECH 18:132-133 (2000).
Bradbury, A., "Recent advances in phage display: the report of the Phage Club first meeting" Immunotechnology, 3(3):227-231 (1997).
Bray, J.K. et al., "Optimized Torsion-Angle Normal Modes Reproduce Conformational Changes More Accurately Than Cartesian Modes" Biophysical Journal 101 2966-2969 (2011).
Breitling, F. et al., "A surface expression vector for antibody screening" Gene, 104(2):147-153 (1991).
Brezinschek, H.P. et al., "Analysis of the human VH gene repertoire. Differential effects of selection and somatic hypermutation on human peripheral CD5(+)/IgM+ and CD5(-31 )/IgM+ B cells" The American Society for Clinical Investigation, Inc., 99(10):2488-2501 (1997).
Broder, Y.C. et al., "The ras recruitment system, a novel approach to the study of protein-protein interactions" Current Biology 8(20):1121-1124 (1998).
Bruggemann, M. et al., Immunoglobulin Heavy Chain Locus of the Rat: Striking Homology to Mouse Antibody Genes, Proc. Natl. Acad. Sci. USA, 83:6075-6079 (1986).

Burton, D.R. et al., "A large array of human monoclonal antibodies to type 1 human immunodeficiency virus from combinatorial libraries of asymptomatic seropostive individuals" Proc. Natl. Acad. Sci., 88(22):10134-10137 (1991).
Butler, J.E. et al., Antibody Repertoire Development in Swine, Dev. Camp. Immunol., 30:199-221 (2006).
Canaán-Haden, L., "Purification and application of a single-chain Fv antibody fragment specific to hepatitis B virus surface antigen" BioTechniques, 19(4) 606-608, 610, 612 passim (1995).
Carroll et al., "Absence of Ig V Region Gene Somatic Hypermutation in Advanced Burkitt's Lymphoma", J. Immunol., 143(2):692-698 (1989).
Casset, F.et al., "A peptide mimetic of an anti-CD4 monoclonal antibody by rational design" Biochemical and Biophysical Research Communications, 307(1):198-205, (2003).
Castelli, L.A. et al., "High-level secretion of correctily processed beta-lactamase from Saccharomyces ceravisiae using a high-copy-number secretion vector" Biomolecular Research Institute, 142(1):113-117 (1994).
Caton, A.J. and Koprowski, H., "Influenza virus hemagglutinin-specific antibodies isolated from a combinatorial expression library are closely related to the immune response of the donor" Proc. Natl. Acad. Science, USA, 87(16):6450-6454 (1990).
Cattaneo, A. and Biocca, S., "The selection of intracellular antibodies" TIBTECH, 17:115-120 (1999).
Cha, J.H. et al., "Cell surface monkey CD9 antigen is a coreceptor that increases diphtheria toxin sensitivity and diphtheria toxin receptor affinity" Journal of Biological Chemistry, 275(10):6901-6907 (2000).
Chang, C.N. et al., "Expression of antibody Fab domains on bacteriophage surfaces. Potential use for antibody selection" J. Immunol, 147(10):3610-3614. (1991).
Chang, H.C. et al., "A general method for facilitating heterodimeric pairing between two proteins: Application to expression of alpha and beta T-cell receptor extracellular segments" Proc Natl. Acad. Sci., USA, 91:11408-11412 (1994).
Charlton, H.R. et al., "Characterisation of a generic monoclonal antibody harvesting system for adsorption of DNA by depth filters and various membranes" Bioseparation 8: 281-291 (1999).
Chaudhary, V.K. et al., "A rapid method of cloning functional variable-region antibody genes in Escherichia coli as single-chain immunotoxins" Proc. Natl. Acad. Sci., 87(3):1066-1070 (1990).
Chen, C.M. et al., "Direct interaction of hepatitis C virus core protein with the cellular lymphotoxin-beta receptor modulates the signal pathway of the lymphotoxin-beta receptor" Journal of Virology, 71(12):9414-9426 (1997).
Chen, W. et al., "Characterization of germline antibody libraries from human umbilical cord blood and selection of monoclonal antibodies to viral envelope glycoproteins: Implications for mechanisms of immune evasion and design of vaccine immunogens" Biochem. Biophys. Res. Commun. 1-6 (2012).
Chiswell, David and McCaffery, John, "Phage antibodies: will new 'coliclonal' antibodies replace monoclonal antibodies?" TIBTECH, 10(3):80-84 (1992).
Chothia, C. and Lesk, A.M., "Canonical structures for the hypervariable regions of immunoglobulins" J. Mol. Biol., 196(4):901-917 (1987).
Chothia, C. et al., "Conformations of immunoglobulin hypervariable regions" Nature, 342(6252):877-883 (1989).
Chothia, C. et al., "Structural repertoire of the human VH segments" J. Mol. Biol., 227(3):799-817 (1992).
Cioe, L., Cloning and Nucleotide Sequence of a Mouse Erythrocyte beta-Spectrin cDNA, Blood, 70:915-920 (1987).
Clackson, T. and Wells, J.A., "In vitro selection from protein and peptide libraries" Trends Biotechnol., 12(5):173-184 (1994).
Clackson, T. et al., "Making antibody fragments using phage display librarires" Nature, 352(6336):624-628 (1991).
Clean copy of involved claims, Filed in Interference No. 105,809, Filed May 20, 2011, pp. 1-6.
Co, M.S. and Queen, C., "Humanized antibodies for therapy" Nature, 351(6326):501-502 (1991).

(56) References Cited

OTHER PUBLICATIONS

Cochet O. et al., "Intracellular expression of an antibody fragment-neutralizing p21 ras promotes tumor regression", Cancer Res.,58(6):1170-1176 (1998).
Collins, A.M. et al., "Partitioning of rearranged Ig genes by mutation analysis demonstrates D-D fusion and V gene replacement in the expressed human repertoire" J. Immunol., 172(1):340-348 (2004).
Collins, A.M. et al., "The reported germline repertoire of human immunoglobulin kappa chain genes is relatively complete and accurate" Immunogenetics, 60(11):669-676 (2008).
Conzelmann, A. et al., Myoinositol gets incorporated into numerous membrane glycoproteins of Saccharomyces cerevisiae; incorporation is dependent on phosphomannomutase (sec53), EMBO Journal, 9(3):653-661 (1990).
Corbett, S.J. et al., "Sequence of the human immunoglobulin diversity (D) segment locus: a systematic analysis provides no evidence for the use of DIR segments, nverted D egments, "minor" D segments or D-D recombination" J. Mol. Bioi., 270:587-597 (1997).
Corrected Adimab Opposition 4, Filed in Interference No. 105,809, Filed Nov. 23, 2011, pp. 1-52.
Courtney, B.C. et al., "A phage display vector with improved stability, applicability and ease of manipulation", Gene, 165(1):139-140 (1995).
Couto, J.R. et al., "Designing human consensus antibodies with minimal positional templates", Cancer Res., (23 Suppl):5973s-5977s (1995).
Crameri, R. and Blaser, K., "Cloning Aspergillus fumigatus allergens by the pJuFo filamentous phage display system" Int Arch Allergy Immunol,110(1):41-45 (1996).
Crameri, R. and Suter, M. , "Display of biologically active proteins on the surface of filamentous phages: a cDNA cloning system for selection of functional gene products linked to the genetic information responsible for their production" Gene, 137(1):69-75 (1993).
Current List of Exhibits, Filed in Interference No. 105,809, Filed Nov. 21, 2011, pp. 1-8.
Cwirla, S.E., et al., "Peptides on phage: a vast library of peptides for identifying ligands" Proc. Natl. Acad. Sci. USA, 87(16):6378-6382 (1990).
Das, S. et al., Evolutionary Dynamics of the Immunoglobulin Heavy Chain Variable Region Genes in Vertebrates, NIH Public Access Author Manuscript from Immunogenetics, 60(1):47-55 (2008).
Davi et al., "High Frequency of Somatic Mutations in the VH Genes Expressed in Prolymphocytic Leukemia", Blood, 88(10):3953-3961 (1996).
Davies, J. and Riechmann, L., "Affinity improvement of single antibody VH domains: residues in all three hypervariable regions affect antigen binding" Immunotechnology 2(3):169-179 (1996).
De Genst, E. et al., Antibody Repertoire Development in Camelids, Dev. Camp. Immunol., 30:187-198 (2006).
de Haard et al., "A Large Non-immunized Human Fab Fragment Phage Library That Permits Rapid Isolation and Kinetic Analysis of High Affinity Antibodies" Journal of Biological Chemistry, 274(26):18218-18230 (1999).
De Jaeger, G. et al., "Analysis of the interaction between single-chain variable fragments and their antigen in a reducing intracellular environment using the two-hybrid system" FEBS Lett., 467(2-3):316-320 (2000).
de Kruif, J. et al., "Selection and application of human single chain Fv antibody fragments from a semi-synthetic phage antibody display library with designed CDR3 regions" Journal of Molecular Biology, 248(1):97-105 (1995).
De Simone, A. et al., "Experimental free energy surfaces reveal the mechanisms of maintenance of protein solubility" PNAS, 108:52 21057-21062 (2011).
Decision—Dyax Response to Order to Show Cause—Bd.R. 41.125(c) in Patent Interference No. 105,809, Dec. 30, 2013.
Decision on Motions in Patent Interference No. 105,809, Nov. 2, 2012.
Declaration Bd.R. 203, Filed in Interference No. 105,809, Filed May 6, 2011, pp. 1-6.
Delves, P.J. "Antibody production: essential techniques" John Wiley & Sons, New York, pp. 90-113 (1997).
Designation of Lead and Backup Counsel, Filed in Interference No. 105,809, Filed May 20, 2011, pp. 1-3.
DiPietro et al., "Limited number of immunoglobulin VH regions expressed in the mutant rabbit 'Alicia'", Eur. J. Immunol., 20:1401-1404 (1990).
Dirkes, G. et al., Sequence and Structure of the Mouse IgH DQ52 5' Region, Immunogenetics, 40:379 (1994).
Dooley, H. et al., Antibody Repertoire Development in Cartilaginous Fish, Dev. Camp. Immunol., 30:43-56 (2006).
Duffy, S. et al., Site-Specific, Enzymatic Biotinylation of Recombinant Proteins in Spodoptera frugiperda Cells Using Biotin Acceptor Peptides, Analytical Biochemistry, 262:122-128 (1998).
Dyax Corrected Substantive Motion 1, Filed in Interference No. 105,809, Filed Sep. 2, 2011, pp. 1-45.
Dyax Exhibit 1000, Filed in Interference No. 105,809, Filed Aug. 19, 2011—Dyax Exhibit List dated Aug. 19, 2011, pp. 1-5.
Dyax Exhibit 1001, Filed in Interference No. 105,809, Filed Aug. 19, 2011—U.S. Pat. No. 7,700,302 Issued Apr. 20, 2010, pp. 1-69.
Dyax Exhibit 1002, Filed in Interference No. 105,809, Filed Aug. 19, 2011—U.S. Appl. No. 12/625,337, filed Nov. 24, 2009, pp. 1-141.
Dyax Exhibit 1003, Filed in Interference No. 105,809, Filed Aug. 19, 2011—*Curriculum Vitae* for Nathalie Scholler (née Buonavista), M.D., Ph.D, pp. 1-18.
Dyax Exhibit 1004, Filed in Interference No. 105,809, Filed Aug. 19, 2011—Boder and Wittrup "Yeast surface display for screening combinatorial polypeptide libraries" Nature Biotechnology 15(6):553-557 (1997).
Dyax Exhibit 1005, Filed in Interference No. 105,809, Filed Aug. 19, 2011—Kieke et al., "Isolation of anti-T cell receptor scFv mutants by yeast surface display" Protein Engineering 10(11):1303-1310 (1997).
Dyax Exhibit 1006, Filed in Interference No. 105,809, Filed Aug. 19, 2011—Cho et al., "A yeast surface display system for the discovery of ligands that trigger cell activation" journal of Immunological Methods 220:179-188 (1998).
Dyax Exhibit 1007, Filed in Interference No. 105,809, Filed Aug. 19, 2011—Boder and Wittrup "Optimal Screening of Surface-Displayed Polypeptide Libraries" Biotechnol. Prog. 14:55-62 (1998).
Dyax Exhibit 1008, Filed in Interference No. 105,809, Filed Aug. 19, 2011—Kieke et al., "Selection of functional T cell receptor mutants from a yeast surface-display library" Proc. Natl. Acad. Sci. 96:5651-5656 (1999).
Dyax Exhibit 1009, Filed in Interference No. 105,809, Filed Aug. 19, 2011—VanAntwerp and Wittrup "Fine Affinity Discrimination by Yeast Surface Display and Flow Cytometry" Biotechnol. Prog. 16:31-37 (2000).
Dyax Exhibit 1010, Filed in Interference No. 105,809, Filed Aug. 19, 2011—Holler et al., "In vitro evolution of a T cell recepto with high affinity for peptide / MHC" Proc. Natl. Acad. Sci. 97(10):5387-5392 (2000).
Dyax Exhibit 1011, Filed in Interference No. 105,809, Filed Aug. 19, 2011—Shusta et al., "Directed evolution of a stable scaffold for T-cell receptor engineering" Nature Biotechnol. 18(7):754-759 (2000).
Dyax Exhibit 1012, Filed in Interference No. 105,809, Filed Aug. 19, 2011—Boder et al., "Directed evolution of antibody fragments with monovalent femtomolar antigen-binding affinity" PNAS 97(20):10701-10705 (2000).
Dyax Exhibit 1013, Filed in Interference No. 105,809, Filed Aug. 19, 2011—Yeung and Wittrup "Quantitative Screening of Yeast Surface-Displayed Polypeptide Libraries by Magnetic Bead Capture" Biotechnol. Prog. 18(2):212-220 (2002).
Dyax Exhibit 1014, Filed in Interference No. 105,809, Filed Aug. 19, 2011—Orr et al., "Rapid Method for Measuring ScFv Thermal Stability by Yeast Surface Display" Biotechnol. Prog. 19:631-638 (2003).

(56) References Cited

OTHER PUBLICATIONS

Dyax Exhibit 1015, Filed in Interference No. 105,809, Filed Aug. 19, 2011—Griffin et al., "Blockade of T Cell Activation Using a Surface-Linked Single-Chain Antibody to CTLA-4 (CD152)" J Immunol. 64(9):4433-4442 (2000).
Dyax Exhibit 1016, Filed in Interference No. 105,809, Filed Aug. 19, 2011—Kieke et al., "High Affinity T Cell Receptors from Yeast Display Libraries Block T Cell Activation by Superantigens" J. Mol. Biol. 307:1305-1315 (2001).
Dyax Exhibit 1017, Filed in Interference No. 105,809, Filed Aug. 19, 2011—Brophy et al., "A yeast display system for engineering functional peptide-MHC complexes" Journal of Immunological Methods 272:235-246 (2003).
Dyax Exhibit 1018, Filed in Interference No. 105,809, Filed Aug. 19, 2011—Starwalt et al., "Directed evolution of a single-chain class II MHC product by yeast display" Protein Engineering 16(2):147-156 (2003).
Dyax Exhibit 1019, Filed in Interference No. 105,809, Filed Aug. 19, 2011—van den Beucken et al., "Affinity maturation of Fab antibody fragments by fluorescent-activated cell sorting of yeast-displayed libraries" FEBS Letters 546:288-294 (2003).
Dyax Exhibit 1020, Filed in Interference No. 105,809, Filed Aug. 19, 2011—Brochure of the 13th Annual Phage and Yeast Display of Antibodies and Protein Conference, pp. 1-7.
Dyax Exhibit 1021, Filed in Interference No. 105,809, Filed Aug. 19, 2011—U.S. Pat. No. 6,610,472 Issued Aug. 26, 2003, pp. 1-72.
Dyax Exhibit 1022, Filed in Interference No. 105,809, Filed Aug. 19, 2011—Walhout et al., "Gateway Recombinational Cloning: Application to the Cloning of Large Numbers of Open Reading Frames or ORFeomes" Methods in Enzymology 328:575-592 (2000).
Dyax Exhibit 1023, Filed in Interference No. 105,809, Filed Aug. 19, 2011—Swers et al., "Shuffled antibody libraries created in vivo homologous recombination and yeast surface display" Nucleic Acids Research 32(3) e36, pp. 1-8 (2004).
Dyax Exhibit 1024, Filed in Interference No. 105,809, Filed Aug. 19, 2011—Swers et al., "Integrated Mimicry of B Cell Antibody Mutagenesis Using Yeast Homologous Recombination" Mol. Biotechnol. 46:57-69 (2011).
Dyax Exhibit 1025, Filed in Interference No. 105,809, Filed Aug. 19, 2011—Abbas et al., "Cellular and Molecular Immunology", 4th ed., p. 43, Figure 3-1,. W.B. Saunders Co. (2000).
Dyax Exhibit 1026, Filed in Interference No. 105,809, Filed Aug. 19, 2011—Lewin, B. "Genes V", p. 99, Oxford University Press (1994).
Dyax Exhibit 1027, Filed in Interference No. 105,809, Filed Aug. 19, 2011—Dranginis et al., "A Biochemical Guide to Yeast Adhesins: Glycoproteins for Social and Antisocial Occasions" Microbiology and Molecular Biology Reviews 71(2)282-294 (2007).
Dyax Exhibit 1027A, Filed in Interference No. 105,809, Filed Aug. 19, 2011—Dranginis et al., "A Biochemical Guide to Yeast Adhesins: Glycoproteins for Social and Antisocial Occasions" Microbiology and Molecular Biology Reviews 71(2)282-294 (2007).
Dyax Exhibit 1028, Filed in Interference No. 105,809, Filed Aug. 19, 2011—Sharifmoghadam, et al., "The fission yeast Map4 protein is a novel adhesin required for mating" FEBS Letters 580:4457-4462 (2006).
Dyax Exhibit 1029, Filed in Interference No. 105,809, Filed Aug. 19, 2011—International Publication No. WO 02/055718 Published Jul. 18, 2002, pp. 1-202.
Dyax Exhibit 1030, Filed in Interference No. 105,809, Filed Aug. 19, 2011—Specification of U.S. Appl. No. 09/703,399 as filed, pp. 1-123.
Dyax Exhibit 1031, Filed in Interference No. 105,809, Filed Aug. 19, 2011—Ma et al., "Plasmid construction by homologous recombination in yeast" Gene 58:201-216 (1987).
Dyax Exhibit 1032, Filed in Interference No. 105,809, Filed Aug. 19, 2011—Wood et al., "The synthesis and in vivo assembly of functional antibodies in yeast" Nature 314:(6010)446-449 (1985).
Dyax Exhibit 1033, Filed in Interference No. 105,809, Filed Aug. 19, 2011—Weaver-Feldhaus et al., "Yeast mating for combinatorial Fab library generation and surface display" FEBS Letters 564:24-34 (2004).
Dyax Exhibit 1034, Filed in Interference No. 105,809, Filed Aug. 19, 2011—Shen et al., "Delineation of Functional Regions within the Subunits of the *Saccharomyces cerevisiae* Cell Adhesion Molecule a-Agglutinin" The Journal of Biological Chemistry 276(19):15768-15775 (2001).
Dyax Exhibit 1035, Filed in Interference No. 105,809, Filed Aug. 19, 2011—Ma et al., "Association of Transport-Defective Light Chains with Immunoglobulin Heavy Chain Binding Protein" Molecular Immunology 27(7):623-630 (1990).
Dyax Exhibit 1036, Filed in Interference No. 105,809, Filed Aug. 19, 2011—Colby et al., "Development of a Human Light Chain Variable Domain ($V_L$) Intracellular Antibody Specific for the Amino Terminus of Huntingtin via Yeast Surface Display" J. Mol. Biol. 901-912 (2004).
Dyax Exhibit 1037, Filed in Interference No. 105,809, Filed Aug. 19, 2011—U.S. Pat. No. 4,946,778 Issued Aug. 7, 1990, pp. 1-69.
Dyax Exhibit 1038, Filed in Interference No. 105,809, Filed Aug. 19, 2011—Hamilton and Gerngross "Glycosylation engineering in yeast: the advent of fully humanized yeast" Current Opinion in Biotechnology 18:387-392 (2007).
Dyax Exhibit 1039, Filed in Interference No. 105,809, Filed Aug. 19, 2011—Bird et al., "Single-Chain Antigen-Binding Proteins" Science 242(4877)423-426 (1998).
Dyax Exhibit 1040, Filed in Interference No. 105,809, Filed Aug. 19, 2011—Boder and Wittrup "Yeast Surface Display for Directed Evolution of Protein Expression, Affinity, and Stability" Methods in Enzymology 328:430-444 (2000).
Dyax Exhibit 1041, Filed in Interference No. 105,809, Filed Aug. 19, 2011—First Declaration of Nathalie Scholler, M.D., Ph.D. filed Aug. 19, 2011, pp. 1-44.
Dyax Exhibit 1042, Filed in Interference No. 105,809, Filed Aug. 19, 2011—U.S. Appl. No. 11/593,957: Non-final Office Action dated Aug. 12, 2008, pp. 1-7.
Dyax Exhibit 1043, Filed in Interference No. 105,809, Filed Aug. 19, 2011—U.S. Appl. No. 11/593,957: Adimab's response to the Non-final Office Action filed Jan. 13, 2009, pp. 1-10.
Dyax Exhibit 1044, Filed in Interference No. 105,809, Filed Aug. 19, 2011—First Declaration of Li Zhu, Ph.D. dated Jan. 13, 2009, pp. 1-2.
Dyax Exhibit 1045, Filed in Interference No. 105,809, Filed Aug. 19, 2011—U.S. Appl. No. 11/593,957: Final Office Action dated Apr. 8, 2009, pp. 1-5.
Dyax Exhibit 1046, Filed in Interference No. 105,809, Filed Aug. 19, 2011—U.S. Appl. No. 11/593,957: Adimab's response to Final Office Action filed Oct. 7, 2009, pp. 1-9.
Dyax Exhibit 1047, Filed in Interference No. 105,809, Filed Aug. 19, 2011—Second Declaration of Li Zhu, Ph.D. filed Oct. 7, 2009, pp. 1.
Dyax Exhibit 1048, Filed in Interference No. 105,809, Filed Aug. 19, 2011—U.S. Appl. No. 11/593,957: Request to Change Inventorship under 37 C.F.R. § 1.48(b) filed Oct. 7, 2009, pp. 1.
Dyax Exhibit 1049, Filed in Interference No. 105,809, Filed Aug. 19, 2011—Sambrook et al., "Molecular Cloning: A Laboratory Manual" pp. 1-2 (1989).
Dyax Exhibit 1050, Filed in Interference No. 105,809, Filed Aug. 19, 2011—Claim chart showing disclosures in the '472 patent for claim 1 of the '302 patent, pp. 1-2.
Dyax Exhibit 1051, Filed in Interference No. 105,809, Filed Aug. 19, 2011—Claim chart showing disclosure in the '472 patent for claims 2-15 of the '302 patent, pp. 1-4.
Dyax Exhibit 1052, Filed in Interference No. 105,809, Filed Aug. 19, 2011—Claim chart showing disclosures in Boder for claim 1 of the '302 patent, pp. 1-2.
Dyax Exhibit 1053, Filed in Interference No. 105,809, Filed Aug. 19, 2011—Claim chart showing disclosures in Boder for claims 2-15 of the '302 patent, pp. 1-2.
Dyax Exhibit 1054, Filed in Interference No. 105,809, Filed Aug. 19, 2011—Claim chart showing disclosures in Boder and Walhout for claim 1 of the '302 patent, pp. 1-2.

(56) References Cited

OTHER PUBLICATIONS

Dyax Exhibit 1055, Filed in Interference No. 105,809, Filed Aug. 19, 2011—Claim chart showing disclosures in Boder and Walhout for claim 2-15 of the '302 patent, pp. 1-5.
Dyax Exhibit 1056, Filed in Interference No. 105,809, Filed Aug. 19, 2011—An on-line document showing publication date of Methods in Enzymology, vol. 328, pp. 1-4.
Dyax Exhibit 1057, Filed in Interference No. 105,809, Filed Aug. 19, 2011—Karu et al., "Recombinant Antibody Technology" ILAR Journal 37(3) pp. 1-9 (1995).
Dyax Exhibit 1058, Filed in Interference No. 105,809, Filed Aug. 19, 2011—U.S. Appl. No. 11/593,957: Complete File History, pp. 1-735.
Dyax Exhibit 1059, Filed in Interference No. 105,809, Filed Sep. 30, 2011—U.S. Appl. No. 12/625,337: Fourth Preliminary Amendment filed Sep. 30, 2011, pp. 1-17.
Dyax Exhibit 1060, Filed in Interference No. 105,809, Filed Sep. 30, 2011—Souriau and Hudson "Recombinant antibodies for cancer diagnosis and therapy" Expert Opin. Biol. Ther. 1(5):845-855 (2001).
Dyax Exhibit 1061, Filed in Interference No. 105,809, Filed Sep. 30, 2011—Liu et al., "Rapid Construction of Recombinant DNA by the Univector Plasmid-Fusion System" Methods in Enzymology 328:530-549 (2000).
Dyax Exhibit 1062, Filed in Interference No. 105,809, Filed Sep. 30, 2011—Hua et al., "Construction of a modular yeast two-hybrid cDNA library from human EST clones for the human genome protein linkage map" Gene 215:143-152 (1998).
Dyax Exhibit 1063, Filed in Interference No. 105,809, Filed Sep. 30, 2011—Abbas et al., Cellular and Molecular Immunology, 4th ed., W.B. Saunders Co., p. 43 (2000).
Dyax Exhibit 1064, Filed in Interference No. 105,809, Filed Sep. 30, 2011—Burke et al., "Methods in Yeast Genetics", pp. 40-41 (2000).
Dyax Exhibit 1065, Filed in Interference No. 105,809, Filed Sep. 30, 2011—U.S. Appl. No. 12/625,337: Third Preliminary Amendment and Suggestion of an Interference under 37 C.F.R. § 41.202(a) filed Jan. 24, 2011, pp. 1-33.
Dyax Exhibit 1066, Filed in Interference No. 105,809, Filed Sep. 30, 2011—Alberts et al., "Molecular Biology of the Cell Third Edition", pp. 1-4 (1994).
Dyax Exhibit 1067, Filed in Interference No. 105,809, Filed Sep. 30, 2011—U.S. Appl. No. 10/262,646, filed Sep. 30, 2002, pp. 1-136.
Dyax Exhibit 1068, Filed in Interference No. 105,809, Filed Sep. 30, 2011—U.S. Appl. No. 60/326,320, filed Oct. 1, 2001, pp. 1-90.
Dyax Exhibit 1069, Filed in Interference No. 105,809, Filed Sep. 30, 2011—Adimab's Substantive Motion 2 (for no interference-in-fact) filed Aug. 19, 2011, pp. 1-25.
Dyax Exhibit 1070, Filed in Interference No. 105,809, Filed Sep. 30, 2011—Marks et al., "By-passing Immunization Human Antibodies from V-gene Libraries Displayed on Phage" J. Mol. Biol. 222:581-597 (1991).
Dyax Exhibit 1071, Filed in Interference No. 105,809, Filed Sep. 30, 2011—Abbas et al., Cellular and Molecular Immunology, Fourth Edition—Section III Maturation, Activation, and Regulation of Lymphocytes, 125-133 (2000).
Dyax Exhibit 1072, Filed in Interference No. 105,809, Filed Sep. 30, 2011—Second Declaration of Nathalie Scholler, M.D., Ph.D. dated Sep. 29, 2011, pp. 1-31.
Dyax Exhibit 1073, Filed in Interference No. 105,809, Filed Sep. 30, 2011—U.S. Appl. No. 10/262,646: Final Office Action with Restriction Requirement dated Mar. 9, 2005, pp. 1-7.
Dyax Exhibit 1074, Filed in Interference No. 105,809, Filed Sep. 30, 2011—U.S. Appl. No. 10/262,646: Response to Restriction Requirement filed Apr. 8, 2005, pp. 1.
Dyax Exhibit 1075, Filed in Interference No. 105,809, Filed Sep. 30, 2011—U.S. Appl. No. 12/625,337: Amendment and Response to Notice to File Missing Parts filed Aug. 17, 2010, pp. 1-9.
Dyax Exhibit 1076, Filed in Interference No. 105,809, Filed Nov. 21, 2011—*Curriculum Vitae* for David M. Kranz, Ph.D, pp. 1-22.
Dyax Exhibit 1077, Filed in Interference No. 105,809, Filed Nov. 21, 2011—Woods and Gietz "High-Efficiency Transformation of Plasmid DNA into Yeast", Methods in Molecular Biology, 177:85-97.
Dyax Exhibit 1078, Filed in Interference No. 105,809, Filed Nov. 21, 2011—David M. Kranz, Ph.D. biography from the University of Illinois, pp. 1-3.
Dyax Exhibit 1079, Filed in Interference No. 105,809, Filed Nov. 21, 2011—US Patent Application 2001/0037016 Published Nov. 1, 2001, pp. 1-85.
Dyax Exhibit 1080, Filed in Interference No. 105,809, Filed Nov. 21, 2011—US Patent Publication No. US 2002/0026653 Published Feb. 28, 2002, pp. 1-25.
Dyax Exhibit 1081, Filed in Interference No. 105,809, Filed Nov. 21, 2011—US Patent Publication No. US 2002/0037280 Published Mar. 28, 2002, pp. 1-51.
Dyax Exhibit 1082, Filed in Interference No. 105,809, Filed Nov. 21, 2011—Alberts et al., Molecular Biology of The Cell, Forth Edition, pp. 293-294 (2001).
Dyax Exhibit 1083, Filed in Interference No. 105,809, Filed Nov. 21, 2011—Alberts et al., Molecular Biology of The Cell, Fourth Edition, pp. 540-5411 (2001).
Dyax Exhibit 1084, Filed in Interference No. 105,809, Filed Nov. 21, 2011—The Hena Protein-Protein Interaction Webpage print out, pp. 1.
Dyax Exhibit 1085, Filed in Interference No. 105,809, Filed Nov. 21, 2011—Deposition of David M. Kranz, Ph.D. dated Oct. 14, 2011, pp. 1-168.
Dyax Exhibit 1086, Filed in Interference No. 105,809, Filed Nov. 21, 2011—Deposition of Nathalie Scholler, M.D., Ph.D. dated Oct. 24, 2011, pp. 1-193.
Dyax Exhibit 1087, Filed in Interference No. 105,809, Filed Nov. 21, 2011—In-Fusion SMARTer Directional cDNA Library Construction Kit User Manual Clontech—Jun. 2011, pp. 1-41.
Dyax Exhibit 1088, Filed in Interference No. 105,809, Filed Nov. 21, 2011—US Patent Publication No. US 2003/0091995 Published May 15, 2003, pp. 1-50.
Dyax Exhibit 1089, Filed in Interference No. 105,809, Filed Nov. 21, 2011—US Patent Publication No. US 2001/0041333 Published Nov. 15, 2001, pp. 1-45.
Dyax Exhibit 1090, Filed in Interference No. 105,809, Filed Nov. 21, 2011—Sheets et al., "Efficient construction of a large nonimmune phage antibody library: The production of high-affinity human single-chain antibodies to protein antigens" Proc. Natl. Acad. Sci. 95:6157-6162 (1998).
Dyax Exhibit 1091, Filed in Interference No. 105,809, Filed Nov. 21, 2011—Third Declaration of Nathalie Scholler, M.D., Ph.D. dated Nov. 20, 2011, pp. 1-40.
Dyax Exhibit 1092, Filed in Interference No. 105,809, Filed Nov. 21, 2011—Shusta et al., "Yeast Polypeptide Fusion Surface Display Levels Predict Thermal Stability and Soluble Secretion Efficiency" JMB 292:949-956 (1999).
Dyax Exhibit 1093, Filed in Interference No. 105,809, Filed Jan. 20, 2012—Boder et al., "Yeast Surface Display of a Noncovalent MHC Class II Heterodimer Complexed With Antigenic Peptide" Biotechnology and Bioengineering 92(4):485-491 (2005).
Dyax Exhibit 1094, Filed in Interference No. 105,809, Filed Jan. 20, 2012—Pepper et al., "A Decade of Yeast Surface Display Technology: Where Are We Now?" Combinatorial Chemistry & High Throughput Screening 11:127-134 (2008).
Dyax Exhibit 1095, Filed in Interference No. 105,809, Filed Jan. 20, 2012—Alberts et al., Molecular Biology of The Cell, Fourth Edition, pp. 275-277 (2002).
Dyax Exhibit 1096, Filed in Interference No. 105,809, Filed Jan. 20, 2012—Lin et al., "Display of a functional hetero-oligomeric catalytic antibody on the yeast cell surface" Appl. Microbiol. Biotechnol. 62:226-232 (2002).

(56) References Cited

OTHER PUBLICATIONS

Dyax Exhibit 1097, Filed in Interference No. 105,809, Filed Jan. 20, 2012—Hubberstey and Wildeman, "Use of interplasmid recombination to generate stable selectable markers for yeast transformation: application to studies of actin gene control" Genome 33(5):696-706 (1990).
Dyax Exhibit 1098, Filed in Interference No. 105,809, Filed Jan. 20, 2012—Dielbandhoesing et al., "Specific Cell Wall Proteins Confer Resistance to Nisin upon Yeast Cells" Applied and Environmental Microbiology 64(10)4047-4052 (1998).
Dyax Exhibit 1099, Filed in Interference No. 105,809, Filed Jan. 20, 2012—Sed1p {Saccharomyces cerevisiae S288c]—Protein—NCBI Reference Sequence: NP_010362.1, pp. 1-2.
Dyax Exhibit 1100, Filed in Interference No. 105,809, Filed Jan. 20, 2012—Tip1p [Saccharomyces cerevisiae S288c]—Protein—NCBI Reference Sequence: NP_009623.1, pp. 1-2.
Dyax Exhibit 1101, Filed in Interference No. 105,809, Filed Jan. 20, 2012—Deposition of David M. Kranz, Ph.D. dated Oct. 14, 2011, pp. 1-54.
Dyax Exhibit 1102, Filed in Interference No. 105,809, Filed Jan. 20, 2012—Tsubouchi and Roeder, "Budding yeast Hed1 down-regulates the mitotic recombination machinery when meiotic recombination is impaired" Genes & Development 20:1766-1775 (2006).
Dyax Exhibit 1103, Filed in Interference No. 105,809, Filed Jan. 20, 2012—Sample Campaign « Adimab, Webpage from www.adimab.com/science-and-technology/technology-overview/sample campaign, pp. 1-2.
Dyax Exhibit 1104, Filed in Interference No. 105,809, Filed Jan. 20, 2012 Corporate Overview « Adimab, Webpage from www.adimab.com/about-adimab/corporate-overview, pp. 1.
Dyax Exhibit 1105, Filed in Interference No. 105,809, Filed Jan. 20, 2012—Manivasakam and Schiestl, High efficiency transformation of *Saccharomyces cerevisiae* by electroporation Nucleic Acids Research 21(18)4414-4415 (1993).
Dyax Exhibit 1106, Filed in Interference No. 105,809, Filed Jan. 20, 2012—Kranz and Voss, "Restricted reassociation of heavy and light chains from hapten-specific monoclonal antibodies" Proc. Natl. Acad. Sci. 78(9):5807-5811 (1981).
Dyax Exhibit 1107, Filed in Interference No. 105,809, Filed Jan. 20, 2012—Decision on Motions and Order for Patent Interference No. 104,424 dated Jul. 28, 2000, pp. 1-62.
Dyax Exhibit 1108, Filed in Interference No. 105,809, Filed Jan. 20, 2012—Stemmer, W. "DNA shuffling by random fragmentation and reassembly: in vitro recombination for molecular evolution" Proc. Natl. Acad. Sci. 91:10747-10751 (1993/1994).
Dyax Exhibit 1109, Filed in Interference No. 105,809, Filed Jan. 20, 2012—Deposition of Eric T. Boder, Ph.D. dated Dec. 20, 2011, pp. 1-106.
Dyax Exhibit 1110, Filed in Interference No. 105,809, Filed Jan. 20, 2012—Second Deposition of David M. Kranz, Ph.D. dated Jan. 3, 2012, pp. 1-133.
Dyax Exhibit 1111, Filed in Interference No. 105,809, Filed Jan. 20, 2012—Second Deposition of Nathalie Scholler, M.D., Ph.D. dated Jan. 12, 2012, pp. 1-94.
Dyax Exhibit 1112, Filed in Interference No. 105,809, Filed Jan. 20, 2012—Fourth Declaration of Nathalie Scholler, M.D., Ph.D. dated Jan. 19, 2012, pp. 1-18.
Dyax Exhibit 1113, Filed in Interference No. 105,809, Filed Jan. 20, 2012—Decision of Yager Miscellaneous Motion 4, filed in Interference No. 104,718 filed Mar. 11, 2002, pp. 1-3.
Dyax Exhibit List, Filed in Interference No. 105,809, Filed Jan. 20, 2012, pp. 1-9.
Dyax Exhibit List, Filed in Interference No. 105,809, Filed Aug. 19, 2011, pp. 1-5.
Dyax Exhibit List, Filed in Interference No. 105,809, Filed Sep. 30, 2011, pp. 1-6.
Dyax List of Exhibits, Filed in Interference No. 105,809, Filed Nov. 21, 2011, pp. 1-7.
Dyax list of proposed motions, Filed in Interference No. 105,809, Filed Jun. 28, 2011, pp. 1-10.
Dyax Miscellaneous Motion 1, Filed in Interference No. 105,809, Filed Feb. 3, 2012, pp. 1-24.
Dyax Notice of Exhibits Served, Filed in Interference No. 105,809, Filed Aug. 19, 2011, pp. 1-2.
Dyax Notice of Filing of Priority Statement, Filed in Interference No. 105,809, Filed Aug. 19, 2011, pp. 1-3.
Dyax Notice of Service of Exhibits, Filed in Interference No. 105,809, Filed Jan. 20, 2012, pp. 1-2.
Dyax Notice of Service of Exhibits, Filed in Interference No. 105,809, Filed Nov. 21, 2011, pp. 1-2.
Dyax Notice of Service of Priority Statement, Filed in Interference No. 105,809, Filed Aug. 26, 2011, pp. 1-3.
Dyax Opposition 1, Filed in Interference No. 105,809, Filed Nov. 21, 2011, pp. 1-45.
Dyax Opposition 2, Filed in Interference No. 105,809, Filed Nov. 21, 2011, pp. 1-4.
Dyax Opposition 3, Filed in Interference No. 105,809, Filed Nov. 21, 2011, pp. 1-38.
Dyax Opposition 4, Filed in Interference No. 105,809, Filed Nov. 21, 2011, pp. 1-49.
Dyax Opposition 5, Filed in Interference No. 105,809, Filed Nov. 21, 2011, pp. 1-30.
Dyax Opposition 6, Filed in Interference No. 105,809, Filed Nov. 21, 2011, pp. 1-36.
Dyax Priority Statement, Filed in Interference No. 105,809, Filed Aug. 19, 2011, pp. 1-11.
Dyax Reply 1, Filed in Interference No. 105,809, Filed Jan. 20, 2012, pp. 1-29.
Dyax Reply 2, Filed in Interference No. 105,809, Filed Jan. 20, 2012, pp. 1-30.
Dyax Reply 3, Filed in Interference No. 105,809, Filed Jan. 20, 2012, pp. 1-25.
Dyax Reply 4, Filed in Interference No. 105,809, Filed Jan. 20, 2012, pp. 1-26.
Dyax Request for Oral Argument, Filed in Interference No. 105,809, Filed Feb. 3, 2012, pp. 1-3.
Dyax Responsive Motion 4, Filed in Interference No. 105,809, Filed Sep. 30, 2011, pp. 1-50.
Dyax Second Notice of Discussions, Filed in Interference No. 105,809, Filed Oct. 6, 2011, pp. 1-3.
Dyax Substantive Motion 1, Filed in Interference No. 105,809, Filed Aug. 19, 2011, pp. 1-30.
Dyax Substantive Motion 2, Filed in Interference No. 105,809, Filed Aug. 19, 2011, pp. 1-31.
Dyax Substantive Motion 3, Filed in Interference No. 105,809, Filed Aug. 19, 2011, pp. 1-28.
Ehlers, M.D., "Synapse structure: glutamate receptors connected by the shanks" Current Biol., 9(22): R848-850 (1999).
Esposito et al., "Phage display of a human antibody against Clostridium tetani toxin", Gene, 148:167-168 (1994).
Fan, Z. and Mendelsohn, J., "Therapeutic application of anti-growth factor receptor antibodies" Curr. Opin. Oncol., 10(1):67-73 (1998).
Fan, Z. et al., "Three-dimensional structure of an Fv from a human IgM immunoglobulin" J. Mol. Biol., 228(1):188-207 (1992).
Feldhaus, M.J. et al., "Oligonucleotide-conjugated beads for transdominant genetic experiments" Nucleic Acids Research, 28(2):534-543 (2000).
Fellouse, F.A. et al., "High-throughput Generation of Synthetic Antibodies from Highly Functional Minimalist Phage-displayed Libraries" Journal of Molecular Biology, 373(4):924-940 (2007).
Fellouse, F.A. et al., "Molecular Recognition by a Binary Code" J. Mol, Biol. 348(5):1153-1162 (2005).
Fellouse, F.A. et al., "Synthetic antibodies from a four-amino-acid code: a dominant role for tyrosine in antigen recoqnition" PNAS, 101(34):12467-12472 (2004).
Fields, S. and Sternglanz, R., "The two-hybrid system: an assay for protein-protein interactions" Trends Genet.,10(8):286-292 (1994).
Fields. S. and Song, O., "A novel genetic system to detect protein-protein interactions" Nature, 340(6230):245-246 (1989).
Finley R.L., Jr. and Brent, R., "Interaction mating reveals binary and ternary connections between *Drosophila* cell cycle regulators" Proc. Natl. Acad. Sci. USA, 91(26):12980-12984 (1994).

(56) References Cited

OTHER PUBLICATIONS

Firth, A.E. and Patrick, W.M., "Glue-It and Pedel-AA: new programmes for analyzing protein diversity in randomized libraries" Nucleic Acids Res., 36:W281-W285 (2008).

Frazer, J. K., and J. D. Capra, "Immunoglobulins: Structure and Function", in Fundamental Immunology, Fourth Edition, William E. Paul, ed., Lippincot-Raven Publishers, Philadelphia, pp. 41-43 and 51-52 (1999).

Friedman, M. L. et al., Neonatal VH, D, and JH, Gene Usage in Rabbit B Lineage Cells, Immunol., 152:632-641 (1994).

Frieman, M. and Cormack, BP, Multiple sequence signals determine the distribution of glycosylphosphatidylinositol proteins between the plasma membrane and cell wall in *Saccharamyces cerevisiae*, Microbiology, 150(Pt 10):3105-3114 (2004).

Fromont-Racine, M. et al., "Toward a functional analysis of the yeast genome through exhaustive two-hybrid screens" Nat. Genet., 16(3):277-282 (1997).

Frykman, S. and Srienc, F., "Quantitating secretion rates of individual cells: design of secretion assays" Biotechnol. & Bioeng., 59(2):214-226 (1998).

Fuh, G., "Synthetic antibodies as therapeutics" Expert Opinion on Biological Therapy, 7(1):73-87 (2007).

Fundamental Immunology, William E. Paul, M.D.ed., 3rd Edition:292-295 (1993).

Fusco, et al., In vivo construction of cDNA libraries for use in the yeast two-hybrid system. Yeast, 15(8):715-720 (1999).

Futcher, AB and Cox, BS, Maintenance of the 2 microns circle plasmid in populations of *Saccharomyces cerevisiae*, Journal of Bacteriology, 154(2):612-622 (1983).

Garcia, R.A. et al., "The neuregulin receptor ErbB-4 interacts with PDZ•containing proteins at neuronal synapses" Proc. Natl. Acad Sci USA, 97(7):3596-3601 (2000).

Gerondakis, S. et al., Immunoglobulin JH Rearrangement in aT-cell Line Reflects Fusion to the DH Locus at a Sequence Lacking the Nonamer Recognition Signal, Immunogenetics, 28:255-259 (1998).

Ghaffari, S.H. et al., Structure and Genomic Organization of a Second Cluster of Immunoglobulin Heavy Chain Gene Segments in the Channel Catfish, J. Immunol., 162:1519-1529 (1999).

Gietz et al., "Improved method for high efficiency transformation of intact yeast cells" Nucleic Acids Res., 20(6):1425 (1992).

Gietz, R.D. and R.H. Schiestl, "Transforming Yeast with DNA" Methods in Molecular and Cellular Biology (Invited Chapter), 5:255-269 (1995).

Gilfillan, S. et al., "Efficient immune responses in mice lacking N-region diversity" Eur. J. Immunol., 25(11):3115-3122 (1995).

Griffin, TJ., et al., Complementary profiling of gene expression at the transcriptome and proteome levels in *Saccharomyces cerevisiae*, Molecular & Cellular Proteomics, 1(4):323-333 (2002).

Griffiths, A.D. et al., "Human anti-self antibodies with high specificity from phage display libraries" EMBO J., 12(2):725-734 (1993).

Griffiths, A.D. et al., "Isolation of high affinity human antibodies directly from large synthetic repertoires," EMBO J., 13(14):3245-3260 (1994).

Grimes E. et al., "Achilles' heel cleavage: creation of rare restriction sites in lambda phage genomes and evaluation of additional operators, repressors and restriction/modification systems" Gene, 90(1):1-7 (1990).

Gu, H. et al., B Cell Development Regulated by Gene Rearrangement: Arrest of Maturation by Membrane-Bound D11 Protein and Selection of DH Element Reading Frames, Cell, 65:47-54 (1991 ).

Gushiken, F.C. et al., "Polymorphism of beta2-glycoprotein I at codons 306 and 316 in patients with systemic lupus erythematosus and antiphospholipid syndrome" Arthritis & Rheumatism, 42(6):1189-1193 (1999).

Hamada, K. et al., Amino acid sequence requirement for efficient incorporation of glycosylphosphatidylinositol-associated proteins into the cell wall of *Saccharomyces cerevisiae*, Journal of Biological Chemistry, 273(41):26946-26953 (1998).

Hanes, J. et al., "Picomolar affinity antibodies from a fully synthetic naive library selected and evolved by ribosome display" Nat Biotechnol. 18:(12):1287-1292 (2000).

Hasan, N. and Szybalski, W., "Control of cloned gene expression by promoter inversion in vivo: construction of improved vectors with a multiple cloning site and the Ptac promoter" Gene, 56(1):145-151 (1987).

Hawkins, R.E. and Winter, G., "Cell selection strategies for making antibodies from variable gene libraries: trapping the memory pool" Eur. J. Immunol., 22(3):867-870 (1992).

Hayman, J. R. et al., Heavy Chain Diversity Region Segments of the Channel Catfish: Structure, Organization, Expression and Phylogenetic Implications, J. Immunol, 164:1916-1924 (2000).

He, M. and Taussig, M.J., "Antibody-ribosome-mRNA (ARM) complexes as efficient selection particles for in vitro display and evolution of antibody combining sites" Nucleic Acids Res., 25(24):5132-5134 (1997).

Heddle, R.J. and Rowley, D., "Dog Immunoglobulins, I. immunochemical characterization of dog serum, parotid saliva, colostrum, milk and small bowel fluid" Immunology, 29(1):185-195 (1975).

Hoet, R.M. et al., "Generation of high-affinity human antibodies by combining donor-derived and synthetic complementarity-determining-region diversity" Nat. Biotechnol., 23(3):344-348 (2005).

Hoet, R.M. et al., "The importance of the light chain for the epitope specificity of human anti-U1 small nuclear RNA autoantibodies present in systemic lupus erythematosus patients" Journal of Immunology,163(6):3304-3312 (1999).

Holliger, P. and Hudson, PJ, Engineered antibody fragments and the rise of single domains, Nature Biotechnology, 23(9):1126-1136 (2005).

Hollinger, P. et al., "Diabodies": small bivalent and bispecific antibody fragments, Proceedings of the National Academy of Science USA, 90(14):6444-6448 (1993).

Holmes, P. and Al-Rubeai, M., "Improved cell line development by a high throughput affinity capture surface display technique to select for high secretors" J. Immunol. Methods, 230(1-2):141-147 (1999).

Hoogenboom et al., "By-passing Immunisation Human Antibodies from Synthetic Repertoires of Germline VH Gene Segments Rearranged in Vitro", J. Mol. Biol., 227:381-388 (1992).

Hoogenboom, H.R. and Winter, G., "By-passing immunisation. Human antibodies from synthetic repertoires of germline VH gene segments rearranged in vitro" J. Mol. Biol., 227(2):381-388 (1992).

Hoogenboom, H.R. et al., "Antibody phage display technology and its applications" Immunotechnology, 4(1):1-20 (1998).

Hoogenboom, H.R. et al., "Multi-subunit proteins on the surface of filamentous phage: methodologies for displaying antibody (Fab) heavy and light chains" Nucleic Acids Research, 19(15):4133-4137 (1991).

Hoogenboom, H.R., "Designing and optimizing library selection strategies for generating high-affinity antibodies" Trends Biotechnol. 15(2):62-70 (1997).

Horwitz A.H. et al., "Secretion of functional antibody and Fab fragments from yeast cells" Proc. Natl. Acad. Sci. USA, 85(22):8678-8682 (1988).

Hoshino, Y. et al., "The rational design of a synthetic polymer nanoparticle that neutralizes a toxic peptide in vivo" PNAS 109(1):33-38 (2012).

Hrncir, Z. and Chýiková et al., "[Anticardiolipin antibodies in diffuse connective tissue diseases in the IgG, IgM and IgA isotypes]" Vnitr. Lek., 36(11):1041-1049 (1990), translation (provided by USPTO) pp. 1-13 (1999).

Hua, S.B. et al., "Construction of a modular yeast two-hybrid cDNA library from human EST clones for the human genome protein linkage map" Gene, 215(1):143-152 (1998).

Hua, S.B. et al., "Minimum length sequence homology required for in vivo cloning by homologous recombination in yeast" Plasmid, 38(2):91-96 (1997).

Huang et al., "A Majority of Ig H Chain cDNA of Normal Human Adult Blood Lymphocytes Resembles cDNA for Fetal Ig and Natural Autoantibodies", J. Immunol., 151:5290-5300 (1993).

Huang, D. and Shusta, E.V. et al., "Secretion and surface display of green fluorescent protein using the yeast *Saccharomyces cerevisiae*" Biotechnol. Prog., 21(2):349-357 (2005).

(56) References Cited

OTHER PUBLICATIONS

Huse, W.D. et al., "Generation of a large combinatorial library of the immunoglobin repertoire in phage lambda" Science 246(4935):1275-1281 (1989).
Huston, J.S. et al., "Protein engineering of antibody binding sites: recovery of specific activity in an anti-digoxin single-chain Fv analogue produced in Escherichia coli" Proc. Natl. Acad. Sci. USA 85(16):5879-5883 (1988).
Interference No. 105809 Decision on Motions, dated Nov. 2, 2012.
Interference No. 105809 Dyax Resp to Order to Show Cause, dated Jan. 4, 2013.
Ivanov, I.I. et al., "Development of the expressed Ig CDR-H3 repertoire is marked by focusing of constraints in length, amino acid use, and charge that are first established in early B cell progenitors," J. Immunol., 174(12):7773-7780 (2005).
Ivanovski et al., "Somatic Hypermutation, Clonal Diversity, and Preferential Expression of the VH 51p1/VL kv325 Immunoglobin Gene Combination in Hepatitis C Virus-Associated Immunocytomas", Blood, 91(7):2433-2442 (1998).
Jackson, K.J., et al., "Identifying highly mutated IGHD genes in the junctions of rearranged human immunoglobulin heavy chain genes," J. Immunol. Methods, 324(1-2):26-37 (2007).
Jacobsson, K. and Frykberg, L., "Phage Display Shot-Gun Cloning of Ligand-Binding Domains of Prokaryotic Receptors Approaches 100% Correct Clones" BioTechniqes, 20(6):1078, 1080-1081 (1996).
Jayaram, M. et al., The yeast plasmid 2mu circle enclodes components required for its high copy propagation, Cell, 34(1):95-104 (1983).
Jenne, C. N. et al., Antibody Repertoire Development in the Sheep, Dev. Camp. Immunol., 30:165-174 (2006).
Jirholt, P. et al., "Exploiting sequence space: shuffling in vivo formed complementarity determining regions into a master framework", Gene, 215(2):471-476 (1998).
Johns M. et al., "In vivo selection of sFv from phage display libraries" J. Immunol. Methods, 239(1-2):137-151 (2000).
Jones, PT. et al., Replacing the complementarity-determining regions in a human antibody with those from a mouse, Nature, 321(6069):522-525 (1986).
Judgment—Bd.R. 127 in Patent Interference No. 105,809, Dec. 30, 2013.
Juul, L. et al., "The normally expressed kappa immunoglobulin light chain gene repertoire and somatic mutations studied by single-sided specific polymerase chain reaction (PCR); frequent occurrence of features often assigned to autoimmunity" Clin. Exp. Immunol., 109(1):194-203 (1997).
Kabat, E. et al., Sequences of Proteins of Immunological Interest, 5th Edition, Public Health Service, National Institutes of Health, Bethesda, MD, 647-669 (1991).
Kaczorowski, T. and Szybalski, W., "Genomic DNA sequencing by SPEL-6 primer walking using hexamer ligation" Gene, 223(1-2):83-91 (1998).
Kang, A.S. et al., "Linkage of recognition and replication functions by assembling combinatorial antibody Fab libraries along phage surfaces" Proc. Natl. Acad. Sci., 88(10):4363-4666 (1991).
Kaufman, Randal J., Selection and Coamplification of Heterologous Genes in Mammalian Cells, Methods in Enzymology, 185:537-566 (1991).
Kaufman, Randal J., Vectors Used for Expression in Mammalian Cells, Methods in Enzymology, 185:487-511 (1991).
Keown, WA et al., Methods for introducing DNA into mammalian cells, Methods in Enzymology, 185:527-537 (1990).
Kieke, M.C. et al., "Isolation of anti-T cell receptor scFv mutants by yeast surface display". Protein Eng. 10(11):1303-1310 (1997).
Kieke, M.C. et al., Selection of functional T cell receptor mutants from a yeast surface-display library, Proc. Natl. Acad. Sci. USA, 96(10):5651-5656 (1999).
Kim, S.C. et al., "Cleaving DNA at any predetermined site with adapter-primers and class-IIS restriction enzymes" Science, 240(4851):504-506 (1988).
Kim, S.C., et al., "Structural requirements for FokI-DNA interaction and oligodeoxyribonucleotide-instructed cleavage" J. Mol. Biol., 258(4):638-649 (1996).
Klein, R. et al., "Expressed human immunoglobulin kappa genes and their hypermutation" Eur. J. Immunol., 23(12):3248-3262 (1993).
Knappik, A. et al., "Fully synthetic human combinatorial antibody libraries (HuCAL) based on modular consensus frameworks and CDRs randomized with trinucleotides" Journal of Molecular Biology, 296(1):57-86 (2000).
Kohler, G. and Milstein, C., Continuous cultures of fused cells secreting antibody of predefined specificity, Nature, 256(5517):495-497 (1975).
Koiwai, O. et al., "Isolation and characterization of bovine and mouse terminal deoxynucleotidyltransferase cDNAs expressible in mammalian cells" Nucleic Acids Res., 14(14):5777-5792 (1986).
Kok, J., Genetics of the proteolytic system of lactic acid bacteria, FEMS Microbiology Reviews, 7(1-2):15-42 (1990).
Kokubu F. et al., Complete structure and organization of immunoglobulin heavy chain constant region genes in a phylogenetically primitive vertebrate, The EMBO Journal, 7(7):1979-1988 (1988).
Kontermann, R.E. and Müller, R., "Intracellular and cell surface displayed single-chain diabodies", J. Immunol. Methods, 226(1-2):179-188 (1999).
Koob, M. and Szybalski, W., "Cleaving yeast and Escherichia coli genomes at a single site" Science, 250(4978):271-273 (1990).
Koob, M. et al., "Conferring new specificity upon restriction endonucleases by combining repressor-operator interaction and methylation" Gene, 74(1):165-167 (1988).
Koob, M. et al., "Conferring operator specificity on restriction endonucleases," Science, 241(4869):1084-1086 (1988).
Koob, M. et al., "RecA-AC: single-site cleavage of plasmids and chromosomes at any predetermined restriction site" Nucleic Acids Res., 20(21):5831-5836 (1992).
Kostrub, C.F. et al., "Use of gap repair in fission yeast to obtain novel alleles of specific genes" Nucleic Acids Research, 26(20):4783-4784 (1998).
Kretzschmar, T. and von Rüden, T., "Antibody discovery: phage display" Curr. Opin. Biotechnol., 13(6):598-602 (2002).
Kur, J. et al., "A novel method for converting common restriction enzymes into rare cutters: integration host factor-mediated Achilles' cleavage (IHF-AC)" Gene, 110(1):1-7 (1992).
Kurosawa, Y. et al., Identification of D Segments of Immunoglobulin Heavy-Chain Genes and Their Rearrangement in T Lymphocytes, Nature, 290:565-570 (1981).
Lake, D.F. et al., "Generation of diverse single-chain proteins using a universal (Gly4-Ser)3 encoding oligonucleotide" BioTechniques, 19(5):700-702 (1995).
Lecrenier, N., et al., "Two-hybrid systematic screening of the yeast proteome" Bioessays. 20(1):1-5 (1998).
Lederman, S. et al., "A single amino acid substitution in a common African allele of the CD4 molecule ablates binding of the monoclonal antibody, OKT4" Mol Immunol. (11):1171-81 (1991).
Lee, C.E., et al., "Reconsidering the human immunoglobulin heavy-chain locus: 1. An evaluation of the expressed human IGHD gene repertoire" Immunogenetics, 57(12):917-925 (2006).
Lee, C.V. et al., "High-affinity human antibodies from phage-displayed synthetic Fab libraries with a single framework scaffold" Journal of Molecular Biology, 340(5):1073-1093 (2004).
Lee, S.Y. et al., "Microbial cell-surface display" Trends Biotechnol., 21(1):45-52 (2003).
Leonard, B. et al., "Co-expression of antibody fab heavy and light chain genes from separate evolved compatible replicons in E. coli" J. Immunol. Methods, 317(1-2):56-63 (2006).
Lerner, R.A. et al.,"Antibodies without immunization" Science,258(5086):1313-314 (1992).
Letter from Michael T. Siekman to Brenda H. Jarrell, dated Nov. 13, 2012.
Lewin, Roger, The universal constructor set, New Scientist, 1746:30-33 (1990).
Lezcano, N. et al., "Dual Signaling Regulated by Calcyon, a D1 Dopamine Receptor Interacting Protein" Science, 287(5458):1660-1664 (2000).

(56) References Cited

OTHER PUBLICATIONS

Li, C.H. et al., "beta-Endorphin omission analogs: dissociation of immunoreactivity from other biological activities" Proc Natl Acad Sci USA. 177(6):3211-3214 (1980).
Li, H. et al., "Biofuels: Biomolecular Engineering Fundamentals and Advances" Annu. Rev. Chem. Biomol. Eng. 1:19-36 (2010).
Li, N et al., "B-Raf kinase inhibitors for cancer treatment" Current Opinion in Investigational Drugs 8(6) 452-456 (2007).
Lieber et al., "Lymphoid V(D)J recombination: Nucleotide insertion at signal joints as well as coding joints", Proc. Natl. Acad. Sci. USA, 85:8588-8592 (1988).
Lieber, M.R., "Site-specific recombination in the immune system", FASEB J., 5:2934-2944 (1991) Liu et al., "Normal Human IgD+ IgM− Germinal Center B Cells can Express up to 80 Mutations in the Variable Region of their IgD Transcripts", Immunity, 4:603-613 (1996).
Link, J. M. et al., The Rhesus Monkey Immunoglobulin /GHD Germline Repertoire, Immunogenetics, 54:240-250 (2002).
List of Exhibits, Filed in Interference No. 105,809, Filed Aug. 19, 2011, pp. 1-4.
Little, M. et al., "Generation of a large complex antibody library from multiple donors" J. Immunol Methods, 231(1-2):3-9 (1999).
Liu et al., "Normal Human IgD+IgM-Germinal Center B Cells can Express up to 80 Mutations in the Variable Region of their IgD Transcripts", Immunity, 4:603-613 (1996).
Liu, Q. et al., "Rapid construction of recombinant DNA by the univector plasmid-fusion system" Methods Enzymol. 328:530-49 (2000).
Love J.C. et al., "A microengraving method for rapid selection of single cells producing antigen-specific antibodies" Nature Biotechnol. 24(6):703-707 (2006).
Lowman, H.B. and Wells, J.A., "Affinity maturation of human growth hormone by monovalent phage display" J. Mol. Biol., 234(3):564-578 (1993).
Lowman, H.B. et al., "Selecting high-affinity binding proteins by monovalent phage display" Biochemistry, 30(45):10832-10838 (1991).
Lundqvist, M. L. et al., Immunoglobulins of the Non-Galliform Birds: Antibody Expression and Repertoire in the Duck, Dev. Camp. Immunol., 30:93-100 (2006).
Ma, H. et al., "Plasmid construction by homologous recombination in yeast" Gene, 58(2-3):201-216 (1987).
MacCallum, R.M. et al., "Antibody-antigen interactions: contact analysis and binding site topography" J. Mol. Biol., 262(5):732-745 (1996).
Mage, R. G. et al., B Cell and Anitbody Repertoire Development in Rabbits: The Requirement of Gut-Associated Lymphoid Tissues, Dev. Camp. Immunol., 30:137-153 (2006).
Malecek, K. et al., Somatic Hypermutation and Junctional Diversification at Ig Heavy Chain Loci in the Nurse Shark, J. Immunol., 175:81 05-8115 (2005).
Manz, R. et al., "Analysis and sorting of live cells according to secreted molecules, relocated to a cell-surface affinity matrix" Proc. Natl. Acad. Sci. USA, 92(6):1921-1925 (1995).
Marks, J.D. et al., "By-passing Immunization. Human Antibodies from V-gene Libraries Displayed on Phage" J. Mol. Biol., 222(3):581-597 (1991).
Marks, J.D. et al., "By-passing Immunization: building high affinity human antibodies by chain shuffling" Biotechnology (NY), 10(7):779-783 (1992).
Martin, A.C., "Accessing the Kabat antibody sequence database by computer" Proteins, 25(1):130-133 (1996).
Martin, A.C.and Thornton, J.M., "Structural families in loops of homologous proteins: automatic classification, modelling and application to antibodies" J. Mol. Biol., 263(5):800-815 (1996).
Marzari, R. et al., "Extending filamentous phage host range by the grafting of a heterologous receptor binding domain" Gene, 185(1):27-33 (1997).
Matolcsy et al., "Molecular Characterization of IgA- and/or IgG-Switched Chronic Lymphocytic Leukemia B Cells", Blood, 89(5):1732-1739 (1997).
Matsuda, F. et al., "The complete nucleotide sequence of the human immunoglobulin heavy chain variable region locus" J. Exp. Med., 188(11):2151-2162 (1998).
Mattila, P.S. et al., "Extensive allelic sequence variation in the J region of the human immunoglobulin heavy chain gene locus" Eur. J. Immunol., 9(:)2578-2582 (1995).
Mazor Y. et al., "Isolation of engineered, full-length antibodies from libraries expressed in *Escherichia coli*" Nature Biotecnol., 25(5):563-565 (2007).
McCafferty et al., "Phage antibodies: filamentous phage displaying antibody variable domains", Nature, 348:552-554 (1990).
McCafferty, J. et al., "Phage antibodies: filamentous phage displaying antibody variable domains" Nature, 348(6301):552-554.
McCormack, W.T., Comparison of latent and nominal rabbit Ig VHa1 allotype cDNA sequences. J. Immunol., 141(6):2063-2071 (1988).
McIntosh et al., "Analysis of Immunoglobulin Gk Antithyroid Peroxidase Antibodies from Different Tissues in Hashimoto's Thyroiditis", J. Clin. Endocrinol. Metab., 82(11):3818-3825 (1997).
Mimran, A. et al., "GCN4-Based Expression System (pGES): Translationally Regulated Yeast Expression Vectors" BioTechniques, 28(3):552-554, 556, 558-560 (2000).
Moll, J.R. et al., "Designed heterodimerizing leucine zippers with a ranger of pIs and stabilities up to 10(-15) M" Protein Science, 10(3):649-55 (2001).
Mollova, S. et al., "Visualising the immune repertoire" BMC Systems Biology, 1(S1):P30 (2007).
Mouquet et al., "Enhanced HIV-1 neutralization by antibody heteroligation", PNAS, published on line before printing, Jan. 4, 2012, doi:10.1073/pnas.1120059109.
Mouquet, H. et al., "Enhanced HIV-1 neutralization by antibody heteroligation" PNAS Early Edition 1-6.
Muhle-Goll, C. et al., "The Leucine Zippers of the HLH-LZ Proteins Max and c-Myc Preferentially Form Heterodimers" Biochemistry, 34(41):13554-13564 (1995).
Mullinax, R.L. et al., "Identification of human antibody fragment clones specific for tetanus toxoid in a bacteriophage lambda immunoexpression library" Proc. Natl. Acad. Sci., 87(20):8095-8099 (1990).
Murray, JA et al., Antagonistic controls regulate copy number of the yeast 2 mu plasmid, EMBO Journal, 6(13):4205-4212 (1987).
Muyldermans, S. et al., Sequence and structure of VH domain from naturally occurring camel heavy chain immunoglobulins lacking light chains, Protein Engineering, 7(9):1129-1135 (1994).
Mézard, C. et al., "Recombination between similar but not identical DNA sequences during yeast transformation occurs within short stretches of identity" Cell, 70(4):659-670 (1992).
Nakamura, Y. et al., "Development of novel whole-cell immunoadsorbents by yeast surface display of the IgG-binding domain" Appl. Microbiol. Biotechnol., 57(4):500-505 (2001).
Nguyen, V. K. et al., Camel Heavy-Chain Antibodies: Diverse Germline VHH and Specific Mechanisms Enlarge the Antiqen-bindinq Repertoire, EMBO J, 19:(5)921-930 (2000).
Nishigaki, K. et al., "Type II restriction endonucleases cleave single-stranded DNAs in general" Nucleic Acids Res, 13(16):5747-5760 (1985).
Nissim et al., "Antibody fragments from a 'single pot' phage display library as immunochemical reagents", The EMBO Journal, 13(3):692-698 (1994).
Notice Designating pro hac vice counsel, Filed in Interference No. 105,809, Filed Oct. 6, 2011, pp. 1-3.
Notice of 4th Preliminary Amendment in Reissue Application, Filed in Interference No. 105,809, Filed Sep. 30, 2011, pp. 1-3.
Notice of Discussions, Filed in Interference No. 105,809, Filed Aug. 12, 2011, pp. 1-3.
Notice of Exhibits List Filed, Filed in Interference No. 105,809, Filed Nov. 21, 2011, pp. 1-3.
Notice of Filing Continuation of Reissue Application, Filed in Interference No. 105,809, Filed Sep. 30, 2011, pp. 1-3.
Notice of Filing of Adimab Priority Statement, Filed in Interference No. 105,809, Filed Aug. 19, 2011, pp. 1-3.
Notice of Filing of Continuation Application, Filed in Interference No. 105,809, Filed Nov. 21, 2011, pp. 1-3.

(56) References Cited

OTHER PUBLICATIONS

Notice of Filing of Reissue Application, Filed in Interference No. 105,809, Filed Aug. 19, 2011, pp. 1-3.
Notice of Filing of Reissue of U.S. Pat. No. 7,005,503, Filed in Interference No. 105,809, Filed Nov. 21, 2011, pp. 1-3.
Notice of Filing of Reissue of U.S. Pat. No. 7,138,496, Filed in Interference No. 105,809, Filed Nov. 21, 2011, pp. 1-3.
Notice of related proceedings filed during interference, Filed in Interference No. 105,809, Filed Jun. 28, 2011, pp. 1-3.
Notice of Related Proceedings, Filed in Interference No. 105,809, Filed May 20, 2011, pp. 1-3.
Notice of Second Preliminary Amendment in Reissue Applicatio, Filed in Interference No. 105,809, Filed Aug. 19, 2011, pp. 1-3.
Notice of Service of Dyax Exhibits, Filed in Interference No. 105,809, Filed Sep. 30, 2011, pp. 1-2.
Notice of Stipulated Extension, Filed in Interference No. 105,809, Filed Sep. 2, 2011, pp. 1-4.
Notice of Stipulation of Extension—Time Period 3, Filed in Interference No. 105,809, Filed Oct. 20, 2011, pp. 1-4.
Notice of Stipulation of Extension—Time Periods 3 & 4, Filed in Interference No. 105,809, Filed Nov. 1, 2011, pp. 1-4.
Notice of Stipulation of Extension—Time Periods 4, 5 & 6, Filed in Interference No. 105,809, Filed Dec. 5, 2011, pp. 1-4.
Notice of Stipulation of Extension of Time Period 2, Filed in Interference No. 105,809, Filed Sep. 21, 2011, pp. 1-4.
Notice of Stipulation of Extension of Time Period 3, Filed in Interference No. 105,809, Filed Nov. 14, 2011, pp. 1-3.
Notice of Stipulation of Extension of Time Periods 4, 5, & 6, Filed in Interference No. 105,809, Filed Jan. 12, 2012, pp. 1-4.
Notice of Stipulation of Extension of Time Periods 5 and 6, Filed in Interference No. 105,809, Filed Jan. 24, 2012, pp. 1-4.
Oldenburg, K.R et al., "Recombination-mediated PCR-directed plasmid construction in vivo in yeast" Nucleic Acids Res, 25(2):451-452 (1997).
Onda, T. et al., "A phage display system for detection of T cell receptor-antigen interactions" Mol Immunol., 32(17-18):1387-1397 (1995).
Order Bd.R. 103 Limited Transfer of Jurisdiction, Filed in Interference No. 105,809, Filed Jul. 25, 2011, pp. 1-2.
Order Bd.R. 104 Authorizing Reply Declaration, Filed in Interference No. 105,809, Filed Dec. 8, 2011, pp. 1-3.
Order Bd.R. 104 Regarding Adimab's Reissue Application, Filed in Interference No. 105,809, Filed Sep. 7, 2011, pp. 1-2.
Order Bd.R. 104, Filed in Interference No. 105,809, Filed Jul. 21, 2011, pp. 1-3.
Order Bd.R. 104—Regarding Related Applications, Filed in Interference No. 105,809, Filed Jul. 1, 2011, pp. 1-2.
Order Bd.R. 109(b)Authorizing Copies of Office Records, Filed in Interference No. 105,809, Filed May 23, 2011, pp. 1-3.
Order Bd.R. 121 Authorizing Motion, Filed in Interference No. 105,809, Filed Aug. 4, 2011, pp. 1-2.
Order Bd.R. 121 Authorizing Motions, Filed in Interference No. 105,809, Filed Sep. 1, 2011, pp. 1-2.
Order Bd.R. 121 Contingently Authorizing Responsive Motion, Filed in Interference No. 105,809, Filed Sep. 13, 2011, pp. 1-3.
Order Bd.R. 121(a) Authorizing Motions, Filed in Interference No. 105,809, Filed Jul. 1, 2011, pp. 1-8.
Order Bd.R. 5(a), Filed in Interference No. 105,809, Filed Sep. 27, 2011, pp. 1-2.
Ornstein, R.L. et al., "An optimized potential function for the calculation of nucleic acid interaction energies I. Base stacking" Biopolyrners, 17:2341-2360 (1978).
Osbourn, J.K., et al., Directed selection of MIP-1alpha neutralizing CCR5 antibodies from phage display human antibody library, Nat. Biotech. 16:778-781 (1998).
Panka, D.J. et al., "Variable region framework differences result in decreased or increased affinity of variant anti-digoxin antibodies" Proc. Natl. Acad. Sci. USA, 85(9):3080-3084 (1988).

Parrott, M.B. et al., "Metabolically biotinylated adenovirus for cell targeting, ligand screening, and vector purification" Mol. Ther., 8(4):688-700 (2003).
Parthasarathy, R. et al., "An immobilized biotin ligase: surface display of *Escherichia coli* BirA on *Saccharomyces cerevisiae*" Biotechnol. Prog., 21(6):1627-1631 (2005).
Pasqualini, R. and Ruoslahti, E., "Organ targeting in vivo using phage display peptide libraries" Nature, 380(6572):364-366 (1996).
Patrick, W.M. et al., "User-friendly algorithms for estimating completeness and diversity in randomized protein-encoding libraries" Protein Engineering, 16(6):451-457 (2003).
Pearson, B.M. et al., "Construction of PCR-ligated long flanking homology cassettes for use in the functional analysis of six unknown open reading frames from the left and right arms of *Saccharomyces cerevisiae* chromosome XV" Yeast, 14(4):391-399 (1998).
Persson, M.A. et al., "Generation of diverse high-affinity human monoclonal antibodies by repertoire cloning" Proc. Natl. Acad. Sci. USA, 88(6):2432-2436 (1991).
Philibert, P. et al., "A focused antibody library for selected scFvs expressed at high levels in the cytoplasm" BMC Biotechnol., 7:81 (2007).
Phizicky, E.M. and Fields, S. et al., "Protein-protein interactions: methods for detection and analysis" Microbiol. Rev. 59(1):94-123 (1995).
Piatesi, A. et al., "Directed evolution for improved secretion of cancer-testis antigen NY-ESO-1 from yeast." Protein Expr. Purif., 48(2):232-42 (2006).
Pickens, L.B. et al., "Metabolic Engineering for the Production of Natural Products" Annu. Rev. Chem. Biomol. Eng. 2:211-236 (2011).
Pini, A. et al., "Design and use of a phage display library. Human antibodies with subnanomolar affinity against a marker of angiogenesis eluted from a two-dimensional gel" Journal of Biological Chemistry, 273(34):21769-21776 (1998).
Pluckthun, A., "Antibody engineering: Advances from the use of *Escherichia coli* expression systems" Biotechnology (NY) 9(6):545-551 (1991).
Pluckthun, A., Antibodies from *Escherichia coli*, The Pharmacology of Monoclonal Antibodies, 113:268-315 (1994).
POA for Mr. Eric Marandett, Filed in Interference No. 105,809, Filed Oct. 6, 2011, pp. 1-3.
Podhajska A.J. and Szybalski W., "Conversion of the FokI endonuclease to a universal restriction enzyme: cleavage of a phage M13mp7 DNA at predetermined sites," Gene, 40(2-3):175-182 (1985).
Podhajska A.J. et al., "Conferring new specificities on restriction enzymes: cleavage at any predetermined site by combining adaptor oligodexynucleotide and class-IIS enzyme" Methods in Enzymology, 216(G):303-309 (1992).
Powell, Richard and McLane, Kathryn Evans, "Construction, assembly and selection of combinatorial antibody libraries." Genetic Engineering with PCR (Horton and Tait, Eds. 1998), vol. 5 of The Current Innovations in Molecular Biol series, Horizon Scientific Press, pp. 155-172.
Prabakaran, P. et al., "Expressed antibody repertoires in human cord blood cells: 454 sequencing and IMGT/High V-QUEST analysis of germline gene usage, junctional diversity, and somatic mutations" Immunogenetics (2011), pp. 1-14.
Prabakaran, P. et al., Supplemental "Expressed antibody repertoires in human cord blood cells: 454 sequencing and IMGT/High V-QUEST analysis of germline gene usage, junctional diversity, and somatic mutations" Immunogenetics (2011), pp. 1-6.
Presta, Leonard G., Antibody engineering, Current Opinion in Biotechnology, 3:395-3999 (1992).
Proba, K. et al., "Antibody scFv fragments without disulfide bonds made by molecular evolution". J Mol Biol. 275(2):245-253 (1998).
Pu, W.T. and Struhl, K., "Dimerization of leucine zippers analyzed by random selection". Nucleic Acids Res. vol. 21(18):4348-55 (1993).
Puga, A et al., "Aromatic hydrocarbon receptor interaction with the retinoblastoma protein potentiates repression of E2F-dependent transcription and cell cycle arrest" Journal Biological Chemistry, 275(4):2943-2950 (2000).

(56) References Cited

OTHER PUBLICATIONS

Pósfai, G. and Szybalski, W. "A simple method for locating methylated bases in DNA using class-IIS restriction enxymes," Gene, 74(1): 179-181 (1988).
Pörtner-Taliana, A. et al., "In vivo selection of single-chain antibodies using a yeast two-hybrid system", J. Immunol. Methods, 238(1-2):161-172 (2000).
Qi, G.R. et al., "Restriction of single-stranded M13 DNA using synthetic oligonucleotides: the structural requirement of restriction enzymes," Biochem. Cell Biol. 65(1):50-55 (1986).
Rader, C and Barbas, C.F. 3rd, "Phage display of combinatorial antibody libraries" Curr. Opin. Biotechnol., 8(4):503-508 (1997).
Rader, C. et al., "A phage display approach for rapid antibody humanization: designed combinatorial V gene libraries" Proc. Natl. Acad. Sci. USA, 95(15):8910-8915 (1998).
Rajan, S. and Sidhu, S., "Simplified Synthetic Antibody Libraries" Methods in Enzymology 202 3-23 (2012).
Rakestraw, J.A. and Wittrup, K.D., "Dissertation Abstracts International", 68(1B):43, abstract only (2006).
Rakestraw, J.A. et al., "A Flow Cytometric Assay for Screening Improved Heterologous Protein Secretion in Yeast." Biotechnol. Prog., 22(4):1200-1208 (2006).
Ratcliffe, M.J.H. et al., Antibodies, Immunoglobulin Genes and the Bursa of Fabricius in Chicken B Cell Development, Dev. Comp. Immunol., 30:101-118 (2006).
Rauchenberger, R. et al., "Human combinatorial Fab library yielding specific and functional antibodies against the human fibroblast growth factor receptor 3" J. Biol. Chem., 278(40):38194-38205 (2003).
Raymond, C.K. et al., "General method for plasmid construction using homologous recombination" BioTechniques, 26(1):134-138, 140-141 (1999).
Real Party-in-interest, Filed in Interference No. 105,809, Filed May 20, 2011, pp. 1-4.
Redeclaration, Filed in Interference No. 105,809, Filed May 23, 2011, pp. 1-2.
Request for file copies, Filed in Interference No. 105,809, Filed May 20, 2011, pp. 1-6.
Retter, I. et al., "VBASE2, an integrative V gene database" Nucleic Acids Res., 33:D671-D674 (2005).
Rhoden, J.J. and Wittrup, K.D., "Dose Dependence of Intratumoral Perivascular Distribution of Monoclonal Antibodies" Journal of Pharmaceutical Sciences 101(2): 860-867 (2012).
Riechmann, L. et al., Reshaping human antibodies for therapy, Nature, 332:323-327 (1988).
Riske, F. et al., "The use of chitosan as a flocculant in mammalian cell culture dramatically improves clarification throughput without adversely impacting momoclonal antibody recovery" Journal of Biotechnology, 128:813-823 (2007).
Roitt, I. et al., "Immunoglobulins: A Family of Proteins", in Immunology, Sixth Edition, Mosby, Harcourt Publishers Limited, London, pp. 67-70 and 80 (2001).
Rudikoff, S. et al., "Single amino acid substitution altering antigen-binding specificity" Proc. Natl. Acad. Sci. USA, 79(6):1979-1983 (1982).
Ruiz, M. et al., "The human immunoglobulin heavy diversity (IGHD) and joining (IGHJ) segments." Exp. Clin. Irnrnunogenet, 16(3):173-184 (1999).
Ryu, D.D. and Nam, D.H., "Recent progress in biomolecular engineering" Biotechnol Prog, 16(1):2-16 (2000).
Saada, R. et al., "Models for antigen receptor gene rearrangement: CDR3 length" Immunol. Cell Biol., 85(4):323-332 (2007).
Sahota et al., "Ig VH Gene Mutational Patterns Indicate Different Tumor Cell Status in Human Myeloma and Monoclonal Gammopathy of Undetermined Significance", Blood, 87(2):746-755 (1996).
Saviranta, P. et al., "Engineering the steroid-specificity of an anti-17beta-estradiol Fab by random mutagenesis and competitive phage panning." Protein Engineering, 11(2):143-152 (1998).
Sblattero, D. and Bradbury, A., "A definitive set of oligonucleotide primers for amplifying human V regions" Immunotechnology, 3(4):271-278 (1998).
Sblattero, D. and Bradbury, A., "Exploiting recombination in single bacteria to make large phage antibody libraries" Nat. Biotechnol., 18(1):75-80 (2000).
Scaviner, D. et al., "Protein displays of the human immunoglobulin heavy, kappa and lambda variable and joining regions." Exp. Clin. Immunogenet., 16(4):234-240 (1999).
Schable, K.F. and Zachau, H.G., "The variable genes of the human immunoglobulin kappa locus" Biol. Chem. Hoppe Seyler, 374(11):1001-1022 (1993).
Schoonbroodt, S. et al., "Oligonucleotide-assisted cleavage and ligation: a novel directional DNA cloning technology to capture cDNAs. Application in the construction of a human immune antibody phage-display library" Nucleic Acids Research, 33(9):e81:2-14 (2005).
Schwager, J. et al., Amino acid sequence of heavy chain from Xenopus levis IgM deduced from cDNA sequence: Implications for evolution of immunoglobulin domains, Proc. Natl. Acad. Sci. USA, 85:2245-2249 (1988).
Seed, B., "Developments in expression cloning." Current Opinion in Biotechnology, 6(5):567-573 (1995).
Sheets, M.D. et al., "Efficient construction of a large nonimmune phage antibody library: The production of high-affinity human single-chain antibodies to protein antigens." Proc. Natl. Acad. Sci. USA, 95(11):6157-6162 (1998).
Shimizu, T. et al., Biased Reading Frames on Pre-Existing DH-JH Coding Joints and Preferential Nucleotide Insertions at VH-DJH Signal Joints of Excision Products of Immunoglobulin Heavy Chain Gene Rearrangements, EMBO J., 11 :(13)4869-4875 (1992).
Shimoda et al., "Natural polyreactive immunoglobulin A antibodies produced in mouse Peyer's patches", Immunology, 97:9-17 (1999).
Shojaei, F. et al., Unusually Long Germline DH Genes Contribute to Large Sized CDR3H in Bovine Antibodies, Mol. Immunol., 40:61-67 (2003).
Shoji, H. et al., "Identification and characterization of a PDZ protein that interacts with activin type II receptors.", J.Biol. Chem., 275(8):5485-5492 (1999).
Short, M.K. et al., "Contribution of antibody heavy chain CDR1 to digoxin binding analyzed by random mutagenesis of phage-displayed Fab 26-10" J. Biol. Chem., 270(48):28541-28550 (1995).
Shusta, E.V. et al., "Directed evolution of a stable scaffold forT-cell receptor engineering" Nat. Biotechnol.,18(7):754-759 (2000).
Shusta, E.V. et al., "Yeast Polypeptide Fusion Surface Display Levels Predict Thermal Stability and Soluble Secretion Efficiency" J. Mol. Biol. 292 949-956 (1999).
Sidhu, S.S, et al., "Phage-displayed antibody libraries of synthetic heavy chain complementarity determining regions" J. Mol. Biol. 338(2):229-310 (2004).
Silverman, J. et al., Multivalent avimer proteins evolved by exon shuffling of a family of human receptor domains, Nature Biotechnology, 23(12):1556-1561 (2005).
Skerra, A., "Alternative non-antibody scaffolds for molecular recognition" Current Opin. Biotechnol. 18(4):295-304 (2007).
Smith, G.P. and Petrenko, V.A., "Phage Display" Chern. Rev., 97(2):391-410 (1997).
Soderlind, E. et al., "Domain libraries: synthetic diversity for de novo design of antibody V-regions" Gene, 160(2): 269-272 (1995).
Soderlind, E. et al., "The immune diversity in a test tube—non-immunised antibody libraries and functional variability in defined protein scaffolds" Combinatorial Chemistry & High Throughput Screening, 4(5):409-416 (2001).
Solem, S.T. et al., Antibody Repertoire Development in Teleosts—A Review with Emphasis on Salmonids and Gadus morhua L, Dev. Camp. Immunol., 30:57-76 (2006).
Souto-Carneiro, M.M. et al., "Characterization of the Hurnan Ig Heavy Chain Antigen Binding Complementarity Determining Region 3 Using a Newly Developed Software Algorithm, Joinsolver," J. Immunol., 172(11):6790-6802 (2004).
Standing Order, Filed in Interference No. 105,809, Filed May 6, 2011, pp. 1-81.

(56) References Cited

OTHER PUBLICATIONS

Stewart, A.K. et al., "High-frequency representation of a single VH gene in the expressed human B cell repertoire" J. Exp. Med., 177(2):409-418 (1993).
Stohl, W. and Hilbert, D.M., "The discovery and development of belimumab: the anti-BLyS-lupus connection" Nature Biology 30(1):69-77 (2012).
Struhl, K. et al., High-frequency transformation of yeast: autonomous replication of hybrid DNA molecules, Proceedings of the National Academy of Science USA, 76(3):1035-1039 (1979).
Suzuki, M. et al., "Light chain determines the binding property of human anti-dsDNA IgG autoantibodies" Biochem. Biophys. Res. Commun., 271(1):240-243 (2000).
Swers, J.S. et al., "Shuffled antibody libraries created by in vivo homologous recombination and yeast surface display" Nuc. Acids. Res. 32(3), e36, 1-8 (2004).
Szybalski W. and Skalka A., "Nobel prizes and restriction enzymes," Gene 4(3):181-182 (1978).
Szybalski W., "Reasons and risks to study restriction/modification enzymes form extreme thermophiles: chilly coldrooms, 13th sample, and 13-codon overlap" Gene, 112(1):1-2 (1992).
Szybalski W., "Universal restriction endonucleases: designing novel cleavage specificities by combining adaptor oligodeoxynucleotide and enzyme moieties" Gene, 40(2-3):169-173 (1985).
Szybalski, W. et al., "Class-IIS restriction enzymes—a review" Gene, 100:13-26 (1991).
Tavladoraki, P. et al., "Transgenic plants expressing a functional single-chain Fv antibody are specifically protected from virus attack" Nature, 366(6454):469-472 (1993).
Terret, N.K. (1998) "Combinational Chemistry", Oxford University Press, pp. 2-5.
Terskikh, A.V. et al., "Peptabody": A new type of high avidity binding protein Proc. Natl. Acad., 94(5):1663-1668 (1997).
Thielking, V, et al., "Accuracy of the EcoRI restriction endonuclease: binding and cleavage studies with oligodeoxynucleotide substrates containing degenerate recognition sequences" Biochemistry, 29(19):4682-4691 (1990).
Tomlinson, I.M. et al., "The repertoire of human germline VH sequences reveals about fifty groups of VH segments with different hypervariable loops" Journal of Molecular Biology, 227(3):776-798 (1992).
Tomlinson, I.M. et al., "The structural repertoire of the human V kappa domain" EMBO J., 14(18):4628-4638 (1995).
Tsurushita, N. et al., "Phage display vectors for in vivo recombination of immunoglobulin heavy and light chain genes to make large combinatorial libraries" Gene, 172(1):59-63 (1996).
Ueda, M. and Tanaka, A., "Genetic immobilization of proteins on the yeast cell surface" Biotechnology Advances, 8(2):121-140 (2000).
Uetz, P. et al., "A comprehensive analysis of protein-protein interactions in *Saccharomyces cerevisiae*" Nature, 403(6770):623-627 (2000).
Urlinger, S. et al., "Exploring the sequence space for tetracycline-dependent transcriptional activators: novel mutations yield expanded range and sensitivity" Proc. Natl. Acad. Sci. USA, 97(14):7963-7968 (2000).
U.S. Appl. No. 13/213,302, Protest Under 37 CFR § 1.291 on behalf of Dyax Corp, May 11, 2012, 491 pages.
U.S. Appl. No. 13/249,581, Protest Under 37 CFR § 1.291 on behalf of Dyax Corp, May 25, 2012, 566 pages.
U.S. Appl. No. 13/300,308, Protest Under 37 CFR § 1.291 on behalf of Dyax Corp, May 25, 2012, 742 pages.
U.S. Appl. No. 13/300,340, Protest Under 37 CFR § 1.291 on behalf of Dyax Corp, May 25, 2012, 734 pages.
U.S. Appl. No. 13/300,534, Protest Under 37 CFR § 1.291 on behalf of Dyax Corp, May 25, 2012, 486 pages.
Van Holten, R.W. and Autenrieth, S.M., "Evaluation of depth filtration to remove prion challenge from an immune globulin preparation" Vox Sanguinis 85:20-24 (2003).
Vander Vaart, J.M. et al., "Comparison of cell wall proteins of *Saccharomyces cerevisiae* as anchors for cell surface expression of heterologous proteins" Appl. Environ. Microbiol., 63(2):615-620 (1997).
Vaswani, S.K. and Hamilton, R.G., "Humanized antibodies as potential therapeutic drugs" Ann. Allergy Athma Immunol., 81(2):105-115 (1998).
Vendel, M.C. et al., "Secretion from bacterial versus mammalian cells yields a recombinant scFv with variable folding properties" Arch. Biochem. Biophys. 1-6 (2012).
Virnekas, B. et al., "Trinucleotide phosphoramidites: ideal reagents for the synthesis of mixed oligonucleotides for random mutagenesis" Nucleic Acids Res., 22(25):5600-5607 (1994).
Visintin. M. et al., "Selection of antibodies for intracellular function using a two-hybrid in vivo system.", Proc. Natl. Acad. Sci. USA 96(21):11723-11728 (1999).
Volpe, J.M. and Kepler, T.B., "Genetic correlates of autoreactivity and autoreactive potential in human Ig heavy chains" Immunome Res., 5:1 (2009).
Volpe, J.M. et al., "SoDA: Implementation of a 3D Alignment Algorithm for Inference of Antigen Receptor Recombinations," Bioinforrnatics, 22(4):438-444 (2006).
Vugmeyster Y., "Biodistribution of [125I]-Labeled Therapeutic Proteins: Application in Protein Drug Development Beyond Oncology" Journal of Pharmaceutical Sciences 99(2) 1028-1045 (2010).
Vugmeyster, Y. et al., "Complex Pharmacokinetics of a Humanized Antibody Against Human Amyloid Beta Peptide, Anti-Abeta Ab2, in Nonclinical Species" Pharm Res, 28:1696-1706 (2011).
Wagner, B., Immunoglobulins and Immunoglobulin Genes of the Horse, Dev. Camp. Immunol., 30:155-164 (2006).
Walhout, A.J. et al., "GATEWAY recombinational cloning: application to the cloning of large numbers of open reading frames or ORFeomes" Methods in Enzymology, 328:575-92 (2000).
Wang, Y. et al., "Many human immunoglobulin heavy-chain IGHV gene polymorphisms have been reported in error" Immunol. Cell. Biol., 86(2):111-115 (epub 2007-2008).
Ward, ES. et al., Binding activities of a repertoire of single immunoglobulin variable domains secreted from *Escherichia coli*, Nature, 341(6242):544-546 (1989).
Weaver-Feldhaus, J.M. et al., "Yeast mating for combinatorial Fab library generation and surface display" FEBS Lett., 564(1-2):24-34 (2004).
Welschof et al., "Amino acid sequence based PCR primers for amplification of rearranced human heavy and light chain immunoglobulin variable region genes", J. Immunol. Meth., 179:203-214 (1995).
Wen et al., "T cells recognize the VH complementarity-determining region 3 of the idiotypic protein of B cell non-Hodgkin's lymphoma", Eur. J. Immunol., 27:1043-1047 (1997).
Wentz, A.E. and Shusta, E.V., "A novel high-throughput screen reveals yeast genes that increase secretion of heterologous proteins" Appl. Environ. Microbiol., 73(4):1189-1198 (2007).
Winkler et al., "Analysis of immunoglobulin variable region genes from human IgG anti-DNA hybridomas", Eur. J. Immunol., 22:1719-1728 (1992).
Winter G. and Milstein C., "Man-made antibodies" Nature, 349(6307):293-299 (1991).
Winter, Greg, "Synthetic human antibodies and a strategy for protein engineering", FEBS Letters, 430:92-94 (1998).
Wu, H. et al., "Humanization of a murine monoclonal antibody by simultaneous optimization of framework and CDR residues" J. Mol. Biol., 294(1):151-162 (1999).
Wörn, A. and Plückthun, A., "An intrinsically stable antibody scFv fragment can tolerate the loss of both disulfide bonds and fold correctly." FEBS Lett., 427(3):357-361 (1998).
Xu et al., "Diversity in the CDR3 Region of VH is Sufficient for Most Antibody Specificities", Immunity, 13:37-45 (2000).
Xu, J.L. and Davis, M.M., "Diversity in the CDR3 region of V(H) is sufficient for most antibody specificities" Immunity, 13(1):37-45 (2000).
Yang, W.P. et al., "CDR walking mutagenesis for the affinity maturation of a potent human anti-HIV-1 antibody into the picomolar range" J. Molecular Biology, 254(3):392-403 (1995).

(56) References Cited

OTHER PUBLICATIONS

Ye, J., The Immunoglobulin /GHD Gene Locus in C57BL/6 Mice, Immunogenetics, 56:399-404 (2004).

Zemlin, M. et al., "Expressed murine and human CDR-H3 intervals of equal length exhibit distinct repertoires that differ in their amino acid composition and predicted range of structures" J. Mol. Biol. 334(4):733-749 (2003).

Zeng et al., "CD146, an epithelial-mesenchymal transition inducer, is associated with triple-negative breast cancer", published on line before print Dec. 30, 2011, doi:1010.1073/pnas.1111053108.

Zeng, Q. et al., "CD146, an epithelial-mesenchymal transition inducer, is associated with triple-negative breast cancer" PNAS Early Edition 1-6.

Zhang, Y., et al., Selection of active scFv to G-protein-coupled receptor CCR5 using surface antigen-mimicking peptides, Biochem. 43:12575-12584 (2004).

Zhao, Y. et al., The Bovine Antibody Repertoire, Dev. Camp. Immunol., 30:175-186 (2006).

Zhu D.L., "Oligodeoxynucleotide-directed cleavage and repair of a single-stranded vector: a method of site-specific mutagenesis" Analytical Biochemistry, 177(1):120-124 (1989).

Zhu, J. and Kahn, C.R., "Analysis of a peptide hormone-receptor interaction in the yeast two-hybrid system" Proc. Natl. Acad. Sci. USA. 94(24):13063-13068 (1997).

Zucconi, A. et al., "Domain repertoires as a tool to derive protein recognition rules" FEBS Letters, 480(1):49-54 (2000).

Silacci, M. et al., Design, construction, and characterization of a large synthetic human antibody phage display library, Proteomics, 5:2340-2350 (2005).

Chen, M. et al., Structure of *Saccharomyces cerevisiae* alpha-agglutinin. Evidence for a yeast cell wall protein with multiple immunoglobulin-like domains with atypical disulfides, J Biol Chem, 270(44):26168-77 (1995).

Georgiou, G. et al., Display of heterologous proteins on the surface of microorganisms From the screening of combinatorial libraries to live recombinant vaccines, Nat Biotechnol., 15:29-34 (1997).

Lipke, P. et al., AGα1 is the structural gene for the *Saccharomyces cerevisiae* alpha-agglutinin, a cell surface glycoprotein involved in cell-cell interactions during mating, Mol Cell Biol, 9(8):3155-65 (1989).

Schreuder, M. et al., Immobilizing proteins on the surface of yeast cells, Trends Biotechnol, 14:115-120 (1996).

* cited by examiner

Figure 7

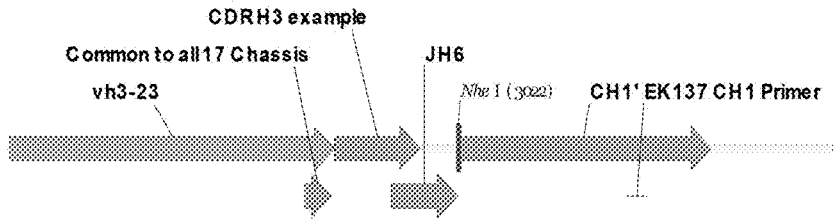

Fragment of p14HC-3-23
745 bp (molecule 7122 bp)

```
                        vh3-23
          E  V  Q  L  L  E  S  G  G  G  L  V  Q  P  G  G  S  L  R  L  S  C  A  A  S  G  F
2616      GAGGTGCAGC TGTTGGAGTC TGGGGGAGGC TTGGTACAGC CTGGGGGGTC CCTGAGACTC TCCTGTGCAG CCTCTGGATT
          CTCCACGTCG ACAACCTCAG ACCCCCTCCG AACCATGTCG GACCCCCCAG GGACTCTGAG AGGACACGTC GGAGACCTAA vh3-23
          T  F  S  S  Y  A  M  S  W  V  R  Q  A  P  G  K  G  L  E  W  V  S  A  I  S  G  S
2696      CACCTTTAGC AGCTATGCCA TGAGCTGGGT CCGCCAGGCT CCAGGGAAGG GGCTGGAGTG GGTCTCAGCT ATTAGTGGTA
          GTGGAAATCG TCGATACGGT ACTCGACCCA GGCGGTCCGA GGTCCCTTCC CCGACCTCAC CCAGAGTCGA TAATCACCAT vh3-23
          G  G  S  T  Y  Y  A  D  S  V  K  G  R  F  T  I  S  R  D  N  S  K  N  T  L  Y
2776      GTGGTGGTAG CACATACTAC GCAGACTCCG TGAAGGGCCG GTTCACCATC TCCAGAGACA ATTCCAAGAA CACGCTGTAT
          CACCACCATC GTGTATGATG CGTCTGAGGC ACTTCCCGGC CAAGTGGTAG AGGTCTCTGT TAAGGTTCTT GTGCGACATA

Common to all 17 Chassis              CDRH3 example
                        vh3-23
          L  Q  M  N  S  L  R  A  E  D  T  A  V  Y  Y  C  A  K  E  G  G  P  G  Y  C  S  S
2856      CTGCAAATGA ACAGCCTGAG AGCCGAGGAC ACGGCGGTGT ACTACTGCGC CAAGGAGGGC GGACCTGGGT ATTGCAGTTC
          GACGTTTACT TGTCGGACTC TCGGCTCCTG TGCCGCCACA TGATGACGCG GTTCCTCCCG CCTGGACCCA TAACGTCAAG JH6
                  CDRH3 example
          T  S  C  Y  T  P  G  G  Y  Y  Y  Y  Y  G  M  D  V  W  G  Q  G  T  T  V  T  V  S
2936      AACTTCTTGT TATACACCAG GAGGCTACTA CTATTACTAC GGCATGGACG TGTGGGGACA AGGTACAACA GTCACCGTCT
          TTGAAGAACA ATATGTGGTC CTCCGATGAT GATAATGATG CCGTACCTGC ACACCCCTGT TCCATGTTGT CAGTGGCAGA CH1'
          JH6
          NheI
          S  A  S  T  K  G  P  S  V  F  P  L  A  P  S  S  K  S  T  S  G  G  T  A  A  L
3016      CCTCAGCTAG CACCAAGGGC CCATCGGTCT TCCCCCTGGC ACCCTCCTCC AAGAGCACCT CTGGGGGCAC AGCGGCCCTG
          GGAGTCGATC GTGGTTCCCG GGTAGCCAGA AGGGGGACCG TGGGAGGAGG TTCTCGTGGA GACCCCGTGT CGCCGGGAC CH1'
                                                                                    EK137 CH1
          Primer
          G  C  L  V  K  D  Y  F  P  E  P  V  T  V  S  W  N  S  G  A  L  T  S  G  V  H  T
3096      GGCTGCCTGG TCAAGGACTA CTTCCCCGAA CCGGTGACGG TGTCGTGGAA CTCAGGCGCC CTGACCAGCG GCGTGCACAC
          CCGACGGACC AGTTCCTGAT GAAGGGGCTT GGCCACTGCC ACAGCACCTT GAGTCCGCGG GACTGGTCGC CGCACGTGTG CH1'
          EK137 CH1 Primer
          F  P  A  V  L  Q  S  S  G  L  Y  S  L  S  S  V  V  T  V  P  S  S  S  L
3176      CTTCCCGGCT GTCCTACAGT CCTCAGGACT CTACTCCCTC AGCAGCGTGG TGACCGTGCC CTCCAGCAGC TTG
          GAAGGGCCGA CAGGATGTCA GGAGTCCTGA GATGAGGGAG TCGTCGCACC ACTGGCACGG GAGGTCGTCG AAC
```

Figure 9

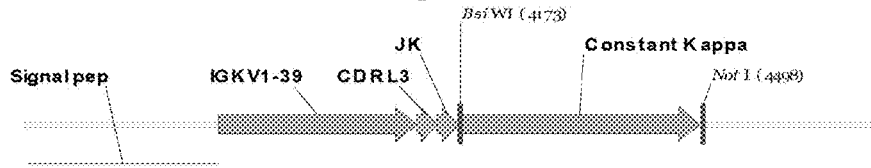

Fragment of p15LC-1-39-LC3-9aa
1128 bp (molecule 7604 bp)

```
                            Signal pep
         ~~~~~~~~~~~~~~~~~~~~~~~~~~~~~~~~~~~~~~~~~~~~~~~~~~~~~~~~~~~~~~~~~~~~~
          M   R   F   P   S   I   F   T   A   V   L   F   A   A   S   S   A   L   A   A   P   A   N   T   T   T   E
    3595  AATGCGCTTT CCGAGCATTT TTACCGCAGT TCTGTTTGCG GCGAGCAGCG CGCTGGCGGC GCCGGCGAAC ACCACCACCG
          TTACGCGAAA GGCTCGTAAA AATGGCGTCA AGACAAACGC CGCTCGTCGC GCGACCGCCG CGGCCGCTTG TGGTGGTGGC
                                          Signal pep
         ~~~~~~~~~~~~~~~~~~~~~~~~~~~~~~~~~~~~~~~~~~~~~~~~~~~~~~~~~~~~~~~~~~~~~
          D   E   T   A   Q   I   P   A   E   A   V   I   D   Y   S   D   L   E   G   D   F   D   A   A   A   L
    3675  AAGATGAAAC CGCGCAGATT CCGGCGGAAG CGGTGATTGA TTATAGCGAT CTGGAAGGCG ATTTTGATGC GGCGGCGCTG
          TTCTACTTTG GCGCGTCTAA GGCCGCCTTC GCCACTAACT AATATCGCTA GACCTTCCGC TAAAACTACG CCGCCGCGAC
                                          Signal pep
         ~~~~~~~~~~~~~~~~~~~~~~~~~~~~~~~~~~~~~~~~~~~~~~~~~~~~~~~~~~~~~~~~~~~~~
          P   L   S   N   S   T   N   N   G   L   S   S   T   N   T   T   I   A   S   I   A   A   K   E   G   V
    3755  CCGCTGAGCA ACAGCACCAA CAACGGCCTG AGCAGCACCA ACACCACCAT TGCGAGCATT GCGGCGAAAG AAGAAGGCGT
          GGCGACTCGT TGTCGTGGTT GTTGCCGGAC TCGTCGTGGT TGTGGTGGTA ACGCTCGTAA CGCCGCTTTC TTCTTCCGCA
          Signal pep
         ~~~~~~~~~~~~~~~~~~~
                                                IGKV1-39
                             ~~~~~~~~~~~~~~~~~~~~~~~~~~~~~~~~~~~~~~~~~~~~~~~~~~~~~~~~~~~~~~~~~~~~~
          Q   L   D   K   R   D   I   Q   M   T   Q   S   P   S   S   L   S   A   S   V   G   D   R   V   T   I   T
    3835  GCAGCTGGAT AAACGCGACA TCCAGATGAC CCAGTCTCCA TCCTCCCTGT CTGCATCTGT AGGAGACAGA GTCACCATCA
          CGTCGACCTA TTTGCGCTGT AGGTCTACTG GGTCAGAGGT AGGAGGGACA GACGTAGACA TCCTCTGTCT CAGTGGTAGT
                                                IGKV1-39
         ~~~~~~~~~~~~~~~~~~~~~~~~~~~~~~~~~~~~~~~~~~~~~~~~~~~~~~~~~~~~~~~~~~~~~
          C   R   A   S   Q   S   I   S   S   Y   L   N   W   Y   Q   Q   K   P   G   K   A   P   K   L   L   I
    3915  CTTGCCGGGC AAGTCAGAGC ATTAGCAGCT ATTTAAATTG GTATCAGCAG AAACCAGGGA AAGCCCCTAA GCTCCTGATC
          GAACGGCCCG TTCAGTCTCG TAATCGTCGA TAAATTTAAC CATAGTCGTC TTTGGTCCCT TTCGGGGATT CGAGGACTAG
                                                IGKV1-39
         ~~~~~~~~~~~~~~~~~~~~~~~~~~~~~~~~~~~~~~~~~~~~~~~~~~~~~~~~~~~~~~~~~~~~~
          Y   A   A   S   S   L   Q   S   G   V   P   S   R   F   S   G   S   G   S   G   T   D   F   T   L   T   I
    3995  TATGCTGCAT CCAGTTTGCA AAGTGGGGTC CCATCAAGGT TCAGTGGCAG TGGATCTGGG ACAGATTTCA CTCTCACCAT
          ATACGACGTA GGTCAAACGT TTCACCCCAG GGTAGTTCCA AGTCACCGTC ACCTAGACCC TGTCTAAAGT GAGAGTGGTA
                                                                              CDRL3
                                                                  ~~~~~~~~~~~~~~~~~~~~~~~~~~~~~~
               IGKV1-39                                                                                JK
         ~~~~~~~~~~~~~~~~~~~~~~~~~~~~~~~~~~~~~~~~~~~~~~~~~                                       ~~~~~~~~~~~~~~
          S   S   L   Q   P   E   D   F   A   T   Y   Y   C   Q   Q   S   Y   S   T   P   L   T   F   G   G   G   T
    4075  CAGCAGTCTG CAACCTGAAG ATTTTGCAAC TTACTACTGT CAACAGAGTT ACAGTACCCC TCTCACTTTT GGCGGAGGGA
          GTCGTCAGAC GTTGGACTTC TAAAACGTTG AATGATGACA GTTGTCTCAA TGTCATGGGG AGAGTGAAAA CCGCCTCCCT
                JK
         ~~~~~~~~~~~~~~~~~~
                                                Constant Kappa
                                  ~~~~~~~~~~~~~~~~~~~~~~~~~~~~~~~~~~~~~~~~~~~~~~~~~~~~~~~~~~~~~~~
                       BsiWI
                       ~~~~~~~
          K   V   E   I   K   R   T   V   A   A   P   S   V   F   I   F   P   P   S   D   E   Q   L   K   S   G
    4155  CCAAGGTTGA GATCAAACGT ACGGTGGCCG CTCCTTCCGT GTTCATCTTC CCTCCCTCCG ACGAGCAGCT GAAGTCCGGC
          GGTTCCAACT CTAGTTTGCA TGCCACCGGC GAGGAAGGCA CAAGTAGAAG GGAGGGAGGC TGCTCGTCGA CTTCAGGCCG
                                          Constant Kappa
         ~~~~~~~~~~~~~~~~~~~~~~~~~~~~~~~~~~~~~~~~~~~~~~~~~~~~~~~~~~~~~~~~~~~~~
          T   A   S   V   V   C   L   L   N   N   F   Y   P   R   E   A   K   V   Q   W   K   V   D   N   A   L   Q
    4235  ACCGCCAGCG TGGTGTGCCT GCTGAACAAC TTCTACCCTC GGGAGGCCAA GGTGCAGTGG AAGGTGGACA ACGCCCTGCA
          TGGCGGTCGC ACCACACGGA CGACTTGTTG AAGATGGGAG CCCTCCGGTT CCACGTCACC TTCCACCTGT TGCGGGACGT
```

Figure 9 (continued)

```
                  Constant Kappa
       ~~~~~~~~~~~~~~~~~~~~~~~~~~~~~~~~~~~~~~~~~~~~~~~~~~~~~~~~~~~~~~~~~~~~~~
        · S   G   N    S   Q   E   S    V   T   E    Q   D   S    K   D   S    T   Y   S   L    S   S   T    L   T   L   S ·
 4315   GAGCGGCAAC TCCCAGGAGT CCGTCACCGA GCAGGACTCC AAGGACAGCA CCTACTCCCT GTCCTCCACC CTGACCCTGT
        CTCGCCGTTG AGGGTCCTCA GGCAGTGGCT CGTCCTGAGG TTCCTGTCGT GGATGAGGGA CAGGAGGTGG GACTGGGACA Constant Kappa
       ~~~~~~~~~~~~~~~~~~~~~~~~~~~~~~~~~~~~~~~~~~~~~~~~~~~~~~~~~~~~~~~~~~~~~~
        · K   A   D    Y   E   K    H   K   V   Y    A   C   E    V   T   H    Q   G   L   S    S   P   V    T   K   S
 4395   CCAAGGCCGA CTACGAGAAG CATAAGGTGT ACGCCTGCGA GGTGACCCAC CAGGGCCTGT CCAGCCCTGT GACCAAGTCC
        GGTTCCGGCT GATGCTCTTC GTATTCCACA TGCGGACGCT CCACTGGGTG GTCCCGGACA GGTCGGGACA CTGGTTCAGG Constant Kappa
       ~~~~~~~~~~~~~~~~~~~~~
                            NotI
                         ~~~~~~~~~
        F   N   R   G    E   C   *
 4475   TTCAACCGGG GCGAGTGCTA GGCGGCCGCA
        AAGTTGGCCC CGCTCACGAT CCGCCGGCGT
```

RATIONALLY DESIGNED, SYNTHETIC ANTIBODY LIBRARIES AND USES THEREFOR

CROSS-REFERENCE TO RELATED APPLICATIONS

This application is a divisional of application Ser. No. 12/210,072, filed Sep. 12, 2008, which claims the benefit of U.S. Provisional Application No. 60/993,785, filed on Sep. 14, 2007; the contents of these applications are hereby incorporated by reference in their entirety.

SEQUENCE LISTING

In accordance with 37 CFR § 1.52(e), the present specification makes reference to a Sequence Listing (submitted electronically as a .txt file named "2009186-0107_SL2_ST25.txt"). The .txt file was generated on May 9, 2017 and is 232,715 bytes in size. The entire contents of the Sequence Listing are herein incorporated by reference.

BACKGROUND OF THE INVENTION

Antibodies have profound relevance as research tools and in diagnostic and therapeutic applications. However, the identification of useful antibodies is difficult and once identified, antibodies often require considerable redesign or 'humanization' before they are suitable for therapeutic applications.

Previous methods for identifying desirable antibodies have typically involved phage display of representative antibodies, for example human libraries derived by amplification of nucleic acids from B cells or tissues, or, alternatively, synthetic libraries. However, these approaches have limitations. For example, most human libraries known in the art contain only the antibody sequence diversity that can be experimentally captured or cloned from the source (e.g., B cells). Accordingly, the human library may completely lack or under-represent certain useful antibody sequences. Synthetic or consensus libraries known in the art have other limitations, such as the potential to encode non-naturally occurring (e.g., non-human) sequences that have the potential to be immunogenic. Moreover, certain synthetic libraries of the art suffer from at least one of two limitations: (1) the number of members that the library can theoretically contain (i.e., theoretical diversity) may be greater than the number of members that can actually be synthesized, and (2) the number of members actually synthesized may be so great as to preclude screening of each member in a physical realization of the library, thereby decreasing the probability that a library member with a particular property may be isolated.

For example, a physical realization of a library (e.g., yeast display, phage display, ribosomal display, etc.) capable of screening $10^{12}$ library members will only sample about 10% of the sequences contained in a library with $10^{13}$ members. Given a median CDRH3 length of about 12.7 amino acids (Rock et al., J. Exp. Med., 1994, 179:323-328), the number of theoretical sequence variants in CDRH3 alone is about $20^{12.7}$, or about $3.3 \times 10^{16}$ variants. This number does not account for known variation that occurs in CDRH1 and CDRH2, heavy chain framework regions, and pairing with different light chains, each of which also exhibit variation in their respective CDRL1, CDRL2, and CDRL3. Finally, the antibodies isolated from these libraries are often not amenable to rational affinity maturation techniques to improve the binding of the candidate molecule.

Accordingly, a need exists for smaller (i.e., able to be synthesized and physically realizable) antibody libraries with directed diversity that systematically represent candidate antibodies that are non-immunogenic (i.e., more human) and have desired properties (e.g., the ability to recognize a broad variety of antigens). However, obtaining such libraries requires balancing the competing objectives of restricting the sequence diversity represented in the library (to enable synthesis and physical realization, potentially with oversampling, while limiting the introduction of non-human sequences) while maintaining a level of diversity sufficient to recognize a broad variety of antigens. Prior to the instant invention, it was known in the art that "[al]though libraries containing heavy chain CDR3 length diversity have been reported, it is impossible to synthesize DNA encoding both the sequence and the length diversity found in natural heavy chain CDR3 repertoires" (Hoet et al., Nat. Biotechnol., 2005, 23: 344, incorporated by reference in its entirety).

Therefore, it would be desirable to have antibody libraries which (a) can be readily synthesized, (b) can be physically realized and, in certain cases, oversampled, (c) contain sufficient diversity to recognize all antigens recognized by the preimmune human repertoire (i.e., before negative selection), (d) are non-immunogenic in humans (i.e., comprise sequences of human origin), and (e) contain CDR length and sequence diversity, and framework diversity, representative of naturally-occurring human antibodies. Embodiments of the instant invention at least provide, for the first time, antibody libraries that have these desirable features.

SUMMARY OF THE INVENTION

The present invention is relates to, at least, synthetic polynucleotide libraries, methods of producing and using the libraries of the invention, kits and computer readable forms including the libraries of the invention. In some embodiments, the libraries of the invention are designed to reflect the preimmune repertoire naturally created by the human immune system and are based on rational design informed by examination of publicly available databases of human antibody sequences. It will be appreciated that certain non-limiting embodiments of the invention are described below. As described throughout the specification, the invention encompasses many other embodiments as well.

In certain embodiments, the invention comprises a library of synthetic polynucleotides, wherein said polynucleotides encode at least $10^6$ unique antibody CDRH3 amino acid sequences comprising:

(i) an N1 amino acid sequence of 0 to about 3 amino acids, wherein each amino acid of the N1 amino acid sequence is among the 12 most frequently occurring amino acids at the corresponding position in N1 amino acid sequences of CDRH3 amino acid sequences that are functionally expressed by human B cells;

(ii) a human CDRH3 DH amino acid sequence, N- and C-terminal truncations thereof, or a sequence of at least about 80% identity to any of them;

(iii) an N2 amino acid sequence of 0 to about 3 amino acids, wherein each amino acid of the N2 amino acid sequence is among the 12 most frequently occurring amino acids at the corresponding position in N2 amino acid sequences of CDRH3 amino acid sequences that are functionally expressed by human B cells; and (iv) a human CDRH3 H3-JH amino acid sequence, N-terminal truncations thereof, or a sequence of at least about 80% identity to any of them.

In other embodiments, the invention comprises a library of synthetic polynucleotides, wherein said polynucleotides encode at least about $10^6$ unique antibody CDRH3 amino acid sequences comprising:
(i) an N1 amino acid sequence of 0 to about 3 amino acids, wherein:
  (a) the most N-terminal N1 amino acid, if present, is selected from a group consisting of R, G, P, L, S, A, V, K, I, Q, T and D;
  (b) the second most N-terminal N1 amino acid, if present, is selected from a group consisting of G, P, R, S, L, V, E, A, D, I, T and K; and
  (c) the third most N-terminal N1 amino acid, if present, is selected from the group consisting of G, R, P, S, L, A, V, T, E, D, K and F;
(ii) a human CDRH3 DH amino acid sequence, N- and C-terminal truncations thereof, or a sequence of at least about 80% identity to any of them;
(iii) an N2 amino acid sequence of 0 to about 3 amino acids, wherein:
  (a) the most N-terminal N2 amino acid, if present, is selected from a group consisting of G, P, R, L, S, A, T, V, E, D, F and H;
  (b) the second most N-terminal N2 amino acid, if present, is selected from a group consisting of G, P, R, S, T, L, A, V, E, Y, D and K; and
  (c) the third most N-terminal N2 amino acid, if present, is selected from the group consisting of G, P, S, R, L, A, T, V, D, E, W and Q; and
(iv) a human CDRH3 H3-JH amino acid sequence, N-terminal truncations thereof, or a sequence of at least about 80% identity to any of them.

In still other embodiments, the invention comprises a library of synthetic polynucleotides, wherein said polynucleotides encode at least about $10^6$ unique antibody CDRH3 amino acid sequences that are at least about 80% identical to an amino acid sequence represented by the following formula:

[X]-[N1]-[DH]-[N2]-[H3-JH], wherein:

(i) X is any amino acid residue or no amino acid residue;
(ii) N1 is an amino acid sequence selected from the group consisting of G, P, R, A, S, L, T, V, GG, GP, GR, GA, GS, GL, GT, GV, PG, RG, AG, SG, LG, TG, VG, PP, PR, PA, PS, PL, PT, PV, RP, AP, SP, LP, TP, VP, GGG, GPG, GRG, GAG, GSG, GLG, GTG, GVG, PGG, RGG, AGG, SGG, LGG, TGG, VGG, GGP, GGR, GGA, GGS, GGL, GGT, GGV, D, E, F, H, I, K, M, Q, W, Y, AR, AS, AT, AY, DL, DT, EA, EK, FH, FS, HL, HW, IS, KV, LD, LE, LR, LS, LT, NR, NT, QE, QL, QT, RA, RD, RE, RF, RH, RL, RR, RS, RV, SA, SD, SE, SF, SI, SK, SL, SQ, SR, SS, ST, SV, TA, TR, TS, TT, TW, VD, VS, WS, YS, AAE, AYH, DTL, EKR, ISR, NTP, PKS, PRP, PTA, PTQ, REL, RPL, SAA, SAL, SGL, SSE, TGL, WGT, and combinations thereof;
(iii) DH is an amino acid sequence selected from the group consisting of all possible reading frames that do not include a stop codon encoded by IGHD1-1 (SEQ ID NO: 501), IGHD1-20 (SEQ ID NO: 503), IGHD1-26 (polynucleotides encoding SEQ ID NOs: 13 and 14), IGHD1-7 (SEQ ID NO: 504), IGHD2-15 (polynucleotides encoding SEQ ID NO: 16), IGHD2-2 (polynucleotides encoding SEQ ID NOs: 10 and 11), IGHD2-21 (SEQ ID NOs: 505 and 506), IGHD2-8 (SEQ ID NO: 507), IGHD3-10 (polynucleotides encoding SEQ ID NOs: 1-3), IGHD3-16 (SEQ ID NO: 508), IGHD3-22 (polynucleotides encoding SEQ ID NO: 4), IGHD3-3 (polynucleotides encoding SEQ ID NO: 9), IGHD3-9 (SEQ ID NO: 509), IGHD4-17 (polynucleotides encoding SEQ ID NO: 12), IGHD4-23 (SEQ ID NO: 510), IGHD4-4 (SEQ ID NO: 511), IGHD-4-11 (SEQ ID NO: 511), IGHD5-12 (SEQ ID NO: 512), IGHD5-24 (SEQ ID NO: 513), IGHD5-5 (polynucleotides encoding SEQ ID NO: 15), IGHD-5-18 (polynucleotides encoding SEQ ID NO: 15), IGHD6-13 (polynucleotides encoding SEQ ID NOs: 7 and 8), IGHD6-19 (polynucleotides encoding SEQ ID NOs: 5 and 6), IGHD6-25 (SEQ ID NO: 514), IGHD6-6 (SEQ ID NO: 515), and IGHD7-27 (SEQ ID NO: 516), and N- and C-terminal truncations thereof;
(iv) N2 is an amino acid sequence selected from the group consisting of G, P, R, A, S, L, T, V, GG, GP, GR, GA, GS, GL, GT, GV, PG, RG, AG, SG, LG, TG, VG, PP, PR, PA, PS, PL, PT, PV, RP, AP, SP, LP, TP, VP, GGG, GPG, GRG, GAG, GSG, GLG, GTG, GVG, PGG, RGG, AGG, SGG, LGG, TGG, VGG, GGP, GGR, GGA, GGS, GGL, GGT, GGV, D, E, F, H, I, K, M, Q, W, Y, AR, AS, AT, AY, DL, DT, EA, EK, FH, FS, HL, HW, IS, KV, LD, LE, LR, LS, LT, NR, NT, QE, QL, QT, RA, RD, RE, RF, RH, RL, RR, RS, RV, SA, SD, SE, SF, SI, SK, SL, SQ, SR, SS, ST, SV, TA, TR, TS, TT, TW, VD, VS, WS, YS, AAE, AYH, DTL, EKR, ISR, NTP, PKS, PRP, PTA, PTQ, REL, RPL, SAA, SAL, SGL, SSE, TGL, WGT, and combinations thereof; and
(v) H3-JH is an amino acid sequence selected from the group consisting of AEYFQH (SEQ ID NO: 17), EYFQH (SEQ ID NO: 583), YFQH (SEQ ID NO: 584), FQH, QH, H, YWYFDL (SEQ ID NO: 18), WYFDL (SEQ ID NO: 585), YFDL (SEQ ID NO: 586), FDL, DL, L, AFDV (SEQ ID NO: 19), FDV, DV, V, YFDY (SEQ ID NO: 20), FDY, DY, Y, NWFDS (SEQ ID NO: 21), WFDS (SEQ ID NO: 587), FDS, DS, S, YYYYYGMDV (SEQ ID NO: 22), YYYYGMDV (SEQ ID NO: 588), YYYGMDV (SEQ ID NO: 589), YYGMDV (SEQ ID NO: 590), YGMDV (SEQ ID NO: 591), GMDV (SEQ ID NO: 592), and MDV, or a sequence of at least 80% identity to any of them.

In still another embodiment, the invention comprises wherein said library consists essentially of a plurality of polynucleotides encoding CDRH3 amino acid sequences that are at least about 80% identical to an amino acid sequence represented by the following formula:

[X]-[N1]-[DH]-[N2]-[H3-JH], wherein:

(i) X is any amino acid residue or no amino acid residue;
(ii) N1 is an amino acid sequence selected from the group consisting of G, P, R, A, S, L, T, V, GG, GP, GR, GA, GS, GL, GT, GV, PG, RG, AG, SG, LG, TG, VG, PP, PR, PA, PS, PL, PT, PV, RP, AP, SP, LP, TP, VP, GGG, GPG, GRG, GAG, GSG, GLG, GTG, GVG, PGG, RGG, AGG, SGG, LGG, TGG, VGG, GGP, GGR, GGA, GGS, GGL, GGT, GGV, D, E, F, H, I, K, M, Q, W, Y, AR, AS, AT, AY, DL, DT, EA, EK, FH, FS, HL, HW, IS, KV, LD, LE, LR, LS, LT, NR, NT, QE, QL, QT, RA, RD, RE, RF, RH, RL, RR, RS, RV, SA, SD, SE, SF, SI, SK, SL, SQ, SR, SS, ST, SV, TA, TR, TS, TT, TW, VD, VS, WS, YS, AAE, AYH, DTL, EKR, ISR, NTP, PKS, PRP, PTA, PTQ, REL, RPL, SAA, SAL, SGL, SSE, TGL, WGT, and combinations thereof;
(iii) DH is an amino acid sequence selected from the group consisting of all possible reading frames that do not include a stop codon encoded by IGHD1-1 (SEQ ID NO: 501), IGHD1-20 (SEQ ID NO: 503), IGHD1-26 (polynucleotides encoding SEQ ID NOs: 13 and 14), IGHD1-7 (SEQ ID NO: 504), IGHD2-15 (polynucleotides encoding SEQ ID NO: 16), IGHD2-2 (polynucleotides encoding SEQ ID NOs: 10 and 11), IGHD2-21 (SEQ ID NOs: 505 and 506), IGHD2-8 (SEQ ID NO: 507), IGHD3-10 (polynucleotides encoding SEQ ID NOs: 1-3), IGHD3-16 (SEQ ID NO: 508), IGHD3-22 (polynucleotides encoding SEQ ID NO: 4), IGHD3-3 (polynucleotides encoding SEQ ID NO: 9), IGHD3-9 (SEQ ID NO: 509), IGHD4-17 (polynucleotides encoding SEQ ID NO: 12), IGHD4-23 (SEQ ID NO: 510), IGHD4-4 (SEQ ID NO: 511), IGHD-4-11 (SEQ ID NO: 511), IGHD5-12 (SEQ ID NO: 512), IGHD5-24 (SEQ ID NO: 513), IGHD5-5 (polynucleotides encoding SEQ ID NO: 15), IGHD-5-18 (polynucleotides encoding SEQ ID NO: 15), IGHD6-13 (polynucleotides encoding SEQ ID NOs: 7 and 8), IGHD6-19 (polynucleotides encoding SEQ ID NOs: 5 and 6), IGHD6-25 (SEQ ID NO: 514), IGHD6-6 (SEQ ID NO: 515), and IGHD7-27 (SEQ ID NO: 516), and N- and C-terminal truncations thereof;

(iv) N2 is an amino acid sequence selected from the group consisting of G, P, R, A, S, L, T, V, GG, GP, GR, GA, GS, GL, GT, GV, PG, RG, AG, SG, LG, TG, VG, PP, PR, PA, PS, PL, PT, PV, RP, AP, SP, LP, TP, VP, GGG, GPG, GRG, GAG, GSG, GLG, GTG, GVG, PGG, RGG, AGG, SGG, LGG, TGG, VGG, GGP, GGR, GGA, GGS, GGL, GGT, GGV, D, E, F, H, I, K, M, Q, W, Y, AR, AS, AT, AY, DL, DT, EA, EK, FH, FS, HL, HW, IS, KV, LD, LE, LR, LS, LT, NR, NT, QE, QL, QT, RA, RD, RE, RF, RH, RL, RR, RS, RV, SA, SD, SE, SF, SI, SK, SL, SQ, SR, SS, ST, SV, TA, TR, TS, TT, TW, VD, VS, WS, YS, AAE, AYH, DTL, EKR, ISR, NTP, PKS, PRP, PTA, PTQ, REL, RPL, SAA, SAL, SGL, SSE, TGL, WGT, and combinations thereof; and (v) H3-JH is an amino acid sequence selected from the group consisting of AEYFQH (SEQ ID NO: 17), EYFQH (SEQ ID NO: 583), YFQH (SEQ ID NO: 584), FQH, QH, H, YWYFDL (SEQ ID NO: 18), WYFDL (SEQ ID NO: 585), YFDL (SEQ ID NO: 586), FDL, DL, L, AFDV (SEQ ID NO: 19), FDV, DV, V, YFDY (SEQ ID NO: 20), FDY, DY, Y, NWFDS (SEQ ID NO: 21), WFDS (SEQ ID NO: 587), FDS, DS, S, YYYYYGMDV (SEQ ID NO: 22), YYYYGMDV (SEQ ID NO: 588), YYYGMDV (SEQ ID NO: 589), YYGMDV (SEQ ID NO: 590), YGMDV (SEQ ID NO: 591), GMDV (SEQ ID NO: 592), and MDV, or a sequence of at least 80% identity to any of them.

In another embodiment, the invention comprises a library of synthetic polynucleotides, wherein said polynucleotides encode one or more full length antibody heavy chain sequences, and wherein the CDRH3 amino acid sequences of the heavy chain comprise:

(i) an N1 amino acid sequence of 0 to about 3 amino acids, wherein each amino acid of the N1 amino acid sequence is among the 12 most frequently occurring amino acids at the corresponding position in N1 amino acid sequences of CDRH3 amino acid sequences that are functionally expressed by human B cells;

(ii) a human CDRH3 DH amino acid sequence, N- and C-terminal truncations thereof, or a sequence of at least about 80% identity to any of them;

(iii) an N2 amino acid sequence of 0 to about 3 amino acids, wherein each amino acid of the N2 amino acid sequence is among the 12 most frequently occurring amino acids at the corresponding position in N2 amino acid sequences of CDRH3 amino acid sequences that are functionally expressed by human B cells; and (iv) a human CDRH3 H3-JH amino acid sequence, N-terminal truncations thereof, or a sequence of at least about 80% identity to any of them.

The following embodiments may be applied throughout the embodiments of the instant invention. In one aspect, one or more CDRH3 amino acid sequences further comprise an N-terminal tail residue. In still another aspect, the N-terminal tail residue is selected from the group consisting of G, D, and E.

In yet another aspect, the N1 amino acid sequence is selected from the group consisting of G, P, R, A, S, L, T, V, GG, GP, GR, GA, GS, GL, GT, GV, PG, RG, AG, SG, LG, TG, VG, PP, PR, PA, PS, PL, PT, PV, RP, AP, SP, LP, TP, VP, GGG, GPG, GRG, GAG, GSG, GLG, GTG, GVG, PGG, RGG, AGG, SGG, LGG, TGG, VGG, GGP, GGR, GGA, GGS, GGL, GGT, GGV, D, E, F, H, I, K, M, Q, W, Y, AR, AS, AT, AY, DL, DT, EA, EK, FH, FS, HL, HW, IS, KV, LD, LE, LR, LS, LT, NR, NT, QE, QL, QT, RA, RD, RE, RF, RH, RL, RR, RS, RV, SA, SD, SE, SF, SI, SK, SL, SQ, SR, SS, ST, SV, TA, TR, TS, TT, TW, VD, VS, WS, YS, AAE, AYH, DTL, EKR, ISR, NTP, PKS, PRP, PTA, PTQ, REL, RPL, SAA, SAL, SGL, SSE, TGL, WGT, and combinations thereof. In certain other aspects, the N1 amino acid sequence may be of about 0 to about 5 amino acids.

In yet another aspect, the N2 amino acid sequence is selected from the group consisting of G, P, R, A, S, L, T, V, GG, GP, GR, GA, GS, GL, GT, GV, PG, RG, AG, SG, LG, TG, VG, PP, PR, PA, PS, PL, PT, PV, RP, AP, SP, LP, TP, VP, GGG, GPG, GRG, GAG, GSG, GLG, GTG, GVG, PGG, RGG, AGG, SGG, LGG, TGG, VGG, GGP, GGR, GGA, GGS, GGL, GGT, GGV, D, E, F, H, I, K, M, Q, W, Y, AR, AS, AT, AY, DL, DT, EA, EK, FH, FS, HL, HW, IS, KV, LD, LE, LR, LS, LT, NR, NT, QE, QL, QT, RA, RD, RE, RF, RH, RL, RR, RS, RV, SA, SD, SE, SF, SI, SK, SL, SQ, SR, SS, ST, SV, TA, TR, TS, TT, TW, VD, VS, WS, YS, AAE, AYH, DTL, EKR, ISR, NTP, PKS, PRP, PTA, PTQ, REL, RPL, SAA, SAL, SGL, SSE, TGL, WGT, and combinations thereof. In certain other aspects, the N2 sequence may be of about 0 to about 5 amino acids.

In yet another aspect, the H3-JH amino acid sequence is selected from the group consisting of AEYFQH (SEQ ID NO: 17), EYFQH (SEQ ID NO: 583), YFQH (SEQ ID NO: 584), FQH, QH, H, YWYFDL (SEQ ID NO: 18), WYFDL (SEQ ID NO: 585), YFDL (SEQ ID NO: 586), FDL, DL, L, AFDV (SEQ ID NO: 19), FDV, DV, V, YFDY (SEQ ID NO: 20), FDY, DY, Y, NWFDS (SEQ ID NO: 21), WFDS (SEQ ID NO: 587), FDS, DS, S, YYYYYGMDV (SEQ ID NO: 22), YYYYGMDV (SEQ ID NO: 588), YYYGMDV (SEQ ID NO: 589), YYGMDV (SEQ ID NO: 590), YGMDV (SEQ ID NO: 591), GMDV (SEQ ID NO: 592), and MDV.

In other embodiments, the invention comprises a library of synthetic polynucleotides encoding a plurality of antibody CDRH3 amino acid sequences, wherein the percent occurrence within the central loop of the CDRH3 amino acid sequences of at least one of the following i-i+1 pairs in the library is within the ranges specified below:

Tyr-Tyr in an amount from about 2.5% to about 6.5%;
Ser-Gly in an amount from about 2.5% to about 4.5%;
Ser-Ser in an amount from about 2% to about 4%;
Gly-Ser in an amount from about 1.5% to about 4%;
Tyr-Ser in an amount from about 0.75% to about 2%;
Tyr-Gly in an amount from about 0.75% to about 2%; and
Ser-Tyr in an amount from about 0.75% to about 2%.

In still other embodiments, the invention comprises a library of synthetic polynucleotides encoding a plurality of antibody CDRH3 amino acid sequences, wherein the percent occurrence within the central loop of the CDRH3 amino acid sequences of at least one of the following i-i+2 pairs in the library is within the ranges specified below:
Tyr-Tyr in an amount from about 2.5% to about 4.5%;
Gly-Tyr in an amount from about 2.5% to about 5.5%;
Ser-Tyr in an amount from about 2% to about 4%;
Tyr-Ser in an amount from about 1.75% to about 3.75%;
Ser-Gly in an amount from about 2% to about 3.5%;
Ser-Ser in an amount from about 1.5% to about 3%;
Gly-Ser in an amount from about 1.5% to about 3%; and
Tyr-Gly in an amount from about 1% to about 2%.

In another embodiment, the invention comprises a library of synthetic polynucleotides encoding a plurality of antibody CDRH3 amino acid sequences, wherein the percent occurrence within the central loop of the CDRH3 amino acid sequences of at least one of the following i-i+3 pairs in the library is within the ranges specified below:
Gly-Tyr in an amount from about 2.5% to about 6.5%;
Ser-Tyr in an amount from about 1% to about 5%;
Tyr-Ser in an amount from about 2% to about 4%;
Ser-Ser in an amount from about 1% to about 3%;
Gly-Ser in an amount from about 2% to about 5%; and
Tyr-Tyr in an amount from about 0.75% to about 2%.

In one aspect of the invention, at least 2, 3, 4, 5, 6, or 7 of the specified i-i+1 pairs in the library are within the specified ranges. In another aspect, the CDRH3 amino acid sequences are human. In yet another aspect, the polynucleotides encode at least about $10^6$ unique CDRH3 amino acid sequences.

In other aspects of the invention, the polynucleotides further encode one or more heavy chain chassis amino acid sequences that are N-terminal to the CDRH3 amino acid sequences, and the one or more heavy chain chassis sequences are selected from the group consisting of about Kabat amino acid 1 to about Kabat amino acid 94 encoded by IGHV1-2 (SEQ ID NO: 24), IGHV1-3 (SEQ ID NO: 423), IGHV1-8 (SEQ ID NOs: 424, 425), IGHV1-18 (SEQ ID NO: 25), IGHV1-24 (SEQ ID NO: 426), IGHV1-45 (SEQ ID NO: 427), IGHV1-46 (SEQ ID NO: 26), IGHV1-58 (SEQ ID NO: 428), IGHV1-69 (SEQ ID NO: 27), IGHV2-5 (SEQ ID NO: 429), IGHV2-26 (SEQ ID NO: 430), IGHV2-70 (SEQ ID NO: 431, 432), IGHV3-7 (SEQ ID NO: 28), IGHV3-9 (SEQ ID NO: 433), IGHV3-11 (SEQ ID NO: 434), IGHV3-13 (SEQ ID NO: 435), IGHV3-15 (SEQ ID NO: 29), IGHV3-20 (SEQ ID NO: 436), IGHV3-21 (SEQ ID NO: 437), IGHV3-23 (SEQ ID NO: 30), IGHV3-30 (SEQ ID NO: 31), IGHV3-33 (SEQ ID NO: 32), IGHV3-43 (SEQ ID NO: 438), IGHV3-48 (SEQ ID NO: 33), IGHV3-49 (SEQ ID NO: 439), IGHV3-53 (SEQ ID NO: 440), IGHV3-64 (SEQ ID NO: 441), IGHV3-66 (SEQ ID NO: 442), IGHV3-72 (SEQ ID NO: 443), IGHV3-73 (SEQ ID NO: 444), IGHV3-74 (SEQ ID NO: 445), IGHV4-4 (SEQ ID NO: 446, 447), IGHV4-28 (SEQ ID NO: 448), IGHV4-31 (SEQ ID NO: 34), IGHV4-34 (SEQ ID NO: 35), IGHV4-39 (SEQ ID NO: 36), IGHV4-59 (SEQ ID NO: 37), IGHV4-61 (SEQ ID NO: 38), IGHV4-B (SEQ ID NO: 39), IGHV5-51 (SEQ ID NO: 40), IGHV6-1 (SEQ ID NO: 449), and IGHV7-4-1 (SEQ ID NO: 450), or a sequence of at least about 80% identity to any of them.

In another aspect, the polynucleotides further encode one or more FRM4 amino acid sequences that are C-terminal to the CDRH3 amino acid sequences, wherein the one or more FRM4 amino acid sequences are selected from the group consisting of a FRM4 amino acid sequence encoded by IGHJ1 (SEQ ID NO: 253), IGHJ2 (SEQ ID NO: 254), IGHJ3 (SEQ ID NO: 255), IGHJ4 (SEQ ID NO: 256), IGHJ5 (SEQ ID NO: 257), and IGHJ6 (SEQ ID NO: 257), or a sequence of at least about 80% identity to any of them. In still another aspect, the polynucleotides further encode one or more immunoglobulin heavy chain constant region amino acid sequences that are C-terminal to the FRM4 sequence.

In yet another aspect, the CDRH3 amino acid sequences are expressed as part of full-length heavy chains. In other aspects, the full-length heavy chains are selected from the group consisting of an IgG1, IgG2, IgG3, and IgG4, or combinations thereof. In one embodiment, the CDRH3 amino acid sequences are from about 2 to about 30, from about 8 to about 19, or from about 10 to about 18 amino acid residues in length. In other aspects, the synthetic polynucleotides of the library encode from about $10^6$ to about $10^{14}$, from about $10^7$ to about $10^{13}$, from about $10^8$ to about $10^{12}$, from about $10^9$ to about $10^{12}$, or from about $10^{10}$ to about $10^{12}$ unique CDRH3 amino acid sequences.

In certain embodiments, the invention comprises a library of synthetic polynucleotides, wherein said polynucleotides encode a plurality of antibody VKCDR3 amino acid sequences comprising about 1 to about 10 of the amino acids found at Kabat positions 89, 90, 91, 92, 93, 94, 95, 95A, 96, and 97, in selected VKCDR3 amino acid sequences derived from a particular IGKV or IGKJ germline sequence.

In one aspect, the synthetic polynucleotides encode one or more of the amino acid sequences listed in Table 33 or a sequence at least about 80% identical to any of them.

In some embodiments, the invention comprises a library of synthetic polynucleotides, wherein said polynucleotides encode a plurality of unique antibody VKCDR3 amino acid sequences that are of at least about 80% identity to an amino acid sequence represented by the following formula:

[VK_Chassis]-[L3-VK]-[X]-[JK*], wherein:

(i) VK_Chassis is an amino acid sequence selected from the group consisting of about Kabat amino acid 1 to about Kabat amino acid 88 encoded by IGKV1-05 (SEQ ID NO: 229), IGKV1-06 (SEQ ID NO: 451), IGKV1-08 (SEQ ID NO: 452, 453), IGKV1-09 (SEQ ID NO: 454), IGKV1-12 (SEQ ID NO: 230), IGKV1-13 (SEQ ID NO: 455), IGKV1-16 (SEQ ID NO: 456), IGKV1-17 (SEQ ID NO: 457), IGKV1-27 (SEQ ID NO: 231), IGKV1-33 (SEQ ID NO: 232), IGKV1-37 (SEQ ID NOs: 458, 459), IGKV1-39 (SEQ ID NO: 233), IGKV1D-16 (SEQ ID NO: 460), IGKV1D-17 (SEQ ID NO: 461), IGKV1D-43 (SEQ ID NO: 462), IGKV1D-8 (SEQ ID NOs: 463, 464), IGKV2-24 (SEQ ID NO: 465), IGKV2-28 (SEQ ID NO: 234), IGKV2-29 (SEQ ID NO: 466), IGKV2-30 (SEQ ID NO: 467), IGKV2-40 (SEQ ID NO: 468), IGKV2D-26 (SEQ ID NO: 469), IGKV2D-29 (SEQ ID NO: 470), IGKV2D-30 (SEQ ID NO: 471), IGKV3-11 (SEQ ID NO: 235), IGKV3-15 (SEQ ID NO: 236), IGKV3-20 (SEQ ID NO: 237), IGKV3D-07 (SEQ ID NO: 472), IGKV3D-11 (SEQ ID NO: 473), IGKV3D-20 (SEQ ID NO: 474), IGKV4-1 (SEQ ID NO: 238), IGKV5-2 (SEQ ID NOs: 475, 476), IGKV6-21 (SEQ ID NOs: 477), and IGKV6D-41, or a sequence of at least about 80% identity to any of them;
(ii) L3-VK is the portion of the VKCDR3 encoded by the IGKV gene segment; and
(iii) X is any amino acid residue; and
(iv) JK* is an amino acid sequence selected from the group consisting of sequences encoded by IGJK1, IGJK2, IGJK3, IGJK4, and IGJK5, wherein the first residue of each IGJK sequence is not present.

In still other aspects, X may be selected from the group consisting of F, L, I, R, W, Y, and P.

In certain embodiments, the invention comprises a library of synthetic polynucleotides, wherein said polynucleotides encode a plurality of VλCDR3 amino acid sequences that are of at least about 80% identity to an amino acid sequence represented by the following formula:

[Vλ_Chassis]-[L3-Vλ]-[Jλ], wherein:

(i) Vλ_Chassis is an amino acid sequence selected from the group consisting of about Kabat amino acid 1 to about Kabat amino acid 88 encoded by IGλV1-36 (SEQ ID NO: 480), IGλV1-40 (SEQ ID NO: 531), IGλV1-44 (SEQ ID NO: 532), IGλV1-47 (SEQ ID NO: 481), IGλV1-51 (SEQ ID NO: 533), IGλV10-54 (SEQ ID NO: 482), IGλV2-11 (SEQ ID NOS: 483, 484), IGλV2-14 (SEQ ID NO: 534), IGλV2-18 (SEQ ID NO: 485), IGλV2-23 (SEQ ID NOS: 486, 487), IGλV2-8 (SEQ ID NO: 488), IGλV3-1 (SEQ ID NO: 535), IGλV3-10 (SEQ ID NO: 489), IGλV3-12 (SEQ ID NO: 490), IGλV3-16 (SEQ ID NO: 491), IGλV3-19 (SEQ ID NO: 536), IGλV3-21 (SEQ ID NO: 537), IGλV3-25 (SEQ ID NO: 492), IGλV3-27 (SEQ ID NO: 493), IGλV3-9 (SEQ ID NO: 494), IGλV4-3 (SEQ ID NO: 495), IGλV4-60 (SEQ ID NO: 496), IGλV4-69 (SEQ ID NO: 538), IGλV5-39 (SEQ ID NO: 497), IGλV5-45 (SEQ ID NO: 540), IGλV6-57 (SEQ ID NO: 539), IGλV7-43 (SEQ ID NO: 541), IGλV7-46 (SEQ ID NO: 498), IGλV8-61 (SEQ ID NO: 499), IGλV9-49 (SEQ ID NO: 500), and IGλV10-54 (SEQ ID NO: 482), or a sequence of at least about 80% identity to any of them;

(ii) L3-Vλ is the portion of the VλCDR3 encoded by the IGλV segment; and (iii) Jλ is an amino acid sequence selected from the group consisting of sequences encoded by IGλJ1-01, IGλJ2-01, IGλJ3-01, IGλJ3-02, IGλJ6-01, IGλJ7-01, and IGλJ7-02, and wherein the first residue of each IGJλ sequence may or may not be deleted.

In further aspects, the invention comprises a library of synthetic polynucleotides, wherein said polynucleotides encode a plurality of antibody proteins comprising:

(i) a CDRH3 amino acid sequence of claim 1; and (ii) a VKCDR3 amino acid sequence comprising about 1 to about 10 of the amino acids found at Kabat positions 89, 90, 91, 92, 93, 94, 95, 95A, 96, and 97, in selected VKCDR3 sequences derived from a particular IGKV or IGKJ germline sequence.

In still further aspects, the invention comprises a library of synthetic polynucleotides, wherein said polynucleotides encode a plurality of antibody proteins comprising:

(i) a CDRH3 amino acid sequence of claim 1; and (ii) a VKCDR3 amino acid sequences of at least about 80% identity to an amino acid sequence represented by the following formula:

[VK_Chassis]-[L3-VK]-[X]-[JK*], wherein:

(a) VK_Chassis is an amino acid sequence selected from the group consisting of about Kabat amino acid 1 to about Kabat amino acid 88 encoded by IGKV1-05 (SEQ ID NO: 229), IGKV1-06 (SEQ ID NO: 451), IGKV1-08 (SEQ ID NO: 452, 453), IGKV1-09 (SEQ ID NO: 454), IGKV1-12 (SEQ ID NO: 230), IGKV1-13 (SEQ ID NO: 455), IGKV1-16 (SEQ ID NO: 456), IGKV1-17 (SEQ ID NO: 457), IGKV1-27 (SEQ ID NO: 231), IGKV1-33 (SEQ ID NO: 232), IGKV1-37 (SEQ ID NOs: 458, 459), IGKV1-39 (SEQ ID NO: 233), IGKV1D-16 (SEQ ID NO: 460), IGKV1D-17 (SEQ ID NO: 461), IGKV1D-43 (SEQ ID NO: 462), IGKV1D-8 (SEQ ID NOs: 463, 464), IGKV2-24 (SEQ ID NO: 465), IGKV2-28 (SEQ ID NO: 234), IGKV2-29 (SEQ ID NO: 466), IGKV2-30 (SEQ ID NO: 467), IGKV2-40 (SEQ ID NO: 468), IGKV2D-26 (SEQ ID NO: 469), IGKV2D-29 (SEQ ID NO: 470), IGKV2D-30 (SEQ ID NO: 471), IGKV3-11 (SEQ ID NO: 235), IGKV3-15 (SEQ ID NO: 236), IGKV3-20, IGKV3D-07 (SEQ ID NO: 472), IGKV3D-11 (SEQ ID NO: 473), IGKV3D-20 (SEQ ID NO: 474), IGKV4-1 (SEQ ID NO: 238), IGKV5-2 (SEQ ID NOs: 475, 476), IGKV6-21 (SEQ ID NOs: 477), and IGKV6D-41, or a sequence of at least about 80% identity to any of them;

(b) L3-VK is the portion of the VKCDR3 encoded by the IGKV gene segment; and (c) X is any amino acid residue; and (d) JK* is an amino acid sequence selected from the group consisting of sequences encoded by IGJK1, IGJK2, IGJK3, IGJK4, and IGJK5, wherein the first residue of each IGJK sequence is not present.

In some aspects, the VKCDR3 amino acid sequence comprises one or more of the sequences listed in Table 33 or a sequence at least about 80% identical to any of them. In other aspects, the antibody proteins are expressed in a heterodimeric form. In yet another aspect, the human antibody proteins are expressed as antibody fragments. In still other aspects of the invention, the antibody fragments are selected from the group consisting of Fab, Fab', F(ab')$_2$, Fv fragments, diabodies, linear antibodies, and single-chain antibodies.

In certain embodiments, the invention comprises an antibody isolated from the polypeptide expression products of any library described herein.

In still other aspects, the polynucleotides further comprise a 5' polynucleotide sequence and a 3' polynucleotide sequence that facilitate homologous recombination.

In one embodiment, the polynucleotides further encode an alternative scaffold.

In another embodiment, the invention comprises a library of polypeptides encoded by any of the synthetic polynucleotide libraries described herein.

In yet another embodiment, the invention comprises a library of vectors comprising any of the polynucleotide libraries described herein. In certain other aspects, the invention comprises a population of cells comprising the vectors of the instant invention.

In one aspect, the doubling time of the population of cells is from about 1 to about 3 hours, from about 3 to about 8 hours, from about 8 to about 16 hours, from about 16 to about 20 hours, or from 20 to about 30 hours. In yet another aspect, the cells are yeast cells. In still another aspect, the yeast is *Saccharomyces cerevisiae*.

In other embodiments, the invention comprises a library that has a theoretical total diversity of N unique CDRH3 sequences, wherein N is about $10^6$ to about $10^{15}$; and wherein the physical realization of the theoretical total CDRH3 diversity has a size of at least about 3N, thereby providing a probability of at least about 95% that any individual CDRH3 sequence contained within the theoretical total diversity of the library is present in the actual library.

In certain embodiments, the invention comprises a library of synthetic polynucleotides, wherein said polynucleotides encode a plurality of antibody VλCDR3 amino acid sequences comprising about 1 to about 10 of the amino acids found at Kabat positions 89, 90, 91, 92, 93, 94, 95, 95A, 95B, 95C, 96, and 97, in selected VλCDR3 sequences encoded by a single germline sequence.

In some embodiments, the invention relates to a library of synthetic polynucleotides encoding a plurality of antibody CDRH3 amino acid sequences, wherein the library has a theoretical total diversity of about $10^6$ to about $10^{15}$ unique CDRH3 sequences.

In still other embodiments, the invention relates to a method of preparing a library of synthetic polynucleotides encoding a plurality of antibody VK amino acid sequences, the method comprising:
- (i) providing polynucleotide sequences encoding:
  - (a) one or more VK_Chassis amino acid sequences selected from the group consisting of about Kabat amino acid 1 to about Kabat amino acid 88 encoded by IGKV1-05 (SEQ ID NO: 229), IGKV1-06 (SEQ ID NO: 451), IGKV1-08 (SEQ ID NO: 452, 453), IGKV1-09 (SEQ ID NO: 454), IGKV1-12 (SEQ ID NO: 230), IGKV1-13 (SEQ ID NO: 455), IGKV1-16 (SEQ ID NO: 456), IGKV1-17 (SEQ ID NO: 457), IGKV1-27 (SEQ ID NO: 231), IGKV1-33 (SEQ ID NO: 232), IGKV1-37 (SEQ ID NOs: 458, 459), IGKV1-39 (SEQ ID NO: 233), IGKV1D-16 (SEQ ID NO: 460), IGKV1D-17 (SEQ ID NO: 461), IGKV1D-43 (SEQ ID NO: 462), IGKV1D-8 (SEQ ID NOs: 463, 464), IGKV2-24 (SEQ ID NO: 465), IGKV2-28 (SEQ ID NO: 234), IGKV2-29 (SEQ ID NO: 466), IGKV2-30 (SEQ ID NO: 467), IGKV2-40 (SEQ ID NO: 468), IGKV2D-26 (SEQ ID NO: 469), IGKV2D-29 (SEQ ID NO: 470), IGKV2D-30 (SEQ ID NO: 471), IGKV3-11 (SEQ ID NO: 235), IGKV3-15 (SEQ ID NO: 236), IGKV3-20 (SEQ ID NO: 237), IGKV3D-07 (SEQ ID NO: 472), IGKV3D-11 (SEQ ID NO: 473), IGKV3D-20 (SEQ ID NO: 474), IGKV4-1 (SEQ ID NO: 238), IGKV5-2 (SEQ ID NOs: 475, 476), IGKV6-21 (SEQ ID NOs: 477), and IGKV6D-41, or a sequence at least about 80% identical to any of them;
  - (b) one or more L3-VK amino acid sequences, wherein L3-VK the portion of the VKCDR3 amino acid sequence encoded by the IGKV gene segment;
  - (c) one or more X residues, wherein X is any amino acid residue; and
  - (d) one or more JK* amino acid sequences, wherein JK* is an amino acid sequence selected from the group consisting amino acid sequences encoded by IGKJ1 (SEQ ID NO: 552), IGKJ2 (SEQ ID NO: 553), IGKJ3 (SEQ ID NO: 554), IGKJ4 (SEQ ID NO: 555), and IGKJ5 (SEQ ID NO: 556), wherein the first amino acid residue of each sequence is not present; and
- (ii) assembling the polynucleotide sequences to produce a library of synthetic polynucleotides encoding a plurality of human VK sequences represented by the following formula:

[VK_Chassis]-[L3-VK]-[X]-[JK*].

In some embodiments, the invention relates to a method of preparing a library of synthetic polynucleotides encoding a plurality of antibody light chain CDR3 sequences, the method comprising:
- (i) determining the percent occurrence of each amino acid residue at each position in selected light chain CDR3 amino acid sequences derived from a single germline polynucleotide sequence;
- (ii) designing synthetic polynucleotides encoding a plurality of human antibody light chain CDR3 amino acid sequences, wherein the percent occurrence of any amino acid at any position within the designed light chain CDR3 amino acid sequences is within at least about 30% of the percent occurrence in the selected light chain CDR3 amino acid sequences derived from a single germline polynucleotide sequence, as determined in (i); and
- (iii) synthesizing one or more polynucleotides that were designed in (ii).

In other embodiments, the invention relates to a method of preparing a library of synthetic polynucleotides encoding a plurality of antibody Vλ amino acid sequences, the method comprising:
- (i) providing polynucleotide sequences encoding:
  - (a) one or more Vλ_Chassis amino acid sequences selected from the group consisting of about Kabat residue 1 to about Kabat residue 88 encoded by IGλV1-36 SEQ ID NO: 480), IGλV1-40 (SEQ ID NO: 531), IGλV1-44 (SEQ ID NO: 532), IGλV1-47 (SEQ ID NO: 481), IGλV1-51 (SEQ ID NO: 533), IGλV10-54 (SEQ ID NO: 482), IGλV2-11 (SEQ ID NO: 483, 484), IGλV2-14 (SEQ ID NO: 534), IGλV2-18 (SEQ ID NO: 485), IGλV2-23 (SEQ ID NO: 486, 487), IGλV2-8 (SEQ ID NO: 488), IGλV3-1 (SEQ ID NO: 535), IGλV3-10 (SEQ ID NO: 489), IGλV3-12 (SEQ ID NO: 490), IGλV3-16 (SEQ ID NO: 491), IGλV3-19 (SEQ ID NO: 536), IGλV3-21 (SEQ ID NO: 537), IGλV3-25 (SEQ ID NO: 492), IGλV3-27 (SEQ ID NO: 493), IGλV3-9 (SEQ ID NO: 494), IGλV4-3 (SEQ ID NO: 495), IGλV4-60 (SEQ ID NO: 496), IGλV4-69 (SEQ ID NO: 538), IGλV5-39 (SEQ ID NO: 497), IGλV5-45 (SEQ ID NO: 540), IGλV6-57 (SEQ ID NO: 539), IGλV7-43 (SEQ ID NO: 541), IGλV7-46 (SEQ ID NO: 498), IGλV8-61 (SEQ ID NO: 499), IGλV9-49 (SEQ ID NO: 500), and IGλV10-54 (SEQ ID NO: 482), or a sequence at least about 80% identical to any of them;
  - (b) one or more L3-Vλ sequences, wherein L3-Vλ is the portion of the VλCDR3 amino acid sequence encoded by the IGλV gene segment;
  - (c) one or more Jλ sequences, wherein Jλ is an amino acid sequence selected from the group consisting of amino acid sequences encoded by IGλJ1-01 (SEQ ID NO: 557), IGλJ2-01 (SEQ ID NO: 558), IGλJ3-01 (SEQ ID NO: 559), IGλJ3-02 (SEQ ID NO: 560), IGλJ6-01 (SEQ ID NO: 561), IGλJ7-01 (SEQ ID NO: 562), and IGλJ7-02 (SEQ ID NO: 563) wherein the first amino acid residue of each sequence may or may not be present; and
- (ii) assembling the polynucleotide sequences to produce a library of synthetic polynucleotides encoding a plurality of human Vλ amino acid sequences represented by the following formula:

[Vλ_Chassis]-[L3-Vλ]-[Jλ].

In certain embodiments, the amino acid sequences encoded by the polynucleotides of the libraries of the invention are human.

The present invention is also directed to methods of preparing a synthetic polynucleotide library comprising providing and assembling the polynucleotide sequences of the instant invention.

In another aspect, the invention comprises a method of preparing the library of synthetic polynucleotides encoding a plurality of antibody CDRH3 amino acid sequences, the method comprising:
(i) providing polynucleotide sequences encoding:
(a) one or more N1 amino acid sequences of about 0 to about 3 amino acids, wherein each amino acid of the N1 amino acid sequence is among the 12 most frequently occurring amino acids at the corresponding position in N1 sequences of CDRH3 amino acid sequences that are functionally expressed by human B cells;
(b) one or more human CDRH3 DH amino acid sequences, N- and C-terminal truncations thereof, or a sequence of at least about 80% identity to any of them;
(c) one or more N2 amino acid sequences of about 0 to about 3 amino acids, wherein each amino acid of the N1 amino acid sequence is among the 12 most frequently occurring amino acids at the corresponding position in N2 amino acid sequences of CDRH3 amino acid sequences that are functionally expressed by human B cells; and
(d) one or more human CDRH3 H3-JH amino acid sequences, N-terminal truncations thereof, or a sequence of at least about 80% identity to any of them; and
(ii) assembling the polynucleotide sequences to produce a library of synthetic polynucleotides encoding a plurality of human antibody CDRH3 amino acid sequences represented by the following formula:

[N1]-[DH]-[N2]-[H3-JH].

In one aspect, one or more of the polynucleotide sequences are synthesized via split-pool synthesis.

In another aspect, the method of the invention further comprises the step of recombining the assembled synthetic polynucleotides with a vector comprising a heavy chain chassis and a heavy chain constant region, to form a full-length heavy chain.

In another aspect, the method of the invention further comprises the step of providing a 5' polynucleotide sequence and a 3' polynucleotide sequence that facilitate homologous recombination. In still another aspect, the method of the invention further comprises the step of recombining the assembled synthetic polynucleotides with a vector comprising a heavy chain chassis and a heavy chain constant region, to form a full-length heavy chain.

In some embodiments, the step of recombining is performed in yeast. In certain embodiments, the yeast is *S. cerevisiae*.

In certain other embodiments, the invention comprises a method of isolating one or more host cells expressing one or more antibodies, the method comprising:
(i) expressing the human antibodies as described herein in one or more host cells;
(ii) contacting the host cells with one or more antigens; and
(iii) isolating one or more host cells having antibodies that bind to the one or more antigens.

In another aspect, the method of the invention further comprises the step of isolating one or more antibodies from the one or more host cells that present the antibodies which recognize the one or more antigens. In yet another aspect, the method of the invention further comprises the step of isolating one or more polynucleotide sequences encoding one or more antibodies from the one or more host cells that present the antibodies which recognize the one or more antigens.

In certain other embodiments, the invention comprises a kit comprising the library of synthetic polynucleotides encoding a plurality of antibody CDRH3 amino acid sequences, or any of the other sequences disclosed herein.

In still other aspects, the CDRH3 amino acid sequences encoded by the libraries of synthetic polynucleotides described herein, or any of the other sequences disclosed herein, are in computer readable form.

BRIEF DESCRIPTION OF THE DRAWINGS

FIG. 7 depicts a schematic diagram of a CDRH3 integrated into a heavy chain vector and the polynucleotide and polypeptide sequences of CDRH3 (amino acid: SEQ ID NO: 847; coding strand: SEQ ID NO: 581; complementary strand: SEQ ID NO: 845).

FIG. 9 depicts a schematic diagram of a CDRL3 integrated into a light chain vector and the polynucleotide and polypeptide sequences of CDRL3 (amino acid: SEQ ID NO: 848; coding strand: SEQ ID NO: 582; complementary strand: SEQ ID NO: 846).

DETAILED DESCRIPTION OF THE INVENTION

Figure 1:
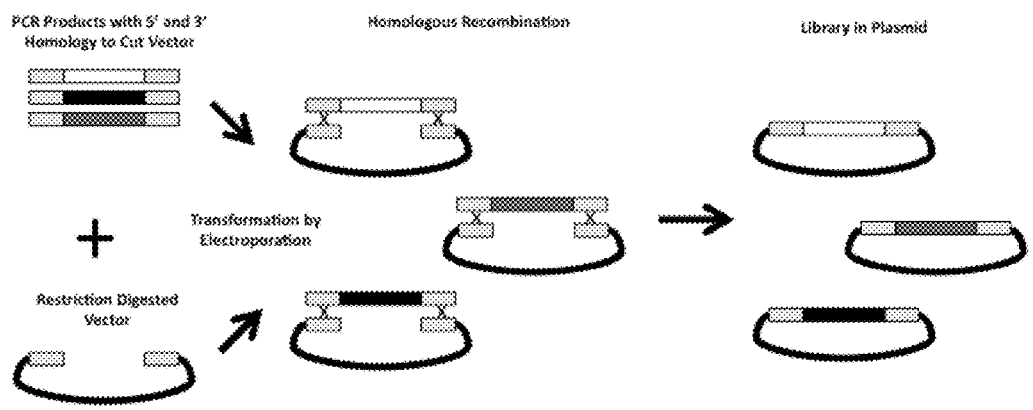
FIG. 1 depicts a schematic of recombination between a fragment (e.g., CDR3) and a vector (e.g., comprising a chassis and constant region) for the construction of a library.

The present invention is directed to, at least, synthetic polynucleotide libraries, methods of producing and using the libraries of the invention, kits and computer readable forms including the libraries of the invention. The libraries taught in this application are described, at least in part, in terms of the components from which they are assembled.

In certain embodiments, the instant invention provides antibody libraries specifically designed based on the composition and CDR length distribution in the naturally occurring human antibody repertoire. It is estimated that, even in the absence of antigenic stimulation, a human makes at least about $10^7$ different antibody molecules. The antigen-binding sites of many antibodies can cross-react with a variety of related but different epitopes. In addition the human antibody repertoire is large enough to ensure that there is an antigen-binding site to fit almost any potential epitope, albeit with low affinity.

The mammalian immune system has evolved unique genetic mechanisms that enable it to generate an almost unlimited number of different light and heavy chains in a remarkably economical way, by combinatorially joining chromosomally separated gene segments prior to transcription. Each type of immunoglobulin (Ig) chain (i.e., κ light, λ light, and heavy) is synthesized by combinatorial assembly of DNA sequences selected from two or more families of gene segments, to produce a single polypeptide chain. Specifically, the heavy chains and light chains each consist of a variable region and a constant (C) region. The variable regions of the heavy chains are encoded by DNA sequences assembled from three families of gene segments: variable (IGHV), joining (IGHJ) and diversity (IGHD). The variable regions of light chains are encoded by DNA sequences assembled from two families of gene segments for each of the kappa and lambda light chains: variable (IGLV) and joining (IGLJ). Each variable region (heavy and light) is also recombined with a constant region, to produce a full-length immunoglobulin chain.

While combinatorial assembly of the V, D and J gene segments make a substantial contribution to antibody variable region diversity, further diversity is introduced in vivo, at the pre-B cell stage, via imprecise joining of these gene segments and the introduction of non-templated nucleotides at the junctions between the gene segments.

After a B cell recognizes an antigen, it is induced to proliferate. During proliferation, the B cell receptor locus undergoes an extremely high rate of somatic mutation that is far greater than the normal rate of genomic mutation. The mutations that occur are primarily localized to the Ig variable regions and comprise substitutions, insertions and deletions. This somatic hypermutation enables the production of B cells that express antibodies possessing enhanced affinity toward an antigen. Such antigen-driven somatic hypermutation fine-tunes antibody responses to a given antigen.

Significant efforts have been made to create antibody libraries with extensive diversity, and to mimic the natural process of affinity maturation of antibodies against various antigens, especially antigens associated with diseases such as autoimmune diseases, cancer, and infectious disease. Antibody libraries comprising candidate binding molecules that can be readily screened against targets are desirable. However, the full promise of an antibody library, which is representative of the preimmune human antibody repertoire, has remained elusive. In addition to the shortcomings enumerated above, and throughout the application, synthetic libraries that are known in the art often suffer from noise (i.e., very large libraries increase the presence of many sequences which do not express well, and/or which misfold), while entirely human libraries that are known in the art may be biased against certain antigen classes (e.g., self-antigens). Moreover, the limitations of synthesis and physical realization techniques restrict the functional diversity of antibody libraries of the art. The present invention provides, for the first time, a fully synthetic antibody library that is representative of the human preimmune antibody repertoire (e.g., in composition and length), and that can be readily screened (i.e., it is physically realizable and, in some cases can be oversampled) using, for example, high throughput methods, to obtain, for example, new therapeutics and/or diagnostics In particular, the synthetic antibody libraries of the instant invention have the potential to recognize any antigen, including self-antigens of human origin. The ability to recognize self-antigens is usually lost in an expressed human library, because self-reactive antibodies are removed by the donor's immune system via negative selection. Another feature of the invention is that screening the antibody library using positive clone selection, for example, by FACS (florescence activated cell sorter) bypasses the standard and tedious methodology of generating a hybridoma library and supernatant screening. Still further, the libraries, or sublibraries thereof, can be screened multiple times, to discover additional antibodies against other desired targets.

Before further description of the invention, certain terms are defined.

1. Definitions

Unless defined otherwise, all technical and scientific terms used herein have the meaning commonly understood by one of ordinary skill in the art relevant to the invention. The definitions below supplement those in the art and are directed to the embodiments described in the current application.

The term "antibody" is used herein in the broadest sense and specifically encompasses at least monoclonal antibodies, polyclonal antibodies, multi-specific antibodies (e.g., bispecific antibodies), chimeric antibodies, humanized antibodies, human antibodies, and antibody fragments. An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes.

"Antibody fragments" comprise a portion of an intact antibody, for example, one or more portions of the antigen-binding region thereof. Examples of antibody fragments include Fab, Fab', F(ab')$_2$, and Fv fragments, diabodies, linear antibodies, single-chain antibodies, and multi-specific antibodies formed from intact antibodies and antibody fragments.

An "intact antibody" is one comprising full-length heavy- and light-chains and an Fc region. An intact antibody is also referred to as a "full-length, heterodimeric" antibody or immunoglobulin.

The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable" regions or "complementarity determining regions" (CDRs). The more conserved (i.e., non-hypervariable) portions of the variable domains are called the "framework" regions (FRM). The variable domains of naturally occurring heavy and light chains each comprise four FRM regions, largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding site (see Kabat et al. Sequences of Proteins of Immunological Interest, 5th Ed. Public Health Service, National Institutes of Health, Bethesda, Md., 1991, incorporated by reference in its entirety). The constant domains are not directly involved in antigen binding, but exhibit various effector functions, such as, for example, antibody-dependent, cell-mediated cytotoxicity and complement activation.

The "chassis" of the invention represent a portion of the antibody heavy chain variable (IGHV) or light chain variable (IGLV) domains that are not part of CDRH3 or CDRL3, respectively. The chassis of the invention is defined as the portion of the variable region of an antibody beginning with the first amino acid of FRM1 and ending with the last amino acid of FRM3. In the case of the heavy chain, the chassis includes the amino acids including from about Kabat position 1 to about Kabat position 94. In the case of the light chains (kappa and lambda), the chassis are defined as including from about Kabat position 1 to about Kabat position 88. The chassis of the invention may contain certain modifications relative to the corresponding germline variable domain sequences presented herein or available in public databases. These modifications may be engineered (e.g., to remove N-linked glycosylation sites) or naturally occurring (e.g., to account for allelic variation). For example, it is known in the art that the immunoglobulin gene repertoire is polymorphic (Wang et al., Immunol. Cell. Biol., 2008, 86: 111; Collins et al., Immunogenetics, 2008, DOI 10.1007/s00251-008-0325-z, published online, each incorporated by reference in its entirety); chassis, CDRs (e.g., CDRH3) and constant regions representative of these allelic variants are also encompassed by the invention. In some embodiments, the allelic variant(s) used in a particular embodiment of the invention may be selected based on the allelic variation present in different patient populations, for example, to identify antibodies that are non-immunogenic in these patient populations. In certain embodiments, the immunogenicity of an antibody of the invention may depend on allelic variation in the major histocompatibility complex (MHC) genes of a patient population. Such allelic variation may also be considered in the design of libraries of the invention. In certain embodiments of the invention, the chassis and constant regions are contained on a vector, and a CDR3 region is introduced between them via homologous recombination.

In some embodiments, one, two or three nucleotides may follow the heavy chain chassis, forming either a partial (if one or two) or a complete (if three) codon. When a full codon is present, these nucleotides encode an amino acid residue that is referred to as the "tail," and occupies position 95.

The "CDRH3 numbering system" used herein defines the first amino acid of CDRH3 as being at Kabat position 95 (the "tail," when present) and the last amino acid of CDRH3 as position 102. The amino acids following the "tail" are called "N1" and, when present, are assigned numbers 96, 96A, 96B, etc. The N1 segment is followed by the "DH" segment, which is assigned numbers 97, 97A, 97B, 97C, etc. The DH segment is followed by the "N2" segment, which, when present, is numbered 98, 98A, 98B, etc. Finally, the most C-terminal amino acid residue of the set of the "H3-JH" segment is designated as number 102. The residue directly before (N-terminal) it, when present, is 101, and the one before (if present) is 100. For reasons of convenience, and which will become apparent elsewhere, the rest of the H3-JH amino acids are numbered in reverse order, beginning with 99 for the amino acid just N-terminal to 100, 99A for the residue N-terminal to 99, and so forth for 99B, 99C, etc. Examples of certain CDRH3 sequence residue numbers may therefore include the following:

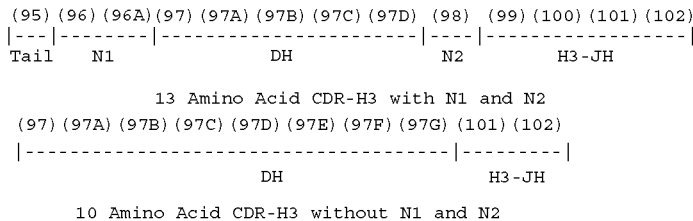

```
(95) (96)(96A)(97) (97A) (97B) (97C) (97D)  (98)   (99)(100)(101)(102)
|---|--------|------------------------|----|------------------|
Tail   N1              DH                N2         H3-JH 13 Amino Acid CDR-H3 with N1 and N2
(97)(97A)(97B)(97C)(97D)(97E)(97F)(97G) (101)(102)
|---------------------------------------|---------|
                   DH                      H3-JH 10 Amino Acid CDR-H3 without N1 and N2
```

As used herein, the term "diversity" refers to a variety or a noticeable heterogeneity. The term "sequence diversity" refers to a variety of sequences which are collectively representative of several possibilities of sequences, for example, those found in natural human antibodies. For example, heavy chain CDR3 (CDRH3) sequence diversity may refer to a variety of possibilities of combining the known human DH and H3-JH segments, including the N1 and N2 regions, to form heavy chain CDR3 sequences. The light chain CDR3 (CDRL3) sequence diversity may refer to a variety of possibilities of combining the naturally occurring light chain variable region contributing to CDRL3 (i.e., L3-VL) and joining (i.e., L3-JL) segments, to form light chain CDR3 sequences. As used herein, H3-JH refers to the portion of the IGHJ gene contributing to CDRH3. As used herein, L3-VL and L3-JL refer to the portions of the IGLV and IGLJ genes (kappa or lambda) contributing to CDRL3, respectively.

As used herein, the term "expression" includes any step involved in the production of a polypeptide including, but not limited to, transcription, post-transcriptional modification, translation, post-translational modification, and secretion.

As used herein, the term "host cell" is intended to refer to a cell into which a polynucleotide of the invention. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "length diversity" refers to a variety in the length of a particular nucleotide or amino acid sequence. For example, in naturally occurring human antibodies, the heavy chain CDR3 sequence varies in length, for example, from about 3 amino acids to over about 35 amino acids, and the light chain CDR3 sequence varies in length, for example, from about 5 to about 16 amino acids. Prior to the instant invention, it was known in the art that it is possible to design antibody libraries containing sequence diversity or length diversity (see, e.g., Hoet et al., Nat. Biotechnol., 2005, 23: 344; Kretzschmar and von Ruden, Curr. Opin. Biotechnol., 2002 13: 598; and Rauchenberger et al., J. Biol. Chem., 2003 278: 38194, each of which is incorporated by reference in its entirety); however, the instant invention is directed to, at least, the design of synthetic antibody libraries containing the sequence diversity and length diversity of naturally occurring human sequences. In some cases, synthetic libraries containing sequence and length diversity have been synthesized, however these libraries contain too much theoretical diversity to synthesize the entire designed repertoire and/or too many theoretical members to physically realize or oversample the entire library.

As used herein, a sequence designed with "directed diversity" has been specifically designed to contain both sequence diversity and length diversity. Directed diversity is not stochastic.

As used herein, "stochastic" describes a process of generating a randomly determined sequence of amino acids, which is considered as a sample of one element from a probability distribution.

The term "library of polynucleotides" refers to two or more polynucleotides having a diversity as described herein, specifically designed according to the methods of the invention. The term "library of polypeptides" refers to two or more polypeptides having a diversity as described herein, specifically designed according to the methods of the invention. The term "library of synthetic polynucleotides" refers to a polynucleotide library that includes synthetic polynucleotides. The term "library of vectors" refers herein to a library of at least two different vectors. As used herein, the term "human antibody libraries," at least includes, a polynucleotide or polypeptide library which has been designed to represent the sequence diversity and length diversity of naturally occurring human antibodies.

As described throughout the specification, the term "library" is used herein in its broadest sense, and also may include the sub-libraries that may or may not be combined to produce libraries of the invention.

As used herein, the term "synthetic polynucleotide" refers to a molecule formed through a chemical process, as opposed to molecules of natural origin, or molecules derived via template-based amplification of molecules of natural origin (e.g., immunoglobulin chains cloned from populations of B cells via PCR amplification are not "synthetic" used herein). In some instances, for example, when referring to libraries of the invention that comprise multiple components (e.g., N1, DH, N2, and/or H3-JH), the invention encompasses libraries in which at least one of the aforementioned components is synthetic. By way of illustration, a library in which certain components are synthetic, while other components are of natural origin or derived via template-based amplification of molecules of natural origin, would be encompassed by the invention.

The term "split-pool synthesis" refers to a procedure in which the products of a plurality of first reactions are combined (pooled) and then separated (split) before participating in a plurality of second reactions. Example 9, describes the synthesis of 278 DH segments (products), each in a separate reaction. After synthesis, these 278 segments are combined (pooled) and then distributed (split) amongst 141 columns for the synthesis of the N2 segments. This enables the pairing of each of the 278 DH segments with each of the 141 N2 segments. As described elsewhere in the specification, these numbers are non-limiting.

"Preimmune" antibody libraries have similar sequence diversities and length diversities to naturally occurring human antibody sequences before these sequences have undergone negative selection or somatic hypermutation. For example, the set of sequences described in Lee et al. (Immunogenetics, 2006, 57: 917, incorporated by reference in its entirety) is believed to represent sequences from the preimmune repertoire. In certain embodiments of the invention, the sequences of the invention will be similar to these sequences (e.g., in terms of composition and length). In certain embodiments of the invention, such antibody libraries are designed to be small enough to chemically synthesize and physically realize, but large enough to encode antibodies with the potential to recognize any antigen. In one embodiment of the invention, an antibody library comprises about $10^7$ to about $10^{20}$ different antibodies and/or polynucleotide sequences encoding the antibodies of the library. In some embodiments, the libraries of the instant invention are designed to include $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or $10^{20}$ different antibodies and/or polynucleotide sequences encoding the antibodies. In certain embodiments, the libraries of the invention may comprise or encode about $10^3$ to about $10^5$, about $10^5$ to about $10^7$, about $10^7$ to about $10^9$, about $10^9$ to about $10^{11}$, about $10^{11}$ to about $10^{13}$, about $10^{13}$ to about $10^{15}$, about $10^{15}$ to about $10^{17}$, or about $10^{17}$ to about $10^{20}$ different antibodies. In certain embodiments of the invention, the diversity of the libraries may be characterized as being greater than or less than one or more of the diversities enumerated above, for example greater than about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or, $10^{20}$ or less than about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or $10^{20}$. In certain other embodiments of the invention, the probability of an antibody of interest being present in a physical realization of a library with a size as enumerated above is at least about 0.0001%, 0.001%, 0.01%, 0.1%, 1%, 5%, 10%, 20%, 30%, 40%, 50%, 60%, 70%, 80%, 85%, 90%, 95%, 99%, 99.5%, or 99.9% (see Library Sampling, in the Detailed Description, for more information on the probability of a particular sequence being present in a physical realization of a library). The antibody libraries of the invention may also include antibodies directed to, for example, self (i.e., human) antigens. The antibodies of the present invention may not be present in expressed human libraries for reasons including because self-reactive antibodies are removed by the donor's immune system via negative selection. However, novel heavy/light chain pairings may in some cases create self-reactive antibody specificity (Griffiths et al. U.S. Pat. No. 5,885,793, incorporated by reference in its entirety). In certain embodiments of the invention, the number of unique heavy chains in a library may be about 10, 50, $10^2$, 150, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, or more. In certain embodiments of the invention, the number of unique light chains in a library may be about 5, 10, 25, 50, $10^2$, 150, 500, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, or more.

As used herein, the term "human antibody CDRH3 libraries," at least includes, a polynucleotide or polypeptide library which has been designed to represent the sequence diversity and length diversity of naturally occurring human antibodies. "Preimmune" CDRH3 libraries have similar sequence diversities and length diversities to naturally occurring human antibody CDRH3 sequences before these sequences undergo negative selection and somatic hypermutation. Known human CDRH3 sequences are represented in various data sets, including Jackson et al., J. Immunol. Methods, 2007, 324: 26; Martin, Proteins, 1996, 25: 130; and Lee et al., Immunogenetics, 2006, 57: 917, each of which is incorporated by reference in its entirety. In certain embodiments of the invention, such CDRH3 libraries are designed to be small enough to chemically synthesize and physically realize, but large enough to encode CDRH3s with the potential to recognize any antigen. In one embodiment of the invention, an antibody library includes about $10^6$ to about $10^{15}$ different CDRH3 sequences and/or polynucleotide sequences encoding said CDRH3 sequences. In some embodiments, the libraries of the instant invention are designed to about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or $10^{16}$, different CDRH3 sequences and/or polynucleotide sequences encoding said CDRH3 sequences. In some embodiments, the libraries of the invention may include or encode about $10^3$ to about $10^6$, about $10^6$ to about $10^8$, about $10^8$ to about $10^{10}$, about $10^{10}$ to about $10^{12}$, about $10^{12}$ to about $10^{14}$, or about $10^{14}$ to about $10^{16}$ different CDRH3 sequences. In certain embodiments of the invention, the diversity of the libraries may be characterized as being greater than or less than one or more of the diversities enumerated above, for example greater than about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or $10^{16}$ or less than about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$ or $10^{16}$. In certain embodiments of the invention, the probability of a CDRH3 of interest being present in a physical realization of a library with a size as enumerated above is at least about 0.0001%, 0.001%, 0.01%, 0.1%, 1%, 2%, 3%, 4%, 5%, 6%, 7%, 8%, 9%, 10%, 15%, 20%, 25%, 30%, 40%, 50%, 60%, 70%, 80%, 85%, 90%, 95%, 99%, 99.5%, or 99.9% (see Library Sampling, in the Detailed Description, for more information on the probability of a particular sequence being present in a physical realization of a library). The preimmune CDRH3 libraries of the invention may also include CDRH3s directed to, for example, self (i.e., human) antigens. Such CDRH3s may not be present in expressed human libraries, because self-reactive CDRH3s are removed by the donor's immune system via negative selection.

Libraries of the invention containing "VKCDR3" sequences and "VλCDR3" sequences refer to the kappa and lambda sub-sets of the CDRL3 sequences, respectively. These libraries may be designed with directed diversity, to collectively represent the length and sequence diversity of the human antibody CDRL3 repertoire. "Preimmune" versions of these libraries have similar sequence diversities and length diversities to naturally occurring human antibody CDRL3 sequences before these sequences undergo negative selection. Known human CDRL3 sequences are represented in various data sets, including the NCBI database (see Appendix A and Appendix B for light chain sequence data sets) and Martin, Proteins, 1996, 25: 130 incorporated by reference in its entirety. In certain embodiments of the invention, such CDRL3 libraries are designed to be small enough to chemically synthesize and physically realize, but large enough to encode CDRL3s with the potential to recognize any antigen.

In one embodiment of the invention, an antibody library comprises about $10^5$ different CDRL3 sequences and/or polynucleotide sequences encoding said CDRL3 sequences. In some embodiments, the libraries of the instant invention are designed to comprise about $10^1$, $10^2$, $10^3$, $10^4$, $10^6$, $10^7$, or $10^8$ different CDRL3 sequences and/or polynucleotide sequences encoding said CDRL3 sequences. In some embodiments, the libraries of the invention may comprise or encode about $10^1$ to about $10^3$, about $10^3$ to about $10^5$, or about $10^5$ to about $10^8$ different CDRL3 sequences. In certain embodiments of the invention, the diversity of the libraries may be characterized as being greater than or less than one or more of the diversities enumerated above, for example greater than about $10^1$, $10^2$, $10^3$, $10^4$, $10^5$, $10^6$, $10^7$, or $10^8$ or less than about $10^1$, $10^2$, $10^3$, $10^4$, $10^5$, $10^6$, $10^7$, or $10^8$. In certain embodiments of the invention, the probability of a CDRL3 of interest being present in a physical realization of a library with a size as enumerated above is at least about 0.0001%, 0.001%, 0.01%, 0.1%, 1%, 5%, 10%, 20%, 30%, 40%, 50%, 60%, 70%, 80%, 85%, 90%, 95%, 99%, 99.5%, or 99.9% (see Library Sampling, in the Detailed Description, for more information on the probability of a particular sequence being present in a physical realization of a library). The preimmune CDRL3 libraries of the invention may also include CDRL3s directed to, for example, self (i.e., human) antigens. Such CDRL3s may not be present in expressed human libraries, because self-reactive CDRL3s are removed by the donor's immune system via negative selection.

As used herein, the term "known heavy chain CDR3 sequences" refers to heavy chain CDR3 sequences in the public domain that have been cloned from populations of human B cells. Examples of such sequences are those published or derived from public data sets, including, for example, Zemlin et al., JMB, 2003, 334: 733; Lee et al., Immunogenetics, 2006, 57: 917; and Jackson et al. J. Immunol. Methods, 2007, 324: 26, each of which are incorporated by reference in their entirety.

As used herein, the term "known light chain CDR3 sequences" refers to light chain CDR3 sequences (e.g., kappa or lambda) in the public domain that have been cloned from populations of human B cells. Examples of such sequences are those published or derived from public data sets, including, for example, the NCBI database (see Appendices A and B filed herewith).

As used herein the term "antibody binding regions" refers to one or more portions of an immunoglobulin or antibody variable region capable of binding an antigen(s). Typically, the antibody binding region is, for example, an antibody light chain (or variable region or one or more CDRs thereof), an antibody heavy chain (or variable region or one or more CDRs thereof), a heavy chain Fd region, a combined antibody light and heavy chain (or variable regions thereof) such as a Fab, F(ab')$_2$, single domain, or single chain antibodies (scFv), or any region of a full length antibody that recognizes an antigen, for example, an IgG (e.g., an IgG1, IgG2, IgG3, or IgG4 subtype), IgA1, IgA2, IgD, IgE, or IgM antibody.

The term "framework region" refers to the art-recognized portions of an antibody variable region that exist between the more divergent (i.e., hypervariable) CDRs. Such framework regions are typically referred to as frameworks 1 through 4 (FRM1, FRM2, FRM3, and FRM4) and provide a scaffold for the presentation of the six CDRs (three from the heavy chain and three from the light chain) in three dimensional space, to form an antigen-binding surface.

The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al., Nature, 1989, 342: 877; Martin and Thornton, J. Mol. Biol., 1996, 263: 800, each of which is incorporated by reference in its entirety). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues. The term "canonical structure" may also include considerations as to the linear sequence of the antibody, for example, as catalogued by Kabat (Kabat et al., in "Sequences of Proteins of Immunological Interest," 5$^{th}$ Edition, U.S. Department of Heath and Human Services, 1992). The Kabat numbering scheme is a widely adopted standard for numbering the amino acid residues of an antibody variable domain in a consistent manner. Additional structural considerations can also be used to determine the canonical structure of an antibody. For example, those differences not fully reflected by Kabat numbering can be described by the numbering system of Chothia et al. and/or revealed by other techniques, for example, crystallography and two or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al., and their implications for construing canonical aspects of antibody structure, are described in the literature.

The terms "CDR", and its plural "CDRs", refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions, including the numbering system described herein. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum et al., (Kabat et al., in "Sequences of Proteins of Immunological Interest," 5$^{th}$ Edition, U.S. Department of Health and Human Services, 1992; Chothia et al., J. Mol. Biol., 1987, 196: 901; and MacCallum et al., J. Mol. Biol., 1996, 262: 732, each of which is incorporated by reference in its entirety).

The term "amino acid" or "amino acid residue" typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (H is or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a nonpolar side chain (e.g., Ala, Cys, Ile, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gln, Gly, His, Met, Phe, Ser, Thr, Trp, and Tyr).

The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides may be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety.

The terms "theoretical diversity", "theoretical total diversity", or "theoretical repertoire" refer to the maximum number of variants in a library design. For example, given an amino acid sequence of three residues, where residues one and three may each be any one of five amino acid types and residue two may be any one of 20 amino acid types, the theoretical diversity is 5×20×5=500 possible sequences. Similarly if sequence X is constructed by combination of 4 amino acid segments, where segment 1 has 100 possible sequences, segment 2 has 75 possible sequences, segment 3 has 250 possible sequences, and segment 4 has 30 possible sequences, the theoretical total diversity of fragment X would be 100×75×200×30, or $5.6×10^5$ possible sequences.

The term "physical realization" refers to a portion of the theoretical diversity that can actually be physically sampled, for example, by any display methodology. Exemplary display methodology include: phage display, ribosomal display, and yeast display. For synthetic sequences, the size of the physical realization of a library depends on (1) the fraction of the theoretical diversity that can actually be synthesized, and (2) the limitations of the particular screening method. Exemplary limitations of screening methods include the number of variants that can be screened in a particular assay (e.g., ribosome display, phage display, yeast display) and the transformation efficiency of a host cell (e.g., yeast, mammalian cells, bacteria) which is used in a screening assay. For the purposes of illustration, given a library with a theoretical diversity of $10^{12}$ members, an exemplary physical realization of the library (e.g., in yeast, bacterial cells, ribosome display, etc.; details provided below) that can maximally include $10^{11}$ members will, therefore, sample about 10% of the theoretical diversity of the library. However, if less than $10^{11}$ members of the library with a theoretical diversity of $10^{12}$ are synthesized, and the physical realization of the library can maximally include $10^{11}$ members, less than 10% of the theoretical diversity of the library is sampled in the physical realization of the library. Similarly, a physical realization of the library that can maximally include more than $10^{12}$ members would "oversample" the theoretical diversity, meaning that each member may be present more than once (assuming that the entire $10^{12}$ theoretical diversity is synthesized).

The term "all possible reading frames" encompasses at least the three forward reading frames and, in some embodiments, the three reverse reading frames.

The term "antibody of interest" refers to any antibody that has a property of interest that is isolated from a library of the invention. The property of interest may include, but is not limited to, binding to a particular antigen or epitope, blocking a binding interaction between two molecules, or eliciting a certain biological effect.

The term "functionally expressed" refers to those immunoglobulin genes that are expressed by human B cells and that do not contain premature stop codons.

The term "full-length heavy chain" refers to an immunoglobulin heavy chain that contains each of the canonical structural domains of an immunoglobulin heavy chain, including the four framework regions, the three CDRs, and the constant region. The term "full-length light chain" refers to an immunoglobulin light chain that contains each of the canonical structural domains of an immunoglobulin light chain, including the four framework regions, the three CDRs, and the constant region.

The term "unique," as used herein, refers to a sequence that is different (e.g. has a different chemical structure) from every other sequence within the designed theoretical diversity. It should be understood that there are likely to be more than one copy of many unique sequences from the theoretical diversity in a particular physical realization. For example, a library comprising three unique sequences may comprise nine total members if each sequence occurs three times in the library. However, in certain embodiments, each unique sequence may occur only once.

The term "heterologous moiety" is used herein to indicate the addition of a composition to an antibody wherein the composition is not normally part of the antibody. Exemplary heterologous moieties include drugs, toxins, imaging agents, and any other compositions which might provide an activity that is not inherent in the antibody itself.

As used herein, the term "percent occurrence of each amino acid residue at each position" refers to the percentage of instances in a sample in which an amino acid is found at a defined position within a particular sequence. For example, given the following three sequences:
K V R
K Y P
K R P,
K occurs in position one in 100% of the instances and P occurs in position three in about 67% of the instances. In certain embodiments of the invention, the sequences selected for comparison are human immunoglobulin sequences.

As used herein, the term "most frequently occurring amino acids" at a specified position of a sequence in a population of polypeptides refers to the amino acid residues that have the highest percent occurrence at the indicated position in the indicated polypeptide population. For example, the most frequently occurring amino acids in each of the three most N-terminal positions in N1 sequences of CDRH3 sequences that are functionally expressed by human B cells are listed in Table 21, and the most frequently occurring amino acids in each of the three most N-terminal positions in N2 sequences of CDRH3 sequences that are functionally expressed by human B cells are listed in Table 22.

For the purposes of analyzing the occurrence of certain duplets (Example 13) and the information content (Example 14) of the libraries of the invention, and other libraries, a "central loop" of CDRH3 is defined. If the C-terminal 5 amino acids from Kabat CDRH3 (95-102) are removed, then the remaining sequence is termed the "central loop". Thus, considering the duplet occurrence calculations of Example 13, using a CDRH3 of size 6 or less would not contribute to the analysis of the occurrence of duplets. A CDRH3 of size 7 would contribute only to the i-i+1 data set, a CDRH3 of size 8 would also contribute to the i-i+2 data set, and a CDRH3 of size 9 and larger would also contribute to the i-i+3 data set. For example, a CDR H3 of size 9 may have amino acids at positions 95-96-97-98-99-100-100A-101-102, but only the first four residues (bolded) would be part of the central loop and contribute to the pair-wise occurrence (duplet) statistics. As a further example, a CDRH3 of size 14 may have the sequence: 95-96-97-98-99-100-100A-100B-100C-100D-100E-100F-101-102. Here, only the first nine residues (bolded) contribute to the central loop.

Library screening requires a genotype-phenotype linkage. The term "genotype-phenotype linkage" is used in a manner consistent with its art-recognized meaning and refers to the fact that the nucleic acid (genotype) encoding a protein with a particular phenotype (e.g., binding an antigen) can be isolated from a library. For the purposes of illustration, an antibody fragment expressed on the surface of a phage can be isolated based on its binding to an antigen (e.g., Ladner et al.). The binding of the antibody to the antigen simultaneously enables the isolation of the phage containing the nucleic acid encoding the antibody fragment. Thus, the phenotype (antigen-binding characteristics of the antibody fragment) has been "linked" to the genotype (nucleic acid encoding the antibody fragment). Other methods of maintaining a genotype-phenotype linkage include those of Wittrup et al. (U.S. Pat. Nos. 6,300,065, 6,331,391, 6,423,538, 6,696,251, 6,699,658, and US Pub. No. 20040146976, each of which is incorporated by reference in its entirety), Miltenyi (U.S. Pat. No. 7,166,423, incorporated by reference in its entirety), Fandl (U.S. Pat. No. 6,919,183, US Pub No. 20060234311, each incorporated by reference in its entirety), Clausell-Tormos et al. (Chem. Biol., 2008, 15: 427, incorporated by reference in its entirety), Love et al. (Nat. Biotechnol., 2006, 24: 703, incorporated by reference in its entirety), and Kelly et al. (Chem. Commun., 2007, 14: 1773, incorporated by reference in its entirety). Any method which localizes the antibody protein with the gene encoding the antibody, in a way in which they can both be recovered while the linkage between them is maintained, is suitable.

2. Design of the Libraries

The antibody libraries of the invention are designed to reflect certain aspects of the preimmune repertoire as naturally created by the human immune system. Certain libraries of the invention are based on rational design informed by the collection of human V, D, and J genes, and other large databases of human heavy and light chain sequences (e.g., publicly known germline sequences; sequences from Jackson et al., J. Immunol. Methods, 2007, 324: 26, incorporated by reference in its entirety; sequences from Lee et al., Immunogenetics, 2006, 57: 917, incorporated by reference in its entirety; and sequences compiled for rearranged VK and Vλ—see Appendices A and B filed herewith). Additional information may be found, for example, in Scaviner et al., Exp. Clin. Immunogenet., 1999, 16: 234; Tomlinson et al., J. Mol. Biol., 1992, 227: 799; and Matsuda et al., J. Exp. Med., 1998, 188: 2151 each incorporated by reference in its entirety. In certain embodiments of the invention, cassettes representing the possible V, D, and J diversity found in the human repertoire, as well as junctional diversity (i.e., N1 and N2), are synthesized de novo as single or double-stranded DNA oligonucleotides. In certain embodiments of the invention, oligonucleotide cassettes encoding CDR sequences are introduced into yeast along with one or more acceptor vectors containing heavy or light chain chassis sequences. No primer-based PCR amplification or template-directed cloning steps from mammalian cDNA or mRNA are employed. Through standard homologous recombination, the recipient yeast recombines the cassettes (e.g., CDR3s) with the acceptor vector(s) containing the chassis sequence(s) and constant regions, to create a properly ordered synthetic, full-length human heavy chain and/or light chain immunoglobulin library that can be genetically propagated, expressed, displayed, and screened. One of ordinary skill in the art will readily recognize that the chassis contained in the acceptor vector can be designed so as to produce constructs other than full-length human heavy chains and/or light chains. For example, in certain embodiments of the invention, the chassis may be designed to encode portions of a polypeptide encoding an antibody fragment or subunit of an antibody fragment, so that a sequence encoding an antibody fragment, or subunit thereof, is produced when the oligonucleotide cassette containing the CDR is recombined with the acceptor vector.

In certain embodiments, the invention provides a synthetic, preimmune human antibody repertoire comprising about $10^7$ to about $10^{20}$ antibody members, wherein the repertoire comprises:

(a) selected human antibody heavy chain chassis (i.e., amino acids 1 to 94 of the heavy chain variable region, using Kabat's definition);

(b) a CDRH3 repertoire, designed based on the human IGHD and IGHJ germline sequences, the CDRH3 repertoire comprising the following:
  (i) optionally, one or more tail regions;
  (ii) one or more N1 regions, comprising about 0 to about 10 amino acids selected from the group consisting of fewer than 20 of the amino acid types preferentially encoded by the action of terminal deoxynucleotidyl transferase (TdT) and functionally expressed by human B cells;
  (iii) one or DH segments, based on one or more selected IGHD segments, and one or more N- or C-terminal truncations thereof;
  (iv) one or more N2 regions, comprising about 0 to about 10 amino acids selected from the group consisting of fewer than 20 of the amino acids preferentially encoded by the activity of TdT and functionally expressed by human B cells; and
  (v) one or more H3-JH segments, based on one or more IGHJ segments, and one or more N-terminal truncations thereof (e.g., down to XXWG);

(c) one or more selected human antibody kappa and/or lambda light chain chassis; and (d) a CDRL3 repertoire designed based on the human IGLV and IGLJ germline sequences, wherein "L" may be a kappa or lambda light chain.

The heavy chain chassis may be any sequence with homology to Kabat residues 1 to 94 of an immunoglobulin heavy chain variable domain. Non-limiting examples of heavy chain chassis are included in the Examples, and one of ordinary skill in the art will readily recognize that the principles presented therein, and throughout the specification, may be used to derive additional heavy chain chassis.

As described above, the heavy chain chassis region is followed, optionally, by a "tail" region. The tail region comprises zero, one, or more amino acids that may or may not be selected on the basis of comparing naturally occurring heavy chain sequences. For example, in certain embodiments of the invention, heavy chain sequences available in the art may be compared, and the residues occurring most frequently in the tail position in the naturally occurring sequences included in the library (e.g., to produce sequences that most closely resemble human sequences). In other embodiments, amino acids that are used less frequently may be used. In still other embodiments, amino acids selected from any group of amino acids may be used. In certain embodiments of the invention, the length of the tail is zero (no residue) or one (e.g., G/D/E) amino acid. For the purposes of clarity, and without being bound by theory, in the naturally occurring human repertoire, the first ⅔ of the codon encoding the tail residue is provided by the FRM3 region of the VH gene. The amino acid at this position in naturally occurring heavy chain sequences may thus be considered to be partially encoded by the IGHV gene (⅔) and partially encoded by the CDRH3 (⅓). However, for the purposes of clearly illustrating certain aspects of the invention, the entire codon encoding the tail residue (and, therefore, the amino acid derived from it) is described herein as being part of the CDRH3 sequence.

As described above, there are two peptide segments derived from nucleotides which are added by TdT in the naturally occurring human antibody repertoire. These segments are designated N1 and N2 (referred to herein as N1 and N2 segments, domains, regions or sequences). In certain embodiments of the invention, N1 and N2 are about 0, 1, 2, or 3 amino acids in length. Without being bound by theory, it is thought that these lengths most closely mimic the N1 and N2 lengths found in the human repertoire (see FIG. 2). In other embodiments of the invention, N1 and N2 may be about 4, 5, 6, 7, 8, 9, or 10 amino acids in length. Similarly, the composition of the amino acid residues utilized to produce the N1 and N2 segments may also vary. In certain embodiments of the invention, the amino acids used to produce N1 and N2 segments may be selected from amongst the eight most frequently occurring amino acids in the N1 and N2 domains of the human repertoire (e.g., G, R, S, P, L, A, V, and T). In other embodiments of the invention, the amino acids used to produce the N1 and N2 segments may be selected from the group consisting of fewer than about 20, 19, 18, 17, 16, 15, 14, 13, 12, 11, 10, 9, 8, 7, 6, 5, 4, or 3 of the amino acids preferentially encoded by the activity of TdT and functionally expressed by human B cells. Alternatively, N1 and N2 may comprise amino acids selected from any group of amino acids. It is not required that N1 and N2 be of a similar length or composition, and independent variation of the length and composition of N1 and N2 is one method by which additional diversity may be introduced into the library.

The DH segments of the libraries are based on the peptides encoded by the naturally occurring IGHD gene repertoire, with progressive deletion of residues at the N- and C-termini IGHD genes may be read in multiple reading frames, and peptides representing these reading frames, and their N- and C-terminal deletions are also included in the libraries of the invention. In certain embodiments of the invention, DH segments as short as three amino acid residues may be included in the libraries. In other embodiments of the invention, DH segments as short as about 1, 2, 4, 5, 6, 7, or 8 amino acids may be included in the libraries.

The H3-JH segments of the libraries are based on the peptides encoded by the naturally occurring IGHJ gene repertoire, with progressive deletion of residues at the N-terminus. The N-terminal portion of the IGHJ segment that makes up part of the CDRH3 is referred to herein as H3-JH. In certain embodiments of the invention, the H3-JH segment may be represented by progressive N-terminal deletions of one or more H3-JH residues, down to two H3-JH residues. In other embodiments of the invention, the H3-JH segments of the library may contain N-terminal deletions (or no deletions) down to about 6, 5, 4, 3, 2, 1, or 0 H3-JH residues.

The light chain chassis of the libraries may be any sequence with homology to Kabat residues 1 to 88 of naturally occurring light chain (κ or 2) sequences. In certain embodiments of the invention, the light chain chassis of the invention are synthesized in combinatorial fashion, utilizing VL and JL segments, to produce one or more libraries of light chain sequences with diversity in the chassis and CDR3 sequences. In other embodiments of the invention, the light chain CDR3 sequences are synthesized using degenerate oligonucleotides or trinucleotides and recombined with the light chain chassis and light chain constant region, to form full-length light chains.

The instant invention also provides methods for producing and using such libraries, as well as libraries comprising one or more immunoglobulin domains or antibody fragments. Design and synthesis of each component of the claimed antibody libraries is provided in more detail below.

2.1. Design of the Antibody Library Chassis Sequences

One step in building certain libraries of the invention is the selection of chassis sequences, which are based on naturally occurring variable domain sequences (e.g., IGHV and IGLV). This selection can be done arbitrarily, or by the selection of chassis that meet certain criteria. For example, the Kabat database, an electronic database containing non-redundant rearranged antibody sequences, can be queried for those heavy and light chain germline sequences that are most frequently represented. The BLAST search algorithm, or more specialized tools such as SoDA (Volpe et al., Bioinformatics, 2006, 22: 438-44, incorporated by reference in its entirety), can be used to compare rearranged antibody sequences with germline sequences, using the V BASE2 database (Retter et al., Nucleic Acids Res., 2005, 33: D671-D674), or similar collections of human V, D, and J genes, to identify the germline families that are most frequently used to generate functional antibodies.

Several criteria can be utilized for the selection of chassis for inclusion in the libraries of the invention. For example, sequences that are known (or have been determined) to express poorly in yeast, or other organisms used in the invention (e.g., bacteria, mammalian cells, fungi, or plants) can be excluded from the libraries. Chassis may also be chosen based on their representation in the peripheral blood of humans. In certain embodiments of the invention, it may be desirable to select chassis that correspond to germline sequences that are highly represented in the peripheral blood of humans. In other embodiments, it may be desirable to select chassis that correspond to germline sequences that are less frequently represented, for example, to increase the canonical diversity of the library. Therefore, chassis may be selected to produce libraries that represent the largest and most structurally diverse group of functional human antibodies. In other embodiments of the invention, less diverse chassis may be utilized, for example, if it is desirable to produce a smaller, more focused library with less chassis variability and greater CDR variability. In some embodiments of the invention, chassis may be selected based on both their expression in a cell of the invention (e.g., a yeast cell) and the diversity of canonical structures represented by the selected sequences. One may therefore produce a library with a diversity of canonical structures that express well in a cell of the invention.

2.1.1. Design of the Heavy Chain Chassis Sequences

In certain embodiments of the invention, the antibody library comprises variable heavy domains and variable light domains, or portions thereof. Each of these domains is built from certain components, which will be more fully described in the examples provided herein. In certain embodiments, the libraries described herein may be used to isolate fully human antibodies that can be used as diagnostics and/or therapeutics. Without being bound by theory, antibodies with sequences most similar or identical to those most frequently found in peripheral blood (for example, in humans) may be less likely to be immunogenic when administered as therapeutic agents.

Without being bound by theory, and for the purposes of illustrating certain embodiments of the invention, the VH domains of the library may be considered to comprise three primary components: (1) a VH "chassis", which includes amino acids 1 to 94 (using Kabat numbering), (2) the CDRH3, which is defined herein to include the Kabat CDRH3 proper (positions 95-102), and (3) the FRM4 region, including amino acids 103 to 113 (Kabat numbering). The overall VH structure may therefore be depicted schematically (not to scale) as:

The selection and design of VH chassis sequences based on the human IGHV germline repertoire will become more apparent upon review of the examples provided herein. In certain embodiments of the invention, the VH chassis sequences selected for use in the library may correspond to all functionally expressed human IGHV germline sequences. Alternatively, IGHV germline sequences may be selected for representation in a library according to one or more criteria. For example, in certain embodiments of the invention, the selected IGHV germline sequences may be among those that are most highly represented among antibody molecules isolated from the peripheral blood of healthy adults, children, or fetuses.

In certain embodiments, it may be desirable to base the design of the VH chassis on the utilization of IGHV germline sequences in adults, children, or fetuses with a disease, for example, an autoimmune disease. Without being bound by theory, it is possible that analysis of germline sequence usage in the antibody molecules isolated from the peripheral blood of individuals with autoimmune disease may provide information useful for the design of antibodies recognizing human antigens.

In some embodiments, the selection of IGHV germline sequences for representation in a library of the invention may be based on their frequency of occurrence in the peripheral blood. For the purposes of illustration, four IGHV1 germline sequences (IGHV1-2 (SEQ ID NO: 24), IGHV1-18 (SEQ ID NO: 25), IGHV1-46 (SEQ ID NO: 26), and IGHV1-69 (SEQ ID NO: 27)) comprise about 80% of the IGHV1 family repertoire in peripheral blood. Thus, the specific IGHV1 germline sequences selected for representation in the library may include those that are most frequently occurring and that cumulatively comprise at least about 80% of the IGHV1 family repertoire found in peripheral blood. An analogous approach can be used to select specific IGHV germline sequences from any other IGHV family (i.e., IGHV1, IGHV2, IGHV3, IGHV4, IGHV5, IGHV6, and IGHV7). The specific germline sequences chosen for representation of a particular IGHV family in a library of the invention may therefore comprise at least about 100%, 99%, 98%, 97%, 96% 95%, 94%, 93%, 92%, 91% 90%, 89%, 88%, 87%, 86%, 85%, 84%, 83%, 82%, 81%, 80%, 75%, 70%, 65%, 60%, 55%, 50%, 45%, 40%, 35%, 30%, 25%, 20%, 15%, 10%, 5%, or 0% of the particular IGHV family member repertoire found in peripheral blood.

In some embodiments, the selected IGHV germline sequences may be chosen to maximize the structural diversity of the VH chassis library. Structural diversity may be evaluated by, for example, comparing the lengths, compositions, and canonical structures of CDRH1 and CDRH2 in the IGHV germline sequences. In human IGHV sequences, the CDRH1 (Kabat definition) may have a length of 5, 6 or 7 amino acids, while CDRH2 (Kabat definition) may have length of 16, 17, 18 or 19 amino acids. The amino acid compositions of the IGHV germline sequences and, in particular, the CDR domains, may be evaluated by sequence alignments, as presented in the Examples. Canonical structure may be assigned, for example, according to the methods described by Chothia et al., J. Mol. Biol., 1992, 227: 799, incorporated by reference in its entirety.

In certain embodiments of the invention, it may be advantageous to design VH chassis based on IGHV germline sequences that may maximize the probability of isolating an antibody with particular characteristics. For example, without being bound by theory, in some embodiments it may be advantageous to restrict the IGHV germline sequences to include only those germline sequences that are utilized in antibodies undergoing clinical development, or antibodies that have been approved as therapeutics. On the other hand, in some embodiments, it may be advantageous to produce libraries containing VH chassis that are not represented amongst clinically utilized antibodies. Such libraries may be capable of yielding antibodies with novel properties that are advantageous over those obtained with the use of "typical" IGHV germline sequences, or enabling studies of the structures and properties of "atypical" IGHV germline sequences or canonical structures.

One of ordinary skill in the art will readily recognize that a variety of other criteria can be used to select IGHV germline sequences for representation in a library of the invention. Any of the criteria described herein may also be combined with any other criteria. Further exemplary criteria include the ability to be expressed at sufficient levels in certain cell culture systems, solubility in particular antibody formats (e.g., whole immunoglobulins and antibody fragments), and the thermodynamic stability of the individual domains, whole immunoglobulins, or antibody fragments. The methods of the invention may be applied to select any IGHV germline sequence that has utility in an antibody library of the instant invention.

In certain embodiments of the invention, the VH chassis of the libraries may comprise from about Kabat residue 1 to about Kabat residue 94 of one or more of the following IGHV germline sequences: IGHV1-2 (SEQ ID NO: 24), IGHV1-3 (SEQ ID NO: 423), IGHV1-8 (SEQ ID NO: 424, 425), IGHV1-18 (SEQ ID NO: 25), IGHV1-24 (SEQ ID NO: 426), IGHV1-45 (SEQ ID NO: 427), IGHV1-46 (SEQ ID NO: 26), IGHV1-58 (SEQ ID NO: 428), IGHV1-69 (SEQ ID NO: 27), IGHV2-5 (SEQ ID NO: 429), IGHV2-26 (SEQ ID NO: 430), IGHV2-70 (SEQ ID NO: 431, 432), IGHV3-7 (SEQ ID NO: 28), IGHV3-9 (SEQ ID NO: 433), IGHV3-11 (SEQ ID NO: 434), IGHV3-13 (SEQ ID NO: 435), IGHV3-15 (SEQ ID NO: 29), IGHV3-20 (SEQ ID NO: 436), IGHV3-21 (SEQ ID NO: 437), IGHV3-23 (SEQ ID NO: 30), IGHV3-30 (SEQ ID NO: 31), IGHV3-33 (SEQ ID NO: 32), IGHV3-43 (SEQ ID NO: 438), IGHV3-48 (SEQ ID NO: 33), IGHV3-49 (SEQ ID NO: 439), IGHV3-53 (SEQ ID NO: 440), IGHV3-64 (SEQ ID NO: 441), IGHV3-66 (SEQ ID NO: 442), IGHV3-72 (SEQ ID NO: 443), IGHV3-73 (SEQ ID NO: 444), IGHV3-74 (SEQ ID NO: 445), IGHV4-4 (SEQ ID NO: 446, 447), IGHV4-28 (SEQ ID NO: 448), IGHV4-31 (SEQ ID NO: 34), IGHV4-34 (SEQ ID NO: 35), IGHV4-39 (SEQ ID NO: 36), IGHV4-59 (SEQ ID NO: 37), IGHV4-61 (SEQ ID NO: 38), IGHV4-B (SEQ ID NO: 39), IGHV5-51 (SEQ ID NO: 40), IGHV6-1 (SEQ ID NO: 449), and IGHV7-4-1 (SEQ ID NO: 450). In some embodiments of the invention, a library may contain one or more of these sequences, one or more allelic variants of these sequences, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences.

In other embodiments, the VH chassis of the libraries may comprise from about Kabat residue 1 to about Kabat residue 94 of the following IGHV germline sequences: IGHV1-2 (SEQ ID NO: 24), IGHV1-18 (SEQ ID NO: 25), IGHV1-46 (SEQ ID NO: 26), IGHV1-69 (SEQ ID NO: 27), IGHV3-7 (SEQ ID NO: 28), IGHV3-15 (SEQ ID NO: 29), IGHV3-23 (SEQ ID NO: 30), IGHV3-30 (SEQ ID NO: 31), IGHV3-33 (SEQ ID NO: 32), IGHV3-48 (SEQ ID NO: 33), IGHV4-31 (SEQ ID NO: 34), IGHV4-34 (SEQ ID NO: 35), IGHV4-39 (SEQ ID NO: 36), IGHV4-59 (SEQ ID NO: 37), IGHV4-61 (SEQ ID NO: 38), IGHV4-B (SEQ ID NO: 39), and IGHV5-51 (SEQ ID NO: 40). In some embodiments of the invention, a library may contain one or more of these sequences, one or more allelic variants of these sequences, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences. The amino acid sequences of these chassis are presented in Table 5.

2.1.1.1. Heavy Chain Chassis Variants

While the selection of the VH chassis with sequences based on the IGHV germline sequences is expected to support a large diversity of CDRH3 sequences, further diversity in the VH chassis may be generated by altering the amino acid residues comprising the CDRH1 and/or CDRH2 regions of each chassis selected for inclusion in the library (see Example 2).

In certain embodiments of the invention, the alterations or mutations in the amino acid residues comprising the CDRH1 and CDRH2 regions, or other regions, of the IGHV germline sequences are made after analyzing the sequence identity within data sets of rearranged human heavy chain sequences that have been classified according to the identity of the original IGHV germline sequence from which the rearranged sequences are derived. For example, from a set of rearranged antibody sequences, the IGHV germline sequence of each antibody is determined, and the rearranged sequences are classified according to the IGHV germline sequence. This determination is made on the basis of sequence identity.

Next, the occurrence of any of the 20 amino acid residues at each position in these sequences is determined. In certain embodiments of the invention, one may be particularly interested in the occurrence of different amino acid residues at the positions within CDRH1 and CDRH2, for example if increasing the diversity of the antigen-binding portion of the VH chassis is desired. In other embodiments of the invention, it may be desirable to evaluate the occurrence of different amino acid residues in the framework regions. Without being bound by theory, alterations in the framework regions may impact antigen binding by altering the spatial orientation of the CDRs.

After the occurrence of amino acids at each position of interest has been identified, alterations may be made in the VH chassis sequence, according to certain criteria. In some embodiments, the objective may be to produce additional VH chassis with sequence variability that mimics the variability observed in the heavy chain domains of rearranged human antibody sequences (derived from respective IGHV germline sequences) as closely as possible, thereby potentially obtaining sequences that are most human in nature (i.e., sequences that most closely mimic the composition and length of human sequences). In this case, one may synthesize additional VH chassis sequences that include mutations naturally found at a particular position and include one or more of these VH chassis sequences in a library of the invention, for example, at a frequency that mimics the frequency found in nature. In another embodiment of the invention, one may wish to include VH chassis that represent only mutations that most frequently occur at a given position in rearranged human antibody sequences. For example, rather than mimicking the human variability precisely, as described above, and with reference to exemplary Tables 6 and 7, one may choose to include only top 19, 18, 17, 16, 15, 14, 13, 12, 11, 10, 9, 8, 7, 6, 5, 4, 3, 2, or 1, amino acid residues that most frequently occur at each position. For the purposes of illustration, and with reference to Table 6, if one wished to include the top four most frequently occurring amino acid residues at position 31 of the VH1-69 sequence, then position 31 in the VH1-69 sequence would be varied to include S, N, T, and R. Without being bound by theory, it is thought that the introduction of diversity by mimicking the naturally occurring composition of the rearranged heavy chain sequences is likely to produce antibodies that are most human in composition. However, the libraries of the invention are not limited to heavy chain sequences that are diversified by this method, and any criteria can be used to introduce diversity into the heavy chain chassis, including random or rational mutagenesis. For example, in certain embodiments of the invention, it may be preferable to substitute neutral and/or smaller amino acid residues for those residues that occur in the IGHV germline sequence. Without being bound by theory, neutral and/or smaller amino acid residues may provide a more flexible and less sterically hindered context for the display of a diversity of CDR sequences.

Example 2 illustrates the application of this method to heavy chains derived from a particular IGHV germline. One of ordinary skill in the art will readily recognize that this method can be applied to any germline sequence, and can be used to generate at least about 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 1000, $10^4$, $10^5$, $10^6$, or more variants of each heavy chain chassis.

2.1.2. Design of the Light Chain Chassis Sequences

The light chain chassis of the invention may be based on kappa and/or lambda light chain sequences. The principles underlying the selection of light chain variable (IGLV) germline sequences for representation in the library are analogous to those employed for the selection of the heavy chain sequences (described above and in Examples 1 and 2). Similarly, the methods used to introduce variability into the selected heavy chain chassis may also be used to introduce variability into the light chain chassis.

Without being bound by theory, and for the purposes of illustrating certain embodiments of the invention, the VL domains of the library may be considered to comprise three primary components: (1) a VL "chassis", which includes amino acids 1 to 88 (using Kabat numbering), (2) the VLCDR3, which is defined herein to include the Kabat CDRL3 proper (positions 89-97), and (3) the FRM4 region, including amino acids 98 to 107 (Kabat numbering). The overall VL structure may therefore be depicted schematically (not to scale) as:

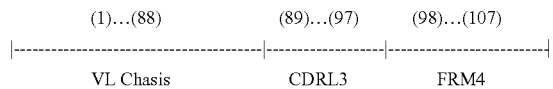

In certain embodiments of the invention, the VL chassis of the libraries include one or more chassis based on IGKV germline sequences. In certain embodiments of the invention, the VL chassis of the libraries may comprise from about Kabat residue 1 to about Kabat residue 88 of one or more of the following IGKV germline sequences: IGKV1-05 (SEQ ID NO: 229), IGKV1-06 (SEQ ID NO: 451), IGKV1-08 (SEQ ID NO: 452, 453), IGKV1-09 (SEQ ID NO: 454), IGKV1-12 (SEQ ID NO: 230), IGKV1-13 (SEQ ID NO: 455), IGKV1-16 (SEQ ID NO: 456), IGKV1-17 (SEQ ID NO: 457), IGKV1-27 (SEQ ID NO: 231), IGKV1-33 (SEQ ID NO: 232), IGKV1-37 (SEQ ID NOs: 458, 459), IGKV1-39 (SEQ ID NO: 233), IGKV1D-16 (SEQ ID NO: 460), IGKV1D-17 (SEQ ID NO: 461), IGKV1D-43 (SEQ ID NO: 462), IGKV1D-8 (SEQ ID NOs: 463, 464), IGKV2-24 (SEQ ID NO: 465), IGKV2-28 (SEQ ID NO: 234), IGKV2-29 (SEQ ID NO: 466), IGKV2-30 (SEQ ID NO: 467), IGKV2-40 (SEQ ID NO: 468), IGKV2D-26 (SEQ ID NO: 469), IGKV2D-29 (SEQ ID NO: 470), IGKV2D-30 (SEQ ID NO: 471), IGKV3-11 (SEQ ID NO: 235), IGKV3-15 (SEQ ID NO: 236), IGKV3-20 (SEQ ID NO: 237), IGKV3D-07 (SEQ ID NO: 472), IGKV3D-11 (SEQ ID NO: 473), IGKV3D-20 (SEQ ID NO: 474), IGKV4-1 (SEQ ID NO: 238), IGKV5-2 (SEQ ID NOs: 475, 476), IGKV6-21 (SEQ ID NOs: 477), and IGKV6D-41. In some embodiments of the invention, a library may contain one or more of these sequences, one or more allelic variants of these sequences, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences.

In other embodiments, the VL chassis of the libraries may comprise from about Kabat residue 1 to about Kabat residue 88 of the following IGKV germline sequences: IGKV1-05 (SEQ ID NO: 229), IGKV1-12 (SEQ ID NO: 230), IGKV1-27 (SEQ ID NO: 231), IGKV1-33 (SEQ ID NO: 232), IGKV1-39 (SEQ ID NO: 233), IGKV2-28 (SEQ ID NO: 234), IGKV3-11 (SEQ ID NO: 235), IGKV3-15 (SEQ ID NO: 236), IGKV3-20 (SEQ ID NO: 237), and IGKV4-1 (SEQ ID NO: 238). In some embodiments of the invention, a library may contain one or more of these sequences, one or more allelic variants of these sequences, or encode an amino acid sequence at least 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences. The amino acid sequences of these chassis are presented in Table 11.

In certain embodiments of the invention, the VL chassis of the libraries include one or more chassis based on IGλV germline sequences. In certain embodiments of the invention, the VL chassis of the libraries may comprise from about Kabat residue 1 to about Kabat residue 88 of one or more of the following IGλV germline sequences: IGλV3-1 (SEQ ID NO: 535), IGλV3-21 (SEQ ID NO: 537), IGλV2-14 (SEQ ID NO: 534), IGλV1-40 (SEQ ID NO: 531), IGλV3-19 (SEQ ID NO: 536), IGλV1-51 (SEQ ID NO: 533), IGλV1-44 (SEQ ID NO: 532), IGλV6-57 (SEQ ID NO: 539), IGλV2-8, IGλV3-25, IGλV2-23, IGλV3-10, IGλV4-69 (SEQ ID NO: 538), IGλV1-47, IGλV2-11, IGλV7-43 (SEQ ID NO: 541), IGλV7-46, IGλV5-45 (SEQ ID NO: 540), IGλV4-60, IGλV10-54 (SEQ ID NO: 482), IGλV8-61 (SEQ ID NO: 499), IGλV3-9 (SEQ ID NO: 494), IGλV1-36 (SEQ ID NO: 480), IGλV2-18 (SEQ ID NO: 485), IGλV3-16 (SEQ ID NO: 491), IGλV3-27 (SEQ ID NO: 493), IGλV4-3 (SEQ ID NO: 495), IGλV5-39 (SEQ ID NO: 497), IGλV9-49 (SEQ ID NO: 500), and IGλV3-12 (SEQ ID NO: 490). In some embodiments of the invention, a library may contain one or more of these sequences, one or more allelic variants of these sequences, or encode an amino acid sequence at least about 99.9%, 99.5%, 99%, 98%, 97%, 96%, 95%, 94%, 93%, 92%, 91%, 90%, 85%, 80%, 75%, 70%, 65%, 60%, 55%, or 50% identical to one or more of these sequences.

In other embodiments, the VL chassis of the libraries may comprise from about Kabat residue 1 to about Kabat residue 88 of the following IGλV germline sequences: IGλV3-1 (SEQ ID NO: 535), IGλV3-21 (SEQ ID NO: 537), IGλV2-14 (SEQ ID NO: 534), IGλV1-40 (SEQ ID NO: 531), IGλV3-19 (SEQ ID NO: 536), IGλV1-51 (SEQ ID NO: 533), IGλV1-44 (SEQ ID NO: 532), IGλV6-57 (SEQ ID NO: 539), IGλV4-69 (SEQ ID NO: 538), IGλV7-43 (SEQ ID NO: 541), and IGλV5-45 (SEQ ID NO: 540). In some embodiments of the invention, a library may contain one or more of these sequences, one or more allelic variants of these sequences, or encode an amino acid sequence at least about 99.9%, 99.5%, 99%, 98%, 97%, 96%, 95%, 94%, 93%, 92%, 91%, 90%, 85%, 80%, 75%, 70%, 65%, 60%, 55%, or 50% identical to one or more of these sequences. The amino acid sequences of these chassis are presented in Table 14.

2.2. Design of the Antibody Library CDRH3 Components

It is known in the art that diversity in the CDR3 region of the heavy chain is sufficient for most antibody specificities (Xu and Davis, Immunity, 2000, 13: 27-45, incorporated by reference in its entirety) and that existing successful libraries have been created using CDRH3 as the major source of diversification (Hoogenboom et al., J. Mol. Biol., 1992, 227: 381; Lee et al., J. Mol. Biol., 2004, 340: 1073 each of which is incorporated by reference in its entirety). It is also known that both the DH region and the N1/N2 regions contribute to the CDRH3 functional diversity (Schroeder et al., J. Immunol., 2005, 174: 7773 and Mathis et al., Eur J. Immunol., 1995, 25: 3115, each of which is incorporated by reference in its entirety). For the purposes of the present invention, the CDHR3 region of naturally occurring human antibodies can be divided into five segments: (1) the tail segment, (2) the N1 segment, (3) the DH segment, (4) the N2 segment, and (5) the JH segment. As exemplified below, the tail, N1 and N2 segments may or may not be present.

In certain embodiments of the invention, the method for selecting amino acid sequences for the synthetic CDRH3 libraries includes a frequency analysis and the generation of the corresponding variability profiles of existing rearranged antibody sequences. In this process, which is described in more detail in the Examples section, the frequency of occurrence of a particular amino acid residue at a particular position within rearranged CDRH3s (or any other heavy or light chain region) is determined Amino acids that are used more frequently in nature may then be chosen for inclusion in a library of the invention.

2.2.1. Design and Selection of the DH Segment Repertoire

In certain embodiments of the invention, the libraries contain CDRH3 regions comprising one or more segments designed based on the IGHD gene germline repertoire. In some embodiments of the invention, DH segments selected for inclusion in the library are selected and designed based on the most frequent usage of human IGHD genes, and progressive N-terminal and C-terminal deletions thereof, to mimic the in vivo processing of the IGHD gene segments. In some embodiments of the invention, the DH segments of the library are about 3 to about 10 amino acids in length. In some embodiments of the invention, the DH segments of the library are about 0, 1, 2, 3, 4, 5, 6, 7, 8, 9, or 10 amino acids in length, or a combination thereof. In certain embodiments, the libraries of the invention may contain DH segments with a wide distribution of lengths (e.g., about 0 to about 10 amino acids). In other embodiments, the length distribution of the DH may be restricted (e.g., about 1 to about 5 amino acids, about 3 amino acids, about 3 and about 5 amino acids, and so on). In certain embodiments of the library, the shortest DH segments may be about 0, 1, 2, 3, 4, 5, 6, 7, 8, 9, or 10 amino acids.

In certain embodiments of the invention, libraries may contain DH segments representative of any reading frame of any IGHD germline sequence. In certain embodiments of the invention, the DH segments selected for inclusion in a library include one or more of the following IGHD sequences, or their derivatives (i.e., any reading frame and any degree of N-terminal and C-terminal truncation): IGHD3-10 (SEQ ID NOs: 1-3), IGHD3-22 (SEQ ID NOs: 239, 4, 240), IGHD6-19 (SEQ ID NOs: 5, 6, 241), IGHD6-13 (SEQ ID NOs: 7, 8, 242), IGHD3-3 (SEQ ID NOs: 243, 244, 9), IGHD2-2 (SEQ ID NOs: 245, 10, 11), IGHD4-17 (SEQ ID NOs: 246, 12, 247), IGHD1-26 (SEQ ID NOs: 13, 248 and 14), IGHD5-5/5-18 (SEQ ID NOs: 249, 250, 15), IGHD2-15 (SEQ ID NOs: 251, 16, 252), IGHD6-6 (encoded by SEQ ID NO: 515), IGHD3-9 (encoded by SEQ ID NO: 509), IGHD5-12 (encoded by SEQ ID NO: 512), IGHD5-24 (encoded by SEQ ID NO: 513), IGHD2-21 (encoded by SEQ ID NOs: 505 and 506), IGHD3-16 (encoded by SEQ ID NO: 508), IGHD4-23 (encoded by SEQ ID NO: 510), IGHD1-1 (encoded by SEQ ID NO: 501), IGHD1-7 (encoded by SEQ ID NO: 504), IGHD4-4/4-11 (encoded by SEQ ID NO: 511), IGHD1-20 (encoded by SEQ ID NO: 503), IGHD7-27, IGHD2-8, and IGHD6-25. In some embodiments of the invention, a library may contain one or more of these sequences, allelic variants thereof, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences.

For the purposes of illustration, progressive N-terminal and C-terminal deletions of IGHD3-10, reading frame 1, are enumerated in the Table 1. N-terminal and C-terminal deletions of other IGHD sequences and reading frames are also encompassed by the invention, and one of ordinary skill in the art can readily determine these sequences using, for example, the non-limiting exemplary data presented in Table 16. and/or the methods outlined above. Table 18 (Example 5) enumerates certain DH segments used in certain embodiments of the invention.

TABLE 1

Example of Progressive N- and C-terminal Deletions of Reading Frame 1 for Gene IGHD3-10, Yielding DH Segments

| DH | SEQ ID NO: |
|---|---|
| VLLWFGELL | 1 |
| VLLWFGEL | 593 |
| VLLWFGE | 594 |
| VLLLWFG | 595 |
| VLLWF | 596 |
| VLLW | 597 |
| VLL | |
| LLWFGELL | 598 |
| LLWFGEL | 599 |
| LLWFGE | 600 |
| LLWFG | 601 |
| LLWF | 602 |
| LLW | |
| LWFGELL | 603 |
| LWFGEL | 604 |
| LWFGE | 605 |
| LWFG | 606 |
| LWF | |
| WFGELL | 607 |
| WFGEL | 608 |
| WFGE | 609 |
| WFG | |
| FGELL | 610 |
| FGEL | 611 |
| FGE | |
| GELL | 612 |
| GEL | |
| ELL | |

In certain embodiments of the invention, the DH segments selected for inclusion in a library include one or more of the following IGHD sequences, or their derivatives (i.e., any reading frame and any degree N-terminal and C-terminal truncation): IGHD3-10 (SEQ ID NOs: 1-3), IGHD3-22 (SEQ ID NOs: 239, 4, 240), IGHD6-19 (SEQ ID NOs: 5, 6, 241), IGHD6-13 (SEQ ID NOs: 7, 8, 242), IGHD3-03 (SEQ ID NOs: 243, 244, 9), IGHD2-02 (SEQ ID NOs: 245, 10, 11), IGHD4-17 (SEQ ID NOs: 246, 12, 247), IGHD1-26

(SEQ ID NOs: 13, 248 and 14), IGHD5-5/5-18 (SEQ ID NOs: 249, 250, 15), and IGHD2-15 (SEQ ID NOs: 251, 16, 252). In some embodiments of the invention, a library may contain one or more of these sequences, allelic variants thereof, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences.

In certain embodiments of the invention, the DH segments selected for inclusion in a library include one or more of the following IGHD sequences, wherein the notation "_x" denotes the reading frame of the gene, or their derivatives (i.e., any degree of N-terminal or C-terminal truncation): IGHD1-26_1 (SEQ ID NO: 13), IGHD1-26_3 (SEQ ID NO: 14), IGHD2-2_2 (SEQ ID NO: 10), IGHD2-2_3 (SEQ ID NO: 11), IGHD2-15_2 (SEQ ID NO: 16), IGHD3-3_3 (SEQ ID NO: 9), IGHD3-10_1 (SEQ ID NO: 1), IGHD3-10_2 (SEQ ID NO: 2), IGHD3-10_3 (SEQ ID NO: 3), IGHD3-22_2 (SEQ ID NO: 4), IGHD4-17_2 (SEQ ID NO: 12), IGHD5-5_3 (SEQ ID NO: 15), IGHD6-13_1 (SEQ ID NO: 7), IGHD6-13_2 (SEQ ID NO: 8), IGHD6-19_1 (SEQ ID NO: 5), and IGHD6-19_2 (SEQ ID NO: 6). In some embodiments of the invention, a library may contain one or more of these sequences, allelic variants thereof, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences.

In certain embodiments of the invention, the libraries are designed to reflect a pre-determined length distribution of N- and C-terminal deleted IGHD segments. For example, in certain embodiments of the library, the DH segments of the library may be designed to mimic the natural length distribution of DH segments found in the human repertoire. For example, the relative occurrence of different IGHD segments in rearranged human antibody heavy chain domains from Lee et al. (Immunogenetics, 2006, 57: 917, incorporated by reference in its entirety). Table 2 shows the relative occurrence of the top 68% of IGHD segments from Lee et al.

TABLE 2

Relative Occurrence of Top 68% of IGHD Gene Usage from Lee et al.

| IGHD Reading Frame | Sequence (Parent) | SEQ ID NO: | Relative Occurrence |
|---|---|---|---|
| IGHD3-10_1 | VLLWFGELL | 1 | 4.3% |
| IGHD3-10_2 | YYYGSGSYYN | 2 | 8.4% |
| IGHD3-10_3 | ITMVRGVII | 3 | 4.0% |
| IGHD3-22_2 | YYYDSSGYYY | 4 | 15.6% |
| IGHD6-19_1 | GYSSGWY | 5 | 7.4% |
| IGHD6-19_2 | GIAVAG | 6 | 6.0% |
| IGHD6-13_1 | GYSSSWY | 7 | 8.4% |
| IGHD6-13_2 | GIAAAG | 8 | 5.3% |

TABLE 2-continued

Relative Occurrence of Top 68% of IGHD Gene Usage from Lee et al.

| IGHD Reading Frame | Sequence (Parent) | SEQ ID NO: | Relative Occurrence |
|---|---|---|---|
| IGHD3-3_3 | ITIFGVVII | 9 | 7.4% |
| IGHD2-2_2 | GYCSSTSCYT | 10 | 5.2% |
| IGHD2-2_3 | DIVVVPAAM | 11 | 4.1% |
| IGHD4-17_2 | DYGDY | 12 | 6.8% |
| IGHD1-26_1 | GIVGATT | 13 | 2.9% |
| IGHD1-26_3 | YSGSYY | 14 | 4.3% |
| IGHD5-5_3 | GYSYGY | 15 | 4.3% |
| IGHD2-15_2 | GYCSGGSCYS | 16 | 5.6% |

In certain embodiments, these relative occurrences may be used to design a library with DH prevalence that is similar to the IGHD usage found in peripheral blood. In other embodiments of the invention, it may be preferable to bias the library toward longer or shorter DH segments, or DH segments of a particular composition. In other embodiments, it may be desirable to use all DH segments selected for the library in equal proportion.

In certain embodiments of the invention, the most commonly used reading-frames of the ten most frequently occurring IGHD sequences are utilized, and progressive N-terminal and C-terminal deletions of these sequences are made, thus providing a total of 278 non-redundant DH segments that are used to create a CDRH3 repertoire of the instant invention (Table 18). In some embodiments of the invention, the methods described above can be applied to produce libraries comprising the top 1, 2, 3, 4, 5, 6, 7, 8, 9, 10, 11, 12, 13, 14, 15, 16, 17, 18, 19, 20, 21, 22, 23, 24, or 25 expressed IGHD sequences, and progressive N-terminal and C-terminal deletions thereof. As with all other components of the library, while the DH segments may be selected from among those that are commonly expressed, it is also within the scope of the invention to select these gene segments based on the fact that they are less commonly expressed. This may be advantageous, for example, in obtaining antibodies toward self-antigens or in further expanding the diversity of the library. Alternatively, DH segments can be used to add compositional diversity in a manner that is strictly relative to their occurrence in actual human heavy chain sequences.

In certain embodiments of the invention, the progressive deletion of IGHD genes containing disulfide loop encoding segments may be limited, so as to leave the loop intact and to avoid the presence of unpaired cysteine residues. In other embodiments of the invention, the presence of the loop can be ignored and the progressive deletion of the IGHD gene segments can occur as for any other segments, regardless of the presence of unpaired cysteine residues. In still other embodiments of the invention, the cysteine residues can be mutated to any other amino acid.

2.2.2. Design and Selection of the H3-JH Segment Repertoire

There are six IGHJ (joining) segments, IGHJ1 (SEQ ID NO: 253), IGHJ2 (SEQ ID NO: 254), IGHJ3 (SEQ ID NO: 255), IGHJ4 (SEQ ID NO: 256), IGHJ5 (SEQ ID NO: 257), and IGHJ6 (SEQ ID NO: 258). The amino acid sequences of the parent segments and the progressive N-terminal deletions are presented in Table 20 (Example 5). Similar to the N- and C-terminal deletions that the IGHD genes undergo, natural variation is introduced into the IGHJ genes by N-terminal "nibbling", or progressive deletion, of one or more codons by exonuclease activity.

The H3-JH segment refers to the portion of the IGHJ segment that is part of CDRH3. In certain embodiments of the invention, the H3-JH segment of a library comprises one or more of the following sequences: AEYFQH (SEQ ID NO: 17), EYFQH (SEQ ID NO: 583), YFQH (SEQ ID NO: 584), FQH, QH, H, YWYFDL (SEQ ID NO: 18), WYFDL (SEQ ID NO: 585), YFDL (SEQ ID NO: 586), FDL, DL, L, AFDV (SEQ ID NO: 19), FDV, DV, V, YFDY (SEQ ID NO: 20), FDY, DY, Y, NWFDS (SEQ ID NO: 21), WFDS (SEQ ID NO: 587), FDS, DS, S, YYYYYGMDV (SEQ ID NO: 22), YYYYGMDV (SEQ ID NO: 588), YYYGMDV (SEQ ID NO: 589), YYGMDV (SEQ ID NO: 590), YGMDV (SEQ ID NO: 591), GMDV (SEQ ID NO: 592), MDV, and DV. In some embodiments of the invention, a library may contain one or more of these sequences, allelic variations thereof, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 60%, 55%, or 50% identical to one or more of these sequences.

In other embodiments of the invention, the H3-JH segment may comprise about 0, 1, 2, 3, 4, 5, 6, 7, 8, 9, or more amino acids. For example, the H3-JH segment of JH1_4 (Table 20) has a length of three residues, while non-deleted JH6 has an H3-JH segment length of nine residues. The FRM4-JH region of the IGHJ segment begins with the sequence WG(Q/R)G (SEQ ID NO: 23) and corresponds to the portion of the IGHJ segment that makes up part of framework 4. In certain embodiments of the invention, as enumerated in Table 20, there are 28 H3-JH segments that are included in a library. In certain other embodiments, libraries may be produced by utilizing about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the IGHJ segments enumerated above or in Table 20.

2.2.3. Design and Selection of the N1 and N2 Segment Repertoires

Terminal deoxynucleotidyl transferase (TdT) is a highly conserved enzyme from vertebrates that catalyzes the attachment of 5' triphosphates to the 3' hydroxyl group of single- or double-stranded DNA. Hence, the enzyme acts as a template-independent polymerase (Koiwai et al., Nucleic Acids Res., 1986, 14: 5777; Basu et al., Biochem. Biophys. Res. Comm., 1983, 111: 1105, each incorporated by reference in its entirety). In vivo, TdT is responsible for the addition of nucleotides to the V-D and D-J junctions of antibody heavy chains (Alt and Baltimore, PNAS, 1982, 79: 4118; Collins et al., J. Immunol., 2004, 172: 340, each incorporated by reference in its entirety). Specifically, TdT is responsible for creating the N1 and N2 (non-templated) segments that flank the D (diversity) region.

Figure 2:
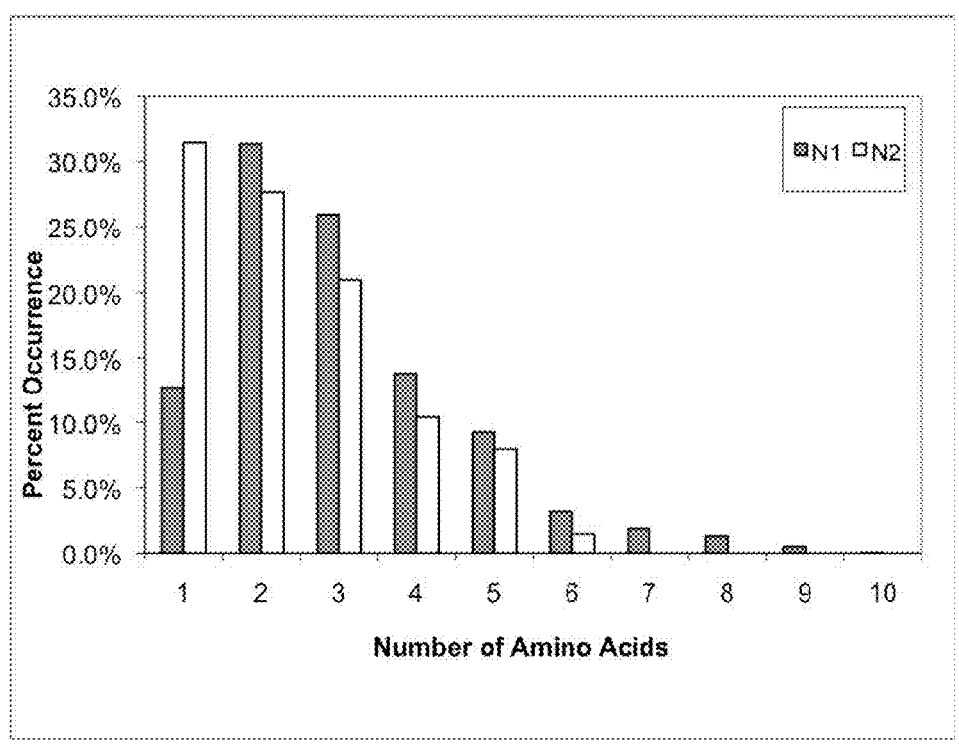
FIG. 2 depicts the length distribution of the N1 and N2 regions of rearranged human antibody sequences compiled from Jackson et al. (J. Immunol Methods, 2007, 324: 26, incorporated by reference in its entirety).

In certain embodiments of the invention, the length and composition of the N1 and N2 segments are designed rationally, according to statistical biases in amino acid usage found in naturally occurring N1 and N2 segments in human antibodies. One embodiment of a library produced via this method is described in Example 5. According to data compiled from human databases (Jackson et al., J. Immunol. Methods, 2007, 324: 26, incorporated by reference in its entirety), there are an average of 3.02 amino acid insertions for N1 and 2.4 amino acid insertions for N2, not taking into account insertions of two nucleotides or less (FIG. 2). In certain embodiments of the invention, N1 and N2 segments are restricted to lengths of zero to three amino acids. In other embodiments of the invention, N1 and N2 may be restricted to lengths of less than about 4, 5, 6, 7, 8, 9, or 10 amino acids.

In some embodiments of the invention, the composition of these sequences may be chosen according to the frequency of occurrence of particular amino acids in the N1 and N2 sequences of natural human antibodies (for examples of this analysis, see, Tables 21 to 23, in Example 5). In certain embodiments of the invention, the eight most commonly occurring amino acids in these regions (i.e., G, R, S, P, L, A, T, and V) are used to design the synthetic N1 and N2 segments. In other embodiments of the invention about the most 1, 2, 3, 4, 5, 6, 7, 8, 9, 10, 11, 12, 13, 14, 15, 16, 17, 18, or 19 most commonly occurring amino acids may be used in the design of the synthetic N1 and N2 segments. In still other embodiments, all 20 amino acids may be used in these segments. Finally, while it is possible to base the designed composition of the N1 and N2 segments of the invention on the composition of naturally occurring N1 and N2 segments, this is not a requirement. The N1 and N2 segments may comprise amino acids selected from any group of amino acids, or designed according to other criteria considered for the design of a library of the invention. A person of ordinary skill in the art would readily recognize that the criteria used to design any portion of a library of the invention may vary depending on the application of the particular library. It is an object of the invention that it may be possible to produce a functional library through the use of N1 and N2 segments selected from any group of amino acids, no N1 or N2 segments, or the use of N1 and N2 segments with compositions other than those described herein.

One important difference between the libraries of the current invention and other libraries known in the art is the consideration of the composition of naturally occurring duplet and triplet amino acid sequences during the design of the library. Table 23 shows the top twenty-five naturally occurring duplets in the N1 and N2 regions. Many of these can be represented by the general formula (G/P)(G/R/S/P/L/A/V/T) or (R/S/L/A/V/T)(G/P). In certain embodiments of the invention, the synthetic N1 and N2 regions may comprise all of these duplets. In other embodiments, the library may comprise the top 2, 3, 4, 5, 6, 7, 8, 9, 10, 11, 12, 13, 14, 15, 16, 17, 18, 19, 20, 21, 22, 23, 24, or 25 most common naturally occurring N1 and/or N2 duplets. In other embodiments of the invention, the libraries may include duplets that are less frequently occurring (i.e., outside of the top 25). The composition of these additional duplets or triplets could readily be determined, given the methods taught herein.

Finally, the data from the naturally occurring triplet N1 and N2 regions demonstrates that the naturally occurring N1 and N2 triplet sequences can often be represented by the formulas (G)(G)(G/R/S/P/L/A/V/T), (G)(R/S/P/L/A/V/T)(G), or (R/S/P/L/A/V/T)(G)(G). In certain embodiments of the invention, the library may comprise the top 2, 3, 4, 5, 6, 7, 8, 9, 10, 11, 12, 13, 14, 15, 16, 17, 18, 19, 20, 21, 22, 23, 24, or 25 most commonly occurring N1 and/or N2 triplets. In other embodiments of the invention, the libraries may include triplets that are less frequently occurring (i.e., outside of the top 25). The composition of these additional duplets or triplets could readily be determined, given the methods taught herein.

In certain embodiments of the invention, there are about 59 total N1 segments and about 59 total N2 segments used to create a library of CDRH3s. In other embodiments of the invention, the number of N1 segments, N2 segments, or both is increased to about 141 (see, for example, Example 5). In other embodiments of the invention, one may select a total of about 0, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 1000, $10^4$, or more N1 and/or N2 segments for inclusion in a library of the invention.

One of ordinary skill in the art will readily recognize that, given the teachings of the instant specification, it is well within the realm of normal experimentation to extend the analysis detailed herein, for example, to generate additional rankings of naturally occurring duplet and triplet (or higher order) N regions that extend beyond those presented herein (e.g., using sequence alignment, the SoDA algorithm, and any database of human sequences (Volpe et al., Bioinformatics, 2006, 22: 438-44, incorporated by reference in its entirety). An ordinarily skilled artisan would also recognize that, based on the information taught herein, it is now possible to produce libraries that are more diverse or less diverse (i.e., more focused) by varying the number of distinct amino acid sequences used in the N1 pool and/or N2 pool.

As described above, many alternative embodiments are envisioned, in which the compositions and lengths of the N1 and N2 segments vary from those presented in the Examples herein. In some embodiments, sub-stoichiometric synthesis of trinucleotides may be used for the synthesis of N1 and N2 segments. Sub-stoichiometric synthesis with trinucleotides is described in Knappik et al. (U.S. Pat. No. 6,300,064, incorporated by reference in its entirety). The use of sub-stoichiometric synthesis would enable synthesis with consideration of the length variation in the N1 and N2 sequences.

In addition to the embodiments described above, a model of the activity of TdT may also be used to determine the composition of the N1 and N2 sequences in a library of the invention. For example, it has been proposed that the probability of incorporating a particular nucleotide base (A, C, G, T) on a polynucleotide, by the activity of TdT, is dependent on the type of base and the base that occurs on the strand directly preceding the base to be added. Jackson et al., (J. Immunol. Methods, 2007, 324: 26, incorporated by reference in its entirety) have constructed a Markov model describing this process. In certain embodiments of the invention, this model may be used to determine the composition of the N1 and/or N2 segments used in libraries of the invention. Alternatively, the parameters presented in Jackson et al. could be further refined to produce sequences that more closely mimic human sequences.

2.2.4. Design of a CDRH3 Library Using the N1, DH, N2, and H3-JH Segments

The CDRH3 libraries of the invention comprise an initial amino acid (in certain exemplary embodiments, G, D, E) or lack thereof (designated herein as position 95), followed by the N1, DH, N2, and H3-JH segments. Thus, in certain embodiments of the invention, the overall design of the CDRH3 libraries can be represented by the following formula:

[G/D/E/-]-[N1]-[DH]-[N2]-[H3-JH].

While the compositions of each portion of a CDRH3 of a library of the invention are more fully described above, the composition of the tail presented above (G/D/E/-) is non-limiting, and that any amino acid (or no amino acid) can be used in this position. Thus, certain embodiments of the invention may be represented by the following formula:

[X]-[N1]-[DH]-[N2]-[H3-JH], wherein [X] is any amino acid residue or no residue.

In certain embodiments of the invention, a synthetic CDRH3 repertoire is combined with selected VH chassis sequences and heavy chain constant regions, via homologous recombination. Therefore, in certain embodiments of the invention, it may be necessary to include DNA sequences flanking the 5' and 3' ends of the synthetic CDRH3 libraries, to facilitate homologous recombination between the synthetic CDRH3 libraries and vectors containing the selected chassis and constant regions. In certain embodiments, the vectors also contain a sequence encoding at least a portion of the non-nibbled region of the IGHJ gene (i.e., FRM4-JH). Thus, a polynucleotide encoding an N-terminal sequence (e.g., CA(K/R/T)) may be added to the synthetic CDRH3 sequences, wherein the N-terminal polynucleotide is homologous with FRM3 of the chassis, while a polynucleotide encoding a C-terminal sequence (e.g., WG(Q/R)G; SEQ ID NO: 23) may be added to the synthetic CDRH3, wherein the C-terminal polynucleotide is homologous with FRM4-JH. Although the sequence WG(Q/R)G (SEQ ID NO: 23) is presented in this exemplary embodiment, additional amino acids, C-terminal to this sequence in FRM4-JH may also be included in the polynucleotide encoding the C-terminal sequence. The purpose of the polynucleotides encoding the N-terminal and C-terminal sequences, in this case, is to facilitate homologous recombination, and one of ordinary skill in the art would recognize that these sequences may be longer or shorter than depicted below. Accordingly, in certain embodiments of the invention, the overall design of the CDRH3 repertoire, including the sequences required to facilitate homologous recombination with the selected chassis, can be represented by the following formula (regions homologous with vector underlined):

CA[R/K/T]-[X]-[N1]-[DH]-[N2]-[H3-JH]-[WG(Q/R) G].

In other embodiments of the invention, the CDRH3 repertoire can be represented by the following formula, which excludes the T residue presented in the schematic above:

CA[R/K]-[X]-[N1]-[DH]-[N2]-[H3-JH]-[WG(Q/R) G].

References describing collections of V, D, and J genes include Scaviner et al., Exp. Clin, Immunogenet., 1999, 16: 243 and Ruiz et al., Exp. Clin Immunogenet, 1999, 16: 173, each incorporated by reference in its entirety.

2.2.5. CDRH3 Length Distributions

As described throughout this application, in addition to accounting for the composition of naturally occurring CDRH3 segments, the instant invention also takes into account the length distribution of naturally occurring CDRH3 segments. Surveys by Zemlin et al. (JMB, 2003, 334: 733, incorporated by reference in its entirety) and Lee et al. (Immunogenetics, 2006, 57: 917, incorporated by reference in its entirety) provide analyses of the naturally occurring CDRH3 lengths. These data show that about 95% of naturally occurring CDRH3 sequences have a length from about 7 to about 23 amino acids. In certain embodiments, the instant invention provides rationally designed antibody libraries with CDRH3 segments which directly mimic the size distribution of naturally occurring CDRH3 sequences. In certain embodiments of the invention, the length of the CDRH3s may be about 2 to about 30, about 3 to about 35, about 7 to about 23, about 3 to about 28, about 5 to about 28, about 5 to about 26, about 5 to about 24, about 7 to about 24, about 7 to about 22, about 8 to about 19, about 9 to about 22, about 9 to about 20, about 10 to about 18, about 11 to about 20, about 11 to about 18, about 13 to about 18, or about 13 to about 16 residues in length.

In certain embodiments of the invention, the length distribution of a CDRH3 library of the invention may be defined based on the percentage of sequences within a certain length range. For example, in certain embodiments of the invention, CDRH3s with a length of about 10 to about 18 amino acid residues comprise about 84% to about 94% of the sequences of a the library. In some embodiments, sequences within this length range comprise about 89% of the sequences of a library.

In other embodiments of the invention, CDRH3s with a length of about 11 to about 17 amino acid residues comprise about 74% to about 84% of the sequences of a library. In some embodiments, sequences within this length range comprise about 79% of the sequences of a library.

In still other embodiments of the invention, CDRH3s with a length of about 12 to about 16 residues comprise about 57% to about 67% of the sequences of a library. In some embodiments, sequences within this length range comprise about 62% of the sequences of a library.

In certain embodiments of the invention, CDRH3s with a length of about 13 to about 15 residues comprise about 35% to about 45% of the sequences of a library. In some embodiments, sequences within this length range comprise about 40% of the sequences of a library.

2.3. Design of the Antibody Library CDRL3 Components

The CDRL3 libraries of the invention can be generated by one of several approaches. The actual version of the CDRL3 library made and used in a particular embodiment of the invention will depend on objectives for the use of the library. More than one CDRL3 library may be used in a particular embodiment; for example, a library containing CDRH3 diversity, with kappa and lambda light chains is within the scope of the invention.

In certain embodiments of the invention, a CDRL3 library is a VKCDR3 (kappa) library and/or a VλCDR3 (lambda) library. The CDRL3 libraries described herein differ significantly from CDRL3 libraries in the art. First, they consider length variation that is consistent with what is observed in actual human sequences. Second, they take into consideration the fact that a significant portion of the CDRL3 is encoded by the IGLV gene. Third, the patterns of amino acid variation within the IGLV gene-encoded CDRL3 portions are not stochastic and are selected based on depending on the identity of the IGLV gene. Taken together, the second and third distinctions mean that CDRL3 libraries that faithfully mimic observed patterns in human sequences cannot use a generic design that is independent of the chassis sequences in FRM1 to FRM3. Fourth, the contribution of JL to CDRL3 is also considered explicitly, and enumeration of each amino acid residue at the relevant positions is based on the compositions and natural variations of the JL genes themselves.

As indicated above, and throughout the application, a unique aspect of the design of the libraries of the invention is the germline or "chassis-based" aspect, which is meant to preserve more of the integrity and variability of actual human sequences. This is in contrast to other codon-based synthesis or degenerate oligonucleotide synthesis approaches that have been described in the literature and that aim to produce "one-size-fits-all" (e.g., consensus) libraries (e.g. Knappik, et al., J Mol Biol, 2000, 296: 57; Akamatsu et al., J Immunol, 1993, 151: 4651, each incorporated by reference in its entirety).

In certain embodiments of the invention, patterns of occurrence of particular amino acids at defined positions within VL sequences are determined by analyzing data available in public or other databases, for example, the NCBI database (see, for example, GI numbers in Appendices A and B filed herewith). In certain embodiments of the invention, these sequences are compared on the basis of identity and assigned to families on the basis of the germline genes from which they are derived. The amino acid composition at each position of the sequence, in each germline family, may then be determined. This process is illustrated in the Examples provided herein.

2.3.1. Minimalist VKCDR3 Libraries

In certain embodiments of the invention, the light chain CDR3 library is a VKCDR3 library. Certain embodiments of the invention may use only the most common VKCDR3 length, nine residues; this length occurs in a dominant proportion (greater than about 70%) of human VKCDR3 sequences. In human VKCDR3 sequences of length nine, positions 89-95 are encoded by the IGKV gene and positions 96-97 are encoded by the IGKJ gene. Analysis of human kappa light chain sequences indicates that there are not strong biases in the usage of the IGKJ genes. Therefore, in certain embodiments of the invention, each of the five the IGKJ genes can be represented in equal proportions to create a combinatorial library of (M VK chassis)×(5 JK genes), or a library of size M×5. However, in other embodiments of the invention, it may be desirable to bias IGKJ gene representation, for example to restrict the size of the library or to weight the library toward IGKJ genes known to have particular properties.

As described in Example 6.1, examination of the first amino acid encoded by the IGKJ gene (position 96) indicated that the seven most common residues found at this position are L, Y, R, W, F, P, and I. These residues cumulatively account for about 85% of the residues found in position 96 in naturally occurring kappa light chain sequences. In certain embodiments of the invention, the amino acid residue at position 96 may be one of these seven residues. In other embodiments of the invention, the amino acid at this position may be chosen from amongst any of the other 13 amino acid residues. In still other embodiments of the invention, the amino acid residue at position 96 may be chosen from amongst the top 1, 2, 3, 4, 5, 6, 7, 8, 9, 10, 11, 12, 13, 14, 15, 16, 17, 18, 19, or 20 amino acids that occur at position 96, or even residues that never occur at position 96. Similarly, the occurrence of the amino acids selected to occupy position 96 may be equivalent or weighted. In certain embodiments of the invention, it may be desirable to include each of the amino acids selected for inclusion in position 96 at equivalent amounts. In other embodiments of the invention, it may be desirable to bias the composition of position 96 to include particular residues more or less frequently than others. For example, as presented in Example 6.1, arginine occurs at position 96 most frequently when the IGKJ1 (SEQ ID NO: 552) germline sequence is used. Therefore, in certain embodiments of the invention, it may be desirable to bias amino acid usage at position 96 according to the origin of the IGKJ germline sequence(s) and/or the IGKV germline sequence(s) selected for representation in a library.

Therefore, in certain embodiments of the invention, a minimalist VKCDR3 library may be represented by one or more of the following amino acid sequences:

[VK_Chassis]-[L3-VK]-[F/L/I/R/W/Y/P]-[JK*]

[VK_Chassis]-[L3-VK]-[X]-[JK*]

In these schematic exemplary sequences, VK_Chassis represents any VK chassis selected for inclusion in a library of the invention (e.g., see Table 11). Specifically, VK_Chassis comprises about Kabat residues 1 to 88 of a selected IGKV sequence. L3-VK represents the portion of the VKCDR3 encoded by the chosen IGKV gene (in this embodiment, Kabat residues 89-95). F, L, I, R, W, Y, and P are the seven most commonly occurring amino acids at position 96 of VKCDR3s with length nine, X is any amino acid, and JK* is an IGKJ amino acid sequence without the N-terminal residue (i.e., the N-terminal residue is substituted with F, L, I, R, W, Y, P, or X). Thus, in one possible embodiment of the minimalist VKCDR3 library, 70 members could be produced by utilizing 10 VK chassis, each paired with its respective L3-VK, 7 amino acids at position 96 (i.e., X), and one JK* sequence. Another embodiment of the library may have 350 members, produced by combining 10 VK chassis, each paired with its respective L3-VK, with 7 amino acids at position 96, and all 5 JK* genes. Still another embodiment of the library may have 1,125 members, produced by combining 15 VK chassis, each paired with its respective H3-JK, with 15 amino acids at position 96 and all 5 JK* genes, and so on. A person of ordinary skill in the art will readily recognize that many other combinations are possible. Moreover, while it is believed that maintaining the pairing between the VK chassis and the L3-VK results in libraries that are more similar to human kappa light chain sequences in composition, the L3-VK regions may also be combinatorially varied with different VK chassis regions, to create additional diversity.

2.3.2. VKCDR3 Libraries of About $10^5$ Complexity

Figure 3:
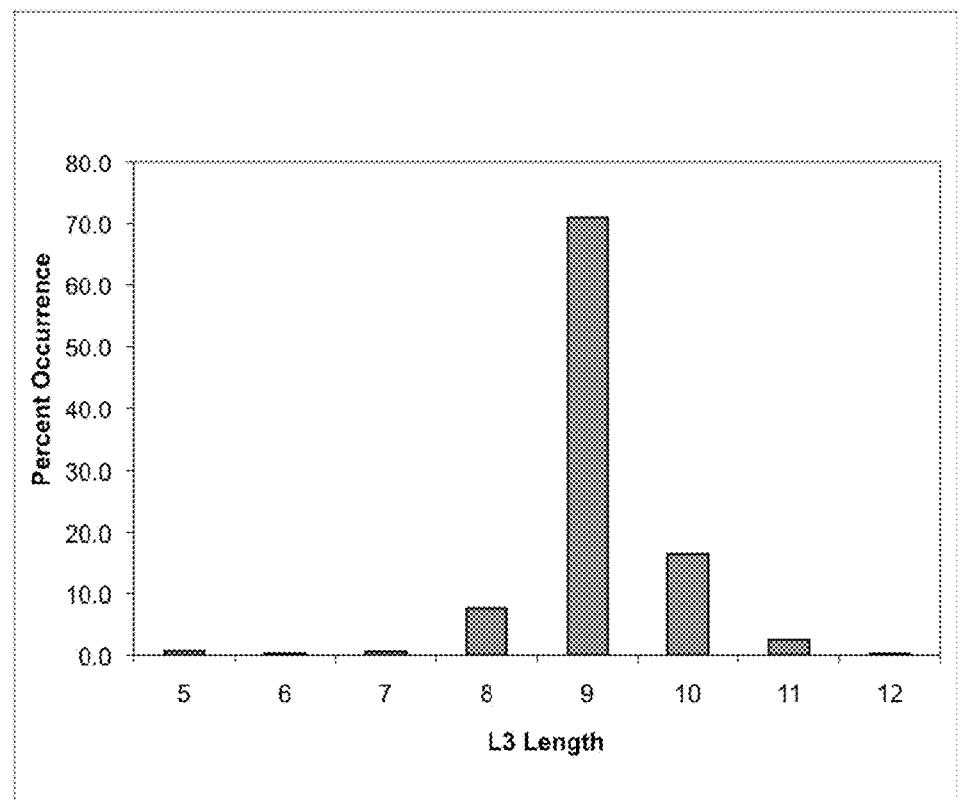
FIG. 3 depicts the length distribution of the CDRL3 regions of rearranged human kappa light chain sequences compiled from the NCBI database (Appendix A).

While the dominant length of VKCDR3 sequences in humans is about nine amino acids, other lengths appear at measurable frequencies that cumulatively approach almost about 30% of VKCDR3 sequences. In particular, VKCDR3 of lengths 8 and 10 represent about 8.5% and about 16%, respectively, of VKCDR3 lengths in representative samples (Example 6.2; FIG. 3). Thus, more complex VKCDR3 libraries may include CDR lengths of 8, 10, and 11 amino acids. Such libraries could account for a greater percentage of the length distribution observed in collections of human VKCDR3 sequences, or even introduce VKCDR3 lengths that do not occur frequently in human VKCDR3 sequences (e.g., less than eight residues or greater than 11 residues).

The inclusion of a diversity of kappa light chain length variations in a library of the invention also enables one to include sequence variability that occurs outside of the amino acid at the VK-JK junction (i.e., position 96, described above). In certain embodiments of the invention, the patterns of sequence variation within the VK, and/or JK segments can be determined by aligning collections of sequences derived from particular germline sequences. In certain embodiments of the invention, the frequency of occurrence of amino acid residues within VKCDR3 can be determined by sequence alignments (e.g., see Example 6.2 and Table 30). In some embodiments of the invention, this frequency of occurrence may be used to introduce variability into the VK_Chassis, L3-VK and/or JK segments that are used to synthesize the VKCDR3 libraries. In certain embodiments of the invention, the top 1, 2, 3, 4, 5, 6, 7, 8, 9, 10, 11, 12, 13, 14, 15, 16, 17, 18, 19, or 20 amino acids that occur at any particular position in a naturally occurring repertoire may be included at that position in a VKCDR3 library of the invention. In certain embodiments of the invention, the percent occurrence of any amino acid at any particular position within the VKCDR3 or a VK light chain may be about 0%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100%. In certain embodiments of the invention, the percent occurrence of any amino acid at any position within a VKCDR3 or kappa light chain library of the invention may be within at least about 1%, 2%, 3%, 4%, 5%, 6%, 7%, 8%, 9% 10%, 15%, 20%, 30%, 40%, 50%, 60%, 70%, 80%, 90%, 100%, 120%, 140%, 160%, 180%, or 200% of the percent occurrence of any amino acid at any position within a naturally occurring VKCDR3 or kappa light chain domain.

In some embodiments of the invention, a VKCDR3 library may be synthesized using degenerate oligonucleotides (see Table 31 for IUPAC base symbol definitions). In some embodiments of the invention, the limits of oligonucleotide synthesis and the genetic code may require the inclusion of more or fewer amino acids at a particular position in the VKCDR3 sequences. An illustrative embodiment of this approach is provided in Example 6.2.

2.3.3. More Complex VKCDR3 Libraries

The limitations inherent in using the genetic code and degenerate oligonucleotide synthesis may, in some cases, require the inclusion of more or fewer amino acids at a particular position within VKCDR3 (e.g., Example 6.2, Table 32), in comparison to those amino acids found at that position in nature. This limitation can be overcome through the use of a codon-based synthesis approach (Virnekas et al. Nucleic Acids Res., 1994, 22: 5600, incorporated by reference in its entirety), which enables precise synthesis of oligonucleotides encoding particular amino acids and a finer degree of control over the proportion of any particular amino acid incorporated at any position. Example 6.3 describes this approach in greater detail.

In some embodiments of the invention, a codon-based synthesis approach may be used to vary the percent occurrence of any amino acid at any particular position within the VKCDR3 or kappa light chain. In certain embodiments, the percent occurrence of any amino acid at any position in a VKCDR3 or kappa light chain sequence of the library may be about 0%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100%. In some embodiments of the invention, the percent occurrence of any amino acid at any position may be about 1%, 2%, 3%, or 4%. In certain embodiments of the invention, the percent occurrence of any amino acid at any position within a VKCDR3 or kappa light chain library of the invention may be within at least about 1%, 2%, 3%, 4%, 5%, 6%, 7%, 8%, 9%, 10%, 15%, 20%, 30%, 40%, 50%, 60%, 70%, 80%, 90%, 100%, 120%, 140%, 160%, 180%, or 200% of the percent occurrence of any amino acid at any position within a naturally occurring VKCDR3 or kappa light chain domain.

In certain embodiments of the invention, the VKCDR3 (and any other sequence used in the library, regardless of whether or not it is part of VKCDR3) may be altered to remove undesirable amino acid motifs. For example, peptide sequences with the pattern N-X-(S or T)-Z, where X and Z are different from P, will undergo post-translational modification (N-linked glycosylation) in a number of expression systems, including yeast and mammalian cells. In certain embodiments of the invention, the introduction of N residues at certain positions may be avoided, so as to avoid the introduction of N-linked glycosylation sites. In some embodiments of the invention, these modifications may not be necessary, depending on the organism used to express the library and the culture conditions. However, even in the event that the organism used to express libraries with potential N-linked glycosylation sites is incapable of N-linked glycosylation (e.g., bacteria), it may still be desirable to avoid N-X-(S/T) sequences, as the antibodies isolated from such libraries may be expressed in different systems (e.g., yeast, mammalian cells) later (e.g., toward clinical development), and the presence of carbohydrate moieties in the variable domains, and the CDRs in particular, may lead to unwanted modifications of activity.

In certain embodiments of the invention, it may be preferable to create the individual sub-libraries of different lengths (e.g., one or more of lengths 5, 6, 7, 8, 9, 10, 11, or more) separately, and then mix the sub-libraries in proportions that reflect the length distribution of VKCDR3 in human sequences; for example, in ratios approximating the 1:9:2 distribution that occurs in natural VKCDR3 sequences of lengths 8, 9, and 10 (see FIG. 3). In other embodiments, it may be desirable to mix these sub-libraries at ratios that are different from the distribution of lengths in natural VKCDR3 sequences, for example, to produce more focused libraries or libraries with particular properties.

2.3.4. VλCDR3 Libraries

The principles used to design the minimalist VλCDR3 libraries of the invention are similar to those enumerated above, for the VKCDR3 libraries, and are explained in more detail in the Examples. One difference between the VλCDR3 libraries of the invention and the VKCDR3 libraries of the invention is that, unlike the IGKV genes, the contribution of the IGVλ genes to CDRL3 (i.e., L3-Vλ) is not constrained to a fixed number of amino acid residues. Therefore, while the combination of the VK (including L3-VK) and JK segments, with inclusion of position 96, yields CDRL3 with a length of only 9 residues, length variation may be obtained within a VλCDR3 library even when only the Vλ (including L3-Vλ) and Jλ segments are considered.

As for the VKCDR3 sequences, additional variability may be introduced into the VλCDR3 sequences via the same methods outlined above, namely determining the frequency of occurrence of particular residues within VλCDR3 sequences and synthesizing the oligonucleotides encoding the desired compositions via degenerate oligonucleotide synthesis or trinucleotides-based synthesis.

2.4. Synthetic Antibody Libraries

In certain embodiments of the invention, both the heavy and light chain chassis sequences and the heavy and light chain CDR3 sequences are synthetic. The polynucleotide sequences of the instant invention can be synthesized by various methods. For example, sequences can be synthesized by split pool DNA synthesis as described in Feldhaus et al., Nucleic Acids Research, 2000, 28: 534; Omstein et al., Biopolymers, 1978, 17: 2341; and Brenner and Lerner, PNAS, 1992, 87: 6378 (each of which is incorporated by reference in its entirety).

In some embodiments of the invention, cassettes representing the possible V, D, and J diversity found in the human repertoire, as well as junctional diversity, are synthesized de novo either as double-stranded DNA oligonucleotides, single-stranded DNA oligonucleotides representative of the coding strand, or single-stranded DNA oligonucleotides representative of the non-coding strand. These sequences can then be introduced into a host cell along with an acceptor vector containing a chassis sequence and, in some cases a portion of FRM4 and a constant region. No primer-based PCR amplification from mammalian cDNA or mRNA or template-directed cloning steps from mammalian cDNA or mRNA need be employed.

2.5. Construction of Libraries by Yeast Homologous Recombination

In certain embodiments, the present invention exploits the inherent ability of yeast cells to facilitate homologous recombination at high efficiency. The mechanism of homologous recombination in yeast and its applications are briefly described below.

As an illustrative embodiment, homologous recombination can be carried out in, for example, *Saccharomyces cerevisiae*, which has genetic machinery designed to carry out homologous recombination with high efficiency. Exemplary *S. cerevisiae* strains include EM93, CEN.PK2, RM11-1a, YJM789, and BJ5465. This mechanism is believed to have evolved for the purpose of chromosomal repair, and is also called "gap repair" or "gap filling". By exploiting this mechanism, mutations can be introduced into specific loci of the yeast genome. For example, a vector carrying a mutant gene can contain two sequence segments that are homologous to the 5' and 3' open reading frame (ORF) sequences of a gene that is intended to be interrupted or mutated. The vector may also encode a positive selection marker, such as a nutritional enzyme allele (e.g., URA3) and/or an antibiotic resistant marker (e.g., Geneticin/G418), flanked by the two homologous DNA segments. Other selection markers and antibiotic resistance markers are known to one of ordinary skill in the art. In some embodiments of the invention, this vector (e.g., a plasmid) is linearized and transformed into the yeast cells. Through homologous recombination between the plasmid and the yeast genome, at the two homologous recombination sites, a reciprocal exchange of the DNA content occurs between the wild type gene in the yeast genome and the mutant gene (including the selection marker gene(s)) that is flanked by the two homologous sequence segments. By selecting for the one or more selection markers, the surviving yeast cells will be those cells in which the wild-type gene has been replaced by the mutant gene (Pearson et al., Yeast, 1998, 14: 391, incorporated by reference in its entirety). This mechanism has been used to make systematic mutations in all 6,000 yeast genes, or open reading frames (ORFs), for functional genomics studies. Because the exchange is reciprocal, a similar approach has also been used successfully to clone yeast genomic DNA fragments into a plasmid vector (Iwasaki et al., Gene, 1991, 109: 81, incorporated by reference in its entirety).

By utilizing the endogenous homologous recombination machinery present in yeast, gene fragments or synthetic oligonucleotides can also be cloned into a plasmid vector without a ligation step. In this application of homologous recombination, a target gene fragment (i.e., the fragment to be inserted into a plasmid vector, e.g., a CDR3) is obtained (e.g., by oligonucleotides synthesis, PCR amplification, restriction digestion out of another vector, etc.). DNA sequences that are homologous to selected regions of the plasmid vector are added to the 5' and 3' ends of the target gene fragment. These homologous regions may be fully synthetic, or added via PCR amplification of a target gene fragment with primers that incorporate the homologous sequences. The plasmid vector may include a positive selection marker, such as a nutritional enzyme allele (e.g., URA3), or an antibiotic resistance marker (e.g., Geneticin/G418). The plasmid vector is then linearized by a unique restriction cut located in-between the regions of sequence homology shared with the target gene fragment, thereby creating an artificial gap at the cleavage site. The linearized plasmid vector and the target gene fragment flanked by sequences homologous to the plasmid vector are co-transformed into a yeast host strain. The yeast is then able to recognize the two stretches of sequence homology between the vector and target gene fragment and facilitate a reciprocal exchange of DNA content through homologous recombination at the gap. As a consequence, the target gene fragment is inserted into the vector without ligation.

The method described above has also been demonstrated to work when the target gene fragments are in the form of single stranded DNA, for example, as a circular M13 phage derived form, or as single stranded oligonucleotides (Simon and Moore, Mol. Cell Biol., 1987, 7: 2329; Ivanov et al., Genetics, 1996, 142: 693; and DeMarini et al., 2001, 30: 520., each incorporated by reference in its entirety). Thus, the form of the target that can be recombined into the gapped vector can be double stranded or single stranded, and derived from chemical synthesis, PCR, restriction digestion, or other methods.

Several factors may influence the efficiency of homologous recombination in yeast. For example, the efficiency of the gap repair is correlated with the length of the homologous sequences flanking both the linearized vector and the target gene. In certain embodiments, about 20 or more base pairs may be used for the length of the homologous sequence, and about 80 base pairs may give a near-optimized result (Hua et al., Plasmid, 1997, 38: 91; Raymond et al., Genome Res., 2002, 12: 190, each incorporated by reference in its entirety). In certain embodiments of the invention, at least about 5, 10, 15, 20, 21, 22, 23, 24, 25, 26, 27, 28, 29, 30, 31, 32, 33, 34 35, 36, 37, 38, 39, 40, 45, 50, 55, 60, 65, 70, 75, 80, 85, 90, 95, 100, 110, 120, 130, 140, 150, 160, 170, 180, 187, 190, or 200 homologous base pairs may be used to facilitate recombination. In other embodiments, between about 20 and about 40 base pairs are utilized. In addition, the reciprocal exchange between the vector and gene fragment is strictly sequence-dependent, i.e. it does not cause a frame shift. Therefore, gap-repair cloning assures the insertion of gene fragments with both high efficiency and precision. The high efficiency makes it possible to clone two, three, or more targeted gene fragments simultaneously into the same vector in one transformation attempt (Raymond et al., Biotechniques, 1999, 26: 134, incorporated by reference in its entirety). Moreover, the nature of precision sequence conservation through homologous recombination makes it possible to clone selected genes or gene fragments into expression or fusion vectors for direct functional examination (El-Deiry et al., Nature Genetics, 1992, 1: 4549; Ishioka et al., PNAS, 1997, 94: 2449, each incorporated by reference in its entirety).

Libraries of gene fragments have also been constructed in yeast using homologous recombination. For example, a human brain cDNA library was constructed as a two-hybrid fusion library in vector pJG4-5 (Guidotti and Zervos, Yeast, 1999, 15: 715, incorporated by reference in its entirety). It has also been reported that a total of 6,000 pairs of PCR primers were used for amplification of 6,000 known yeast ORFs for a study of yeast genomic protein interactions (Hudson et al., Genome Res., 1997, 7: 1169, incorporated by reference in its entirety). In 2000, Uetz et al. conducted a comprehensive analysis-of protein-protein interactions in *Saccharomyces cerevisiae* (Uetz et al., Nature, 2000, 403: 623, incorporated by reference in its entirety). The protein-protein interaction map of the budding yeast was studied by using a comprehensive system to examine two-hybrid interactions in all possible combinations between the yeast proteins (Ito et al., PNAS, 2000, 97: 1143, incorporated by reference in its entirety), and the genomic protein linkage map of Vaccinia virus was studied using this system (McCraith et al., PNAS, 2000, 97: 4879, incorporated by reference in its entirety).

In certain embodiments of the invention, a synthetic CDR3 (heavy or light chain) may be joined by homologous recombination with a vector encoding a heavy or light chain chassis, a portion of FRM4, and a constant region, to form a full-length heavy or light chain. In certain embodiments of the invention, the homologous recombination is performed directly in yeast cells. In some embodiments, the method comprises:

(a) transforming into yeast cells:
  (i) a linearized vector encoding a heavy or light chain chassis, a portion of FRM4, and a constant region, wherein the site of linearization is between the end of FRM3 of the chassis and the beginning of the constant region; and
  (ii) a library of CDR3 insert nucleotide sequences that are linear and double stranded, wherein each of the CDR3 insert sequences comprises a nucleotide sequence encoding CDR3 and 5'- and 3'-flanking sequences that are sufficiently homologous to the termini of the vector of (i) at the site of linearization to enable homologous recombination to occur between the vector and the library of CDR3 insert sequences; and
(b) allowing homologous recombination to occur between the vector and the CDR3 insert sequences in the transformed yeast cells, such that the CDR3 insert sequences are incorporated into the vector, to produce a vector encoding full-length heavy chain or light chain.

As specified above, the CDR3 inserts may have a 5' flanking sequence and a 3' flanking sequence that are homologous to the termini of the linearized vector. When the CDR3 inserts and the linearized vectors are introduced into a host cell, for example, a yeast cell, the "gap" (the linearization site) created by linearization of the vector is filled by the CDR3 fragment insert through recombination of the homologous sequences at the 5' and 3' termini of these two linear double-stranded DNAs (i.e., the vector and the insert). Through this event of homologous recombination, libraries of circular vectors encoding full-length heavy or light chains comprising variable CDR3 inserts is generated. Particular instances of these methods are presented in the Examples.

Subsequent analysis may be carried out to determine the efficiency of homologous recombination that results in correct insertion of the CDR3 sequences into the vectors. For example, PCR amplification of the CDR3 inserts directly from selected yeast clones may reveal how many clones are recombinant. In certain embodiments, libraries with minimum of about 90% recombinant clones are utilized. In certain other embodiments libraries with a minimum of about 1%, 5% 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% recombinant clones are utilized. The same PCR amplification of selected clones may also reveal the insert size.

To verify the sequence diversity of the inserts in the selected clones, a PCR amplification product with the correct size of insert may be "fingerprinted" with restriction enzymes known to cut or not cut within the amplified region. From a gel electrophoresis pattern, it may be determined whether the clones analyzed are of the same identity or of the distinct or diversified identity. The PCR products may also be sequenced directly to reveal the identity of inserts and the fidelity of the cloning procedure, and to prove the independence and diversity of the clones. FIG. 1 depicts a schematic of recombination between a fragment (e.g., CDR3) and a vector (e.g., comprising a chassis, portion of FRM4, and constant region) for the construction of a library.

2.6. Expression and Screening Systems

Libraries of polynucleotides generated by any of the techniques described herein, or other suitable techniques, can be expressed and screened to identify antibodies having desired structure and/or activity. Expression of the antibodies can be carried out, for example, using cell-free extracts (and e.g., ribosome display), phage display, prokaryotic cells (e.g., bacterial display), or eukaryotic cells (e.g., yeast display). In certain embodiments of the invention, the antibody libraries are expressed in yeast.

In other embodiments, the polynucleotides are engineered to serve as templates that can be expressed in a cell-free extract. Vectors and extracts as described, for example in U.S. Pat. Nos. 5,324,637; 5,492,817; 5,665,563, (each incorporated by reference in its entirety) can be used and many are commercially available. Ribosome display and other cell-free techniques for linking a polynucleotide (i.e., a genotype) to a polypeptide (i.e., a phenotype) can be used, e.g., Profusion™ (see, e.g., U.S. Pat. Nos. 6,348,315; 6,261,804; 6,258,558; and 6,214,553, each incorporated by reference in its entirety).

Alternatively, the polynucleotides of the invention can be expressed in an *E. coli* expression system, such as that described by Pluckthun and Skerra. (Meth. Enzymol., 1989, 178: 476; Biotechnology, 1991, 9: 273, each incorporated by reference in its entirety). The mutant proteins can be expressed for secretion in the medium and/or in the cytoplasm of the bacteria, as described by Better and Horwitz, Meth. Enzymol., 1989, 178: 476, incorporated by reference in its entirety. In some embodiments, the single domains encoding VH and VL are each attached to the 3' end of a sequence encoding a signal sequence, such as the ompA, phoA or pelB signal sequence (Lei et al., J. Bacteriol., 1987, 169: 4379, incorporated by reference in its entirety). These gene fusions are assembled in a dicistronic construct, so that they can be expressed from a single vector, and secreted into the periplasmic space of *E. coli* where they will refold and can be recovered in active form. (Skerra et al., Biotechnology, 1991, 9: 273, incorporated by reference in its entirety). For example, antibody heavy chain genes can be concurrently expressed with antibody light chain genes to produce antibodies or antibody fragments.

In other embodiments of the invention, the antibody sequences are expressed on the membrane surface of a prokaryote, e.g., *E. coli*, using a secretion signal and lipidation moiety as described, e.g., in US20040072740; US20030100023; and US20030036092 (each incorporated by reference in its entirety).

Higher eukaryotic cells, such as mammalian cells, for example myeloma cells (e.g., NS/0 cells), hybridoma cells, Chinese hamster ovary (CHO), and human embryonic kidney (HEK) cells, can also be used for expression of the antibodies of the invention. Typically, antibodies expressed in mammalian cells are designed to be secreted into the culture medium, or expressed on the surface of the cell. The antibody or antibody fragments can be produced, for example, as intact antibody molecules or as individual VH and VL fragments, Fab fragments, single domains, or as single chains (scFv) (Huston et al., PNAS, 1988, 85: 5879, incorporated by reference in its entirety).

Alternatively, antibodies can be expressed and screened by anchored periplasmic expression (APEx 2-hybrid surface display), as described, for example, in Jeong et al., PNAS, 2007, 104: 8247 (incorporated by reference in its entirety) or by other anchoring methods as described, for example, in Mazor et al., Nature Biotechnology, 2007, 25: 563 (incorporated by reference in its entirety).

In other embodiments of the invention, antibodies can be selected using mammalian cell display (Ho et al., PNAS, 2006, 103: 9637, incorporated by reference in its entirety).

The screening of the antibodies derived from the libraries of the invention can be carried out by any appropriate means. For example, binding activity can be evaluated by standard immunoassay and/or affinity chromatography. Screening of the antibodies of the invention for catalytic function, e.g., proteolytic function can be accomplished using a standard assays, e.g., the hemoglobin plaque assay as described in U.S. Pat. No. 5,798,208 (incorporated by reference in its entirety). Determining the ability of candidate antibodies to bind therapeutic targets can be assayed in vitro using, e.g., a BIACORE™ instrument, which measures binding rates of an antibody to a given target or antigen based on surface plasmon resonance. In vivo assays can be conducted using any of a number of animal models and then subsequently tested, as appropriate, in humans. Cell-based biological assays are also contemplated.

One aspect of the instant invention is the speed at which the antibodies of the library can be expressed and screened. In certain embodiments of the invention, the antibody library can be expressed in yeast, which have a doubling time of less than about 3, 4, 5, 6, 7, 8, 9, 10, 11, 12, 13, 14, 15, 16, 17, 18, 19, 20, 21, 22, 23, or 24 hours. In some embodiments, the doubling times are about 1 to about 3 hours, about 2 to about 4, about 3 to about 8 hours, about 3 to about 24, about 5 to about 24, about 4 to about 6 about 5 to about 22, about 6 to about 8, about 7 to about 22, about 8 to about 10 hours, about 7 to about 20, about 9 to about 20, about 9 to about 18, about 11 to about 18, about 11 to about 16, about 13 to about 16, about 16 to about 20, or about 20 to about 30 hours. In certain embodiments of the invention, the antibody library is expressed in yeast with a doubling time of about 16 to about 20 hours, about 8 to about 16 hours, or about 4 to about 8 hours. Thus, the antibody library of the instant invention can be expressed and screened in a matter of hours, as compared to previously known techniques which take several days to express and screen antibody libraries. A limiting step in the throughput of such screening processes in mammalian cells is simply the time required to iteratively regrow populations of isolated cells, which, in some cases, have doubling times greater than the doubling times of the yeast used in the current invention.

In certain embodiments of the invention, the composition of a library may be defined after one or more enrichment steps (for example by screening for antigen binding, or other properties). For example, a library with a composition comprising about x % sequences or libraries of the invention may be enriched to contain about 2x %, 3x %, 4x %, 5x %, 6x %, 7x %, 8x %, 9x %, 10x %, 20x %, 25x %, 40x %, 50x %, 60x % 75x %, 80x %, 90x %, 95x %, or 99x % sequences or libraries of the invention, after one or more screening steps. In other embodiments of the invention, the sequences or libraries of the invention may be enriched about 2-fold, 3-fold, 4-fold, 5-fold, 6-fold, 7-fold, 8-fold, 9-fold, 10-fold, 100-fold, 1,000-fold, or more, relative to their occurrence prior to the one or more enrichment steps. In certain embodiments of the invention, a library may contain at least a certain number of a particular type of sequence(s), such as CDRH3s, CDRL3s, heavy chains, light chains, or whole antibodies (e.g., at least about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or $10^{20}$). In certain embodiments, these sequences may be enriched during one or more enrichment steps, to provide libraries comprising at least about $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, or $10^{19}$ of the respective sequence(s).

2.7. Mutagenesis Approaches for Affinity Maturation

As described above, antibody leads can be identified through a selection process that involves screening the antibodies of a library of the invention for binding to one or more antigens, or for a biological activity. The coding sequences of these antibody leads may be further mutagenized in vitro or in vivo to generate secondary libraries with diversity introduced in the context of the initial antibody leads. The mutagenized antibody leads can then be further screened for binding to target antigens or biological activity, in vitro or in vivo, following procedures similar to those used for the selection of the initial antibody lead from the primary library. Such mutagenesis and selection of primary antibody leads effectively mimics the affinity maturation process naturally occurring in a mammal that produces antibodies with progressive increases in the affinity to an antigen. In one embodiment of the invention, only the CDRH3 region is mutagenized. In another embodiment of the invention, the whole variable region is mutagenized. In other embodiments of the invention one or more of CDRH1, CDRH2, CDRH3, CDRL1, CDRL2, and/ CDRL3 may be mutagenized. In some embodiments of the invention, "light chain shuffling" may be used as part of the affinity maturation protocol. In certain embodiments, this may involve pairing one or more heavy chains with a number of light chains, to select light chains that enhance the affinity and/or biological activity of an antibody. In certain embodiments of the invention, the number of light chains to which the one or more heavy chains can be paired is at least about 2, 5, 10, 100, 1000, $10^4$, $10^5$, $10^6$, $10^7$, $10^8$, $10^9$, or $10^{10}$. In certain embodiments of the invention, these light chains are encoded by plasmids. In other embodiments of the invention, the light chains may be integrated into the genome of the host cell.

The coding sequences of the antibody leads may be mutagenized by a wide variety of methods. Examples of methods of mutagenesis include, but are not limited to site-directed mutagenesis, error-prone PCR mutagenesis, cassette mutagenesis, and random PCR mutagenesis. Alternatively, oligonucleotides encoding regions with the desired mutations can be synthesized and introduced into the sequence to be mutagenized, for example, via recombination or ligation.

Site-directed mutagenesis or point mutagenesis may be used to gradually change the CDR sequences in specific regions. This may be accomplished by using oligonucleotide-directed mutagenesis or PCR. For example, a short sequence of an antibody lead may be replaced with a synthetically mutagenized oligonucleotide in either the heavy chain or light chain region, or both. The method may not be efficient for mutagenizing large numbers of CDR sequences, but may be used for fine tuning of a particular lead to achieve higher affinity toward a specific target protein.

Cassette mutagenesis may also be used to mutagenize the CDR sequences in specific regions. In a typical cassette mutagenesis, a sequence block, or a region, of a single template is replaced by a completely or partially randomized sequence. However, the maximum information content that can be obtained may be statistically limited by the number of random sequences of the oligonucleotides. Similar to point mutagenesis, this method may also be used for fine tuning of a particular lead to achieve higher affinity towards a specific target protein.

Error-prone PCR, or "poison" PCR, may be used to mutagenize the CDR sequences by following protocols described in Caldwell and Joyce, PCR Methods and Applications, 1992, 2: 28; Leung et al., Technique, 1989, 1: 11; Shafikhani et al., Biotechniques, 1997, 23: 304; and Stemmer et al., PNAS, 1994, 91: 10747 (each of which is incorporated by reference in its entirety).

Conditions for error prone PCR may include (a) high concentrations of $Mn^{2+}$ (e.g., about 0.4 to about 0.6 mM) that efficiently induces malfunction of Taq DNA polymerase; and (b) a disproportionally high concentration of one nucleotide substrate (e.g., dGTP) in the PCR reaction that causes incorrect incorporation of this high concentration substrate into the template and produces mutations. Additionally, other factors such as, the number of PCR cycles, the species of DNA polymerase used, and the length of the template, may affect the rate of misincorporation of "wrong" nucleotides into the PCR product. Commercially available kits may be utilized for the mutagenesis of the selected antibody library, such as the "Diversity PCR random mutagenesis kit" (CLONTECH™).

The primer pairs used in PCR-based mutagenesis may, in certain embodiments, include regions matched with the homologous recombination sites in the expression vectors. This design allows facile re-introduction of the PCR products back into the heavy or light chain chassis vectors, after mutagenesis, via homologous recombination.

Other PCR-based mutagenesis methods can also be used, alone or in conjunction with the error prone PCR described above. For example, the PCR amplified CDR segments may be digested with DNase to create nicks in the double stranded DNA. These nicks can be expanded into gaps by other exonucleases such as Bal 31. The gaps may then be filled by random sequences by using DNA Klenow polymerase at a low concentration of regular substrates dGTP, dATP, dTTP, and dCTP with one substrate (e.g., dGTP) at a disproportionately high concentration. This fill-in reaction should produce high frequency mutations in the filled gap regions. These method of DNase digestion may be used in conjunction with error prone PCR to create a high frequency of mutations in the desired CDR segments.

The CDR or antibody segments amplified from the primary antibody leads may also be mutagenized in vivo by exploiting the inherent ability of mutation in pre-B cells. The Ig genes in pre-B cells are specifically susceptible to a high-rate of mutation. The Ig promoter and enhancer facilitate such high rate mutations in a pre-B cell environment while the pre-B cells proliferate. Accordingly, CDR gene segments may be cloned into a mammalian expression vector that contains a human Ig enhancer and promoter. This construct may be introduced into a pre-B cell line, such as 38B9, which allows the mutation of the VH and VL gene segments naturally in the pre-B cells (Liu and Van Ness, Mol. Immunol., 1999, 36: 461, incorporated by reference in its entirety). The mutagenized CDR segments can be amplified from the cultured pre-B cell line and re-introduced back into the chassis-containing vectors) via, for example, homologous recombination.

In some embodiments, a CDR "hit" isolated from screening the library can be re-synthesized, using degenerate codons or trinucleotides, and re-cloned into the heavy or light chain vector using gap repair.

3. Library Sampling

In certain embodiments of the invention, a library of the invention comprises a designed, non-random repertoire wherein the theoretical diversity of particular components of the library (for example, CDRH3), but not necessarily all components or the entire library, can be over-sampled in a physical realization of the library, at a level where there is a certain degree of statistical confidence (e.g., 95%) that any given member of the theoretical library is present in the physical realization of the library at least at a certain frequency (e.g., at least once, twice, three times, four times, five times, or more) in the library.

In a library, it is generally assumed that the number of copies of a given clone obeys a Poisson probability distribution (see Feller, W. *An Introduction to Probability Theory and Its Applications,* 1968, Wiley New York, incorporated by reference in its entirety). The probability of a Poisson random number being zero, corresponding to the probability of missing a given component member in an instance of a library (see below), is $e^{-N}$, where N is the average of the random number. For example, if there are $10^6$ possible theoretical members of a library and a physical realization of the library has $10^7$ members, with an equal probability of each member of the theoretical library being sampled, then the average number of times that each member occurs in the physical realization of the library is $10^7/10^6=10$, and the probability that the number of copies of a given member is zero is $e^{-N}=e^{-10}=0.000045$; or a 99.9955% chance that there is at least one copy of any of the $10^6$ theoretical members in this 10× oversampled library. For a 2.3× oversampled library one is 90% confident that a given component is present. For a 3× oversampled library one is 95% confident that a given component is present. For a 4.6× oversampled library one is 99% confident a given clone is present, and so on.

Therefore, if M is the maximum number of theoretical library members that can be feasibly physically realized, then M/3 is the maximum theoretical repertoire size for which one can be 95% confident that any given member of the theoretical library will be sampled. It is important to note that there is a difference between a 95% chance that a given member is represented and a 95% chance that every possible member is represented. In certain embodiments, the instant invention provides a rationally designed library with diversity so that any given member is 95% likely to be represented in a physical realization of the library. In other embodiments of the invention, the library is designed so that any given member is at least about 0.0001%, 0.001%, 0.01%, 0.1%, 1%, 5%, 10%, 20%, 30%, 40%, 50%, 60%, 70%, 80%, 85%, 90%, 95%, 99%, 99.5%, or 99.9% likely to be represented in a physical realization of the library. For a review, see, e.g., Firth and Patrick, Biomol. Eng., 2005, 22: 105, and Patrick et al., Protein Engineering, 2003, 16: 451, each of which is incorporated by reference in its entirety.

In certain embodiments of the invention, a library may have a theoretical total diversity of X unique members and the physical realization of the theoretical total diversity may contain at least about 1×, 2×, 3×, 4×, 5×, 6×, 7×, 8×9×, 10×, or more members. In some embodiments, the physical realization of the theoretical total diversity may contain about 1× to about 2×, about 2× to about 3×, about 3× to about 4×, about 4× to about 5×, about 5× to about 6× members. In other embodiments, the physical realization of the theoretical total diversity may contain about 1× to about 3×, or about 3× to about 5× total members.

An assumption underlying all directed evolution experiments is that the amount of molecular diversity theoretically possible is enormous compared with the ability to synthesize it, physically realize it, and screen it. The likelihood of finding a variant with improved properties in a given library is maximized when that library is maximally diverse. Patrick et al. used simple statistics to derive a series of equations and computer algorithms for estimating the number of unique sequence variants in libraries constructed by randomized oligonucleotide mutagenesis, error-prone PCR and in vitro recombination. They have written a suite of programs for calculating library statistics, such as GLUE, GLUE-IT, PEDEL, PEDEL-AA, and DRIVeR. These programs are described, with instructions on how to access them, in Patrick et al., Protein Engineering, 2003, 16: 451 and Firth et al., Nucleic Acids Res., 2008, 36: W281 (each of which is incorporated by reference in its entirety).

It is possible to construct a physical realization of a library in which some components of the theoretical diversity (such as CDRH3) are oversampled, while other aspects (VH/VL pairings) are not. For example, consider a library in which $10^8$ CDRH3 segments are designed to be present in a single VH chassis, and then paired with $10^5$ VL genes to produce $10^{13}$ (=$10^8*10^5$) possible full heterodimeric antibodies. If a physical realization of this library is constructed with a diversity of $10^9$ transformant clones, then the CDRH3 diversity is oversampled ten-fold (=$10^9/10^8$), however the possible VH/VL pairings are undersampled by $10^{-4}$ (=$10^9/10^{13}$). In this example, on average, each CDRH3 is paired only with 10 samples of the VL from the possible $10^5$ partners. In certain embodiments of the invention, it is the CDRH3 diversity that is preferably oversampled.

3.1. Other Variants of the Polynucleotide Sequences of the Invention

In certain embodiments, the invention relates to a polynucleotide that hybridizes with a polynucleotide taught herein, or that hybridizes with the complement of a polynucleotide taught herein. For example, an isolated polynucleotide that remains hybridized after hybridization and washing under low, medium, or high stringency conditions to a polynucleotide taught herein or the complement of a polynucleotide taught herein is encompassed by the present invention.

Exemplary low stringency conditions include hybridization with a buffer solution of about 30% to about 35% formamide, about 1 M NaCl, about 1% SDS (sodium dodecyl sulphate) at about 37° C., and a wash in about 1× to about 2×SSC (20×SSC=3.0 M NaCl/0.3 M trisodium citrate) at about 50° C. to about 55° C.

Exemplary moderate stringency conditions include hybridization in about 40% to about 45% formamide, about 1 M NaCl, about 1% SDS at about 37° C., and a wash in about 0.5× to about 1× SSC at abut 55° C. to about 60° C.

Exemplary high stringency conditions include hybridization in about 50% formamide, about 1 M NaCl, about 1% SDS at about 37° C., and a wash in about 0.1×SSC at about 60° C. to about 65° C.

Optionally, wash buffers may comprise about 0.1% to about 1% SDS.

The duration of hybridization is generally less than about 24 hours, usually about 4 to about 12 hours.

3.2. Sub-Libraries and Larger Libraries Comprising the Libraries or Sub-Libraries of the Invention As described throughout the application, the libraries of the current invention are distinguished, in certain embodiments, by their human-like sequence composition and length, and the ability to generate a physical realization of the library which contains all members of (or, in some cases, even oversamples) a particular component of the library. Libraries comprising combinations of the libraries described herein (e.g., CDRH3 and CDRL3 libraries) are encompassed by the invention. Sub-libraries comprising portions of the libraries described herein are also encompassed by the invention (e.g., a CDRH3 library in a particular heavy chain chassis or a sub-set of the CDRH3 libraries). One of ordinary skill in the art will readily recognize that each of the libraries described herein has several components (e.g., CDRH3, VH, CDRL3, VL, etc.), and that the diversity of these components can be varied to produce sub-libraries that fall within the scope of the invention.

Moreover, libraries containing one of the libraries or sub-libraries of the invention also fall within the scope of the invention. For example, in certain embodiments of the invention, one or more libraries or sub-libraries of the invention may be contained within a larger library, which may include sequences derived by other means, for example, non-human or human sequence derived by stochastic or semi-stochastic synthesis. In certain embodiments of the invention, at least about 1% of the sequences in a polynucleotide library may be those of the invention (e.g., CDRH3 sequences, CDRL3 sequences, VH sequences, VL sequences), regardless of the composition of the other 99% of sequences. In other embodiments of the invention, at least about 0.001%, 0.01%, 0.1%, 2%, 5%, 10%, 20%, 30%, 40%, 50%, 60%, 70%, 80%, 81%, 82%, 83%, 84%, 85%, 86%, 87%, 88%, 89%, 90%, 91,%, 92%, 93%, 94%, 95%, 96%, 97%, 98% or 99% of the sequences in any polynucleotide library may be those of the invention, regardless of the composition of the other sequences. In some embodiments, the sequences of the invention may comprise about 0.001% to about 1%, about 1% to about 2%, about 2% to about 5%, about 5% to about 10%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 99% of the sequences in any polynucleotide library, regardless of the composition of the other sequences. Thus, libraries more diverse than one or more libraries or sub-libraries of the invention, but yet still comprising one or more libraries or sub-libraries of the invention, in an amount in which the one or more libraries or sub-libraries of the invention can be effectively screened and from which sequences encoded by the one or more libraries or sub-libraries of the invention can be isolated, also fall within the scope of the invention.

3.3. Alternative Scaffolds

In certain embodiments of the invention, the amino acid products of a library of the invention (e.g., a CDRH3 or CDRL3) may be displayed on an alternative scaffold. Several of these scaffolds have been shown to yield molecules with specificities and affinities that rival those of antibodies. Exemplary alternative scaffolds include those derived from fibronectin (e.g., AdNectin), the β-sandwich (e.g., iMab), lipocalin (e.g., Anticalin), EETI-II/AGRP, BPTI/LACI-D1/ITI-D2 (e.g., Kunitz domain), thioredoxin (e.g., peptide aptamer), protein A (e.g., Affibody), ankyrin repeats (e.g., DARPin), γB-crystallin/ubiquitin (e.g., Affilin), CTLD$_3$ (e.g., Tetranectin), and (LDLR-A module)$_3$ (e.g., Avimers). Additional information on alternative scaffolds are provided in Binz et al., Nat. Biotechnol., 2005 23: 1257 and Skerra, Current Opin. in Biotech., 2007 18: 295-304, each of which is incorporated by reference in its entirety.

4. Other Embodiments Of The Invention

In certain embodiments, the invention comprises a synthetic preimmune human antibody CDRH3 library comprising $10^7$ to $10^8$ polynucleotide sequences representative of the sequence diversity and length diversity found in known heavy chain CDR3 sequences.

In other embodiments, the invention comprises a synthetic preimmune human antibody CDRH3 library comprising polynucleotide sequences encoding CDRH3 represented by the following formula:

[G/D/E/-][N1][DH][N2][H3-JH], wherein [G/D/E/-] is zero to one amino acids in length, [N1] is zero to three amino acids, [DH] is three to ten amino acids in length, [N2] is zero to three amino acids in length, and [H3-JH] is two to nine amino acids in length.

In certain embodiments of the invention, [G/D/E/-] is represented by an amino acid sequence selected from the group consisting of: G, D, E, and nothing.

In some embodiments of the invention, [N1] is represented by an amino acid sequence selected from the group consisting of: G, R, S, P, L, A, V, T, (G/P)(G/R/S/P/L/A/V/T), (R/S/L/A/V/T)(G/P), GG(G/R/S/P/L/A/V/T), G(R/S/P/L/A/V/T)G, (R/S/P/L/A/V/T)GG, and nothing.

In certain embodiments of the invention, [N2] is represented by an amino acid sequence selected from the group consisting of: G, R, S, P, L, A, V, T, (G/P)(G/R/S/P/L/A/V/T), (R/S/L/A/V/T)(G/P), GG(G/R/S/P/L/A/V/T), G(R/S/P/L/A/V/T)G, (R/S/P/L/A/V/T)GG, and nothing.

In some embodiments of the invention, [DH] comprises a sequence selected from the group consisting of: IGHD3-10 reading frame 1 (SEQ ID NO: 1), IGHD3-10 reading frame 2 (SEQ ID NO: 2), IGHD3-10 reading frame 3 (SEQ ID NO: 3), IGHD3-22 reading frame 2 (SEQ ID NO: 4), IGHD6-19 reading frame 1 (SEQ ID NO: 5), IGHD6-19 reading frame 2 (SEQ ID NO: 6), IGHD6-13 reading frame 1 (SEQ ID NO: 7), IGHD6-13 reading frame 2 (SEQ ID NO: 8), IGHD3-03 reading frame 3 (SEQ ID NO: 9), IGHD2-02 reading frame 2 (SEQ ID NO: 10), IGHD2-02 reading frame 3 (SEQ ID NO: 11), IGHD4-17 reading frame 2 (SEQ ID NO: 12), IGHD1-26 reading frame 1 (SEQ ID NO: 13), IGHD1-26 reading frame 3 (SEQ ID NO: 14), IGHD5-5/5-18 reading frame 3 (SEQ ID NO: 15), IGHD2-15 reading frame 2 (SEQ ID NO: 16), and all possible N-terminal and C-terminal truncations of the above-identified IGHDs down to three amino acids.

In certain embodiments of the invention, [H3-JH] comprises a sequence selected from the group consisting of: AEYFQH (SEQ ID NO: 17), EYFQH (SEQ ID NO: 583), YFQH (SEQ ID NO: 584), FQH, QH, YWYFDL (SEQ ID NO: 18), WYFDL (SEQ ID NO: 585), YFDL (SEQ ID NO: 586), FDL, DL, AFDV (SEQ ID NO: 19), FDV, DV, YFDY (SEQ ID NO: 20), FDY, DY, NWFDS (SEQ ID NO: 21), WFDS (SEQ ID NO: 587), FDS, DS, YYYYYGMDV (SEQ ID NO: 22), YYYYGMDV (SEQ ID NO: 588), YYYGMDV (SEQ ID NO: 589), YYGMDV (SEQ ID NO: 590), YGMDV (SEQ ID NO: 591), GMDV (SEQ ID NO: 592), MDV, and DV.

In some embodiments of the invention, the sequences represented by [G/D/E/-][N1][ext-DH][N2][H3-JH] comprise a sequence of about 3 to about 26 amino acids in length.

In certain embodiments of the invention, the sequences represented by [G/D/E/-][N1][ext-DH][N2][H3-JH] comprise a sequence of about 7 to about 23 amino acids in length.

In some embodiments of the invention, the library comprises about $10^7$ to about $10^{10}$ sequences.

In certain embodiments of the invention, the library comprises about $10^7$ sequences.

In some embodiments of the invention, the polynucleotide sequences of the libraries further comprise a 5' polynucleotide sequence encoding a framework 3 (FRM3) region on the corresponding N-terminal end of the library sequence, wherein the FRM3 region comprises a sequence of about 1 to about 9 amino acid residues.

In certain embodiments of the invention, the FRM3 region comprises a sequence selected from the group consisting of CAR, CAK, and CAT.

In some embodiments of the invention, the polynucleotide sequences further comprise a 3' polynucleotide sequence encoding a framework 4 (FRM4) region on the corresponding C-terminal end of the library sequence, wherein the FRM4 region comprises a sequence of about 1 to about 9 amino acid residues.

In certain embodiments of the invention, the library comprises a FRM4 region comprising a sequence selected from WGRG (SEQ ID NO: 23) and WGQG (SEQ ID NO: 23).

In some embodiments of the invention, the polynucleotide sequences further comprise an FRM3 region coding for a corresponding polypeptide sequence comprising a sequence selected from the group consisting of CAR, CAK, and CAT; and an FRM4 region coding for a corresponding polypeptide sequence comprising a sequence selected from WGRG (SEQ ID NO: 23) and WGQG (SEQ ID NO: 23).

In certain embodiments of the invention, the polynucleotide sequences further comprise 5' and 3' sequences which facilitate homologous recombination with a heavy chain chassis.

In some embodiments, the invention comprises a synthetic preimmune human antibody light chain library comprising polynucleotide sequences encoding human antibody kappa light chains represented by the formula:

[IGKV(1-95)][F/L/I/R/W/Y][JK].

In certain embodiments of the invention, [IGKV (1-95)] is selected from the group consisting of IGKV3-20 (SEQ ID NO: 237) (1-95), IGKV1-39 (SEQ ID NO: 233) (1-95), IGKV3-11 (SEQ ID NO: 235) (1-95), IGKV3-15 (SEQ ID NO: 236) (1-95), IGKV1-05 (SEQ ID NO: 229) (1-95), IGKV4-01, IGKV2-28 (SEQ ID NO: 234) (1-95), IGKV 1-33 (1-95), IGKV1-09 (SEQ ID NO: 454) (1-95), IGKV1-12 (SEQ ID NO: 230) (1-95), IGKV2-30 (SEQ ID NO: 467) (1-95), IGKV1-27 (SEQ ID NO: 231) (1-95), IGKV1-16 (SEQ ID NO: 456) (1-95), and truncations of said group up to and including position 95 according to Kabat.

In some embodiments of the invention, [F/L/I/R/W/Y] is an amino acid selected from the group consisting of F, L, I, R, W, and Y.

In certain embodiments of the invention, [JK] comprises a sequence selected from the group consisting of TFGQGTKVEIK (SEQ ID NO: 528) and TFGGGT (SEQ ID NO: 529).

In some embodiments of the invention, the light chain library comprises a kappa light chain library.

In certain embodiments of the invention, the polynucleotide sequences further comprise 5' and 3' sequences which facilitate homologous recombination with a light chain chassis.

In some embodiments, the invention comprises a method for producing a synthetic preimmune human antibody CDRH3 library comprising $10^7$ to $10^8$ polynucleotide sequences, said method comprising:

a) selecting the CDRH3 polynucleotide sequences encoded by the CDRH3 sequences, as follows:
{0 to 5 amino acids selected from the group consisting of fewer than ten of the amino acids preferentially encoded by terminal deoxynucleotidyl transferase (TdT) and preferentially functionally expressed by human B cells}, followed by
{all possible N or C-terminal truncations of IGHD alone and all possible combinations of N and C-terminal truncations}, followed by
{0 to 5 amino acids selected from the group consisting of fewer than ten of the amino acids preferentially encoded by TdT and preferentially functionally expressed by human B cells}, followed by
{all possible N-terminal truncations of IGHJ, down to DXWG, wherein X is S, V, L, or Y}; and b) synthesizing the CDRH3 library described in a) by chemical synthesis, wherein a synthetic preimmune human antibody CDRH3 library is produced.

In certain embodiments, the invention comprises a synthetic preimmune human antibody CDRH3 library comprising $10^7$ to $10^{10}$ polynucleotide sequences representative of known human IGHD and IGHJ germline sequences encoding CDRH3, represented by the following formula:
{0 to 5 amino acids selected from the group consisting of fewer than ten of the amino acids preferentially encoded by terminal deoxynucleotidyl transferase (TdT) and preferentially functionally expressed by human B cells}, followed by {all possible N or C-terminal truncations of IGHD alone and all possible combinations of N and C-terminal truncations}, followed by
{0 to 5 amino acids selected from the group consisting of fewer than ten of the amino acids preferentially encoded by TdT and preferentially functionally expressed by human B cells}, followed by
{all possible N-terminal truncations of IGHJ, down to DXWG (SEQ ID NO: 530), wherein X is S, V, L, or Y}.

In certain embodiments, the invention comprises a synthetic preimmune human antibody heavy chain variable domain library comprising $10^7$ to $10^{10}$ polynucleotide sequences encoding human antibody heavy chain variable domains, said library comprising:

a) an antibody heavy chain chassis, and
b) a CDRH3 repertoire designed based on the human IGHD and IGHJ germline sequences, as follows:
{0 to 5 amino acids selected from the group consisting of fewer than ten of the amino acids preferentially encoded by terminal deoxynucleotidyl transferase (TdT) and preferentially functionally expressed by human B cells}, followed by
{all possible N or C-terminal truncations of IGHD alone and all possible combinations of N and C-terminal truncations}, followed by
{0 to 5 amino acids selected from the group consisting of fewer than ten of the amino acids preferentially encoded by TdT and preferentially functionally expressed by human B cells}, followed by {all possible N-terminal truncations of IGHJ, down to DXWG (SEQ ID NO: 530), wherein X is S, V, L, or Y}.

In some embodiments of the invention, the synthetic preimmune human antibody heavy chain variable domain library is expressed as a full length chain selected from the group consisting of an IgG1 full length chain, an IgG2 full length chain, an IgG3 full length chain, and an IgG4 full length chain.

In certain embodiments of the invention, the human antibody heavy chain chassis is selected from the group consisting of IGHV4-34 (SEQ ID NO: 35), IGHV3-23 (SEQ ID NO: 30), IGHV5-51 (SEQ ID NO: 40), IGHV1-69 (SEQ ID NO: 27), IGHV3-30 (SEQ ID NO: 31), IGHV4-39 (SEQ ID NO: 36), IGHV1-2 (SEQ ID NO: 24), IGHV1-18 (SEQ ID NO: 25), IGHV2-5 (SEQ ID NO: 429), IGHV2-70 (SEQ ID NO: 431, 432), IGHV3-7 (SEQ ID NO: 28), IGHV6-1 (SEQ ID NO: 449), IGHV1-46 (SEQ ID NO: 26), IGHV3-33 (SEQ ID NO: 32), IGHV4-31 (SEQ ID NO: 34), IGHV4-4 (SEQ ID NO: 446, 447), IGHV4-61 (SEQ ID NO: 38), and IGHV3-15 (SEQ ID NO: 29).

In some embodiments of the invention, the synthetic preimmune human antibody heavy chain variable domain library comprises $10^7$ to $10^{10}$ polynucleotide sequences encoding human antibody heavy chain variable domains, said library comprising:
a) an antibody heavy chain chassis, and
b) a synthetic preimmune human antibody CDRH3 library.

In some embodiments of the invention, the polynucleotide sequences are single-stranded coding polynucleotide sequences.

In certain embodiments of the invention, the polynucleotide sequences are single-stranded non-coding polynucleotide sequences.

In some embodiments of the invention, the polynucleotide sequences are double-stranded polynucleotide sequences.

In certain embodiments, the invention comprises a population of replicable cells with a doubling time of four hours or less, in which a synthetic preimmune human antibody repertoire is expressed.

In some embodiments of the invention, the population of replicable cells are yeast cells.

In certain embodiments, the invention comprises a method of generating a full-length antibody library comprising transforming a cell with a preimmune human antibody heavy chain variable domain library and a synthetic preimmune human antibody light chain library.

In some embodiments, the invention comprises a method of generating a full-length antibody library comprising transforming a cell with a preimmune human antibody heavy chain variable domain library and a synthetic preimmune human antibody light chain library.

In certain embodiments, the invention comprises a method of generating an antibody library comprising synthesizing polynucleotide sequences by split-pool DNA synthesis.

In some embodiments of the invention, the polynucleotide sequences are selected from the group consisting of single-stranded coding polynucleotide sequences, single-stranded non-coding polynucleotide sequences, and double-stranded polynucleotide sequences.

In certain embodiments, the invention comprises a synthetic full-length preimmune human antibody library comprising about $10^7$ to about $10^{10}$ polynucleotide sequences representative of the sequence diversity and length diversity found in known heavy chain CDR3 sequences.

In certain embodiments, the invention comprises a method of selecting an antibody of interest from a human antibody library, comprising providing a synthetic preimmune human antibody CDRH3 library comprising a theoretical diversity of (N) polynucleotide sequences representative of the sequence diversity and length diversity found in known heavy chain CDR3 sequences, wherein the physical realization of that diversity is an actual library of a size at least 3(N), thereby providing a 95% probability that a single antibody of interest is present in the library, and selecting an antibody of interest.

In some embodiments of the invention, the theoretical diversity is about $10^7$ to about $10^8$ polynucleotide sequences.

EXAMPLES

This invention is further illustrated by the following examples which should not be construed as limiting. The contents of all references, patents and published patent applications cited throughout this application are hereby incorporated by reference.

In general, the practice of the present invention employs, unless otherwise indicated, conventional techniques of chemistry, molecular biology, recombinant DNA technology, PCR technology, immunology (especially, e.g., antibody technology), expression systems (e.g., yeast expression, cell-free expression, phage display, ribosome display, and PROFUSION™), and any necessary cell culture that are within the skill of the art and are explained in the literature. See, e.g., Sambrook, Fritsch and Maniatis, *Molecular Cloning: Cold Spring Harbor Laboratory Press* (1989); *DNA Cloning*, Vols. 1 and 2, (D. N. Glover, Ed. 1985); *Oligonucleotide Synthesis* (M. J. Gait, Ed. 1984); *PCR Handbook Current Protocols in Nucleic Acid Chemistry*, Beaucage, Ed. John Wiley & Sons (1999) (Editor); *Oxford Handbook of Nucleic Acid Structure*, Neidle, Ed., Oxford Univ Press (1999); *PCR Protocols: A Guide to Methods and Applications*, Innis et al., Academic Press (1990); *PCR Essential Techniques: Essential Techniques*, Burke, Ed., John Wiley & Son Ltd (1996); *The PCR Technique: RT-PCR*, Siebert, Ed., Eaton Pub. Co. (1998); *Antibody Engineering Protocols* (Methods in Molecular Biology), 510, Paul, S., Humana Pr (1996); *Antibody Engineering: A Practical Approach* (Practical Approach Series, 169), McCafferty, Ed., Irl Pr (1996); *Antibodies: A Laboratory Manual*, Harlow et al., C.S.H.L. Press, Pub. (1999); *Current Protocols in Molecular Biology*, eds. Ausubel et al., John Wiley & Sons (1992); *Large-Scale Mammalian Cell Culture Technology*, Lubiniecki, A., Ed., Marcel Dekker, Pub., (1990); *Phage Display: A Laboratory Manual*, C. Barbas (Ed.), CSHL Press, (2001); *Antibody Phage Display*, P O'Brien (Ed.), Humana Press (2001); Border et al., Nature Biotechnology, 1997, 15: 553; Border et al., Methods Enzymol., 2000, 328: 430; ribosome display as described by Pluckthun et al. in U.S. Pat. No. 6,348,315, and Profusion™ as described by Szostak et al. in U.S. Pat. Nos. 6,258,558; 6,261,804; and 6,214,553; and bacterial periplasmic expression as described in US20040058403A1. Each of the references cited in this paragraph is incorporated by reference in its entirety.

Further details regarding antibody sequence analysis using Kabat conventions and programs to screen aligned nucleotide and amino acid sequences may be found, e.g., in Johnson et al., Methods Mol. Biol., 2004, 248: 11; Johnson et al., Int. Immunol., 1998, 10: 1801; Johnson et al., Methods Mol. Biol., 1995, 51: 1; Wu et al., Proteins, 1993, 16: 1; and Martin, Proteins, 1996, 25: 130. Each of the references cited in this paragraph is incorporated by reference in its entirety.

Further details regarding antibody sequence analysis using Chothia conventions may be found, e.g., in Chothia et al., J. Mol. Biol., 1998, 278: 457; Morea et al., Biophys. Chem., 1997, 68: 9; Morea et al., J. Mol. Biol., 1998, 275: 269; Al-Lazikani et al., J. Mol. Biol., 1997, 273: 927. Barre et al., Nat. Struct. Biol., 1994, 1: 915; Chothia et al., J. Mol. Biol., 1992, 227: 799; Chothia et al., Nature, 1989, 342: 877; and Chothia et al., J. Mol. Biol., 1987, 196: 901. Further analysis of CDRH3 conformation may be found in Shirai et al., FEBS Lett., 1999, 455: 188 and Shirai et al., FEBS Lett., 1996, 399: 1. Further details regarding Chothia analysis are described, for example, in Chothia et al., Cold Spring Harb. Symp. Quant Biol., 1987, 52: 399. Each of the references cited in this paragraph is incorporated by reference in its entirety.

Further details regarding CDR contact considerations are described, for example, in MacCallum et al., J. Mol. Biol., 1996, 262: 732, incorporated by reference in its entirety.

Further details regarding the antibody sequences and databases referred to herein are found, e.g., in Tomlinson et al., J. Mol. Biol., 1992, 227: 776, VBASE2 (Retter et al., Nucleic Acids Res., 2005, 33: D671); BLAST (www.ncbi.nlm.nih.gov/BLAST/); CDHIT (bioinformatics.ljcrf.edu/cd-hi/); EMBOSS (www.hgmp.mrc.ac.uk/Software/EMBOSS/); PHYLIP (evolution.genetics.washington.edu/phylip.html); and FASTA (fasta.bioch.virginia.edu). Each of the references cited in this paragraph is incorporated by reference in its entirety.

Example 1

Design of an Exemplary VH Chassis Library

This example demonstrates the selection and design of exemplary, non-limiting VH chassis sequences of the invention. VH chassis sequences were selected by examining collections of human IGHV germline sequences (Scaviner et al., Exp. Clin. Immunogenet., 1999, 16: 234; Tomlinson et al., J. Mol. Biol., 1992, 227: 799; Matsuda et al., J. Exp. Med., 1998, 188: 2151, each incorporated by reference in its entirety). As discussed in the Detailed Description, as well as below, a variety of criteria can be used to select VH chassis sequences, from these data sources or others, for inclusion in the library.

Table 3 (adapted from information provided in Scaviner et al., Exp. Clin. Immunogenet., 1999, 16: 234; Matsuda et cd., J. Exp. Med., 1998, 188: 2151; and Wang et al. Immunol. Cell. Biol., 2008, 86: 111, each incorporated by reference in its entirety) lists the CDRH1 and CDRH2 length, the canonical structure and the estimated relative occurrence in peripheral blood, for the proteins encoded by each of the human IGHV germline sequences.

TABLE 3

IGHV Characteristics and Occurrence in Antibodies from Peripheral Blood

| IGHV Germline | Length of CDRH1 | Length of CDRH2 | Canonical Structures[1] | Estimated Relative Occurrence in Peripheral Blood[2] |
|---|---|---|---|---|
| IGHV1-2 | 5 | 17 | 1-3 | 37 |
| IGHV1-3 | 5 | 17 | 1-3 | 15 |
| IGHV1-8 | 5 | 17 | 1-3 | 13 |
| IGHV1-18 | 5 | 17 | 1-2 | 25 |
| IGHV1-24 | 5 | 17 | 1-U | 5 |
| IGHV1-45 | 5 | 17 | 1-3 | 0 |
| IGHV1-46 | 5 | 17 | 1-3 | 25 |
| IGHV1-58 | 5 | 17 | 1-3 | 2 |
| IGHV1-69 | 5 | 17 | 1-2 | 58 |
| IGHV2-5 | 7 | 16 | 3-1 | 10 |
| IGHV2-26 | 7 | 16 | 3-1 | 9 |
| IGHV2-70 | 7 | 16 | 3-1 | 13 |
| IGHV3-7 | 5 | 17 | 1-3 | 26 |
| IGHV3-9 | 5 | 17 | 1-3 | 15 |
| IGHV3-11 | 5 | 17 | 1-3 | 13 |
| IGHV3-13 | 5 | 16 | 1-1 | 3 |
| IGHV3-15 | 5 | 19 | 1-4 | 14 |
| IGHV3-20 | 5 | 17 | 1-3 | 3 |
| IGHV3-21 | 5 | 17 | 1-3 | 19 |
| IGHV3-23 | 5 | 17 | 1-3 | 80 |
| IGHV3-30 | 5 | 17 | 1-3 | 67 |
| IGHV3-33 | 5 | 17 | 1-3 | 28 |
| IGHV3-43 | 5 | 17 | 1-3 | 2 |
| IGHV3-48 | 5 | 17 | 1-3 | 21 |
| IGHV3-49 | 5 | 19 | 1-U | 8 |
| IGHV3-53 | 5 | 16 | 1-1 | 7 |
| IGHV3-64 | 5 | 17 | 1-3 | 2 |
| IGHV3-66 | 5 | 17 | 1-3 | 3 |
| IGHV3-72 | 5 | 19 | 1-4 | 2 |
| IGHV3-73 | 5 | 19 | 1-4 | 3 |
| IGHV3-74 | 5 | 17 | 1-3 | 14 |
| IGHV4-4 | 5 | 16 | 1-1 | 33 |
| IGHV4-28 | 6 | 16 | 2-1 | 1 |
| IGHV4-31 | 7 | 16 | 3-1 | 25 |
| IGHV4-34 | 5 | 16 | 1-1 | 125 |
| IGHV4-39 | 7 | 16 | 3-1 | 63 |
| IGHV4-59 | 5 | 16 | 1-1 | 51 |
| IGHV4-61 | 7 | 16 | 3-1 | 23 |
| IGHV4-B | 6 | 16 | 2-1 | 7 |
| IGHV5-51 | 5 | 17 | 1-2 | 52 |
| IGHV6-1 | 7 | 18 | 3-5 | 26 |
| IGHV7-4-1 | 5 | 17 | 1-2 | 8 |

[1]Adapted from Chothia et al., J. Mol. Biol., 1992, 227: 799
[2]Adapted from Table S1 of Wang et al., Immunol. Cell. Biol., 2008, 86: 111

In the currently exemplified library, 17 germline sequences were chosen for representation in the VH chassis of the library (Table 4). As described in more detail below, these sequences were selected based on their relatively high representation in the peripheral blood of adults, with consideration given to the structural diversity of the chassis and the representation of particular germline sequences in antibodies used in the clinic. These 17 sequences account for about 76% of the total sample of heavy chain sequences used to derive the results of Table 4. As outlined in the Detailed Description, these criteria are non-limiting, and one of ordinary skill in the art will readily recognize that a variety of other criteria can be used to select the VH chassis sequences, and that the invention is not limited to a library comprising the 17 VH chassis genes presented in Table 4.

TABLE 4

VH Chassis Selected for Use in the Exemplary Library

| VH Chassis | Relative Occurrence | Length of CDRH1 | Length of CDRH2 | Comment |
|---|---|---|---|---|
| VH1-2 | 37 | 5 | 17 | Among highest usage for VH1 family |
| VH1-18 | 25 | 5 | 17 | Among highest usage for VH1 family |
| VH1-46 | 25 | 5 | 17 | Among highest usage for VH1 family |
| VH1-69 | 58 | 5 | 17 | Highest usage for VH1 family. The four chosen VH1 chassis represent about 80% of the VH1 repertoire. |
| VH3-7 | 26 | 5 | 17 | Among highest usage in VH3 family |
| VH3-15 | 14 | 5 | 19 | Not among highest usage, but it has unique structure (H2 of length 19). Highest occurrence among those with such structure. |
| VH3-23 | 80 | 5 | 17 | Highest usage in VH3 family. |
| VH3-30 | 67 | 5 | 17 | Among highest usage in VH3 family |
| VH3-33 | 28 | 5 | 17 | Among highest usage in VH3 family |
| VH3-48 | 21 | 5 | 17 | Among highest usage in VH3 family. The six chosen VH3 chassis account for about 70% of the VH3 repertoire. |
| VH4-31 | 25 | 7 | 16 | Among highest usage in VH4 family |
| VH4-34 | 125 | 5 | 16 | Highest usage in VH4 family |
| VH4-39 | 63 | 7 | 16 | Among highest usage in VH4 family |
| VH4-59 | 51 | 5 | 16 | Among highest usage in VH4 family |
| VH4-61 | 23 | 7 | 16 | Among highest usage in VH4 family |
| VH4-B | 7 | 6 | 16 | Not among highest usage in VH4 family, but has unique structure (H1 of length 6). The 6 chosen VH4 chassis account for close to 90% of the VH4 family repertoire |
| VH5-51 | 52 | 5 | 17 | High usage |

In this particular embodiment of the library, VH chassis derived from sequences in the IGHV2, IGHV6 and IGHV7 germline families were not included. As described in the Detailed Description, this exemplification is not meant to be limiting, as, in some embodiments, it may be desirable to include one or more of these families, particularly as clinical information on antibodies with similar sequences becomes available, to produce libraries with additional diversity that is potentially unexplored, or to study the properties and potential of these IGHV families in greater detail. The modular design of the library of the present invention readily permits the introduction of these, and other, VH chassis sequences. The amino acid sequences of the VH chassis utilized in this particular embodiment of the library, which are derived from the IGHV germline sequences, are presented in Table 5. The details of the derivation procedures are presented below.

TABLE 5

Amino Acid Sequences for VH Chassis Selected for Inclusion in the Exemplary Library

| Chassis | SEQ ID NO: | FRM1 | CDRH1 | FRM2 | CDRH2 | FRM3 |
|---|---|---|---|---|---|---|
| VH1-2 | 24 | QVQLVQSGAEVKKPGASVKVSCKASGYTFT | GYYMH | WVRQAPGQGLEWMG | WINPNSGGTNYAQKFQG | RVTMTRDTSISTAYMELSRLRSDDTAVYYCAR |

TABLE 5-continued

Amino Acid Sequences for VH Chassis Selected
for Inclusion in the Exemplary Library

| Chassis | SEQ ID NO: | FRM1 | CDRH1 | FRM2 | CDRH2 | FRM3 |
|---|---|---|---|---|---|---|
| VH1-18 | 25 | QVQLVQSGAEVKKPGASVKVSCKASGYTFT | SYGIS | WVRQAPGQGLEWMG | WISAYNGNTNYAQKLQG | RVTMTTDTSTSTAYMELRSLRSDDTAVYYCAR |
| VH1-46 | 26 | QVQLVQSGAEVKKPGASVKVSCKASGYTFT | SYYMH | WVRQAPGQGLEWMG | IINPSGGSTSYAQKFQG | RVTMTRDTSTSTVYMELSSLRSEDTAVYYCAR |
| VH1-69 | 27 | QVQLVQSGAEVKKPGSSVKVSCKASGGTFS | SYAIS | WVRQAPGQGLEWMG | GIIPIFGTANYAQKFQG | RVTITADKSTSTAYMELSSLRSEDTAVYYCAR |
| VH3-7 | 28 | EVQLVESGGGLVQPGGSLRLSCAASGFTFS | SYWMS | WVRQAPGKGLEWVA | NIKQDGSEKYYVDSVKG | RFTISRDNAKNSLYLQMNSLRAEDTAVYYCAR |
| VH3-15[1] | 29 | EVQLVESGGGLVKPGGSLRLSCAASGFTFS | NAWMS | WVRQAPGKGLEWVG | RIKSKTDGGTTDYAAPVKG | RFTISRDDSKNTLYLQMNSLRAEDTAVYYCAR |
| VH3-23 | 30 | EVQLLESGGGLVQPGGSLRLSCAASGFTFS | SYAMS | WVRQAPGKGLEWVS | AISGSGGSTYYADSVKG | RFTISRDNSKNTLYLQMNSLRAEDTAVYYCAK |
| VH3-30 | 31 | QVQLVESGGGVVQPGRSLRLSCAASGFTFS | SYGMH | WVRQAPGKGLEWVA | VISYDGSNKYYADSVKG | RFTISRDNSKNTLYLQMNSLRAEDTAVYYCAR |
| VH3-33 | 32 | QVQLVESGGGVVQPGRSLRLSCAASGFTFS | SYGMH | WVRQAPGKGLEWVA | VIWYDGSNKYYADSVKG | RFTISRDNSKNTLYLQMNSLRAEDTAVYYCAR |
| VH3-48 | 33 | EVQLVESGGGLVQPGGSLRLSCAASGFTFS | SYSMN | WVRQAPGKGLEWVS | YISSSSSTIYYADSVKG | RFTISRDNAKNSLYLQMNSLRAEDTAVYYCAR |
| VH4-31 | 34 | QVQLQESGPGLVKPSQTLSLTCTVSGGSIS | SGGYYWS | WIRQHPGKGLEWIG | YIYYSGSTYYNPSLKS | RVTISVDTSKNQFSLKLSSVTAADTAVYYCAR |
| VH4-34[2] | 35 | QVQLQQWGAGLLKPSETLSLTCAVYGGSFS | GYYWS | WIRQPPGKGLEWIG | EIDHSGSTNYNPSLKS | RVTISVDTSKNQFSLKLSSVTAADTAVYYCAR |
| VH4-39 | 36 | QLQLQESGPGLVKPSETLSLTCTVSGGSIS | SSSYYWG | WIRQPPGKGLEWIG | SIYYSGSTYYNPSLKS | RVTISVDTSKNQFSLKLSSVTAADTAVYYCAR |
| VH4-59 | 37 | QVQLQESGPGLVKPSETLSLTCTVSGGSIS | SYYWS | WIRQPPGKGLEWIG | YIYYSGSTNYNPSLKS | RVTISVDTSKNQFSLKLSSVTAADTAVYYCAR |
| VH4-61 | 38 | QVQLQESGPGLVKPSETLSLTCTVSGGSVS | SGSYYWS | WIRQPPGKGLEWIG | YIYYSGSTNYNPSLKS | RVTISVDTSKNQFSLKLSSVTAADTAVYYCAR |
| VH4-B | 39 | QVQLQESGPGLVKPSETLSLTCAVSGYSIS | SGYYWG | WIRQPPGKGLEWIG | SIYHSGSTYYNPSLKS | RVTISVDTSKNQFSLKLSSVTAADTAVYYCAR |

TABLE 5-continued

Amino Acid Sequences for VH Chassis Selected
for Inclusion in the Exemplary Library

| Chassis | SEQ ID NO: | FRM1 | CDRH1 | FRM2 | CDRH2 | FRM3 |
|---|---|---|---|---|---|---|
| VH5-51 | 40 | EVQLVQSG AEVKKPGE SLKISCKG SGYSFT | SYWIG | WVRQMPG KGLEWMG | IIYPGDS DTRYSPS FQG | QVTISADKSI STAYLQWSSL KASDTAVYYC AR |

[1]The original KT sequence in VH3-15 was mutated to RA (bold/underlined) and TT to AR (bold/underlined), in order to match other VH3 family members selected for inclusion in the library. The modification to RA was made so that no unique sequence stretches of up to about 20 amino acids are created. Without being bound by theory, this modification is expected to reduce the odds of introducing novel T-cell epitopes in the VH3-15-derived chassis sequence. The avoidance of T cell epitopes is an additional criterion that can be considered in the design of certain libraries of the invention.
[2]The original NHS motif in VH4-34 was mutated to DHS, in order to remove a possible N-linked glycosylation site in CDR-H2. In certain embodiments of the invention, for example, if the library is transformed into yeast, this may prevent unwanted N-linked glycosylation.

Table 5 provides the amino acid sequences of the seventeen chassis. In nucleotide space, most of the corresponding germline nucleotide sequences include two additional nucleotides on the 3' end (i.e., two-thirds of a codon). In most cases, those two nucleotides are GA. In many cases, nucleotides are added to the 3' end of the IGHV-derived gene segment in vivo, prior to recombination with the IGHD gene segment. Any additional nucleotide would make the resulting codon encode one of the following two amino acids: Asp (if the codon is GAC or GAT) or Glu (if the codon is GAA or GAG). One, or both, of the two 3'-terminal nucleotides may also be deleted in the final rearranged heavy chain sequence. If only the A is deleted, the resulting amino acid is very frequently a G. If both nucleotides are deleted, this position is "empty," but followed by a general V-D addition or an amino acid encoded by the IGHD gene. Further details are presented in Example 5. This first position, after the CAR or CAK motif at the C-terminus of FRM3 (Table 5), is designated the "tail." In the currently exemplified embodiment of the library, this residue may be G, D, E, or nothing. Thus, adding the tail to any chassis enumerated above (Table 5) can produce one of the following four schematic sequences, wherein the residue following the VH chassis is the tail:

(1) [VH_Chassis]-[G]
(2) [VH_Chassis]-[D]
(3) [VH_Chassis]-[E]
(4) [VH_Chassis]

These structures can also be represented in the format:

[VH_Chassis]-[G/D/E/-], wherein the hyphen symbol (–) indicates an empty or null position.

Using the CDRH3 numbering system defined in the Definitions section, the above sequences could be denoted to have amino acid 95 as G, D, or E, for instances (1), (2), and (3), respectively, while the sequence of instance 4 would have no position 95, and CDRH3 proper would begin at position 96 or 97.

In some embodiments of the invention, VH3-66, with canonical structure 1-1 (five residues in CDRH1 and 16 for CDRH2) may be included in the library. The inclusion of VH3-66 may compensate for the removal of other chassis from the library, which may not express well in yeast under some conditions (e.g., VH4-34 and VH4-59).

Example 2

Design of VH Chassis Variants with Variation within CDRH1 and CDRH2

This example demonstrates the introduction of further diversity into the VH chassis by creating mutations in the CDRH1 and CDRH2 regions of each chassis shown in Example 1. The following approach was used to select the positions and nature of the amino acid variation for each chassis: First, the sequence identity between rearranged human heavy chain antibody sequences was analyzed (Lee et al., Immunogenetics, 2006, 57: 917; Jackson et al., J. Immunol. Methods, 2007, 324: 26) and they were classified by the origin of their respective IGHV germline sequence. As an illustrative example, about 200 sequences in the data set exhibited greatest identity to the IGHV1-69 germline, indicating that they were likely to have been derived from IGHV1-69. Next, the occurrence of amino acid residues at each position within the CDRH1 and CDRH2 segments, in each germline family selected in Example 1 was determined. For VH1-69, these occurrences are illustrated in Tables 6 and 7. Second, neutral and/or smaller amino acid residues were favored, where possible, as replacements. Without being bound by theory, the rationale for the choice of these amino acid residues is the desire to provide a more flexible and less sterically hindered context for the display of a diversity of CDR sequences.

TABLE 6

Occurrence of Amino Acid Residues at Each Position Within IGHV1-69-derived CDRH1 Sequences

|   | 31<br>S | 32<br>Y | 33<br>A | 34<br>I | 35<br>S |
|---|---|---|---|---|---|
| A | 1 | 0 | 129 | 0 | 0 |
| C | 0 | 1 | 0 | 0 | 2 |
| D | 0 | 5 | 1 | 0 | 0 |
| E | 0 | 0 | 0 | 0 | 0 |
| F | 0 | 9 | 1 | 8 | 0 |
| G | 0 | 0 | 24 | 0 | 3 |
| H | 2 | 11 | 0 | 0 | 4 |
| I | 2 | 0 | 0 | 159 | 1 |
| K | 3 | 0 | 0 | 0 | 0 |
| L | 0 | 10 | 2 | 5 | 0 |
| M | 1 | 0 | 0 | 0 | 0 |
| N | 21 | 2 | 2 | 0 | 27 |
| P | 0 | 0 | 1 | 0 | 0 |
| Q | 1 | 1 | 0 | 0 | 5 |
| R | 9 | 0 | 0 | 0 | 1 |
| S | 133 | 3 | 7 | 0 | 129 |
| T | 12 | 1 | 10 | 0 | 12 |
| V | 0 | 0 | 7 | 13 | 0 |
| W | 0 | 0 | 0 | 0 | 0 |
| Y | 0 | 142 | 1 | 0 | 1 |

TABLE 7

Occurrence of Amino Acid Residues at Each Position Within IGHV1-69-derived CDRH2 Sequences

|   | 50<br>G | 51<br>I | 52<br>I | 52A<br>P | 53<br>I | 54<br>F | 55<br>G | 56<br>T | 57<br>A | 58<br>N | 59<br>Y | 60<br>A | 61<br>Q | 62<br>K | 63<br>F | 64<br>Q | 65<br>G |
|---|---|---|---|---|---|---|---|---|---|---|---|---|---|---|---|---|---|
| A | 0 | 0 | 7 | 0 | 2 | 0 | 4 | 3 | 132 | 0 | 0 | 178 | 0 | 0 | 0 | 0 | 0 |
| C | 0 | 0 | 0 | 0 | 0 | 0 | 0 | 0 | 0 | 0 | 0 | 0 | 0 | 0 | 0 | 0 | 0 |
| D | 1 | 0 | 0 | 0 | 0 | 0 | 11 | 0 | 1 | 21 | 0 | 0 | 0 | 2 | 0 | 0 | 12 |
| E | 2 | 0 | 0 | 0 | 0 | 0 | 4 | 0 | 0 | 2 | 0 | 1 | 1 | 4 | 0 | 2 | 0 |
| F | 0 | 1 | 0 | 1 | 7 | 119 | 0 | 0 | 0 | 0 | 0 | 0 | 0 | 0 | 180 | 0 | 0 |
| G | 135 | 0 | 1 | 0 | 0 | 0 | 155 | 0 | 3 | 1 | 0 | 0 | 0 | 0 | 0 | 0 | 173 |
| H | 0 | 0 | 0 | 0 | 1 | 0 | 0 | 0 | 0 | 4 | 4 | 0 | 3 | 0 | 0 | 4 | 0 |
| I | 0 | 166 | 159 | 0 | 132 | 2 | 0 | 0 | 34 | 0 | 2 | 1 | 0 | 0 | 0 | 0 | 0 |
| K | 1 | 0 | 0 | 0 | 0 | 0 | 0 | 4 | 1 | 5 | 0 | 0 | 2 | 156 | 0 | 3 | 0 |
| L | 0 | 1 | 2 | 0 | 16 | 37 | 0 | 1 | 0 | 0 | 0 | 0 | 0 | 0 | 3 | 2 | 0 |
| M | 0 | 6 | 2 | 0 | 9 | 1 | 0 | 3 | 0 | 0 | 0 | 0 | 0 | 0 | 0 | 0 | 0 |
| N | 0 | 0 | 1 | 0 | 2 | 0 | 5 | 0 | 0 | 132 | 1 | 0 | 0 | 8 | 0 | 0 | 0 |
| P | 0 | 2 | 0 | 181 | 1 | 3 | 0 | 0 | 15 | 0 | 0 | 3 | 6 | 0 | 0 | 0 | 0 |
| Q | 0 | 0 | 0 | 0 | 0 | 0 | 1 | 0 | 1 | 0 | 0 | 0 | 173 | 2 | 0 | 164 | 0 |
| R | 44 | 0 | 0 | 0 | 0 | 0 | 0 | 0 | 1 | 4 | 0 | 3 | 0 | 0 | 13 | 0 | 9 | 0 |
| S | 1 | 0 | 1 | 1 | 2 | 6 | 3 | 5 | 8 | 7 | 0 | 2 | 0 | 1 | 0 | 0 | 0 |
| T | 1 | 1 | 7 | 2 | 2 | 1 | 0 | 127 | 15 | 8 | 3 | 1 | 0 | 0 | 0 | 0 | 0 |
| V | 0 | 8 | 5 | 0 | 11 | 4 | 0 | 4 | 8 | 0 | 0 | 0 | 0 | 0 | 0 | 0 | 0 |
| W | 0 | 0 | 0 | 0 | 0 | 1 | 0 | 0 | 0 | 0 | 0 | 0 | 0 | 0 | 0 | 0 | 0 |
| Y | 0 | 0 | 0 | 0 | 0 | 11 | 1 | 0 | 0 | 0 | 176 | 0 | 0 | 0 | 1 | 1 | 0 |

The original germline sequence is provided in the second row of the tables, in bold font, beneath the residue number (Kabat system). The entries in the table indicate the number of times a given amino acid residue (first column) is observed at the indicated CDRH1 (Table 6) or CDRH2 (Table 7) position. For example, at position 33 the amino acid type G (glycine) is observed 24 times in the set of IGHV1-69-based sequences that were examined. Thus, applying the criteria above, variants were constructed with N at position 31, L at position 32 (H can be charged, under some conditions), G and T at position 33, no variants at position 34 and N at position 35, resulting in the following VH1-69 chassis CDRH1 single-amino acid variant sequences:

```
                                    (SEQ ID NO: 41)
NYAIS (SEQ ID NO: 42)
SLAIS (SEQ ID NO: 43)
SYGIS (SEQ ID NO: 44)
SYTIS (SEQ ID NO: 45)
SYAIN
```

Similarly, the analysis that produced Table 7 provided a basis for choosing the following single-amino acid variant sequences for VH1-69 chassis CDRH2s:

```
                                    (SEQ ID NO: 46)
SIIPIFGTANYAQKFQG (SEQ ID NO: 47)
GIAPIFGTANYAQKFQG (SEQ ID NO: 48)
GIIPILGTANYAQKFQG (SEQ ID NO: 49)
GIIPIFGTASYAQKFQG
```

A similar approach was used to design and construct variants of the other selected chassis; the resulting CDRH1 and CDRH2 variants for each of the exemplary chassis are provided in Table 8. One of ordinary skill in the art will readily recognize that the methods described herein can be applied to create variants of other VH chassis and VL chassis.

TABLE 8

VH Chassis Variants

| Chassis | CDRH1 | SEQ ID NO: | CDRH2 | SEQ ID NO: | Chassis | CDRH1 | SEQ ID NO: | CDRH2 | SEQ ID NO: |
|---|---|---|---|---|---|---|---|---|---|
| 1-18.0 | SYGIS | 50 | WISAYNGNTNYAQKLQG | 56 | 3-48.0 | SYSMN | 129 | YISSSSSTIYYADSVKG | 136 |
| 1-18.1 | NYGIS | 51 | WISAYNGNTNYAQKLQG | 56 | 3-48.1[1] | NYSMN | 130 | YISSSSSTIYYADSVKG | 136 |
| 1-18.2 | SNGIS | 52 | WISAYNGNTNYAQKLQG | 56 | 3-48.2 | IYSMN | 131 | YISSSSSTIYYADSVKG | 136 |
| 1-18.3 | SYAIS | 53 | WISAYNGNTNYAQKLQG | 56 | 3-48.3 | SNSMN | 132 | YISSSSSTIYYADSVKG | 136 |
| 1-18.4 | SYGIT | 54 | WISAYNGNTNYAQKLQG | 56 | 3-48.4 | SYEMN | 133 | YISSSSSTIYYADSVKG | 136 |
| 1-18.5 | SYGIH | 55 | WISAYNGNTNYAQKLQG | 56 | 3-48.5 | SYNMN | 134 | YISSSSSTIYYADSVKG | 136 |
| 1-18.6 | SYGIS | 50 | SISAYNGNTNYAQKLQG | 57 | 3-48.6 | SYSMT | 135 | YISSSSSTIYYADSVKG | 136 |
| 1-18.7 | SYGIS | 50 | WISTYNGNTNYAQKLQG | 58 | 3-48.7 | SYSMN | 129 | TISSSSSTIYYADSVKG | 137 |
| 1-18.8 | SYGIS | 50 | WISPYNGNTNYAQKLQG | 59 | 3-48.8 | SYSMN | 129 | YISGSSSTIYYADSVKG | 138 |
| 1-18.9 | SYGIS | 50 | WISAYNGNTYYAQKLQG | 60 | 3-48.9 | SYSMN | 129 | YISSSSSTILYADSVKG | 139 |
| 1-2.0 | GYYMH | 61 | WINPNSGGTNYAQKFQG | 67 | 3-7.0 | SYWMS | 140 | NIKQDGSEKYYVDSVKG | 152 |
| 1-2.1 | DYYMH | 62 | WINPNSGGTNYAQKFQG | 67 | 3-7.1 | TYWMS | 141 | NIKQDGSEKYYVDSVKG | 152 |
| 1-2.2 | RYYMH | 63 | WINPNSGGTNYAQKFQG | 67 | 3-7.2 | NYWMS | 142 | NIKQDGSEKYYVDSVKG | 152 |
| 1-2.3 | GSYMH | 64 | WINPNSGGTNYAQKFQG | 67 | 3-7.3 | SSWMS | 143 | NIKQDGSEKYYVDSVKG | 152 |
| 1-2.4 | GYSMH | 65 | WINPNSGGTNYAQKFQG | 67 | 3-7.4 | SYGMS | 144 | NIKQDGSEKYYVDSVKG | 152 |
| 1-2.5 | GYYMQ | 66 | WINPNSGGTNYAQKFQG | 67 | 3-7.5 | SYWMT | 145 | NIKQDGSEKYYVDSVKG | 152 |
| 1-2.6 | GYYMH | 61 | SINPNSGGTNYAQKFQG | 68 | 3-7.6 | SYWMS | 140 | SIKQDGSEKYYVDSVKG | 153 |
| 1-2.7 | GYYMH | 61 | WINPSSGGTNYAQKFQG | 69 | 3-7.7 | SYWMS | 140 | NINQDGSEKYYVDSVKG | 154 |
| 1-2.8 | GYYMH | 61 | WINPNSGGTKYAQKFQG | 70 | 3-7.8 | SYWMS | 140 | NIKSSDGSEKYYVDSVKG | 155 |
| 1-2.9 | GYYMH | 61 | WINPNSGGTSYAQKFQG | 71 | 3-7.9 | SYWMS | 140 | NIKQDGSEKQYVDSVKG | 156 |
| 1-46.0 | SYYMH | 72 | IINPSGGSTSYAQKFQG | 79 | 4-31.0 | SGGYYWS | 147 | YIYYSGSTYYNPSLKS | 157 |
| 1-46.1 | NYYMH | 73 | IINPSGGSTSYAQKFQG | 79 | 4-31.1 | SGSYYWS | 148 | YIYYSGSTYYNPSLKS | 157 |
| 1-46.2 | SSYMH | 74 | IINPSGGSTSYAQKFQG | 79 | 4-31.2 | SGTYYWS | 149 | YIYYSGSTYYNPSLKS | 157 |
| 1-46.3 | SYSMH | 75 | IINPSGGSTSYAQKFQG | 79 | 4-31.3 | SGGTYWS | 150 | YIYYSGSTYYNPSLKS | 157 |
| 1-46.4 | SYYIH | 76 | IINPSGGSTSYAQKFQG | 79 | 4-31.4 | SGGYSWS | 151 | YIYYSGSTYYNPSLKS | 157 |

TABLE 8-continued

VH Chassis Variants

| Chassis | CDRH1 | SEQ ID NO: | CDRH2 | SEQ ID NO: | Chassis | CDRH1 | SEQ ID NO: | CDRH2 | SEQ ID NO: |
|---|---|---|---|---|---|---|---|---|---|
| 1-46.5 | SYYMV | 77 | IINPSGGST SYAQKFQG | 79 | 4-31.5 | SGGYYWS | 147 | SIYYSGSTY YNPSLKS | 158 |
| 1-46.6 | SYYMS | 78 | IINPSGGST SYAQKFQG | 79 | 4-31.6 | SGGYYWS | 147 | NIYYSGSTY YNPSLKS | 159 |
| 1-46.7 | SYYMH | 72 | VINPSGGST SYAQKFQG | 80 | 4-31.7 | SGGYYWS | 147 | YIYYSGNTY YNPSLKS | 160 |
| 1-46.8 | SYYMH | 72 | IINPGGGST SYAQKFQG | 81 | 4-31.8 | SGGYYWS | 147 | YIYYSGSTS YNPSLKS | 161 |
| 1-46.9 | SYYMH | 72 | IINPSGGST TYAQKFQG | 82 | 4-31.9 | SGGYYWS | 147 | YIYYSGSTV YNPSLKS | 162 |
| 1-69.0 | SYAIS | 83 | GIIPIFGTA NYAQKFQG | 84 | 4-34.0 | GYYWS | 163 | EIDHSGSTN YNPSLKS | 166 |
| 1-69.1 | NYAIS | 41 | GIIPIFGTA NYAQKFQG | 84 | 4-34.1 | DYYWS | 164 | EIDHSGSTN YNPSLKS | 166 |
| 1-69.2 | SLAIS | 42 | GIIPIFGTA NYAQKFQG | 84 | 4-34.2 | GYYWT | 165 | EIDHSGSTN YNPSLKS | 166 |
| 1-69.3 | SYGIS | 43 | GIIPIFGTA NYAQKFQG | 84 | 4-34.3 | GYYWS | 163 | DIDHSGSTN YNPSLKS | 167 |
| 1-69.4 | SYTIS | 44 | GIIPIFGTA NYAQKFQG | 84 | 4-34.4 | GYYWS | 163 | EISHSGSTN YNPSLKS | 168 |
| 1-69.5 | SYAIN | 45 | GIIPIFGTA NYAQKFQG | 84 | 4-34.5 | GYYWS | 163 | EIDQSGSTN YNPSLKS | 169 |
| 1-69.6 | SYAIS | 83 | SIIPIFGTA NYAQKFQG | 46 | 4-34.6 | GYYWS | 163 | EIDHGGSTN YNPSLKS | 170 |
| 1-69.7 | SYAIS | 83 | GIAPIFGTA NYAQKFQG | 47 | 4-34.7 | GYYWS | 163 | EIDHSGNTN YNPSLKS | 171 |
| 1-69.8 | SYAIS | 83 | GIIPILGTA NYAQKFQG | 48 | 4-34.8 | GYYWS | 163 | EIDHSGSTS YNPSLKS | 172 |
| 1-69.9 | SYAIS | 83 | GIIPIFGTA SYAQKFQG | 49 | 4-34.9 | GYYWS | 163 | EIDHSGSTD YNPSLKS | 173 |
| 3-15.0 | NAWMS | 85 | RIKSKTDGG TTDYAAPVKG | 91 | 4-39.0 | SSSYYWG | 174 | SIYYSGSTY YNPSLKS | 181 |
| 3-15.1 | KAWMS | 86 | RIKSKTDGG TTDYAAPVKG | 91 | 4-39.1 | TSSYYWG | 175 | SIYYSGSTY YNPSLKS | 181 |
| 3-15.2 | DAWMS | 87 | RIKSKTDGG TTDYAAPVKG | 91 | 4-39.2 | SNSYYWG | 176 | SIYYSGSTY YNPSLKS | 181 |
| 3-15.3 | NALMS | 88 | RIKSKTDGG TTDYAAPVKG | 91 | 4-39.3 | SSDYYWG | 177 | SIYYSGSTY YNPSLKS | 181 |
| 3-15.4 | NAAMS | 89 | RIKSKTDGG TTDYAAPVKG | 91 | 4-39.4 | SSNYYWG | 178 | SIYYSGSTY YNPSLKS | 181 |
| 3-15.5 | NAWMN | 90 | RIKSKTDGG TTDYAAPVKG | 91 | 4-39.5 | SSRYYWG | 179 | SIYYSGSTY YNPSLKS | 181 |
| 3-15.6 | NAWMS | 85 | SIKSKTDGG TTDYAAPVKG | 92 | 4-39.6 | SSSYAWG | 180 | SIYYSGSTY YNPSLKS | 181 |
| 3-15.7 | NAWMS | 85 | RIKSTTDGG TTDYAAPVKG | 93 | 4-39.7 | SSSYYWG | 174 | NIYYSGSTY YNPSLKS | 182 |
| 3-15.8 | NAWMS | 85 | RIKSKADGG TTDYAAPVKG | 94 | 4-39.8 | SSSYYWG | 174 | SISYSGSTY YNPSLKS | 183 |
| 3-15.9 | NAWMS | 85 | RIKSKTDGG TTGYAAPVKG | 95 | 4-39.9 | SSSYYWG | 174 | SIYYSGSTS YNPSLKS | 184 |

TABLE 8-continued

VH Chassis Variants

| Chassis | CDRH1 | SEQ ID NO: | CDRH2 | SEQ ID NO: | Chassis | CDRH1 | SEQ ID NO: | CDRH2 | SEQ ID NO: |
|---|---|---|---|---|---|---|---|---|---|
| 3-23.0 | SYAMS | 96 | AISGSGGST YYADSVKG | 100 | 4-59.0 | SYYWS | 185 | YIYYSGSTN YNPSLKS | 189 |
| 3-23.1 | NYAMS | 97 | AISGSGGST YYADSVKG | 100 | 4-59.1 | TYYWS | 186 | YIYYSGSTN YNPSLKS | 189 |
| 3-23.2 | TYAMS | 98 | AISGSGGST YYADSVKG | 100 | 4-59.2 | SSYWS | 187 | YIYYSGSTN YNPSLKS | 189 |
| 3-23.3 | SSAMS | 99 | AISGSGGST YYADSVKG | 100 | 4-59.3 | SYSWS | 188 | YIYYSGSTN YNPSLKS | 189 |
| 3-23.4 | SYAMS | 96 | GISGSGGST YYADSVKG | 101 | 4-59.4 | SYYWS | 185 | FIYYSGSTN YNPSLKS | 190 |
| 3-23.5 | SYAMS | 96 | SISGSGGST YYADSVKG | 102 | 4-59.5 | SYYWS | 185 | HIYYSGSTN YNPSLKS | 191 |
| 3-23.6 | SYAMS | 96 | TISGSGGST YYADSVKG | 103 | 4-59.6 | SYYWS | 185 | SIYYSGSTN YNPSLKS | 192 |
| 3-23.7 | SYAMS | 96 | VISGSGGST YYADSVKG | 104 | 4-59.7 | SYYWS | 185 | YIYSSGSTN YNPSLKS | 193 |
| 3-23.8 | SYAMS | 96 | AISASGGST YYADSVKG | 105 | 4-59.8 | SYYWS | 185 | YIYYSGSTD YNPSLKS | 194 |
| 3-23.9 | SYAMS | 96 | AISGSGGST SYADSVKG | 106 | 4-59.9 | SYYWS | 185 | YIYYSGSTT YNPSLKS | 195 |
| 3-30.0 | SYGMH | 107 | VISYDGSNK YYADSVKG | 111 | 4-61.0 | SGSYYWS | 196 | YIYYSGSTN YNPSLKS | 202 |
| 3-30.1 | NYGMH | 108 | VISYDGSNK YYADSVKG | 111 | 4-61.1 | SGGYYWS | 197 | YIYYSGSTN YNPSLKS | 202 |
| 3-30.2 | SYAMH | 109 | VISYDGSNK YYADSVKG | 111 | 4-61.2 | SGNYYWS | 198 | YIYYSGSTN YNPSLKS | 202 |
| 3-30.3 | SYGFH | 110 | VISYDGSNK YYADSVKG | 111 | 4-61.3 | SGSSYWS | 199 | YIYYSGSTN YNPSLKS | 202 |
| 3-30.4 | SYGMH | 107 | FISYDGSNK YYADSVKG | 112 | 4-61.4 | SGSYSWS | 200 | YIYYSGSTN YNPSLKS | 202 |
| 3-30.5 | SYGMH | 107 | LISYDGSNK YYADSVKG | 113 | 4-61.5 | SGSYYWT | 201 | YIYYSGSTN YNPSLKS | 202 |
| 3-30.6 | SYGMH | 107 | VISSDGSNK YYADSVKG | 114 | 4-61.6 | SGSYYWS | 196 | RIYYSGSTN YNPSLKS | 203 |
| 3-30.7 | SYGMH | 107 | VISYDGNNK YYADSVKG | 115 | 4-61.7 | SGSYYWS | 196 | SIYYSGSTN YNPSLKS | 204 |
| 3-30.8 | SYGMH | 107 | VISYDGSIK YYADSVKG | 116 | 4-61.8 | SGSYYWS | 196 | YIYTSGSTN YNPSLKS | 205 |
| 3-30.9 | SYGMH | 107 | VISYDGSNQ YYADSVKG | 117 | 4-61.9 | SGSYYWS | 196 | YIYYSGSTS YNPSLKS | 206 |
| 3-33.0 | SYGMH | 118 | VIWYDGSNK YYADSVKG | 124 | 4-B.0 | SGYYWG | 207 | SIYHSGSTY YNPSLKS | 212 |
| 3-33.1 | TYGMH | 119 | VIWYDGSNK YYADSVKG | 124 | 4-B.1 | SAYYWG | 208 | SIYHSGSTY YNPSLKS | 212 |
| 3-33.2 | NYGMH | 120 | VIWYDGSNK YYADSVKG | 124 | 4-B.2 | SGSYWG | 209 | SIYHSGSTY YNPSLKS | 212 |
| 3-33.3 | SSGMH | 121 | VIWYDGSNK YYADSVKG | 124 | 4-B.3 | SGYNWG | 210 | SIYHSGSTY YNPSLKS | 212 |
| 3-33.4 | SYAMH | 122 | VIWYDGSNK YYADSVKG | 124 | 4-B.4 | SGYYWA | 211 | SIYHSGSTY YNPSLKS | 212 |

TABLE 8-continued

VH Chassis Variants

| Chassis | CDRH1 | SEQ ID NO: | CDRH2 | SEQ ID NO: | Chassis | CDRH1 | SEQ ID NO: | CDRH2 | SEQ ID NO: |
|---|---|---|---|---|---|---|---|---|---|
| 3-33.5 | SYGMN | 123 | VIWYDGSNK YYADSVKG | 124 | 4-B.5 | SGYYWG | 207 | TIYHSGSTY YNPSLKS | 213 |
| 3-33.6 | SYGMH | 118 | LIWYDGSNK YYADSVKG | 125 | 4-B.6 | SGYYWG | 207 | SSYHSGSTY YNPSLKS | 214 |
| 3-33.7 | SYGMH | 118 | FIWYDGSNK YYADSVKG | 126 | 4-B.7 | SGYYWG | 207 | SIYHSGNTY YNPSLKS | 215 |
| 3-33.8 | SYGMH | 118 | VIWYDGSNK SYADSVKG | 127 | 4-B.8 | SGYYWG | 207 | SIYHSGSTN YNPSLKS | 216 |
| 3-33.9 | SYGMH | 118 | VIWYDGSNK GYADSVKG | 128 | 4-B.9 | SGYYWG | 207 | SIYHSGSTG YNPSLKS | 217 |
| | | | | | 5-51.0 | SYWIG | 218 | IIYPGDSDT RYSPSFQG | 224 |
| | | | | | 5-51.1 | TYWIG | 219 | IIYPGDSDT RYSPSFQG | 224 |
| | | | | | 5-51.2 | NYWIG | 220 | IIYPGDSDT RYSPSFQG | 224 |
| | | | | | 5-51.3 | SNWIG | 221 | IIYPGDSDT RYSPSFQG | 224 |
| | | | | | 5-51.4 | SYYIG | 222 | IIYPGDSDT RYSPSFQG | 224 |
| | | | | | 5-51.5 | SYWIS | 223 | IIYPGDSDT RYSPSFQG | 224 |
| | | | | | 5-51.6 | SYWIG | 218 | SIYPGDSDT RYSPSFQG | 225 |
| | | | | | 5-51.7 | SYWIG | 218 | IIYPADSDT RYSPSFQG | 226 |
| | | | | | 5-51.8 | SYWIG | 218 | IIYPGDSST RYSPSFQG | 227 |
| | | | | | 5-51.9 | SYWIG | 218 | IIYPGDSDT TYSPSFQG | 228 |

[1]Contains an N-linked glycosylation site which can be removed, if desired, as described herein.

As specified in the Detailed Description, other criteria can be used to select which amino acids are to be altered and the identity of the resulting altered sequence. This is true for any heavy chain chassis sequence, or any other sequence of the invention. The approach outlined above is meant for illustrative purposes and is non-limiting.

Example 3

Design of an Exemplary VK Chassis Library

This example describes the design of an exemplary VK chassis library. One of ordinary skill in the art will recognize that similar principles may be used to design a Vλ library, or a library containing both VK and Vλ chassis. Design of a Vλ chassis library is presented in Example 4.

As was previously demonstrated in Example 1, for IGHV germline sequences, the sequence characteristics and occurrence of human IGKV germline sequences in antibodies from peripheral blood were analyzed. The data are presented in Table 9.

TABLE 9

IGKV Gene Characteristics and Occurrence in Antibodies from Peripheral Blood

| IGKV Gene | Alternative Names | CDRL1 Length | CDRL2 Length | Canonical Structures[1] | Estimated Relative Occurrence in Peripheral Blood[2] |
|---|---|---|---|---|---|
| IGKV1-05 | L12 | 11 | 7 | 2-1-(U) | 69 |
| IGKV1-06 | L11 | 11 | 7 | 2-1-(1) | 14 |

TABLE 9-continued

IGKV Gene Characteristics and Occurrence
in Antibodies from Peripheral Blood

| IGKV Gene | Alternative Names | CDRL1 Length | CDRL2 Length | Canonical Structures[1] | Estimated Relative Occurrence in Peripheral Blood[2] |
|---|---|---|---|---|---|
| IGKV1-08 | L9 | 11 | 7 | 2-1-(1) | 9 |
| IGKV1-09 | L8 | 11 | 7 | 2-1-(1) | 24 |
| IGKV1-12 | L5, L19 | 11 | 7 | 2-1-(1) | 32 |
| IGKV1-13 | L4, L18 | 11 | 7 | 2-1-(1) | 13 |
| IGKV1-16 | L1 | 11 | 7 | 2-1-(1) | 15 |
| IGKV1-17 | A30 | 11 | 7 | 2-1-(1) | 34 |
| IGKV1-27 | A20 | 11 | 7 | 2-1-(1) | 27 |
| IGKV1-33 | O8, O18 | 11 | 7 | 2-1-(1) | 43 |
| IGKV1-37 | O14, O4 | 11 | 7 | 2-1-(1) | 3 |
| IGKV1-39 | O2, O12 | 11 | 7 | 2-1-(1) | 147 |
| IGKV1D-16 | L15 | 11 | 7 | 2-1-(1) | 6 |
| IGKV1D-17 | L14 | 11 | 7 | 2-1-(1) | 1 |
| IGKV1D-43 | L23 | 11 | 7 | 2-1-(1) | 1 |
| IGKV1D-8 | L24 | 11 | 7 | 2-1-(1) | 1 |
| IGKV2-24 | A23 | 16 | 7 | 4-1-(1) | 8 |
| IGKV2-28 | A19, A3 | 16 | 7 | 4-1-(1) | 62 |
| IGKV2-29 | A18 | 16 | 7 | 4-1-(1) | 6 |
| IGKV2-30 | A17 | 16 | 7 | 4-1-(1) | 30 |
| IGKV2-40 | O1, O11 | 17 | 7 | 3-1-(1) | 3 |
| IGKV2D-26 | A8 | 16 | 7 | 4-1-(1) | 0 |
| IGKV2D-29 | A2 | 16 | 7 | 4-1-(1) | 20 |
| IGKV2D-30 | A1 | 16 | 7 | 4-1-(1) | 4 |
| IGKV3-11 | L6 | 11 | 7 | 2-1-(1) | 87 |
| IGKV3-15 | L2 | 11 | 7 | 2-1-(1) | 53 |
| IGKV3-20 | A27 | 12 | 7 | 6-1-(1) | 195 |
| IGKV3D-07 | L25 | 12 | 7 | 6-1-(1) | 0 |
| IGKV3D-11 | L20 | 11 | 7 | 2-1-(U) | 0 |
| IGKV3D-20 | A11 | 12 | 7 | 6-1-(1) | 2 |
| IGKV4-1 | B3 | 17 | 7 | 3-1-(1) | 83 |
| IGKV5-2 | B2 | 11 | 7 | 2-1-(1) | 1 |
| IGKV6-21 | A10, A26 | 11 | 7 | 2-1-(1) | 6 |
| IGKV6D-41 | A14 | 11 | 7 | 2-1-(1) | 0 |

[1]Adapted from Tomlinson et al. EMBO J., 1995, 14: 4628, incorporated by reference in its entirety. The number in parenthesis refers to canonical structures in CDRL3, if one assuming the most common length (see Example 5 for further detail about CDRL3).

[2]Estimated from sets of human VK sequences compiled from the NCBI database; full set of GI numbers provided in Appendix A.

The 14 most commonly occurring IGKV germline genes (bolded in column 6 of Table 9) account for just over 90% of the usage of the entire repertoire in peripheral blood. From the analysis of Table 9, ten IGKV germline genes were selected for representation as chassis in the currently exemplified library (Table 10). All but V1-12 and V1-27 are among the top 10 most commonly occurring. IGKV germline genes VH2-30, which was tenth in terms of occurrence in peripheral blood, was not included in the currently exemplified embodiment of the library, in order to maintain the proportion of chassis with short (i.e., 11 or 12 residues in length) CDRL1 sequences at about 80% in the final set of 10 chassis. V1-12 was included in its place. V1-17 was more similar to other members of the V1 family that were already selected; therefore, V1-27 was included, instead of V1-17. In other embodiments, the library could include 12 chassis (e.g., the ten of Table 10 plus V1-17 and V2-30), or a different set of any "N" chassis, chosen strictly by occurrence (Table 9) or any other criteria. The ten chosen VK chassis account for about 80% of the usage in the data set believed to be representative of the entire kappa light chain repertoire.

TABLE 10

VK Chassis Selected for Use in the Exemplary Library

| Chassis | CDR-L1 Length | CDR-L2 Length | Canonical Structures | Estimated Relative Occurrence in Peripheral Blood |
|---|---|---|---|---|
| VK1-5 | 11 | 7 | 2-1-(U) | 69 |
| VK1-12 | 11 | 7 | 2-1-(1) | 32 |
| VK1-27 | 11 | 7 | 2-1-(1) | 27 |
| VK1-33 | 11 | 7 | 2-1-(1) | 43 |
| VK1-39 | 11 | 7 | 2-1-(1) | 147 |
| VK2-28 | 16 | 7 | 4-1-(1) | 62 |
| VK3-11 | 11 | 7 | 2-1-(1) | 87 |
| VK3-15 | 11 | 7 | 2-1-(1) | 53 |
| VK3-20 | 12 | 7 | 6-1-(1) | 195 |
| VK4-1 | 17 | 7 | 3-1-(1) | 83 |

The amino acid sequences of the selected VK chassis enumerated in Table 10 are provided in Table 11.

TABLE 11

Amino Acid Sequences for VK Chassis Selected for Inclusion in the Exemplary Library

| Chassis | FRM1 | CDRL1 | FRM2 | CDRL2 | FRM3 | CDRL3[1] | SEQ ID NO: |
|---|---|---|---|---|---|---|---|
| VK1-5 | DIQMTQS PSTLSAS VGDRVTI TC | RASQSI SSWLA | WYQQKP GKAPKL LIY | DASSLE S | GVPSRFSGSGSGT EFTLTISSLQPDD FATYYC | QQYNS YS | 229 |
| VK1-12 | DIQMTQS PSSVSAS VGDRVTI TC | RASQGI SSWLA | WYQQKP GKAPKL LIY | AASSLQ S | GVPSRFSGSGSGT DFTLTISSLQPED FATYYC | QQANS FP | 230 |
| VK1-27 | DIQMTQS PSSLSAS VGDRVTI TC | RASQGI SNYLA | WYQQKP GKVPKL LIY | AASTLQ S | GVPSRFSGSGSGT DFTLTISSLQPED VATYYC | QKYNS AP | 231 |
| VK1-33 | DIQMTQS PSSLSAS VGDRVTI TC | QASQDI SNYLN | WYQQKP GKAPKL LIY | DASNLE T | GVPSRFSGSGSGT DFTFTISSLQPED IATYYC | QQYDN LP | 232 |
| VK1-39 | DIQMTQS PSSLSAS VGDRVTI TC | RASQSI SSYLN | WYQQKP GKAPKL LIY | AASSLQ S | GVPSRFSGSGSGT DFTLTISSLQPED FATYYC | QQSYS TP | 233 |
| VK2-28 | DIVMTQS PLSLPVT PGEPASI SC | RSSQSL LHSNGY NYLD | WYLQKP GQSPQL LIY | LGSNRA S | GVPDRFSGSGSGT DFTLKISRVEAED VGVYYC | MQALQ TP | 234 |
| VK3-11 | EIVLTQS PATLSLS PGERATL SC | RASQSV SSYLA | WYQQKP GQAPRL LIY | DASNRA T | GIPARFSGSGSGT DFTLTISSLEPED FAVYYC | QQRSN WP | 235 |
| VK3-15 | EIVMTQS PATLSVS PGERATL SC | RASQSV SSNLA | WYQQKP GQAPRL LIY | GASTRA T | GIPARFSGSGSGT EFTLTISSLQSED FAVYYC | QQYNN WP | 236 |
| VK3-20 | EIVLTQS PGTLSLS PGERATL SC | RASQSV SSSYLA | WYQQKP GQAPRL LIY | GASSRA T | GIPDRFSGSGSGT DFTLTISRLEPED FAVYYC | QQYGS SP | 237 |
| VK4-1 | DIVMTQS PDSLAVS LGERATI NC | KSSQSV LYSSNN KNYLA | WYQQKP GQPPKL LIY | WASTRE S | GVPDRFSGSGSGT DFTLTISSLQAED VAVYYC | QQYYS TP | 238 |

[1]Note that the portion of the IGKV gene contributing to VKCDR3 is not considered part of the chassis as described herein. The VK chassis is defined as Kabat residues 1 to 88 of the IGKV-encoded sequence, or from the start of FRM1 to the end of FRM3. The portion of the VKCDR3 sequence contributed by the IGKV gene is referred to herein as the L3-VK region.

Example 4

Design of an Exemplary Vλ Chassis Library

This example, describes the design of an exemplary Vλ chassis library. As was previously demonstrated in Examples 1-3, for the VH and VK chassis sequences, the sequence characteristics and occurrence of human IgλN germline-derived sequences in peripheral blood were analyzed. As with the assignment of other sequences set forth herein to germline families, assignment of Vλ sequences to a germline family was performed via SoDA and VBASE2 (Volpe and Kepler, Bioinformatics, 2006, 22: 438; Mollova et al., BMS Systems Biology, 2007, IS: P30, each incorporated by reference in its entirety). The data are presented in Table 12.

TABLE 12

IGλV Gene Characteristics and Occurrence in Peripheral Blood

| IGλV Gene | Alternative Name | Canonical Structures[1] | Contribution of IGVλ Gene to CDRL3 | Estimated Relative Occurrence in Peripheral Blood[2] |
|---|---|---|---|---|
| IGλV3-1 | 3R | 11-7(*) | 8 | 11.5 |
| IGλV3-21 | 3H | 11-7(*) | 9 | 10.5 |
| IGλV2-14 | 2A2 | 14-7(A) | 9 | 10.1 |
| IGλV1-40 | 1E | 14-7(A) | 9 | 7.7 |
| IGλV3-19 | 3L | 11-7(*) | 9 | 7.6 |
| IGλV1-51 | 1B | 13-7(A) | 9 | 7.4 |
| IGλV1-44 | 1C | 13-7(A) | 9 | 7.0 |
| IGλV6-57 | 6A | 13-7(B) | 7 | 6.1 |
| IGλV2-8 | 2C | 14-7(A) | 9 | 4.7 |
| IGλV3-25 | 3M | 11-7(*) | 9 | 4.6 |
| IGλV2-23 | 2B2 | 14-7(A) | 9 | 4.3 |
| IGλV3-10 | 3P | 11-7(*) | 9 | 3.4 |
| IGλV4-69 | 4B | 12-11(*) | 7 | 3.0 |
| IGλV1-47 | 1G | 13-7(A) | 9 | 2.9 |
| IGλV2-11 | 2E | 14-7(A) | 9 | 1.3 |
| IGλV7-43 | 7A | 14-7(B) | 8 | 1.3 |
| IGλV7-46 | 7B | 14-7(B) | 8 | 1.1 |
| IGλV5-45 | 5C | 14-11(*) | 8 | 1.0 |
| IGλV4-60 | 4A | 12-11(*) | 7 | 0.7 |
| IGλV10-54 | 8A | 14-7(B) | 8 | 0.7 |
| IGλV8-61 | 10A | 13-7(C) | 9 | 0.7 |
| IGλV3-9 | 3J | 11-7(*) | 8 | 0.6 |
| IGλV1-36 | 1A | 13-7(A) | 9 | 0.4 |
| IGλV2-18 | 2D | 14-7(A) | 9 | 0.3 |
| IGλV3-16 | 3A | 11-7(*) | 9 | 0.2 |
| IGλV3-27 | | 11-7(*) | 7 | 0.2 |
| IGλV4-3 | 5A | 14-11(*) | 8 | 0.2 |
| IGλV5-39 | 4C | 12-11(*) | 12 | 0.2 |
| IGλV9-49 | 9A | 12-12(*) | 12 | 0.2 |
| IGλV3-12 | 3I | 11-7(*) | 9 | 0.1 |

[1]Adapted from Williams et al. J. Mol. Biol. 1996: 264, 220-32. The (*) indicates that the canonical structure is entirely defined by the lengths of CDRs L1 and L2. When distinct structures are possible for identical L1 and L2 length combinations, the structure present in a given gene is set forth as A, B, or C.
[2]Estimated from a set of human Vλ sequences compiled from the NCBI database; full set of GI codes set forth in Appendix B.

To choose a subset of the sequences from Table 12 to serve as chassis, those represented at less than 1% in peripheral blood (as extrapolated from analysis of published sequences corresponding to the GI codes provided in Appendix B) were first discarded. From the remaining 18 germline sequences, the top occurring genes for each unique canonical structure and contribution to CDRL3, as well as any germline gene represented at more than the 5% level, were chosen to constitute the exemplary Vλ chassis. The list of 11 such sequences is given in Table 13, below. These 11 sequences represent approximately 73% of the repertoire in the examined data set (Appendix B).

TABLE 13

Vλ Chassis Selected for Use in the Exemplary Library

| Chassis | CDRL1 Length | CDRL2 Length | Canonical Structure | Relative Occurrence |
|---|---|---|---|---|
| Vλ3-1 | 11 | 7 | 11-7(*) | 11.5 |
| Vλ3-21 | 11 | 7 | 11-7(*) | 10.5 |
| Vλ2-14 | 14 | 7 | 14-7(A) | 10.1 |
| Vλ1-40 | 14 | 7 | 14-7(A) | 7.7 |
| Vλ3-19 | 11 | 7 | 11-7(*) | 7.6 |
| Vλ1-51 | 13 | 7 | 13-7(A) | 7.4 |
| Vλ1-44 | 13 | 7 | 13-7(A) | 7.0 |
| Vλ6-57 | 13 | 7 | 13-7(B) | 6.1 |
| Vλ4-69 | 12 | 11 | 12-11(*) | 3.0 |
| Vλ7-43 | 14 | 7 | 14-7(B) | 1.3 |
| Vλ5-45 | 11 | 11 | 14-11(*) | 1.0 |

The amino acid sequences of the selected Vλ chassis enumerated in Table 13 are provided in Table 14, below.

TABLE 14

Amino Acid Sequences for Vλ Chassis Selected for Inclusion in the Exemplary Library

| Chassis | FRM1 | CDRL1 | FRM2 | CDRL2 | FRM3 | CDRL3[2] |
|---|---|---|---|---|---|---|
| Vλ1-40 SEQ ID NO: 531 | QSVLTQP PSVSGAP GQRVTIS C | TGSSSN IGAGYD ---VH | WYQQLP GTAPKL LIY | GN---- SNRPS | GVPDRFSGSKSG-- TSASLAITGLQAEDE ADYYC | QSYDSS LSG |

TABLE 14-continued

Amino Acid Sequences for Vλ Chassis Selected
for Inclusion in the Exemplary Library

| Chassis | FRM1 | CDRL1 | FRM2 | CDRL2 | FRM3 | CDRL3[2] |
|---|---|---|---|---|---|---|
| Vλ1-44 SEQ ID NO: 532 | QSVLTQP PSASGTP GQRVTIS C | SGSSSN IGSNT- ---VN | WYQQLP GTAPKL LIY | SN---- NQRPS | GVPDRFSGSKSG-- TSASLAISGLQSEDE ADYYC | AAWDDS LNG |
| Vλ1-51 SEQ ID NO: 533 | QSVLTQP PSVSAAP GQKVTIS C | SGSSSN IGNNY- ---VS | WYQQLP GTAPKL LIY | DN---- NKRPS | GIPDRFSGSKSG-- TSATLGITGLQTGDE ADYYC | GTWDSS LSA |
| Vλ2-14 SEQ ID NO: 534 | QSALTQP ASVSGSP GQSITIS C | TGTSSD VGGYNY ---VS | WYQQHP GKAPKL MIY | EV---- SNRPS | GVSNRFSGSKSG-- NTASLTISGLQAEDE ADYYC | SSYTSS STL |
| Vλ3-1[1] SEQ ID NO: 535 | SYELTQP PSVSVSP GQTASIT C | SGDKLG DKY--- ---AS | WYQQKP GQSPVL VIY | QD---- SKRPS | GIPERFSGSNSG-- NTATLTISGTQAMDE ADYYC | QAWDSS TA- |
| Vλ3-19 SEQ ID NO: 536 | SSELTQD PAVSVAL GQTVRIT C | QGDSLR SYY--- ---AS | WYQQKP GQAPVL VIY | GK---- NNRPS | GIPDRFSGSSSG-- NTASLTITGAQAEDE ADYYC | NSRDSS GNH |
| Vλ3-21 SEQ ID NO: 537 | SYVLTQP PSVSVAP GKTARIT C | GGNNIG SKS--- ---VH | WYQQKP GQAPVL VIY | YD---- SDRPS | GIPERFSGSNSG-- NTATLTISRVEAGDE ADYYC | QVWDSS SDH |
| Vλ4-69 SEQ ID NO: 538 | QLVLTQS PSASASL GASVKLT C | TLSSGH SSYA-- ---IA | WHQQQP EKGPRY LMK | LNSDGS HSKGD | GIPDRFSGSSSG-- AERYLTISSLQSEDE ADYYC | QTWGTG I-- |
| Vλ6-57 SEQ ID NO: 539 | NFMLTQP HSVSESP GKTVTIS C | TRSSGS IASNY- ---VQ | WYQQRP GSSPTT VIY | ED---- NQRPS | GVPDRFSGSIDSSSN SASLTISGLKTEDEA DYYC | QSYDSS N-- |
| Vλ5-45 SEQ ID NO: 540 | QAVLTQP ASLSASP GASASLT C | TLRSGI NVGTYR ---IY | WYQQKP GSPPQY LLR | YKSDSD KQQGS | GVPSRFSGSKDASAN AGILLISGLQSEDEA DYYC | MIWHSS AS- |
| Vλ7-43 SEQ ID NO: 541 | QTVVTQE PSLTVSP GGTVTLT C | ASSTGA VTSGYY ---PN | WFQQKP GQAPRA LIY | ST---- SNKHS | WTPARFSGSLLG-- GKAALTLSGVQPEDE AEYYC | LLYYGG AQ- |

[1]The last amino acid in CDRL1 of the Vλ3-1 chassis, S, differs from the corresponding one in the IGλV3-1 germline gene, C. This was done to avoid having a potentially unpaired CYS (C) amino acid in the resulting synthetic light chain.
[2]Note that, as for the Vκ chassis, the portion of the IGλV gene contributing to VλCDR3 is not considered part of the chassis as described herein. The Vλ chassis is defined as Kabat residues 1 to 88 of the IGλV-encoded sequence, or from the start of FRM1 to the end of FRM3. The portion of the VλCDR3 sequence contributed by the IGλV gene is referred to herein as the L3-Vλ region.

Example 5

Design of a CDRH3 Library

This example describes the design of a CDHR3 library from its individual components. In nature, the CDRH3 sequence is derived from a complex process involving recombination of three different genes, termed IGHV, IGHD and IGHJ. In addition to recombination, these genes may also undergo progressive nucleotide deletions: from the 3' end of the IGHV gene, either end of the IGHD gene, and/or the 5' end of the IGHJ gene. Non-templated nucleotide additions may also occur at the junctions between the V, D and J sequences. Non-templated additions at the V-D junction are referred to as "N1", and those at the D-J junction are referred to as "N2". The D gene segments may be read in three forward and, in some cases, three reverse reading frames.

In the design of the present exemplary library, the codon (nucleotide triplet) or single amino acid was designated as a fundamental unit, to maintain all sequences in the desired reading frame. Thus, all deletions or additions to the gene segments are carried out via the addition or deletion of amino acids or codons, and not single nucleotides. According to the CDRH3 numbering system of this application, CDRH3 extends from amino acid number 95 (when present; see Example 1) to amino acid 102.

Example 5.1

Selection of the DH Segments

In this illustrative example, selection of DH gene segments for use in the library was performed according to principles similar to those used for the selection of the chassis sequences. First, an analysis of IGHD gene usage was performed, using data from Lee et al., Immunogenetics, 2006, 57: 917; Corbett et al., PNAS, 1982, 79: 4118; and Souto-Carneiro et al., J. Immunol., 2004, 172: 6790 (each incorporated by reference in its entirety), with preference for representation in the library given to those IGHD genes most frequently observed in human sequences. Second, the degree of deletion on either end of the IGHD gene segments was estimated by comparison with known heavy chain sequences, using the SoDA algorithm (Volpe et al., Bioinformatics, 2006, 22: 438, incorporated by reference in its entirety) and sequence alignments. For the presently exemplified library, progressively deleted DH segments, as short as three amino acids, were included. As enumerated in the Detailed Description, other embodiments of the invention comprise DH segments with deletions to a different length, for example, about 1, 2, 4, 5, 6, 7, 8, 9, or 10 amino acids. Table 15 shows the relative occurrence of IGHD gene usage in human antibody heavy chain sequences isolated mainly from peripheral blood B cells (list adapted from Lee et al., Immunogenetics, 2006, 57: 917, incorporated by reference in its entirety).

TABLE 15

Usage of IGHD Genes Based on Relative Occurrence in Peripheral Blood*

| IGHD Gene | Estimated Relative Occurrence in Peripheral Blood[3] |
|---|---|
| IGHD3-10 | 117 |
| IGHD3-22 | 111 |
| IGHD6-19 | 95 |
| IGHD6-13 | 93 |
| IGHD3-3 | 82 |
| IGHD2-2 | 63 |
| IGHD4-17 | 61 |
| IGHD1-26 | 51 |
| IGHD5-5/5-18[1] | 49 |
| IGHD2-15 | 47 |
| IGHD6-6 | 38 |
| IGHD3-9 | 32 |
| IGHD5-12 | 29 |
| IGHD5-24 | 29 |
| IGHD2-21 | 28 |
| IGHD3-16 | 18 |
| IGHD4-23 | 13 |
| IGHD1-1 | 9 |
| IGHD1-7 | 9 |
| IGHD4-4/4-11[2] | 7 |
| IGHD1-20 | 6 |
| IGHD7-27 | 6 |
| IGHD2-8 | 4 |
| IGHD6-25 | 3 |

[1]Although distinct genes in the genome, the nucleotide sequences of IGHD5-5 and IGHD5-18 are 100% identical and thus indistinguishable in rearranged VH sequences.
[2]IGHD4-4 and IGHD4-11 are also 100% identical.
[3]Adapted from Lee et al. Immunogenetics, 2006, 57: 917, by merging the information for distinct alleles of the same IGHD gene.
*IGHD1-14 may also be included in the libraries of the invention.

The translations of the ten most commonly expressed IGHD gene sequences found in naturally occurring human antibodies, in three reading frames, are shown in Table 16. As in Table 15, data regarding IGHD sequence usage and reading frame statistics were derived from Lee et al., 2006, and data regarding IGHD sequence reading frame usage were further complemented by data derived from Corbett et al., PNAS, 1982, 79: 4118 and Souto-Carneiro et al., J. Immunol, 2004, 172: 6790, each of which is incorporated by reference in its entirety.

| IGHD | RF 1 | SEQ ID NO | RF 2 | SEQ ID NO | RF 3 | SEQ ID NO |
|---|---|---|---|---|---|---|
| IGHD3-10 | VLLWFGELL | 1 | YYYGSGSYYN | 2 | ITMVRGVII | 3 |
| IGHD3-22 | VLLL###WLLL | 239 | YYYDSSGYYY | 4 | ITMIVVVIT | 240 |
| IGHD6-19 | GYSSGWY | 5 | GIAVAG | 6 | V#QWLV | 241 |
| IGHD6-13 | GYSSSWY | 7 | GIAAAG | 8 | V#QQLV | 242 |
| IGHD3-03 | VLRFLEWLLY | 243 | YYDFWSGYYT | 244 | ITIFGVVII | 9 |
| IGHD2-02 | WIL##YQLLC | 245 | GYCSSTSCYT | 10 | DIVVVPAAM | 11 |
| IGHD4-17 | #LR#L | 246 | DYGDY | 12 | TTVT | 247 |
| IGHD1-26 | GIVGATT | 13 | V#WELL | 248 | YSGSYY | 14 |
| IGHD5-5/5-18 | VDTAMVT | 249 | WIQLWL | 250 | GYSYGY | 15 |
| IGHD2-15 | RIL#WW#LLL | 251 | GYCSGGSCYS | 16 | DIVVVAAT | 252 |

In the presently exemplified library, the top 10 IGHD genes most frequently used in heavy chain sequences occurring in peripheral blood were chosen for representation in the library. Other embodiments of the library could readily utilize more or fewer D genes. The amino acid sequences of the selected IGHD genes, including the most commonly used reading frames and the total number of variants after progressive N- and C-terminal deletion to a minimum of three residues, are listed in Table 17. As depicted in Table 17, only the most commonly occurring alleles of certain IGHD genes were included in the illustrative library. This is, however, not required, and other embodiments of the invention may utilize IGHD reading frames that occur less frequently in the peripheral blood.

TABLE 17

D Genes Selected for use in the Exemplary Library

| IGHD Gene[1] | Amino Acid Sequence | SEQ ID NO: | Total Number of Variants[2] |
|---|---|---|---|
| IGHD1-26_1 | GIVGATT | 13 | 15 |
| IGHD1-26_3 | YSGSYY | 14 | 10 |
| IGHD2-2_2 | GYCSSTSCYT | 10 | 9[3] |
| IGHD2-2_3 | DIVVVPAAM | 11 | 28 |
| IGHD2-15_2 | GYCSGGSCYS | 16 | 9 |
| IGHD3-3_3 | ITIFGVVII | 9 | 28 |
| IGHD3-10_1 | VLLWFGELL | 1 | 28 |
| IGHD3-10_2 | YYYGSGSYYN | 2 | 36 |
| IGHD3-10_3 | ITMVRGVII | 3 | 28 |
| IGHD3-22_2 | YYYDSSGYYY | 4 | 36 |
| IGHD4-17_2 | DYGDY | 12 | 6 |
| IGHD5-5_3 | GYSYGY | 15 | 10 |
| IGHD6-13_1 | GYSSSWY | 7 | 15 |
| IGHD6-13_2 | GIAAAG | 8 | 10 |

TABLE 17-continued

D Genes Selected for use in the Exemplary Library

| IGHD Gene[1] | Amino Acid Sequence | SEQ ID NO: | Total Number of Variants[2] |
|---|---|---|---|
| IGHD6-19_1 | GYSSGWY | 5 | 15 |
| IGHD6-19_2 | GIAVAG | 6 | 10 |

[1]The reading frame (RF) is specified as _RF after the name of the gene.
[2]In most cases the total number of variants is given by (N-1) times (N-2) divided by two, where N is the total length in amino acids of the intact D segment.
[3]As detailed herein, the number of variants for segments containing a putative disulfide bond (two C or Cys residues) is limited in this illustrative embodiment.

For each of the selected sequences of Table 17, variants were generated by systematic deletion from the N- and/or C-termini, until there were three amino acids remaining. For example, for the IGHD4-17_2 above, the full sequence DYGDY (SEQ ID NO: 12) may be used to generate the progressive deletion variants: DYGD (SEQ ID NO: 613), YGDY (SEQ ID NO: 614), DYG, GDY and YGD. In general, for any full-length sequence of size N, there will be a total of (N−1)*(N−2)/2 total variants, including the original full sequence. For the disulfide-loop-encoding segments, as exemplified by reading frame 2 of both IGHD2-2 and IGHD2-15, (i.e., IGHD2-2_2 and IGH2-15_2), the progressive deletions were limited, so as to leave the loop intact i.e., only amino acids N-terminal to the first Cys, or C-terminal to the second Cys, were deleted in the respective DH segment variants. The foregoing strategy was used to avoid the presence of unpaired cysteine residues in the exemplified version of the library. However, as discussed in the Detailed Description, other embodiments of the library may include unpaired cysteine residues, or the substitution of these cysteine residues with other amino acids. In the cases where the truncation of the IGHD gene is limited by the presence of the Cys residues, only 9 variants (including the original full sequence) were generated; e.g., for IGHD2-22, the variants would be: GYCSSTSCYT (SEQ ID NO: 10), GYCSSTSCY (SEQ ID NO: 615), YCSSTSCYT (SEQ ID NO: 616), CSSTSCYT (SEQ ID NO: 617), GYCSSTSC (SEQ ID NO: 618), YCSSTSCY (SEQ ID NO: 619), CSST-SCY (SEQ ID NO: 620), YCSSTSC (SEQ ID NO: 621) and CSSTSC (SEQ ID NO: 622).

According to the criteria outlined above, 293 DH sequences were obtained from the selected IGHD gene segments, including the original IGHD gene segments. Certain sequences are redundant. For example, it is possible to obtain the YYY variant from either IGHD3-10_2 (full sequence YYYGSGSYYN (SEQ ID NO: 2)), or in two different ways from IGHD3-22_2 (SEQ ID NO: 4) (YYYDSSGYYY). When redundant sequences are removed, the number of unique DH segment sequences in this illustrative embodiment of the library is 278. These sequences are enumerated in Table 18.

TABLE 18

DH Gene Segments Used in the Presently Exemplified Library*

| DH Segment Designation[1] | Peptide | SEQ ID NO: | DH Segment Designation | Peptide | SEQ ID NO: |
|---|---|---|---|---|---|
| IGHD1-26_1-1 | ATT | | IGHD3-10_2-20 | YYGSG | 713 |
| IGHD1-26_1-2 | GAT | | IGHD3-10_2-21 | YYYGS | 714 |
| IGHD1-26_1-3 | GIV | | IGHD3-10_2-22 | GSGSYY | 715 |

TABLE 18-continued

DH Gene Segments Used in the Presently Exemplified Library*

| DH Segment Designation[1] | Peptide | SEQ ID NO: | DH Segment Designation | Peptide | SEQ ID NO: |
|---|---|---|---|---|---|
| IGHD1-26_1-4 | IVG | | IGHD3-10_2-23 | SGSYYN | 716 |
| IGHD1-26_1-5 | VGA | | IGHD3-10_2-24 | YGSGSY | 717 |
| IGHD1-26_1-6 | GATT | 623 | IGHD3-10_2-25 | YYGSGS | 718 |
| IGHD1-26_1-7 | GIVG | 624 | IGHD3-10_2-26 | YYYGSG | 719 |
| IGHD1-26_1-8 | IVGA | 625 | IGHD3-10_2-27 | GSGSYYN | 720 |
| IGHD1-26_1-9 | VGAT | 626 | IGHD3-10_2-28 | YGSGSYY | 721 |
| IGHD1-26_1-10 | GIVGA | 627 | IGHD3-10_2-29 | YYGSGSY | 722 |
| IGHD1-26_1-11 | IVGAT | 628 | IGHD3-10_2-30 | YYYGSGS | 723 |
| IGHD1-26_1-12 | VGATT | 629 | IGHD3-10_2-31 | YGSGSYYN | 724 |
| IGHD1-26_1-13 | GIVGAT | 630 | IGHD3-10_2-32 | YYGSGSYY | 725 |
| IGHD1-26_1-14 | IVGATT | 631 | IGHD3-10_2-33 | YYYGSGSY | 726 |
| IGHD1-26_1-15 | GIVGATT | 13 | IGHD3-10_2-34 | YYGSGSYYN | 727 |
| IGHD1-26_3-1 | YSG | | IGHD3-10_2-35 | YYYGSGSYY | 728 |
| IGHD1-26_3-2 | YSGS | 632 | IGHD3-10_2-36 | YYYGSGSYYN | 2 |
| IGHD1-26_3-3 | YSGSY | 633 | IGHD3-10_3-1 | GVI | |
| IGHD1-26_3-4 | YSGSYY | 14 | IGHD3-10_3-2 | ITM | |
| IGHD2-02_2-1 | CSSTSC | 622 | IGHD3-10_3-3 | MVR | |
| IGHD2-02_2-2 | CSSTSCY | 620 | IGHD3-10_3-4 | RGV | |
| IGHD2-02_2-3 | YCSSTSC | 621 | IGHD3-10_3-5 | TMV | |
| IGHD2-02_2-4 | CSSTSCYT | 617 | IGHD3-10_3-6 | VII | |
| IGHD2-02_2-5 | GYCSSTSC | 618 | IGHD3-10_3-7 | VRG | |
| IGHD2-02_2-6 | YCSSTSCY | 619 | IGHD3-10_3-8 | GVII | 729 |
| IGHD2-02_2-7 | GYCSSTSCY | 615 | IGHD3-10_3-9 | ITMV | 730 |
| IGHD2-02_2-8 | YCSSTSCYT | 616 | IGHD3-10_3-10 | MVRG | 731 |
| IGHD2-02_2-9 | GYCSSTSCYT | 10 | IGHD3-10_3-11 | RGVI | 732 |
| IGHD2-02_3-1 | AAM | | IGHD3-10_3-12 | TMVR | 733 |
| IGHD2-02_3-2 | DIV | | IGHD3-10_3-13 | VRGV | 734 |
| IGHD2-02_3-3 | IVV | | IGHD3-10_3-14 | ITMVR | 735 |
| IGHD2-02_3-4 | PAA | | IGHD3-10_3-15 | MVRGV | 736 |
| IGHD2-02_3-5 | VPA | | IGHD3-10_3-16 | RGVII | 737 |
| IGHD2-02_3-6 | VVP | | IGHD3-10_3-17 | TMVRG | 738 |
| IGHD2-02_3-7 | VVV | | IGHD3-10_3-18 | VRGVI | 739 |
| IGHD2-02_3-8 | DIVV | 634 | IGHD3-10_3-19 | ITMVRG | 740 |
| IGHD2-02_3-9 | IVVV | 635 | IGHD3-10_3-20 | MVRGVI | 741 |
| IGHD2-02_3-10 | PAAM | 636 | IGHD3-10_3-21 | TMVRGV | 742 |
| IGHD2-02_3-11 | VPAA | 637 | IGHD3-10_3-22 | VRGVII | 743 |
| IGHD2-02_3-12 | VVPA | 638 | IGHD3-10_3-23 | ITMVRGV | 744 |

TABLE 18-continued

DH Gene Segments Used in the Presently Exemplified Library*

| DH Segment Designation[1] | Peptide | SEQ ID NO: | DH Segment Designation | Peptide | SEQ ID NO: |
|---|---|---|---|---|---|
| IGHD2-02_3-13 | VVVP | 639 | IGHD3-10_3-24 | MVRGVII | 745 |
| IGHD2-02_3-14 | DIVVV | 640 | IGHD3-10_3-25 | TMVRGVI | 746 |
| IGHD2-02_3-15 | IVVVP | 641 | IGHD3-10_3-26 | ITMVRGVI | 747 |
| IGHD2-02_3-16 | VPAAM | 642 | IGHD3-10_3-27 | TMVRGVII | 748 |
| IGHD2-02_3-17 | VVPAA | 643 | IGHD3-10_3-28 | ITMVRGVII | 3 |
| IGHD2-02_3-18 | VVVPA | 644 | IGHD3-22_2-1 | DSS | |
| IGHD2-02_3-19 | DIVVVP | 645 | IGHD3-22_2-2 | GYY | |
| IGHD2-02_3-20 | IVVVPA | 646 | IGHD3-22_2-3 | SGY | |
| IGHD2-02_3-21 | VVPAAM | 647 | IGHD3-22_2-4 | SSG | |
| IGHD2-02_3-22 | VVVPAA | 648 | IGHD3-22_2-5 | YDS | |
| IGHD2-02_3-23 | DIVVVPA | 649 | IGHD3-22_2-6 | YYD | |
| IGHD2-02_3-24 | IVVVPAA | 650 | IGHD3-22_2-7 | DSSG | 749 |
| IGHD2-02_3-25 | VVVPAAM | 651 | IGHD3-22_2-8 | GYYY | 750 |
| IGHD2-02_3-26 | DIVVVPAA | 652 | IGHD3-22_2-9 | SGYY | 751 |
| IGHD2-02_3-27 | IVVVPAAM | 653 | IGHD3-22_2-10 | SSGY | 752 |
| IGHD2-02_3-28 | DIVVVPAAM | 11 | IGHD3-22_2-11 | YDSS | 753 |
| IGHD2-15_2-1 | CSGGSC | 654 | IGHD3-22_2-12 | YYDS | 754 |
| IGHD2-15_2-2 | CSGGSCY | 655 | IGHD3-22_2-13 | YYYD | 755 |
| IGHD2-15_2-3 | YCSGGSC | 656 | IGHD3-22_2-14 | DSSGY | 756 |
| IGHD2-15_2-4 | CSGGSCYS | 657 | IGHD3-22_2-15 | SGYYY | 757 |
| IGHD2-15_2-5 | GYCSGGSC | 658 | IGHD3-22_2-16 | SSGYY | 758 |
| IGHD2-15_2-6 | YCSGGSCY | 659 | IGHD3-22_2-17 | YDSSG | 759 |
| IGHD2-15_2-7 | GYCSGGSCY | 660 | IGHD3-22_2-18 | YYDSS | 760 |
| IGHD2-15_2-8 | YCSGGSCYS | 661 | IGHD3-22_2-19 | YYYDS | 761 |
| IGHD2-15_2-9 | GYCSGGSCYS | 16 | IGHD3-22_2-20 | DSSGYY | 762 |
| IGHD3-03_3-1 | FGV | | IGHD3-22_2-21 | SSGYYY | 763 |
| IGHD3-03_3-2 | GVV | | IGHD3-22_2-22 | YDSSGY | 764 |
| IGHD3-03_3-3 | IFG | | IGHD3-22_2-23 | YDSSG | 765 |
| IGHD3-03_3-4 | ITI | | IGHD3-22_2-24 | YYYDSS | 766 |
| IGHD3-03_3-5 | TIF | | IGHD3-22_2-25 | DSSGYYY | 767 |
| IGHD3-03_3-6 | VVI | | IGHD3-22_2-26 | YDSSGYY | 768 |
| IGHD3-03_3-7 | FGVV | 662 | IGHD3-22_2-27 | YDSSGY | 769 |
| IGHD3-03_3-8 | GVVI | 663 | IGHD3-22_2-28 | YYYDSSG | 770 |
| IGHD3-03_3-9 | IFGV | 664 | IGHD3-22_2-29 | YDSSGYYY | 771 |
| IGHD3-03_3-10 | ITIF | 665 | IGHD3-22_2-30 | YDSSGYY | 772 |
| IGHD3-03_3-11 | TIFG | 666 | IGHD3-22_2-31 | YYYDSSGY | 773 |
| IGHD3-03_3-12 | VVII | 667 | IGHD3-22_2-32 | YYDSSGYYY | 774 |

TABLE 18-continued

DH Gene Segments Used in the Presently Exemplified Library*

| DH Segment Designation[1] | Peptide | SEQ ID NO: | DH Segment Designation | Peptide | SEQ ID NO: |
|---|---|---|---|---|---|
| IGHD3-03_3-13 | FGVVI | 668 | IGHD3-22_2-33 | YYYDSSGYY | 775 |
| IGHD3-03_3-14 | GVVII | 669 | IGHD3-22_2-34 | YYYDSSGYYY | 4 |
| IGHD3-03_3-15 | IFGVV | 670 | IGHD4-17_2-1 | DYG | |
| IGHD3-03_3-16 | ITIFG | 671 | IGHD4-17_2-2 | GDY | |
| IGHD3-03_3-17 | TIFGV | 672 | IGHD4-17_2-3 | YGD | |
| IGHD3-03_3-18 | FGVVII | 673 | IGHD4-17_2-4 | DYGD | 613 |
| IGHD3-03_3-19 | IFGVVI | 674 | IGHD4-17_2-5 | YGDY | 614 |
| IGHD3-03_3-20 | ITIFGV | 675 | IGHD4-17_2-6 | DYGDY | 12 |
| IGHD3-03_3-21 | TIFGVV | 676 | IGHD5-5_3-1 | SYG | |
| IGHD3-03_3-22 | IFGVVII | 677 | IGHD5-5_3-2 | YGY | |
| IGHD3-03_3-23 | ITIFGVV | 678 | IGHD5-5_3-3 | YSY | |
| IGHD3-03_3-24 | TIFGVVI | 679 | IGHD5-5_3-4 | GYSY | 776 |
| IGHD3-03_3-25 | ITIFGVVI | 680 | IGHD5-5_3-5 | SYGY | 777 |
| IGHD3-03_3-26 | TIFGVVII | 681 | IGHD5-5_3-6 | YSYG | 778 |
| IGHD3-03_3-27 | ITIFGVVII | 9 | IGHD5-5_3-7 | GYSYG | 779 |
| IGHD3-10_1-1 | ELL | | IGHD5-5_3-8 | YSYGY | 780 |
| IGHD3-10_1-2 | FGE | | IGHD5-53-9 | GYSYGY | 15 |
| IGHD3-10_1-3 | GEL | | IGHD6-13_1-1 | SSS | |
| IGHD3-10_1-4 | LLW | | IGHD6-13_1-2 | SSW | |
| IGHD3-10_1-5 | LWF | | IGHD6-13_1-3 | SWY | |
| IGHD3-10_1-6 | VLL | | IGHD6-13_1-4 | SSSW | 781 |
| IGHD3-10_1-7 | WFG | | IGHD6-13_1-5 | SSWY | 782 |
| IGHD3-10_1-8 | FGEL | 682 | IGHD6-13_1-6 | YSSS | 783 |
| IGHD3-10_1-9 | GELL | 683 | IGHD6-13_1-7 | GYSSS | 784 |
| IGHD3-10_1-10 | LLWF | 684 | IGHD6-13_1-8 | SSSWY | 785 |
| IGHD3-10_1-11 | LWFG | 685 | IGHD6-13_1-9 | YSSSW | 786 |
| IGHD3-10_1-12 | VLLW | 686 | IGHD6-13_1-10 | GYSSSW | 787 |
| IGHD3-10_1-13 | WFGE | 687 | IGHD6-13_1-11 | YSSSWY | 788 |
| IGHD3-10_1-14 | FGELL | 688 | IGHD6-13_1-12 | GYSSSWY | 7 |
| IGHD3-10_1-15 | LLWFG | 689 | IGHD6-19_1-1 | GWY | |
| IGHD3-10_1-16 | LWFGE | 690 | IGHD6-19_1-2 | GYS | |
| IGHD3-10_1-17 | VLLWF | 691 | IGHD6-19_1-3 | SGW | |
| IGHD3-10_1-18 | WFGEL | 692 | IGHD6-19_1-4 | YSS | |
| IGHD3-10_1-19 | LLWFGE | 693 | IGHD6-19_1-5 | GYSS | 789 |
| IGHD3-10_1-20 | LWFGEL | 694 | IGHD6-19_1-6 | SGWY | 790 |
| IGHD3-10_1-21 | VLLWFG | 695 | IGHD6-19_1-7 | SSGW | 791 |
| IGHD3-10_1-22 | WFGELL | 696 | IGHD6-19_1-8 | YSSG | 792 |

TABLE 18-continued

DH Gene Segments Used in the Presently Exemplified Library*

| DH Segment Designation[1] | Peptide | SEQ ID NO: | DH Segment Designation | Peptide | SEQ ID NO: |
|---|---|---|---|---|---|
| IGHD3-10_1-23 | LLWFGEL | 697 | IGHD6-19_1-9 | GYSSG | 793 |
| IGHD3-10_1-24 | LWFGELL | 698 | IGHD6-19_1-10 | SSGWY | 794 |
| IGHD3-10_1-25 | VLLWFGE | 699 | IGHD6-19_1-11 | YSSGW | 795 |
| IGHD3-10_1-26 | LLWFGELL | 700 | IGHD6-19_1-12 | GYSSGW | 796 |
| IGHD3-10_1-27 | VLLWFGEL | 701 | IGHD6-19_1-13 | YSSGWY | 797 |
| IGHD3-10_1-28 | VLLWFGELL | 1 | IGHD6-19_1-14 | GYSSGWY | 5 |
| IGHD3-10_2-1 | GSG | | IGHD6-19_2-1 | AVA | |
| IGHD3-10_2-2 | GSY | | IGHD6-19_2-2 | GIA | |
| IGHD3-10_2-3 | SGS | | IGHD6-19_2-3 | IAV | |
| IGHD3-10_2-4 | SYY | | IGHD6-19_2-4 | VAG | |
| IGHD3-10_2-5 | YGS | | IGHD6-19_2-5 | AVAG | 798 |
| IGHD3-10_2-6 | YYG | | IGHD6-19_2-6 | GIAV | 799 |
| IGHD3-10_2-7 | YYN | | IGHD6-19_2-7 | IAVA | 800 |
| IGHD3-10_2-8 | YYY | | IGHD6-19_2-8 | GIAVA | 801 |
| IGHD3-10_2-9 | GSGS | 702 | IGHD6-19_2-9 | IAVAG | 802 |
| IGHD3-10_2-10 | GSYY | 703 | IGHD6-19_2-10 | GIAVAG | 6 |
| IGHD3-10_2-11 | SGSY | 704 | IGHD6-13_2-1 | AAA | |
| IGHD3-10_2-12 | SYYN | 705 | IGHD6-13_2-2 | AAG | |
| IGHD3-10_2-13 | YGSG | 706 | IGHD6-13_2-3 | IAA | |
| IGHD3-10_2-14 | YYGS | 707 | IGHD6-13_2-4 | AAAG | 803 |
| IGHD3-10_2-15 | YYYG | 708 | IGHD6-132-5 | GIAA | 804 |
| IGHD3-10_2-16 | GSGSY | 709 | IGHD6-132-6 | IAAA | 805 |
| IGHD3-10_2-17 | GSYYN | 710 | IGHD6-13_2-7 | GIAAA | 806 |
| IGHD3-10_2-18 | SGSYY | 711 | IGHD6-13_2-8 | IAAAG | 807 |
| IGHD3-102-19 | YGSGS | 712 | IGHD6-132-9 | GIAAAG | 8 |

[1]The sequence designation is formatted as follows: (IGHD Gene Name)_(Reading Frame)-(Variant Number)
*Note that the origin of certain variants is rendered somewhat arbitrary when redundant segments are deleted from the library (i.e., certain segments may have their origins with more than one parent, including the one specified in the table).

Table 19 shows the length distribution of the 278 DH segments selected according to the methods described above.

TABLE 19

Length Distributions of DH Segments Selected for Inclusion in the Exemplary Library

| DH Size | Number of Occurrences |
|---|---|
| 3 | 78 |
| 4 | 64 |
| 5 | 50 |
| 6 | 38 |
| 7 | 27 |
| 8 | 20 |
| 9 | 12 |
| 10 | 4 |

As specified above, based on the CDRH3 numbering system defined in this application, IGHD-derived amino acids (i.e., DH segments) are numbered beginning with position 97, followed by positions 97A, 97B, etc. In the currently exemplified embodiment of the library, the shortest DH segment has three amino acids: 97, 97A and 97B, while the longest DH segment has 10 amino acids: 97, 97A, 97B, 97C, 97D, 97E, 97F, 97G, 97H and 97I.

Example 5.2

Selection of the H3-JH Segments

There are six human germline IGHJ genes. During in vivo assembly of antibody genes, these segments are progressively deleted at their 5' end. In this exemplary embodiment of the library, IGHJ gene segments with no deletions, or with 1, 2, 3, 4, 5, 6, or 7 deletions (at the amino acid level), yielding JH segments as short as 13 amino acids, were included (Table 20). Other embodiments of the invention, in which the IGHJ gene segments are progressively deleted (at their 5'/N-terminal end) to yield 15, 14, 12, or 11 amino acids are also contemplated.

TABLE 20

IGHJ Gene Segments Selected for use in the Exemplary Library

| IGHJ Segment | [H3-JH]-[FRM4][1] | SEQ ID NO: | H3-JH | SEQ ID NO: |
|---|---|---|---|---|
| JH1 parent or JH1_1 | AEYFQHWGQGTLVTVSS | 253 | AEYFQH | 17 |
| JH1_2 | EYFQHWGQGTLVTVSS | 808 | EYFQH | 830 |
| JH1_3 | YFQHWGQGTLVTVSS | 809 | YFQH | 831 |
| JH1_4 | FQHWGQGTLVTVSS | 810 | FQH | |
| JH1_5 | QHWGQGTLVTVSS | 811 | QH | |
| JH2 parent or JH2_1 | YWYFDLWGRGTLVTVSS | 254 | YWYFDL | 18 |
| JH2_2 | WYFDLWGRGTLVTVSS | 812 | WYFDL | 832 |
| JH2_3 | YFDLWGRGTLVTVSS | 813 | YFDL | 833 |
| JH2_4 | FDLWGRGTLVTVSS | 814 | FDL | |
| JH2_5 | DLWGRGTLVTVSS | 815 | DL | |
| JH3 parent or JH3_1 | AFDVWGQGTMVTVSS | 255 | AFDV | 19 |
| JH3_2 | FDVWGQGTMVTVSS | 816 | FDV | |
| JH3_3 | DVWGQGTMVTVSS | 817 | DV | |
| JH3 parent or JH3_1 | AFDIWGQGTMVTVSS | 849 | AFDV | 852 |
| JH3_2 | FDIWGQGTMVTVSS | 850 | FDI | |
| JH3_3 | DIWGQGTMVTVSS | 851 | DI | |
| JH4 parent or JH4_1 | YFDYWGQGTLVTVSS | 256 | YFDY | 20 |
| JH4_2 | FDYWGQGTLVTVSS | 818 | FDY | |
| JH4_3 | DYWGQGTLVTVSS | 819 | DY | |
| JH5 parent or JH5_1 | NWFDSWGQGTLVTVSS | 257 | NWFDS | 21 |
| JH5_2 | WFDSWGQGTLVTVSS | 820 | WFDS | 834 |
| JH5_3 | FDSWGQGTLVTVSS | 821 | FDS | |
| JH5_4 | DSWGQGTLVTVSS | 822 | DS | |
| JH5 parent or JH5_1 | NWFDPWGQGTLVTVSS | 853 | NWFDP | 857 |
| JH5_2 | WFDPWGQGTLVTVSS | 854 | WFDS | 858 |
| JH5_3 | FDPWGQGTLVTVSS | 855 | FDP | |
| JH5_4 | DPWGQGTLVTVSS | 856 | DP | |
| JH6 parent or JH6_1 | YYYYYGMDVWGQGTTVTVSS | 258 | YYYYYGMDV | 22 |
| JH6_2 | YYYYGMDVWGQGTTVTVSS | 823 | YYYYGMDV | 835 |
| JH6_3 | YYYGMDVWGQGTTVTVSS | 824 | YYYGMDV | 836 |
| JH6_4 | YYGMDVWGQGTTVTVSS | 825 | YYGMDV | 837 |
| JH6_5 | YGMDVWGQGTTVTVSS | 826 | YGMDV | 838 |
| JH6_6 | GMDVWGQGTTVTVSS | 827 | GMDV | 839 |
| JH6_7 | MDVWGQGTTVTVSS | 828 | MDV | |
| JH6_8 | DVWGQGTMVTVSS | 829 | DV | |

[1]H3-JH is defined as the portion of the IGHJ segment included within the Kabat definition of CDRH3; FRM4 is defined as the portion of the IGHJ segment encoding framework region four.

According to the CDRH3 numbering system of this application, the contribution of, for example, JH6_1 to CDRH3, would be designated by positions 99F, 99E, 99D, 99C, 99B, 99A, 100, 101 and 102 (Y, Y, Y, Y, Y, G, M, D and V, respectively). Similarly, the JH4_3 sequence would contribute amino acid positions 101 and 102 (D and Y, respectively) to CDRH3. However, in all cases of the exemplified library, the JH segment will contribute amino acids 103 to 113 to the FRM4 region, in accordance with the standard Kabat numbering system for antibody variable regions (Kabat, op. cit. 1991). This may not be the case in other embodiments of the library.

Example 5.3

Selection of the N1 and N2 Segments

While the consideration of V-D-J recombination enhanced by mimicry of the naturally occurring process of progressive deletion (as exemplified above) can generate enormous diversity, the diversity of the CDRH3 sequences in vivo is further amplified by non-templated addition of a varying number of nucleotides at the V-D junction and the D-J junction.

N1 and N2 segments located at the V-D and D-J junctions, respectively, were identified in a sample containing about 2,700 antibody sequences (Jackson et al., J. Immunol. Methods, 2007, 324: 26) also analyzed by the SoDA method of Volpe et al., Bioinformatics, 2006, 22: 438-44; (both Jackson et al., and Volpe et al., are incorporated by reference in their entireties). Examination of these sequences revealed patterns in the length and composition of N1 and N2. For the construction of the currently exemplified CDRH3 library, specific short amino acid sequences were derived from the above analysis and used to generate a number of N1 and N2 segments that were incorporated into the CDRH3 design, using the synthetic scheme described herein.

As described in the Detailed Description, certain embodiments of the invention include N1 and N2 segments with rationally designed length and composition, informed by statistical biases in these parameters that are found by comparing naturally occurring N1 and N2 segments in human antibodies. According to data compiled from human databases (see, e.g., Jackson et al., J. Immunol. Methods, 2007, 324: 26, incorporated by reference in its entirety), there are an average of about 3.02 amino acid insertions for N1 and about 2.4 amino acid insertions for N2, not taking into account insertions of two nucleotides or less. FIG. 2 shows the length distributions of the N1 and N2 regions in human antibodies. In this exemplary embodiment of the invention, N1 and N2 were fixed to a length of 0, 1, 2, or 3 amino acids. The naturally occurring composition of these sequences in human antibodies was used as a guide for the inclusion of different amino acid residues.

The naturally occurring composition of single amino acid, two amino acids, and three amino acids N1 additions is defined in Table 21, and the naturally occurring composition of the corresponding N2 additions is defined in Table 22. The most frequently occurring duplets in the N1 and N2 set are compiled in Table 23.

TABLE 21

Composition of Naturally Occurring 1, 2, and 3 Amino Acid N1 Additions*

| Position 1 | Number of Occurrences | Position 2 | Number of Occurrences | Position 3 | Number of Occurrences |
|---|---|---|---|---|---|
| R | 251 | G | 97 | G | 101 |
| G | 249 | P | 67 | R | 66 |
| P | 173 | R | 67 | P | 47 |
| L | 130 | S | 42 | S | 47 |
| S | 117 | L | 39 | L | 38 |
| A | 84 | V | 33 | A | 33 |
| V | 62 | E | 24 | V | 28 |
| K | 61 | A | 21 | T | 27 |
| I | 55 | D | 18 | E | 24 |
| Q | 51 | I | 18 | D | 22 |
| T | 51 | T | 18 | K | 18 |
| D | 50 | K | 16 | F | 14 |
| E | 49 | Y | 16 | I | 13 |
| F | 3 | H | 13 | W | 13 |
| H | 32 | F | 12 | N | 10 |
| N | 30 | Q | 11 | Y | 10 |
| W | 28 | N | 5 | H | 8 |
| Y | 21 | W | 5 | Q | 5 |
| M | 16 | C | 4 | C | 3 |
| C | 3 | M | 4 | M | 3 |
|   | 1546 |   | 530 |   | 530 |

*Defined as the sequence C-terminal to "CARX" (SEQ ID NO: 840), or equivalent, of VH, wherein "X" is the "tail" (e.g., D, E, G, or no amino acid residue).

TABLE 22

Composition of Naturally Occurring 1, 2, and 3 Amino Acid N2 Additions*

| Position 1 | Number of Occurrences | Position 2 | Number of Occurrences | Position 3 | Number of Occurrences |
|---|---|---|---|---|---|
| G | 242 | G | 244 | G | 156 |
| P | 219 | P | 138 | P | 79 |
| R | 180 | R | 86 | S | 54 |
| L | 132 | S | 85 | R | 51 |
| S | 123 | T | 77 | L | 49 |

TABLE 22-continued

Composition of Naturally Occurring 1, 2, and 3 Amino Acid N2 Additions*

| Position 1 | Number of Occurrences | Position 2 | Number of Occurrences | Position 3 | Number of Occurrences |
|---|---|---|---|---|---|
| A | 97 | L | 74 | A | 41 |
| T | 78 | A | 69 | T | 31 |
| V | 75 | V | 46 | V | 29 |
| E | 57 | E | 41 | D | 23 |
| D | 56 | Y | 38 | E | 23 |
| F | 54 | D | 36 | W | 23 |
| H | 54 | K | 30 | Q | 19 |
| Q | 53 | F | 29 | F | 17 |
| I | 49 | W | 27 | Y | 17 |
| N | 45 | H | 24 | H | 16 |
| Y | 40 | I | 23 | I | 11 |
| K | 35 | Q | 23 | K | 11 |
| W | 29 | N | 21 | N | 8 |
| M | 20 | M | 8 | C | 6 |
| C | 6 | C | 5 | M | 6 |
|   | 1644 |   | 1124 |   | 670 |

*Defined as the sequence C-terminal to the D segment but not encoded by IGHJ genes.

TABLE 23

Top Twenty-Five Naturally Occurring N1 and N2 Duplets

| Sequence | Number of Occurrences | Cumulative Frequency | Individual Frequency |
|---|---|---|---|
| GG | 17 | 0.037 | 0.037 |
| PG | 15 | 0.070 | 0.033 |
| RG | 15 | 0.103 | 0.033 |
| PP | 13 | 0.132 | 0.029 |
| GP | 12 | 0.158 | 0.026 |
| GL | 11 | 0.182 | 0.024 |
| PT | 10 | 0.204 | 0.022 |
| TG | 10 | 0.226 | 0.022 |
| GV | 9 | 0.246 | 0.020 |
| RR | 9 | 0.266 | 0.020 |
| SG | 8 | 0.284 | 0.018 |
| RP | 7 | 0.299 | 0.015 |
| IG | 6 | 0.312 | 0.013 |
| GS | 6 | 0.325 | 0.013 |
| SR | 6 | 0.338 | 0.013 |
| PA | 6 | 0.352 | 0.013 |
| LP | 6 | 0.365 | 0.013 |
| VG | 6 | 0.378 | 0.013 |
| KG | 6 | 0.389 | 0.011 |
| GW | 5 | 0.400 | 0.011 |
| FP | 5 | 0.411 | 0.011 |
| LG | 5 | 0.422 | 0.011 |
| RS | 5 | 0.433 | 0.011 |
| TP | 5 | 0.444 | 0.011 |
| EG | 5 | 0.455 | 0.011 |

Example 5.3.1

Selection of the N1 Segments

Analysis of the identified N1 segments, located at the junction between V and D, revealed that the eight most frequently occurring amino acid residues were G, R, S, P, L, A, T and V (Table 21). The number of amino acid additions in the N1 segment was frequently none, one, two, or three (FIG. 2). The addition of four or more amino acids was relatively rare. Therefore, in the currently exemplified embodiment of the library, the N1 segments were designed to include zero, one, two or three amino acids. However, in other embodiments, N1 segments of four, five, or more amino acids may also be utilized. G and P were always among the most commonly occurring amino acid residues in the N1 regions. Thus, in the present exemplary embodiment of the library, the N1 segments that are dipeptides are of the form GX, XG, PX, or XP, where X is any of the eight most commonly occurring amino acids listed above. Due to the fact that G residues were observed more frequently than P residues, the tripeptide members of the exemplary N1 library have the form GXG, GGX, or XGG, where X is, again, one of the eight most frequently occurring amino acid residues listed above. The resulting set of N1 sequences used in the present exemplary embodiment of the library, include the "zero" addition amounts to 59 sequences, which are listed in Table 24.

TABLE 24

N1 Sequences Selected for Inclusion in the Exemplary Library

| Segment Type | Sequences | Number |
|---|---|---|
| "Zero" | (no addition) V segment joins directly to D segment | 1 |
| Monomers | G, P, R, A, S, L, T, V | 8 |
| Dimers | GG, GP, GR, GA, GS, GL, GT, GV, PG, RG, AG, SG, LG, TG, VG, PP, PR, PA, PS, PL, PT, PV, RP, AP, SP, LP, TP, VP | 28 |
| Trimers | GGG, GPG, GRG, GAG, GSG, GLG, GTG, GVG, PGG, RGG, AGG, SGG, LGG, TGG, VGG, GGP, GGR, GGA, GGS, GGL, GGT, GGV | 22 |

In accordance with the CDRH3 numbering system of the application, the sequences enumerated in Table 24 contribute the following positions to CDRH3: the monomers contribute position 96, the dimers to 96 and 96A, and the trimers to 96, 96A and 96B. In alternative embodiments, where tetramers and longer segments could be included among the N1 sequences, the corresponding numbers would go on to include 96C, and so on.

Example 5.3.2

Selection of the N2 Segments

Similarly, analysis of the identified N2 segments, located at the junction between D and J, revealed that the eight most frequently occurring amino acid residues were also G, R, S, P, L, A, T and V (Table 22). The number of amino acid additions in the N2 segment was also frequently none, one, two, or three (FIG. 2). For the design of the N2 segments in the exemplary library, an expanded set of sequences was utilized. Specifically, the sequences in Table 25 were used, in addition to the 59 sequences enumerated in Table 24, for N1.

TABLE 25

Extra Sequences in N2 Additions

| Segment Type | Sequence | Number New | Number Total |
|---|---|---|---|
| Monomers | D, E, F, H, I, K, M, Q, W, Y | 10 | 18 |
| Dimers | AR, AS, AT, AY, DL, DT, EA, EK, FH, FS, HL, HW, IS, KV, LD, LE, LR, LS, LT, NR, NT, QE, QL, QT, RA, RD, RE, RF, RH, RL, RR, RS, RV, SA, SD, SE, SF, SI, SK, SL, SQ, SR, SS, ST, SV, TA, TR, TS, TT, TW, VD, VS, WS, YS | 54 | 82 |
| Trimers | AAE, AYH, DTL, EKR, ISR, NTP, PKS, PRP, PTA, PTQ, REL, RPL, SAA, SAL, SGL, SSE, TGL, WGT | 18 | 40 |

The presently exemplified embodiment of the library, therefore, contains 141 total N2 sequences, including the "zero" state. One of ordinary skill in the art will readily recognize that these 141 sequences may also be used in the N1 region, and that such embodiments are within the scope of the invention. In addition, the length and compositional diversity of the N1 and N2 sequences can be further increased by utilizing amino acids that occur less frequently than G, R, S, P, L, A, T and V, in the N1 and N2 regions of naturally occurring antibodies, and including N1 and N2 segments of four, five, or more amino acids in the library. Tables 21 to 23 and FIG. 2 provides information about the composition and length of the N1 and N2 sequences in naturally occurring antibodies that is useful for the design of additional N1 and N2 regions which mimic the natural composition and length.

In accordance with the CDRH3 numbering system of the application, N2 sequences will begin at position 98 (when present) and extend to 98A (dimers) and 98B (trimers). Alternative embodiments may occupy positions 98C, 98D, and so on.

Example 5.4

A CDRH3 Library

When the "tail" (i.e., G/D/E/-) is considered, the CDRH3 in the exemplified library may be represented by the general formula:

[G/D/E/-]-[N1]-[DH]-[N2]-[H3-JH]

In the currently exemplified, non-limiting, embodiment of the library, [G/D/E/-] represents each of the four possible terminal amino acid "tails"; N1 can be any of the 59 sequences in Table 24; DH can be any of the 278 sequences in Table 18; N2 can be any of the 141 sequences in Tables 24 and 25; and H3-JH can be any of the 28 H3-JH sequences in Table 20. The total theoretical diversity or repertoire size of this CDRH3 library is obtained by multiplying the variations at each of the components, i.e., $4 \times 59 \times 278 \times 141 \times 28 = 2.59 \times 10^8$.

Figure 23:
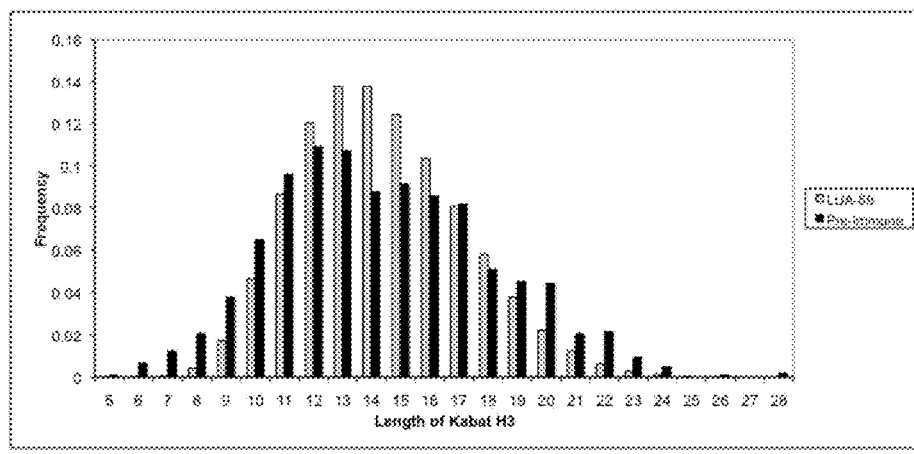
FIG. 23 depicts the frequency of occurrence of different CDRH3 lengths in an exemplary library of the invention, versus the preimmune repertoire of Lee et al. (Immunogenetics, 2006, 57: 917, incorporated by reference in its entirety).

However, as described in the previous examples, redundancies may be eliminated from the library. In the presently exemplified embodiment, the tail and N1 segments were combined, and redundancies were removed from the library. For example, considering the VH chassis, tail, and N1 regions, the sequence [VH_Chassis]-[G] may be obtained in two different ways: [VH_Chassis]+[G]+[nothing] or [VH_Chassis]+[nothing]+[G]. Removal of redundant sequences resulted in a total of 212 unique [G/D/E/-]-[N1] segments out of the 236 possible combinations (i.e., 4 tails×59 N1). Therefore, the actual diversity of the presently exemplified CDRH3 library is $212 \times 278 \times 141 \times 28 = 2.11 \times 10^8$. FIG. 23 depicts the frequency of occurrence of different CDRH3 lengths in this library, versus the preimmune repertoire of Lee et al.

Table 26 further illustrates specific exemplary sequences from the CDRH3 library described above, using the CDRH3 numbering system of the present application. In instances where a position is not used, the hyphen symbol (-) is included in the table instead.

TABLE 26

Examples of Designed CDRH3 Sequences According to the Library Exemplified in Examples 1 to 5

| | [Tail] | [N1] | | | [DH] | | | | | | | | | [N2] | | |
|---|---|---|---|---|---|---|---|---|---|---|---|---|---|---|---|---|
| | 95 | 96 | 96A | 96B | 97 | 97A | 97B | 97C | 97D | 97E | 97F | 97G | 97H | 97I | 98 | 98A | 98B |
| No. 1 | G | — | — | — | Y | Y | Y | — | — | — | — | — | — | — | — | — | — |
| No. 2 | D | G | — | — | G | Y | C | S | G | G | S | C | Y | S | Y | — | — |
| No. 3 | E | R | — | — | I | T | I | F | G | V | — | — | — | — | G | G | — |
| No. 4 | — | P | P | — | V | L | L | W | F | G | E | L | L | — | D | — | — |
| No. 5 | G | G | S | G | Y | Y | Y | G | S | G | S | Y | Y | N | P | — | — |
| No. 6 | D | — | — | — | R | G | V | I | I | — | — | — | — | — | M | — | — |
| No. 7 | E | S | G | — | Y | Y | Y | D | S | S | G | Y | Y | Y | T | G | L |
| No. 8 | — | S | — | — | D | Y | G | D | Y | — | — | — | — | — | S | I | — |
| No. 9 | — | P | G | — | W | F | G | — | — | — | — | — | — | — | P | S | — |
| No. 10 | — | — | — | — | C | S | G | G | S | C | — | — | — | — | A | Y | — |

| | [H3-JH] | | | | | | | | CDRH3 |
|---|---|---|---|---|---|---|---|---|---|
| | 99E | 99D | 99C | 99B | 99A | 99 | 100 | 101 | 102 | Length |
| No. 1 | — | — | — | — | — | — | — | D | V | 6 |
| No. 2 | — | — | — | — | — | — | F | Q | H | 16 |
| No. 3 | — | — | — | — | — | Y | F | D | Y | 14 |
| No. 4 | — | — | — | — | — | — | — | D | L | 14 |
| No. 5 | — | — | — | A | E | Y | F | Q | H | 21 |
| No. 6 | Y | Y | Y | Y | Y | G | M | D | V | 16 |
| No. 7 | — | — | — | — | W | Y | F | D | L | 21 |
| No. 8 | — | — | — | — | — | — | F | D | I | 11 |
| No. 9 | — | — | — | Y | Y | G | M | D | V | 13 |
| No. 10 | — | — | — | — | N | W | F | D | P | 13 |

Sequence Identifiers:
No. 1 (SEQ ID NO: 542);
No. 2 (SEQ ID NO: 543);
No. 3 (SEQ ID NO: 544);
No. 4 (SEQ ID NO: 545);
No. 5 (SEQ ID NO: 546);
No. 6 (SEQ ID NO: 547);
No. 7 (SEQ ID NO: 548);
No. 8 (SEQ ID NO: 549);
No. 9 (SEQ ID NO: 550);
No. 10 (SEQ ID NO: 551).

Example 6

Design of VKCDR3 Libraries

This example describes the design of a number of exemplary VKCDR3 libraries. As specified in the Detailed Description, the actual version(s) of the VKCDR3 library made or used in particular embodiments of the invention will depend on the objectives for the use of the library. In this example the Kabat numbering system for light chain variable regions was used.

In order to facilitate examination of patterns of occurrence, human kappa light chain sequences were obtained from the publicly available NCBI database (Appendix A). As for the heavy chain sequences (Example 2), each of the sequences obtained from the publicly available database was assigned to its closest germline gene, on the basis of sequence identity. The amino acid compositions at each position were then determined within each kappa light chain subset.

Example 6.1

A Minimalist VKCDR3 Library

This example describes the design of a "minimalist" VKCDR3 library, wherein the VKCDR3 repertoire is restricted to a length of nine residues. Examination of the VKCDR3 lengths of human sequences shows that a dominant proportion (over 70%) has nine amino acids within the Kabat definition of CDRL3: positions 89 through 97. Thus, the currently exemplified minimalist design considers only VKCDR3 of length nine. Examination of human kappa light chain sequences shows that there are not strong biases in the usage of IGKJ genes; there are five such IKJ genes in humans. Table 27 depicts IGKJ gene usage amongst three data sets, namely Juul et al. (Clin. Exp. Immunol., 1997, 109: 194, incorporated by reference in its entirety), Klein and Zachau (Eur. J. Immunol., 1993, 23: 3248, incorporated by reference in its entirety), and the kappa light chain data set provided in Appendix A (labeled LUA).

TABLE 27

IGKJ Gene Usage in Various Data Sets

| Gene | Klein | Juul | LUA |
|---|---|---|---|
| IGKJ1 | 35.0% | 29.0% | 29.3% |
| IGKJ2 | 25.0% | 23.0% | 24.1% |
| IGKJ3 | 7.0% | 8.0% | 12.1% |
| IGKJ4 | 26.0% | 24.0% | 26.5% |
| IGKJ5 | 6.0% | 18.0% | 8.0% |

Thus, a simple combinatorial of "M" VK chassis and the 5 IGKJ genes would generate a library of size M×5. In the Kabat numbering system, for VKCDR3 of length nine, amino acid number 96 is the first encoded by the IGKJ gene. Examination of the amino acid occupying this position in human sequences showed that the seven most common residues are L, Y, R, W, F, P, and I, cumulatively accounting for about 85% of the residues found in position 96. The remaining 13 amino acids account for the other 15%. The occurrence of all 20 amino acids at position 96 is presented in Table 28.

TABLE 28

Occurrence of 20 Amino Acid Residues at Position 96 in Human VK Data Set

| Type | Number | Percent | Cumulative |
|---|---|---|---|
| L | 333 | 22.3 | 22.3 |
| Y | 235 | 15.8 | 38.1 |
| R | 222 | 14.9 | 52.9 |
| W | 157 | 10.5 | 63.5 |
| F | 148 | 9.9 | 73.4 |
| I | 96 | 6.4 | 79.8 |
| P | 90 | 6.0 | 85.9 |
| Q | 53 | 3.6 | 89.4 |
| N | 39 | 2.6 | 92.0 |
| H | 31 | 2.1 | 94.1 |
| V | 21 | 1.4 | 95.5 |
| G | 20 | 1.3 | 96.8 |
| C | 14 | 0.9 | 97.8 |
| K | 7 | 0.5 | 98.3 |
| S | 6 | 0.4 | 98.7 |
| A | 5 | 0.3 | 99.0 |
| D | 5 | 0.3 | 99.3 |
| E | 5 | 0.3 | 99.7 |
| T | 5 | 0.3 | 100.0 |
| M | 0 | 0.0 | 100.0 |

To determine the origins of the seven residues most commonly found in position 96, known human IGKJ amino acid sequences were examined (Table 29).

TABLE 29

Known Human IGKJ Amino Acid Sequences

| Gene | Sequence | SEQ ID NO: |
|---|---|---|
| IGKJ1 | WTFGQGTKVEIK | 552 |
| IGKJ2 | YTFGQGTKLEIK | 553 |
| IGKJ3 | FTFGPGTKVDIK | 554 |
| IGKJ4 | LTFGGGTKVEIK | 555 |
| IGKJ5 | ITFGQGTRLEIK | 556 |

Without being bound by theory, five of the seven most commonly occurring amino acids found in position 96 of rearranged human sequences appear to originate from the first amino acid encoded by each of the five human IGKJ genes, namely, W, Y, F, L, and I.

Less evident were the origins of the P and R residues. Without being bound by theory, most of the human IGKV gene nucleotide sequences end with the sequence CC, which occurs after (i.e., 3' to) the end of the last full codon (e.g., that encodes the C-terminal residue shown in Table 11). Therefore, regardless of which nucleotide is placed after this sequence (i.e., CCX, where X may be any nucleotide) the codon will encode a proline (P) residue. Thus, when the IGKJ gene undergoes progressive deletion (just as in the IGHJ of the heavy chain; see Example 5), the first full amino acid is lost and, if no deletions have occurred in the IGKV gene, a P residue will result.

To determine the origin of the arginine residue at position 96, the origin of IGKJ genes in rearranged kappa light chain sequences containing R at position 96 were analyzed. The analysis indicated that R occurred most frequently at position 96 when the IGKJ gene was IGKJ1 (SEQ ID NO: 552). The germline W (position 1; Table 29) for IGKJ1 (SEQ ID NO: 552) is encoded by TGG. Without being bound by theory, a single nucleotide change of T to C (yielding CGG) or A (yielding AGG) will, therefore, result in codons encoding Arg (R). A change to G (yielding GGG) results in a codon encoding Gly (G). R occurs about ten times more often at position 96 in human sequences than G (when the IGKJ gene is IGKJ1 (SEQ ID NO: 552)), and it is encoded by CGG more often than AGG. Therefore, without being bound by theory, C may originate from one of the aforementioned two Cs at the end of IGKV gene. However, regardless of the mechanism(s) of occurrence, R and P are among the most frequently observed amino acid types at position 96, when the length of VKCDR3 is 9. Therefore, a minimalist VKCDR3 library may be represented by the following amino acid sequence:

[VK_Chassis]-[L3-VK]-[F/L/I/R/W/Y/P]-[TFGGGT-KVEIK(SEQ ID NO:841)]

In this sequence, VK_Chassis represents any selected VK chassis (for non-limiting examples, see Table 11), specifically Kabat residues 1 to 88 encoded by the IGKV gene. L3-VK represents the portion of the VKCDR3 encoded by the chosen IGKV gene (in this embodiment, residues 89-95). F/L/I/R/W/Y/P represents any one of amino residues F, L, I, R, W, Y, or P. In this exemplary representation, IKJ4 (minus the first residue) has been depicted. Without being bound by theory, apart from IGKJ4 (SEQ ID NO: 555) being among the most commonly used IGKJ genes in humans, the GGG amino acid sequence is expected to lead to larger conformational flexibility than any of the alternative IGKJ genes, which contain a GXG amino acid sequence, where X is an amino acid other than G. In some embodiments, it may be advantageous to produce a minimalist pre-immune repertoire with a higher degree of conformational flexibility. Considering the ten VK chassis depicted in Table 11, one implementation of the minimalist VKCDR3 library would have 70 members resulting from the combination of 10 VK chassis by 7 junction (position 96) options and one IGKJ-derived sequence (e.g., IGKJ4 (SEQ ID NO: 555)). Although this embodiment of the library has been depicted using IGKJ4 (SEQ ID NO: 555), it is possible to design a minimalist VKCDR3 library using one of the other four IGKJ sequences. For example, another embodiment of the library may have 350 members (10 VK chassis by 7 junctions by 5 IGKJ genes).

One of ordinary skill in the art will readily recognize that one or more minimalist VKCDR3 libraries may be constructed using any of the IGKJ genes. Using the notation above, these minimalist VKCDR3 libraries may have sequences represented by, for example:

JK1: [VK_Chassis]-[L3-VK]-[F/L/I/R/W/Y/P]-[TF-GQGTKVEIK(SEQ ID NO: 528)];

JK2: [VK_Chassis]-[L3-VK]-[F/L/I/R/W/Y/P]-[TF-GQGTKLEIK(SEQ ID NO: 842)];

JK3: [VK_Chassis]-[L3-VK]-[F/L/I/R/W/Y/P]-[TFG-PGTKVDIK(SEQ ID NO: 843); and

JK5: [VK_Chassis]-[L3-VK]-[F/L/I/R/W/Y/P]-[TF-GQGTRLEIK(SEQ ID NO: 844].

Example 6.2

A VKCDR3 Library of About $10^5$ Complexity

In this example, the nine residue VKCDR3 repertoire described in Example 6.1 is expanded to include VKCDR3 lengths of eight and ten residues. Moreover, while the previously enumerated VKCDR3 library included the VK chassis and portions of the IGKJ gene not contributing to VKCDR3, the presently exemplified version focuses only on residues comprising a portion of VKCDR3. This embodiment may be favored, for example, when recombination with a vector which already contains VK chassis sequences and constant region sequences is desired.

While the dominant length of VKCDR3 sequences in humans is nine amino acids, other lengths appear at measurable rates that cumulatively approach almost 30% of kappa light chain sequences. In particular, VKCDR3 of lengths 8 and 10 represent, respectively, about 8.5% and about 16% of sequences in representative samples (FIG. 3). Thus, a more complex VKCDR3 library includes CDR lengths of 8 to 10 amino acids; this library accounts for over 95% of the length distribution observed in typical collections of human VKCDR3 sequences. This library also enables the inclusion of additional variation outside of the junction between the VK and JK genes. The present example describes such a library. The library comprises 10 sub-libraries, each designed around one of the 10 exemplary VK chassis depicted in Table 11. Clearly, the approach exemplified here can be generalized to consider M different chassis, where M may be less than or more than 10.

To characterize the variability within the polypeptide segment occupying Kabat positions 89 to 95, human kappa light chain sequence collections derived from each of the ten germline sequences of Example 3 were aligned and compared separately (i.e., within the germline group). This analysis enabled us to discern the patterns of sequence variation at each individual position in each kappa light chain sequence, grouped by germline. The table below shows the results for sequences derived from IGKV1-39 (SEQ ID NO: 233).

TABLE 30

Percent Occurrence of Amino Acid Types in IGKV1-39-Derived Sequences

| Amino Acid | P89 | P90 | P91 | P92 | P93 | P94 | P95 |
|---|---|---|---|---|---|---|---|
| A | 0 | 0 | 1 | 0 | 0 | 4 | 1 |
| C | 0 | 0 | 0 | 0 | 0 | 0 | 0 |
| D | 0 | 0 | 1 | 1 | 3 | 0 | 0 |
| E | 0 | 1 | 0 | 0 | 0 | 0 | 0 |
| F | 0 | 0 | 0 | 5 | 0 | 2 | 0 |
| G | 0 | 0 | 2 | 1 | 2 | 0 | 0 |
| H | 1 | 1 | 0 | 4 | 0 | 0 | 0 |
| I | 0 | 0 | 1 | 0 | 4 | 5 | 1 |
| K | 0 | 0 | 0 | 1 | 2 | 0 | 0 |
| L | 3 | 0 | 0 | 1 | 1 | 3 | 7 |
| M | 0 | 0 | 0 | 0 | 0 | 1 | 0 |
| N | 0 | 0 | 3 | 2 | 6 | 2 | 0 |
| P | 0 | 0 | 0 | 0 | 0 | 4 | 85 |
| Q | 96 | 97 | 0 | 0 | 0 | 0 | 0 |
| R | 0 | 0 | 0 | 0 | 5 | 0 | 2 |
| S | 0 | 0 | 80 | 4 | 65 | 6 | 3 |
| T | 0 | 0 | 9 | 0 | 10 | 65 | 1 |

TABLE 30-continued

Percent Occurrence of Amino Acid Types in IGKV1-39-Derived Sequences

| Amino Acid | P89 | P90 | P91 | P92 | P93 | P94 | P95 |
|---|---|---|---|---|---|---|---|
| V | 0 | 0 | 0 | 0 | 0 | 1 | 1 |
| W | 0 | 0 | 0 | 0 | 0 | 0 | 0 |
| Y | 0 | 0 | 2 | 80 | 0 | 3 | 0 |

For example, at position 89, two amino acids, Q and L, account for about 99% of the observed variability, and thus in the currently exemplified library (see below), only Q and L were included in position 89. In larger libraries, of course, additional, less frequently occurring amino acid types (e.g., H), may also be included.

Similarly, at position 93 there is more variation, with amino acid types S, T, N, R and I being among the most frequently occurring. The currently exemplified library thus aimed to include these five amino acids at position 93, although clearly others could be included in more diverse libraries. However, because this library was constructed via standard chemical oligonucleotide synthesis, one is bound by the limits of the genetic code, so that the actual amino acid set represented at position 93 of the exemplified library consists of S, T, N, R, P and H, with P and H replacing I (see exemplary 9 residue VKCDR3 in Table 32, below). This limitation may be overcome by using codon-based synthesis of oligonucleotides, as described in Example 6.3, below. A similar approach was followed at the other positions and for the other sequences: analysis of occurrences of amino acid type per position, choice from among most frequently occurring subset, followed by adjustment as dictated by the genetic code.

As indicated above, the library employs a practical and facile synthesis approach using standard oligonucleotide synthesis instrumentation and degenerate oligonucleotides. To facilitate description of the library, the IUPAC code for degenerate nucleotides, as given in Table 31, will be used.

TABLE 31

Degenerate Base Symbol Definition

| IUPAC Symbol | Base Pair Composition |
|---|---|
| A | A (100%) |
| C | C (100%) |
| G | G (100%) |
| T | T (100%) |
| R | A (50%) G (50%) |
| Y | C (50%) T (50%) |
| W | A (50%) T (50%) |
| S | C (50%) G (50%) |
| M | A (50%) C (50%) |
| K | G (50%) T (50%) |
| B | C (33%) G (33%) T (33%) (*) |
| D | A (33%) G (33%) T (33%) |
| H | A (33%) C (33%) T (33%) |
| V | A (33%) C (33%) G (33%) |
| N | A (25%) C (25%) G (25%) T (25%) |

(*) 33% is short hand here for 1/3 (i.e., 33.3333 . . . %)

Using the VK1-39 chassis with VKCDR3 of length nine as an example, the VKCDR3 library may be represented by the following four oligonucleotides (left column in Table 32), with the corresponding amino acids encoded at each position of CDRL3 (Kabat numbering) provided in the columns on the right.

TABLE 32

Exemplary Oligonucleotides Encoding a VK1-39 CDR3 Library

| Oligonucleotide Sequence | 89 | 90 | 91 | 92 | 93 | 94 | 95 | 95A | 96 | 97 |
|---|---|---|---|---|---|---|---|---|---|---|
| CWGSAAWCATHCMVTABTCCTTWCACT (SEQ ID NO: 307) | LQ | EQ | ST | FSY | HNPRST | IST | P | — | FY | T |
| CWGSAAWCATHCMVTABTCCTMTCACT (SEQ ID NO: 308) | LQ | EQ | ST | FSY | HNPRST | IST | P | — | IL | T |
| CWGSAAWCATHCMVTABTCCTWGGACT (SEQ ID NO: 309) | LQ | EQ | ST | FSY | HNPRST | IST | P | — | WR | T |
| CWGSAAWCATHCMVTABTCCTCBTACT (SEQ ID NO: 310) | LQ | EQ | ST | FSY | HNPRST | IST | P | PLR | — | T |

For example, the first codon (CWG) of the first nucleotide of Table 32, corresponding to Kabat position 89, represents 50% CTG and 50% CAG, which encode Leu (L) and Gln (Q), respectively. Thus, the expressed polypeptide would be expected to have L and Q each about 50% of the time. Similarly, for Kabat position 95A of the fourth oligonucleotide, the codon CBT represents ⅓ each of CCT, CGT and CTT, corresponding in turn to ⅓ each of Pro (P), Leu (L) and Arg (R) upon translation. By multiplying the number of options available at each position of the peptide sequence, one can obtain the complexity, in peptide space, contributed by each oligonucleotide. For the VK1-39 example above, the numbers are 864 for the first three oligonucleotides and 1,296 for the fourth oligonucleotide. Thus, the oligonucleotides encoding VK1-39 CDR3s of length nine contribute 3,888 members to the library. However, as shown in Table 32, sequences with L or R at position 95A (when position 96 is empty) are identical to those with L or R at position 96 (and 95A empty). Therefore, the 3,888 number overestimates the LR contribution and the actual number of unique members is slightly lower, at 3,024. As depicted in Table 33, for the complete list of oligonucleotides that represent VKCDR3 of sizes 8, 9, and 10, for all 10 VK chassis, the overall complexity is about $1.3 \times 10^5$ or $1.2 \times 10^5$ unique sequences after correcting for over-counting of the LR contribution for the size 9 VKCDR3.

TABLE 33

Degenerate Oligonucleotides Encoding an Exemplary VKCDR3 Library

| Chassis | CDRL3 Length | Junction Type (1) | Degenerate Oligonucleotide | SEQ ID NO: | 89 | 90 | 91 | 92 | 93 | 94 | 95 | 95A | 96 | 97 |
|---|---|---|---|---|---|---|---|---|---|---|---|---|---|---|
| VK1-5 | 8 | 1 | CASCASTM CVRTRSTT WCTWCACT | 259 | HQ | HQ | SY | DGHNRS | AGST | FY | — | — | FY | T |
| VK1-5 | 8 | 2 | CASCASTM CVRTRSTT WCMTCACT | 260 | HQ | HQ | SY | DGHNRS | AGST | FY | — | — | IL | T |
| VK1-5 | 8 | 3 | CASCASTM CVRTRSTT WCWGGACT | 261 | HQ | HQ | SY | DGHNRS | AGST | FY | — | — | WR | T |
| VK1-5 | 8 | 4 | CASCASTM CVRTRSTT WCYCTACT | 262 | HQ | HQ | SY | DGHNRS | AGST | FY | PS | — | — | T |
| VK1-5 | 9 | 1 | CASCASTM CVRTRSTT WCYCTTWC ACT | 263 | HQ | HQ | SY | DGHNRS | AGST | FY | PS | — | FY | T |
| VK1-5 | 9 | 2 | CASCASTM CVRTRSTT WCYCTMTC ACT | 264 | HQ | HQ | SY | DGHNRS | AGST | FY | PS | — | IL | T |
| VK1-5 | 9 | 3 | CASCASTM CVRTRSTT WCYCTWGG ACT | 265 | HQ | HQ | SY | DGHNRS | AGST | FY | PS | — | WR | T |
| VK1-5 | 9 | 4 | CASCASTM CVRTRSTT WCYCTYCT ACT | 266 | HQ | HQ | SY | DGHNRS | AGST | FY | PS | PS | — | T |

TABLE 33-continued

Degenerate Oligonucleotides Encoding an Exemplary VKCDR3 Library

| Chassis | CDRL3 Length | Junction Type (1) | Degenerate Oligonucleotide | SEQ ID NO: | 89 | 90 | 91 | 92 | 93 | 94 | 95 | 95A | 96 | 97 |
|---|---|---|---|---|---|---|---|---|---|---|---|---|---|---|
| VK1-5 | 10 | 1 | CASCASTMCVRTRSTTWCYCTCBTTWCACT | 267 | HQ | HQ | SY | DGHNRS | AGST | FY | PS | PLR | FY | T |
| VK1-5 | 10 | 2 | CASCASTMCVRTRSTTWCYCTCBTMTCACT | 268 | HQ | HQ | SY | DGHNRS | AGST | FY | PS | PLR | IL | T |
| VK1-5 | 10 | 3 | CASCASTMCVRTRSTTWCYCTCBTWGGACT | 269 | HQ | HQ | SY | DGHNRS | AGST | FY | PS | PLR | WR | T |
| VK1-12 | 8 | 1 | CASCASDCTRVCARTTTSTWCACT | 270 | HQ | HQ | AST | ADGNST | NS | FL | — | — | FY | T |
| VK1-12 | 8 | 2 | CASCASDCTRVCARTTTSMTCACT | 271 | HQ | HQ | AST | ADGNST | NS | FL | — | — | IL | T |
| VK1-12 | 8 | 3 | CASCASDCTRVCARTTTSWGGACT | 272 | HQ | HQ | AST | ADGNST | NS | FL | — | — | WR | T |
| VK1-12 | 8 | 4 | CASCASDCTRVCARTTTSCCTACT | 273 | HQ | HQ | AST | ADGNST | NS | FL | P | — | — | T |
| VK1-12 | 9 | 1 | CASCASDCTRVCARTTTSCCTTWCACT | 274 | HQ | HQ | AST | ADGNST | NS | FL | P | — | FY | T |
| VK1-12 | 9 | 2 | CASCASDCTRVCARTTTSCCTMTCACT | 275 | HQ | HQ | AST | ADGNST | NS | FL | P | — | IL | T |
| VK1-12 | 9 | 3 | CASCASDCTRVCARTTTSCCTWGGACT | 276 | HQ | HQ | AST | ADGNST | NS | FL | P | — | WR | T |
| VK1-12 | 9 | 4 | CASCASDCTRVCARTTTSCCTCBTACT | 277 | HQ | HQ | AST | ADGNST | NS | FL | P | PLR | — | T |
| VK1-12 | 10 | 1 | CASCASDCTRVCARTTTSCCTCBTTWCACT | 278 | HQ | HQ | AST | ADGNST | NS | FL | P | PLR | FY | T |
| VK1-12 | 10 | 2 | CASCASDCTRVCARTTTSCCTCBTMTCACT | 279 | HQ | HQ | AST | ADGNST | NS | FL | P | PLR | IL | T |
| VK1-12 | 10 | 3 | CASCASDCTRVCARTTTSCCTCBTWGGACT | 280 | HQ | HQ | AST | ADGNST | NS | FL | P | PLR | WR | T |
| VK1-27 | 8 | 1 | CASMAGTWCRRTASKGBATWCACT | 281 | HQ | KQ | FY | DGNS | RST | AGV | — | — | FY | T |
| VK1-27 | 8 | 2 | CASMAGTWCRRTASKGBAMTCACT | 282 | HQ | KQ | FY | DGNS | RST | AGV | — | — | IL | T |

TABLE 33-continued

Degenerate Oligonucleotides Encoding an Exemplary VKCDR3 Library

| Chassis | CDRL3 Length | Junction Type (1) | Degenerate Oligonucleotide | SEQ ID NO: | 89 | 90 | 91 | 92 | 93 | 94 | 95 | 95A | 96 | 97 |
|---|---|---|---|---|---|---|---|---|---|---|---|---|---|---|
| VK1-27 | 8 | 3 | CASMAGTWCRRTASKGBAWGGACT | 283 | HQ | KQ | FY | DGNS | RST | AGV | — | — | WR | T |
| VK1-27 | 8 | 4 | CASMAGTWCRRTASKGBACCTACT | 284 | HQ | KQ | FY | DGNS | RST | AGV | P | — | — | T |
| VK1-27 | 9 | 1 | CASMAGTWCRRTASKGBACCTTWCACT | 285 | HQ | KQ | FY | DGNS | RST | AGV | P | — | FY | T |
| VK1-27 | 9 | 2 | CASMAGTWCRRTASKGBACCTMTCACT | 286 | HQ | KQ | FY | DGNS | RST | AGV | P | — | IL | T |
| VK1-27 | 9 | 3 | CASMAGTWCRRTASKGBACCTWGGACT | 287 | HQ | KQ | FY | DGNS | RST | AGV | P | — | WR | T |
| VK1-27 | 9 | 4 | CASMAGTWCRRTASKGBACCTCBTACT | 288 | HQ | KQ | FY | DGNS | RST | AGV | P | PLR | — | T |
| VK1-27 | 10 | 1 | CASMAGTWCRRTASKGBACCTCBTTWCACT | 289 | HQ | KQ | FY | DGNS | RST | AGV | P | PLR | FY | T |
| VK1-27 | 10 | 2 | CASMAGTWCRRTASKGBACCTCBTMTCACT | 290 | HQ | KQ | FY | DGNS | RST | AGV | P | PLR | IL | T |
| VK1-27 | 10 | 3 | CASMAGTWCRRTASKGBACCTCBTWGGACT | 291 | HQ | KQ | FY | DGNS | RST | AGV | P | PLR | WR | T |
| VK1-33 | 8 | 1 | CASCWTTMCRATRVCBWTTWCACT | 292 | HQ | HL | SY | DN | ADGNST | DFHLVY | — | — | FY | T |
| VK1-33 | 8 | 2 | CASCWTTMCRATRVCBWTMTCACT | 293 | HQ | HL | SY | DN | ADGNST | DFHLVY | — | — | IL | T |
| VK1-33 | 8 | 3 | CASCWTTMCRATRVCBWTWGGACT | 294 | HQ | HL | SY | DN | ADGNST | DFHLVY | — | — | WR | T |
| VK1-33 | 8 | 4 | CASCWTTMCRATRVCBWTCCTACT | 295 | HQ | HL | SY | DN | ADGNST | DFHLVY | P | — | — | T |
| VK1-33 | 9 | 1 | CASCWTTMCRATRVCBWTCCTTWCACT | 296 | HQ | HL | SY | DN | ADGNST | DFHLVY | P | — | FY | T |
| VK1-33 | 9 | 2 | CASCWTTMCRATRVCBWTCCTMTCACT | 297 | HQ | HL | SY | DN | ADGNST | DFHLVY | P | — | IL | T |
| VK1-33 | 9 | 3 | CASCWTTMCRATRVCBWTCCTWGGACT | 298 | HQ | HL | SY | DN | ADGNST | DFHLVY | P | — | WR | T |

TABLE 33-continued

Degenerate Oligonucleotides Encoding an Exemplary VKCDR3 Library

| Chassis | CDRL3 Length | Junction Type (1) | Degenerate Oligonucleotide | SEQ ID NO: | 89 | 90 | 91 | 92 | 93 | 94 | 95 | 95A | 96 | 97 |
|---|---|---|---|---|---|---|---|---|---|---|---|---|---|---|
| VK1-33 | 9 | 4 | CASCWTTMCRATRVCBWTCCTCBTACT | 299 | HQ | HL | SY | DN | ADGNST | DFHLVY | P | PLR | — | T |
| VK1-33 | 10 | 1 | CASCWTTMCRATRVCBWTCCTCBTTWCACT | 300 | HQ | HL | SY | DN | ADGNST | DFHLVY | P | PLR | FY | T |
| VK1-33 | 10 | 2 | CASCWTTMCRATRVCBWTCCTCBTMTCACT | 301 | HQ | HL | SY | DN | ADGNST | DFHLVY | P | PLR | IL | T |
| VK1-33 | 10 | 3 | CASCWTTMCRATRVCBWTCCTCBTWGGACT | 302 | HQ | HL | SY | DN | ADGNST | DFHLVY | P | PLR | WR | T |
| VK1-39 | 8 | 1 | CWGSAAWCATHCMVTABTTWCACT | 303 | LQ | EQ | ST | FSY | HNPRST | IST | — | — | FY | T |
| VK1-39 | 8 | 2 | CWGSAAWCATHCMVTABTMTCACT | 304 | LQ | EQ | ST | FSY | HNPRST | IST | — | — | IL | T |
| VK1-39 | 8 | 3 | CWGSAAWCATHCMVTABTWGGACT | 305 | LQ | EQ | ST | FSY | HNPRST | IST | — | — | WR | T |
| VK1-39 | 8 | 4 | CWGSAAWCATHCMVTABTCCTACT | 306 | LQ | EQ | ST | FSY | HNPRST | IST | P | — | — | T |
| VK1-39 | 9 | 1 | CWGSAAWCATHCMVTABTCCTTWCACT | 307 | LQ | EQ | ST | FSY | HNPRST | IST | P | — | FY | T |
| VK1-39 | 9 | 2 | CWGSAAWCATHCMVTABTCCTMTCACT | 308 | LQ | EQ | ST | FSY | HNPRST | IST | P | — | IL | T |
| VK1-39 | 9 | 3 | CWGSAAWCATHCMVTABTCCTWGGACT | 309 | LQ | EQ | ST | FSY | HNPRST | IST | P | — | WR | T |
| VK1-39 | 9 | 4 | CWGSAAWCATHCMVTABTCCTCBTACT | 310 | LQ | EQ | ST | FSY | HNPRST | IST | P | PLR | — | T |
| VK1-39 | 10 | 1 | CWGSAAWCATHCMVTABTCCTCBTTWCACT | 311 | LQ | EQ | ST | FSY | HNPRST | IST | P | PLR | FY | T |
| VK1-39 | 10 | 2 | CWGSAAWCATHCMVTABTCCTCBTMTCACT | 312 | LQ | EQ | ST | FSY | HNPRST | IST | P | PLR | IL | T |
| VK1-39 | 10 | 3 | CWGSAAWCATHCMVTABTCCTCBTWGGACT | 313 | LQ | EQ | ST | FSY | HNPRST | IST | P | PLR | WR | T |

TABLE 33-continued

Degenerate Oligonucleotides Encoding an Exemplary VKCDR3 Library

| Chassis | CDRL3 Length | Junction Type (1) | Degenerate Oligonucleotide | SEQ ID NO: | 89 | 90 | 91 | 92 | 93 | 94 | 95 | 95A | 96 | 97 |
|---|---|---|---|---|---|---|---|---|---|---|---|---|---|---|
| VK3-11 | 8 | 1 | CASCASAGWRGKRVCTSGTWCACT | 314 | HQ | HQ | RS | GRS | ADGNST | SW | — | — | FY | T |
| VK3-11 | 8 | 2 | CASCASAGWRGKRVCTSGMTCACT | 315 | HQ | HQ | RS | GRS | ADGNST | SW | — | — | IL | T |
| VK3-11 | 8 | 3 | CASCASAGWRGKRVCTSGWGGACT | 316 | HQ | HQ | RS | GRS | ADGNST | SW | — | — | WR | T |
| VK3-11 | 8 | 4 | CASCASAGWRGKRVCTSGCCTACT | 317 | HQ | HQ | RS | GRS | ADGNST | SW | P | — | — | T |
| VK3-11 | 9 | 1 | CASCASAGWRGKRVCTSGCCTTWCACT | 318 | HQ | HQ | RS | GRS | ADGNST | SW | P | — | FY | T |
| VK3-11 | 9 | 2 | CASCASAGWRGKRVCTSGCCTMTCACT | 319 | HQ | HQ | RS | GRS | ADGNST | SW | P | — | IL | T |
| VK3-11 | 9 | 3 | CASCASAGWRGKRVCTSGCCTWGGACT | 320 | HQ | HQ | RS | GRS | ADGNST | SW | P | — | WR | T |
| VK3-11 | 9 | 4 | CASCASAGWRGKRVCTSGCCTCBTACT | 321 | HQ | HQ | RS | GRS | ADGNST | SW | P | PLR | — | T |
| VK3-11 | 10 | 1 | CASCASAGWRGKRVCTSGCCTCBTTWCACT | 322 | HQ | HQ | RS | GRS | ADGNST | SW | P | PLR | FY | T |
| VK3-11 | 10 | 2 | CASCASAGWRGKRVCTSGCCTCBTMTCACT | 323 | HQ | HQ | RS | GRS | ADGNST | SW | P | PLR | IL | T |
| VK3-11 | 10 | 3 | CASCASAGWRGKRVCTSGCCTCBTWGGACT | 324 | HQ | HQ | RS | GRS | ADGNST | SW | P | PLR | WR | T |
| VK3-15 | 8 | 1 | CASCASTMCVRTRRKTGGTWCACT | 325 | HQ | HQ | SY | DGHNRS | DEGKNRS | W | — | — | FY | T |
| VK3-15 | 8 | 2 | CASCASTMCVRTRRKTGGMTCACT | 326 | HQ | HQ | SY | DGHNRS | DEGKNRS | W | — | — | IL | T |
| VK3-15 | 8 | 3 | CASCASTMCVRTRRKTGGWGGACT | 327 | HQ | HQ | SY | DGHNRS | DEGKNRS | W | — | — | WR | T |
| VK3-15 | 8 | 4 | CASCASTMCVRTRRKTGGCCTACT | 328 | HQ | HQ | SY | DGHNRS | DEGKNRS | W | P | — | — | T |
| VK3-15 | 9 | 1 | CASCASTMCVRTRRKTGGCCTTWCACT | 329 | HQ | HQ | SY | DGHNRS | DEGKNRS | W | P | — | FY | T |

TABLE 33-continued

Degenerate Oligonucleotides Encoding an Exemplary VKCDR3 Library

| Chassis | CDRL3 Length | Junction Type (1) | Degenerate Oligonucleotide | SEQ ID NO: | 89 | 90 | 91 | 92 | 93 | 94 | 95 | 95A | 96 | 97 |
|---|---|---|---|---|---|---|---|---|---|---|---|---|---|---|
| VK3-15 | 9 | 2 | CASCASTMCVRTRRKTGGCCTMTCACT | 330 | HQ | HQ | SY | DGHNRS | DEGKNRS | W | P | — | IL | T |
| VK3-15 | 9 | 3 | CASCASTMCVRTRRKTGGCCTWGGACT | 331 | HQ | HQ | SY | DGHNRS | DEGKNRS | W | P | — | WR | T |
| VK3-15 | 9 | 4 | CASCASTMCVRTRRKTGGCCTCBTACT | 332 | HQ | HQ | SY | DGHNRS | DEGKNRS | W | P | PLR | — | T |
| VK3-15 | 10 | 1 | CASCASTMCVRTRRKTGGCCTCBTTWCACT | 333 | HQ | HQ | SY | DGHNRS | DEGKNRS | W | P | PLR | FY | T |
| VK3-15 | 10 | 2 | CASCASTMCVRTRRKTGGCCTCBTMTCACT | 334 | HQ | HQ | SY | DGHNRS | DEGKNRS | W | P | PLR | IL | T |
| VK3-15 | 10 | 3 | CASCASTMCVRTRRKTGGCCTCBTWGGACT | 335 | HQ | HQ | SY | DGHNRS | DEGKNRS | W | P | PLR | WR | T |
| VK3-20 | 8 | 1 | CASCASTWCGRTRVKKCATWCACT | 336 | HQ | HQ | FY | DG | ADEGKNRST | AS | — | — | FY | T |
| VK3-20 | 8 | 2 | CASCASTWCGRTRVKKCAMTCACT | 337 | HQ | HQ | FY | DG | ADEGKNRST | AS | — | — | IL | T |
| VK3-20 | 8 | 3 | CASCASTWCGRTRVKKCAWGGACT | 338 | HQ | HQ | FY | DG | ADEGKNRST | AS | — | — | WR | T |
| VK3-20 | 8 | 4 | CASCASTWCGRTRVKKCACCTACT | 339 | HQ | HQ | FY | DG | ADEGKNRST | AS | P | — | — | T |
| VK3-20 | 9 | 1 | CASCASTWCGRTRVKKCACCTTWCACT | 340 | HQ | HQ | FY | DG | ADEGKNRST | AS | P | — | FY | T |
| VK3-20 | 9 | 2 | CASCASTWCGRTRVKKCACCTMTCACT | 341 | HQ | HQ | FY | DG | ADEGKNRST | AS | P | — | IL | T |
| VK3-20 | 9 | 3 | CASCASTWCGRTRVKKCACCTWGGACT | 342 | HQ | HQ | FY | DG | ADEGKNRST | AS | P | — | WR | T |
| VK3-20 | 9 | 4 | CASCASTWCGRTRVKKCACCTCBTACT | 343 | HQ | HQ | FY | DG | ADEGKNRST | AS | P | PLR | — | T |
| VK3-20 | 10 | 1 | CASCASTWCGRTRVKKCACCTCBTTWCACT | 344 | HQ | HQ | FY | DG | ADEGKNRST | AS | P | PLR | FY | T |

TABLE 33-continued

Degenerate Oligonucleotides Encoding an Exemplary VKCDR3 Library

| Chassis | CDRL3 Length | Junction Type (1) | Degenerate Oligonucleotide | SEQ ID NO: | 89 | 90 | 91 | 92 | 93 | 94 | 95 | 95A | 96 | 97 |
|---|---|---|---|---|---|---|---|---|---|---|---|---|---|---|
| VK3-20 | 10 | 2 | CASCASTWCGRTRVKKCACCTCBTMTCACT | 345 | HQ | HQ | FY | DG | ADEGKNRST | AS | P | PLR | IL | T |
| VK3-20 | 10 | 3 | CASCASTWCGRTRVKKCACCTCBTWGGACT | 346 | HQ | HQ | FY | DG | ADEGKNRST | AS | P | PLR | WR | T |
| VK2-28 | 8 | 1 | ATGCASRBTCKTSASABTTWCACT | 347 | M | HQ | AGISTV | LR | DEHQ | IST | — | — | FY | T |
| VK2-28 | 8 | 2 | ATGCASRBTCKTSASABTMTCACT | 348 | M | HQ | AGISTV | LR | DEHQ | IST | — | — | IL | T |
| VK2-28 | 8 | 3 | ATGCASRBTCKTSASABTWGGACT | 349 | M | HQ | AGISTV | LR | DEHQ | IST | — | — | WR | T |
| VK2-28 | 8 | 4 | ATGCASRBTCKTSASABTCCTACT | 350 | M | HQ | AGISTV | LR | DEHQ | IST | P | — | — | T |
| VK2-28 | 9 | 1 | ATGCASRBTCKTSASABTCCTTWCACT | 351 | M | HQ | AGISTV | LR | DEHQ | IST | P | — | FY | T |
| VK2-28 | 9 | 2 | ATGCASRBTCKTSASABTCCTMTCACT | 352 | M | HQ | AGISTV | LR | DEHQ | IST | P | — | IL | T |
| VK2-28 | 9 | 3 | ATGCASRBTCKTSASABTCCTWGGACT | 353 | M | HQ | AGISTV | LR | DEHQ | IST | P | — | WR | T |
| VK2-28 | 9 | 4 | ATGCASRBTCKTSASABTCCTCBTACT | 354 | M | HQ | AGISTV | LR | DEHQ | IST | P | PLR | — | T |
| VK2-28 | 10 | 1 | ATGCASRBTCKTSASABTCCTCBTTWCACT | 355 | M | HQ | AGISTV | LR | DEHQ | IST | P | PLR | FY | T |
| VK2-28 | 10 | 2 | ATGCASRBTCKTSASABTCCTCBTMTCACT | 356 | M | HQ | AGISTV | LR | DEHQ | IST | P | PLR | IL | T |
| VK2-28 | 10 | 3 | ATGCASRBTCKTSASABTCCTCBTWGGACT | 357 | M | HQ | AGISTV | LR | DEHQ | IST | P | PLR | WR | T |
| VK4-1 | 8 | 1 | CASCASTWCTWCRVCABTTWCACT | 358 | HQ | HQ | FY | FY | ADGNST | IST | — | — | FY | T |
| VK4-1 | 8 | 2 | CASCASTWCTWCRVCABTMTCACT | 359 | HQ | HQ | FY | FY | ADGNST | IST | — | — | IL | T |
| VK4-1 | 8 | 3 | CASCASTWCTWCRVCABTWGGACT | 360 | HQ | HQ | FY | FY | ADGNST | IST | — | — | WR | T |

TABLE 33-continued

Degenerate Oligonucleotides Encoding an Exemplary VKCDR3 Library

| Chassis | CDRL3 Length | Junction Type (1) | Degenerate Oligonucleotide | SEQ ID NO: | 89 | 90 | 91 | 92 | 93 | 94 | 95 | 95A | 96 | 97 |
|---|---|---|---|---|---|---|---|---|---|---|---|---|---|---|
| VK4-1 | 8 | 4 | CASCASTWCTWCRVCABTCCTACT | 361 | HQ | HQ | FY | FY | ADGNST | IST | P | — | — | T |
| VK4-1 | 9 | 1 | CASCASTWCTWCRVCABTCCTTWCACT | 362 | HQ | HQ | FY | FY | ADGNST | IST | P | — | FY | T |
| VK4-1 | 9 | 2 | CASCASTWCTWCRVCABTCCTMTCACT | 363 | HQ | HQ | FY | FY | ADGNST | IST | P | — | IL | T |
| VK4-1 | 9 | 3 | CASCASTWCTWCRVCABTCCTWGGACT | 364 | HQ | HQ | FY | FY | ADGNST | IST | P | — | WR | T |
| VK4-1 | 9 | 4 | CASCASTWCTWCRVCABTCCTCBTACT | 365 | HQ | HQ | FY | FY | ADGNST | IST | P | PLR | — | T |
| VK4-1 | 10 | 1 | CASCASTWCTWCRVCABTCCTCBTTWCACT | 366 | HQ | HQ | FY | FY | ADGNST | IST | P | PLR | FY | T |
| VK4-1 | 10 | 2 | CASCASTWCTWCRVCABTCCTCBTMTCACT | 367 | HQ | HQ | FY | FY | ADGNST | IST | P | PLR | IL | T |
| VK4-1 [Alternative for VK1-33] (2) | 10 | 3 | CASCASTWCTWCRVCABTCCTCBTWGGACT | 368 | HQ | HQ | FY | FY | ADGNST | IST | P | PLR | WR | T |
| VK1-33 | 8 | 1 | CASCWATMCRATRVCBWTTWCACT | 369 | HQ | QL | SY | DN | ADGNST | DFHLVY | — | — | FY | T |
| VK1-33 | 8 | 2 | CASCWATMCRATRVCBWTMTCACT | 370 | HQ | QL | SY | DN | ADGNST | DFHLVY | — | — | IL | T |
| VK1-33 | 8 | 3 | CASCWATMCRATRVCBWTWGGACT | 371 | HQ | QL | SY | DN | ADGNST | DFHLVY | — | — | WR | T |
| VK1-33 | 8 | 4 | CASCWATMCRATRVCBWTCCTACT | 372 | HQ | QL | SY | DN | ADGNST | DFHLVY | P | — | — | T |
| VK1-33 | 9 | 1 | CASCWATMCRATRVCBWTCCTTWCACT | 373 | HQ | QL | SY | DN | ADGNST | DFHLVY | P | — | FY | T |
| VK1-33 | 9 | 2 | CASCWATMCRATRVCBWTCCTMTCACT | 374 | HQ | QL | SY | DN | ADGNST | DFHLVY | P | — | IL | T |
| VK1-33 | 9 | 3 | CASCWATMCRATRVCBWTCCTWGGACT | 375 | HQ | QL | SY | DN | ADGNST | DFHLVY | P | — | WR | T |

TABLE 33-continued

Degenerate Oligonucleotides Encoding an Exemplary VKCDR3 Library

| Chassis | CDRL3 Length | Junction Type (1) | Degenerate Oligonucleotide | SEQ ID NO: | 89 | 90 | 91 | 92 | 93 | 94 | 95 | 95A | 96 | 97 |
|---|---|---|---|---|---|---|---|---|---|---|---|---|---|---|
| VK1-33 | 9 | 4 | CASCWATM CRATRVCB WTCCTCBT ACT | 376 | HQ | QL | SY | DN | ADGNS T | DFH LVY | P | PLR | — | T |
| VK1-33 | 10 | 1 | CASCWATM CRATRVCB WTCCTCBT TWCACT | 377 | HQ | QL | SY | DN | ADGNS T | DFH LVY | P | PLR | FY | T |
| VK1-33 | 10 | 2 | CASCWATM CRATRVCB WTCCTCBT MTCACT | 378 | HQ | QL | SY | DN | ADGNS T | DFH LVY | P | PLR | IL | T |
| VK1-33 | 10 | 3 | CASCWATM CRATRVCB WTCCTCBT WGGACT | 379 | HQ | QL | SY | DN | ADGNS T | DFH LVY | P | PLR | WR | T |

(1) Junction type 1 has position 96 as FY, type 2 as IL, type 3 as RW, and type 4 has a deletion.
(2) Two embodiments are shown for the VK1-33 library. In one embodiment, the second codon was CWT. In another embodiment, it was CWA or CWG.

Example 6.3

More Complex VKCDR3 Libraries

This example demonstrates how a more faithful representation of amino acid variation at each position may be obtained by using a codon-based synthesis approach (Virnekas et al. Nucleic Acids Res., 1994, 22: 5600). This synthetic scheme also allows for finer control of the proportions of particular amino acids included at a position. For example, as described above for the VK1-39 sequences, position 89 was designed as 50% Q and 50% L; however, as Table 30 shows, Q is used much more frequently than L. The more complex VKCDR3 libraries of the present example account for the different relative occurrence of Q and L, for example, 90% Q and 10% L. Such control is better exercised within codon-based synthetic schemes, especially when multiple amino acid types are considered.

This example also describes an implementation of a codon-based synthetic scheme, using the ten VK chassis described in Table 11. Similar approaches, of course, can be implemented with more or fewer such chassis. As indicated in the Detailed Description, a unique aspect of the design of the present libraries, as well as those of the preceding examples, is the germline or chassis-based aspect, which is meant to preserve more of the integrity and variation of actual human kappa light chain sequences. This is in contrast to other codon-based synthesis or degenerate oligonucleotide synthesis approaches that have been described in the literature and that aim to produce "one-size-fits-all" (e.g., consensus) kappa light chain libraries (e.g. Knappik, et al., J Mol Biol, 2000, 296: 57; Akamatsu et al., J Immunol, 1993, 151: 4651).

With reference to Table 30, obtained for VK1-39, one can thus design the length nine VKCDR3 library of Table 34. Here, for practical reasons, the proportions at each position are denoted in multiples of five percentage points. As better synthetic schemes are developed, finer resolution may be obtained—for example to resolutions of one, two, three, or four percent.

TABLE 34

Amino Acid Composition (%) at Each VKCDR3 Position for VK1-39 Library With CDR Length of Nine Residues

| Amino Acid | 89 | 90 | 91 | 92 | 93 | 94 | 95 | 96 (*) | 97 (*) |
|---|---|---|---|---|---|---|---|---|---|
| A |  |  |  |  |  | 5 |  |  | 5 |
| D |  |  |  | 5 | 5 |  |  |  |  |
| E |  | 5 |  |  |  | 5 |  |  |  |
| F |  |  |  |  | 5 |  |  | 10 |  |
| G |  |  |  | 5 | 5 | 5 |  | 5 |  |
| H | 5 | 5 |  |  | 5 |  | 5 |  |  |
| I |  |  |  |  |  | 5 |  | 5 |  |
| K |  |  |  |  |  | 5 |  |  |  |
| L | 10 |  |  |  |  | 5 | 10 | 20 |  |
| M |  |  |  |  |  |  |  |  |  |
| N |  |  | 0 | 0 | 5 | 0 |  | 5 |  |
| P |  |  |  |  |  |  | 5 | 85 | 5 |
| Q | 85 | 90 |  |  |  |  |  |  | 5 |
| R |  |  |  |  |  | 5 |  | 5 | 10 |
| S |  |  | 80 | 5 | 60 | 5 |  |  | 5 |
| T |  |  | 10 |  | 10 | 65 |  |  | 90 |
| V |  |  |  |  |  |  |  | 5 |  |
| W |  |  |  |  |  |  |  | 15 |  |
| Y |  |  | 5 | 75 |  | 5 |  | 15 |  |
| Number Different | 3 | 3 | 4 | 6 | 8 | 8 | 3 | 11 | 3 |

(*) The composition of positions 96 and 97, determined largely by junction and IGKJ diversity, could be the same for length 9 VK CDR3 of all chassis.

The library of Table 34 would have $1.37 \times 10^6$ unique polypeptide sequences, calculated by multiplying together the numbers in the bottom row of the table.

The underlined 0 entries for Asn (N) at certain positions represent regions where the possibility of having N-linked glycosylation sites in the VKCDR3 has been minimized or eliminated. Peptide sequences with the pattern N-X-(S or T)-Z, where X and Z are different from P, may undergo post-translational modification in a number of expression systems, including yeast and mammalian cells. Moreover, the nature of such modification depends on the specific cell type and, even for a given cell type, on culture conditions. N-linked glycosylation may be disadvantageous when it occurs in a region of the antibody molecule likely to be involved in antigen binding (e.g., a CDR), as the function of the antibody may then be influenced by factors that may be difficult to control. For example, considering position 91 above, one can observe that position 92 is never P. Position 94 is not P in 95% of the cases. However, position 93 is S or T in 75% (65+10) of the cases. Thus, allowing N at position 91 would generate the undesirable motif N-X-(T/S)-Z (with both X and Z distinct from P), and a zero occurrence has therefore been implemented, even though N is observed with some frequency in actual human sequences (see Table 30). A similar argument applies for N at positions 92 and 94. It should be appreciated, however, that if the antibody library were to be expressed in a system incapable of N-linked glycosylation, such as bacteria, or under culture conditions in which N-linked glycosylation did not occur, this consideration may not apply. However, even in the event that the organism used to express libraries with potential N-linked glycosylation sites is incapable of N-linked glycosylation (e.g., bacteria), it may still be desirable to avoid N-X-(S/T) sequences, as the antibodies isolated from such libraries may be expressed in different systems (e.g., yeast, mammalian cells) later (e.g., toward clinical development), and the presence of carbohydrate moieties in the variable domains, and the CDRs in particular, may lead to unwanted modifications of activity. These embodiments are also included within the scope of the invention. To our knowledge, VKCDR3 libraries known in the art have not considered this effect, and thus a proportion of their members may have the undesirable qualities mentioned above.

We also designed additional sub-libraries, related to the library outlined in Table 34, for VKCDR3 of lengths 8 and 10. In these embodiments, the compositions at positions 89 to 94 and 97 remain the same as those depicted in Table 34. Additional diversity, introduced at positions 95 and 95A, the latter being defined for VKCDR3 of length 10 only, are illustrated in Table 35.

TABLE 35

Amino Acid Composition (%) for VK1-39 Libraries of Lengths 8 and 10

| Amino Acid | Position 95 - Length 8 (*) | Position 95 - Length 10 (**) | Position 95A - Length 10 |
|---|---|---|---|
| A | | | |
| D | | | |
| E | | | |
| F | 5 | | |
| G | | | 5 |
| H | | | |
| I | 10 | | 5 |
| K | | | |
| L | 20 | 10 | 10 |
| M | | | |
| N | | | |
| P | 25 | 85 | 60 |
| Q | | | |
| R | 10 | 5 | 10 |
| S | 5 | | 5 |
| T | | | 5 |
| V | 5 | | |
| W | 10 | | |
| Y | 10 | | |
| Number Different | 9 | 3 | 8 |

(*) Position 96 is deleted in VKCDR3 of size 8.
(**) This is the same composition as in VKCDR3 of size 9.

The total number of unique members in the VK1-39 library of length 8, thus, can be obtained as before, and is $3.73 \times 10^5$ (or, $3 \times 3 \times 4 \times 6 \times 8 \times 8 \times 9 \times 3$). Similarly, the complexity of the VK1-39 library of length 10 would be $10.9 \times 10^6$ (or 8 times that of the library of size 9, as there is additional 8-fold variation at the insertion position 95A). Thus, there would be a total of $12.7 \times 10^6$ unique members in the overall VK1-39 library, as obtained by summing the number of unique members for each of the specified lengths. In certain embodiments of the invention, it may be preferable to create the individual sub-libraries of lengths 8, 9 and 10 separately, and then mix the sub-libraries in proportions that reflect the length distribution of VKCDR3 in human sequences; for example, in ratios approximating the 1:9:2 distribution that occurs in natural VKCDR3 sequences (see FIG. 3). The present invention provides the compositions and methods for one of ordinary skill synthesizing VKCDR3 libraries corresponding to other VK chassis.

Example 7

A Minimalist Vλ CDR3 Library

This example describes the design of a minimalist VλCDR3 library. The principles used in designing this library (or more complex Vλ libraries) are similar to those used to design the VKCDR3 libraries. However, unlike the VK genes, the contribution of the IgλV segment to CDRL3 is not constrained to a fixed number of amino acids. Therefore, length variation may be obtained in a minimalist VλCDR3 library even when only considering combinations between Vλ chassis and Jλ sequences.

Figure 4:
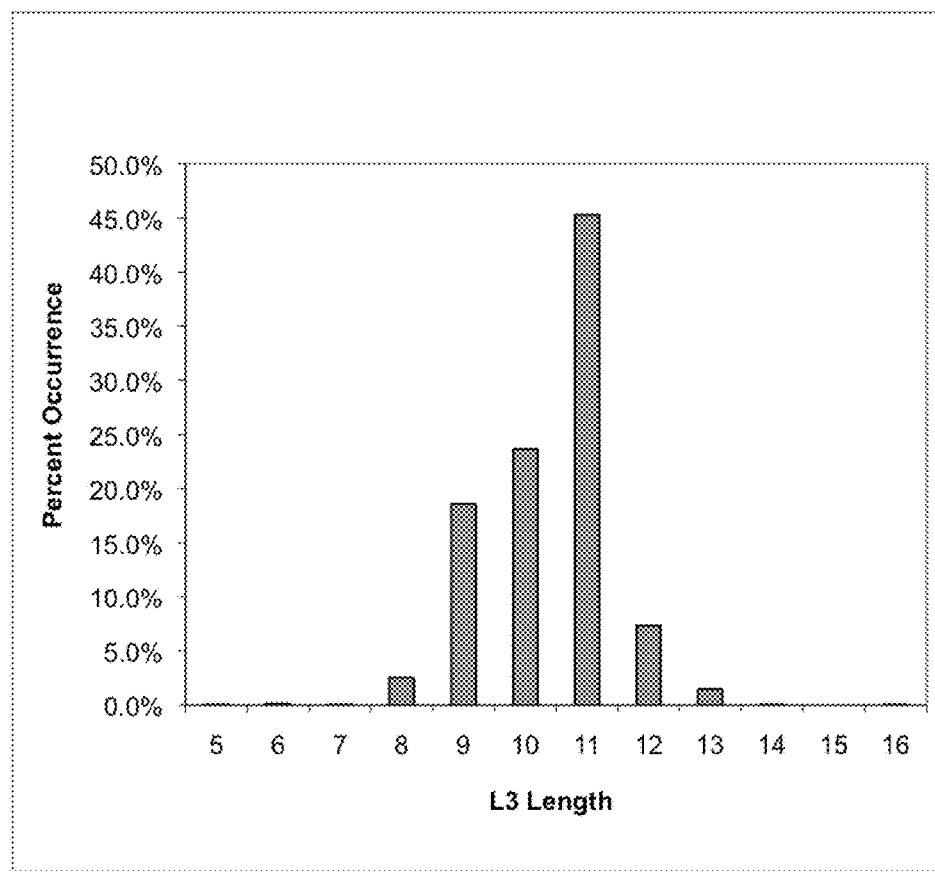
FIG. 4 depicts the length distribution of the CDRL3 regions of rearranged human lambda light chain sequences compiled from the NCBI database (Appendix B).

Examination of the Vλ CDR3 lengths of human sequences shows that lengths of 9 to 12 account for almost about 95% of sequences, and lengths of 8 to 12 account for about 97% of sequences (FIG. 4). Table 36 shows the usage (percent occurrence) of the six known IGλJ genes in the rearranged human lambda light chain sequences compiled from the NCBI database (see Appendix B), and Table 37 shows the sequences encoded by the genes.

TABLE 36

IGλJ Gene Usage in the Lambda Light Chain Sequences Compiled from the NCBI Database (see Appendix B)

| Gene_Allele | LUA |
|---|---|
| Jλ1_01 | 20.2% |
| Jλ2_01 | 42.2% |
| Jλ3_02 | 36.2% |
| Jλ6_01 | 0.6% |
| Jλ7_01 | 0.9% |

TABLE 37

Observed Human IGλJ Amino Acid Sequences

| Gene | Sequence | SEQ ID NO: |
|---|---|---|
| IGλJ1-01 | YVFGTGTKVTVL | 557 |
| IGλJ2-01 | VVFGGGTKLTVL | 558 |
| IGλJ3-01 | WVFGGGTKLTVL | 559 |
| IGλJ3-02 | VVFGGGTKLTVL | 560 |
| IGλJ6-01 | NVFGSGTKVTVL | 561 |

TABLE 37-continued

Observed Human IGλJ Amino Acid Sequences

| Gene | Sequence | SEQ ID NO: |
|---|---|---|
| IGλJ7-01 | AVFGGGTQLTVL | 562 |
| IGλJ7-02 | AVFGGGTQLTAL | 563 |

IGλJ3-01 and IGλJ7-02 are not represented among the sequences that were analyzed; therefore, they were not included in Table 36. As illustrated in Table 36, IGλJ1-01, IGλJ2-01, and IGλJ3-02 are over-represented in their usage, and have thus been bolded in Table 37. In some embodiments of the invention, for example, only these three over-represented sequences may be utilized. In other embodiments of the invention, one may use all six segments, any 1, 2, 3, 4, or 5 of the 6 segments, or any combination thereof may be utilized.

As shown in Table 14, the portion of CDRL3 contributed by the IGλV gene segment is 7, 8, or 9 amino acids. The remainder of CDRL3 and FRM4 are derived from the IGλJ sequences (Table 37). The IGλJ sequences contribute either one or two amino acids to CDRL3. If two amino acids are contributed by IGλJ, the contribution is from the N-terminal two residues of the IGλJ segment: YV (IGλJ1-01), VV (IGλJ2-01), WV (IGλJ3-01), VV (IGλJ3-02), or AV (IGλJ7-01 and IGλJ7-02). If one amino acid is contributed from IGλJ, it is a V residue, which is formed after the deletion of the N-terminal residue of a IGλJ segment.

In this non-limiting exemplary embodiment of the invention, the FRM4 segment was fixed as FGGGTKLTVL, corresponding to IGλJ2-01 and IGλJ3-02 (i.e., portions of SEQ ID NOs: 558 and 560).

Seven of the 11 selected chassis (Vλ1-40 (SEQ ID NO: 531), Vλ3-19 (SEQ ID NO: 536), Vλ3-21 (SEQ ID NO: 537), Vλ6-57 (SEQ ID NO: 539), Vλ1-44 (SEQ ID NO: 532), Vλ1-51 (SEQ ID NO: 533), and Vλ4-69 (SEQ ID NO: 538)) have an additional two nucleotides following the last full codon. In four of those seven cases, analysis of the data set provided in Appendix B showed that the addition of a single nucleotide (i.e. without being limited by theory, via the activity of TdT) lead to a further increase in CDRL3 length. This effect can be considered by introducing variants for the L3-Vλ sequences contributed by these four ION sequences (Table 38).

Thus, the final set of chassis in the currently exemplified embodiment of the invention is 15: eleven contributed by the chassis in Table 14 and an additional four contributed by the chassis of Table 38. The corresponding L3-Vλ domains of the 15 chassis contribute from 7 to 10 amino acids to CDRL3. When considering the amino acids contributed by the IGλJ sequences, the total variation in the length of CDRL3 is 8 to 12 amino acids, approximating the distribution in FIG. 4. Thus, in this exemplary embodiment of the invention, the minimalist Vλ library may be represented by the following: 15 Chassis×5 IGλJ-derived segments=75 sequences. Here, the 15 chassis are Vλ1-40 (SEQ ID NO: 531), Vλ1-44 (SEQ ID NO: 532), Vλ1-51 (SEQ ID NO: 533), Vλ2-14 (SEQ ID NO: 534), Vλ3-1* (SEQ ID NO: 535), Vλ3-19 (SEQ ID NO: 536), Vλ3-21 (SEQ ID NO: 537), Vλ4-69 (SEQ ID NO: 538), Vλ6-57 (SEQ ID NO: 539), Vλ5-45 (SEQ ID NO: 540), Vλ7-43 (SEQ ID NO: 541), Vλ1-40+ (SEQ ID NO: 564), Vλ3-19+ (SEQ ID NO: 565), Vλ3-21+ (SEQ ID NO: 566), and Vλ6-57+ (SEQ ID NO: 567). The 5 IGλJ-derived segments are YVFGGGT-KLTVL (IGλJ1; SEQ ID NO: 568), VVFGGGTKLTVL (IGλJ2; SEQ ID NO: 558), WVFGGGTKLTVL (IGλJ3; SEQ ID NO: 559), AVFGGGTKLTVL (IGλJ7; SEQ ID NO: 569), and -VFGGGTKLTVL (from any of the preceding sequences).

Example 8

Matching to "Reference" Antibodies

CDRH3 sequences of human antibodies of interest that are known in the art, (e.g., antibodies that have been used in the clinic) have close counterparts in the designed library of the invention. A set of fifteen CDRH3 sequences from clinically relevant antibodies is presented in Table 39.

TABLE 39

CDRH3 Sequences of Reference Antibodies

| Antibody Name | Target | Origin | Status | CDHR3 sequence | SEQ ID NO: |
|---|---|---|---|---|---|
| CAB1 | TNF-α | Phage display-human library | FDA Approved | AKVSYLST ASSLDY | 380 |

TABLE 38

Variants with an additional residue in CDRL3

| Name | Locus | FRM1 | CDR1 | FRM2 | CDR2 | FRM3 | CDR3/ L3-Vλ | SEQ ID NO: |
|---|---|---|---|---|---|---|---|---|
| 1E+ | IGVλ1-40+ | QSVLTQPP SVSGAPGQ RVTISC | TGSSSNI GAGYD-- -VH | WYQQLPG TAPKLLI | YGN--- -SNRPS | GVPDRFSGSKSG --TSASLAITGL QAEDEADYYC | QSYDSS LSGS | 564 |
| 3L+ | IGVλ3-19+ | SSELTQDP AVSVALGQ TVRITC | QGDSLRS -YY---- -AS | WYQQKPG QAPVLVI | YGK--- -NNRPS | GIPDRFSGSSSG --NTASLTITGA QAEDEADYYC | NSRDSS GNHH/Q | 565 |
| 3H+ | IGVλ3-21+ | SYVLTQPP SVSVAPGK TARITC | GGNNIGS KS----- -VH | WYQQKPG QAPVLVI | YYD--- -SDRPS | GIPERFSGSNSG --NTATLTISRV EAGDEADYYC | QVWDSS SDHP | 566 |
| 6A+ | IGVλ6_57+ | NFMLTQPH SVSESPGK TVTISC | TRSSGSI ASNY--- -VQ | WYQQRPG SSPTTVI | YED--- -NQRPS | GVPDRFSGSIDS SSNSASLTISGL KTEDEADYYC | QSYDSS NH/Q-- | 567 |

(+)sequences are derived from their parents by the addition of an amino acid at the end of the respective CDR3 (bold underlined). H/Q can be introduced in a single sequence by use of the degenerate codon CAW or similar.

TABLE 39-continued

CDRH3 Sequences of Reference Antibodies

| Antibody Name | Target | Origin | Status | CDHR3 sequence | SEQ ID NO: |
|---|---|---|---|---|---|
| CAB2 | EGFR | Transgenic mouse | FDA Approved | VRDRVTGA FDI | 381 |
| CAB3 | IL-12/IL-23 | Phage display-human library | Phase III | KTHGSHDN | 382 |
| CAB4 | Interleukin-1-β | Transgenic mouse | Phase III | ARDLRTGP FDY | 383 |
| CAB5 | RANKL | Transgenic mouse | Phase III | AKDPGTTV IMSWFDP | 384 |
| CAB6 | IL-12/IL-23 | Transgenic mouse | Phase III | ARRRPGQG YFDF | 385 |
| CAB7 | TNF-α | Transgenic mouse | Phase III | ARDRGASA GGNYYYYG MDV | 386 |
| CAB8 | CTLA4 | Transgenic mouse | Phase III | ARDPRGAT LYYYYGM DV | 387 |
| CAB9 | CD20 | Transgenic mouse | Phase III | AKDIQYGN YYYGMDV | 388 |
| CAB10 | CD4 | Transgenic mouse | Phase III | ARVINWFD P | 389 |
| CAB11 | CTLA4 | Transgenic mouse | Phase III | ARTGWLGP FDY | 390 |
| CAB12 | IGF1-R | Transgenic mouse | Phase II | AKDLGWSD SYYYYYGM DV | 391 |
| CAB13 | EGFR | Transgenic mouse | Phase II | ARDGITMV RGVMKDYF DY | 392 |
| CAB14 | EGFR | Phage display-human library | Phase II | ARVSIFGV GTFDY | 393 |
| CAB15 | BLyS | Phage display-human library | Phase II | ARSRDLLL FPHHALSP | 394 |

Each of the above sequences was compared to each of the members of the library of Example 5, and the member, or members, with the same length and fewest number of amino acid mismatches was, or were, recorded. The results are summarized in Table 40, below. For most of the cases, matches with 80% identity or better were found in the exemplified CDRH3 library. To the extent that the specificity and binding affinity of each of these antibodies is influenced by their CDRH3 sequence, without being bound by theory, one or more of these library members could have measurable affinity to the relevant targets.

TABLE 40

Match of Reference Antibody CDRH3 to Designed Library

| Antibody Name | Number of Mismatches (*) | Length | % Identity of Best Match |
|---|---|---|---|
| CAB1 | 5 | 14 | 64% |
| CAB2 | 2 | 11 | 82% |
| CAB3 | 4 | 8 | 50% |
| CAB4 | 2 | 11 | 82% |
| CAB5 | 3 | 15 | 80% |
| CABG | 3 | 12 | 75% |
| CAB7 | 2 | 20 | 90% |
| CAB8 | 0 | 19 | 100% |
| CAB9 | 3 | 15 | 80% |
| CAB10 | 1 | 9 | 89% |
| CAB11 | 1 | 11 | 91% |
| CAB12 | 2 | 18 | 89% |
| CAB13 | 2 | 18 | 89% |
| CAB14 | 1 | 13 | 92% |
| CAB15 | 7 | 16 | 56% |

(*) For the best-matching sequence(s) in library

Given that a physical realization of a library with about $10^8$ distinct members could, in practice, contain every single member, then such sequences with close percent identity to antibodies of interest would be present in the physical realization of the library. This example also highlights one of many distinctions of the libraries of the current invention over those of the art; namely, that the members of the libraries of the invention may be precisely enumerated. In contrast, CDRH3 libraries known in the art cannot be explicitly enumerated in the manner described herein. For example, many libraries known in the art (e.g., Hoet et al., Nat. Biotechnol., 2005, 23: 344; Griffiths et al., EMBO J., 1994, 13: 3245; Griffiths et al., EMBO J., 1993, 12: 725; Marks et al., J. Mol. Biol., 1991, 222: 581, each incorporated by reference in its entirety) are derived by cloning of natural human CDRH3 sequences and their exact composition is not characterized, which precludes enumeration.

Synthetic libraries produced by other (e.g., random or semi-random/biased) methods (Knappik, et al., J Mol Biol, 2000, 296: 57, incorporated by reference in its entirety) tend to have very large numbers of unique members. Thus, while matches to a given input sequence (for example, at 80% or greater) may exist in a theoretical representation of such libraries, the probability of synthesizing and then producing a physical realization of the theoretical library that contains such a sequence and then selecting an antibody corresponding to such a match, in practice, may be remotely small. For example, a CDRH3 of length 19 in the Knappik library may have over $10^{19}$ distinct sequences. In a practical realization of such a library a tenth or so of the sequences may have length 19 and the largest total library may have in the order of $10^{10}$ to $10^{12}$ transformants; thus, the probability of a given pre-defined member being present, in practice, is effectively zero (less than one in ten million). Other libraries (e.g., Enzelberger et al. WO2008053275 and Ladner US20060257937, each incorporated by reference in its entirety) suffer from at least one of the limitations described throughout this application.

Thus, for example, considering antibody CAB14, there are seven members of the designed library of Example 5 that differ at just one amino acid position from the sequence of the CDRH3 of CAB14 (given in Table 39). Since the total length of this CDRH3 sequence is 13, the percent of identical amino acids is 12/13 or about 92% for each of these 7 sequences of the library of the invention. It can be estimated that the probability of obtaining such a match (or better) in the library of Knappik et al. is about $1.4 \times 10^{-9}$; it would be lower still, about $5.5 \times 10^{-10}$, in a library with equal amino acid proportions (i.e., completely random). Therefore, in a physical realization of the library with about $10^{10}$ transformants of which about a tenth may have length 13, there may be one or two instances of these best matches. However, with longer sequences such as CAB 12, the probability of having members in the Knappik library with about 89% or better matching are under about $10^{-15}$, so that the expected number of instances in a physical realization of the library is essentially zero. To the extent that sequences of interest resemble actual human CDRH3 sequences, there will be close matches in the library of Example 5, which was designed to mimic human sequences. Thus, one of the many relative advantages of the present library, versus those in the art, becomes more apparent as the length of the CDRH3 increases.

Example 9

Split Pool Synthesis of Oligonucleotides Encoding the DH, N2, and H3-JH Segments This example outlines the procedures used to synthesize the oligonucleotides used to construct the exemplary libraries of the invention. Custom Primer Support™ 200 dT40S resin (GE Healthcare) was used to synthesize the oligonucleotides, using a loading of about 39 µmol/g of resin. Columns (diameter=30 µm) and frits were purchased from Biosearch Technologies, Inc. A column bed volume of 30 µL was used in the synthesis, with 120 nmol of resin loaded in each column. A mixture of dichloromethane (DCM) and methanol (MeOH), at a ratio of 400/122 (v/v) was used to load the resin. Oligonucleotides were synthesized using a Dr. Oligo® 192 oligonucleotide synthesizer and standard phosphorothioate chemistry.

The split pool procedure for the synthesis of the [DH]-[N2]-[H3-JH]oligonucleotides was performed as follows: First, oligonucleotide leader sequences, containing a randomly chosen 10 nucleotide sequence (ATGCACAGTT; SEQ ID NO: 395), a BsrDI recognition site (GCAATG), and a two base "overlap sequence" (TG, AC, AG, CT, or GA) were synthesized. The purpose of each of these segments is explained below. After synthesis of this 18 nucleotide sequence, the DH segments were synthesized; approximately 1 g of resin (with the 18 nucleotide segment still conjugated) was suspended in 20 mL of DCM/MeOH. About 60 µL of the resulting slurry (120 nmol) was distributed inside each of 278 oligonucleotide synthesis columns. These 278 columns were used to synthesize the 278 DH segments of Table 18, 3' to the 18 nucleotide segment described above. After synthesis, the 278 DH segments were pooled as follows: the resin and frits were pushed out of the columns and collected inside a 20 mL syringe barrel (without plunger). Each column was then washed with 0.5 mL MeOH, to remove any residual resin that was adsorbed to the walls of the column. The resin in the syringe barrel was washed three times with MeOH, using a low porosity glass filter to retain the resin. The resin was then dried and weighed.

The pooled resin (about 1.36 g) containing the 278 DH segments was subsequently suspended in about 17 mL of DCM/MeOH, and about 60 µL of the resulting slurry was distributed inside each of two sets of 141 columns. The 141 N2 segments enumerated in Tables 24 and 25 were then synthesized, in duplicate (282 total columns), 3' to the 278 DH segments synthesized in the first step. The resin from the 282 columns was then pooled, washed, and dried, as described above.

The pooled resin obtained from the N2 synthesis (about 1.35 g) was suspended in about 17 mL of DCM/MeOH, and about 60 µL of the resulting slurry was distributed inside each of 280 columns, representing 28 H3-JH segments synthesized ten times each. A portion (described more fully below) of each of the 28 IGHJ segments, including H3-JH of Table 20 were then synthesized, 3' to the N2 segments, in ten of the columns. Final oligonucleotides were cleaved and deprotected by exposure to gaseous ammonia (85° C., 2 h, 60 psi).

Split pool synthesis was used to synthesize the exemplary CDRH3 library. However, it is appreciated that recent advances in oligonucleotide synthesis, which enable the synthesis of longer oligonucleotides at higher fidelity and the production of the oligonucleotides of the library by synthetic procedures that involve splitting, but not pooling, may be used in alternative embodiments of the invention. The split pool synthesis described herein is, therefore, one possible means of obtaining the oligonucleotides of the library, but is not limiting. One other possible means of synthesizing the oligonucleotides described in this application is the use of trinucleotides. This may be expected to increase the fidelity of the synthesis, since frame shift mutants would be reduced or eliminated.

Example 10

Construction of the CDRH3 and Heavy Chain Libraries

This example outlines the procedures used to create exemplary CDRH3 and heavy chain libraries of the invention. A two step process was used to create the CDRH3 library. The first step involved the assembly of a set of vectors encoding the tail and N1 segments, and the second step involved utilizing the split pool nucleic acid synthesis procedures outlined in Example 9 to create oligonucleotides encoding the DH, N2, and H3-JH segments. The chemically synthesized oligonucleotides were then ligated into the vectors, to yield CDRH3 residues 95-102, based on the numbering system described herein. This CDRH3 library was subsequently amplified by PCR and recombined into a plurality of vectors containing the heavy chain chassis variants described in Examples 1 and 2. CDRH1 and CDRH2 variants were produced by QuikChange® Mutagenesis (Stratagene™), using the oligonucleotides encoding the ten heavy chain chassis of Example 1 as a template. In addition to the heavy chain chassis, the plurality of vectors contained the heavy chain constant regions (i.e., CH1, CH2, and CH3) from IgG1, so that a full-length heavy chain was formed upon recombination of the CDRH3 with the vector containing the heavy chain chassis and constant regions. In this exemplary embodiment, the recombination to produce the full-length heavy chains and the expression of the full-length heavy chains were both performed in S. cerevisiae.

To generate full-length, heterodimeric IgGs, comprising a heavy chain and a light chain, a light chain protein was also expressed in the yeast cell. The light chain library used in this embodiment was the kappa light chain library, wherein the VKCDR3s were synthesized using degenerate oligonucleotides (see Example 6.2). Due to the shorter length of the oligonucleotides encoding the light chain library (in comparison to those encoding the heavy chain library), the light chain CDR3 oligonucleotides could be synthesized de novo, using standard procedures for oligonucleotide synthesis, without the need for assembly from sub-components (as in the heavy chain CDR3 synthesis). One or more light chains can be expressed in each yeast cell which expresses a particular heavy chain clone from a library of the invention. One or more light chains have been successfully expressed from both episomal (e.g., plasmid) vectors and from integrated sites in the yeast genome.

Below are provided further details on the assembly of the individual components for the synthesis of a CDRH3 library of the invention, and the subsequent combination of the exemplary CDRH3 library with the vectors containing the chassis and constant regions. In this particular exemplary embodiment of the invention, the steps involved in the process may be generally characterized as (i) synthesis of 424 vectors encoding the tail and N1 regions; (ii) ligation of oligonucleotides encoding the [DH]-[N2]-[H3-JH] segments into these 424 vectors; (iii) PCR amplification of the CDRH3 sequences from the vectors produced in these ligations; and (iv) homologous recombination of these PCR-amplified CDRH3 domains into the yeast expression vectors containing the chassis and constant regions.

Example 10.1

Synthesis of Vectors Encoding the Tail and N1 Regions

This example demonstrates the synthesis of 424 vectors encoding the tail and N1 regions of CDRH3. In this exemplary embodiment of the invention, the tail was restricted to G, D, E, or nothing, and the N1 region was restricted to one of the 59 sequences shown in Table 24. As described throughout the specification, many other embodiments are possible.

In the first step of the process, a single "base vector" (pJM204, a pUC-derived cloning vector) was constructed, which contained (i) a nucleic acid sequence encoding two amino acids that are common to the C-terminal portion of all 28 IGHJ segments (SS), and (ii) a nucleic acid sequence encoding a portion of the CH1 constant region from IgG1. Thus, the base vector contains an insert encoding a sequence that can be depicted as:

[SS]-[CH1~], wherein SS is a common portion of the C-terminus of the 28 IGHJ segments and CH1~ is a portion of the CH1 constant region from IgG1, namely:

(SEQ ID NO: 396)
ASTKGPSVFPLAPSSKSTSGGTAALGCLVKDYFPEPVTVSWNSGALT
SGVHTFPAVLQSSGLYSLSSVVTVPSSSLG.

Next, 424 different oligonucleotides were cloned into the base vector, upstream (i.e., 5') from the region encoding the [SS]-[CH1~]. These 424 oligonucleotides were synthesized by standard methods and each encoded a C-terminal portion of one of the 17 heavy chain chassis enumerated in Table 5, plus one of four exemplary tail segments (G/D/E/-), and one of 59 exemplary N1 segments (Table 24). These 424 oligonucleotides, therefore, encode a plurality of sequences that may be represented by:

[~FRM3]-[G/D/E/-]-[N1], wherein ~FRM3 represents a C-terminal portion of a FRM3 region from one of the 17 heavy chain chassis of Table 5, G/D/E/- represents G, D, E, or nothing, and N1 represents one of the 59 N1 sequences enumerated in Table 24. As described throughout the specification, the invention is not limited to the chassis exemplified in Table 5, their CDRH1 and CDRH2 variants (Table 8), the four exemplary tail options used in this example, or the 59 N1 segments presented in Table 24.

The oligonucleotide sequences represented by the sequences above were synthesized in two groups: one group containing a ~FRM3 region identical to the corresponding region on 16 of the 17 the heavy chain chassis enumerated in Table 5, and another group containing a ~FRM3 region that is identical to the corresponding region on VH3-15. In the former group, an oligonucleotide encoding DTAVYYCA R (SEQ ID NO: 397) was used for ~FRM3. During subsequent PCR amplification, the V residue of VH5-51 was altered to an M, to correspond to the VH5-51 germline sequence. In the latter group (that with a sequence common to VH3-15), a larger oligonucleotide, encoding the sequence AISGSGGSTYYADSVKGRFTISRDNSKNT-LYLQMNSLRAEDTAVYYCAK (SEQ ID NO: 398) was used for ~FRM3. Each of the two oligonucleotides encoding the ~FRM3 regions were paired with oligonucleotides encoding one of the four tail regions (G/D/E/-) and one of the 59 N1 segments, yielding a total of 236 possible combinations for each ~FRM3 (i.e., 1×4×59), or a total of 472 possible combinations when both ~FRM3 sequences are considered. However, 48 of these combinations are redundant and only a single representation of these sequences was used in the currently exemplified CDRH3 library, yielding 424 unique oligonucleotides encoding [~FRM3]-[G/D/E/-]-[N1] sequences.

After the oligonucleotides encoding the [~FRM3]-[G/D/E/-]-[N1] and [SS]-[CH1~] segments were cloned into the vector, as described above, additional sequences were added to the vector to facilitate the subsequent insertion of the oligonucleotides encoding the [DH]-[N2]-[H3-JH] fragments synthesized during the split pool synthesis. These additional sequences comprise a polynucleotide encoding a selectable marker protein, flanked on each side by a recognition site for a type II restriction enzyme, for example:

[Type II RS 1]-[selectable marker protein]-[Type II RS 2].

In this exemplary embodiment, the selectable marker protein is ccdB and the type II restriction enzyme recognition sites are specific for BsrDI and BbsI. In certain strains of *E. coli*, the ccdB protein is toxic, thereby preventing the growth of these bacteria when the gene is present.

An example of the 5' end of one of the 212 vectors with a ~FRM3 region based on the VH3-23 chassis, D tail residue and an N1 segment of length zero is presented below (SEQ ID NO: 570):

```
                                                                      VH3-23
                                                          ~~~~~~~~~~~~~~~~~~~~~~~~~~~~~~~
                                                           A  I  S    G  S  G    G  S  T  Y •
  961                                                     GCTATTAG TGGTAGTGGT GGTAGCACAT
                                                          CGATAATC ACCATCACCA CCATCGTGTA
                            VH3-23
        ~~~~~~~~~~~~~~~~~~~~~~~~~~~~~~~~~~~~~~~~~~~~~~~~~~~~~~~~~~~~~~~~~~~~~~~~~~~~~~~~~~~~~~
      • Y  A  D    S  V  K    G  R  F  T    I  S  R    D  N  S    K  N  T  L    Y  L  Q    M  N  S
 1041 ACTACGCAGA CTCCGTGAAG GGCCGGTTCA CCATCTCCAG AGACAATTCC AAGAACACGC TGTATCTGCA AATGAACAGC
      TGATGCGTCT GAGGCACTTC CCGGCCAAGT GGTAGAGGTC TCTGTTAAGG TTCTTGTGCG ACATAGACGT TTACTTGTCG
              VH3-23                                                           ccdB
      ~~~~~~~~~~~~~~~~~~~~~~~~~~~~~~~~~~~~~~~~~           ~~~~~~~~~~~~~~~~~~~~~~~~~~~~~~~
                                         BsrDI
                                         ~~~~~~
      L  R  A  E    D  T  A    V  Y  Y    C  A  K
 1121 CTGAGAGCCG AGGACACGGC GGTGTACTAC TGCGCCAAGG ACCATTGCGC TTAGCCTAGG TTATATTCCC CAGAACATCA
      GACTCTCGGC TCCTGTGCCG CCACATGATG ACGCGGTTCC TGGTAACGCG AATCGGATCC AATATAAGGG GTCTTGTAGT
```

An example of one of the 212 vectors with a ~FRM3 region based on one of the other 16 chassis, with a D residue as the tail and an N1 segment of length zero is presented below (SEQ ID NO: 571):

```
                                                                     Framework 3
                                                          ~~~~~~~~~~~~~~~~~~~~~~~~~~~~~~~
                                                          D  T  A    V  Y  Y    C    A  R
  961                                                     GACACGGCG GTGTACTACT GCGCCAGAGA
                                                          CTGTGCCGC CACATGATGA CGCGGTCTCT
                                          ccdB
        ~~~~~~~~~~~~~~~~~~~~~~~~~~~~~~~~~~~~~~~~~~~~~~~~~~~~~~~~~~~~~~~~~~~~~~~~~~~~~~~~~~~~~~
      BsrDI
      ~~~~~~
 1041 CCATTGCGCT TAGCCTAGGT TATATTCCCC AGAACATCAG GTTAATGGCG TTTTTGATGT CATTTTCGCG GTGGCTGAGA
      GGTAACGCGA ATCGGATCCA ATATAAGGGG TCTTGTAGTC CAATTACCGC AAAAACTACA GTAAAAGCGC CACCGACTCT
                                          ccdB
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 1121 TCAGCCACTT CTTCCCCGAT AACGGAAACC GGCACACTGG CCATATCGGT GGTCATCATG CGCCAGCTTT CATCCCCGAT
      AGTCGGTGAA GAAGGGGCTA TTGCCTTTGG CCGTGTGACC GGTATAGCCA CCAGTAGTAC GCGGTCGAAA GTAGGGGCTA
                                          ccdB
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 1201 ATGCACCACC GGGTAAAGTT CACGGGAGAC TTTATCTGAC AGCAGACGTG CACTGGCCAG GGGGATCACC ATCCGTCGCC
      TACGTGGTGG CCCATTTCAA GTGCCCTCTG AAATAGACTG TCGTCTGCAC GTGACCGGTC CCCCTAGTGG TAGGCAGCGG
                                          ccdB
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 1281 CGGGCGTGTC AATAATATCA GTCTGTACAT CCACAAACAG ACGATAACGG CTCTCTCTTT TATAGGTGTA AACCTTAAAC
      GCCCGCACAG TTATTATAGT CAGACATGTA GGTGTTTGTC TGCTATTGCC GAGAGAGAAA ATATCCACAT TTGGAATTTG
                                          ccdB
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 1361 TGCATTTCAC CAGCCCCTGT TCTCGTCAGC AAAAGAGCCG TTCATTTCAA TAAACCGGGC GACCTCAGCC ATCCCTTCCT
      ACGTAAAGTG GTCGGGGACA AGAGCAGTCG TTTTCTCGGC AAGTAAAGTT ATTTGGCCCG CTGGAGTCGG TAGGGAAGGA
                                          ccdB
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 1441 GATTTTCCGC TTTCCAGCGT TCGGCACGCA GACGACGGGC TTCATTCTGC ATGGTTGTGC TTACCAGACC GGAGATATTG
      CTAAAAGGCG AAAGGTCGCA AGCCGTGCGT CTGCTGCCCG AAGTAAGACG TACCAACACG AATGGTCTGG CCTCTATAAC
                                          ccdB
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 1521 ACATCATATA TGCCTTGAGC AACTGATAGC TGTCGCTGTC AACTGTCACT GTAATACGCT GCTTCATAGC ATACCTCTTT
      TGTAGTATAT ACGGAACTCG TTGACTATCG ACAGCGACAG TTGACAGTGA CATTATGCGA CGAAGTATCG TATGGAGAAA
                                          ccdB
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~
 1601 TTGACATACT TCGGGTATAC ATATCAGTAT ATATTCTTAT ACCGCAAAAA TCAGCGCGCA AATATGCATA CTGTTATCTG
      AACTGTATGA AGCCCATATG TATAGTCATA TATAAGAATA TGGCGTTTTT AGTCGCGCGT TTATACGTAT GACAATAGAC
              ccdB                                                             CH1
      ~~~~~~~~~~~~~~~~~~~~~~~~~~~~~~~~~~~~~~~~~           ~~~~~~~~~~~~~~~~~~~~~~~~~~~~~~~~~~~~~
                             BbsI
                             ~~~~~~~
                                                           A  S  T  K    G  P  S    V  F  P  L    A  P  S •
 1681 GCTTTTAGTA AGCCGCCTAG GTCATCAGAA GACAACTCAG CTAGCACCAA GGGCCCATCG GTCTTTCCCC TGGCACCCTC
      CGAAAATCAT TCGGCGGATC CAGTAGTCTT CTGTTGAGTC GATCGTGGTT CCCGGGTAGC CAGAAAGGGG ACCGTGGGAG
                                          CH1
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      • S  K  S    T  S  G  G    T  A  A    L  G  C    L  V  K  D    Y  F  P    E  P  V    T  V  S  W •
 1761 CTCCAAGAGC ACCTCTGGGG GCACAGCGGC CCTGGGCTGC CTGGTCAAGG ACTACTTCCC CGAACCGGTG ACGGTGTCGT
      GAGGTTCTCG TGGAGACCCC CGTGTCGCCG GGACCCGACG GACCAGTTCC TGATGAAGGG GCTTGGCCAC TGCCACAGCA
```

-continued

```
                                             CH1
       ~~~~~~~~~~~~~~~~~~~~~~~~~~~~~~~~~~~~~~~~~~~~~~~~~~~~~~~~~
         • N   S   G   A  L  T   S   G   V   H   T   F   P   A  V  L   Q   S  S  G    L
  1841  GGAACTCAGG CGCCCTGACC AGCGGCGTGC ACACCTTCCC GGCTGTCCTA CAGTCCTCAG GACTC
        CCTTGAGTCC GCGGGACTGG TCGCCGCACG TGTGGAAGGG CCGACAGGAT GTCAGGAGTC CTGAG
```

Figure 5:
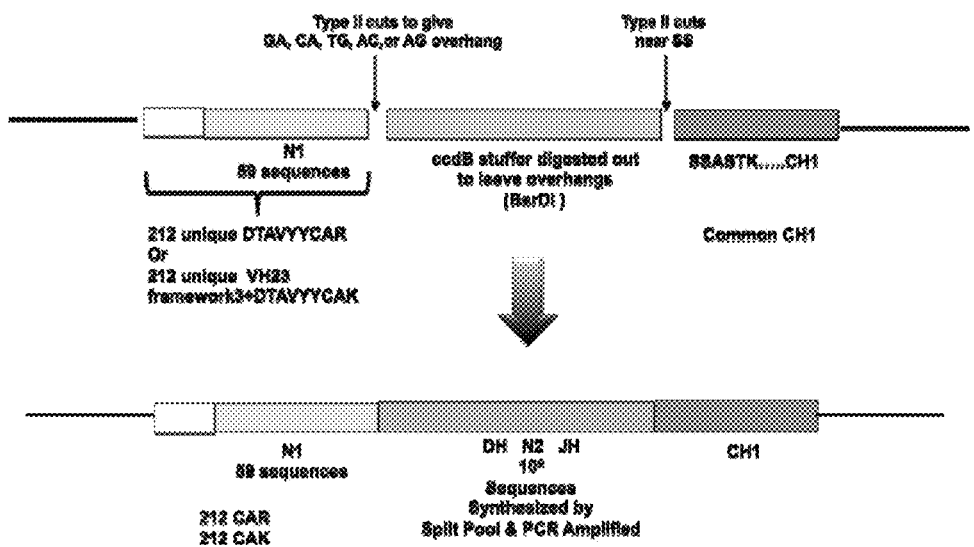
FIG. 5 depicts a schematic representation of the 424 cloning vectors used in the synthesis of the CDRH3 regions before and after ligation of the [DH]-[N2]-[JH] segment (DTAVYYCAR: SEQ ID NO: 579; DTAVYYCAK: SEQ ID NO: 578; SSASTK: SEQ ID NO: 580).

All 424 vectors were sequence verified. A schematic diagram of the content of the 424 vectors, before and after cloning of the [DH]-[N2]-[H3-JH] fragment is presented in FIG. 5. Below is an exemplary sequence from one of the 424 vectors containing a FRM3 region from VH3-23 (SEQ ID NO: 572).

segments that was not synthesized in the split pool synthesis. The amplified oligonucleotides were then digested with the restriction enzymes BsrDI (cleaves adjacent to the DH segment) and BbsI (cleaves near the end of the JH segment). The cleaved oligonucleotides were then purified and ligated into the 424 vectors which had previously been digested

```
                                                    primer EMK135
                                               ~~~~~~~~~~~~~~~~~~~~~~~~~~~
                                    VH3-23
              ~~~~~~~~~~~~~~~~~~~~~~~~~~~~~~~~~~~~~~~~~~~~~~~~~~~~~~~~~~~~~~~~
                    A   I   S   G   S   G   G   S   T   Y   Y   A   D   S   V   K   G   R   F
   561           GCTATTA GTGGTAGTGG TGGTAGCACA TACTACGCAG ACTCCGTGAA GGGCCGGTTC
                 CGATAAT CACCATCACC ACCATCGTGT ATGATGCGTC TGAGGCACTT CCCGGCCAAG
                        VH3-23
              ~~~~~~~~~~~~~~~~~~~~~~~~~~~~~~~~~~~~~~~~~~~~~~~~~~~~~~~~~~~~~~~~~
            T   I   S   R   D   N   S   K   N   T   L   Y   L   Q   M   N   S   L   R   A   E   D   T   A   V   Y   Y •
   641    ACCATCTCCA GAGACAATTC CAAGAACACG CTGTATCTGC AAATGAACAG CCTGAGAGCC GAGGACACGG CGGTGTACTA
          TGGTAGAGGT CTCTGTTAAG GTTCTTGTGC GACATAGACG TTTACTTGTC GGACTCTCGG CTCCTGTGCC GCCACATGAT VH3-23                                        D                                   J1
         ~~~~~~~~~~           ~~~~~~~~~~~~~~~~~~~~~~~~~~~~~~~~~~~~~~       ~~~~~~~~~~~~~~~~~~~~~~
                                                                                    JH6
                                                                           ~~~~~~~~~~~~~~~~~~~~~
                         N1_9                                    N2
                      ~~~~~~~~~~~~~~~~                        ~~~~~~~~~~~~
          • C   A   K    D   A   G   G   Y   Y   Y   G   S   G   S   Y   Y   N   A   A   A   Y   Y   Y   Y   Y   G   M •
   721   CTGCGCCAAG GACGCCGGAG GATATTATTA TGGGTCAGGA AGCTATTACA ACGCTGCGGC TTACTACTAC TATTATGGCA
         GACGCGGTTC CTGCGGCCTC CTATAATAAT ACCCAGTCCT TCGATAATGT TGCGACGCCG AATGATGATG ATAATACCGT
                         JH6
              ~~~~~~~~~~~~~~~~~~~~~~~~~~~~~~~~~~~~~~~~~~~~~~~~
           J1                                                                                 CH1
         ~~~~~~~~                                                                ~~~~~~~~~~~~~~~~~~~~~~~~~~~~~~~~~~~~~
                                                                                   NheI
                                                                                 ~~~~~~~
          • D   V   W   G   Q   G   T   T   V   T   V   S   S   A   S   T   K   G   P   S   V   F   P   L   A   P
   801   TGGACGTGTG GGGACAAGGT ACAACAGTCA CCGTCTCCTC AGCTAGCACC AAGGGCCCAT CGGTCTTTCC CCTGGCACCC
         ACCTGCACAC CCCTGTTCCA TGTTGTCAGT GGCAGAGGAG TCGATCGTGG TTCCCGGGTA GCCAGAAAGG GGACCGTGGG
                                                                CH1
              ~~~~~~~~~~~~~~~~~~~~~~~~~~~~~~~~~~~~~~~~~~~~~~~~~~~~~~~~~~~~~~~~~~~~~~~~~~~~~~~~~~~~~~
             S   S   K   S   T   S   G   G   T   A   A   L   G   C   L   V   K   D   Y   F   P   E   P   V   T   V   S •
   881    TCCTCCAAGA GCACCTCTGG GGGCACAGCG GCCCTGGGCT GCCTGGTCAA GGACTACTTC CCCGAACCGG TGACGGTGTC
          AGGAGGTTCT CGTGGAGACC CCCGTGTCGC CGGGACCCGA CGGACCAGTT CCTGATGAAG GGGCTTGGCC ACTGCCACAG
                                                                CH1
              ~~~~~~~~~~~~~~~~~~~~~~~~~~~~~~~~~~~~~~~~~~~~~~~~~~~~~~~~~~~~~~~~~~~~~~~~~~~~~~~~~~~~~~
          • W   N   S   G   A   L   T   S   G   V   H   T   F   P   A   V   L   Q   S   S   G   L   Y   S   L   S   S •
   961    GTGGAACTCA GGCGCCCTGA CCAGCGGCGT GCACACCTTC CCGGCTGTCC TACAGTCCTC AGGACTCTAC TCCCTCAGCA
          CACCTTGAGT CCGCGGGACT GGTCGCCGCA CGTGTGGAAG GGCCGACAGG ATGTCAGGAG TCCTGAGATG AGGGAGTCGT
                         CH1
              ~~~~~~~~~~~~~~~~~~~~~~~~~~~~~~~~~
          • V   V   T   V   P   S   S   S   L   G
  1041   GCGTGGTGAC CGTGCCCTCC AGCAGCTTGG GC
         CGCACCACTG GCACGGGAGG TCGTCGAACC CG
```

Example 10.2

Cloning of the Oligonucleotides Encoding the DH, N2, H3-JH Segments into the Vectors Containing the Tail and N1 Segments This example describes the cloning of the oligonucleotides encoding the [D]-[N2]-[H3-JH] segments (made via split pool synthesis; Example 9) into the 424 vectors produced in Example 10.1. To summarize, the [DH]-[N2]-[H3-JH] oligonucleotides produced via split pool synthesis were amplified by PCR, to produce double-stranded oligonucleotides, to introduce restriction sites that would create overhangs complementary to those on the vectors (i.e., BsrDI and BbsI), and to complete the 3' portion of the IGHJ with BsrDI and BbsI. After ligation, the reactions were purified, ethanol precipitated, and resolubilized.

This process for one of the [DH]-[N2]-[H3-JH] oligonucleotides synthesized in the split pool synthesis is illustrated below. The following oligonucleotide (SEQ ID NO: 399) is one of the oligonucleotides synthesized during the split pool synthesis:

```
 1   ATGCACAGTTGCAATGTGTATTACTATGGATCTGGTTCTTA 50
     CTATAATGT

51   GGGCGGATATTATTACTACTATGGTATGGACGTATGGGGGC 99
     AAGGGACC
```

The first 10 nucleotides (ATGCACAGTT; SEQ ID NO: 395) represent a portion of a random sequence that is increased to 20 base pairs in the PCR amplification step, below. This portion of the sequence increases the efficiency of BsrDI digestion and facilitates the downstream purification of the oligonucleotides.

Nucleotides 11-16 (underlined) represent the BsrDI recognition site. The two base overlap sequence that follows this site (in this example TG; bold) was synthesized to be complementary to the two base overhang created by digesting certain of the 424 vectors with BsrDI (i.e., depending on the composition of the tail/N1 region of the particular vector). Other oligonucleotides contain different two-base overhangs, as described below.

The two base overlap is followed by the DH gene segment (nucleotides 19-48), in this example, by a 30 bp sequence (TATTACTATGGATCTGGTTCTTACTATAAT, SEQ ID NO: 400) which encodes the ten residue DH segment YYYGSGSYYN (i.e., IGHD3-10_2 of Table 17; SEQ ID NO: 2).

The region of the oligonucleotide encoding the DH segment is followed, in this example, by a nine base region (GTGGGCGGA; bold; nucleotides 49-57), encoding the N2 segment (in this case VGG; Table 24).

The remainder of this exemplary oligonucleotide represents the portion of the JH segment that is synthesized during the split pool synthesis (TATTATTACTACTATGGTATGGACGTATGGGGGCAAGGGACC; SEQ ID NO: 401; nucleotides 58-99; underlined), encoding the sequence YYYYYGMDVWGQGT (Table 20; residues 1-14 of SEQ ID NO: 258). The balance of the IGHJ segment is added during the subsequent PCR amplification described below.

After the split pool-synthesized oligonucleotides were cleaved from the resin and deprotected, they served as a template for a PCR reaction which added an additional randomly chosen 10 nucleotides (e.g., GACGAGCTTC; SEQ ID NO: 402) to the 5' end and the rest of the IGHJ segment plus the BbsI restriction site to the 3' end. These additions facilitate the cloning of the [DH]-[N2]-[JH] oligonucleotides into the 424 vectors. As described above (Example 9), the last round of the split pool synthesis involves 280 columns: 10 columns for each of the oligonucleotides encoding one of 28 H3-JH segments. The oligonucleotide products obtained from these 280 columns are pooled according to the identity of their H3-JH segments, for a total of 28 pools. Each of these 28 pools is then amplified in five separate PCR reactions, using five forward primers that each encode a different two base overlap (preceding the DH segment; see above) and one reverse primer that has a sequence corresponding to the familial origin of the H3-JH segment being amplified. The sequences of these 11 primers are provided below:

```
Forward primers
AC
                                   (SEQ ID NO: 403)
GACGAGCTTCAATGCACAGTTGCAATGAC AG
                                   (SEQ ID NO: 404)
GACGAGCTTCAATGCACAGTTGCAATGAG CT
                                   (SEQ ID NO: 405)
GACGAGCTTCAATGCACAGTTGCAATGCT GA
                                   (SEQ ID NO: 406)
GACGAGCTTCAATGCACAGTTGCAATGGA TG
                                   (SEQ ID NO: 407)
GACGAGCTTCAATGCACAGTTGCAATGTG Reverse Primers
JH1
                                   (SEQ ID NO: 408)
TGCATCAGTGCGACTAACGGAAGACTCTGAGGAGACGGTGACCAAGG
TGCCCTGGCCCCA JH2
                                   (SEQ ID NO: 409)
TGCATCAGTGCGACTAACGGAAGACTCTGAGGAGACAGTGACCAAGG
TGCCACGGCCCCA JH3
                                   (SEQ ID NO: 410)
TGCATCAGTGCGACTAACGGAAGACTCTGAAGAGACGGTGACCATTG
TCCCTTGGCCCCA JH4
                                   (SEQ ID NO: 411)
TGCATCAGTGCGACTAACGGAAGACTCTGAGGAGACGGTGACCAAGG
TTCCTTGGCCCCA JH5
                                   (SEQ ID NO: 412)
TGCATCAGTGCGACTAACGGAAGACTCTGAGGAGACGGTGACCAAGG
TTCCCTGGCCCCA JH6
                                   (SEQ ID NO: 413)
TGCATCAGTGCGACTAACGGAAGACTCTGAGGAGACGGTGACCGTGG
TCCCTTGCCCCCA
```

Amplifications were performed using Taq polymerase, under standard conditions. The oligonucleotides were amplified for eight cycles, to maintain the representation of sequences of different lengths. Melting of the strands was performed at 95° C. for 30 seconds, with annealing at 58° C. and a 15 second extension time at 72° C.

Using the exemplary split-pool derived oligonucleotide enumerated above as an example, the PCR amplification was performed using the TG primer and the JH6 primer, where the annealing portion of the primers has been underlined:

```
TG
                                   (SEQ ID NO: 407)
GACGAGCTTCAATGCACAGTTGCAATGTG

JH6
                                   (SEQ ID NO: 413)
TGCATCAGTGCGACTAACGGAAGACTCTGAGGAGACGGTGACCGTGG
TCCCTTGCCCCCA
```

The portion of the TG primer that is 5' to the annealing portion includes the random 10 base pairs described above. The portion of the JH6 primer that is 5' to the annealing portion includes the balance of the JH6 segment and the BbsI restriction site. The following PCR product (SEQ ID NO: 414) is formed in the reaction (added sequences underlined):

```
GACGAGCTTCATGCACAGTTGCAATGTGTATTACTATGGATCTGGTT

CTTACTATAATGTGGGCGGATATTATTACTACTATGGTATGGACGTA

TGGGGGCAAGGGACCACGGTCACCGTCTCCTCAGAGTCTTCCGTTAG

TCGCACTGATGCAG
```

The PCR products from each reaction were then combined into five pools, based on the forward primer that was used in the reaction, creating sets of sequences yielding the same two-base overhang after BsrDI digestion. The five pools of PCR products were then digested with BsRDI and BbsI (100 µg of PCR product; 1 mL reaction volume; 200 U BbsI; 100 U BsrDI; 2 h; 37° C.; NEB Buffer 2). The digested oligonucleotides were extracted twice with phenol/chloroform, ethanol precipitated, air dried briefly and resolubilized in 300 µL of TE buffer by sitting overnight at 4° C.

Each of the 424 vectors described in the preceding sections was then digested with BsrDI and BbsI, each vector yielding a two base overhang that was complimentary to one of those contained in one of the five pools of PCR products. Thus, one of the five pools of restriction digested PCR products are ligated into each of the 424 vectors, depending on their compatible ends, for a total of 424 ligations.

Example 10.3

PCR Amplification of the CDRH3 from the 424 Vectors

This example describes the PCR amplification of the CDRH3 regions from the 424 vectors described above. As set forth above, the 424 vectors represent two sets: one for the VH3-23 family, with FRM3 ending in CAK (212 vectors) and one for the other 16 chassis, with FRM3 ending in CAR (212 vectors). The CDRH3s in the VH3-23-based vectors were amplified using a reverse primer (EK137; see Table 41) recognizing a portion of the CH1 region of the plasmid and the VH3-23-specific primer EK135 (see Table 41). Amplification of the CDRH3s from the 212 vectors with FRM3 ending in CAR was performed using the same reverse primer (EK137) and each of five FRM3-specific primers shown in Table 41 (EK139, EK140, EK141, EK143, and EK144). Therefore, 212 VH3-23 amplifications and 212×5 FRM3 PCR reactions were performed, for a total of 1,272 reactions. An additional PCR reaction amplified the CDRH3 from the 212 VH3-23-based vectors, using the EK 133 forward primer, to allow the amplicons to be cloned into the other 5 VH3 family member chassis while making the last three amino acids of these chassis CAK instead of the original CAR (VH3-23*). The primers used in each reaction are shown in Table 41.

TABLE 41

Primers Used for Amplification of CDRH3 Sequences

| Primer No. | Compatible Chassis | Primer Sequence | SEQ ID NO |
|---|---|---|---|
| EK135 | VH3-23 | CACATACTACGCAGACTCCGTG | 415 |
| EK133 | VH3-48; VH3-7; VH3-15; VH3-30; VH3-33; VH3-23* | CAAATGAACAGCCTGAGAGCCG AGGACACGGCGGTGTACTACTG | 416 |
| EK139 | VH4-B; VH4-31; VH4-34; VH4-39; VH4-59; VH4-61 | AAGCTGAGTTCTGTGACCGCCG CAGACACGGCGGTGTACTACTG | 417 |
| EK140 | VH1-46; VH1-69 | GAGCTGAGCAGCCTGAGATCTG AGGACACGGCGGTGTACTACTG | 418 |

TABLE 41-continued

Primers Used for Amplification of CDRH3 Sequences

| Primer No. | Compatible Chassis | Primer Sequence | SEQ ID NO |
|---|---|---|---|
| EK141 | VH1-2 | GAGCTGAGCAGGCTGAGATCTG ACGACACGGCGGTGTACTACTG | 419 |
| EK143 | VH5-51 | CAGTGGAGCAGCCTGAAGGCCT CGGACACGGCGATGTACTACTG | 420 |
| EK144 | VH1-18 | GAGCTGAGGAGCCTGAGATCTG ACGACACGGCGGTGTACTACTG | 421 |
| EK137 | CH1 Rev. Primer | GTAGGACAGCCGGGAAGG | 422 |

Example 10.4

Homologous Recombination of PCR Amplified CDRH3 Regions into Heavy Chain Chassis After amplification, reaction products were pooled according to the respective VH chassis that they would ultimately be cloned into. Table 42 enumerates these pools, with the PCR primers used to obtain the CDRH3 sequences in each pool provided in the last two columns.

TABLE 42

PCR Primers Used to Amplify CDRH3 Regions from 424 Vectors

| Pool # (Arbitrary) | HC Chassis Target | 5' Primer | 3' Primer |
|---|---|---|---|
| 1 | 1-46 | EK140 | EK137 |
|  | 1-69 | EK140 | EK137 |
| 2 | 1-2 | EK141 | EK137 |
| 3 | 1-18 | EK144 | EK137 |
| 4 | 4-B | EK139 | EK137 |
|  | 4-31 | EK139 | EK137 |
|  | 4-34[2] | EK139 | EK137 |
|  | 4-39 | EK139 | EK137 |
|  | 4-59 | EK139 | EK137 |
|  | 4-61 | EK139 | EK137 |
| 5 | 5-51 | EK143 | EK137 |
| 6 | 3-15[1] | EK133 | EK137 |
|  | 3-7 | EK133 | EK137 |
|  | 3-33 | EK133 | EK137 |
|  | 3-33 | EK133 | EK137 |
|  | 3-48 | EK133 | EK137 |
| 7 | 3-23 | EMK135 | EK137 |
| 8 | 3-23* | EK133 | EK137 |

*Allowed the amplicons to be cloned into the other 5 VH3 family member chassis (i.e., other than VH3-23), while making the last three amino acids of these chassis CAK instead of the original CAR.
[1]As described in Table 5, the original KT sequence in VH3-15 was mutated to RA, and the original TT to AR.
[2]As described in Table 5, the potential site for N-linked glycosylation was removed from CDRH2 of this chassis.

Figure 6:
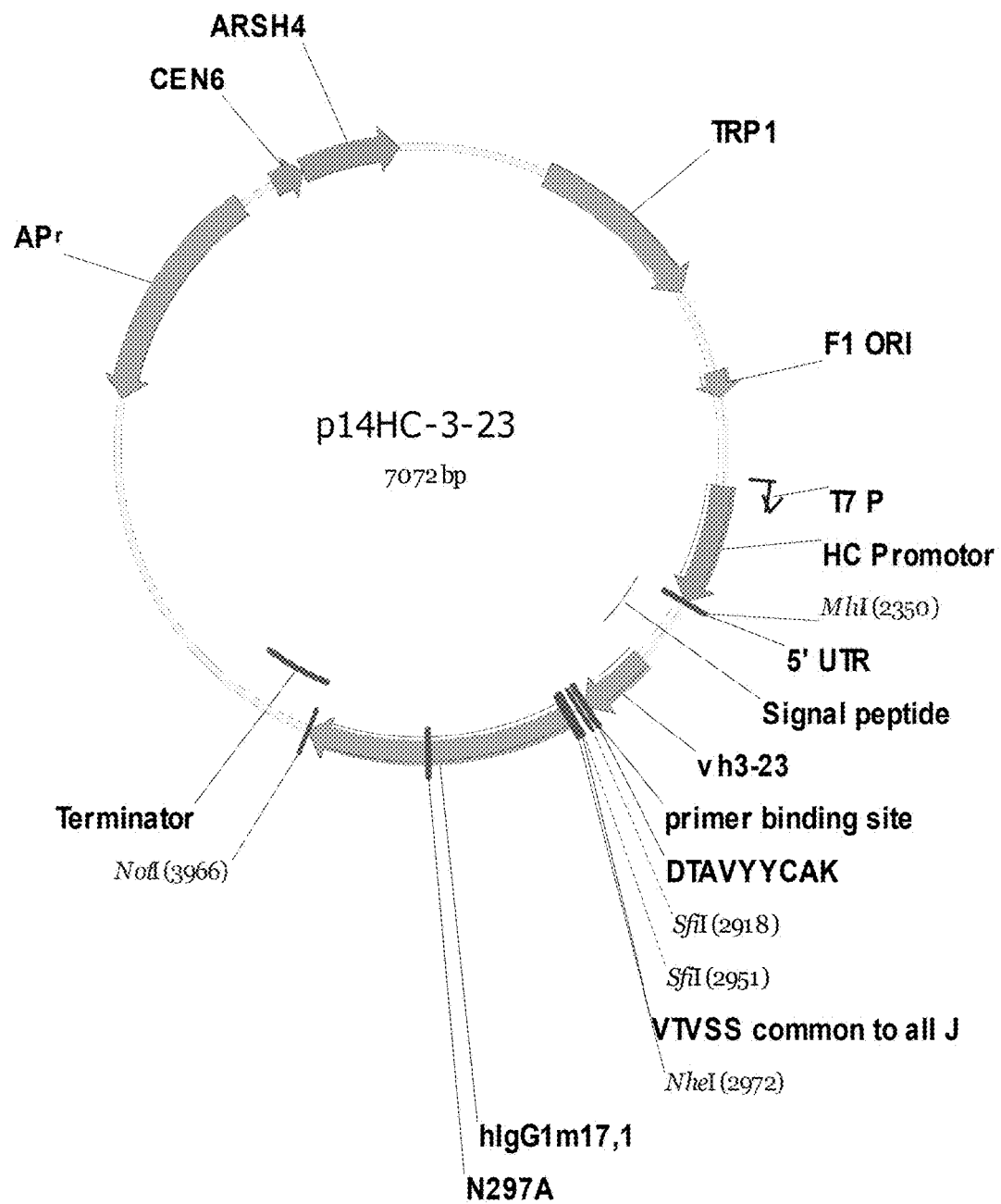
FIG. 6 depicts a schematic structure of a heavy chain vector, prior to recombination with a CDRH3.

After pooling of the amplified CDRH3 regions, according to the process outlined above, the heavy chain chassis expression vectors were pooled according to their origin and cut, to create a "gap" for homologous recombination with the amplified CDRH3s. FIG. 6 shows a schematic structure of a heavy chain vector, prior to recombination with a CDRH3. In this exemplary embodiment of the invention, there were a total of 152 vectors encoding heavy chain chassis and IgG1 constant regions, but no CDRH3. These 152 vectors represent 17 individual variable heavy chain gene families (Table 5; Examples 1 and 2). Fifteen of the families were represented by the heavy chain chassis sequences described in Table 5 and the CDRH1/H2 variants described in Table 8 (i.e., 150 vectors). VH 3-30 differs from VH3-33 by a single amino acid; thus VH3-30 was included in the VH3-33 pool of variants. The 4-34 VH family member was kept separate from all others and, in this exemplary embodiment, no variants of it were included in the library. Thus, a total of 16 pools, representing 17 heavy chain chassis, were generated from the 152 vectors.

The vector pools were digested with the restriction enzyme SfiI, which cuts at two sites in the vector that are located between the end of the FRM3 of the variable domain and the start of the CH1 (SEQ ID NO: 573).

TABLE 43

Occurrence of Heavy Chain Chassis in Data Sets Used to Design Library, Expected (Designed) Library, and Actual (Observed) Library

| Chassis | Relative Occurrence in Data Sets (1) | Expected (2) | Observed (3) |
|---|---|---|---|
| VH1-2 | 5.1 | 6.0 | 6.4 |
| VH1-18 | 3.4 | 3.7 | 3.8 |
| VH1-46 | 3.4 | 5.2 | 4.7 |
| VH1-69 | 8.0 | 8.0 | 10.7 |
| VH3-7 | 3.6 | 6.1 | 4.5 |
| VH3-15 | 1.9 | 6.9 | 3.6 |
| VH3-23 | 11.0 | 13.2 | 17.1 |

```
                                           VH3-48
     ~~~~~~~~~~~~~~~~~~~~~~~~~~~~~~~~~~~~~~~~~~~~~~~~~~~~~~~~~~~~~~~~~~~~~~~~~~~~~
       S   V   K    G   R   F   T    I   S   R    D   N   A    K   N   S    L   Y   L   Q    M   N   S    L   R   A   E   •
2801   CTCTGTGAAG  GGCCGATTCA  CCATCTCCAG  AGACAATGCC  AAGAACTCAC  TGTATCTGCA  AATGAACAGC  CTGAGAGCTG
       GAGACACTTC  CCGGCTAAGT  GGTAGAGGTC  TCTGTTACGG  TTCTTGAGTG  ACATAGACGT  TTACTTGTCG  GACTCTCGAC
               Constant DTAVYYCAR
        ~~~~~~~~~~~~~~~~~~~~~~~~~~~~~~~

VH3-48                                                                              VTVSS common to all J
     ~~                                                                                  ~~~~~
                              SfiI                                             SfiI
                     ~~~~~~~~~~~~~~~~~~                               ~~~~~~~~~~~~~~
     •  D   T    A   V   Y   Y    C   A   R
                                                                                            V    T    •
2881 AGGACACGGC  GGTGTACTAC  TGCGCCAGAG  GCCAATAGGG  CCAACTATAA  CAGGGGTACC  CCGGCCAATA  AGGCCGTCAC
     TCCTGTGCCG  CCACATGATG  ACGCGGTCTC  CGGTTATCCC  GGTTGATATT  GTCCCCATGG  GGCCGGTTAT  TCCGGCAGTG
     VTVSS common to all J
     ~~~~~~~~~~~
                                         hIgG1m17,1
                  ~~~~~~~~~~~~~~~~~~~~~~~~~~~~~~~~~~~~~~~~~~~~~~~~~~~~~~~~~~~~~~~~~~~~~~~~~~~~~~
            NheI
            ~~~~~~
     • V    S   S    A   S   T   K    G   P   S    V   F   P    L   A   P   S    S   K   S    T   S   G    G   T   A
2961 CGTCTCCTCA  GCTAGCACCA  AGGGCCCATC  GGTCTTCCCC  CTGGCACCCT  CCTCCAAGAG  CACCTCTGGG  GGCACAGCGG
     GCAGAGGAGT  CGATCGTGGT  TCCCGGGTAG  CCAGAAGGGG  GACCGTGGGA  GGAGGTTCTC  GTGGAGACCC  CCGTGTCGCC
```

The gapped vector pools were then mixed with the appropriate (i.e., compatible) pool of CDRH3 amplicons, generated as described above, at a 50:1 insert to vector ratio. The mixture was then transformed into electrocompetent yeast (*S. cerevisiae*), which already contained plasmids or integrated genes comprising a VK light chain library (described below). The degree of library diversity was determined by plating a dilution of the electroporated cells on a selectable agar plate. In this exemplified embodiment of the invention, the agar plate lacked tryptophan and the yeast lacked the ability to endogenously synthesize tryptophan. This deficiency was remedied by the inclusion of the TRP marker on the heavy chain chassis plasmid, so that any yeast receiving the plasmid and recombining it with a CDRH3 insert would grow. The electroporated cells were then outgrown approximately 100-fold, in liquid media lacking tryptophan. Aliquots of the library were frozen in 50% glycerol and stored at −80° C. Each transformant obtained at this stage represents a clone that can express a full IgG molecule. A schematic diagram of a CDRH3 integrated into a heavy chain vector and the accompanying sequences are provided in FIG. 7.

A heavy chain library pool was then produced, based on the approximate representation of the heavy chain family members as depicted in Table 43.

TABLE 43-continued

Occurrence of Heavy Chain Chassis in Data Sets Used to Design Library, Expected (Designed) Library, and Actual (Observed) Library

| Chassis | Relative Occurrence in Data Sets (1) | Expected (2) | Observed (3) |
|---|---|---|---|
| VH3-33/30 | 13.1 | 12.5 | 6.6 |
| VH3-48 | 2.9 | 6.3 | 7.5 |
| VH4-31 | 3.4 | 2.5 | 4.3 |
| VH4-34 | 17.2 | 7.0 | 4.7 |
| VH4-39 | 8.7 | 3.9 | 3.0 |
| VH4-59 | 7.0 | 7.8 | 9.2 |
| VH4-61 | 3.2 | 1.9 | 2.4 |
| VH4-B | 1.0 | 1.4 | 0.8 |
| VH5-51 | 7.2 | 7.7 | 10.5 |

(1) As detailed in Example 1, these 17 sequences account for about 76% of the entire sample of human VH sequences used to represent the human repertoire.
(2) Based on pooling of sub-libraries of each chassis type.
(3) Usage in 531 sequences from library; cf. FIG. 20.

Example 10.5

K94R Mutation in VH3-23 and R94K Mutation in VH3-33, VH3-30, VH3-7, and VH3-48

This example describes the mutation of position 94 in VH3-23, VH3-33, VH3-30, VH3-7, and VH3-48. In VH3-23, the amino acid at this position was mutated from K to R.

In VH3-33, VH3-30, VH3-7, and VH3-48, this amino acid was mutated from R to K. In VH3-32, this position was mutated from K to R. The purpose of making these mutations was to enhance the diversity of CDRH3 presentation in the library. For example, in naturally occurring VH3-23 sequences, about 90% have K at position 94, while about 10% have position R. By making these changes the diversity of the CDRH3 presentation is increased, as is the overall diversity of the library.

Amplification was performed using the 424 vectors as a template. For the K94R mutation, the vectors containing the sequence DTAVYYCAK (VH3-23; SEQ ID NO: 578) were amplified with a PCR primer that changed the K to a R and added 5' tail for homologous recombination with the VH3-48, VH3-33, VH-30, and VH3-7. The "T" base in 3-48 does not change the amino acid encoded and thus the same primer with a T::C mismatch still allows homologous recombination into the 3-48 chassis.

Furthermore, the amplification products from the 424 vectors (produced as described above) containing the DTAVYYCAR (SEQ ID NO: 579) sequence can be homologously recombined into the VH3-23 (CAR) vector, changing R to K in this framework and thus further increasing the diversity of CDRH3 presentation in this chassis.

```
VH3-48 (240)
                                         SEQ ID NO: (574)
240
TCTGCAAATGAACAGCCTGAGAGCTGAGGACACGGCGGTGTACT
       294
ACTGCGCCAGA

VH3-33/30 (240)
                                         SEQ ID NO: (575)
TCTGCAAATGAACAGCCTGAGAGCCGAGGACACGGCGGTGTACT
ACTGCGCCAGA

VH3-7 (240)
                                         SEQ ID NO: (576)
TCTGCAAATGAACAGCCTGAGAGCCGAGGACACGGCGGTGTACT
ACTGCGCCAGA

VH3-23 (240)
                                         SEQ ID NO: (577)
TCTGCAAATGAACAGCCTGAGAGCCGAGGACACGGCGGTGTACT
ACTGCGCCAAG
```

Example 11

VK Library Construction

This example describes the construction of a VK library of the invention. The exemplary VK library described herein corresponds to the VKCDR3 library of about $10^5$ complexity, described in Example 6.2. As described in Example 6, and throughout the application, other VK libraries are within the scope of the invention, as are Vλ libraries.

Figure 8:
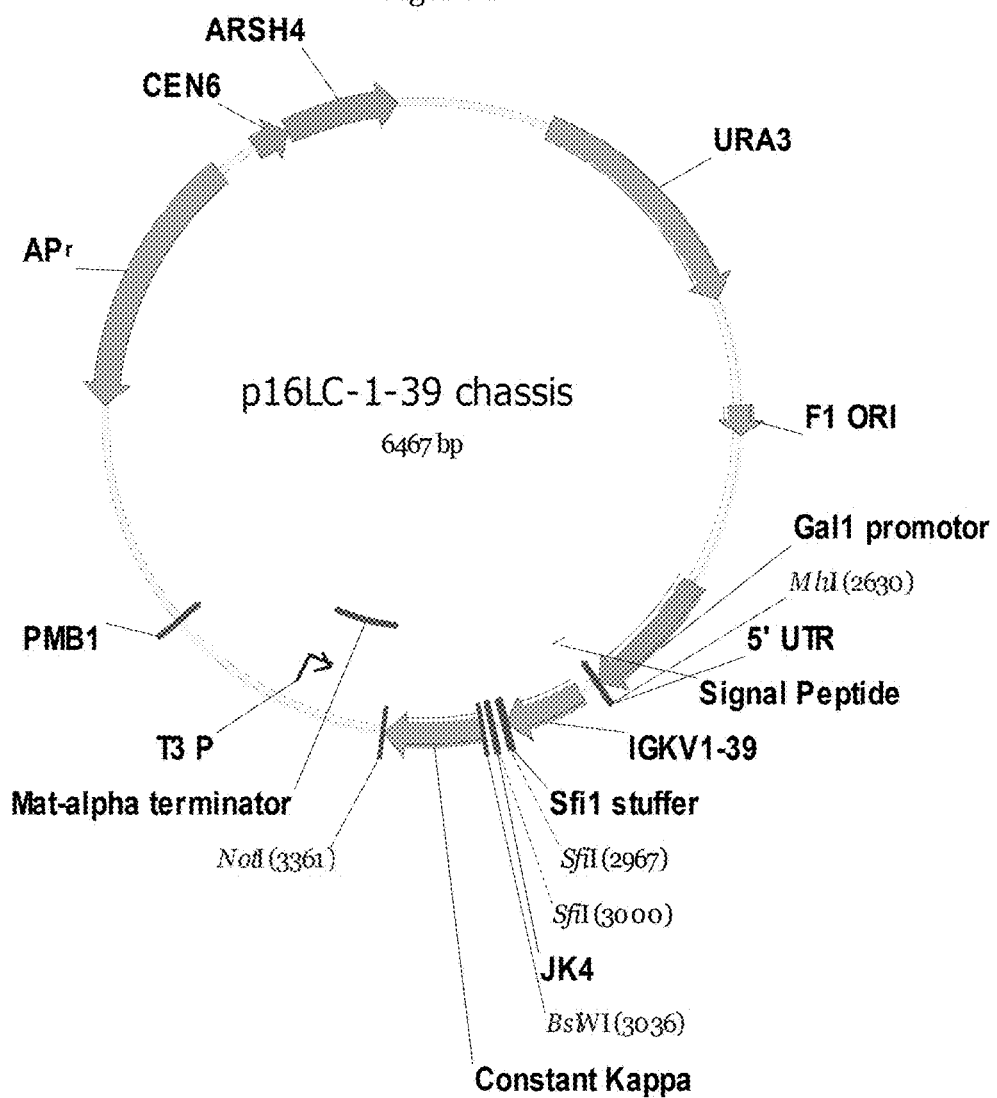
FIG. 8 depicts a schematic structure of a kappa light chain vector, prior to recombination with a CDRL3.

Ten VK chassis were synthesized (Table 11), which did not contain VKCDR3, but instead had two SfiI restriction sites in the place of VKCDR3, as for the heavy chain vectors. The kappa constant region followed the SfiI restriction sites. FIG. 8 shows a schematic structure of a light chain vector, prior to recombination with a CDRL3.

Ten VKCDR oligonucleotide libraries were then synthesized, as described in Example 6.2, using degenerate oligonucleotides (Table 33). The oligonucleotides were then PCR amplified, as separate pools, to make them double stranded and to add additional nucleotides required for efficient homologous recombination with the gapped (by SfiI) vector containing the VK chassis and constant region sequences. The VKCDR3 pools in this embodiment of the invention represented lengths 8, 9, and 10 amino acids, which were mixed post-PCR at a ratio 1:8:1. The pools were then cloned into the respective SfiI gapped VK chassis via homologous recombination, as described for the CDRH3 regions, set forth above. A schematic diagram of a CDRL3 integrated into a light chain vector and the accompanying sequence are provided in FIG. 9.

A kappa light chain library pool was then produced, based on the approximate representation of the VK family members found in the circulating pool of B cells. The 10 kappa variable regions used and the relative frequency in the final library pool are shown in Table 44.

TABLE 44

Occurrence of VK Chassis in Data Sets Used to Design Library, Expected (Designed) Library, and Actual (Observed) Library

| Chassis | Relative Occurrence in Data Sets (1) | Expected (2) | Observed (3) |
|---|---|---|---|
| VK1-5 | 8.6 | 7.1 | 5.8 |
| VK1-12 | 4.0 | 3.6 | 3.5 |
| VK1-27 | 3.3 | 3.6 | 8.1 |
| VK1-33 | 5.3 | 7.1 | 3.5 |
| VK1-39 | 18.5 | 21.4 | 17.4 |
| VK2-28 | 7.7 | 7.1 | 5.8 |
| VK3-11 | 10.9 | 10.7 | 20.9 |
| VK3-15 | 6.6 | 7.1 | 4.7 |
| VK3-20 | 24.5 | 21.4 | 18.6 |
| VK4-1 | 10.4 | 10.7 | 11.6 |

(1) As indicated in Example 3, these 10 chassis account for about 80% of the occurrences in the entire data set of VK sequences examined.
(2) Rounded off ratios from the data in column 2, then normalized for actual experimental set up. The relative rounded ratios are 6 for VK1-39 and VK3-20, 3 for VK3-11 and VK4-1, 2 for VK-15, VK1-33, VK2-28 and VK3-15, and 1 for VK1-12 and VK1-27.
(3) Chassis usage in set of 86 sequences obtained from library; see also FIG. 22.

Example 12

Characterization of Exemplary Libraries

This example shows the characteristics of exemplary libraries of the invention, constructed according to the methods described herein.

Example 12.1

Characterization of the Heavy Chains

Figure 10:
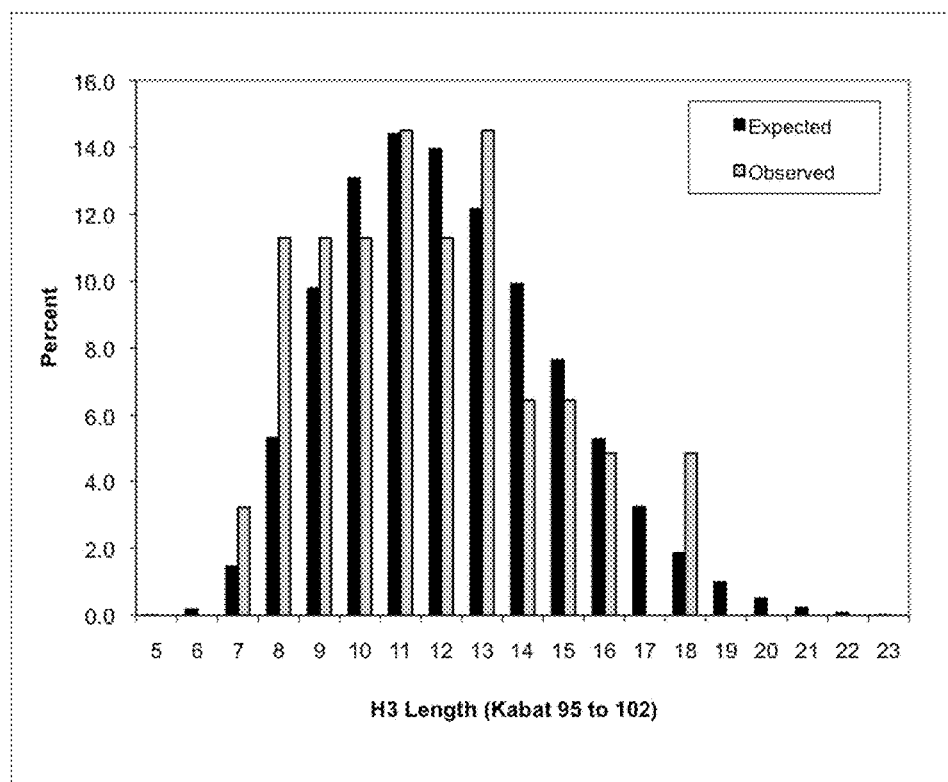
FIG. 10 depicts the length distribution of the CDRH3 domain (Kabat positions 95-102) from 96 colonies obtained by transformation with 10 of the 424 vectors synthesized as described in Example 10 (observed), as compared to the expected (i.e., designed) distribution.
Figure 11:
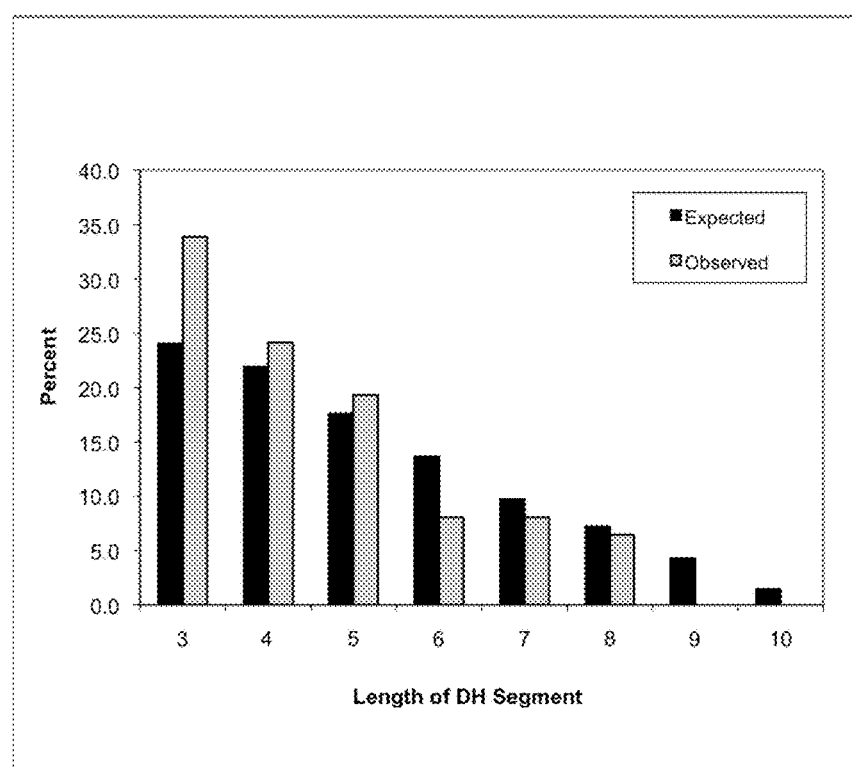
FIG. 11 depicts the length distribution of the DH segment from 96 colonies obtained by transformation with 10 of the 424 vectors synthesized as described in Example 10 (observed), as compared to the expected (i.e., designed) distribution.
Figure 12:
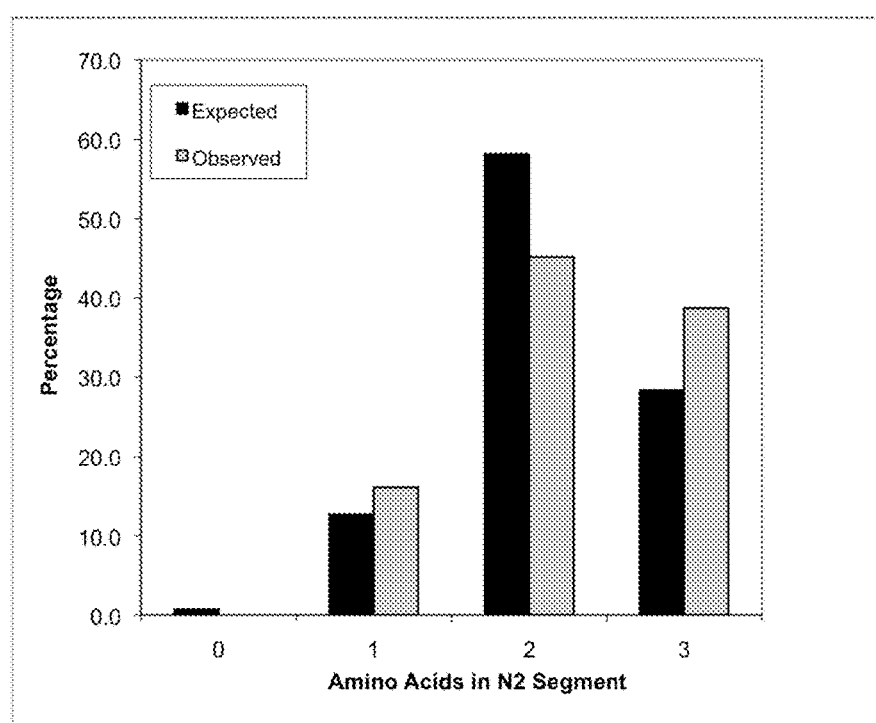
FIG. 12 depicts the length distribution of the N2 segment from 96 colonies obtained by transformation with 10 of the 424 vectors synthesized as described in Example 10 (observed), as compared to the expected (i.e., designed) distribution.
Figure 13:
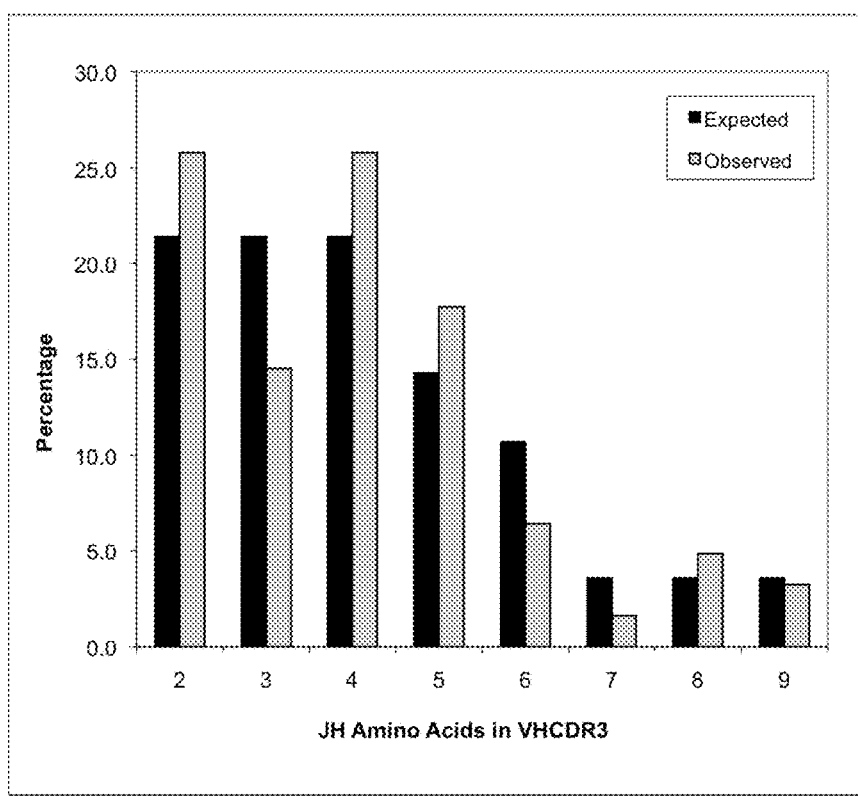
FIG. 13 depicts the length distribution of the H3-JH segment from 96 colonies obtained by transformation with 10 of the 424 vectors synthesized as described in Example 10 (observed), as compared to the expected (i.e., designed) distribution.

To characterize the product of the split pool synthesis, ten of the 424 vectors containing the [Tail]-[N1]-[DH]-[N2]-[H3-JH] product were selected at random and transformed into *E. coli*. The split pool product had a theoretical diversity of about $1.1 \times 10^6$ (i.e., 278×141×28). Ninety-six colonies were selected from the transformation and forward and reverse sequences were generated for each clone. Of the 96 sequencing reactions, 90 yielded sequences from which the CDRH3 region could be identified, and about 70% of these sequences matched a designed sequence in the library. The length distribution of the sequenced CDRH3 segments from the ten vectors, as compared to the theoretical distribution (based on design), is provided in FIG. 10. The length distribution of the individual DH, N2, and H3-JH segments obtained from the ten vectors are shown in FIGS. 11-13.

Figure 14:
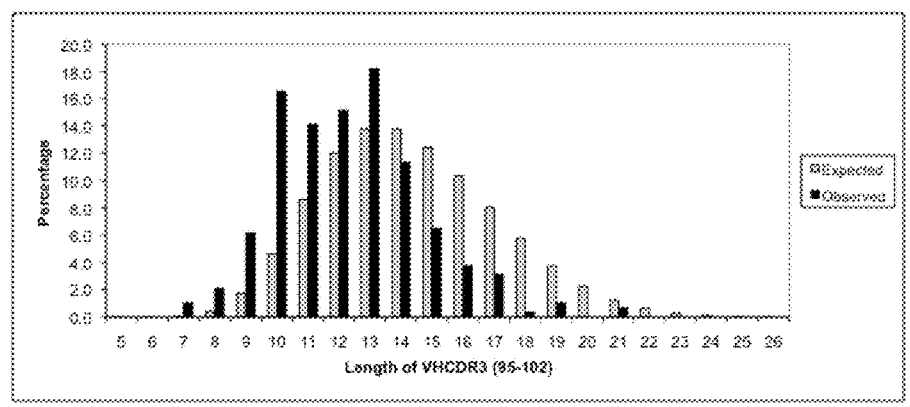
FIG. 14 depicts the length distribution of the CDRH3 domains from 291 sequences prepared from yeast cells transformed according to the method outlined in Example 10.4, namely the co-transformation of vectors containing heavy chain chassis and constant regions with a CDRH3 insert (observed), as compared to the expected (i.e., designed) distribution.
Figure 15:
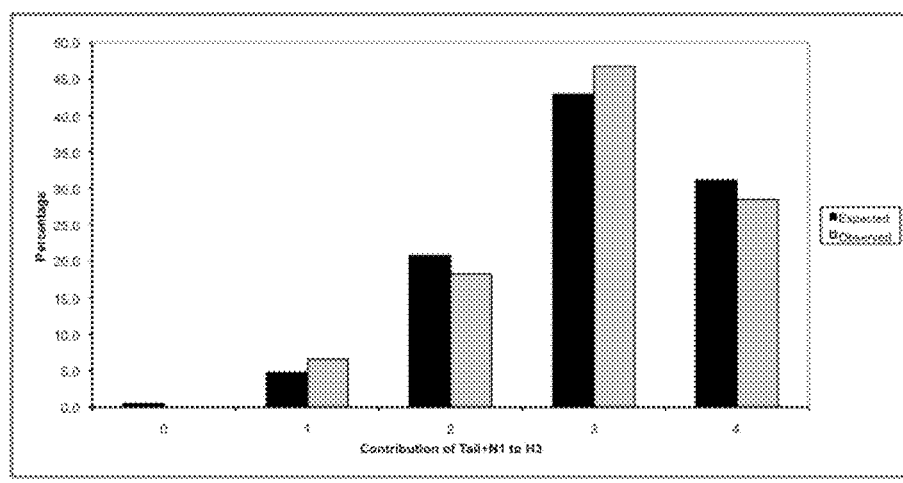
FIG. 15 depicts the length distribution of the [Tail]-[N1] region from the 291 sequences prepared from yeast cells transformed according to the protocol outlined in Example 10.4 (observed), as compared to the expected (i.e., designed) distribution.
Figure 16:
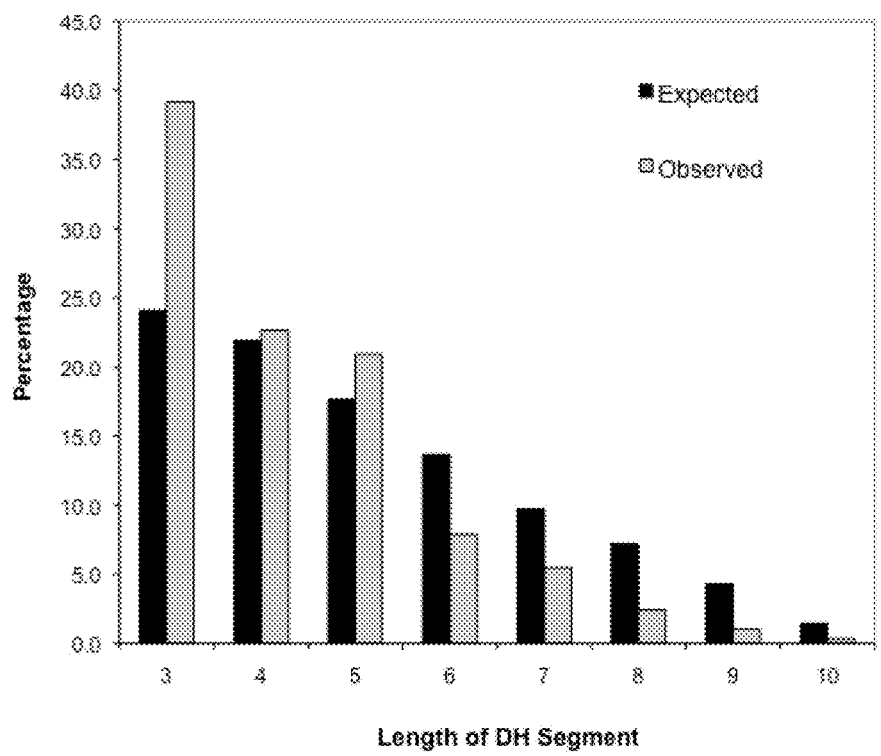
FIG. 16 depicts the length distribution of the DH region from the 291 sequences prepared from yeast cells transformed according to the protocol outlined in Example 10.4 (observed), as compared to the theoretical (i.e., designed) distribution.
Figure 17:
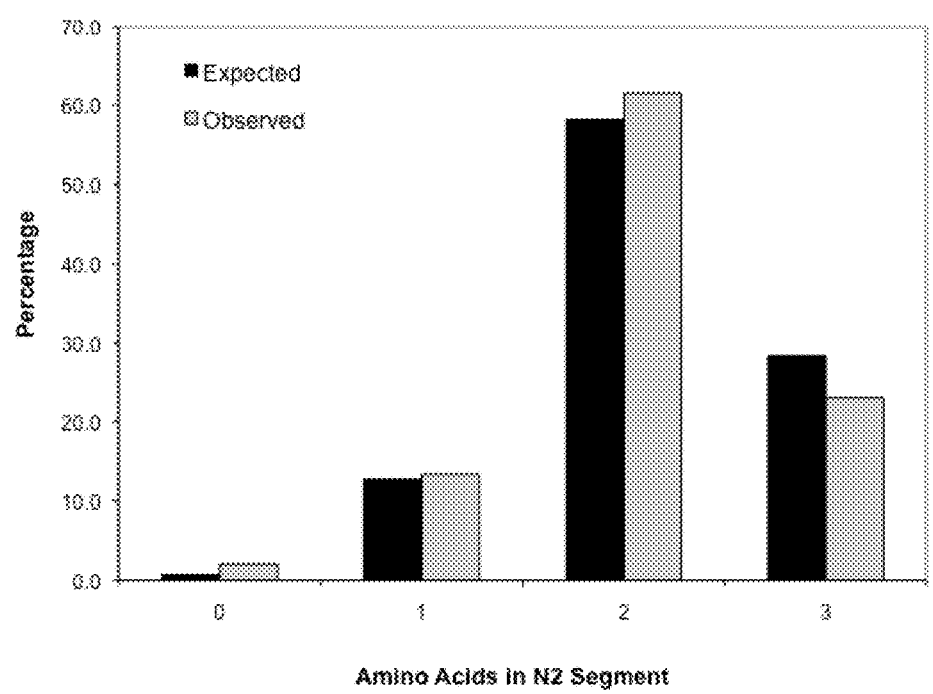
FIG. 17 depicts the length distribution of the N2 region from the 291 sequences prepared from yeast cells transformed according to the protocol outlined in Example 10.4 (observed), as compared to the theoretical (i.e., designed) distribution.
Figure 18:
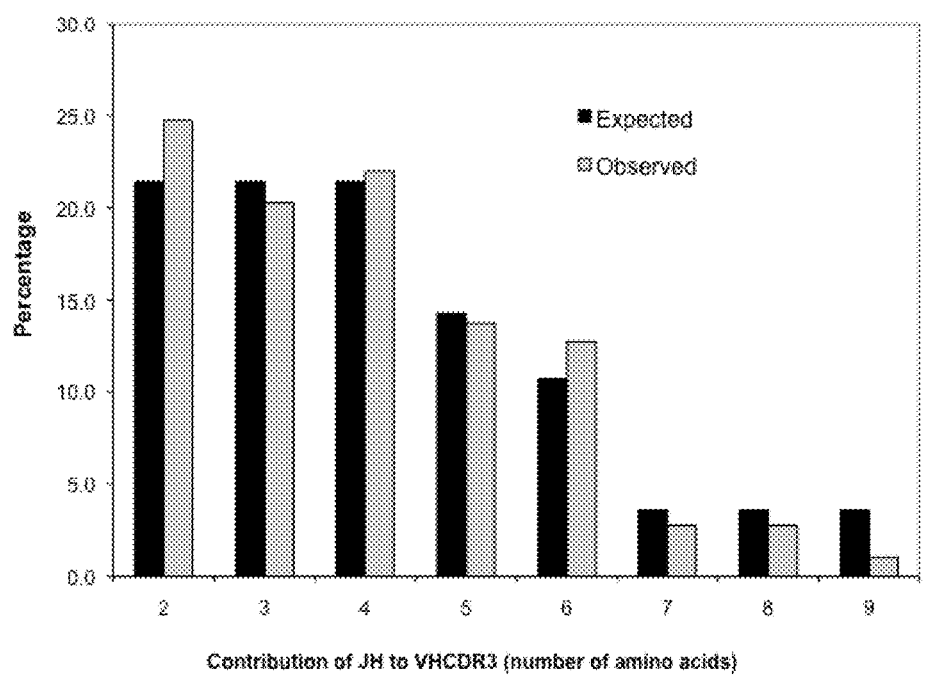
FIG. 18 depicts the length distribution of the H3-JH region from the 291 sequences prepared from yeast cells transformed according to the protocol outlined in Example 10.4 (observed), as compared to the theoretical (i.e., designed) distribution.
Figure 19:
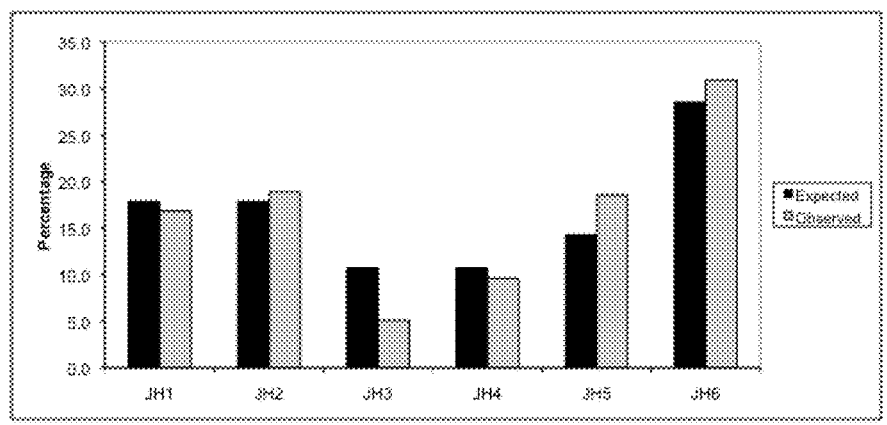
FIG. 19 depicts the familial origin of the JH segments identified in the 291 sequences (observed), as compared to the theoretical (i.e., designed) familial origin.
Figure 20:
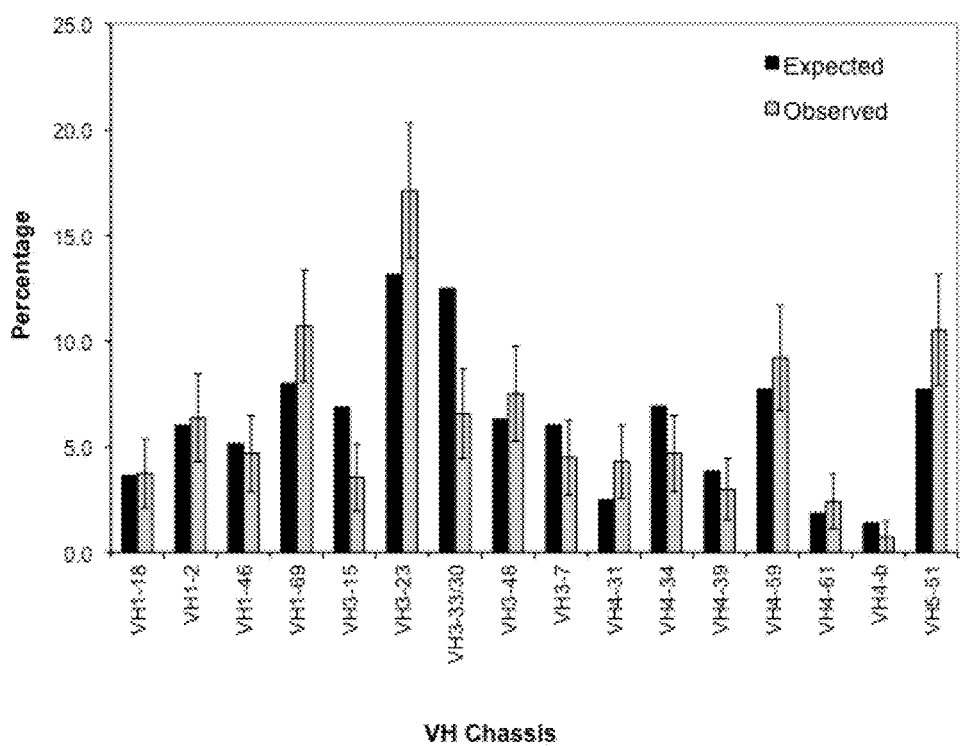
FIG. 20 depicts the representation of each of the 16 chassis of the library (observed), as compared to the theoretical (i.e., designed) chassis representation. VH3-23 is represented twice; once ending in CAR and once ending in CAK. These representations were combined, as were the ten variants of VH3-33 with one variant of VH3-30.

Once the length distribution of the CDRH3 components of the library that were contained in the vector matched design were verified, the CDRH3 domains and heavy chain family representation in yeast that had been transformed according to the process described in Example 10.4 were characterized. Over 500 single-pass sequences were obtained. Of these, 531 yielded enough sequence information to identify the heavy chain chassis and 291 yielded enough sequence information to characterize the CDRH3. These CDRH3 domains have been integrated with the heavy chain chassis and constant region, according to the homologous recombination processes described herein. The length distribution of the CDRH3 domains from 291 sequences, compared to the theoretical length distribution, is shown in FIG. 14. The mean theoretical length was 14.4±4 amino acids, while the average observed length was 14.3±3 amino acids. The observed length of each portion of the CDRH3, as compared to theoretical, is presented in FIGS. 15-18. FIG. 19 depicts the familial origin of the JH segments identified in the 291 sequences, and FIG. 20 shows the representation of 16 of the chassis of the library. The VH3-15 chassis was not represented amongst these sequences. This was corrected later by introducing yeast transformants containing the VH3-15 chassis, with CDRH3 diversity, into the library at the desired composition.

Example 12.2

Characterization of the Light Chains

Figure 21:
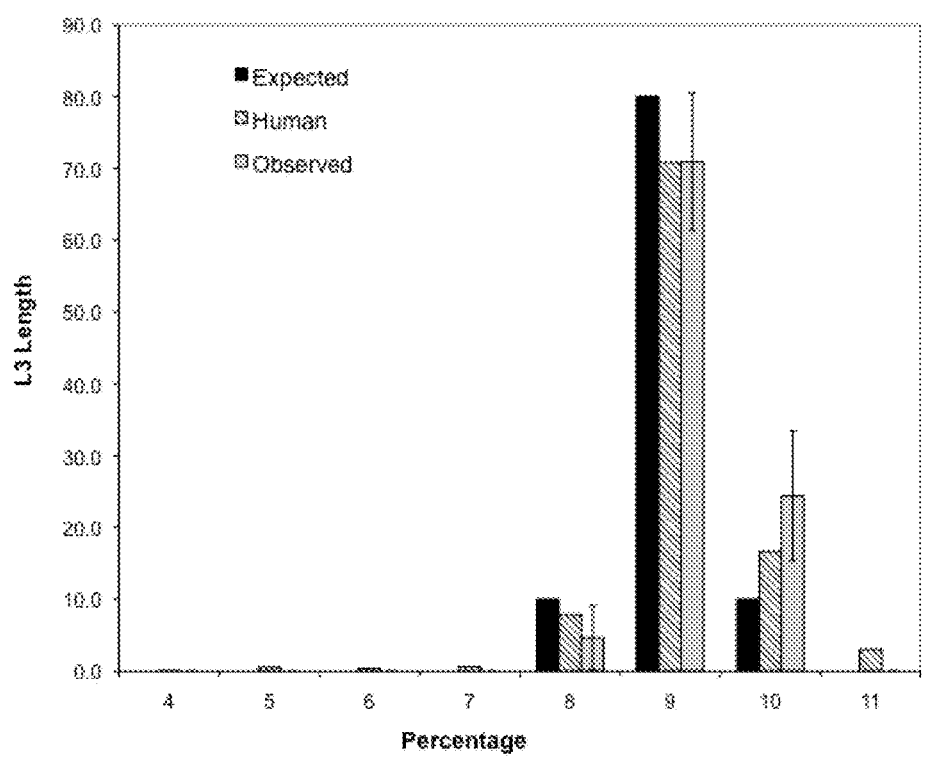
FIG. 21 depicts a comparison of the CDRL3 length from 86 sequences selected from the VKCDR3 library of Example 6.2 (observed) to human sequences (human) and the designed sequences (designed).
Figure 22:
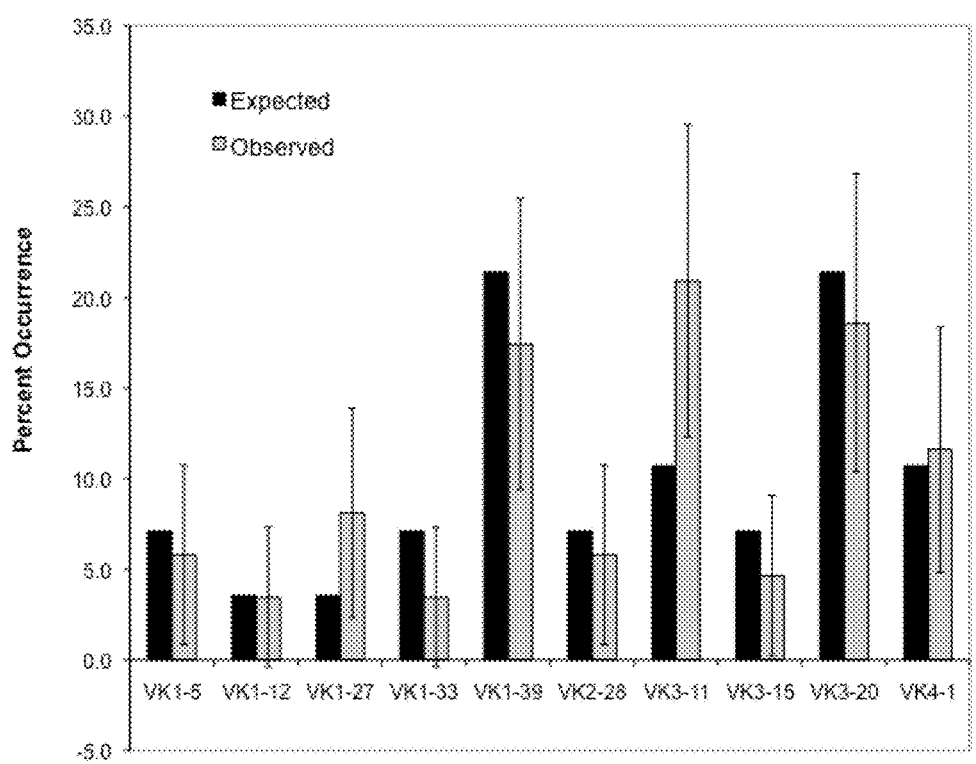
FIG. 22 depicts the representation of the light chain chassis amongst the 86 sequences selected from the library (observed), as compared to the theoretical (i.e., designed) chassis representation.

The length distribution of the CDRL3 components, from the VKCDR3 library described in Example 6.2, were determined after yeast transformation via the methods described in Example 10.4. A comparison of the CDRL3 length from 86 sequences of the library to the human sequences and designed sequences is provided in FIG. 21. FIG. 22 shows the representation of the light chain chassis from amongst the 86 sequences selected from the library. About 91% of the CDRL3 sequences were exact matches to the design, and about 9% differed by a single amino acid.

Example 13

Characterization of the Composition of the Designed CDRH3 Libraries

This example presents data on the composition of the CDRH3 domains of exemplary libraries, and a comparison to other libraries of the art. More specifically, this example presents an analysis of the occurrence of the 400 possible amino acid pairs (20 amino acids×20 amino acids) occurring in the CDRH3 domains of the libraries. The prevalence of these pairs is computed by examination of the nearest neighbor (i-i+1; designated IP1), next nearest neighbor (i-i+2; designated IP2), and next-next nearest neighbor (i-i+3; designated IP3) of the i residue in CDRH3. Libraries previously known in the art (e.g., Knappik et al., J. Mol. Biol., 2000, 296: 57; Sidhu et al., J. Mol. Biol., 2004, 338: 299; and Lee et al., J. Mol. Biol. 2004, 340: 1073, each of which is incorporated by reference in its entirety) have only considered the occurrence of the 20 amino acids at individual positions within CDRH3, while maintaining the same composition across the center of CDRH3, and not the pair-wise occurrences considered herein. In fact, according to Sidhu et al. (J. Mol. Biol., 2004, 338: 299, incorporated by reference in its entirety), "[i]n CDR-H3, there was some bias towards certain residue types, but all 20 natural amino acid residues occurred to a significant extent, and there was very little position-specific bias within the central portion of the loop". Thus, the present invention represents the first recognition that, surprisingly, a position-specific bias does exist within the central portion of the CDRH3 loop, when the occurrences of amino acid pairs recited above are considered. This example shows that the libraries described herein more faithfully reproduce the occurrence of these pairs as found in human sequences, in comparison to other libraries of the art. The composition of the libraries described herein may thus be considered more "human" than other libraries of the art.

To examine the pair-wise composition of CDRH3 domains, a portion of CDRH3 beginning at position 95 was chosen. For the purposes of comparison with data presented in Knappik et al. and Lee et al., the last five residues in each of the analyzed CDRH3s were ignored. Thus, for the purposes of this analysis, both members of the pair i-i+X (X=1 to 3) must fall within the region starting at position 95 and ending at (but including) the sixth residue from the C-terminus of the CDRH3. The analyzed portion is termed the "central loop" (see Definitions).

To estimate pair distributions in representative libraries of the invention, a sampling approach was used. A number of sequences were generated by choosing randomly and, in turn, one of the 424 tail plus N1 segments, one of the 278 DH segments, one of the 141 N2 segments and one of the 28 JH segments (the latter truncated to include only the 95 to 102 Kabat CDRH3). The process was repeated 10,000 times to generate a sample of 10,000 sequences. By choosing a different seed for the random number generation, an independent sample of another 10,000 sequences was also generated and the results for pair distributions were observed to be nearly the same. For the calculations presented herein, a third and much larger sample of 50,000 sequences was used. A similar approach was used for the alternative library embodiment (N-1-141), whereby the first segment was selected from 1068 tail+N1 segments (resulting after eliminating redundant sequences from 2 times 4 times 141 or 1128 possible combinations).

The pair-wise composition of Knappik et al. was determined based on the percent occurrences presented in FIG. 7a of Knappik et al. (p. 71). The relevant data are reproduced below, in Table 45.

TABLE 45

Composition of CDRH3 positions 95-100s (corresponding to positions 95-99B of the libraries of the current invention) of CDRH3 of Knappik et al. (from FIG. 7a of Knappik et al.)

| Amino Acid | Planned (%) | Found (%) |
|---|---|---|
| A | 4.1 | 3.0 |
| C | 1.0 | 1.0 |
| D | 4.1 | 4.2 |
| E | 4.1 | 2.3 |
| F | 4.1 | 4.9 |
| G | 15.0 | 10.8 |
| H | 4.1 | 4.6 |
| I | 4.1 | 4.5 |
| K | 4.1 | 2.9 |
| L | 4.1 | 6.6 |
| M | 4.1 | 3.3 |
| N | 4.1 | 4.5 |
| P | 4.1 | 4.8 |
| Q | 4.1 | 2.9 |
| R | 4.1 | 4.1 |
| S | 4.1 | 5.6 |
| T | 4.1 | 4.5 |
| V | 4.1 | 3.7 |
| W | 4.1 | 2.0 |
| Y | 15.0 | 19.8 |

The pair-wise composition of Lee et al. was determined based on the libraries depicted in Table 5 of Lee et al., where the positions corresponding to those CDRH3 regions analyzed from the current invention and from Knappik et al. are composed of an "XYZ" codon in Lee et al. The XYZ codon of Lee et al. is a degenerate codon with the following base compositions:

position 1 (X): 19% A, 17% C, 38% G, and 26% T;
position 2 (Y): 34% A, 18% C, 31% G, and 17% T; and
position 3 (Z): 24% G and 76% T.

When the approximately 2% of codons encoding stop codons are excluded (these do not occur in functionally expressed human CDRH3 sequences), and the percentages are re-normalized to 100%, the following amino acid representation can be deduced from the composition of the XYZ codon of Lee et al. (Table 46).

TABLE 46

Composition of CDRH3 of Lee et al., Based on the Composition of the Degenerate XYZ Codon.

| Type | Percent |
|---|---|
| A | 6.99% |
| C | 6.26% |
| D | 10.03% |
| E | 3.17% |
| F | 3.43% |
| G | 12.04% |
| H | 4.49% |
| I | 2.51% |
| K | 1.58% |
| L | 4.04% |
| M | 0.79% |
| N | 5.02% |
| P | 3.13% |
| Q | 1.42% |
| R | 6.83% |
| S | 9.35% |
| T | 3.49% |
| V | 6.60% |
| W | 1.98% |
| Y | 6.86% |

The occurrences of each of the 400 amino acid pairs, in each of the IP1, IP2, and IP3 configurations, can be computed for Knappik et al. and Lee et al. by multiplying together the individual amino acid compositions. For example, for Knappik et al., the occurrence of YS pairs in the library is calculated by multiplying 15% by 4.1%, to yield 6.1%; note that the occurrence of SY pairs would be the same. Similarly, for the XYZ codon-based libraries of Lee et al., the occurrence of YS pairs would be 6.86% (Y) multiplied by 9.35% (S), to give 6.4%; the same, again, for SY.

For the human CDRH3 sequences, the calculation is performed by ignoring the last five amino acids in the Kabat definition. By ignoring the C-terminal 5 amino acids of the human CDRH3, these sequences may be compared to those of Lee et al., based on the XYZ codons. While Lee et al. also present libraries with "NNK" and "NNS" codons, the pair-wise compositions of these libraries are even further away from human CDRH3 pair-wise composition. The XYZ codon was designed by Lee et al. to replicate, to some extent, the individual amino acid type biases observed in CDRH3.

An identical approach was used for the libraries of the invention, after using the methods described above to produce sample sequences. While it is possible to perform these calculations with all sequences in the library, independent random samples of 10,000 to 20,000 members gave indistinguishable results. The numbers reported herein were thus generated from samples of 50,000 members.

Three tables were generated for IP1, IP2 and IP3, respectively (Tables 47, 48, and 49). Out of the 400 pairs, a selection from amongst the 20 most frequently occurring is included in the tables. The sample of about 1,000 human sequences (Lee et al., 2006) is denoted as "Preimmune," a sample of about 2,500 sequences (Jackson et al., 2007) is denoted as "Humabs," and the more affinity matured subset of the latter, which excludes all of the Preimmune set, is denoted as "Matured." Synthetic libraries in the art are denoted as HuCAL (Knappik, et al., 2000) and XYZ (Lee et al., e 2004). Two representative libraries of the invention are included: LUA-59 includes 59 N1 segments, 278 DH segments, 141 N2 segments, and 28 H3-JH segments (see Examples, above). LUA-141 includes 141 N1 segments, 278 DH segments, 141 N2 segments, and 28 H3-JH segments (see Examples, above). Redundancies created by combination of the N1 and tail sequences were removed from the dataset in each respective library. In certain embodiments, the invention may be defined based on the percent occurrence of any of the 400 amino acid pairs, particularly those in Tables 47-49. In certain embodiments, the invention may be defined based on at least 1, 2, 3, 4, 5, 6, 7, 8, 9, 10, 11, 12, 13, 14, 15, 16, 17, 18, 19, 20, or more of these pairs. In certain embodiments of the invention, the percent occurrence of certain pairs of amino acids may fall within ranges indicated by "LUA−" (lower boundary) and "LUA+" (higher boundary), in the following tables. In some embodiments of the invention, the lower boundary for the percent occurrence of any amino acid pairs may be about 0.1, 0.25, 0.5, 0.75, 1, 1.25, 1.5, 1.75, 2, 2.25, 2.5, 2.75, 3, 3.25, 3.5, 3.75, 4, 4.25, 4.5, 4.75, and 5. In some embodiments of the invention, the higher boundary for the percent occurrence of any amino acid pairs may be about 0.1, 0.25, 0.5, 0.75, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, and 8. According to the present invention, any of the lower boundaries recited may be combined with any of the higher boundaries recited, to establish ranges, and vice-versa.

TABLE 47

Percent Occurrence of i − i + 1 (IP1) Amino Acid Pairs in Human Sequences, Exemplary Libraries of the Invention, and the Libraries of Knappik et al. and Lee et al.

| Pairs | Preimmune | Humabs | Matured | LUA-59 | LUA-141 | HuCAL | XYZ | LUA− | LUA+ | Range | HuCAL | XYZ |
|---|---|---|---|---|---|---|---|---|---|---|---|---|
| YY | 5.87 | 4.44 | 3.27 | 5.83 | 5.93 | 2.25 | 0.47 | 2.50 | 6.50 | 4.00 | 0 | 0 |
| SG | 3.54 | 3.41 | 3.26 | 3.90 | 3.72 | 0.61 | 1.13 | 2.50 | 4.50 | 2.00 | 0 | 0 |
| SS | 3.35 | 2.65 | 2.26 | 2.82 | 3.08 | 0.16 | 0.88 | 2.00 | 4.00 | 2.00 | 0 | 0 |
| GS | 2.59 | 2.37 | 2.20 | 3.82 | 3.52 | 0.61 | 1.13 | 1.50 | 4.00 | 2.50 | 0 | 0 |
| GY | 2.55 | 2.34 | 2.12 | 3.15 | 2.56 | 2.25 | 0.83 | 2.00 | 3.50 | 1.50 | 1 | 0 |
| GG | 2.19 | 2.28 | 2.41 | 6.78 | 3.51 | 2.25 | 1.45 | 2.00 | 7.00 | 5.00 | 1 | 0 |

TABLE 47-continued

Percent Occurrence of i – i + 1 (IP1) Amino Acid Pairs in Human Sequences,
Exemplary Libraries of the Invention, and the Libraries of Knappik et al. and Lee et al.

| Pairs | Preimmune | Humabs | Matured | LUA-59 | LUA-141 | HuCAL | XYZ | LUA− | LUA+ | Range | HuCAL | XYZ |
|---|---|---|---|---|---|---|---|---|---|---|---|---|
| YS | 1.45 | 1.30 | 1.23 | 1.40 | 1.52 | 0.61 | 0.64 | 0.75 | 2.00 | 1.25 | 0 | 0 |
| YG | 1.35 | 1.21 | 1.10 | 1.64 | 1.69 | 2.25 | 0.83 | 0.75 | 2.00 | 1.25 | 0 | 1 |
| SY | 1.31 | 1.07 | 0.90 | 1.65 | 1.77 | 0.61 | 0.64 | 0.75 | 2.00 | 1.25 | 0 | 0 |
| YD | 1.67 | 1.40 | 1.17 | 0.88 | 0.90 | 0.61 | 0.69 | 0.75 | 2.25 | 1.50 | 0 | 0 |
| DS | 1.53 | 1.31 | 1.16 | 1.20 | 1.46 | 0.16 | 0.94 | 0.75 | 2.00 | 1.25 | 0 | 1 |
| DY | 1.40 | 1.23 | 1.11 | 0.34 | 0.48 | 0.61 | 0.69 | 0.25 | 2.00 | 1.75 | 1 | 1 |
| VV | 1.37 | 0.94 | 0.64 | 2.30 | 2.30 | 0.16 | 0.44 | 0.50 | 2.50 | 2.00 | 0 | 0 |
| GD | 1.20 | 1.21 | 1.25 | 0.49 | 0.44 | 0.61 | 1.21 | 0.25 | 1.75 | 1.50 | 1 | 1 |
| AA | 1.16 | 0.93 | 0.75 | 1.27 | 1.46 | 0.16 | 0.49 | 0.60 | 1.50 | 0.90 | 0 | 0 |
| RG | 1.08 | 1.26 | 1.38 | 1.69 | 1.38 | 0.61 | 0.82 | 1.00 | 2.00 | 1.00 | 0 | 0 |
| VA | 0.91 | 0.66 | 0.46 | 0.36 | 0.35 | 0.16 | 0.46 | 0.25 | 1.00 | 0.75 | 0 | 1 |
| GV | 0.84 | 0.89 | 0.95 | 2.87 | 2.16 | 0.61 | 0.79 | 0.80 | 3.00 | 2.20 | 0 | 0 |
| CS | 0.82 | 0.55 | 0.38 | 0.79 | 0.80 | 0.04 | 0.59 | 0.50 | 1.00 | 0.50 | 0 | 1 |
| GR | 0.74 | 0.90 | 1.00 | 1.01 | 0.79 | 0.61 | 0.82 | 0.70 | 1.25 | 0.55 | 0 | 1 |

The pairs in bold comprise about 19% to about 24% of occurrences (among the possible 400 pairs) for the Preimmune (Lee, et al., 2006), Humabs (Jackson, et al., 2007) and matured (Jackson minus Lee) sets. They account for about 27% to about 31% of the occurrences in the LUA libraries, but only about 12% in the HuCAL library and about 8% in the "XYZ" library. This is a reflection of the fact that pair-wise biases do exist in the human and LUA libraries, but not in the others.
The last 2 columns indicate whether the corresponding pair-wise compositions fall within the LUA− and LUA+ boundaries: 0 if outside, 1 if within.

TABLE 48

Percent Occurrence of i – i + 2 (IP2) Amino Acid Pairs in Human Sequences,
Exemplary Libraries of the Invention, and the Libraries of Knappik et al. and Lee et al.

| Pairs | Preimmune | Humabs | Matured | LUA-59 | LUA-141 | HuCAL | XYZ | LUA− | LUA+ | Range | HuCAL | XYZ |
|---|---|---|---|---|---|---|---|---|---|---|---|---|
| YY | 3.57 | 2.59 | 1.78 | 2.99 | 3.11 | 2.25 | 0.47 | 2.5 | 4.5 | 2 | 0 | 0 |
| GY | 3.34 | 2.91 | 2.56 | 4.96 | 3.78 | 2.25 | 0.83 | 2.5 | 5.5 | 3 | 0 | 0 |
| SY | 2.94 | 2.41 | 2.01 | 3.03 | 3.42 | 0.61 | 0.64 | 2 | 4 | 2 | 0 | 0 |
| YS | 2.88 | 2.34 | 1.95 | 3.24 | 3.32 | 0.61 | 0.64 | 1.75 | 3.75 | 2 | 0 | 0 |
| SG | 2.60 | 2.29 | 2.05 | 2.84 | 2.96 | 0.61 | 1.13 | 2 | 3.5 | 1.5 | 0 | 0 |
| SS | 2.27 | 2.01 | 1.84 | 2.30 | 2.50 | 0.16 | 0.88 | 1.5 | 3 | 1.5 | 0 | 0 |
| GS | 2.16 | 2.12 | 2.10 | 2.96 | 2.32 | 0.61 | 1.13 | 1.5 | 3 | 1.5 | 0 | 0 |
| GG | 1.92 | 2.25 | 2.44 | 6.23 | 3.68 | 2.25 | 1.45 | 1.5 | 7 | 5.5 | 1 | 0 |
| YG | 1.17 | 1.14 | 1.15 | 1.39 | 1.47 | 2.25 | 0.83 | 1 | 2 | 1 | 0 | 0 |
| DS | 2.03 | 1.67 | 1.40 | 1.21 | 1.48 | 0.16 | 0.94 | 1 | 2.5 | 1.5 | 0 | 0 |
| YD | 1.71 | 1.39 | 1.11 | 0.89 | 0.92 | 0.61 | 0.69 | 0.75 | 1.75 | 1 | 0 | 0 |
| VG | 1.35 | 1.17 | 1.01 | 1.75 | 1.54 | 0.61 | 0.79 | 1 | 2 | 1 | 0 | 0 |
| DY | 1.06 | 1.02 | 0.99 | 0.23 | 0.40 | 0.61 | 0.69 | 0.2 | 1.2 | 1 | 1 | 1 |
| WG | 1.06 | 0.76 | 0.53 | 0.85 | 0.91 | 0.61 | 0.24 | 0.75 | 1.25 | 0.5 | 0 | 0 |
| RY | 0.98 | 1.00 | 0.96 | 0.70 | 0.91 | 0.61 | 0.47 | 0.6 | 1 | 0.4 | 1 | 0 |
| GC | 0.97 | 0.75 | 0.64 | 0.94 | 0.81 | 0.15 | 0.75 | 0.5 | 1 | 0.5 | 0 | 1 |
| DG | 0.95 | 1.05 | 1.08 | 1.78 | 1.05 | 0.61 | 1.21 | 0.75 | 2 | 1.25 | 0 | 1 |
| GD | 0.94 | 0.88 | 0.86 | 0.47 | 0.36 | 0.61 | 1.21 | 0.25 | 1 | 0.75 | 1 | 0 |
| VV | 0.94 | 0.59 | 0.35 | 0.95 | 0.90 | 0.16 | 0.44 | 0.5 | 1 | 0.5 | 0 | 0 |
| AA | 0.90 | 0.73 | 0.59 | 0.72 | 0.74 | 0.16 | 0.49 | 0.5 | 1 | 0.5 | 0 | 0 |

The pairs in bold comprise about 18% to about 23% of occurrences (among the possible 400 pairs) for the Preimmune (Lee, et al., 2006), Humabs (Jackson, et al., 2007) and matured (Jackson minus Lee) sets. They account for about 27% to about 30% of the occurrences in the LUA libraries, but only about 12% in the HuCAL library and about 8% in the "XYZ" library.
Because of the nature of the construction of the central loops in the HuCAL and XYZ libraries, these numbers are the same for the IP1, IP2, and IP3 pairs.
The last 2 columns indicate whether the corresponding pair-wise compositions fall within the LUA− and LUA+ boundaries: 0 if outside, 1 if within.

TABLE 49

Percent Occurrence of i – i + 3 (IP3) Amino Acid Pairs in Human Sequences,
Exemplary Libraries of the Invention, and the Libraries of Knappik et al. and Lee et al.

| Pairs | Preimmune | Humabs | Matured | LUA-59 | LUA-141 | HuCAL | XYZ | LUA− | LUA+ | Range | HuCAL | XYZ |
|---|---|---|---|---|---|---|---|---|---|---|---|---|
| GY | 3.55 | 2.85 | 2.32 | 5.80 | 4.42 | 2.25 | 0.83 | 2.5 | 6.5 | 4 | 0 | 0 |
| SY | 3.38 | 3.01 | 2.67 | 3.78 | 4.21 | 0.61 | 0.64 | 1 | 5 | 4 | 0 | 0 |
| YS | 3.18 | 2.56 | 2.05 | 3.20 | 3.33 | 0.61 | 0.64 | 2 | 4 | 2 | 0 | 0 |
| SS | 2.26 | 1.74 | 1.37 | 1.81 | 2.18 | 0.16 | 0.88 | 1 | 3 | 2 | 0 | 0 |
| GS | 2.23 | 2.13 | 2.00 | 4.60 | 3.33 | 0.61 | 1.13 | 2 | 5 | 3 | 0 | 0 |
| YG | 2.14 | 1.65 | 1.35 | 2.69 | 2.79 | 2.25 | 0.83 | 1.5 | 3 | 1.5 | 1 | 0 |
| YY | 1.86 | 1.48 | 1.12 | 1.18 | 1.27 | 2.25 | 0.47 | 0.75 | 2 | 1.25 | 0 | 0 |
| GG | 1.60 | 1.87 | 2.11 | 4.73 | 2.84 | 2.25 | 1.45 | 1.5 | 5 | 3.5 | 1 | 0 |
| SG | 0.90 | 1.04 | 1.12 | 0.93 | 1.25 | 0.61 | 1.13 | 0.75 | 1.5 | 0.75 | 0 | 1 |
| DG | 2.01 | 1.94 | 1.84 | 2.51 | 2.03 | 0.61 | 1.21 | 1.5 | 3 | 1.5 | 0 | 0 |

TABLE 49-continued

Percent Occurrence of i – i + 3 (IP3) Amino Acid Pairs in Human Sequences,
Exemplary Libraries of the Invention, and the Libraries of Knappik et al. and Lee et al.

| Pairs | Preimmune | Humabs | Matured | LUA-59 | LUA-141 | HuCAL | XYZ | LUA– | LUA+ | Range | HuCAL | XYZ |
|---|---|---|---|---|---|---|---|---|---|---|---|---|
| DS | 1.48 | 1.31 | 1.22 | 0.41 | 0.55 | 0.16 | 0.94 | 0.25 | 1.5 | 1.25 | 0 | 1 |
| VA | 1.18 | 0.83 | 0.55 | 1.48 | 1.46 | 0.16 | 0.46 | 0.5 | 2 | 1.5 | 0 | 0 |
| AG | 1.13 | 1.09 | 1.03 | 0.97 | 1.04 | 0.61 | 0.84 | 0.9 | 2 | 1.1 | 0 | 0 |
| TY | 1.05 | 0.90 | 0.76 | 1.01 | 1.16 | 0.61 | 0.24 | 0.75 | 1.75 | 1 | 0 | 0 |
| PY | 1.02 | 0.88 | 0.79 | 1.23 | 0.86 | 0.61 | 0.21 | 0.75 | 1.75 | 1 | 0 | 0 |
| RS | 1.02 | 0.88 | 0.77 | 0.38 | 0.55 | 0.16 | 0.64 | 0.25 | 1.25 | 1 | 0 | 1 |
| RY | 1.02 | 1.12 | 1.14 | 0.68 | 0.88 | 0.61 | 0.47 | 0.65 | 1.25 | 0.6 | 0 | 0 |
| LY | 1.01 | 0.88 | 0.75 | 0.69 | 0.76 | 0.61 | 0.28 | 0.65 | 1.25 | 0.6 | 0 | 0 |
| DY | 0.93 | 0.84 | 0.77 | 0.72 | 0.95 | 0.61 | 0.69 | 0.7 | 1.3 | 0.6 | 0 | 0 |
| GC | 0.90 | 0.62 | 0.48 | 0.86 | 0.68 | 0.15 | 0.75 | 0.5 | 1 | 0.5 | 0 | 1 |

The pairs in bold comprise about 18% to about 23% of occurrences (among the possible 400 pairs) for the Preimmune (Lee, et al., 2006), Humabs (Jackson, et al., 2007) and matured (Jackson minus Lee) sets. They account for 26% to 29% of the occurrences in the LUA libraris, but only about 12% in the HuCAL library and about 8% for the "XYZ" library. Because of the nature of the construction of the central loops in the HuCAL and XYZ libraries, these numbers are the same for the IP1, IP2, and IP3 pairs.
The last 2 columns indicate whether the corresponding pair-wise compositions fall within the LUA– and LUA+ boundaries: 0 if outside, 1 if within.

The analysis provided in this example demonstrates that the composition of the libraries of the present invention more closely mimics the composition of human sequences than other libraries known in the art. Synthetic libraries of the art do not intrinsically reproduce the composition of the "central loop" portion actual human CDRH3 sequences at the level of pair percentages. The libraries of the invention have a more complex pair-wise composition that closely reproduces that observed in actual human CDRH3 sequences. The exact degree of this reproduction versus a target set of actual human CDRH3 sequences may be optimized, for example, by varying the compositions of the segments used to design the CDRH3 libraries. Moreover, it is also possible to utilize these metrics to computationally design libraries that exactly mimic the pair-wise compositional prevalence found in human sequences.

Example 14

Information Content of Exemplary Libraries

One way to quantify the observation that certain libraries, or collection of sequences, may be intrinsically more complex or "less random" than others is to apply information theory (Shannon, Bell Sys. Tech. J., 1984, 27: 379; Martin et al., Bioinformatics, 2005, 21: 4116; Weiss et al., J. Theor. Biol., 2000, 206: 379, each incorporated by reference in its entirety). For example, a metric can be devised to quantify the fact that a position with a fixed amino acid represents less "randomness" than a position where all 20 amino acids may occur with equal probability. Intermediate situations should lead, in turn, to intermediate values of such a metric. According to information theory this metric can be represented by the formula:

$$I = \sum_{i=1}^{N} f_i \log_2 f_i$$

Here, $f_i$ is the normalized frequency of occurrence of i, which may be an amino acid type (in which case N would be equal to 20). When all $f_i$ are zero except for one, the value of I is zero. In any other case the value of I would be smaller, i.e., negative, and the lowest value is achieved when all $f_i$ values are the same and equal to N. For the amino acid case, N is 20, and the resulting value of I would be –4.322. Because I is defined with base 2 logarithms, the units of I are bits.

The I value for the HuCAL and XYZ libraries at the single position level may be derived from Tables 45 and 46, respectively, and are equal to –4.08 and –4.06. The corresponding single residue frequency occurrences in the non-limiting exemplary libraries of the invention and the sets of human sequences previously introduced, taken within the "central loop" as defined above, are provided in Table 50.

TABLE 50

Amino Acid Type Frequencies in Central Loop

| Type | Preimmune | Humabs | Matured | LUA-59 | LUA-141 |
|---|---|---|---|---|---|
| A | 5.46 | 5.51 | 5.39 | 5.71 | 6.06 |
| C | 1.88 | 1.46 | 1.22 | 1.33 | 1.34 |
| D | 7.70 | 7.51 | 7.38 | 4.76 | 5.23 |
| E | 2.40 | 2.90 | 3.28 | 3.99 | 4.68 |
| F | 2.29 | 2.60 | 2.81 | 1.76 | 2.17 |
| G | 14.86 | 15.42 | 15.82 | 24.90 | 18.85 |
| H | 1.46 | 1.79 | 2.01 | 0.20 | 0.67 |
| I | 3.71 | 3.26 | 2.99 | 3.99 | 4.34 |
| K | 1.06 | 1.27 | 1.44 | 0.21 | 0.67 |
| L | 4.48 | 4.84 | 5.16 | 4.12 | 4.54 |
| M | 1.18 | 1.03 | 0.93 | 0.94 | 1.03 |
| N | 1.81 | 2.43 | 2.84 | 0.41 | 0.65 |
| P | 4.12 | 4.10 | 4.13 | 5.68 | 3.96 |
| Q | 1.60 | 1.77 | 1.95 | 0.21 | 0.68 |
| R | 5.05 | 5.90 | 6.41 | 3.35 | 4.11 |
| S | 12.61 | 11.83 | 11.37 | 11.18 | 12.77 |
| T | 4.59 | 5.11 | 5.47 | 4.36 | 4.95 |
| V | 6.21 | 5.55 | 5.12 | 8.13 | 7.67 |
| W | 2.79 | 2.91 | 3.07 | 1.57 | 1.98 |
| Y | 14.74 | 12.81 | 11.24 | 13.20 | 13.63 |

The information content of these sets, computed by the formula given above, would then be –3.88, –3.93, –3.96, –3.56, and –3.75, for the preimmune, human, matured, LUA-59 and LUA-141 sets, respectively. As the frequencies deviate more from completely uniform (5% for each of the 20), then numbers tend to be larger, or less negative.

The identical approach can be used to analyze pair compositions, or frequencies, by calculating the sum in the formula above over the 20×20 or 400 values of the frequencies for each of the pairs. It can be shown that any pair frequency made up of the simple product of two singleton frequency sets is equal to the sum of the individual singleton I values. If the two singleton frequency sets are the same or approximately so, this means that I (independent pairs)=2*I (singles). It is thus possible to define a special case of the mutual information, MI, for a general set of pair frequencies as MI (pair)=I(pair)–2*I (singles) to measure the amount of information gained by the structure of the pair frequencies themselves (compare to the standard definitions in Martin et al., 2005, for example, after considering that I (X)=−H(X) in their notation). When there is no such structure, the value of MI is simply zero.

Values of MI computed from the pair distributions discussed above (over the entire set of 400 values) are given in Table 51.

TABLE 51

Mutual Information Within Central Loop of CDRH3

| Library or Set | i - i + 1 | i - i + 2 | i - i + 3 |
|---|---|---|---|
| Preimmune | 0.226 | 0.192 | 0.163 |
| Humabs | 0.153 | 0.128 | 0.111 |
| Matured | 0.124 | 0.107 | 0.100 |
| LUA-59 | 0.422 | 0.327 | 0.278 |
| LUA-141 | 0.376 | 0.305 | 0.277 |
| HuCAL | 0.000 | 0.000 | 0.000 |
| XYZ | 0.000 | 0.000 | 0.000 |

It is notable that the MI values decrease within sets of human sequences as those sequences undergo further somatic mutation, a process that over many independent sequences is essentially random. It is also worth noting that the MI values decrease as the pairs being considered sit further and further apart, and this is the case for both sets of human sequences, and exemplary libraries of the invention. In both cases, as the two amino acids in a pair become further separated the odds of their straddling an actual segment (V, D, J plus V-D or D-J insertions) increase, and their pair frequencies become closer to a simple product of singleton frequencies.

Table 52 contains sequence information on certain immunoglobulin gene segments cited in the application. These sequences are non-limiting, and it is recognized that allelic variants exist and encompassed by the present invention. Accordingly, the methods present herein can be utilized with mutants of these sequences.

TABLE 52

Sequence Information for Certain Immunoglobulin Gene Segments Cited Herein

| SEQ ID NO: | Sequence | Peptide or Nucleotide Sequence | Observations |
|---|---|---|---|
| 423 | IGHV1-3 | QVQLVQSGAEVKKPGASVKVSCKASGYTFTSYAMHWVRQ APGQRLEWMGWINAGNGNTKYSQKFQGRVTITRDTSAST AYMELSSLRSEDTAVYYCAR | |
| 424 | IGHV1-8_v1 | QVQLVQSGAEVKKPGASVKVSCKASGYTFTSYDINWVRQ ATGQGLEWMGWMNPNSGNTGYAQKFQGRVTMTRNTSIS TAYMELSSLRSEDTAVYYCAR | |
| 425 | IGHV1-8_v2 | QVQLVQSGAEVKKPGASVKVSCKASGYTFTSYDINWVRQ ATGQGLEWMGWMNPNSGNTGYAQKFQGRVTMTRDTSIS TAYMELSSLRSEDTAVYYCAR | N to D mutation avoids NTS potential glycosylation site in the original germline sequence (v1 above). XTS, where X is not N, and NTZ, where Z is not S or T are also options. NPS is yet another option that is much less likely to be N-linked glycosylated. |
| 426 | IGHV1-24 | QVQLVQSGAEVKKPGASVKVSCKVSGYTLTELSMHWVRQ APGKGLEWMGGFDPEDGETIYAQKFQGRVTMTEDTSTDT AYMELSSLRSEDTAVYYCAT | |
| 427 | IGHV1-45 | QMQLVQSGAEVKKTGSSVKVSCKASGYTFTYRYLHWVRQ APGQALEWMGWITPFNGNTNYAQKFQDRVTITRDRSMST AYMELSSLRSEDTAMYYCAR | |
| 428 | IGHV1-58 | QMQLVQSGPEVKKPGTSVKVSCKASGFTFTSSAVQWVRQ ARGQRLEWIGWIVVGSGNTNYAQKFQERVTITRDMSTSTA YMELSSLRSEDTAVYYCAA | |
| 429 | IGHV2-5 | QITLKESGPTLVKPTQTLTLTCTFSGFSLSTSGVGVGWIRQ PPGKALEWLALIYWDDDKRYSPSLKSRLTITKDTSKNQVVL TMTNMDPVDTATYYCAHR | |
| 430 | IGHV2-26 | QVTLKESGPVLVKPTETLTLTCTVSGFSLSNARMGVSWIRQ PPGKALEWLAHIFSNDEKSYSTSLKSRLTISKDTSKSQVVLT MTNMDPVDTATYYCARI | |
| 431 | IGHV2-70_v1 | RVTLRESGPALVKPTQTLTLTCTFSGFSLSTSGMCVSWIRQ PPGKALEWLARIDWDDDKYYSTSLKTRLTISKDTSKNQVVL TMTNMDPVDTATYYCARI | |
| 432 | IGHV2-70_v2 | RVTLRESGPALVKPTQTLTLTCTFSGFSLSTSGMGVSWIRQ PPGKALEWLARIDWDDDKYYSTSLKTRLTISKDTSKNQVVL TMTNMDPVDTATYYCARI | C to G mutation avoids unpaired Cys in v1 above. G was chosen by analogy to other germline sequences, but other amino acid types, R, S, T, as non-limiting examples, are possible. |

TABLE 52-continued

Sequence Information for Certain
Immunoglobulin Gene Segments Cited Herein

| SEQ ID NO: | Sequence | Peptide or Nucleotide Sequence | Observations |
|---|---|---|---|
| 433 | IGHV3-9 | EVQLVESGGGLVQPGRSLRLSCAASGFTFDDYAMHWVRQ APGKGLEWVSGISWNSGSIGYADSVKGRFTISRDNAKNSL YLQMNSLRAEDTALYYCAKD | |
| 434 | IGHV3-11 | QVQLVESGGGLVKPGGSLRLSCAASGFTFSDYYMSWIRQ APGKGLEWVSYISSSGSTIYYADSVKGRFTISRDNAKNSLY LQMNSLRAEDTAVYYCAR | |
| 435 | IGHV3-13 | EVQLVESGGGLVQPGGSLRLSCAASGFTFSSYDMHWVRQ ATGKGLEWVSAIGTAGDTYYPGSVKGRFTISRENAKNSLYL QMNSLRAGDTAVYYCAR | |
| 436 | IGHV3-20 | EVQLVESGGGVVRPGGSLRLSCAASGFTFDDYGMSWVR QAPGKGLEWVSGINWNGGSTGYADSVKGRFTISRDNAKN SLYLQMNSLRAEDTALYHCAR | |
| 437 | IGHV3-21 | EVQLVESGGGLVKPGGSLRLSCAASGFTFSSYSMNWVRQ APGKGLEWVSSISSSSYIYYADSVKGRFTISRDNAKNSLY LQMNSLRAEDTAVYYCAR | |
| 438 | IGHV3-43 | EVQLVESGGWVQPGGSLRLSCAASGFTFDDYTMHWVRQ APGKGLEWVSLISWDGGSTYYADSVKGRFTISRDNSKNSL YLQMNSLRTEDTALYYCAKD | |
| 439 | IGHV3-49 | EVQLVESGGGLVQPGRSLRLSCTASGFTFGDYAMSWVRQ APGKGLEWVGFIRSKAYGGTTEYAASVKGRFTISRDDSKSI AYLQMNSLKTEDTAVYYCTR | |
| 440 | IGHV3-53 | EVQLVESGGGLIQPGGSLRLSCAASGFTVSSNYMSWVRQ APGKGLEWVSVIYSGGSTYYADSVKGRFTISRDNSKNTLYL QMNSLRAEDTAVYYCAR | |
| 441 | IGHV3-64 | EVQLVESGGGLVQPGGSLRLSCSASGFTFSSYAMHWVRQ APGKGLEYVSAISSNGGSTYYADSVKGRFTISRDNSKNTLY LQMSSLRAEDTAVYYCVK | |
| 442 | IGHV3-66 | EVQLVESGGGLVQPGGSLRLSCAASGFTVSSNYMSVVRQ APGKGLEWVSVIYSGGSTYYADSVKGRFTISRDNSKNTLYL QMNSLRAEDTAVYYCAR | |
| 443 | IGHV3-72 | EVQLVESGGGLVQPGGSLRLSCAASGFTFSDHYMDWVRQ APGKGLEWVGRTRNKANSYTTEYAASVKGRFTISRDDSKN SLYLQMNSLKTEDTAVYYCAR | |
| 444 | IGHV3-73 | EVQLVESGGGLVQPGGSLKLSCAASGFTFSGSAMHWVRQ ASGKGLEWVGRIRSKANSYATAYAASVKGRFTISRDDSKN TAYLQMNSLKTEDTAVYYCTR | |
| 445 | IGHV3-74 | EVQLVESGGGLVQPGGSLRLSCAASGFTFSSYWMHWVR QAPGKGLVWVSRINSDGSSTSYADSVKGRFTISRDNAKNT LYLQMNSLRAEDTAVYYCAR | |
| 446 | IGHV4-4v1 | QVQLQESGPGLVKPSGTLSLTCAVSGGSISSSNWWSVVR QPPGKGLEWIGEIYHSGSTNYNPSLKSRVTISVDKSKNQFS LKLSSVTAADTAVYYCAR | Contains CDRH1 with size 6 (Kabat definition); canonical structure H1-2. Sequence corresponds to allele *02 of IGHV4-4. |
| 447 | IGHV4-4v2 | QVQLQESGPGLVKPSETLSLTCTVSGGSISSYYWSWIRQP AGKGLEWIGRIYTSGSTNYNPSLKSRVTMSVDTSKNQFSL KLSSVTAADTAVYYCAR | Contains CDRH1 with size 5 (Kabat definition); canonical structure H1-1. Sequence corresponds to allele *07 of IGHV4-4 |
| 448 | IGHV4-28 | QVQLQESGPGLVKPSDTLSLTCAVSGYSISSSNWWGWIR QPPGKGLEWIGYIYYSGSTYYNPSLKSRVTMSVDTSKNQF SLKLSSVTAVDTAVYYCAR | |
| 449 | IGHV6-1 | QVQLQQSGPGLVKPSQTLSLTCAISGDSVSSNSAAWNWIR QSPSRGLEWLGRTYYRSKVVYNDYAVSVKSRITINPDTSKN QFSLQLNSVTPEDTAVYYCAR | |

TABLE 52-continued

Sequence Information for Certain
Immunoglobulin Gene Segments Cited Herein

| SEQ ID NO: | Sequence | Peptide or Nucleotide Sequence | Observations |
|---|---|---|---|
| 450 | IGHV7-4-1 | QVQLVQSGSELKKPGASVKVSCKASGYTFTSYAMNWVRQ APGQGLEWMGWINTNTGNPTYAQGFTGRFVFSLDTSVST AYLQISSLKAEDTAVYYCAR | |
| 451 | IGKV1-06 | AIQMTQSPSSLSASVGDRVTITCRASQGIRNDLGWYQQKP GKAPKLLIYAASSLQSGVPSRFSGSGSGTDFTLTISSLQPE DFATYYCLQDYNYP | |
| 452 | IGKV1-08_v1 | AIRMTQSPSSFSASTGDRVTITCRASQGISSYLAWYQQKP GKAPKLLIYAASTLQSGVPSRFSGSGSGTDFTLTISCLQSE DFATYYCQQYYSYP | |
| 453 | IGKV1-08_v2 | AIRMTQSPSSFSASTGDRVTITCRASQGISSYLAWYQQKP GKAPKLLIYAASTLQSGVPSRFSGSGSGTDFTLTISSLQSE DFATYYCQQYYSYP | C to S mutation avoids unpaired Cys. in v1 above. S was chosen by analogy to other germline sequences, but amino acid types, N, R, S, as non-limiting examples, are also possible |
| 454 | IGKV1-09 | DIQLTQSPSFLSASVGDRVTITCRASQGISSYLAVVYQQKPG KAPKLLIYAASTLQSGVPSRFSGSGSGTEFTLTISSLQPEDF ATYYCQQLNSYP | |
| 455 | IGKV1-13 | AIQLTQSPSSLSASVGDRVTITCRASQGISSALAWYQQKPG KAPKLLIYDASSLESGVPSRFSGSGSGTDFTLTISSLQPEDF ATYYCQQFNSYP | |
| 456 | IGKV1-16 | DIQMTQSPSSLSASVGDRVTITCRASQGISNYLAWFQQKP GKAPKSLIYAASSLQSGVPSRFSGSGSGTDFTLTISSLQPE DFATYYCQQYNSYP | |
| 457 | IGKV1-17 | DIQMTQSPSSLSASVGDRVTITCRASQGIRNDLGWYQQKP GKAPKRLIYAASSLQSGVPSRFSGSGSGTEFTLTISSLQPE DFATYYCLQHNSYP | |
| 458 | IGKV1-37_v1 | DIQLTQSPSSLSASVGDRVTITCRVSQGISSYLNVVYRQKPG KVPKLLIYSASNLQSGVPSRFSGSGSGTDFTLTISSLQPED VATYYGQRTYNAP | |
| 459 | IGKV1-37_v2 | DIQLTQSPSSLSASVGDRVTITCRVSQGISSYLNWYRQKPG KVPKLLIYSASNLQSGVPSRFSGSGSGTDFTLTISSLQPED VATYYCQRTYNAP | Restores conserved Cys, missing in v1 above, just prior to CDRL3. |
| 460 | IGKV1D-16 | DIQMTQSPSSLSASVGDRVTITCRASQGISSWLAWYQQKP EKAPKSLIYAASSLQSGVPSRFSGSGSGTDFTLTISSLQPE DFATYYCQQYNSYP | |
| 461 | IGKV1D-17 | NIQMTQSPSAMSASVGDRVTITCRARQGISNYLAWFQQKP GKVPKHLIYAASSLQSGVPSRFSGSGSGTEFTLTISSLQPE DFATYYCLQHNSYP | |
| 462 | IGKV1D-43 | AIRMTQSPFSLSASVGDRVTITCWASQGISSYLAWYQQKP AKAPKLFIYYASSLQSGVPSRFSGSGSGTDYTLTISSLQPE DFATYYCQQYYSTP | |
| 463 | IGKV1D-8_v1 | VIWMTQSPSLLSASTGDRVTISCRMSQGISSYLAWYQQKP GKAPELLIYAASTLQSGVPSRFSGSGSGTDFTLTISCLQSE DFATYYCQQYYSFP | |
| 464 | IGKV1D-8_v2 | VIWMTQSPSLLSASTGDRVTISCRMSQGISSYLAWYQQKP GKAPELLIYAASTLQSGVPSRFSGSGSGTDFTLTISSLQSE DFATYYCQQYYSFP | C to S mutation avoids unpaired Cys. in v1 above. S was chosen by analogy to other germline sequences, but amino acid types, N, R, S, as non-limiting examples, are also possible |
| 465 | IGKV2-24 | DIVMTQTPLSSPVTLGQPASISCRSSQSLVHSDGNTYLSWL QQRPGQPPRLLIYKISNRFSGVPDRFSGSGAGTDFTLKISR VEAEDVGVYYCMQATQFP | |
| 466 | IGKV2-29 | DIVMTQTFLSLSVTRQQPASISCKSSQSLLHSDGVTYLYWY LQRPQQSPQLLTYEVSSRFSGVPDRFSGSGSGTDFTLKIS RVEAEDVGVYYCMQGTHLP | |

TABLE 52-continued

Sequence Information for Certain
Immunoglobulin Gene Segments Cited Herein

| SEQ ID NO: | Sequence | Peptide or Nucleotide Sequence | Observations |
|---|---|---|---|
| 467 | IGKV2-30 | DVVMTQSPLSLPVTLGQPASISCRSSQSLVYSDGNTYLNW FQQRPGQSPRRLIYKVSNRDSGVPDRFSGSGSGTDFTLKI SRVEAEDVGVYYCMQGTHWP | |
| 468 | IGKV2-40 | DIVMTQTPLSLPVTPGEPASISCRSSQSLLDSDDGNTYLDW YLQKPGQSPQLLIYTLSYRASGVPDRFSGSGSGTDFTLKIS RVEAEDVGVYYCMQRIEFP | |
| 469 | IGKV2D-26 | EIVMTQTPLSLSITPGEQASMSCRSSQSLLHSDGYTYLYWF LQKARPVSTLLIYEVSNRFSGVPDRFSGSGSGTDFTLKISR VEAEDFGVYYCMQDAQD | |
| 470 | IGKV2D-29 | DIVMTQTPLSLSVTPGQPASISCKSSQSLLHSDGKTYLYWY LQKPGQPPQLLIYEVSNRFSGVPDRFSGSGSGTDFTLKISR VEAEDVGVYYCMQSIQLP | |
| 471 | IGKV2D-30 | DVVMTQSPLSLPVTLGQPASISCRSSQSLVYSDGNTYLNW FQQRPGQSPRRLIYKVSNWDSGVPDRFSGSGSGTDFTLKI SRVEAEDVGVYYCMQGTHWP | |
| 472 | IGKV3D-07 | EIVMTQSPATLSLSPGERATLSCRASQSVSSSYLSWYQQK PGQAPRLLIYGASTRATGIPARFSGSGSGTDFTLTISSLQPE DFAVYYCQQDYNLP | |
| 473 | IGKV3D-11 | EIVLTQSPATLSLSPGERATLSCRASQGVSSYLAVVYQQKP GQAPRLLIYDASNRATGIPARFSGSGPGTDFTLTISSLEPED FAVYYCQQRSNWH | |
| 474 | IGKV3D-20 | EIVLTQSPATLSLSPGERATLSCGASQSVSSSYLAWYQQK PGLAPRLLIYDASSRATGIPDRFSGSGSGTDFTLTISRLEPE DFAVYYCQQYGSSP | |
| 475 | IGKV5-2_v1 | ETTLTQSPAFMSATPGDKVNISCKASQDIDDDMNWYQQKP GEAAIFIIQEATTLVPGIPPRFSGSGYGTDFTLTINNIESEDA AYYFCLQHDNFP | |
| 476 | IGKV5-2_v2 | ETTLTQSPAFMSATPGDKVTISCKASQDIDDDMNWYQQKP GEAAIFIIQEATTLVPGIPPRFSGSGYGTDFTLTINNIESEDA AYYFCLQHDNFP | N to D mutation avoids NIS potential glycosylation site in v1 above. XIS, where X is not N, and NIZ, where Z is not S or T are also options. NPS is yet another option that is much less likely to be N-linked glycosylated. |
| 477 | IGKV6-21 | EIVLTQSPDFQSVTPKEKVTITCRASQSIGSSLHWYQQKPD QSPKLLIKYASQSFSGVPSRFSGSGSGTDFTLTINSLEAED AATYYCHQSSSLP | |
| 478 | IGKV6D-21 | EIVLTQSPDFQSVTPKEKVTITCRASQSIGSSLHWYQQKPD QSPKLLIKYASQSFSGVPSRFSGSGSGTDFTLTINSLEAED AATYYCHQSSSLP | |
| 479 | IGKV7-3 | DIVLTQSPASLAVSPGQRATITCRASESVSFLGINLIHWYQQ KPGQPPKLLIYQASNKDTGVPARFSGSGSGTDFTLTINPVE ANDTANYYCLQSKNFP | |
| 480 | IGλV1-36 | QSVLTQPPSVSEAPRQRVTISCSGSSSNIGNNAVNWYQQL PGKAPKLLIYYDDLLPSGVSDRFSGSKSGTSASLAISGLQS EDEADYYCAAWDDSLNG | |
| 481 | IGλV1-47 | QSVLTQPPSASGTPGQRVTISCSGSSSNIGSNYVYWYQQL PGTAPKLLIYRNNQRPSGVPDRFSGSKSGTSASLAISGLRS EDEADYYCAAWDDSLSG | |
| 482 | IGλV10-54 | QAGLTQPPSVSKGLRQTATLTCTGNSNNVGNQGAAWLQQ HQGHPPKLLSYRNNNRPSGISERLSASRSGNTASLTITGLQ PEDEADYYCSAWDSSLSA | |
| 483 | IGλV2-11_v1 | QSALTQPRSVSGSPGQSVTISCTGTSSDVGGYNYVSWYQ QHPGKAPKLMIYDVSKRPSGVPDRFSGSKSGNTASLTISGL QAEDEADYYCCSYAGSYTF | |

TABLE 52-continued

Sequence Information for Certain Immunoglobulin Gene Segments Cited Herein

| SEQ ID NO: | Sequence | Peptide or Nucleotide Sequence | Observations |
|---|---|---|---|
| 484 | IGλV2-11_v2 | QSALTQPRSVSGSPGQSVTISCTGTSSDVGGYNYVSWYQ QHPGKAPKLMIYDVSKRPSGVPDRFSGSKSGNTASLTISGL QAEDEADYYCSSYAGSYTF | C to S mutation avoids unpaired Cys in v1 above. S was chosen by analogy to other germline sequences, but other amino acid types, such as Q, G, A, L, as non-limiting examples, are also possible |
| 485 | IGλV2-18 | QSALTQPPSVSGSPGQSVTISCTGTSSDVGSYNRVSWYQ QPPGTAPKLMIYEVSNRPSGVPDRFSGSKSGNTASLTISGL QAEDEADYYCSLYTSSSTF | |
| 486 | IGλV2-23_v1 | QSALTQPASVSGSPGQSITISCTGTSSDVGSYNLVSWYQQ HPGKAPKLMIYEGSKRPSGVSNRFSGSKSGNTASLTISGL QAEDEADYYCCSYAGSSTL | |
| 487 | IGλV2-23_v2 | QSALTQPASVSGSPGQSITISCTGTSSDVGSYNLVSWYQQ HPGKAPKLMIYEGSKRPSGVSNRFSGSKSGNTASLTISGL QAEDEADYYCSSYAGSSTL | C to S mutation avoids unpaired Cys in v1 above. S was chosen by analogy to other germline sequences, but other amino acid types, such as Q, G, A, L, as non-limiting examples, are also possible |
| 488 | IGλV2-8 | QSALTQPPSASGSPGQSVTISCTGTSSDVGGYNYVSWYQ QHPGKAPKLMIYEVSKRPSGVPDRFSGSKSGNTASLTVSG LQAEDEADYYCSSYAGSNNF | |
| 489 | IGλV3-10 | SYELTQPPSVSVSPGQTARITCSGDALPKKYAYWYQQKSG QAPVLVIYEDSKRPSGIPERFSGSSSGTMATLTISGAQVED EADYYCYSTDSSGNH | |
| 490 | IGλV3-12 | SYELTQPHSVSVATAQMARITCGGNNIGSKAVHWYQQKP GQDPVLVIYSDSNRPSGIPERFSGSNPGNTTTLTISRIEAGD EADYYCQVWDSSSDH | |
| 491 | IGλV3-16 | SYELTQPPSVSVSLGQMARITCSGEALPKKYAYWYQQKPG QFPVLVIYKDSERPSGIPERFSGSSSGTIVTLTISGVQAEDE ADYYCLSADSSGTY | |
| 492 | IGλV3-25 | SYELMQPPSVSVSPGQTARITCSGDALPKQYAYWYQQKP GQAPVLVIYKDSERPSGIPERFSGSSSGTTVTLTISGVQAE DEADYYCQSADSSGTY | |
| 493 | IGλV3-27 | SYELTQPSSVSVSPGQTARITCSGDVLAKKYARWFQQKPG QAPVLVIYKDSERPSGIPERFSGSSSGTTVTLTISGAQVEDE ADYYCYSAADNN | |
| 494 | IGλV3-9 | SYELTQPLSVSVALGQTARITCGGNNIGSKNVHWYQQKPG QAPVLVIYRDSNRPSGIPERFSGSNSGNTATLTISRAQAGD EADYYCQVWDSSTA | |
| 495 | IGλV4-3 | LPVLTQPPSASALLGASIKLTCTLSSEHSTYTIEWYQQRPG RSPQYIMKVKSDGSHSKGDGIPDRFMGSSSGADRYLTFSN LQSDDEAEYHCGESHTIDGQVG | |
| 496 | IGλV4-60 | QPVLTQSSSASASLGSSVKLTCTLSSGHSSYIIAWHQQQP GKAPRYLMKLEGSGSYNKGSGVPDRFSGSSSGADRYLTIS NLQLEDEADYYCETWDSNT | |
| 497 | IGλV5-39 | QPVLTQPTSLSASPGASARFTCTLRSGINVGTYRIYWYQQK PGSLPRYLLRYKSDSDKQQGSGVPSRFSGSKDASTNAGLL LISGLQSEDEADYYCAIWYSSTS | |
| 498 | IGλV7-46 | QAVVTQEPSLTVSPGGTVTLTCGSSTGAVTSGHYPYWFQ QKPGQAPRTLIYDTSNKHSWTPARFSGSLLGGKAALTLSG AQPEDEAEYYCLLSYSGAR | |

TABLE 52-continued

Sequence Information for Certain
Immunoglobulin Gene Segments Cited Herein

| SEQ ID NO: | Sequence | Peptide or Nucleotide Sequence | Observations |
| --- | --- | --- | --- |
| 499 | IGλV8-61 | QTVVTQEPSFSVSPGGTVTLTCGLSSGSVSTSYYPSWYQ QTPGQAPRTLIYSTNTRSSGVPDRFSGSILGNKAALTITGA QADDESDYYCVLYMGSGI | |
| 500 | IGλV9-49 | QPVLTQPPSASASLGASVTLTCTLSSGYSNYKVDWYQQRP GKGPRFVMRVGTGGIVGSKGDGIPDRFSVLGSGLNRYLTI KNIQEEDESDYHCGADHGSGSNFV | |
| 501 | IGHD1-1 | GGTACAACTGGAACGAC | See (1) below. |
| 502 | IGHD1-14 | GGTATAACCGGAACCAC | |
| 503 | IGHD1-20 | GGTATAACTGGAACGAC | |
| 504 | IGHD1-7 | GGTATAACTGGAACTAC | |
| 505 | IGHD2-21_v1 | AGCATATTGTGGTGGTGATTGCTATTCC | |
| 506 | IGHD2-21_v2 | AGCATATTGTGGTGGTGACTGCTATTCC | Common allelic variant encoding a different amino acid sequence, compared to v1, in 2 of 3 forward reading frames. |
| 507 | IGHD2-8 | AGGATATTGTACTAATGGTGTATGCTATACC | |
| 508 | IGHD3-16 | GTATTATGATTACGTTTGGGGGAGTTATGCTTATACC | |
| 509 | IGHD3-9 | GTATTACGATATTTTGACTGGTTATTATAAC | |
| 510 | IGHD4-23 | TGACTACGGTGGTAACTCC | |
| 511 | IGHD4-4/4-11 | TGACTACAGTAACTAC | |
| 512 | IGHD5-12 | GTGGATATAGTGGCTACGATTAC | |
| 513 | IGHD5-24 | GTAGAGATGGCTACAATTAC | |
| 514 | IGHD6-25 | GGGTATAGCAGCGGCTAC | |
| 515 | IGHD6-6 | GAGTATAGCAGCTCGTCC | |
| 516 | IGHD7-27 | CTAACTGGGGA | |

(1) Each of the IGHD nucleotide sequences can be read in three (3) forward reading frames, and, possibly, in 3 reverse reading frames. For example, the nucleotide sequence given for IGHD1-1, depending on how it inserts in full V-DJ rearrangement, may encode the full peptide sequences: GTTGT (SEQ ID NO: 517), VQLER (SEQ ID NO: 518) and YNWND (SEQ ID NO: 519) in the forward direction, and VVPVV (SEQ ID NO: 520), SFQLY (SEQ ID NO: 521) and RSSCT (SEQ ID NO: 522) in the reverse direction. Each of these sequences, in turn, could generate progressively deleted segments as explained in the Examples to produce suitable components for libraries of the invention.

Example 15

Selection of Antibodies from the Library

Figure 24:
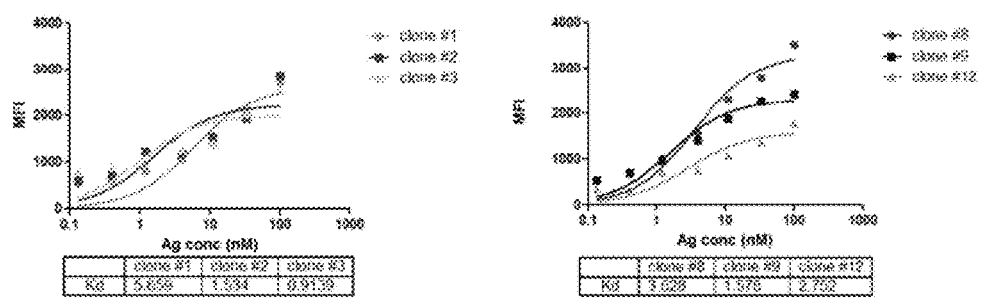
FIG. 24 depicts binding curves for 6 antibodies selected from a library of the invention.

In this example, the selection of antibodies from a library of the invention (described in Examples 9-11 and other Examples) is demonstrated. These selections demonstrate that the libraries of the invention encode antibody proteins capable of binding to antigens. In one selection, antibodies specific for "Antigen X", a protein antigen, were isolated from the library using the methods described herein. FIG. 24 shows binding curves for six clones specifically binding Antigen X, and their Kd values. This selection was performed using yeast with the heavy chain on a plasmid vector and the kappa light chain library integrated into the genome of the yeast.

Figure 25:
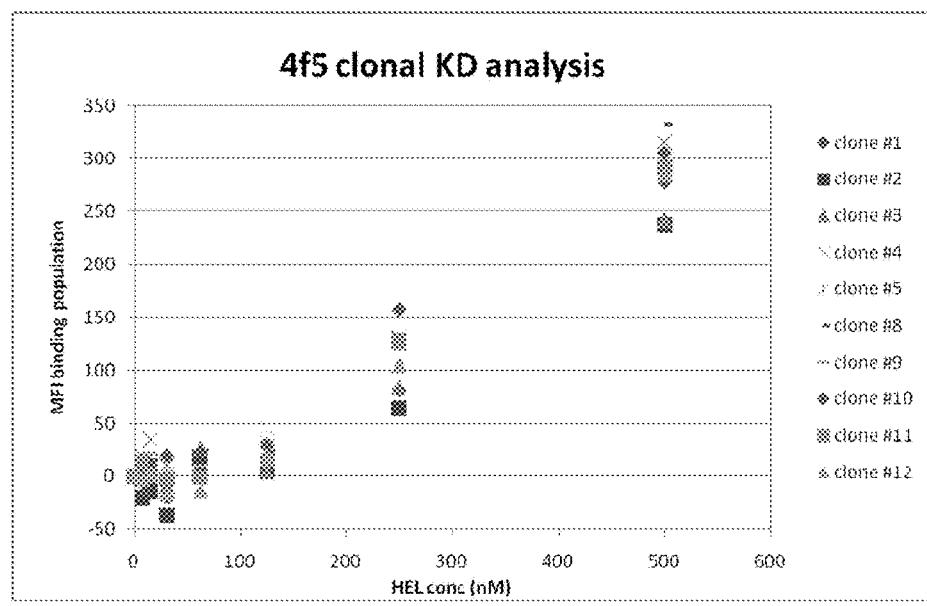
FIG. 25 depicts binding curves for 10 antibodies selected from a library of the invention binding to hen egg white lysozyme.

In a separate selection, antibodies specific for a model antigen, hen egg white lysozyme (HEL) were isolated. FIG. 25 shows the binding curves for 10 clones specifically binding HEL; each gave a Kd>500 nM. This selection was performed using yeast with the heavy chain on a plasmid vector and the kappa light chain library on a plasmid vector. The sequences of the heavy and light chains were determined for clones isolated from the library and it was demonstrated that multiple clones were present. A portion of the FRM3s (underlined) and the entire CDRH3s from four clones are shown below (Table 53 and Table 54, the latter using the numbering system of the invention).

TABLE 53

Sequences of CDRH3, and a Portion of FRM3, from Four HEL Binders

| Seq Name | SEQ ID NO: | FRM3 and CDRH3 | Tail | N1 | DH | N2 | H3-JH |
|---|---|---|---|---|---|---|---|
| CR080362 | 523 | AKGPSVPAARAEYFQH | G | PS | VPA | AR | AEYFQH |
| CR080363 | 524 | AREGGLGYYYREWYFDL | E | GGL | GYYY | RE | WYFDL |
| CR080372 | 525 | AKPDYGAEYFQH | — | P | DYG | — | AEYFQH |
| EK080902 | 526 | AKEIVVPSAEYFQH | E | — | IVV | PS | AEYFQH |

TABLE 54

Sequences of CDRH3 from Four HEL Binders in Numbering System of the Invention, According to the Numbering System of the Invention

| | [Tail] | [N1] | | | | [DH] | | | | [N2] | |
|---|---|---|---|---|---|---|---|---|---|---|---|
| Clones | 95 | 96 | 96A | 96B | 97 | 97A | 97B | 97C | 97D | 98 | 98A | 98B |
| CR080362 | G | P | S | — | V | P | A | — | — | A | R | — |
| CR080363 | E | G | G | L | G | Y | Y | Y | — | R | E | — |
| CR080372 | — | P | — | — | D | Y | G | — | — | — | — | — |
| EK080902 | E | — | — | — | I | V | V | — | — | P | S | — |

| | [H3-JH] | | | | | | | | CDRH3 |
|---|---|---|---|---|---|---|---|---|---|
| Clones | 99E | 99D | 99C | 99B | 99A | 99 | 100 | 101 | 102 | Length |
| CR080362 | — | — | — | A | E | Y | F | Q | H | 14 |
| CR080363 | — | — | — | — | W | Y | F | D | L | 15 |
| CR080372 | — | — | — | A | E | Y | F | Q | H | 10 |
| EK080902 | — | — | — | A | E | Y | F | Q | H | 12 |

Sequence Identifiers:
CR080362 (SEQ ID NO: 523);
CR080363 (SEQ ID NO: 524);
CR080372 (SEQ ID NO: 525);
EK080902 (SEQ ID NO: 526)

The heavy chain chassis isolated were VH3-23.0 (for EK080902 and CR080363), VH3-23.6 (for CR080362), and VH3-23.4 (for CR080372). These variants are defined in Table 8 of Example 2. Each of the four heavy chain CDRH3 sequences matched a designed sequence from the exemplified library. The CDRL3 sequence of one of the clones (ED080902) was also determined, and is shown below, with the surrounding FRM regions underlined:

CDRL3:
(SEQ ID NO: 527)
YYCQESFHIPYTFGGG.

In this case, the CDRL3 matched the design of a degenerate VK1-39 oligonucleotide sequence in row 49 of Table 33. The relevant portion of this table is reproduced below, with the amino acids occupying each position of the isolated CDRL3 bolded and underlined:

| Chassis | CDR Length | Junction type | Degenerate Oligonucleotide | SEQ ID | 89 | 90 | 91 | 92 | 93 | 94 | 95 | 96 | 97 |
|---|---|---|---|---|---|---|---|---|---|---|---|---|---|
| VK1-39 | 9 | 1 | CWGSAAWCATHC MVTABTCCTTWC ACT | 307 | LQ | EQ | ST | FSY | HNPRST | IST | P | FY | T |

EQUIVALENTS

Those skilled in the art will recognize, or be able to ascertain using no more than routine experimentation, many equivalents to the specific embodiments and methods described herein. Such equivalents are intended to be encompassed by the scope of the following claims.

What is claimed is:

1. An antibody isolated from a library comprising synthetic polynucleotides that encode an antibody heavy chain and an antibody light chain containing at least about $10^6$ unique antibody CDRH3 amino acid sequences, wherein each of the polynucleotides encoding the at least about $10^6$ unique antibody CDRH3 amino acid sequences has an antibody CDRH3 amino acid sequence represented by the following formula:

[X]-[N1]-[DH]-[N2]-[H3-JH], wherein (i) X is selected from the group consisting of G, D, E and nothing;

(ii) N1 is an amino acid sequence selected from the group consisting of G, P, R, A, S, L, T, V, GG, GP, GR, GA, GS, GL, GT, GV, PG, RG, AG, SG, LG, TG, VG, PP, PR, PA, PS, PL, PT, PV, RP, AP, SP, LP, TP, VP, IG, KG, GW, FP, EG, GGG, GPG, GRG, GAG, GSG, GLG, GTG, GVG, PGG, RGG, AGG, SGG, LGG, TGG, VGG, GGP, GGR, GGA, GGS, GGL, GGT, GGV, D, E, F, H, I, K, M, Q, W, Y, AR, AS, AT, AY, DL, DT, EA, EK, FH, FS, HL, HW, IS, KV, LD, LE, LR, LS, LT, NR, NT, QE, QL, QT, RA, RD, RE, RF, RH, RL, RR, RS, RV, SA, SD, SE, SF, SI, SK, SL, SQ, SR, SS, ST, SV, TA, TR, TS, TT, TW, VD, VS, WS, YS, AAE, AYH, DTL, EKR, ISR, NTP, PKS, PRP, PTA, PTQ, REL, RPL, SAA, SAL, SGL, SSE, TGL, WGT;

(iii) DH is all of a human CDRH3 DH amino acid sequence, wherein the DH amino acid sequence is selected from the group consisting of ATT, GAT, GIV, IVG, VGA, VLLLWLLL (SEQ ID NO: 239), ITMIVVVIT (SEQ ID NO: 240), VQWLV (SEQ ID NO: 241), VQQLV (SEQ ID NO: 242), VLRFLEWLLY (SEQ ID NO: 243), YYDFWSGYYT (SEQ ID NO: 244), WILYQLLC (SEQ ID NO: 245), LRL (SEQ ID NO: 246), TTVT (SEQ ID NO: 247), VWELL (SEQ ID NO: 248), VDTAMVT (SEQ ID NO: 249), WIQLWL (SEQ ID NO: 250), RILWWLLL (SEQ ID NO: 251), DIVVVVAAT (SEQ ID NO: 252), VLLLWFG (SEQ ID NO: 595), GATT (SEQ ID NO: 623), GIVG (SEQ ID NO: 624), IVGA (SEQ ID NO: 625), VGAT (SEQ ID NO: 626), GIVGA (SEQ ID NO: 627), IVGAT (SEQ ID NO: 628), VGATT (SEQ ID NO: 629), GIVGAT (SEQ ID NO: 630), IVGATT (SEQ ID NO: 631), GIVGATT (SEQ ID NO: 13), YSG, YSGS (SEQ ID NO: 632), YSGSY (SEQ ID NO: 633), YSGSYY (SEQ ID NO: 14), CSSTSC (SEQ ID NO: 622), CSSTSCY (SEQ ID NO: 620), YCSSTSC (SEQ ID NO: 621), CSSTSCYT (SEQ ID NO: 617), GYCSSTSC (SEQ ID NO: 618), YCSSTSCY (SEQ ID NO: 619), GYCSSTSCY (SEQ ID NO: 615), YCSSTSCYT (SEQ ID NO: 616), GYCSSTSCYT (SEQ ID NO:10), AAM, DIV, IVY, PAA, VPA, VVP, VVV, DIVV (SEQ ID NO: 634), IVVV (SEQ ID NO: 635), PAAM (SEQ ID NO: 636), VPAA (SEQ ID NO: 637), VVPA (SEQ ID NO: 638), VVVP (SEQ ID NO: 639), DIVVY (SEQ ID NO: 640), IVVVP (SEQ ID NO: 641), VPAAM (SEQ ID NO: 642), VVPAA (SEQ ID NO: 643), VVVPA (SEQ ID NO: 644), DIVVVP (SEQ ID NO: 645), IVVVPA (SEQ ID NO: 646), VVPAAM (SEQ ID NO: 647), VVVPAA (SEQ ID NO: 648), DIVVVPA (SEQ ID NO: 649), IVVVPAA (SEQ ID NO: 650), VVVPAAM (SEQ ID NO: 651), DIVVVPAA (SEQ ID NO: 652), IVVVPAAM (SEQ ID NO: 653), DIVVVPAAM (SEQ ID NO: 11), CSGGSC (SEQ ID NO: 654), CSGGSCY (SEQ ID NO: 655), YCSGGSC (SEQ ID NO: 656), CSGGSCYS (SEQ ID NO: 657), GYCSGGSC (SEQ ID NO: 658), YCSGGSCY (SEQ ID NO: 659), GYCSGGSCY (SEQ ID NO: 660), YCSGGSCYS (SEQ ID NO: 661), GYCSGGSCYS (SEQ ID NO: 16), FGV, GVV, IFG, ITI, TIF, VVI, FGVV (SEQ ID NO: 662), GVVI (SEQ ID NO: 663), IFGV (SEQ ID NO: 664), ITIF (SEQ ID NO: 665), TIFG (SEQ ID NO: 666), VVII (SEQ ID NO: 667), FGVVI (SEQ ID NO: 668), GVVII (SEQ ID NO: 669), IFGVV (SEQ ID NO: 670), ITIFG (SEQ ID NO: 671), TIFGV (SEQ ID NO: 672), FGVVII (SEQ ID NO: 673), IFGVVI (SEQ ID NO: 674), ITIFGV (SEQ ID NO: 675), TIFGVV(SEQ ID NO: 676), IFGVVII (SEQ ID NO: 677), ITIFGVV (SEQ ID NO: 678), TIFGVVI (SEQ ID NO: 679), ITIFGVVI (SEQ ID NO: 680), TIFGVVII(SEQ ID NO: 681), ITIFGVVII (SEQ ID NO: 9), ELL, FGE, GEL, LLW, LWF, VLL, WFG, FGEL (SEQ ID NO: 682), GELL (SEQ ID NO: 683), LLWF (SEQ ID NO: 684), LWFG (SEQ ID NO: 685), VLLW (SEQ ID NO: 686), WFGE (SEQ ID NO: 687), FGELL (SEQ ID NO: 688), LLWFG (SEQ ID NO: 689), LWFGE (SEQ ID NO: 690), VLLWF (SEQ ID NO: 691), WFGEL (SEQ ID NO: 692), LLWFGE (SEQ ID NO: 693), LWFGEL (SEQ ID NO: 694), VLLWFG (SEQ ID NO: 695), WFGELL (SEQ ID NO: 696), LLWFGEL (SEQ ID NO: 697), LWFGELL (SEQ ID NO: 698), VLLWFGE (SEQ ID NO: 699), LLWFGELL (SEQ ID NO: 700), VLLWFGEL (SEQ ID NO: 701), VLLWFGELL (SEQ ID NO: 1), GSG, GSY, SGS, SYY, YGS, YYG, YYN, YYY, GSGS (SEQ ID NO: 702), GSYY (SEQ ID NO: 703), SGSY (SEQ ID NO: 704), SYYN (SEQ ID NO: 705), YGSG (SEQ ID NO: 706), YYGS (SEQ ID NO: 707), YYYG (SEQ ID NO: 708), GSGSY (SEQ ID NO: 709), GSYYN (SEQ ID NO: 710), SGSYY (SEQ ID NO: 711), YGSGS (SEQ ID NO: 712), YYGSG (SEQ ID NO: 713), YYYGS (SEQ ID NO: 714), GSGSYY (SEQ ID NO: 715), SGSYYN (SEQ ID NO: 716), YGSGSY (SEQ ID NO: 717), YYGSGS (SEQ ID NO: 718), YYYGSG (SEQ ID NO: 719), GSGSYYN (SEQ ID NO: 720), YGSGSYY (SEQ ID NO: 721), YYGSGSY (SEQ ID NO: 722), YYYGSGS (SEQ ID NO: 723), YGSGSYYN (SEQ ID NO: 724), YYGSGSYY (SEQ ID NO: 725), YYYGSGSY (SEQ ID NO: 726), YYGSGSYYN (SEQ ID NO: 727), YYYGSGSYY (SEQ ID NO: 728), YYYGSGSYYN (SEQ ID NO: 2), GVI, ITM, MVR, RGV, TMV, VII, VRG, GVII (SEQ ID NO: 729), ITMV (SEQ ID NO: 730), MVRG (SEQ ID NO: 731), RGVI (SEQ ID NO: 732), TMVR (SEQ ID NO: 733), VRGV (SEQ ID NO: 734), ITMVR (SEQ ID NO: 735), MVRGV (SEQ ID NO: 736), RGVII (SEQ ID NO: 737), TMVRG (SEQ ID NO: 738), VRGVI (SEQ ID NO: 739), ITMVRG (SEQ ID NO: 740), MVRGVI (SEQ ID NO: 741), TMVRGV (SEQ ID NO: 742), VRGVII (SEQ ID NO: 743), ITMVRGV (SEQ ID NO: 744), MVRGVII (SEQ ID NO: 745), TMVRGVI (SEQ ID NO: 746), ITMVRGVI (SEQ ID NO: 747), TMVRGVII (SEQ ID NO: 748), ITMVRGVII (SEQ ID NO: 3), DSS, GYY, SGY, SSG, YDS, YYD, DSSG (SEQ ID NO: 749), GYYY (SEQ ID NO: 750), SGYY (SEQ ID NO: 751), SSGY (SEQ ID NO: 752), YDSS (SEQ ID NO: 753), YYDS (SEQ ID NO: 754), YYYD (SEQ ID NO: 755), DSSGY (SEQ ID NO: 756), SGYYY (SEQ ID NO: 757), SSGYY (SEQ ID NO: 758), YDSSG (SEQ ID NO: 759), YYDSS (SEQ ID NO: 760), YYYDS (SEQ ID NO: 761), DSSGYY (SEQ ID NO: 762), SSGYYY (SEQ ID NO: 763), YDSSGY (SEQ ID NO: 764), YYDSSG (SEQ ID NO: 765), YYYDSS (SEQ ID NO: 766), DSSGYYY (SEQ ID NO: 767), YDSSGYY (SEQ ID NO: 768), YYDSSGY (SEQ ID NO: 769), YYYDSSG (SEQ ID NO: 770), YDSSGYYY (SEQ ID NO: 771), YYDSSGYY (SEQ ID NO: 772), YYYDSSGY (SEQ ID NO: 773), YYDSSGYYY (SEQ ID NO: 774), YYYDSSGYY (SEQ ID NO: 775), YYYDSSGYYY (SEQ ID NO: 4), DYG, GDY, YGD, DYGD (SEQ ID NO: 613), YGDY (SEQ ID NO: 614), DYGDY (SEQ ID NO: 12), SYG, YGY, YSY, GYSY (SEQ ID NO: 776), SYGY (SEQ ID NO: 777), YSYG (SEQ ID NO: 778), GYSYG (SEQ ID NO: 779), YSYGY (SEQ ID NO: 780), GYSYGY (SEQ ID NO: 15), SSS, SSW, SWY, SSSW (SEQ ID NO: 781), SSWY (SEQ ID NO: 782), YSSS (SEQ ID NO: 783), GYSSS (SEQ ID NO: 784), SSSWY (SEQ ID NO: 785), YSSSW(SEQ ID NO: 786), GYSSSW (SEQ ID NO: 787), YSSSWY (SEQ ID NO: 788), GYSSSWY (SEQ ID NO: 7), GWY, GYS, SGW, YSS, GYSS (SEQ ID NO: 789), SGWY (SEQ ID NO: 790), SSGW (SEQ ID NO: 791), YSSG (SEQ ID NO: 792), GYSSG (SEQ ID NO: 793), SSGWY (SEQ ID NO: 794), YSSGW (SEQ ID NO: 795), GYSSGW (SEQ ID NO: 796), YSSGWY (SEQ ID NO: 797), GYSSGWY (SEQ ID NO: 5), AVA, GIA, IAV, VAG, AVAG (SEQ ID NO: 798), GIAV (SEQ ID NO: 799), IAVA (SEQ ID NO: 800), GIAVA (SEQ ID NO: 801), IAVAG (SEQ ID NO: 802), GIAVAG (SEQ ID NO: 6), AAA, AAG, IAA, AAAG (SEQ ID NO: 803), GIAA (SEQ ID NO: 804), IAAA (SEQ ID NO: 805), GIAAA (SEQ ID NO: 806), IAAAG (SEQ ID NO: 807), and GIAAAG (SEQ ID NO: 8);

(iv) N2 is an amino acid sequence selected from the group consisting of G, P, R, A, S, L, T, V, GG, GP, GR, GA, GS, GL, GT, GV, PG, RG, AG, SG, LG, TG, VG, PP, PR, PA, PS, PL, PT, PV, RP, AP, SP, LP, TP, VP, IG, KG, GW, FP, EG, GGG, GPG, GRG, GAG, GSG, GLG, GTG, GVG, PGG, RGG, AGG, SGG, LGG, TGG, VGG, GGP, GGR, GGA, GGS, GGL, GGT, GGV, D, E, F, H, I, K, M, Q, W, Y, AR, AS, AT, AY, DL, DT, EA, EK, FH, FS, HL, HW, IS, KV, LD, LE, LR, LS, LT, NR, NT, QE, QL, QT, RA, RD, RE, RF, RH, RL, RR, RS, RV, SA, SD, SE, SF, SI, SK, SL, SQ, SR, SS, ST, SV, TA, TR, TS, TT, TW, VD, VS, WS, YS, AAE, AYH, DTL, EKR, ISR, NTP, PKS, PRP, PTA, PTQ, REL, RPL, SAA, SAL, SGL, SSE, TGL, WGT;

(v) H3-JH is all of a human CDRH3 H3-JH amino acid sequence, wherein the H3-JH amino acid sequence is selected from the group consisting of AEYFQH (SEQ ID NO: 17), EYFQH (SEQ ID NO: 583), YFQH (SEQ ID NO: 584), FQH, QH, H YWYFDL (SEQ ID NO: 18), WYFDL (SEQ ID NO: 585), YFDL (SEQ ID NO: 586), FDL, DL, L, AFDV (SEQ ID NO: 19), FDV, DV, V, YFDY (SEQ ID NO: 20), FDY, DY, Y, NWFDS (SEQ ID NO: 21), WFDS (SEQ ID NO: 587), FDS, DS, S, YYYYYGMDV (SEQ ID NO: 22), YYYYGMDV (SEQ ID NO: 588), YYYGMDV (SEQ ID NO: 589), YYGMDV (SEQ ID NO: 590), YGMDV (SEQ ID NO: 591), GMDV (SEQ ID NO: 592), MDV, AFDI (SEQ ID NO: 852), FDI, DI, NWFDP (SEQ ID NO: 857), WFDP (SEQ ID NO: 858), FDP, and DP;

wherein the diversity of the polynucleotides encoding the at least about $10^6$ unique antibody CDRH3 amino acid sequences is created by each of the polynucleotides having a CDRH3 sequence that is different from the CDRH3 sequence of every other polynucleotide;

wherein the antibody heavy chain is a variable domain with framework (FRM) and complementary determining regions (CDR) comprising FRMH1-CDRH1-FRM2-CDRH2-FRMH3-CDRH3-FRMH4; and a VKCDR3 amino acid sequence comprising about 1 to about 10 of the amino acids found at Kabat positions 89, 90, 91, 92, 93, 94, 95, 95A, 96, and 97, in selected VKCDR3 amino acid sequences derived from a particular IGKV or IGKJ germline sequence;

wherein the antibody light chain is a variable domain with framework (FRM) and complementary determining regions (CDR) comprising FRMVK1-VKCDR1-FRMVK2-VKCDR2-FRMVK3-VKCDR3-FRMVK4.

2. The antibody of claim 1, wherein the antibody is expressed in a heterodimeric form.

3. The antibody of claim 1, wherein the antibody is expressed as an antibody fragment.

4. The antibody of claim 1, wherein the antibody is selected from the group consisting of a Fab fragment, a Fab' fragment, a F(ab')₂ fragment, an Fv fragment, a diabody, linear antibody, and a single-chain antibody.

5. An antibody isolated from a library comprising synthetic polynucleotides that encode an antibody heavy chain and an antibody light chain containing at least about $10^6$ unique antibody CDRH3 amino acid sequences, wherein each of the polynucleotides encoding the at least about $10^6$ unique antibody CDRH3 amino acid sequences has an antibody CDRH3 amino acid sequence represented by the following formula:

[X]-[N1]-[DH]-[N2]-[H3-JH], wherein (i) X is selected from the group consisting of G, D, E and nothing;

(ii) N1 is an amino acid sequence selected from the group consisting of G, P, R, A, S, L, T, V, GG, GP, GR, GA, GS, GL, GT, GV, PG, RG, AG, SG, LG, TG, VG, PP, PR, PA, PS, PL, PT, PV, RP, AP, SP, LP, TP, VP, IG, KG, GW, FP, EG, GGG, GPG, GRG, GAG, GSG, GLG, GTG, GVG, PGG, RGG, AGG, SGG, LGG, TGG, VGG, GGP, GGR, GGA, GGS, GGL, GGT, GGV, D, E, F, H, I, K, M, Q, W, Y, AR, AS, AT, AY, DL, DT, EA, EK, FH, FS, HL, HW, IS, KV, LD, LE, LR, LS, LT, NR, NT, QE, QL, QT, RA, RD, RE, RF, RH, RL, RR, RS, RV, SA, SD, SE, SF, SI, SK, SL, SQ, SR, SS, ST, SV, TA, TR, TS, TT, TW, VD, VS, WS, YS, AAE, AYH, DTL, EKR, ISR, NTP, PKS, PRP, PTA, PTQ, REL, RPL, SAA, SAL, SGL, SSE, TGL, WGT;

(iii) DH is all of a human CDRH3 DH amino acid sequence, wherein the DH amino acid sequence is selected from the group consisting of ATT, GAT, GIV, IVG, VGA, VLLLWLLL (SEQ ID NO: 239), ITMIV-VVIT (SEQ ID NO: 240), VQWLV (SEQ ID NO: 241), VQQLV (SEQ ID NO: 242), VLRFLEWLLY (SEQ ID NO: 243), YYDFWSGYYT (SEQ ID NO: 244), WILY-QLLC (SEQ ID NO: 245), LRL (SEQ ID NO: 246), TTVT (SEQ ID NO: 247), VWELL (SEQ ID NO: 248), VDTAMVT (SEQ ID NO: 249), WIQLWL (SEQ ID NO: 250), RILWWLLL (SEQ ID NO: 251), DIV-VVVAAT (SEQ ID NO: 252), VLLLWFG (SEQ ID NO: 595), GATT (SEQ ID NO: 623), GIVG (SEQ ID NO: 624), IVGA (SEQ ID NO: 625), VGAT (SEQ ID NO: 626), GIVGA (SEQ ID NO: 627), IVGAT (SEQ ID NO: 628), VGATT (SEQ ID NO: 629), GIVGAT (SEQ ID NO: 630), IVGATT (SEQ ID NO: 631), GIVGATT (SEQ ID NO: 13), YSG, YSGS (SEQ ID NO: 632), YSGSY (SEQ ID NO: 633), YSGSYY (SEQ ID NO: 14), CSSTSC (SEQ ID NO: 622), CSSTSCY (SEQ ID NO: 620), YCSSTSC (SEQ ID NO: 621), CSSTSCYT (SEQ ID NO: 617), GYCSSTSC (SEQ ID NO: 618), YCSSTSCY (SEQ ID NO: 619), GYCSST-SCY (SEQ ID NO: 615), YCSSTSCYT (SEQ ID NO: 616), GYCSSTSCYT (SEQ ID NO:10), AAM, DIV, IVY, PAA, VPA, VVP, VVV, DIVV (SEQ ID NO: 634), IVVV (SEQ ID NO: 635), PAAM (SEQ ID NO: 636), VPAA (SEQ ID NO: 637, VVPA (SEQ ID NO: 638), VVVP (SEQ ID NO: 639), DIVVY (SEQ ID NO: 640), IVVVP (SEQ ID NO: 641), VPAAM (SEQ ID NO: 642), VVPAA (SEQ ID NO: 643), VVVPA (SEQ ID NO: 644), DIVVVP (SEQ ID NO: 645), IVVVPA (SEQ ID NO: 646), VVPAAM (SEQ ID NO: 647), VVVPAA (SEQ ID NO: 648), DIVVPA (SEQ ID NO: 649), IVVVPAA (SEQ ID NO: 650), VVVPAAM (SEQ ID NO: 651), DIVVVPAA (SEQ ID NO: 652), IVVVPAAM (SEQ ID NO: 653), DIVVVPAAM (SEQ ID NO: 11), CSGGSC (SEQ ID NO: 654), CSGGSCY (SEQ ID NO: 655), YCSGGSC (SEQ ID NO: 656), CSGGSCYS (SEQ ID NO: 657), GYCSGGSC (SEQ ID NO: 658), YCSGGSCY (SEQ ID NO: 659), GYC-SGGSCY (SEQ ID NO: 660), YCSGGSCYS (SEQ ID NO: 661), GYCSGGSCYS (SEQ ID NO: 16), FGV, GVV, IFG, ITI, TIF, VVI, FGVV (SEQ ID NO: 662), GVVI (SEQ ID NO: 663), IFGV (SEQ ID NO: 664), ITIF (SEQ ID NO: 665), TIFG (SEQ ID NO: 666), VVII (SEQ ID NO: 667), FGVVI (SEQ ID NO: 668), GVVII (SEQ ID NO: 669), IFGVV (SEQ ID NO: 670), ITIFG (SEQ ID NO: 671), TIFGV (SEQ ID NO: 672), FGVVII (SEQ ID NO: 673), IFGVVI (SEQ ID NO: 674), ITIFGV (SEQ ID NO: 675), TIFGVV (SEQ ID NO: 676), IFGVVII (SEQ ID NO: 677), ITIFGVV (SEQ ID NO: 678), TIFGVVI (SEQ ID NO: 679), ITIFGVVI (SEQ ID NO: 680), TIFGVVII (SEQ ID NO: 681), ITIFGVVII (SEQ ID NO: 9), ELL, FGE, GEL, LLW, LWF, VLL, WFG, FGEL (SEQ ID NO: 682), GELL (SEQ ID NO: 683), LLWF (SEQ ID NO: 684), LWFG (SEQ ID NO: 685), VLLW (SEQ ID NO: 686), WFGE (SEQ ID NO: 687), FGELL (SEQ ID NO: 688), LLWFG (SEQ ID NO: 689), LWFGE (SEQ ID NO: 690), VLLWF (SEQ ID NO: 691), WFGEL (SEQ ID NO: 692), LLWFGE (SEQ ID NO: 693), LWFGEL (SEQ ID NO: 694), VLLWFG (SEQ ID NO: 695), WFGELL (SEQ ID NO: 696), LLWFGEL (SEQ ID NO: 697), LWFGELL (SEQ ID NO: 698), VLLWFGE (SEQ ID NO: 699), LLWFGELL (SEQ ID NO: 700), VLLWFGEL (SEQ ID NO: 701), VLLWFGELL (SEQ ID NO: 1), GSG, GSY, SGS, SYY, YGS, YYG, YYN, YYY, GSGS (SEQ ID NO: 702), GSYY (SEQ ID NO: 703), SGSY (SEQ ID NO: 704), SYYN (SEQ ID NO: 705), YGSG (SEQ ID NO: 706), YYGS (SEQ ID NO: 707), YYYG (SEQ ID NO: 708), GSGSY (SEQ ID NO: 709), GSYYN (SEQ ID NO: 710), SGSYY (SEQ ID NO: 711), YGSGS (SEQ ID NO: 712), YYGSG (SEQ ID NO: 713), YYYGS (SEQ ID NO: 714), GSGSYY (SEQ ID NO: 715), SGSYYN (SEQ ID NO: 716), YGSGSY (SEQ ID NO: 717), YYGSGS (SEQ ID NO: 718), YYYGSG (SEQ ID NO: 719), GSGSYYN (SEQ ID NO: 720), YGSGSYY (SEQ ID NO: 721), YYGSGSY (SEQ ID NO: 722), YYYGSGS (SEQ ID NO: 723), YGSGSYYN (SEQ ID NO: 724), YYGSGSYY (SEQ ID NO: 725), YYYGSGSY (SEQ ID NO: 726), YYGSGSYYN (SEQ ID NO: 727), YYYGSGSYY (SEQ ID NO: 728), YYYGSGSYYN (SEQ ID NO: 2), GVI, ITM, MVR, RGV, TMV, VII, VRG, GVII (SEQ ID NO: 729), ITMV (SEQ ID NO: 730), MVRG (SEQ ID NO: 731), RGVI (SEQ ID NO: 732), TMVR (SEQ ID NO: 733), VRGV (SEQ ID NO: 734), ITMVR (SEQ ID NO: 735), MVRGV (SEQ ID NO: 736), RGVII (SEQ ID NO: 737), TMVRG (SEQ ID NO: 738), VRGVI (SEQ ID NO: 739), ITMVRG (SEQ ID NO: 740), MVRGVI (SEQ ID NO: 741), TMVRGV (SEQ ID NO: 742), VRGVII (SEQ ID NO: 743), ITMVRGV (SEQ ID NO: 744), MVRGVII (SEQ ID NO: 745), TMVRGVI (SEQ ID NO: 746), ITMVRGVI (SEQ ID NO: 747), TMVRGVII (SEQ ID NO: 748), ITMVRGVII (SEQ ID NO: 3), DSS, GYY, SGY, SSG, YDS, YYD, DSSG (SEQ ID NO: 749), GYYY (SEQ ID NO: 750), SGYY (SEQ ID NO: 751), SSGY (SEQ ID NO: 752), YDSS (SEQ ID NO: 753), YYDS (SEQ ID NO: 754), YYYD (SEQ ID NO: 755), DSSGY (SEQ ID NO: 756), SGYYY (SEQ ID NO: 757), SSGYY (SEQ ID NO: 758), YDSSG (SEQ ID NO: 759), YYDSS (SEQ ID NO: 760), YYYGS (SEQ ID NO: 761), DSSGYY (SEQ ID NO: 762), SSGYYY (SEQ ID NO: 763), YDSSGY (SEQ ID NO: 764), YYDSSG (SEQ ID NO: 765), YYYDSS (SEQ ID NO: 766), DSSGYYY (SEQ ID NO: 767), YDSSGYY (SEQ ID NO: 768), YYDSSGY (SEQ ID NO: 769), YYYDSSG (SEQ ID NO: 770), YDSSGYYY (SEQ ID NO: 771), YYDSSGYY (SEQ ID NO: 772), YYYDSSGY (SEQ ID NO: 773), YYDSSGYYY (SEQ ID NO: 774), YYYDSSGYY (SEQ ID NO: 775), YYYDSSGYYY (SEQ ID NO: 4), DYG, GDY, YGD, DYGD (SEQ ID NO: 613), YGDY (SEQ ID NO: 614), DYGDY (SEQ ID NO: 12), SYG, YGY, YSY, GYSY (SEQ ID NO: 776), SYGY (SEQ ID NO: 777), YSYG (SEQ ID NO: 778), GYSYG (SEQ ID NO: 779), YSYGY (SEQ ID NO: 780), GYSYGY (SEQ ID NO: 15), SSS, SSW, SWY, SSSW (SEQ ID NO: 781), SSWY (SEQ ID NO: 782), YSSS (SEQ ID NO: 783), GYSSS (SEQ ID NO: 784), SSSWY (SEQ ID NO: 785), YSSSW(SEQ ID NO: 786), GYSSSW (SEQ ID NO: 787), YSSSWY (SEQ ID NO: 788), GYSSSWY (SEQ ID NO: 7) , GWY, GYS, SGW, YSS, GYSS (SEQ ID NO: 789), SGWY (SEQ ID NO: 790), SSGW (SEQ ID NO: 791), YSSG (SEQ ID NO: 792), GYSSG (SEQ ID NO: 793), SSGWY (SEQ ID NO: 794), YSSGW (SEQ ID NO: 795), GYSSGW (SEQ ID NO: 796), YSSGWY (SEQ ID NO: 797), GYSSGWY (SEQ ID NO: 5), AVA, GIA, IAV, VAG, AVAG (SEQ ID NO: 798), GIAV (SEQ ID NO: 799), IAVA (SEQ ID NO: 800), GIAVA (SEQ ID NO: 801), IAVAG (SEQ ID NO: 802), GIAVAG (SEQ ID NO: 6), AAA, AAG, IAA, AAAG (SEQ ID NO: 803), GIAA (SEQ ID NO: 804), IAAA (SEQ ID NO: 805), GIAAA (SEQ ID NO: 806), IAAAG (SEQ ID NO: 807), and GIAAAG (SEQ ID NO: 8);

(iv) N2 is an amino acid sequence selected from the group consisting of G, P, R, A, S, L, T, V, GG, GP, GR, GA, GS, GL, GT, GV, PG, RG, AG, SG, LG, TG, VG, PP, PR, PA, PS, PL, PT, PV, RP, AP, SP, LP, TP, VP, IG, KG, GW, FP, EG, GGG, GPG, GRG, GAG, GSG, GLG, GTG, GVG, PGG, RGG, AGG, SGG, LGG, TGG, VGG, GGP, GGR, GGA, GGS, GGL, GGT, GGV, D, E, F, H, I, K, M, Q, W, Y, AR, AS, AT, AY, DL, DT, EA, EK, FH, FS, HL, HW, IS, KV, LD, LE, LR, LS, LT, NR, NT, QE, QL, QT, RA, RD, RE, RF, RH, RL, RR, RS, RV, SA, SD, SE, SF, SI, SK, SL, SQ, SR, SS, ST, SV, TA, TR, TS, TT, TW, VD, VS, WS, YS, AAE, AYH, DTL, EKR, ISR, NTP, PKS, PRP, PTA, PTQ, REL, RPL, SAA, SAL, SGL, SSE, TGL, WGT;

(v) H3-JH is all of a human CDRH3 H3-JH amino acid sequence, wherein the H3-JH amino acid sequence is selected from the group consisting of AEYFQH (SEQ ID NO: 17), EYFQH (SEQ ID NO: 583), YFQH (SEQ ID NO: 584), FQH, QH, H YWYFDL (SEQ ID NO: 18), WYFDL (SEQ ID NO: 585), YFDL (SEQ ID NO: 586), FDL, DL, L, AFDV (SEQ ID NO: 19), FDV, DV, V, YFDY (SEQ ID NO: 20), FDY, DY, Y, NWFDS (SEQ ID NO: 21), WFDS (SEQ ID NO: 587), FDS, DS, S, YYYYYGMDV (SEQ ID NO: 22), YYYYG-MDV (SEQ ID NO: 588), YYYGMDV (SEQ ID NO: 589), YYGMDV (SEQ ID NO: 590), YGMDV (SEQ ID NO: 591), GMDV (SEQ ID NO: 592), MDV, AFDI (SEQ ID NO: 852), FDI, DI, NWFDP (SEQ ID NO: 857), WFDP (SEQ ID NO: 858), FDP, and DP;

wherein the diversity of the polynucleotides encoding the at least about $10^6$ unique antibody CDRH3 amino acid sequences is created by each of the polynucleotides having a CDRH3 sequence that is different from the CDRH3 sequence of every other polynucleotide;

wherein the antibody heavy chain is a variable domain with framework (FRM) and complementary determining regions (CDR) comprising FRMH1-CDRH1-FRMH2-CDRH2-FRMH3-CDRH3-FRMH4; and a VKCDR3 amino acid sequence of at least about 80% identity to an amino acid sequence represented by the following formula:

[VK_Chassis]-[L3-VK]-[X]-[JK*], wherein:

(a) VK_Chassis is an amino acid sequence selected from the group consisting of about Kabat amino acid 1 to about Kabat amino acid 88 encoded by IGKV1-05, IGKV1-06, IGKV1-08, IGKV1-09, IGKV1-12, IGKV1-13, IGKV1-16, IGKV1-17, IGKV1-27, IGKV1-33, IGKV1-37, IGKV1-39, IGKV1D-16, IGKV1D-17, IGKV1D-43, IGKV1D-8, IGKV2-24, IGKV2-28, IGKV2-29, IGKV2-30, IGKV2-40, IGKV2D-26, IGKV2D-29, IGKV2D-30, IGKV3-11, IGKV3-15, IGKV3-20, IGKV3D-07, IGKV3D-11, IGKV3D-20, IGKV4-1, IGKV5-2, IGKV6-21, and IGKV6D-41, or a sequence of at least about 80% identity to any of them;

(b) L3-VK is the portion of the VKCDR3 encoded by the IGKV gene segment; and (c) X is any amino acid residue; and (d) JK* is an amino acid sequence selected from the group consisting of amino acid sequences encoded by IGJK1, IGJK2, IGJK3, IGJK4, and IGJK5, wherein the first residue of each IGJK amino acid sequence is not present;

wherein the antibody light chain is a variable domain with framework (FRM) and complementary determining regions (CDR) comprising FRMVK1-VKCDR1-FRMVK2-VKCDR2-FRMVK3-VKCDR3-FRMVK4.

6. The antibody according to claim 5 wherein the antibody is expressed in heterodimeric form.

7. The antibody according to claim 5, wherein the antibody is a full-length antibody, a Fab fragment, a Fab' fragment, a F(ab')$_2$ fragment, an Fv fragment, a diabody, a linear antibody, and a single-chain antibody.

* * * * *

```
                             SEQUENCE LISTING

<160> NUMBER OF SEQ ID NOS: 858

<210> SEQ ID NO 1
<211> LENGTH: 9
<212> TYPE: PRT
<213> ORGANISM: Homo sapiens

<400> SEQUENCE: 1

Val Leu Leu Trp Phe Gly Glu Leu Leu
1               5

<210> SEQ ID NO 2
<211> LENGTH: 10
<212> TYPE: PRT
<213> ORGANISM: Homo sapiens

<400> SEQUENCE: 2

Tyr Tyr Tyr Gly Ser Gly Ser Tyr Tyr Asn
1               5                   10

<210> SEQ ID NO 3
<211> LENGTH: 9
<212> TYPE: PRT
<213> ORGANISM: Homo sapiens

<400> SEQUENCE: 3

Ile Thr Met Val Arg Gly Val Ile Ile
1               5

<210> SEQ ID NO 4
<211> LENGTH: 10
<212> TYPE: PRT
<213> ORGANISM: Homo sapiens

<400> SEQUENCE: 4

Tyr Tyr Tyr Asp Ser Ser Gly Tyr Tyr Tyr
1               5                   10

<210> SEQ ID NO 5
<211> LENGTH: 7
<212> TYPE: PRT
<213> ORGANISM: Homo sapiens

<400> SEQUENCE: 5

Gly Tyr Ser Ser Gly Trp Tyr
1               5

<210> SEQ ID NO 6
<211> LENGTH: 6
<212> TYPE: PRT
<213> ORGANISM: Homo sapiens

<400> SEQUENCE: 6

Gly Ile Ala Val Ala Gly
1               5

<210> SEQ ID NO 7
<211> LENGTH: 7
<212> TYPE: PRT
<213> ORGANISM: Homo sapiens
```

-continued

```
<400> SEQUENCE: 7

Gly Tyr Ser Ser Ser Trp Tyr
1               5

<210> SEQ ID NO 8
<211> LENGTH: 6
<212> TYPE: PRT
<213> ORGANISM: Homo sapiens

<400> SEQUENCE: 8

Gly Ile Ala Ala Ala Gly
1               5

<210> SEQ ID NO 9
<211> LENGTH: 9
<212> TYPE: PRT
<213> ORGANISM: Homo sapiens

<400> SEQUENCE: 9

Ile Thr Ile Phe Gly Val Val Ile Ile
1               5

<210> SEQ ID NO 10
<211> LENGTH: 10
<212> TYPE: PRT
<213> ORGANISM: Homo sapiens

<400> SEQUENCE: 10

Gly Tyr Cys Ser Ser Thr Ser Cys Tyr Thr
1               5                   10

<210> SEQ ID NO 11
<211> LENGTH: 9
<212> TYPE: PRT
<213> ORGANISM: Homo sapiens

<400> SEQUENCE: 11

Asp Ile Val Val Val Pro Ala Ala Met
1               5

<210> SEQ ID NO 12
<211> LENGTH: 5
<212> TYPE: PRT
<213> ORGANISM: Homo sapiens

<400> SEQUENCE: 12

Asp Tyr Gly Asp Tyr
1               5

<210> SEQ ID NO 13
<211> LENGTH: 7
<212> TYPE: PRT
<213> ORGANISM: Homo sapiens

<400> SEQUENCE: 13

Gly Ile Val Gly Ala Thr Thr
1               5

<210> SEQ ID NO 14
<211> LENGTH: 6
<212> TYPE: PRT
<213> ORGANISM: Homo sapiens

<400> SEQUENCE: 14
```

Tyr Ser Gly Ser Tyr Tyr
1               5

<210> SEQ ID NO 15
<211> LENGTH: 6
<212> TYPE: PRT
<213> ORGANISM: Homo sapiens

<400> SEQUENCE: 15

Gly Tyr Ser Tyr Gly Tyr
1               5

<210> SEQ ID NO 16
<211> LENGTH: 10
<212> TYPE: PRT
<213> ORGANISM: Homo sapiens

<400> SEQUENCE: 16

Gly Tyr Cys Ser Gly Gly Ser Cys Tyr Ser
1               5                   10

<210> SEQ ID NO 17
<211> LENGTH: 6
<212> TYPE: PRT
<213> ORGANISM: Homo sapiens

<400> SEQUENCE: 17

Ala Glu Tyr Phe Gln His
1               5

<210> SEQ ID NO 18
<211> LENGTH: 6
<212> TYPE: PRT
<213> ORGANISM: Homo sapiens

<400> SEQUENCE: 18

Tyr Trp Tyr Phe Asp Leu
1               5

<210> SEQ ID NO 19
<211> LENGTH: 4
<212> TYPE: PRT
<213> ORGANISM: Homo sapiens

<400> SEQUENCE: 19

Ala Phe Asp Val
1

<210> SEQ ID NO 20
<211> LENGTH: 4
<212> TYPE: PRT
<213> ORGANISM: Homo sapiens

<400> SEQUENCE: 20

Tyr Phe Asp Tyr
1

<210> SEQ ID NO 21
<211> LENGTH: 5
<212> TYPE: PRT
<213> ORGANISM: Homo sapiens

<400> SEQUENCE: 21

Asn Trp Phe Asp Ser
1               5

-continued

<210> SEQ ID NO 22
<211> LENGTH: 9
<212> TYPE: PRT
<213> ORGANISM: Homo sapiens

<400> SEQUENCE: 22

Tyr Tyr Tyr Tyr Tyr Gly Met Asp Val
1               5

<210> SEQ ID NO 23
<211> LENGTH: 4
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Gln or Arg

<400> SEQUENCE: 23

Trp Gly Xaa Gly
1

<210> SEQ ID NO 24
<211> LENGTH: 98
<212> TYPE: PRT
<213> ORGANISM: Homo sapiens

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 25
<211> LENGTH: 98
<212> TYPE: PRT
<213> ORGANISM: Homo sapiens

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys

```
                    85                  90                  95

Ala Arg

<210> SEQ ID NO 26
<211> LENGTH: 98
<212> TYPE: PRT
<213> ORGANISM: Homo sapiens

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 27
<211> LENGTH: 98
<212> TYPE: PRT
<213> ORGANISM: Homo sapiens

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 28
<211> LENGTH: 98
<212> TYPE: PRT
<213> ORGANISM: Homo sapiens

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 29
<211> LENGTH: 100
<212> TYPE: PRT
<213> ORGANISM: Homo sapiens

<400> SEQUENCE: 29

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
             35                  40                  45

Gly Arg Ile Lys Ser Lys Thr Asp Gly Gly Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg
            100

<210> SEQ ID NO 30
<211> LENGTH: 98
<212> TYPE: PRT
<213> ORGANISM: Homo sapiens

<400> SEQUENCE: 30

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 31
<211> LENGTH: 98
<212> TYPE: PRT
<213> ORGANISM: Homo sapiens

<400> SEQUENCE: 31

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30
```

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 32
<211> LENGTH: 98
<212> TYPE: PRT
<213> ORGANISM: Homo sapiens

<400> SEQUENCE: 32

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 33
<211> LENGTH: 98
<212> TYPE: PRT
<213> ORGANISM: Homo sapiens

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 34
<211> LENGTH: 99
<212> TYPE: PRT
<213> ORGANISM: Homo sapiens

<400> SEQUENCE: 34

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg

<210> SEQ ID NO 35
<211> LENGTH: 97
<212> TYPE: PRT
<213> ORGANISM: Homo sapiens

<400> SEQUENCE: 35

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg

<210> SEQ ID NO 36
<211> LENGTH: 99
<212> TYPE: PRT
<213> ORGANISM: Homo sapiens

<400> SEQUENCE: 36

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg

<210> SEQ ID NO 37
<211> LENGTH: 97

<212> TYPE: PRT
<213> ORGANISM: Homo sapiens

<400> SEQUENCE: 37

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 38
<211> LENGTH: 99
<212> TYPE: PRT
<213> ORGANISM: Homo sapiens

<400> SEQUENCE: 38

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 39
<211> LENGTH: 98
<212> TYPE: PRT
<213> ORGANISM: Homo sapiens

<400> SEQUENCE: 39

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg

<210> SEQ ID NO 40
<211> LENGTH: 98
<212> TYPE: PRT
<213> ORGANISM: Homo sapiens

<400> SEQUENCE: 40

Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Ser Tyr
            20                  25                  30
Trp Ile Gly Trp Val Arg Gln Met Pro Gly Lys Gly Leu Glu Trp Met
        35                  40                  45
Gly Ile Ile Tyr Pro Gly Asp Ser Asp Thr Arg Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Val Tyr Tyr Cys
                85                  90                  95
Ala Arg

<210> SEQ ID NO 41
<211> LENGTH: 5
<212> TYPE: PRT
<213> ORGANISM: Homo sapiens

<400> SEQUENCE: 41

Asn Tyr Ala Ile Ser
1               5

<210> SEQ ID NO 42
<211> LENGTH: 5
<212> TYPE: PRT
<213> ORGANISM: Homo sapiens

<400> SEQUENCE: 42

Ser Leu Ala Ile Ser
1               5

<210> SEQ ID NO 43
<211> LENGTH: 5
<212> TYPE: PRT
<213> ORGANISM: Homo sapiens

<400> SEQUENCE: 43

Ser Tyr Gly Ile Ser
1               5

<210> SEQ ID NO 44
<211> LENGTH: 5
<212> TYPE: PRT
<213> ORGANISM: Homo sapiens

<400> SEQUENCE: 44

Ser Tyr Thr Ile Ser
1               5

<210> SEQ ID NO 45
<211> LENGTH: 5
<212> TYPE: PRT
<213> ORGANISM: Homo sapiens

```
<400> SEQUENCE: 45

Ser Tyr Ala Ile Asn
1               5

<210> SEQ ID NO 46
<211> LENGTH: 17
<212> TYPE: PRT
<213> ORGANISM: Homo sapiens

<400> SEQUENCE: 46

Ser Ile Ile Pro Ile Phe Gly Thr Ala Asn Tyr Ala Gln Lys Phe Gln
1               5                   10                  15

Gly

<210> SEQ ID NO 47
<211> LENGTH: 17
<212> TYPE: PRT
<213> ORGANISM: Homo sapiens

<400> SEQUENCE: 47

Gly Ile Ala Pro Ile Phe Gly Thr Ala Asn Tyr Ala Gln Lys Phe Gln
1               5                   10                  15

Gly

<210> SEQ ID NO 48
<211> LENGTH: 17
<212> TYPE: PRT
<213> ORGANISM: Homo sapiens

<400> SEQUENCE: 48

Gly Ile Ile Pro Ile Leu Gly Thr Ala Asn Tyr Ala Gln Lys Phe Gln
1               5                   10                  15

Gly

<210> SEQ ID NO 49
<211> LENGTH: 17
<212> TYPE: PRT
<213> ORGANISM: Homo sapiens

<400> SEQUENCE: 49

Gly Ile Ile Pro Ile Phe Gly Thr Ala Ser Tyr Ala Gln Lys Phe Gln
1               5                   10                  15

Gly

<210> SEQ ID NO 50
<211> LENGTH: 5
<212> TYPE: PRT
<213> ORGANISM: Homo sapiens

<400> SEQUENCE: 50

Ser Tyr Gly Ile Ser
1               5

<210> SEQ ID NO 51
<211> LENGTH: 5
<212> TYPE: PRT
<213> ORGANISM: Homo sapiens

<400> SEQUENCE: 51

Asn Tyr Gly Ile Ser
1               5
```

<210> SEQ ID NO 52
<211> LENGTH: 5
<212> TYPE: PRT
<213> ORGANISM: Homo sapiens

<400> SEQUENCE: 52

Ser Asn Gly Ile Ser
1               5

<210> SEQ ID NO 53
<211> LENGTH: 5
<212> TYPE: PRT
<213> ORGANISM: Homo sapiens

<400> SEQUENCE: 53

Ser Tyr Ala Ile Ser
1               5

<210> SEQ ID NO 54
<211> LENGTH: 5
<212> TYPE: PRT
<213> ORGANISM: Homo sapiens

<400> SEQUENCE: 54

Ser Tyr Gly Ile Thr
1               5

<210> SEQ ID NO 55
<211> LENGTH: 5
<212> TYPE: PRT
<213> ORGANISM: Homo sapiens

<400> SEQUENCE: 55

Ser Tyr Gly Ile His
1               5

<210> SEQ ID NO 56
<211> LENGTH: 17
<212> TYPE: PRT
<213> ORGANISM: Homo sapiens

<400> SEQUENCE: 56

Trp Ile Ser Ala Tyr Asn Gly Asn Thr Asn Tyr Ala Gln Lys Leu Gln
1               5                   10                  15

Gly

<210> SEQ ID NO 57
<211> LENGTH: 17
<212> TYPE: PRT
<213> ORGANISM: Homo sapiens

<400> SEQUENCE: 57

Ser Ile Ser Ala Tyr Asn Gly Asn Thr Asn Tyr Ala Gln Lys Leu Gln
1               5                   10                  15

Gly

<210> SEQ ID NO 58
<211> LENGTH: 17
<212> TYPE: PRT
<213> ORGANISM: Homo sapiens

<400> SEQUENCE: 58

Trp Ile Ser Thr Tyr Asn Gly Asn Thr Asn Tyr Ala Gln Lys Leu Gln
1               5                   10                  15

Gly

<210> SEQ ID NO 59
<211> LENGTH: 17
<212> TYPE: PRT
<213> ORGANISM: Homo sapiens

<400> SEQUENCE: 59

Trp Ile Ser Pro Tyr Asn Gly Asn Thr Asn Tyr Ala Gln Lys Leu Gln
1               5                   10                  15

Gly

<210> SEQ ID NO 60
<211> LENGTH: 17
<212> TYPE: PRT
<213> ORGANISM: Homo sapiens

<400> SEQUENCE: 60

Trp Ile Ser Ala Tyr Asn Gly Asn Thr Tyr Tyr Ala Gln Lys Leu Gln
1               5                   10                  15

Gly

<210> SEQ ID NO 61
<211> LENGTH: 5
<212> TYPE: PRT
<213> ORGANISM: Homo sapiens

<400> SEQUENCE: 61

Gly Tyr Tyr Met His
1               5

<210> SEQ ID NO 62
<211> LENGTH: 5
<212> TYPE: PRT
<213> ORGANISM: Homo sapiens

<400> SEQUENCE: 62

Asp Tyr Tyr Met His
1               5

<210> SEQ ID NO 63
<211> LENGTH: 5
<212> TYPE: PRT
<213> ORGANISM: Homo sapiens

<400> SEQUENCE: 63

Arg Tyr Tyr Met His
1               5

<210> SEQ ID NO 64
<211> LENGTH: 5
<212> TYPE: PRT
<213> ORGANISM: Homo sapiens

<400> SEQUENCE: 64

Gly Ser Tyr Met His
1               5

<210> SEQ ID NO 65
<211> LENGTH: 5
<212> TYPE: PRT

<213> ORGANISM: Homo sapiens

<400> SEQUENCE: 65

Gly Tyr Ser Met His
1               5

<210> SEQ ID NO 66
<211> LENGTH: 5
<212> TYPE: PRT
<213> ORGANISM: Homo sapiens

<400> SEQUENCE: 66

Gly Tyr Tyr Met Gln
1               5

<210> SEQ ID NO 67
<211> LENGTH: 17
<212> TYPE: PRT
<213> ORGANISM: Homo sapiens

<400> SEQUENCE: 67

Trp Ile Asn Pro Asn Ser Gly Gly Thr Asn Tyr Ala Gln Lys Phe Gln
1               5                   10                  15

Gly

<210> SEQ ID NO 68
<211> LENGTH: 17
<212> TYPE: PRT
<213> ORGANISM: Homo sapiens

<400> SEQUENCE: 68

Ser Ile Asn Pro Asn Ser Gly Gly Thr Asn Tyr Ala Gln Lys Phe Gln
1               5                   10                  15

Gly

<210> SEQ ID NO 69
<211> LENGTH: 17
<212> TYPE: PRT
<213> ORGANISM: Homo sapiens

<400> SEQUENCE: 69

Trp Ile Asn Pro Ser Ser Gly Gly Thr Asn Tyr Ala Gln Lys Phe Gln
1               5                   10                  15

Gly

<210> SEQ ID NO 70
<211> LENGTH: 17
<212> TYPE: PRT
<213> ORGANISM: Homo sapiens

<400> SEQUENCE: 70

Trp Ile Asn Pro Asn Ser Gly Gly Thr Lys Tyr Ala Gln Lys Phe Gln
1               5                   10                  15

Gly

<210> SEQ ID NO 71
<211> LENGTH: 17
<212> TYPE: PRT
<213> ORGANISM: Homo sapiens

<400> SEQUENCE: 71

Trp Ile Asn Pro Asn Ser Gly Gly Thr Ser Tyr Ala Gln Lys Phe Gln

```
1               5                   10                  15

Gly

<210> SEQ ID NO 72
<211> LENGTH: 5
<212> TYPE: PRT
<213> ORGANISM: Homo sapiens

<400> SEQUENCE: 72

Ser Tyr Tyr Met His
1               5

<210> SEQ ID NO 73
<211> LENGTH: 5
<212> TYPE: PRT
<213> ORGANISM: Homo sapiens

<400> SEQUENCE: 73

Asn Tyr Tyr Met His
1               5

<210> SEQ ID NO 74
<211> LENGTH: 5
<212> TYPE: PRT
<213> ORGANISM: Homo sapiens

<400> SEQUENCE: 74

Ser Ser Tyr Met His
1               5

<210> SEQ ID NO 75
<211> LENGTH: 5
<212> TYPE: PRT
<213> ORGANISM: Homo sapiens

<400> SEQUENCE: 75

Ser Tyr Ser Met His
1               5

<210> SEQ ID NO 76
<211> LENGTH: 5
<212> TYPE: PRT
<213> ORGANISM: Homo sapiens

<400> SEQUENCE: 76

Ser Tyr Tyr Ile His
1               5

<210> SEQ ID NO 77
<211> LENGTH: 5
<212> TYPE: PRT
<213> ORGANISM: Homo sapiens

<400> SEQUENCE: 77

Ser Tyr Tyr Met Val
1               5

<210> SEQ ID NO 78
<211> LENGTH: 5
<212> TYPE: PRT
<213> ORGANISM: Homo sapiens

<400> SEQUENCE: 78

Ser Tyr Tyr Met Ser
```

```
1               5
```

<210> SEQ ID NO 79
<211> LENGTH: 17
<212> TYPE: PRT
<213> ORGANISM: Homo sapiens

<400> SEQUENCE: 79

```
Ile Ile Asn Pro Ser Gly Gly Ser Thr Ser Tyr Ala Gln Lys Phe Gln
1               5                   10                  15

Gly
```

<210> SEQ ID NO 80
<211> LENGTH: 17
<212> TYPE: PRT
<213> ORGANISM: Homo sapiens

<400> SEQUENCE: 80

```
Val Ile Asn Pro Ser Gly Gly Ser Thr Ser Tyr Ala Gln Lys Phe Gln
1               5                   10                  15

Gly
```

<210> SEQ ID NO 81
<211> LENGTH: 17
<212> TYPE: PRT
<213> ORGANISM: Homo sapiens

<400> SEQUENCE: 81

```
Ile Ile Asn Pro Gly Gly Gly Ser Thr Ser Tyr Ala Gln Lys Phe Gln
1               5                   10                  15

Gly
```

<210> SEQ ID NO 82
<211> LENGTH: 17
<212> TYPE: PRT
<213> ORGANISM: Homo sapiens

<400> SEQUENCE: 82

```
Ile Ile Asn Pro Ser Gly Gly Ser Thr Thr Tyr Ala Gln Lys Phe Gln
1               5                   10                  15

Gly
```

<210> SEQ ID NO 83
<211> LENGTH: 5
<212> TYPE: PRT
<213> ORGANISM: Homo sapiens

<400> SEQUENCE: 83

```
Ser Tyr Ala Ile Ser
1               5
```

<210> SEQ ID NO 84
<211> LENGTH: 17
<212> TYPE: PRT
<213> ORGANISM: Homo sapiens

<400> SEQUENCE: 84

```
Gly Ile Ile Pro Ile Phe Gly Thr Ala Asn Tyr Ala Gln Lys Phe Gln
1               5                   10                  15

Gly
```

<210> SEQ ID NO 85
<211> LENGTH: 5
<212> TYPE: PRT
<213> ORGANISM: Homo sapiens

<400> SEQUENCE: 85

Asn Ala Trp Met Ser
1               5

<210> SEQ ID NO 86
<211> LENGTH: 5
<212> TYPE: PRT
<213> ORGANISM: Homo sapiens

<400> SEQUENCE: 86

Lys Ala Trp Met Ser
1               5

<210> SEQ ID NO 87
<211> LENGTH: 5
<212> TYPE: PRT
<213> ORGANISM: Homo sapiens

<400> SEQUENCE: 87

Asp Ala Trp Met Ser
1               5

<210> SEQ ID NO 88
<211> LENGTH: 5
<212> TYPE: PRT
<213> ORGANISM: Homo sapiens

<400> SEQUENCE: 88

Asn Ala Leu Met Ser
1               5

<210> SEQ ID NO 89
<211> LENGTH: 5
<212> TYPE: PRT
<213> ORGANISM: Homo sapiens

<400> SEQUENCE: 89

Asn Ala Ala Met Ser
1               5

<210> SEQ ID NO 90
<211> LENGTH: 5
<212> TYPE: PRT
<213> ORGANISM: Homo sapiens

<400> SEQUENCE: 90

Asn Ala Trp Met Asn
1               5

<210> SEQ ID NO 91
<211> LENGTH: 19
<212> TYPE: PRT
<213> ORGANISM: Homo sapiens

<400> SEQUENCE: 91

Arg Ile Lys Ser Lys Thr Asp Gly Gly Thr Thr Asp Tyr Ala Ala Pro
1               5                   10                  15

Val Lys Gly

```
<210> SEQ ID NO 92
<211> LENGTH: 19
<212> TYPE: PRT
<213> ORGANISM: Homo sapiens

<400> SEQUENCE: 92

Ser Ile Lys Ser Lys Thr Asp Gly Gly Thr Thr Asp Tyr Ala Ala Pro
1               5                   10                  15

Val Lys Gly

<210> SEQ ID NO 93
<211> LENGTH: 19
<212> TYPE: PRT
<213> ORGANISM: Homo sapiens

<400> SEQUENCE: 93

Arg Ile Lys Ser Thr Thr Asp Gly Gly Thr Thr Asp Tyr Ala Ala Pro
1               5                   10                  15

Val Lys Gly

<210> SEQ ID NO 94
<211> LENGTH: 19
<212> TYPE: PRT
<213> ORGANISM: Homo sapiens

<400> SEQUENCE: 94

Arg Ile Lys Ser Lys Ala Asp Gly Gly Thr Thr Asp Tyr Ala Ala Pro
1               5                   10                  15

Val Lys Gly

<210> SEQ ID NO 95
<211> LENGTH: 19
<212> TYPE: PRT
<213> ORGANISM: Homo sapiens

<400> SEQUENCE: 95

Arg Ile Lys Ser Lys Thr Asp Gly Gly Thr Thr Gly Tyr Ala Ala Pro
1               5                   10                  15

Val Lys Gly

<210> SEQ ID NO 96
<211> LENGTH: 5
<212> TYPE: PRT
<213> ORGANISM: Homo sapiens

<400> SEQUENCE: 96

Ser Tyr Ala Met Ser
1               5

<210> SEQ ID NO 97
<211> LENGTH: 5
<212> TYPE: PRT
<213> ORGANISM: Homo sapiens

<400> SEQUENCE: 97

Asn Tyr Ala Met Ser
1               5

<210> SEQ ID NO 98
<211> LENGTH: 5
<212> TYPE: PRT
<213> ORGANISM: Homo sapiens
```

```
<400> SEQUENCE: 98

Thr Tyr Ala Met Ser
1               5

<210> SEQ ID NO 99
<211> LENGTH: 5
<212> TYPE: PRT
<213> ORGANISM: Homo sapiens

<400> SEQUENCE: 99

Ser Ser Ala Met Ser
1               5

<210> SEQ ID NO 100
<211> LENGTH: 17
<212> TYPE: PRT
<213> ORGANISM: Homo sapiens

<400> SEQUENCE: 100

Ala Ile Ser Gly Ser Gly Gly Ser Thr Tyr Tyr Ala Asp Ser Val Lys
1               5                   10                  15

Gly

<210> SEQ ID NO 101
<211> LENGTH: 17
<212> TYPE: PRT
<213> ORGANISM: Homo sapiens

<400> SEQUENCE: 101

Gly Ile Ser Gly Ser Gly Gly Ser Thr Tyr Tyr Ala Asp Ser Val Lys
1               5                   10                  15

Gly

<210> SEQ ID NO 102
<211> LENGTH: 17
<212> TYPE: PRT
<213> ORGANISM: Homo sapiens

<400> SEQUENCE: 102

Ser Ile Ser Gly Ser Gly Gly Ser Thr Tyr Tyr Ala Asp Ser Val Lys
1               5                   10                  15

Gly

<210> SEQ ID NO 103
<211> LENGTH: 17
<212> TYPE: PRT
<213> ORGANISM: Homo sapiens

<400> SEQUENCE: 103

Thr Ile Ser Gly Ser Gly Gly Ser Thr Tyr Tyr Ala Asp Ser Val Lys
1               5                   10                  15

Gly

<210> SEQ ID NO 104
<211> LENGTH: 17
<212> TYPE: PRT
<213> ORGANISM: Homo sapiens

<400> SEQUENCE: 104

Val Ile Ser Gly Ser Gly Gly Ser Thr Tyr Tyr Ala Asp Ser Val Lys
1               5                   10                  15
```

Gly

<210> SEQ ID NO 105
<211> LENGTH: 17
<212> TYPE: PRT
<213> ORGANISM: Homo sapiens

<400> SEQUENCE: 105

Ala Ile Ser Ala Ser Gly Gly Ser Thr Tyr Tyr Ala Asp Ser Val Lys
1               5                   10                  15

Gly

<210> SEQ ID NO 106
<211> LENGTH: 17
<212> TYPE: PRT
<213> ORGANISM: Homo sapiens

<400> SEQUENCE: 106

Ala Ile Ser Gly Ser Gly Gly Ser Thr Ser Tyr Ala Asp Ser Val Lys
1               5                   10                  15

Gly

<210> SEQ ID NO 107
<211> LENGTH: 5
<212> TYPE: PRT
<213> ORGANISM: Homo sapiens

<400> SEQUENCE: 107

Ser Tyr Gly Met His
1               5

<210> SEQ ID NO 108
<211> LENGTH: 5
<212> TYPE: PRT
<213> ORGANISM: Homo sapiens

<400> SEQUENCE: 108

Asn Tyr Gly Met His
1               5

<210> SEQ ID NO 109
<211> LENGTH: 5
<212> TYPE: PRT
<213> ORGANISM: Homo sapiens

<400> SEQUENCE: 109

Ser Tyr Ala Met His
1               5

<210> SEQ ID NO 110
<211> LENGTH: 5
<212> TYPE: PRT
<213> ORGANISM: Homo sapiens

<400> SEQUENCE: 110

Ser Tyr Gly Phe His
1               5

<210> SEQ ID NO 111
<211> LENGTH: 17
<212> TYPE: PRT
<213> ORGANISM: Homo sapiens

<400> SEQUENCE: 111

Val Ile Ser Tyr Asp Gly Ser Asn Lys Tyr Tyr Ala Asp Ser Val Lys
1               5                   10                  15

Gly

<210> SEQ ID NO 112
<211> LENGTH: 17
<212> TYPE: PRT
<213> ORGANISM: Homo sapiens

<400> SEQUENCE: 112

Phe Ile Ser Tyr Asp Gly Ser Asn Lys Tyr Tyr Ala Asp Ser Val Lys
1               5                   10                  15

Gly

<210> SEQ ID NO 113
<211> LENGTH: 17
<212> TYPE: PRT
<213> ORGANISM: Homo sapiens

<400> SEQUENCE: 113

Leu Ile Ser Tyr Asp Gly Ser Asn Lys Tyr Tyr Ala Asp Ser Val Lys
1               5                   10                  15

Gly

<210> SEQ ID NO 114
<211> LENGTH: 17
<212> TYPE: PRT
<213> ORGANISM: Homo sapiens

<400> SEQUENCE: 114

Val Ile Ser Ser Asp Gly Ser Asn Lys Tyr Tyr Ala Asp Ser Val Lys
1               5                   10                  15

Gly

<210> SEQ ID NO 115
<211> LENGTH: 17
<212> TYPE: PRT
<213> ORGANISM: Homo sapiens

<400> SEQUENCE: 115

Val Ile Ser Tyr Asp Gly Asn Asn Lys Tyr Tyr Ala Asp Ser Val Lys
1               5                   10                  15

Gly

<210> SEQ ID NO 116
<211> LENGTH: 17
<212> TYPE: PRT
<213> ORGANISM: Homo sapiens

<400> SEQUENCE: 116

Val Ile Ser Tyr Asp Gly Ser Ile Lys Tyr Tyr Ala Asp Ser Val Lys
1               5                   10                  15

Gly

<210> SEQ ID NO 117
<211> LENGTH: 17
<212> TYPE: PRT
<213> ORGANISM: Homo sapiens

<400> SEQUENCE: 117

```
Val Ile Ser Tyr Asp Gly Ser Asn Gln Tyr Tyr Ala Asp Ser Val Lys
1               5                   10                  15

Gly

<210> SEQ ID NO 118
<211> LENGTH: 5
<212> TYPE: PRT
<213> ORGANISM: Homo sapiens

<400> SEQUENCE: 118

Ser Tyr Gly Met His
1               5

<210> SEQ ID NO 119
<211> LENGTH: 5
<212> TYPE: PRT
<213> ORGANISM: Homo sapiens

<400> SEQUENCE: 119

Thr Tyr Gly Met His
1               5

<210> SEQ ID NO 120
<211> LENGTH: 5
<212> TYPE: PRT
<213> ORGANISM: Homo sapiens

<400> SEQUENCE: 120

Asn Tyr Gly Met His
1               5

<210> SEQ ID NO 121
<211> LENGTH: 5
<212> TYPE: PRT
<213> ORGANISM: Homo sapiens

<400> SEQUENCE: 121

Ser Ser Gly Met His
1               5

<210> SEQ ID NO 122
<211> LENGTH: 5
<212> TYPE: PRT
<213> ORGANISM: Homo sapiens

<400> SEQUENCE: 122

Ser Tyr Ala Met His
1               5

<210> SEQ ID NO 123
<211> LENGTH: 5
<212> TYPE: PRT
<213> ORGANISM: Homo sapiens

<400> SEQUENCE: 123

Ser Tyr Gly Met Asn
1               5

<210> SEQ ID NO 124
<211> LENGTH: 17
<212> TYPE: PRT
<213> ORGANISM: Homo sapiens

<400> SEQUENCE: 124
```

```
Val Ile Trp Tyr Asp Gly Ser Asn Lys Tyr Tyr Ala Asp Ser Val Lys
1               5                   10                  15

Gly

<210> SEQ ID NO 125
<211> LENGTH: 17
<212> TYPE: PRT
<213> ORGANISM: Homo sapiens

<400> SEQUENCE: 125

Leu Ile Trp Tyr Asp Gly Ser Asn Lys Tyr Tyr Ala Asp Ser Val Lys
1               5                   10                  15

Gly

<210> SEQ ID NO 126
<211> LENGTH: 17
<212> TYPE: PRT
<213> ORGANISM: Homo sapiens

<400> SEQUENCE: 126

Phe Ile Trp Tyr Asp Gly Ser Asn Lys Tyr Tyr Ala Asp Ser Val Lys
1               5                   10                  15

Gly

<210> SEQ ID NO 127
<211> LENGTH: 17
<212> TYPE: PRT
<213> ORGANISM: Homo sapiens

<400> SEQUENCE: 127

Val Ile Trp Tyr Asp Gly Ser Asn Lys Ser Tyr Ala Asp Ser Val Lys
1               5                   10                  15

Gly

<210> SEQ ID NO 128
<211> LENGTH: 17
<212> TYPE: PRT
<213> ORGANISM: Homo sapiens

<400> SEQUENCE: 128

Val Ile Trp Tyr Asp Gly Ser Asn Lys Gly Tyr Ala Asp Ser Val Lys
1               5                   10                  15

Gly

<210> SEQ ID NO 129
<211> LENGTH: 5
<212> TYPE: PRT
<213> ORGANISM: Homo sapiens

<400> SEQUENCE: 129

Ser Tyr Ser Met Asn
1               5

<210> SEQ ID NO 130
<211> LENGTH: 5
<212> TYPE: PRT
<213> ORGANISM: Homo sapiens

<400> SEQUENCE: 130

Asn Tyr Ser Met Asn
1               5
```

```
<210> SEQ ID NO 131
<211> LENGTH: 5
<212> TYPE: PRT
<213> ORGANISM: Homo sapiens

<400> SEQUENCE: 131

Ile Tyr Ser Met Asn
1               5

<210> SEQ ID NO 132
<211> LENGTH: 5
<212> TYPE: PRT
<213> ORGANISM: Homo sapiens

<400> SEQUENCE: 132

Ser Asn Ser Met Asn
1               5

<210> SEQ ID NO 133
<211> LENGTH: 5
<212> TYPE: PRT
<213> ORGANISM: Homo sapiens

<400> SEQUENCE: 133

Ser Tyr Glu Met Asn
1               5

<210> SEQ ID NO 134
<211> LENGTH: 5
<212> TYPE: PRT
<213> ORGANISM: Homo sapiens

<400> SEQUENCE: 134

Ser Tyr Asn Met Asn
1               5

<210> SEQ ID NO 135
<211> LENGTH: 5
<212> TYPE: PRT
<213> ORGANISM: Homo sapiens

<400> SEQUENCE: 135

Ser Tyr Ser Met Thr
1               5

<210> SEQ ID NO 136
<211> LENGTH: 17
<212> TYPE: PRT
<213> ORGANISM: Homo sapiens

<400> SEQUENCE: 136

Tyr Ile Ser Ser Ser Ser Ser Thr Ile Tyr Tyr Ala Asp Ser Val Lys
1               5                   10                  15

Gly

<210> SEQ ID NO 137
<211> LENGTH: 17
<212> TYPE: PRT
<213> ORGANISM: Homo sapiens

<400> SEQUENCE: 137

Thr Ile Ser Ser Ser Ser Ser Thr Ile Tyr Tyr Ala Asp Ser Val Lys
1               5                   10                  15
```

Gly

<210> SEQ ID NO 138
<211> LENGTH: 17
<212> TYPE: PRT
<213> ORGANISM: Homo sapiens

<400> SEQUENCE: 138

Tyr Ile Ser Gly Ser Ser Ser Thr Ile Tyr Tyr Ala Asp Ser Val Lys
1               5                   10                  15

Gly

<210> SEQ ID NO 139
<211> LENGTH: 17
<212> TYPE: PRT
<213> ORGANISM: Homo sapiens

<400> SEQUENCE: 139

Tyr Ile Ser Ser Ser Ser Ser Thr Ile Leu Tyr Ala Asp Ser Val Lys
1               5                   10                  15

Gly

<210> SEQ ID NO 140
<211> LENGTH: 5
<212> TYPE: PRT
<213> ORGANISM: Homo sapiens

<400> SEQUENCE: 140

Ser Tyr Trp Met Ser
1               5

<210> SEQ ID NO 141
<211> LENGTH: 5
<212> TYPE: PRT
<213> ORGANISM: Homo sapiens

<400> SEQUENCE: 141

Thr Tyr Trp Met Ser
1               5

<210> SEQ ID NO 142
<211> LENGTH: 5
<212> TYPE: PRT
<213> ORGANISM: Homo sapiens

<400> SEQUENCE: 142

Asn Tyr Trp Met Ser
1               5

<210> SEQ ID NO 143
<211> LENGTH: 5
<212> TYPE: PRT
<213> ORGANISM: Homo sapiens

<400> SEQUENCE: 143

Ser Ser Trp Met Ser
1               5

<210> SEQ ID NO 144
<211> LENGTH: 5
<212> TYPE: PRT
<213> ORGANISM: Homo sapiens

<400> SEQUENCE: 144

```
Ser Tyr Gly Met Ser
1               5

<210> SEQ ID NO 145
<211> LENGTH: 5
<212> TYPE: PRT
<213> ORGANISM: Homo sapiens

<400> SEQUENCE: 145

Ser Tyr Trp Met Thr
1               5

<210> SEQ ID NO 146
<211> LENGTH: 17
<212> TYPE: PRT
<213> ORGANISM: Homo sapiens

<400> SEQUENCE: 146

Asn Ile Lys Gln Asp Gly Ser Glu Lys Tyr Tyr Val Asp Ser Val Lys
1               5                   10                  15

Gly

<210> SEQ ID NO 147
<211> LENGTH: 7
<212> TYPE: PRT
<213> ORGANISM: Homo sapiens

<400> SEQUENCE: 147

Ser Gly Gly Tyr Tyr Trp Ser
1               5

<210> SEQ ID NO 148
<211> LENGTH: 7
<212> TYPE: PRT
<213> ORGANISM: Homo sapiens

<400> SEQUENCE: 148

Ser Gly Ser Tyr Tyr Trp Ser
1               5

<210> SEQ ID NO 149
<211> LENGTH: 7
<212> TYPE: PRT
<213> ORGANISM: Homo sapiens

<400> SEQUENCE: 149

Ser Gly Thr Tyr Tyr Trp Ser
1               5

<210> SEQ ID NO 150
<211> LENGTH: 7
<212> TYPE: PRT
<213> ORGANISM: Homo sapiens

<400> SEQUENCE: 150

Ser Gly Gly Thr Tyr Trp Ser
1               5

<210> SEQ ID NO 151
<211> LENGTH: 7
<212> TYPE: PRT
<213> ORGANISM: Homo sapiens

<400> SEQUENCE: 151
```

Ser Gly Gly Tyr Ser Trp Ser
1               5

<210> SEQ ID NO 152
<211> LENGTH: 17
<212> TYPE: PRT
<213> ORGANISM: Homo sapiens

<400> SEQUENCE: 152

Asn Ile Lys Gln Asp Gly Ser Glu Lys Tyr Tyr Val Asp Ser Val Lys
1               5                   10                  15

Gly

<210> SEQ ID NO 153
<211> LENGTH: 17
<212> TYPE: PRT
<213> ORGANISM: Homo sapiens

<400> SEQUENCE: 153

Ser Ile Lys Gln Asp Gly Ser Glu Lys Tyr Tyr Val Asp Ser Val Lys
1               5                   10                  15

Gly

<210> SEQ ID NO 154
<211> LENGTH: 17
<212> TYPE: PRT
<213> ORGANISM: Homo sapiens

<400> SEQUENCE: 154

Asn Ile Asn Gln Asp Gly Ser Glu Lys Tyr Tyr Val Asp Ser Val Lys
1               5                   10                  15

Gly

<210> SEQ ID NO 155
<211> LENGTH: 17
<212> TYPE: PRT
<213> ORGANISM: Homo sapiens

<400> SEQUENCE: 155

Asn Ile Lys Ser Asp Gly Ser Glu Lys Tyr Tyr Val Asp Ser Val Lys
1               5                   10                  15

Gly

<210> SEQ ID NO 156
<211> LENGTH: 17
<212> TYPE: PRT
<213> ORGANISM: Homo sapiens

<400> SEQUENCE: 156

Asn Ile Lys Gln Asp Gly Ser Glu Lys Gln Tyr Val Asp Ser Val Lys
1               5                   10                  15

Gly

<210> SEQ ID NO 157
<211> LENGTH: 16
<212> TYPE: PRT
<213> ORGANISM: Homo sapiens

<400> SEQUENCE: 157

Tyr Ile Tyr Tyr Ser Gly Ser Thr Tyr Tyr Asn Pro Ser Leu Lys Ser
1               5                   10                  15

<210> SEQ ID NO 158
<211> LENGTH: 16
<212> TYPE: PRT
<213> ORGANISM: Homo sapiens

<400> SEQUENCE: 158

Ser Ile Tyr Tyr Ser Gly Ser Thr Tyr Tyr Asn Pro Ser Leu Lys Ser
1               5                   10                  15

<210> SEQ ID NO 159
<211> LENGTH: 16
<212> TYPE: PRT
<213> ORGANISM: Homo sapiens

<400> SEQUENCE: 159

Asn Ile Tyr Tyr Ser Gly Ser Thr Tyr Tyr Asn Pro Ser Leu Lys Ser
1               5                   10                  15

<210> SEQ ID NO 160
<211> LENGTH: 16
<212> TYPE: PRT
<213> ORGANISM: Homo sapiens

<400> SEQUENCE: 160

Tyr Ile Tyr Tyr Ser Gly Asn Thr Tyr Tyr Asn Pro Ser Leu Lys Ser
1               5                   10                  15

<210> SEQ ID NO 161
<211> LENGTH: 16
<212> TYPE: PRT
<213> ORGANISM: Homo sapiens

<400> SEQUENCE: 161

Tyr Ile Tyr Tyr Ser Gly Ser Thr Ser Tyr Asn Pro Ser Leu Lys Ser
1               5                   10                  15

<210> SEQ ID NO 162
<211> LENGTH: 16
<212> TYPE: PRT
<213> ORGANISM: Homo sapiens

<400> SEQUENCE: 162

Tyr Ile Tyr Tyr Ser Gly Ser Thr Val Tyr Asn Pro Ser Leu Lys Ser
1               5                   10                  15

<210> SEQ ID NO 163
<211> LENGTH: 5
<212> TYPE: PRT
<213> ORGANISM: Homo sapiens

<400> SEQUENCE: 163

Gly Tyr Tyr Trp Ser
1               5

<210> SEQ ID NO 164
<211> LENGTH: 5
<212> TYPE: PRT
<213> ORGANISM: Homo sapiens

<400> SEQUENCE: 164

Asp Tyr Tyr Trp Ser
1               5

```
<210> SEQ ID NO 165
<211> LENGTH: 5
<212> TYPE: PRT
<213> ORGANISM: Homo sapiens

<400> SEQUENCE: 165

Gly Tyr Tyr Trp Thr
1               5

<210> SEQ ID NO 166
<211> LENGTH: 16
<212> TYPE: PRT
<213> ORGANISM: Homo sapiens

<400> SEQUENCE: 166

Glu Ile Asp His Ser Gly Ser Thr Asn Tyr Asn Pro Ser Leu Lys Ser
1               5                   10                  15

<210> SEQ ID NO 167
<211> LENGTH: 16
<212> TYPE: PRT
<213> ORGANISM: Homo sapiens

<400> SEQUENCE: 167

Asp Ile Asp His Ser Gly Ser Thr Asn Tyr Asn Pro Ser Leu Lys Ser
1               5                   10                  15

<210> SEQ ID NO 168
<211> LENGTH: 16
<212> TYPE: PRT
<213> ORGANISM: Homo sapiens

<400> SEQUENCE: 168

Glu Ile Ser His Ser Gly Ser Thr Asn Tyr Asn Pro Ser Leu Lys Ser
1               5                   10                  15

<210> SEQ ID NO 169
<211> LENGTH: 16
<212> TYPE: PRT
<213> ORGANISM: Homo sapiens

<400> SEQUENCE: 169

Glu Ile Asp Gln Ser Gly Ser Thr Asn Tyr Asn Pro Ser Leu Lys Ser
1               5                   10                  15

<210> SEQ ID NO 170
<211> LENGTH: 16
<212> TYPE: PRT
<213> ORGANISM: Homo sapiens

<400> SEQUENCE: 170

Glu Ile Asp His Gly Gly Ser Thr Asn Tyr Asn Pro Ser Leu Lys Ser
1               5                   10                  15

<210> SEQ ID NO 171
<211> LENGTH: 16
<212> TYPE: PRT
<213> ORGANISM: Homo sapiens

<400> SEQUENCE: 171

Glu Ile Asp His Ser Gly Asn Thr Asn Tyr Asn Pro Ser Leu Lys Ser
1               5                   10                  15

<210> SEQ ID NO 172
<211> LENGTH: 16
```

<212> TYPE: PRT
<213> ORGANISM: Homo sapiens

<400> SEQUENCE: 172

Glu Ile Asp His Ser Gly Ser Thr Ser Tyr Asn Pro Ser Leu Lys Ser
1               5                   10                  15

<210> SEQ ID NO 173
<211> LENGTH: 16
<212> TYPE: PRT
<213> ORGANISM: Homo sapiens

<400> SEQUENCE: 173

Glu Ile Asp His Ser Gly Ser Thr Asp Tyr Asn Pro Ser Leu Lys Ser
1               5                   10                  15

<210> SEQ ID NO 174
<211> LENGTH: 7
<212> TYPE: PRT
<213> ORGANISM: Homo sapiens

<400> SEQUENCE: 174

Ser Ser Ser Tyr Tyr Trp Gly
1               5

<210> SEQ ID NO 175
<211> LENGTH: 7
<212> TYPE: PRT
<213> ORGANISM: Homo sapiens

<400> SEQUENCE: 175

Thr Ser Ser Tyr Tyr Trp Gly
1               5

<210> SEQ ID NO 176
<211> LENGTH: 7
<212> TYPE: PRT
<213> ORGANISM: Homo sapiens

<400> SEQUENCE: 176

Ser Asn Ser Tyr Tyr Trp Gly
1               5

<210> SEQ ID NO 177
<211> LENGTH: 7
<212> TYPE: PRT
<213> ORGANISM: Homo sapiens

<400> SEQUENCE: 177

Ser Ser Asp Tyr Tyr Trp Gly
1               5

<210> SEQ ID NO 178
<211> LENGTH: 7
<212> TYPE: PRT
<213> ORGANISM: Homo sapiens

<400> SEQUENCE: 178

Ser Ser Asn Tyr Tyr Trp Gly
1               5

<210> SEQ ID NO 179
<211> LENGTH: 7
<212> TYPE: PRT
<213> ORGANISM: Homo sapiens

<400> SEQUENCE: 179

Ser Ser Arg Tyr Tyr Trp Gly
1               5

<210> SEQ ID NO 180
<211> LENGTH: 7
<212> TYPE: PRT
<213> ORGANISM: Homo sapiens

<400> SEQUENCE: 180

Ser Ser Ser Tyr Ala Trp Gly
1               5

<210> SEQ ID NO 181
<211> LENGTH: 16
<212> TYPE: PRT
<213> ORGANISM: Homo sapiens

<400> SEQUENCE: 181

Ser Ile Tyr Tyr Ser Gly Ser Thr Tyr Tyr Asn Pro Ser Leu Lys Ser
1               5                   10                  15

<210> SEQ ID NO 182
<211> LENGTH: 16
<212> TYPE: PRT
<213> ORGANISM: Homo sapiens

<400> SEQUENCE: 182

Asn Ile Tyr Tyr Ser Gly Ser Thr Tyr Tyr Asn Pro Ser Leu Lys Ser
1               5                   10                  15

<210> SEQ ID NO 183
<211> LENGTH: 16
<212> TYPE: PRT
<213> ORGANISM: Homo sapiens

<400> SEQUENCE: 183

Ser Ile Ser Tyr Ser Gly Ser Thr Tyr Tyr Asn Pro Ser Leu Lys Ser
1               5                   10                  15

<210> SEQ ID NO 184
<211> LENGTH: 16
<212> TYPE: PRT
<213> ORGANISM: Homo sapiens

<400> SEQUENCE: 184

Ser Ile Tyr Tyr Ser Gly Ser Thr Ser Tyr Asn Pro Ser Leu Lys Ser
1               5                   10                  15

<210> SEQ ID NO 185
<211> LENGTH: 5
<212> TYPE: PRT
<213> ORGANISM: Homo sapiens

<400> SEQUENCE: 185

Ser Tyr Tyr Trp Ser
1               5

<210> SEQ ID NO 186
<211> LENGTH: 5
<212> TYPE: PRT
<213> ORGANISM: Homo sapiens

<400> SEQUENCE: 186

```
Thr Tyr Tyr Trp Ser
1               5

<210> SEQ ID NO 187
<211> LENGTH: 5
<212> TYPE: PRT
<213> ORGANISM: Homo sapiens

<400> SEQUENCE: 187

Ser Ser Tyr Trp Ser
1               5

<210> SEQ ID NO 188
<211> LENGTH: 5
<212> TYPE: PRT
<213> ORGANISM: Homo sapiens

<400> SEQUENCE: 188

Ser Tyr Ser Trp Ser
1               5

<210> SEQ ID NO 189
<211> LENGTH: 16
<212> TYPE: PRT
<213> ORGANISM: Homo sapiens

<400> SEQUENCE: 189

Tyr Ile Tyr Tyr Ser Gly Ser Thr Asn Tyr Asn Pro Ser Leu Lys Ser
1               5                   10                  15

<210> SEQ ID NO 190
<211> LENGTH: 16
<212> TYPE: PRT
<213> ORGANISM: Homo sapiens

<400> SEQUENCE: 190

Phe Ile Tyr Tyr Ser Gly Ser Thr Asn Tyr Asn Pro Ser Leu Lys Ser
1               5                   10                  15

<210> SEQ ID NO 191
<211> LENGTH: 16
<212> TYPE: PRT
<213> ORGANISM: Homo sapiens

<400> SEQUENCE: 191

His Ile Tyr Tyr Ser Gly Ser Thr Asn Tyr Asn Pro Ser Leu Lys Ser
1               5                   10                  15

<210> SEQ ID NO 192
<211> LENGTH: 16
<212> TYPE: PRT
<213> ORGANISM: Homo sapiens

<400> SEQUENCE: 192

Ser Ile Tyr Tyr Ser Gly Ser Thr Asn Tyr Asn Pro Ser Leu Lys Ser
1               5                   10                  15

<210> SEQ ID NO 193
<211> LENGTH: 16
<212> TYPE: PRT
<213> ORGANISM: Homo sapiens

<400> SEQUENCE: 193

Tyr Ile Tyr Ser Ser Gly Ser Thr Asn Tyr Asn Pro Ser Leu Lys Ser
```

<210> SEQ ID NO 194
<211> LENGTH: 16
<212> TYPE: PRT
<213> ORGANISM: Homo sapiens

<400> SEQUENCE: 194

Tyr Ile Tyr Tyr Ser Gly Ser Thr Asp Tyr Asn Pro Ser Leu Lys Ser
1               5                   10                  15

<210> SEQ ID NO 195
<211> LENGTH: 16
<212> TYPE: PRT
<213> ORGANISM: Homo sapiens

<400> SEQUENCE: 195

Tyr Ile Tyr Tyr Ser Gly Ser Thr Thr Tyr Asn Pro Ser Leu Lys Ser
1               5                   10                  15

<210> SEQ ID NO 196
<211> LENGTH: 7
<212> TYPE: PRT
<213> ORGANISM: Homo sapiens

<400> SEQUENCE: 196

Ser Gly Ser Tyr Tyr Trp Ser
1               5

<210> SEQ ID NO 197
<211> LENGTH: 7
<212> TYPE: PRT
<213> ORGANISM: Homo sapiens

<400> SEQUENCE: 197

Ser Gly Gly Tyr Tyr Trp Ser
1               5

<210> SEQ ID NO 198
<211> LENGTH: 7
<212> TYPE: PRT
<213> ORGANISM: Homo sapiens

<400> SEQUENCE: 198

Ser Gly Asn Tyr Tyr Trp Ser
1               5

<210> SEQ ID NO 199
<211> LENGTH: 7
<212> TYPE: PRT
<213> ORGANISM: Homo sapiens

<400> SEQUENCE: 199

Ser Gly Ser Ser Tyr Trp Ser
1               5

<210> SEQ ID NO 200
<211> LENGTH: 7
<212> TYPE: PRT
<213> ORGANISM: Homo sapiens

<400> SEQUENCE: 200

Ser Gly Ser Tyr Ser Trp Ser
1               5

<210> SEQ ID NO 201
<211> LENGTH: 7
<212> TYPE: PRT
<213> ORGANISM: Homo sapiens

<400> SEQUENCE: 201

Ser Gly Ser Tyr Tyr Trp Thr
1               5

<210> SEQ ID NO 202
<211> LENGTH: 16
<212> TYPE: PRT
<213> ORGANISM: Homo sapiens

<400> SEQUENCE: 202

Tyr Ile Tyr Tyr Ser Gly Ser Thr Asn Tyr Asn Pro Ser Leu Lys Ser
1               5                   10                  15

<210> SEQ ID NO 203
<211> LENGTH: 16
<212> TYPE: PRT
<213> ORGANISM: Homo sapiens

<400> SEQUENCE: 203

Arg Ile Tyr Tyr Ser Gly Ser Thr Asn Tyr Asn Pro Ser Leu Lys Ser
1               5                   10                  15

<210> SEQ ID NO 204
<211> LENGTH: 16
<212> TYPE: PRT
<213> ORGANISM: Homo sapiens

<400> SEQUENCE: 204

Ser Ile Tyr Tyr Ser Gly Ser Thr Asn Tyr Asn Pro Ser Leu Lys Ser
1               5                   10                  15

<210> SEQ ID NO 205
<211> LENGTH: 16
<212> TYPE: PRT
<213> ORGANISM: Homo sapiens

<400> SEQUENCE: 205

Tyr Ile Tyr Thr Ser Gly Ser Thr Asn Tyr Asn Pro Ser Leu Lys Ser
1               5                   10                  15

<210> SEQ ID NO 206
<211> LENGTH: 16
<212> TYPE: PRT
<213> ORGANISM: Homo sapiens

<400> SEQUENCE: 206

Tyr Ile Tyr Tyr Ser Gly Ser Thr Ser Tyr Asn Pro Ser Leu Lys Ser
1               5                   10                  15

<210> SEQ ID NO 207
<211> LENGTH: 6
<212> TYPE: PRT
<213> ORGANISM: Homo sapiens

<400> SEQUENCE: 207

Ser Gly Tyr Tyr Trp Gly
1               5

<210> SEQ ID NO 208

```
<211> LENGTH: 6
<212> TYPE: PRT
<213> ORGANISM: Homo sapiens

<400> SEQUENCE: 208

Ser Ala Tyr Tyr Trp Gly
1               5

<210> SEQ ID NO 209
<211> LENGTH: 6
<212> TYPE: PRT
<213> ORGANISM: Homo sapiens

<400> SEQUENCE: 209

Ser Gly Ser Tyr Trp Gly
1               5

<210> SEQ ID NO 210
<211> LENGTH: 6
<212> TYPE: PRT
<213> ORGANISM: Homo sapiens

<400> SEQUENCE: 210

Ser Gly Tyr Asn Trp Gly
1               5

<210> SEQ ID NO 211
<211> LENGTH: 6
<212> TYPE: PRT
<213> ORGANISM: Homo sapiens

<400> SEQUENCE: 211

Ser Gly Tyr Tyr Trp Ala
1               5

<210> SEQ ID NO 212
<211> LENGTH: 16
<212> TYPE: PRT
<213> ORGANISM: Homo sapiens

<400> SEQUENCE: 212

Ser Ile Tyr His Ser Gly Ser Thr Tyr Tyr Asn Pro Ser Leu Lys Ser
1               5                   10                  15

<210> SEQ ID NO 213
<211> LENGTH: 16
<212> TYPE: PRT
<213> ORGANISM: Homo sapiens

<400> SEQUENCE: 213

Thr Ile Tyr His Ser Gly Ser Thr Tyr Tyr Asn Pro Ser Leu Lys Ser
1               5                   10                  15

<210> SEQ ID NO 214
<211> LENGTH: 16
<212> TYPE: PRT
<213> ORGANISM: Homo sapiens

<400> SEQUENCE: 214

Ser Ser Tyr His Ser Gly Ser Thr Tyr Tyr Asn Pro Ser Leu Lys Ser
1               5                   10                  15

<210> SEQ ID NO 215
<211> LENGTH: 16
<212> TYPE: PRT
```

<213> ORGANISM: Homo sapiens

<400> SEQUENCE: 215

Ser Ile Tyr His Ser Gly Asn Thr Tyr Tyr Asn Pro Ser Leu Lys Ser
1               5                   10                  15

<210> SEQ ID NO 216
<211> LENGTH: 16
<212> TYPE: PRT
<213> ORGANISM: Homo sapiens

<400> SEQUENCE: 216

Ser Ile Tyr His Ser Gly Ser Thr Asn Tyr Asn Pro Ser Leu Lys Ser
1               5                   10                  15

<210> SEQ ID NO 217
<211> LENGTH: 16
<212> TYPE: PRT
<213> ORGANISM: Homo sapiens

<400> SEQUENCE: 217

Ser Ile Tyr His Ser Gly Ser Thr Gly Tyr Asn Pro Ser Leu Lys Ser
1               5                   10                  15

<210> SEQ ID NO 218
<211> LENGTH: 5
<212> TYPE: PRT
<213> ORGANISM: Homo sapiens

<400> SEQUENCE: 218

Ser Tyr Trp Ile Gly
1               5

<210> SEQ ID NO 219
<211> LENGTH: 5
<212> TYPE: PRT
<213> ORGANISM: Homo sapiens

<400> SEQUENCE: 219

Thr Tyr Trp Ile Gly
1               5

<210> SEQ ID NO 220
<211> LENGTH: 5
<212> TYPE: PRT
<213> ORGANISM: Homo sapiens

<400> SEQUENCE: 220

Asn Tyr Trp Ile Gly
1               5

<210> SEQ ID NO 221
<211> LENGTH: 5
<212> TYPE: PRT
<213> ORGANISM: Homo sapiens

<400> SEQUENCE: 221

Ser Asn Trp Ile Gly
1               5

<210> SEQ ID NO 222
<211> LENGTH: 5
<212> TYPE: PRT
<213> ORGANISM: Homo sapiens

<400> SEQUENCE: 222

Ser Tyr Tyr Ile Gly
1               5

<210> SEQ ID NO 223
<211> LENGTH: 5
<212> TYPE: PRT
<213> ORGANISM: Homo sapiens

<400> SEQUENCE: 223

Ser Tyr Trp Ile Ser
1               5

<210> SEQ ID NO 224
<211> LENGTH: 17
<212> TYPE: PRT
<213> ORGANISM: Homo sapiens

<400> SEQUENCE: 224

Ile Ile Tyr Pro Gly Asp Ser Asp Thr Arg Tyr Ser Pro Ser Phe Gln
1               5                   10                  15

Gly

<210> SEQ ID NO 225
<211> LENGTH: 17
<212> TYPE: PRT
<213> ORGANISM: Homo sapiens

<400> SEQUENCE: 225

Ser Ile Tyr Pro Gly Asp Ser Asp Thr Arg Tyr Ser Pro Ser Phe Gln
1               5                   10                  15

Gly

<210> SEQ ID NO 226
<211> LENGTH: 17
<212> TYPE: PRT
<213> ORGANISM: Homo sapiens

<400> SEQUENCE: 226

Ile Ile Tyr Pro Ala Asp Ser Asp Thr Arg Tyr Ser Pro Ser Phe Gln
1               5                   10                  15

Gly

<210> SEQ ID NO 227
<211> LENGTH: 17
<212> TYPE: PRT
<213> ORGANISM: Homo sapiens

<400> SEQUENCE: 227

Ile Ile Tyr Pro Gly Asp Ser Ser Thr Arg Tyr Ser Pro Ser Phe Gln
1               5                   10                  15

Gly

<210> SEQ ID NO 228
<211> LENGTH: 17
<212> TYPE: PRT
<213> ORGANISM: Homo sapiens

<400> SEQUENCE: 228

Ile Ile Tyr Pro Gly Asp Ser Asp Thr Thr Tyr Ser Pro Ser Phe Gln
1               5                   10                  15

Gly

```
<210> SEQ ID NO 229
<211> LENGTH: 95
<212> TYPE: PRT
<213> ORGANISM: Homo sapiens

<400> SEQUENCE: 229

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 230
<211> LENGTH: 95
<212> TYPE: PRT
<213> ORGANISM: Homo sapiens

<400> SEQUENCE: 230

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro
                85                  90                  95

<210> SEQ ID NO 231
<211> LENGTH: 95
<212> TYPE: PRT
<213> ORGANISM: Homo sapiens

<400> SEQUENCE: 231

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
                85                  90                  95
```

<210> SEQ ID NO 232
<211> LENGTH: 95
<212> TYPE: PRT
<213> ORGANISM: Homo sapiens

<400> SEQUENCE: 232

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95

<210> SEQ ID NO 233
<211> LENGTH: 95
<212> TYPE: PRT
<213> ORGANISM: Homo sapiens

<400> SEQUENCE: 233

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 234
<211> LENGTH: 100
<212> TYPE: PRT
<213> ORGANISM: Homo sapiens

<400> SEQUENCE: 234

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

```
Leu Gln Thr Pro
            100

<210> SEQ ID NO 235
<211> LENGTH: 95
<212> TYPE: PRT
<213> ORGANISM: Homo sapiens

<400> SEQUENCE: 235

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 236
<211> LENGTH: 95
<212> TYPE: PRT
<213> ORGANISM: Homo sapiens

<400> SEQUENCE: 236

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95

<210> SEQ ID NO 237
<211> LENGTH: 96
<212> TYPE: PRT
<213> ORGANISM: Homo sapiens

<400> SEQUENCE: 237

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
```

<210> SEQ ID NO 238
<211> LENGTH: 101
<212> TYPE: PRT
<213> ORGANISM: Homo sapiens

<400> SEQUENCE: 238

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 239
<211> LENGTH: 8
<212> TYPE: PRT
<213> ORGANISM: Homo sapiens
<220> FEATURE:
<221> NAME/KEY: VARSPLIC
<222> LOCATION: (4)..(5)

<400> SEQUENCE: 239

Val Leu Leu Leu Trp Leu Leu Leu
1               5

<210> SEQ ID NO 240
<211> LENGTH: 9
<212> TYPE: PRT
<213> ORGANISM: Homo sapiens

<400> SEQUENCE: 240

Ile Thr Met Ile Val Val Val Ile Thr
1               5

<210> SEQ ID NO 241
<211> LENGTH: 5
<212> TYPE: PRT
<213> ORGANISM: Homo sapiens
<220> FEATURE:
<221> NAME/KEY: VARSPLIC
<222> LOCATION: (1)..(2)

<400> SEQUENCE: 241

Val Gln Trp Leu Val
1               5

<210> SEQ ID NO 242
<211> LENGTH: 5
<212> TYPE: PRT
<213> ORGANISM: Homo sapiens
<220> FEATURE:
<221> NAME/KEY: VARSPLIC
<222> LOCATION: (1)..(2)

```
<400> SEQUENCE: 242

Val Gln Gln Leu Val
1               5

<210> SEQ ID NO 243
<211> LENGTH: 10
<212> TYPE: PRT
<213> ORGANISM: Homo sapiens

<400> SEQUENCE: 243

Val Leu Arg Phe Leu Glu Trp Leu Leu Tyr
1               5                   10

<210> SEQ ID NO 244
<211> LENGTH: 10
<212> TYPE: PRT
<213> ORGANISM: Homo sapiens

<400> SEQUENCE: 244

Tyr Tyr Asp Phe Trp Ser Gly Tyr Tyr Thr
1               5                   10

<210> SEQ ID NO 245
<211> LENGTH: 8
<212> TYPE: PRT
<213> ORGANISM: Homo sapiens
<220> FEATURE:
<221> NAME/KEY: VARSPLIC
<222> LOCATION: (3)..(4)

<400> SEQUENCE: 245

Trp Ile Leu Tyr Gln Leu Leu Cys
1               5

<210> SEQ ID NO 246
<211> LENGTH: 3
<212> TYPE: PRT
<213> ORGANISM: Homo sapiens
<220> FEATURE:
<221> NAME/KEY: VARSPLIC
<222> LOCATION: (1)..(2)
<220> FEATURE:
<221> NAME/KEY: VARSPLIC
<222> LOCATION: (2)..(3)
<223> OTHER INFORMATION: Stop codon

<400> SEQUENCE: 246

Leu Arg Leu
1

<210> SEQ ID NO 247
<211> LENGTH: 4
<212> TYPE: PRT
<213> ORGANISM: Homo sapiens

<400> SEQUENCE: 247

Thr Thr Val Thr
1

<210> SEQ ID NO 248
<211> LENGTH: 5
<212> TYPE: PRT
<213> ORGANISM: Homo sapiens
<220> FEATURE:
<221> NAME/KEY: VARSPLIC
<222> LOCATION: (1)..(2)
```

```
<400> SEQUENCE: 248

Val Trp Glu Leu Leu
1               5

<210> SEQ ID NO 249
<211> LENGTH: 7
<212> TYPE: PRT
<213> ORGANISM: Homo sapiens

<400> SEQUENCE: 249

Val Asp Thr Ala Met Val Thr
1               5

<210> SEQ ID NO 250
<211> LENGTH: 6
<212> TYPE: PRT
<213> ORGANISM: Homo sapiens

<400> SEQUENCE: 250

Trp Ile Gln Leu Trp Leu
1               5

<210> SEQ ID NO 251
<211> LENGTH: 8
<212> TYPE: PRT
<213> ORGANISM: Homo sapiens
<220> FEATURE:
<221> NAME/KEY: VARSPLIC
<222> LOCATION: (3)..(4)
<223> OTHER INFORMATION: Stop codon
<220> FEATURE:
<221> NAME/KEY: VARSPLIC
<222> LOCATION: (5)..(6)

<400> SEQUENCE: 251

Arg Ile Leu Trp Trp Leu Leu Leu
1               5

<210> SEQ ID NO 252
<211> LENGTH: 9
<212> TYPE: PRT
<213> ORGANISM: Homo sapiens

<400> SEQUENCE: 252

Asp Ile Val Val Val Val Ala Ala Thr
1               5

<210> SEQ ID NO 253
<211> LENGTH: 17
<212> TYPE: PRT
<213> ORGANISM: Homo sapiens

<400> SEQUENCE: 253

Ala Glu Tyr Phe Gln His Trp Gly Gln Gly Thr Leu Val Thr Val Ser
1               5                   10                  15

Ser

<210> SEQ ID NO 254
<211> LENGTH: 17
<212> TYPE: PRT
<213> ORGANISM: Homo sapiens

<400> SEQUENCE: 254

Tyr Trp Tyr Phe Asp Leu Trp Gly Arg Gly Thr Leu Val Thr Val Ser
1               5                   10                  15
```

Ser

<210> SEQ ID NO 255
<211> LENGTH: 15
<212> TYPE: PRT
<213> ORGANISM: Homo sapiens

<400> SEQUENCE: 255

Ala Phe Asp Val Trp Gly Gln Gly Thr Met Val Thr Val Ser Ser
1               5                   10                  15

<210> SEQ ID NO 256
<211> LENGTH: 15
<212> TYPE: PRT
<213> ORGANISM: Homo sapiens

<400> SEQUENCE: 256

Tyr Phe Asp Tyr Trp Gly Gln Gly Thr Leu Val Thr Val Ser Ser
1               5                   10                  15

<210> SEQ ID NO 257
<211> LENGTH: 16
<212> TYPE: PRT
<213> ORGANISM: Homo sapiens

<400> SEQUENCE: 257

Asn Trp Phe Asp Ser Trp Gly Gln Gly Thr Leu Val Thr Val Ser Ser
1               5                   10                  15

<210> SEQ ID NO 258
<211> LENGTH: 20
<212> TYPE: PRT
<213> ORGANISM: Homo sapiens

<400> SEQUENCE: 258

Tyr Tyr Tyr Tyr Tyr Gly Met Asp Val Trp Gly Gln Gly Thr Thr Val
1               5                   10                  15

Thr Val Ser Ser
            20

<210> SEQ ID NO 259
<211> LENGTH: 24
<212> TYPE: DNA
<213> ORGANISM: Homo sapiens

<400> SEQUENCE: 259
cascastmcv rtrsttwctw cact                                          24

<210> SEQ ID NO 260
<211> LENGTH: 24
<212> TYPE: DNA
<213> ORGANISM: Homo sapiens

<400> SEQUENCE: 260
cascastmcv rtrsttwcmt cact                                          24

<210> SEQ ID NO 261
<211> LENGTH: 24
<212> TYPE: DNA
<213> ORGANISM: Homo sapiens

<400> SEQUENCE: 261
cascastmcv rtrsttwcwg gact                                          24

<210> SEQ ID NO 262
<211> LENGTH: 24
<212> TYPE: DNA
<213> ORGANISM: Homo sapiens

<400> SEQUENCE: 262
cascastmcv rtrsttwcyc tact 24

<210> SEQ ID NO 263
<211> LENGTH: 27
<212> TYPE: DNA
<213> ORGANISM: Homo sapiens

<400> SEQUENCE: 263
cascastmcv rtrsttwcyc ttwcact 27

<210> SEQ ID NO 264
<211> LENGTH: 27
<212> TYPE: DNA
<213> ORGANISM: Homo sapiens

<400> SEQUENCE: 264
cascastmcv rtrsttwcyc tmtcact 27

<210> SEQ ID NO 265
<211> LENGTH: 27
<212> TYPE: DNA
<213> ORGANISM: Homo sapiens

<400> SEQUENCE: 265
cascastmcv rtrsttwcyc twggact 27

<210> SEQ ID NO 266
<211> LENGTH: 27
<212> TYPE: DNA
<213> ORGANISM: Homo sapiens

<400> SEQUENCE: 266
cascastmcv rtrsttwcyc tyctact 27

<210> SEQ ID NO 267
<211> LENGTH: 30
<212> TYPE: DNA
<213> ORGANISM: Homo sapiens

<400> SEQUENCE: 267
cascastmcv rtrsttwcyc tcbttwcact 30

<210> SEQ ID NO 268
<211> LENGTH: 30
<212> TYPE: DNA
<213> ORGANISM: Homo sapiens

<400> SEQUENCE: 268
cascastmcv rtrsttwcyc tcbtmtcact 30

<210> SEQ ID NO 269
<211> LENGTH: 30
<212> TYPE: DNA
<213> ORGANISM: Homo sapiens

<400> SEQUENCE: 269

| | |
|---|---|
| cascastmcv rtrsttwcyc tcbtwggact | 30 |

<210> SEQ ID NO 270
<211> LENGTH: 24
<212> TYPE: DNA
<213> ORGANISM: Homo sapiens

<400> SEQUENCE: 270

| | |
|---|---|
| cascasdctr vcartttstw cact | 24 |

<210> SEQ ID NO 271
<211> LENGTH: 24
<212> TYPE: DNA
<213> ORGANISM: Homo sapiens

<400> SEQUENCE: 271

| | |
|---|---|
| cascasdctr vcartttsmt cact | 24 |

<210> SEQ ID NO 272
<211> LENGTH: 24
<212> TYPE: DNA
<213> ORGANISM: Homo sapiens

<400> SEQUENCE: 272

| | |
|---|---|
| cascasdctr vcartttswg gact | 24 |

<210> SEQ ID NO 273
<211> LENGTH: 24
<212> TYPE: DNA
<213> ORGANISM: Homo sapiens

<400> SEQUENCE: 273

| | |
|---|---|
| cascasdctr vcartttscc tact | 24 |

<210> SEQ ID NO 274
<211> LENGTH: 27
<212> TYPE: DNA
<213> ORGANISM: Homo sapiens

<400> SEQUENCE: 274

| | |
|---|---|
| cascasdctr vcartttscc ttwcact | 27 |

<210> SEQ ID NO 275
<211> LENGTH: 27
<212> TYPE: DNA
<213> ORGANISM: Homo sapiens

<400> SEQUENCE: 275

| | |
|---|---|
| cascasdctr vcartttscc tmtcact | 27 |

<210> SEQ ID NO 276
<211> LENGTH: 27
<212> TYPE: DNA
<213> ORGANISM: Homo sapiens

<400> SEQUENCE: 276

| | |
|---|---|
| cascasdctr vcartttscc twggact | 27 |

<210> SEQ ID NO 277
<211> LENGTH: 27
<212> TYPE: DNA
<213> ORGANISM: Homo sapiens

<400> SEQUENCE: 277

```
cascasdctr vcartttscc tcbtact                                            27

<210> SEQ ID NO 278
<211> LENGTH: 30
<212> TYPE: DNA
<213> ORGANISM: Homo sapiens

<400> SEQUENCE: 278
cascasdctr vcartttscc tcbttwcact                                         30

<210> SEQ ID NO 279
<211> LENGTH: 30
<212> TYPE: DNA
<213> ORGANISM: Homo sapiens

<400> SEQUENCE: 279
cascasdctr vcartttscc tcbtmtcact                                         30

<210> SEQ ID NO 280
<211> LENGTH: 30
<212> TYPE: DNA
<213> ORGANISM: Homo sapiens

<400> SEQUENCE: 280
cascasdctr vcartttscc tcbtwggact                                         30

<210> SEQ ID NO 281
<211> LENGTH: 24
<212> TYPE: DNA
<213> ORGANISM: Homo sapiens

<400> SEQUENCE: 281
casmagtwcr rtaskgbatw cact                                               24

<210> SEQ ID NO 282
<211> LENGTH: 24
<212> TYPE: DNA
<213> ORGANISM: Homo sapiens

<400> SEQUENCE: 282
casmagtwcr rtaskgbamt cact                                               24

<210> SEQ ID NO 283
<211> LENGTH: 24
<212> TYPE: DNA
<213> ORGANISM: Homo sapiens

<400> SEQUENCE: 283
casmagtwcr rtaskgbawg gact                                               24

<210> SEQ ID NO 284
<211> LENGTH: 24
<212> TYPE: DNA
<213> ORGANISM: Homo sapiens

<400> SEQUENCE: 284
casmagtwcr rtaskgbacc tact                                               24

<210> SEQ ID NO 285
<211> LENGTH: 27
<212> TYPE: DNA
<213> ORGANISM: Homo sapiens
```

```
<400> SEQUENCE: 285
casmagtwcr rtaskgbacc ttwcact                                    27

<210> SEQ ID NO 286
<211> LENGTH: 27
<212> TYPE: DNA
<213> ORGANISM: Homo sapiens

<400> SEQUENCE: 286
casmagtwcr rtaskgbacc tmtcact                                    27

<210> SEQ ID NO 287
<211> LENGTH: 27
<212> TYPE: DNA
<213> ORGANISM: Homo sapiens

<400> SEQUENCE: 287
casmagtwcr rtaskgbacc twggact                                    27

<210> SEQ ID NO 288
<211> LENGTH: 27
<212> TYPE: DNA
<213> ORGANISM: Homo sapiens

<400> SEQUENCE: 288
casmagtwcr rtaskgbacc tcbtact                                    27

<210> SEQ ID NO 289
<211> LENGTH: 30
<212> TYPE: DNA
<213> ORGANISM: Homo sapiens

<400> SEQUENCE: 289
casmagtwcr rtaskgbacc tcbttwcact                                 30

<210> SEQ ID NO 290
<211> LENGTH: 30
<212> TYPE: DNA
<213> ORGANISM: Homo sapiens

<400> SEQUENCE: 290
casmagtwcr rtaskgbacc tcbtmtcact                                 30

<210> SEQ ID NO 291
<211> LENGTH: 30
<212> TYPE: DNA
<213> ORGANISM: Homo sapiens

<400> SEQUENCE: 291
casmagtwcr rtaskgbacc tcbtwggact                                 30

<210> SEQ ID NO 292
<211> LENGTH: 24
<212> TYPE: DNA
<213> ORGANISM: Homo sapiens

<400> SEQUENCE: 292
cascwttmcr atrvcbwttw cact                                       24

<210> SEQ ID NO 293
<211> LENGTH: 24
<212> TYPE: DNA
<213> ORGANISM: Homo sapiens
```

<400> SEQUENCE: 293
cascwttmcr atrvcbwtmt cact                                          24

<210> SEQ ID NO 294
<211> LENGTH: 24
<212> TYPE: DNA
<213> ORGANISM: Homo sapiens

<400> SEQUENCE: 294
cascwttmcr atrvcbwtwg gact                                          24

<210> SEQ ID NO 295
<211> LENGTH: 24
<212> TYPE: DNA
<213> ORGANISM: Homo sapiens

<400> SEQUENCE: 295
cascwttmcr atrvcbwtcc tact                                          24

<210> SEQ ID NO 296
<211> LENGTH: 27
<212> TYPE: DNA
<213> ORGANISM: Homo sapiens

<400> SEQUENCE: 296
cascwttmcr atrvcbwtcc ttwcact                                       27

<210> SEQ ID NO 297
<211> LENGTH: 27
<212> TYPE: DNA
<213> ORGANISM: Homo sapiens

<400> SEQUENCE: 297
cascwttmcr atrvcbwtcc tmtcact                                       27

<210> SEQ ID NO 298
<211> LENGTH: 27
<212> TYPE: DNA
<213> ORGANISM: Homo sapiens

<400> SEQUENCE: 298
cascwttmcr atrvcbwtcc twggact                                       27

<210> SEQ ID NO 299
<211> LENGTH: 27
<212> TYPE: DNA
<213> ORGANISM: Homo sapiens

<400> SEQUENCE: 299
cascwttmcr atrvcbwtcc tcbtact                                       27

<210> SEQ ID NO 300
<211> LENGTH: 30
<212> TYPE: DNA
<213> ORGANISM: Homo sapiens

<400> SEQUENCE: 300
cascwttmcr atrvcbwtcc tcbttwcact                                    30

<210> SEQ ID NO 301
<211> LENGTH: 30
<212> TYPE: DNA

<213> ORGANISM: Homo sapiens

<400> SEQUENCE: 301
cascwttmcr atrvcbwtcc tcbtmtcact                     30

<210> SEQ ID NO 302
<211> LENGTH: 30
<212> TYPE: DNA
<213> ORGANISM: Homo sapiens

<400> SEQUENCE: 302
cascwttmcr atrvcbwtcc tcbtwggact                     30

<210> SEQ ID NO 303
<211> LENGTH: 24
<212> TYPE: DNA
<213> ORGANISM: Homo sapiens

<400> SEQUENCE: 303
cwgsaawcat hcmvtabttw cact                           24

<210> SEQ ID NO 304
<211> LENGTH: 24
<212> TYPE: DNA
<213> ORGANISM: Homo sapiens

<400> SEQUENCE: 304
cwgsaawcat hcmvtabtmt cact                           24

<210> SEQ ID NO 305
<211> LENGTH: 24
<212> TYPE: DNA
<213> ORGANISM: Homo sapiens

<400> SEQUENCE: 305
cwgsaawcat hcmvtabtwg gact                           24

<210> SEQ ID NO 306
<211> LENGTH: 24
<212> TYPE: DNA
<213> ORGANISM: Homo sapiens

<400> SEQUENCE: 306
cwgsaawcat hcmvtabtcc tact                           24

<210> SEQ ID NO 307
<211> LENGTH: 27
<212> TYPE: DNA
<213> ORGANISM: Homo sapiens

<400> SEQUENCE: 307
cwgsaawcat hcmvtabtcc ttwcact                        27

<210> SEQ ID NO 308
<211> LENGTH: 27
<212> TYPE: DNA
<213> ORGANISM: Homo sapiens

<400> SEQUENCE: 308
cwgsaawcat hcmvtabtcc tmtcact                        27

<210> SEQ ID NO 309
<211> LENGTH: 27

```
<212> TYPE: DNA
<213> ORGANISM: Homo sapiens

<400> SEQUENCE: 309
cwgsaawcat hcmvtabtcc twggact                                               27

<210> SEQ ID NO 310
<211> LENGTH: 27
<212> TYPE: DNA
<213> ORGANISM: Homo sapiens

<400> SEQUENCE: 310
cwgsaawcat hcmvtabtcc tcbtact                                               27

<210> SEQ ID NO 311
<211> LENGTH: 30
<212> TYPE: DNA
<213> ORGANISM: Homo sapiens

<400> SEQUENCE: 311
cwgsaawcat hcmvtabtcc tcbttwcact                                            30

<210> SEQ ID NO 312
<211> LENGTH: 30
<212> TYPE: DNA
<213> ORGANISM: Homo sapiens

<400> SEQUENCE: 312
cwgsaawcat hcmvtabtcc tcbtmtcact                                            30

<210> SEQ ID NO 313
<211> LENGTH: 30
<212> TYPE: DNA
<213> ORGANISM: Homo sapiens

<400> SEQUENCE: 313
cwgsaawcat hcmvtabtcc tcbtwggact                                            30

<210> SEQ ID NO 314
<211> LENGTH: 24
<212> TYPE: DNA
<213> ORGANISM: Homo sapiens

<400> SEQUENCE: 314
cascasagwr gkrvctsgtw cact                                                  24

<210> SEQ ID NO 315
<211> LENGTH: 24
<212> TYPE: DNA
<213> ORGANISM: Homo sapiens

<400> SEQUENCE: 315
cascasagwr gkrvctsgmt cact                                                  24

<210> SEQ ID NO 316
<211> LENGTH: 24
<212> TYPE: DNA
<213> ORGANISM: Homo sapiens

<400> SEQUENCE: 316
cascasagwr gkrvctsgwg gact                                                  24

<210> SEQ ID NO 317
```

```
<211> LENGTH: 24
<212> TYPE: DNA
<213> ORGANISM: Homo sapiens

<400> SEQUENCE: 317
cascasagwr gkrvctsgcc tact                                            24

<210> SEQ ID NO 318
<211> LENGTH: 27
<212> TYPE: DNA
<213> ORGANISM: Homo sapiens

<400> SEQUENCE: 318
cascasagwr gkrvctsgcc ttwcact                                         27

<210> SEQ ID NO 319
<211> LENGTH: 27
<212> TYPE: DNA
<213> ORGANISM: Homo sapiens

<400> SEQUENCE: 319
cascasagwr gkrvctsgcc tmtcact                                         27

<210> SEQ ID NO 320
<211> LENGTH: 27
<212> TYPE: DNA
<213> ORGANISM: Homo sapiens

<400> SEQUENCE: 320
cascasagwr gkrvctsgcc twggact                                         27

<210> SEQ ID NO 321
<211> LENGTH: 27
<212> TYPE: DNA
<213> ORGANISM: Homo sapiens

<400> SEQUENCE: 321
cascasagwr gkrvctsgcc tcbtact                                         27

<210> SEQ ID NO 322
<211> LENGTH: 30
<212> TYPE: DNA
<213> ORGANISM: Homo sapiens

<400> SEQUENCE: 322
cascasagwr gkrvctsgcc tcbttwcact                                      30

<210> SEQ ID NO 323
<211> LENGTH: 30
<212> TYPE: DNA
<213> ORGANISM: Homo sapiens

<400> SEQUENCE: 323
cascasagwr gkrvctsgcc tcbtmtcact                                      30

<210> SEQ ID NO 324
<211> LENGTH: 30
<212> TYPE: DNA
<213> ORGANISM: Homo sapiens

<400> SEQUENCE: 324
cascasagwr gkrvctsgcc tcbtwggact                                      30
```

```
<210> SEQ ID NO 325
<211> LENGTH: 24
<212> TYPE: DNA
<213> ORGANISM: Homo sapiens

<400> SEQUENCE: 325
cascastmcv rtrrktggtw cact                                              24

<210> SEQ ID NO 326
<211> LENGTH: 24
<212> TYPE: DNA
<213> ORGANISM: Homo sapiens

<400> SEQUENCE: 326
cascastmcv rtrrktggmt cact                                              24

<210> SEQ ID NO 327
<211> LENGTH: 24
<212> TYPE: DNA
<213> ORGANISM: Homo sapiens

<400> SEQUENCE: 327
cascastmcv rtrrktggwg gact                                              24

<210> SEQ ID NO 328
<211> LENGTH: 24
<212> TYPE: DNA
<213> ORGANISM: Homo sapiens

<400> SEQUENCE: 328
cascastmcv rtrrktggcc tact                                              24

<210> SEQ ID NO 329
<211> LENGTH: 27
<212> TYPE: DNA
<213> ORGANISM: Homo sapiens

<400> SEQUENCE: 329
cascastmcv rtrrktggcc ttwcact                                           27

<210> SEQ ID NO 330
<211> LENGTH: 27
<212> TYPE: DNA
<213> ORGANISM: Homo sapiens

<400> SEQUENCE: 330
cascastmcv rtrrktggcc tmtcact                                           27

<210> SEQ ID NO 331
<211> LENGTH: 27
<212> TYPE: DNA
<213> ORGANISM: Homo sapiens

<400> SEQUENCE: 331
cascastmcv rtrrktggcc twggact                                           27

<210> SEQ ID NO 332
<211> LENGTH: 27
<212> TYPE: DNA
<213> ORGANISM: Homo sapiens

<400> SEQUENCE: 332
cascastmcv rtrrktggcc tcbtact                                           27
```

<210> SEQ ID NO 333
<211> LENGTH: 30
<212> TYPE: DNA
<213> ORGANISM: Homo sapiens

<400> SEQUENCE: 333
cascastmcv rtrrktggcc tcbttwcact                                    30

<210> SEQ ID NO 334
<211> LENGTH: 30
<212> TYPE: DNA
<213> ORGANISM: Homo sapiens

<400> SEQUENCE: 334
cascastmcv rtrrktggcc tcbtmtcact                                    30

<210> SEQ ID NO 335
<211> LENGTH: 30
<212> TYPE: DNA
<213> ORGANISM: Homo sapiens

<400> SEQUENCE: 335
cascastmcv rtrrktggcc tcbtwggact                                    30

<210> SEQ ID NO 336
<211> LENGTH: 24
<212> TYPE: DNA
<213> ORGANISM: Homo sapiens

<400> SEQUENCE: 336
cascastwcg rtrvkkcatw cact                                          24

<210> SEQ ID NO 337
<211> LENGTH: 24
<212> TYPE: DNA
<213> ORGANISM: Homo sapiens

<400> SEQUENCE: 337
cascastwcg rtrvkkcamt cact                                          24

<210> SEQ ID NO 338
<211> LENGTH: 24
<212> TYPE: DNA
<213> ORGANISM: Homo sapiens

<400> SEQUENCE: 338
cascastwcg rtrvkkcawg gact                                          24

<210> SEQ ID NO 339
<211> LENGTH: 24
<212> TYPE: DNA
<213> ORGANISM: Homo sapiens

<400> SEQUENCE: 339
cascastwcg rtrvkkcacc tact                                          24

<210> SEQ ID NO 340
<211> LENGTH: 27
<212> TYPE: DNA
<213> ORGANISM: Homo sapiens

<400> SEQUENCE: 340
cascastwcg rtrvkkcacc ttwcact                                       27

```
<210> SEQ ID NO 341
<211> LENGTH: 27
<212> TYPE: DNA
<213> ORGANISM: Homo sapiens

<400> SEQUENCE: 341
cascastwcg rtrvkkcacc tmtcact                                27

<210> SEQ ID NO 342
<211> LENGTH: 27
<212> TYPE: DNA
<213> ORGANISM: Homo sapiens

<400> SEQUENCE: 342
cascastwcg rtrvkkcacc twggact                                27

<210> SEQ ID NO 343
<211> LENGTH: 27
<212> TYPE: DNA
<213> ORGANISM: Homo sapiens

<400> SEQUENCE: 343
cascastwcg rtrvkkcacc tcbtact                                27

<210> SEQ ID NO 344
<211> LENGTH: 30
<212> TYPE: DNA
<213> ORGANISM: Homo sapiens

<400> SEQUENCE: 344
cascastwcg rtrvkkcacc tcbttwcact                             30

<210> SEQ ID NO 345
<211> LENGTH: 30
<212> TYPE: DNA
<213> ORGANISM: Homo sapiens

<400> SEQUENCE: 345
cascastwcg rtrvkkcacc tcbtmtcact                             30

<210> SEQ ID NO 346
<211> LENGTH: 30
<212> TYPE: DNA
<213> ORGANISM: Homo sapiens

<400> SEQUENCE: 346
cascastwcg rtrvkkcacc tcbtwggact                             30

<210> SEQ ID NO 347
<211> LENGTH: 24
<212> TYPE: DNA
<213> ORGANISM: Homo sapiens

<400> SEQUENCE: 347
atgcasrbtc ktsasabttw cact                                   24

<210> SEQ ID NO 348
<211> LENGTH: 24
<212> TYPE: DNA
<213> ORGANISM: Homo sapiens

<400> SEQUENCE: 348
```

```
atgcasrbtc ktsasabtmt cact                                          24

<210> SEQ ID NO 349
<211> LENGTH: 24
<212> TYPE: DNA
<213> ORGANISM: Homo sapiens

<400> SEQUENCE: 349
atgcasrbtc ktsasabtwg gact                                          24

<210> SEQ ID NO 350
<211> LENGTH: 24
<212> TYPE: DNA
<213> ORGANISM: Homo sapiens

<400> SEQUENCE: 350
atgcasrbtc ktsasabtcc tact                                          24

<210> SEQ ID NO 351
<211> LENGTH: 27
<212> TYPE: DNA
<213> ORGANISM: Homo sapiens

<400> SEQUENCE: 351
atgcasrbtc ktsasabtcc ttwcact                                       27

<210> SEQ ID NO 352
<211> LENGTH: 27
<212> TYPE: DNA
<213> ORGANISM: Homo sapiens

<400> SEQUENCE: 352
atgcasrbtc ktsasabtcc tmtcact                                       27

<210> SEQ ID NO 353
<211> LENGTH: 27
<212> TYPE: DNA
<213> ORGANISM: Homo sapiens

<400> SEQUENCE: 353
atgcasrbtc ktsasabtcc twggact                                       27

<210> SEQ ID NO 354
<211> LENGTH: 27
<212> TYPE: DNA
<213> ORGANISM: Homo sapiens

<400> SEQUENCE: 354
atgcasrbtc ktsasabtcc tcbtact                                       27

<210> SEQ ID NO 355
<211> LENGTH: 30
<212> TYPE: DNA
<213> ORGANISM: Homo sapiens

<400> SEQUENCE: 355
atgcasrbtc ktsasabtcc tcbttwcact                                    30

<210> SEQ ID NO 356
<211> LENGTH: 30
<212> TYPE: DNA
<213> ORGANISM: Homo sapiens

<400> SEQUENCE: 356
```

```
atgcasrbtc ktsasabtcc tcbtmtcact                                    30

<210> SEQ ID NO 357
<211> LENGTH: 30
<212> TYPE: DNA
<213> ORGANISM: Homo sapiens

<400> SEQUENCE: 357
atgcasrbtc ktsasabtcc tcbtwggact                                    30

<210> SEQ ID NO 358
<211> LENGTH: 24
<212> TYPE: DNA
<213> ORGANISM: Homo sapiens

<400> SEQUENCE: 358
cascastwct wcrvcabttw cact                                          24

<210> SEQ ID NO 359
<211> LENGTH: 24
<212> TYPE: DNA
<213> ORGANISM: Homo sapiens

<400> SEQUENCE: 359
cascastwct wcrvcabtmt cact                                          24

<210> SEQ ID NO 360
<211> LENGTH: 24
<212> TYPE: DNA
<213> ORGANISM: Homo sapiens

<400> SEQUENCE: 360
cascastwct wcrvcabtwg gact                                          24

<210> SEQ ID NO 361
<211> LENGTH: 24
<212> TYPE: DNA
<213> ORGANISM: Homo sapiens

<400> SEQUENCE: 361
cascastwct wcrvcabtcc tact                                          24

<210> SEQ ID NO 362
<211> LENGTH: 27
<212> TYPE: DNA
<213> ORGANISM: Homo sapiens

<400> SEQUENCE: 362
cascastwct wcrvcabtcc ttwcact                                       27

<210> SEQ ID NO 363
<211> LENGTH: 27
<212> TYPE: DNA
<213> ORGANISM: Homo sapiens

<400> SEQUENCE: 363
cascastwct wcrvcabtcc tmtcact                                       27

<210> SEQ ID NO 364
<211> LENGTH: 27
<212> TYPE: DNA
<213> ORGANISM: Homo sapiens
```

```
<400> SEQUENCE: 364
cascastwct wcrvcabtcc twggact                                        27

<210> SEQ ID NO 365
<211> LENGTH: 27
<212> TYPE: DNA
<213> ORGANISM: Homo sapiens

<400> SEQUENCE: 365
cascastwct wcrvcabtcc tcbtact                                        27

<210> SEQ ID NO 366
<211> LENGTH: 30
<212> TYPE: DNA
<213> ORGANISM: Homo sapiens

<400> SEQUENCE: 366
cascastwct wcrvcabtcc tcbttwcact                                     30

<210> SEQ ID NO 367
<211> LENGTH: 30
<212> TYPE: DNA
<213> ORGANISM: Homo sapiens

<400> SEQUENCE: 367
cascastwct wcrvcabtcc tcbtmtcact                                     30

<210> SEQ ID NO 368
<211> LENGTH: 30
<212> TYPE: DNA
<213> ORGANISM: Homo sapiens

<400> SEQUENCE: 368
cascastwct wcrvcabtcc tcbtwggact                                     30

<210> SEQ ID NO 369
<211> LENGTH: 24
<212> TYPE: DNA
<213> ORGANISM: Homo sapiens

<400> SEQUENCE: 369
cascwatmcr atrvcbwttw cact                                           24

<210> SEQ ID NO 370
<211> LENGTH: 24
<212> TYPE: DNA
<213> ORGANISM: Homo sapiens

<400> SEQUENCE: 370
cascwatmcr atrvcbwtmt cact                                           24

<210> SEQ ID NO 371
<211> LENGTH: 24
<212> TYPE: DNA
<213> ORGANISM: Homo sapiens

<400> SEQUENCE: 371
cascwatmcr atrvcbwtwg gact                                           24

<210> SEQ ID NO 372
<211> LENGTH: 24
<212> TYPE: DNA
<213> ORGANISM: Homo sapiens
```

```
<400> SEQUENCE: 372
cascwatmcr atrvcbwtcc tact                                          24

<210> SEQ ID NO 373
<211> LENGTH: 27
<212> TYPE: DNA
<213> ORGANISM: Homo sapiens

<400> SEQUENCE: 373
cascwatmcr atrvcbwtcc ttwcact                                       27

<210> SEQ ID NO 374
<211> LENGTH: 27
<212> TYPE: DNA
<213> ORGANISM: Homo sapiens

<400> SEQUENCE: 374
cascwatmcr atrvcbwtcc tmtcact                                       27

<210> SEQ ID NO 375
<211> LENGTH: 27
<212> TYPE: DNA
<213> ORGANISM: Homo sapiens

<400> SEQUENCE: 375
cascwatmcr atrvcbwtcc twggact                                       27

<210> SEQ ID NO 376
<211> LENGTH: 27
<212> TYPE: DNA
<213> ORGANISM: Homo sapiens

<400> SEQUENCE: 376
cascwatmcr atrvcbwtcc tcbtact                                       27

<210> SEQ ID NO 377
<211> LENGTH: 30
<212> TYPE: DNA
<213> ORGANISM: Homo sapiens

<400> SEQUENCE: 377
cascwatmcr atrvcbwtcc tcbttwcact                                    30

<210> SEQ ID NO 378
<211> LENGTH: 30
<212> TYPE: DNA
<213> ORGANISM: Homo sapiens

<400> SEQUENCE: 378
cascwatmcr atrvcbwtcc tcbtmtcact                                    30

<210> SEQ ID NO 379
<211> LENGTH: 30
<212> TYPE: DNA
<213> ORGANISM: Homo sapiens

<400> SEQUENCE: 379
cascwatmcr atrvcbwtcc tcbtwggact                                    30

<210> SEQ ID NO 380
<211> LENGTH: 14
<212> TYPE: PRT
```

<213> ORGANISM: Homo sapiens

<400> SEQUENCE: 380

Ala Lys Val Ser Tyr Leu Ser Thr Ala Ser Ser Leu Asp Tyr
1               5                   10

<210> SEQ ID NO 381
<211> LENGTH: 11
<212> TYPE: PRT
<213> ORGANISM: Homo sapiens

<400> SEQUENCE: 381

Val Arg Asp Arg Val Thr Gly Ala Phe Asp Ile
1               5                   10

<210> SEQ ID NO 382
<211> LENGTH: 8
<212> TYPE: PRT
<213> ORGANISM: Homo sapiens

<400> SEQUENCE: 382

Lys Thr His Gly Ser His Asp Asn
1               5

<210> SEQ ID NO 383
<211> LENGTH: 11
<212> TYPE: PRT
<213> ORGANISM: Homo sapiens

<400> SEQUENCE: 383

Ala Arg Asp Leu Arg Thr Gly Pro Phe Asp Tyr
1               5                   10

<210> SEQ ID NO 384
<211> LENGTH: 15
<212> TYPE: PRT
<213> ORGANISM: Homo sapiens

<400> SEQUENCE: 384

Ala Lys Asp Pro Gly Thr Thr Val Ile Met Ser Trp Phe Asp Pro
1               5                   10                  15

<210> SEQ ID NO 385
<211> LENGTH: 12
<212> TYPE: PRT
<213> ORGANISM: Homo sapiens

<400> SEQUENCE: 385

Ala Arg Arg Arg Pro Gly Gln Gly Tyr Phe Asp Phe
1               5                   10

<210> SEQ ID NO 386
<211> LENGTH: 19
<212> TYPE: PRT
<213> ORGANISM: Homo sapiens

<400> SEQUENCE: 386

Ala Arg Asp Arg Gly Ala Ser Ala Gly Gly Asn Tyr Tyr Tyr Gly
1               5                   10                  15

Met Asp Val

<210> SEQ ID NO 387
<211> LENGTH: 18
<212> TYPE: PRT

<213> ORGANISM: Homo sapiens

<400> SEQUENCE: 387

Ala Arg Asp Pro Arg Gly Ala Thr Leu Tyr Tyr Tyr Tyr Gly Met
1               5                   10                  15

Asp Val

<210> SEQ ID NO 388
<211> LENGTH: 15
<212> TYPE: PRT
<213> ORGANISM: Homo sapiens

<400> SEQUENCE: 388

Ala Lys Asp Ile Gln Tyr Gly Asn Tyr Tyr Tyr Gly Met Asp Val
1               5                   10                  15

<210> SEQ ID NO 389
<211> LENGTH: 9
<212> TYPE: PRT
<213> ORGANISM: Homo sapiens

<400> SEQUENCE: 389

Ala Arg Val Ile Asn Trp Phe Asp Pro
1               5

<210> SEQ ID NO 390
<211> LENGTH: 11
<212> TYPE: PRT
<213> ORGANISM: Homo sapiens

<400> SEQUENCE: 390

Ala Arg Thr Gly Trp Leu Gly Pro Phe Asp Tyr
1               5                   10

<210> SEQ ID NO 391
<211> LENGTH: 18
<212> TYPE: PRT
<213> ORGANISM: Homo sapiens

<400> SEQUENCE: 391

Ala Lys Asp Leu Gly Trp Ser Asp Ser Tyr Tyr Tyr Tyr Gly Met
1               5                   10                  15

Asp Val

<210> SEQ ID NO 392
<211> LENGTH: 18
<212> TYPE: PRT
<213> ORGANISM: Homo sapiens

<400> SEQUENCE: 392

Ala Arg Asp Gly Ile Thr Met Val Arg Gly Val Met Lys Asp Tyr Phe
1               5                   10                  15

Asp Tyr

<210> SEQ ID NO 393
<211> LENGTH: 13
<212> TYPE: PRT
<213> ORGANISM: Homo sapiens

<400> SEQUENCE: 393

Ala Arg Val Ser Ile Phe Gly Val Gly Thr Phe Asp Tyr
1               5                   10

<210> SEQ ID NO 394
<211> LENGTH: 16
<212> TYPE: PRT
<213> ORGANISM: Homo sapiens

<400> SEQUENCE: 394

Ala Arg Ser Arg Asp Leu Leu Leu Phe Pro His His Ala Leu Ser Pro
1               5                   10                  15

<210> SEQ ID NO 395
<211> LENGTH: 10
<212> TYPE: DNA
<213> ORGANISM: Artificial Sequence
<220> FEATURE:
<223> OTHER INFORMATION: Random 10 nucleic acids

<400> SEQUENCE: 395
atgcacagtt                                                          10

<210> SEQ ID NO 396
<211> LENGTH: 77
<212> TYPE: PRT
<213> ORGANISM: Homo sapiens

<400> SEQUENCE: 396

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly
65                  70                  75

<210> SEQ ID NO 397
<211> LENGTH: 9
<212> TYPE: PRT
<213> ORGANISM: Homo sapiens

<400> SEQUENCE: 397

Asp Thr Ala Val Tyr Tyr Cys Ala Arg
1               5

<210> SEQ ID NO 398
<211> LENGTH: 49
<212> TYPE: PRT
<213> ORGANISM: Homo sapiens

<400> SEQUENCE: 398

Ala Ile Ser Gly Ser Gly Gly Ser Thr Tyr Tyr Ala Asp Ser Val Lys
1               5                   10                  15

Gly Arg Phe Thr Ile Ser Arg Asp Asn Ser Lys Asn Thr Leu Tyr Leu
                20                  25                  30

Gln Met Asn Ser Leu Arg Ala Glu Asp Thr Ala Val Tyr Tyr Cys Ala
            35                  40                  45

Lys

<210> SEQ ID NO 399
<211> LENGTH: 99

<212> TYPE: DNA
<213> ORGANISM: Homo sapiens

<400> SEQUENCE: 399
atgcacagtt gcaatgtgta ttactatgga tctggttctt actataatgt gggcggatat    60
tattactact atggtatgga cgtatggggg caagggacc                           99

<210> SEQ ID NO 400
<211> LENGTH: 30
<212> TYPE: DNA
<213> ORGANISM: Homo sapiens

<400> SEQUENCE: 400
tattactatg gatctggttc ttactataat                                     30

<210> SEQ ID NO 401
<211> LENGTH: 42
<212> TYPE: DNA
<213> ORGANISM: Homo sapiens

<400> SEQUENCE: 401
tattattact actatggtat ggacgtatgg gggcaaggga cc                       42

<210> SEQ ID NO 402
<211> LENGTH: 10
<212> TYPE: DNA
<213> ORGANISM: Artificial Sequence
<220> FEATURE:
<223> OTHER INFORMATION: Random 10 nucleic acids

<400> SEQUENCE: 402
gacgagcttc                                                           10

<210> SEQ ID NO 403
<211> LENGTH: 29
<212> TYPE: DNA
<213> ORGANISM: Homo sapiens

<400> SEQUENCE: 403
gacgagcttc aatgcacagt tgcaatgac                                      29

<210> SEQ ID NO 404
<211> LENGTH: 29
<212> TYPE: DNA
<213> ORGANISM: Homo sapiens

<400> SEQUENCE: 404
gacgagcttc aatgcacagt tgcaatgag                                      29

<210> SEQ ID NO 405
<211> LENGTH: 29
<212> TYPE: DNA
<213> ORGANISM: Homo sapiens

<400> SEQUENCE: 405
gacgagcttc aatgcacagt tgcaatgct                                      29

<210> SEQ ID NO 406
<211> LENGTH: 29
<212> TYPE: DNA
<213> ORGANISM: Homo sapiens

<400> SEQUENCE: 406

-continued gacgagcttc aatgcacagt tgcaatgga                              29

<210> SEQ ID NO 407
<211> LENGTH: 29
<212> TYPE: DNA
<213> ORGANISM: Homo sapiens

<400> SEQUENCE: 407
gacgagcttc aatgcacagt tgcaatgtg                              29

<210> SEQ ID NO 408
<211> LENGTH: 60
<212> TYPE: DNA
<213> ORGANISM: Homo sapiens

<400> SEQUENCE: 408
tgcatcagtg cgactaacgg aagactctga ggagacggtg accaaggtgc cctggcccca    60

<210> SEQ ID NO 409
<211> LENGTH: 60
<212> TYPE: DNA
<213> ORGANISM: Homo sapiens

<400> SEQUENCE: 409
tgcatcagtg cgactaacgg aagactctga ggagacagtg accaaggtgc cacggcccca    60

<210> SEQ ID NO 410
<211> LENGTH: 60
<212> TYPE: DNA
<213> ORGANISM: Homo sapiens

<400> SEQUENCE: 410
tgcatcagtg cgactaacgg aagactctga agagacggtg accattgtcc cttggcccca    60

<210> SEQ ID NO 411
<211> LENGTH: 60
<212> TYPE: DNA
<213> ORGANISM: Homo sapiens

<400> SEQUENCE: 411
tgcatcagtg cgactaacgg aagactctga ggagacggtg accaaggttc cttggcccca    60

<210> SEQ ID NO 412
<211> LENGTH: 60
<212> TYPE: DNA
<213> ORGANISM: Homo sapiens

<400> SEQUENCE: 412
tgcatcagtg cgactaacgg aagactctga ggagacggtg accaaggttc cctggcccca    60

<210> SEQ ID NO 413
<211> LENGTH: 60
<212> TYPE: DNA
<213> ORGANISM: Homo sapiens

<400> SEQUENCE: 413
tgcatcagtg cgactaacgg aagactctga ggagacggtg accgtggtcc cttgccccca    60

<210> SEQ ID NO 414
<211> LENGTH: 155
<212> TYPE: DNA
<213> ORGANISM: Homo sapiens

<400> SEQUENCE: 414

```
gacgagcttc atgcacagtt gcaatgtgta ttactatgga tctggttctt actataatgt    60
gggcggatat tattactact atggtatgga cgtatggggg caagggacca cggtcaccgt   120
ctcctcagag tcttccgtta gtcgcactga tgcag                              155
```

<210> SEQ ID NO 415
<211> LENGTH: 22
<212> TYPE: DNA
<213> ORGANISM: Homo sapiens

<400> SEQUENCE: 415

```
cacatactac gcagactccg tg                                             22
```

<210> SEQ ID NO 416
<211> LENGTH: 44
<212> TYPE: DNA
<213> ORGANISM: Homo sapiens

<400> SEQUENCE: 416

```
caaatgaaca gcctgagagc cgaggacacg gcggtgtact actg                     44
```

<210> SEQ ID NO 417
<211> LENGTH: 44
<212> TYPE: DNA
<213> ORGANISM: Homo sapiens

<400> SEQUENCE: 417

```
aagctgagtt ctgtgaccgc cgcagacacg gcggtgtact actg                     44
```

<210> SEQ ID NO 418
<211> LENGTH: 44
<212> TYPE: DNA
<213> ORGANISM: Homo sapiens

<400> SEQUENCE: 418

```
gagctgagca gcctgagatc tgaggacacg gcggtgtact actg                     44
```

<210> SEQ ID NO 419
<211> LENGTH: 44
<212> TYPE: DNA
<213> ORGANISM: Homo sapiens

<400> SEQUENCE: 419

```
gagctgagca ggctgagatc tgacgacacg gcggtgtact actg                     44
```

<210> SEQ ID NO 420
<211> LENGTH: 44
<212> TYPE: DNA
<213> ORGANISM: Homo sapiens

<400> SEQUENCE: 420

```
cagtggagca gcctgaaggc ctcggacacg gcgatgtact actg                     44
```

<210> SEQ ID NO 421
<211> LENGTH: 44
<212> TYPE: DNA
<213> ORGANISM: Homo sapiens

<400> SEQUENCE: 421

```
gagctgagga gcctgagatc tgacgacacg gcggtgtact actg                     44
```

<210> SEQ ID NO 422

-continued

```
<211> LENGTH: 18
<212> TYPE: DNA
<213> ORGANISM: Homo sapiens

<400> SEQUENCE: 422
gtaggacagc cgggaagg                                                 18

<210> SEQ ID NO 423
<211> LENGTH: 98
<212> TYPE: PRT
<213> ORGANISM: Homo sapiens

<400> SEQUENCE: 423

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 424
<211> LENGTH: 98
<212> TYPE: PRT
<213> ORGANISM: Homo sapiens

<400> SEQUENCE: 424

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 425
<211> LENGTH: 98
<212> TYPE: PRT
<213> ORGANISM: Homo sapiens

<400> SEQUENCE: 425

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
```

```
                35                  40                  45
Gly Trp Met Asn Pro Asn Ser Gly Asn Thr Gly Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 426
<211> LENGTH: 98
<212> TYPE: PRT
<213> ORGANISM: Homo sapiens

<400> SEQUENCE: 426

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 427
<211> LENGTH: 98
<212> TYPE: PRT
<213> ORGANISM: Homo sapiens

<400> SEQUENCE: 427

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Arg
                20                  25                  30

Tyr Leu His Trp Val Arg Gln Ala Pro Gly Gln Ala Leu Glu Trp Met
            35                  40                  45

Gly Trp Ile Thr Pro Phe Asn Gly Asn Thr Asn Tyr Ala Gln Lys Phe
        50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg

<210> SEQ ID NO 428
<211> LENGTH: 98
<212> TYPE: PRT
<213> ORGANISM: Homo sapiens

<400> SEQUENCE: 428

Gln Met Gln Leu Val Gln Ser Gly Pro Glu Val Lys Lys Pro Gly Thr
1               5                   10                  15
```

Ser Val Lys Val Ser Cys Lys Ala Ser Gly Phe Thr Phe Thr Ser Ser
                20                  25                  30

Ala Val Gln Trp Val Arg Gln Ala Arg Gly Gln Arg Leu Glu Trp Ile
            35                  40                  45

Gly Trp Ile Val Val Gly Ser Gly Asn Thr Asn Tyr Ala Gln Lys Phe
        50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala

<210> SEQ ID NO 429
<211> LENGTH: 100
<212> TYPE: PRT
<213> ORGANISM: Homo sapiens

<400> SEQUENCE: 429

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Val Gly Val Gly Trp Ile Arg Gln Pro Pro Gly Lys Ala Leu Glu
            35                  40                  45

Trp Leu Ala Leu Ile Tyr Trp Asp Asp Asp Lys Arg Tyr Ser Pro Ser
        50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100

<210> SEQ ID NO 430
<211> LENGTH: 100
<212> TYPE: PRT
<213> ORGANISM: Homo sapiens

<400> SEQUENCE: 430

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
                20                  25                  30

Arg Met Gly Val Ser Trp Ile Arg Gln Pro Pro Gly Lys Ala Leu Glu
            35                  40                  45

Trp Leu Ala His Ile Phe Ser Asn Asp Glu Lys Ser Tyr Ser Thr Ser
        50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile
            100

<210> SEQ ID NO 431
<211> LENGTH: 100

-continued

<212> TYPE: PRT
<213> ORGANISM: Homo sapiens

<400> SEQUENCE: 431

Arg Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Arg Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile
            100

<210> SEQ ID NO 432
<211> LENGTH: 100
<212> TYPE: PRT
<213> ORGANISM: Homo sapiens

<400> SEQUENCE: 432

Arg Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala Arg Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile
            100

<210> SEQ ID NO 433
<211> LENGTH: 99
<212> TYPE: PRT
<213> ORGANISM: Homo sapiens

<400> SEQUENCE: 433

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys

```
                85                  90                  95

Ala Lys Asp

<210> SEQ ID NO 434
<211> LENGTH: 98
<212> TYPE: PRT
<213> ORGANISM: Homo sapiens

<400> SEQUENCE: 434

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 435
<211> LENGTH: 97
<212> TYPE: PRT
<213> ORGANISM: Homo sapiens

<400> SEQUENCE: 435

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg

<210> SEQ ID NO 436
<211> LENGTH: 98
<212> TYPE: PRT
<213> ORGANISM: Homo sapiens

<400> SEQUENCE: 436

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Ser Thr Gly Tyr Ala Asp Ser Val
    50                  55                  60
```

-continued

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg

<210> SEQ ID NO 437
<211> LENGTH: 98
<212> TYPE: PRT
<213> ORGANISM: Homo sapiens

<400> SEQUENCE: 437

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 438
<211> LENGTH: 99
<212> TYPE: PRT
<213> ORGANISM: Homo sapiens

<400> SEQUENCE: 438

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr
                20                  25                  30

Thr Met His Trp Val Arg Gln Ala Pro Gly Lys Gly Leu Glu Trp Val
            35                  40                  45

Ser Leu Ile Ser Trp Asp Gly Gly Ser Thr Tyr Tyr Ala Asp Ser Val
        50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp

<210> SEQ ID NO 439
<211> LENGTH: 100
<212> TYPE: PRT
<213> ORGANISM: Homo sapiens

<400> SEQUENCE: 439

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
                20                  25                  30

Ala Met Ser Trp Val Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
 50                  55                  60

Ser Val Lys Gly Arg Phe Thr Ile Ser Arg Asp Asp Ser Lys Ser Ile
 65                  70                  75                  80

Ala Tyr Leu Gln Met Asn Ser Leu Lys Thr Glu Asp Thr Ala Val Tyr
                 85                  90                  95

Tyr Cys Thr Arg
             100

<210> SEQ ID NO 440
<211> LENGTH: 97
<212> TYPE: PRT
<213> ORGANISM: Homo sapiens

<400> SEQUENCE: 440

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Val Ser Ser Asn
                 20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg

<210> SEQ ID NO 441
<211> LENGTH: 98
<212> TYPE: PRT
<213> ORGANISM: Homo sapiens

<400> SEQUENCE: 441

Glu Val Gln Leu Val Glu Ser Gly Gly Gly Leu Val Gln Pro Gly Gly
 1               5                  10                  15

Ser Leu Arg Leu Ser Cys Ser Ala Ser Gly Phe Thr Phe Ser Ser Tyr
                 20                  25                  30

Ala Met His Trp Val Arg Gln Ala Pro Gly Lys Gly Leu Glu Tyr Val
            35                  40                  45

Ser Ala Ile Ser Ser Asn Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Ser Ser Leu Arg Ala Glu Asp Thr Ala Val Tyr Tyr Cys
                 85                  90                  95

Val Lys

<210> SEQ ID NO 442
<211> LENGTH: 97
<212> TYPE: PRT
<213> ORGANISM: Homo sapiens

<400> SEQUENCE: 442

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg

<210> SEQ ID NO 443
<211> LENGTH: 100
<212> TYPE: PRT
<213> ORGANISM: Homo sapiens

<400> SEQUENCE: 443

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
            85                  90                  95

Tyr Cys Ala Arg
            100

<210> SEQ ID NO 444
<211> LENGTH: 100
<212> TYPE: PRT
<213> ORGANISM: Homo sapiens

<400> SEQUENCE: 444

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
            85                  90                  95

Tyr Cys Thr Arg
            100

```
<210> SEQ ID NO 445
<211> LENGTH: 98
<212> TYPE: PRT
<213> ORGANISM: Homo sapiens

<400> SEQUENCE: 445

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 446
<211> LENGTH: 98
<212> TYPE: PRT
<213> ORGANISM: Homo sapiens

<400> SEQUENCE: 446

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg

<210> SEQ ID NO 447
<211> LENGTH: 97
<212> TYPE: PRT
<213> ORGANISM: Homo sapiens

<400> SEQUENCE: 447

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
```

```
                85                  90                  95

Arg

<210> SEQ ID NO 448
<211> LENGTH: 98
<212> TYPE: PRT
<213> ORGANISM: Homo sapiens

<400> SEQUENCE: 448

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Thr Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg

<210> SEQ ID NO 449
<211> LENGTH: 101
<212> TYPE: PRT
<213> ORGANISM: Homo sapiens

<400> SEQUENCE: 449

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg
                100

<210> SEQ ID NO 450
<211> LENGTH: 98
<212> TYPE: PRT
<213> ORGANISM: Homo sapiens

<400> SEQUENCE: 450

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
```

```
                    50                  55                  60
Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg

<210> SEQ ID NO 451
<211> LENGTH: 95
<212> TYPE: PRT
<213> ORGANISM: Homo sapiens

<400> SEQUENCE: 451

Ala Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro
                 85                  90                  95

<210> SEQ ID NO 452
<211> LENGTH: 95
<212> TYPE: PRT
<213> ORGANISM: Homo sapiens

<400> SEQUENCE: 452

Ala Ile Arg Met Thr Gln Ser Pro Ser Ser Phe Ser Ala Ser Thr Gly
  1               5                  10                  15

Asp Arg Val Thr Ile Thr Cys Arg Ala Ser Gln Gly Ile Ser Ser Tyr
                 20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Cys Leu Gln Ser
 65                  70                  75                  80

Glu Asp Phe Ala Thr Tyr Tyr Cys Gln Gln Tyr Tyr Ser Tyr Pro
                 85                  90                  95

<210> SEQ ID NO 453
<211> LENGTH: 95
<212> TYPE: PRT
<213> ORGANISM: Homo sapiens

<400> SEQUENCE: 453

Ala Ile Arg Met Thr Gln Ser Pro Ser Ser Phe Ser Ala Ser Thr Gly
  1               5                  10                  15

Asp Arg Val Thr Ile Thr Cys Arg Ala Ser Gln Gly Ile Ser Ser Tyr
                 20                  25                  30

Leu Ala Trp Tyr Gln Gln Lys Pro Gly Lys Ala Pro Lys Leu Leu Ile
             35                  40                  45
```

```
Tyr Ala Ala Ser Thr Leu Gln Ser Gly Val Pro Ser Arg Phe Ser Gly
         50                  55                  60

Ser Gly Ser Gly Thr Asp Phe Thr Leu Thr Ile Ser Ser Leu Gln Ser
 65                  70                  75                  80

Glu Asp Phe Ala Thr Tyr Tyr Cys Gln Gln Tyr Tyr Ser Tyr Pro
                 85                  90                  95

<210> SEQ ID NO 454
<211> LENGTH: 95
<212> TYPE: PRT
<213> ORGANISM: Homo sapiens

<400> SEQUENCE: 454

Asp Ile Gln Leu Thr Gln Ser Pro Ser Phe Leu Ser Ala Ser Val Gly
 1                5                  10                  15

Asp Arg Val Thr Ile Thr Cys Arg Ala Ser Gln Gly Ile Ser Ser Tyr
                 20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro
                 85                  90                  95

<210> SEQ ID NO 455
<211> LENGTH: 95
<212> TYPE: PRT
<213> ORGANISM: Homo sapiens

<400> SEQUENCE: 455

Ala Ile Gln Leu Thr Gln Ser Pro Ser Ser Leu Ser Ala Ser Val Gly
 1                5                  10                  15

Asp Arg Val Thr Ile Thr Cys Arg Ala Ser Gln Gly Ile Ser Ser Ala
                 20                  25                  30

Leu Ala Trp Tyr Gln Gln Lys Pro Gly Lys Ala Pro Lys Leu Leu Ile
             35                  40                  45

Tyr Asp Ala Ser Ser Leu Glu Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro
                 85                  90                  95

<210> SEQ ID NO 456
<211> LENGTH: 95
<212> TYPE: PRT
<213> ORGANISM: Homo sapiens

<400> SEQUENCE: 456

Asp Ile Gln Met Thr Gln Ser Pro Ser Ser Leu Ser Ala Ser Val Gly
 1                5                  10                  15

Asp Arg Val Thr Ile Thr Cys Arg Ala Ser Gln Gly Ile Ser Asn Tyr
                 20                  25                  30

Leu Ala Trp Phe Gln Gln Lys Pro Gly Lys Ala Pro Lys Ser Leu Ile
             35                  40                  45

Tyr Ala Ala Ser Ser Leu Gln Ser Gly Val Pro Ser Arg Phe Ser Gly
```

-continued

```
                50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95

<210> SEQ ID NO 457
<211> LENGTH: 95
<212> TYPE: PRT
<213> ORGANISM: Homo sapiens

<400> SEQUENCE: 457

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro
                 85                  90                  95

<210> SEQ ID NO 458
<211> LENGTH: 95
<212> TYPE: PRT
<213> ORGANISM: Homo sapiens

<400> SEQUENCE: 458

Asp Ile Gln Leu Thr Gln Ser Pro Ser Ser Leu Ser Ala Ser Val Gly
  1               5                  10                  15

Asp Arg Val Thr Ile Thr Cys Arg Val Ser Gln Gly Ile Ser Ser Tyr
                 20                  25                  30

Leu Asn Trp Tyr Arg Gln Lys Pro Gly Lys Val Pro Lys Leu Leu Ile
             35                  40                  45

Tyr Ser Ala Ser Asn Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Gly Gln Arg Thr Tyr Asn Ala Pro
                 85                  90                  95

<210> SEQ ID NO 459
<211> LENGTH: 95
<212> TYPE: PRT
<213> ORGANISM: Homo sapiens

<400> SEQUENCE: 459

Asp Ile Gln Leu Thr Gln Ser Pro Ser Ser Leu Ser Ala Ser Val Gly
  1               5                  10                  15

Asp Arg Val Thr Ile Thr Cys Arg Val Ser Gln Gly Ile Ser Ser Tyr
                 20                  25                  30

Leu Asn Trp Tyr Arg Gln Lys Pro Gly Lys Val Pro Lys Leu Leu Ile
             35                  40                  45

Tyr Ser Ala Ser Asn Leu Gln Ser Gly Val Pro Ser Arg Phe Ser Gly
         50                  55                  60
```

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Thr Tyr Asn Ala Pro
                85                  90                  95

<210> SEQ ID NO 460
<211> LENGTH: 95
<212> TYPE: PRT
<213> ORGANISM: Homo sapiens

<400> SEQUENCE: 460

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 461
<211> LENGTH: 95
<212> TYPE: PRT
<213> ORGANISM: Homo sapiens

<400> SEQUENCE: 461

Asn Ile Gln Met Thr Gln Ser Pro Ser Ala Met Ser Ala Ser Val Gly
1               5                   10                  15

Asp Arg Val Thr Ile Thr Cys Arg Ala Arg Gln Gly Ile Ser Asn Tyr
            20                  25                  30

Leu Ala Trp Phe Gln Gln Lys Pro Gly Lys Val Pro Lys His Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 462
<211> LENGTH: 95
<212> TYPE: PRT
<213> ORGANISM: Homo sapiens

<400> SEQUENCE: 462

Ala Ile Arg Met Thr Gln Ser Pro Phe Ser Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Ala Lys Ala Pro Lys Leu Phe Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro
                85                  90                  95

<210> SEQ ID NO 463
<211> LENGTH: 95
<212> TYPE: PRT
<213> ORGANISM: Homo sapiens

<400> SEQUENCE: 463

Val Ile Trp Met Thr Gln Ser Pro Ser Leu Leu Ser Ala Ser Thr Gly
1               5                   10                  15

Asp Arg Val Thr Ile Ser Cys Arg Met Ser Gln Gly Ile Ser Ser Tyr
                20                  25                  30

Leu Ala Trp Tyr Gln Gln Lys Pro Gly Lys Ala Pro Glu Leu Leu Ile
            35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Phe Pro
                85                  90                  95

<210> SEQ ID NO 464
<211> LENGTH: 95
<212> TYPE: PRT
<213> ORGANISM: Homo sapiens

<400> SEQUENCE: 464

Val Ile Trp Met Thr Gln Ser Pro Ser Leu Leu Ser Ala Ser Thr Gly
1               5                   10                  15

Asp Arg Val Thr Ile Ser Cys Arg Met Ser Gln Gly Ile Ser Ser Tyr
                20                  25                  30

Leu Ala Trp Tyr Gln Gln Lys Pro Gly Lys Ala Pro Glu Leu Leu Ile
            35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Ser
65                  70                  75                  80

Glu Asp Phe Ala Thr Tyr Tyr Cys Gln Gln Tyr Tyr Ser Phe Pro
                85                  90                  95

<210> SEQ ID NO 465
<211> LENGTH: 100
<212> TYPE: PRT
<213> ORGANISM: Homo sapiens

<400> SEQUENCE: 465

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
                20                  25                  30

Asp Gly Asn Thr Tyr Leu Ser Trp Leu Gln Gln Arg Pro Gly Gln Pro
            35                  40                  45

Pro Arg Leu Leu Ile Tyr Lys Ile Ser Asn Arg Phe Ser Gly Val Pro
50                  55                  60

Asp Arg Phe Ser Gly Ser Gly Ala Gly Thr Asp Phe Thr Leu Lys Ile

```
                 65                  70                  75                  80
Ser Arg Val Glu Ala Glu Asp Val Gly Val Tyr Tyr Cys Met Gln Ala
                 85                  90                  95

Thr Gln Phe Pro
            100

<210> SEQ ID NO 466
<211> LENGTH: 100
<212> TYPE: PRT
<213> ORGANISM: Homo sapiens

<400> SEQUENCE: 466

Asp Ile Val Met Thr Gln Thr Phe Leu Ser Leu Ser Val Thr Arg Gln
1               5                   10                  15

Gln Pro Ala Ser Ile Ser Cys Lys Ser Ser Gln Ser Leu Leu His Ser
                20                  25                  30

Asp Gly Val Thr Tyr Leu Tyr Trp Tyr Leu Gln Arg Pro Gln Gln Ser
            35                  40                  45

Pro Gln Leu Leu Thr Tyr Glu Val Ser Ser Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Leu Pro
            100

<210> SEQ ID NO 467
<211> LENGTH: 100
<212> TYPE: PRT
<213> ORGANISM: Homo sapiens

<400> SEQUENCE: 467

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 468
<211> LENGTH: 101
<212> TYPE: PRT
<213> ORGANISM: Homo sapiens

<400> SEQUENCE: 468

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
                20                  25                  30
```

-continued

Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                85                  90                  95

Arg Ile Glu Phe Pro
            100

<210> SEQ ID NO 469
<211> LENGTH: 99
<212> TYPE: PRT
<213> ORGANISM: Homo sapiens

<400> SEQUENCE: 469

Glu Ile Val Met Thr Gln Thr Pro Leu Ser Leu Ser Ile Thr Pro Gly
 1               5                   10                  15

Glu Gln Ala Ser Met Ser Cys Arg Ser Ser Gln Ser Leu Leu His Ser
                20                  25                  30

Asp Gly Tyr Thr Tyr Leu Tyr Trp Phe Leu Gln Lys Ala Arg Pro Val
            35                  40                  45

Ser Thr Leu Leu Ile Tyr Glu Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Phe Gly Val Tyr Tyr Cys Met Gln Asp
                85                  90                  95

Ala Gln Asp

<210> SEQ ID NO 470
<211> LENGTH: 100
<212> TYPE: PRT
<213> ORGANISM: Homo sapiens

<400> SEQUENCE: 470

Asp Ile Val Met Thr Gln Thr Pro Leu Ser Leu Ser Val Thr Pro Gly
 1               5                   10                  15

Gln Pro Ala Ser Ile Ser Cys Lys Ser Ser Gln Ser Leu Leu His Ser
                20                  25                  30

Asp Gly Lys Thr Tyr Leu Tyr Trp Tyr Leu Gln Lys Pro Gly Gln Pro
            35                  40                  45

Pro Gln Leu Leu Ile Tyr Glu Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 471
<211> LENGTH: 100
<212> TYPE: PRT
<213> ORGANISM: Homo sapiens -continued

<400> SEQUENCE: 471

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 472
<211> LENGTH: 96
<212> TYPE: PRT
<213> ORGANISM: Homo sapiens

<400> SEQUENCE: 472

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

<210> SEQ ID NO 473
<211> LENGTH: 95
<212> TYPE: PRT
<213> ORGANISM: Homo sapiens

<400> SEQUENCE: 473

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His
                85                  90                  95

<210> SEQ ID NO 474
<211> LENGTH: 96
<212> TYPE: PRT

```
<213> ORGANISM: Homo sapiens

<400> SEQUENCE: 474

Glu Ile Val Leu Thr Gln Ser Pro Ala Thr Leu Ser Leu Ser Pro Gly
1               5                   10                  15

Glu Arg Ala Thr Leu Ser Cys Gly Ala Ser Gln Ser Val Ser Ser Ser
                20                  25                  30

Tyr Leu Ala Trp Tyr Gln Gln Lys Pro Gly Leu Ala Pro Arg Leu Leu
            35                  40                  45

Ile Tyr Asp Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 475
<211> LENGTH: 95
<212> TYPE: PRT
<213> ORGANISM: Homo sapiens

<400> SEQUENCE: 475

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Pro Pro Arg Phe Ser Gly
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro
                85                  90                  95

<210> SEQ ID NO 476
<211> LENGTH: 95
<212> TYPE: PRT
<213> ORGANISM: Homo sapiens

<400> SEQUENCE: 476

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Pro Pro Arg Phe Ser Gly
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro
                85                  90                  95

<210> SEQ ID NO 477
<211> LENGTH: 95
<212> TYPE: PRT
<213> ORGANISM: Homo sapiens
```

<400> SEQUENCE: 477

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 478
<211> LENGTH: 95
<212> TYPE: PRT
<213> ORGANISM: Homo sapiens

<400> SEQUENCE: 478

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 479
<211> LENGTH: 99
<212> TYPE: PRT
<213> ORGANISM: Homo sapiens

<400> SEQUENCE: 479

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Phe Leu
            20                  25                  30

Gly Ile Asn Leu Ile His Trp Tyr Gln Gln Lys Pro Gly Gln Pro Pro
        35                  40                  45

Lys Leu Leu Ile Tyr Gln Ala Ser Asn Lys Asp Thr Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Leu Gln Ser Lys
                85                  90                  95

Asn Phe Pro

<210> SEQ ID NO 480
<211> LENGTH: 98
<212> TYPE: PRT

<213> ORGANISM: Homo sapiens

<400> SEQUENCE: 480

Gln Ser Val Leu Thr Gln Pro Pro Ser Val Ser Glu Ala Pro Arg Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly

<210> SEQ ID NO 481
<211> LENGTH: 98
<212> TYPE: PRT
<213> ORGANISM: Homo sapiens

<400> SEQUENCE: 481

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly

<210> SEQ ID NO 482
<211> LENGTH: 98
<212> TYPE: PRT
<213> ORGANISM: Homo sapiens

<400> SEQUENCE: 482

Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Leu Ser
50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95

Ser Ala

<210> SEQ ID NO 483
<211> LENGTH: 99
<212> TYPE: PRT
<213> ORGANISM: Homo sapiens

<400> SEQUENCE: 483

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Phe

<210> SEQ ID NO 484
<211> LENGTH: 99
<212> TYPE: PRT
<213> ORGANISM: Homo sapiens

<400> SEQUENCE: 484

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Tyr Thr Phe

<210> SEQ ID NO 485
<211> LENGTH: 99
<212> TYPE: PRT
<213> ORGANISM: Homo sapiens

<400> SEQUENCE: 485

Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Val Gly Ser Tyr
            20                  25                  30

Asn Arg Val Ser Trp Tyr Gln Gln Pro Pro Gly Thr Ala Pro Lys Leu
        35                  40                  45

Met Ile Tyr Glu Val Ser Asn Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

```
Gln Ala Glu Asp Glu Ala Asp Tyr Tyr Cys Ser Leu Tyr Thr Ser Ser
                85                  90                  95

Ser Thr Phe

<210> SEQ ID NO 486
<211> LENGTH: 99
<212> TYPE: PRT
<213> ORGANISM: Homo sapiens

<400> SEQUENCE: 486

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Leu Val Ser Trp Tyr Gln Gln His Pro Gly Lys Ala Pro Lys Leu
            35                  40                  45

Met Ile Tyr Glu Gly Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Leu

<210> SEQ ID NO 487
<211> LENGTH: 99
<212> TYPE: PRT
<213> ORGANISM: Homo sapiens

<400> SEQUENCE: 487

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Leu Val Ser Trp Tyr Gln Gln His Pro Gly Lys Ala Pro Lys Leu
            35                  40                  45

Met Ile Tyr Glu Gly Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Ser Thr Leu

<210> SEQ ID NO 488
<211> LENGTH: 99
<212> TYPE: PRT
<213> ORGANISM: Homo sapiens

<400> SEQUENCE: 488

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45
```

```
Met Ile Tyr Glu Val Ser Lys Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Ser
                 85                  90                  95

Asn Asn Phe
```

<210> SEQ ID NO 489
<211> LENGTH: 96
<212> TYPE: PRT
<213> ORGANISM: Homo sapiens

<400> SEQUENCE: 489

```
Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Lys Tyr Ala
                 20                  25                  30

Tyr Trp Tyr Gln Gln Lys Ser Gly Gln Ala Pro Val Leu Val Ile Tyr
                 35                  40                  45

Glu Asp Ser Lys Arg Pro Ser Gly Ile Pro Glu Arg Phe Ser Gly Ser
 50                  55                  60

Ser Ser Gly Thr Met Ala Thr Leu Thr Ile Ser Gly Ala Gln Val Glu
 65                  70                  75                  80

Asp Glu Ala Asp Tyr Tyr Cys Tyr Ser Thr Asp Ser Ser Gly Asn His
                 85                  90                  95
```

<210> SEQ ID NO 490
<211> LENGTH: 96
<212> TYPE: PRT
<213> ORGANISM: Homo sapiens

<400> SEQUENCE: 490

```
Ser Tyr Glu Leu Thr Gln Pro His Ser Val Ser Val Ala Thr Ala Gln
 1               5                  10                  15

Met Ala Arg Ile Thr Cys Gly Gly Asn Asn Ile Gly Ser Lys Ala Val
                 20                  25                  30

His Trp Tyr Gln Gln Lys Pro Gly Gln Asp Pro Val Leu Val Ile Tyr
                 35                  40                  45

Ser Asp Ser Asn Arg Pro Ser Gly Ile Pro Glu Arg Phe Ser Gly Ser
 50                  55                  60

Asn Pro Gly Asn Thr Thr Thr Leu Thr Ile Ser Arg Ile Glu Ala Gly
 65                  70                  75                  80

Asp Glu Ala Asp Tyr Tyr Cys Gln Val Trp Asp Ser Ser Ser Asp His
                 85                  90                  95
```

<210> SEQ ID NO 491
<211> LENGTH: 96
<212> TYPE: PRT
<213> ORGANISM: Homo sapiens

<400> SEQUENCE: 491

```
Ser Tyr Glu Leu Thr Gln Pro Pro Ser Val Ser Val Ser Leu Gly Gln
 1               5                  10                  15

Met Ala Arg Ile Thr Cys Ser Gly Glu Ala Leu Pro Lys Lys Tyr Ala
                 20                  25                  30

Tyr Trp Tyr Gln Gln Lys Pro Gly Gln Phe Pro Val Leu Val Ile Tyr
                 35                  40                  45
```

```
Lys Asp Ser Glu Arg Pro Ser Gly Ile Pro Glu Arg Phe Ser Gly Ser
            50                  55                  60

Ser Ser Gly Thr Ile Val Thr Leu Thr Ile Ser Gly Val Gln Ala Glu
 65                  70                  75                  80

Asp Glu Ala Asp Tyr Tyr Cys Leu Ser Ala Asp Ser Ser Gly Thr Tyr
                    85                  90                  95

<210> SEQ ID NO 492
<211> LENGTH: 96
<212> TYPE: PRT
<213> ORGANISM: Homo sapiens

<400> SEQUENCE: 492

Ser Tyr Glu Leu Met Gln Pro Pro Ser Val Ser Val Ser Pro Gly Gln
 1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
            35                  40                  45

Lys Asp Ser Glu Arg Pro Ser Gly Ile Pro Glu Arg Phe Ser Gly Ser
            50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly Thr Tyr
                    85                  90                  95

<210> SEQ ID NO 493
<211> LENGTH: 94
<212> TYPE: PRT
<213> ORGANISM: Homo sapiens

<400> SEQUENCE: 493

Ser Tyr Glu Leu Thr Gln Pro Ser Ser Val Ser Val Ser Pro Gly Gln
 1               5                   10                  15

Thr Ala Arg Ile Thr Cys Ser Gly Asp Val Leu Ala Lys Lys Tyr Ala
            20                  25                  30

Arg Trp Phe Gln Gln Lys Pro Gly Gln Ala Pro Val Leu Val Ile Tyr
            35                  40                  45

Lys Asp Ser Glu Arg Pro Ser Gly Ile Pro Glu Arg Phe Ser Gly Ser
            50                  55                  60

Ser Ser Gly Thr Thr Val Thr Leu Thr Ile Ser Gly Ala Gln Val Glu
 65                  70                  75                  80

Asp Glu Ala Asp Tyr Tyr Cys Tyr Ser Ala Ala Asp Asn Asn
                    85                  90

<210> SEQ ID NO 494
<211> LENGTH: 95
<212> TYPE: PRT
<213> ORGANISM: Homo sapiens

<400> SEQUENCE: 494

Ser Tyr Glu Leu Thr Gln Pro Leu Ser Val Ser Val Ala Leu Gly Gln
 1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
            35                  40                  45
```

```
Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Ala
                85                  90                  95

<210> SEQ ID NO 495
<211> LENGTH: 103
<212> TYPE: PRT
<213> ORGANISM: Homo sapiens

<400> SEQUENCE: 495

Leu Pro Val Leu Thr Gln Pro Ser Ala Ser Ala Leu Leu Gly Ala
1               5                   10                  15

Ser Ile Lys Leu Thr Cys Thr Leu Ser Ser Glu His Ser Thr Tyr Thr
                20                  25                  30

Ile Glu Trp Tyr Gln Gln Arg Pro Gly Arg Ser Pro Gln Tyr Ile Met
            35                  40                  45

Lys Val Lys Ser Asp Gly Ser His Ser Lys Gly Asp Gly Ile Pro Asp
    50                  55                  60

Arg Phe Met Gly Ser Ser Ser Gly Ala Asp Arg Tyr Leu Thr Phe Ser
65                  70                  75                  80

Asn Leu Gln Ser Asp Asp Glu Ala Glu Tyr His Cys Gly Glu Ser His
                85                  90                  95

Thr Ile Asp Gly Gln Val Gly
            100

<210> SEQ ID NO 496
<211> LENGTH: 99
<212> TYPE: PRT
<213> ORGANISM: Homo sapiens

<400> SEQUENCE: 496

Gln Pro Val Leu Thr Gln Ser Ser Ala Ser Ala Ser Leu Gly Ser
1               5                   10                  15

Ser Val Lys Leu Thr Cys Thr Leu Ser Ser Gly His Ser Ser Tyr Ile
                20                  25                  30

Ile Ala Trp His Gln Gln Pro Gly Lys Ala Pro Arg Tyr Leu Met
            35                  40                  45

Lys Leu Glu Gly Ser Gly Ser Tyr Asn Lys Gly Ser Gly Val Pro Asp
    50                  55                  60

Arg Phe Ser Gly Ser Ser Ser Gly Ala Asp Arg Tyr Leu Thr Ile Ser
65                  70                  75                  80

Asn Leu Gln Leu Glu Asp Glu Ala Asp Tyr Tyr Cys Glu Thr Trp Asp
                85                  90                  95

Ser Asn Thr

<210> SEQ ID NO 497
<211> LENGTH: 104
<212> TYPE: PRT
<213> ORGANISM: Homo sapiens

<400> SEQUENCE: 497

Gln Pro Val Leu Thr Gln Pro Thr Ser Leu Ser Ala Ser Pro Gly Ala
1               5                   10                  15

Ser Ala Arg Phe Thr Cys Thr Leu Arg Ser Gly Ile Asn Val Gly Thr
                20                  25                  30
```

```
Tyr Arg Ile Tyr Trp Tyr Gln Gln Lys Pro Gly Ser Leu Pro Arg Tyr
        35                  40                  45

Leu Leu Arg Tyr Lys Ser Asp Ser Asp Lys Gln Gln Gly Ser Gly Val
50                  55                  60

Pro Ser Arg Phe Ser Gly Ser Lys Asp Ala Ser Thr Asn Ala Gly Leu
65                  70                  75                  80

Leu Leu Ile Ser Gly Leu Gln Ser Glu Asp Glu Ala Asp Tyr Tyr Cys
                85                  90                  95

Ala Ile Trp Tyr Ser Ser Thr Ser
                100

<210> SEQ ID NO 498
<211> LENGTH: 98
<212> TYPE: PRT
<213> ORGANISM: Homo sapiens

<400> SEQUENCE: 498

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
        35                  40                  45

Leu Ile Tyr Asp Thr Ser Asn Lys His Ser Trp Thr Pro Ala Arg Phe
50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
                85                  90                  95

Ala Arg

<210> SEQ ID NO 499
<211> LENGTH: 98
<212> TYPE: PRT
<213> ORGANISM: Homo sapiens

<400> SEQUENCE: 499

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile

<210> SEQ ID NO 500
<211> LENGTH: 104
<212> TYPE: PRT
<213> ORGANISM: Homo sapiens

<400> SEQUENCE: 500
```

```
Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Val Met
        35                  40                  45

Arg Val Gly Thr Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Val
            100

<210> SEQ ID NO 501
<211> LENGTH: 17
<212> TYPE: DNA
<213> ORGANISM: Homo sapiens

<400> SEQUENCE: 501
ggtacaactg gaacgac                                                          17

<210> SEQ ID NO 502
<211> LENGTH: 17
<212> TYPE: DNA
<213> ORGANISM: Homo sapiens

<400> SEQUENCE: 502
ggtataaccg gaaccac                                                          17

<210> SEQ ID NO 503
<211> LENGTH: 17
<212> TYPE: DNA
<213> ORGANISM: Homo sapiens

<400> SEQUENCE: 503
ggtataactg gaacgac                                                          17

<210> SEQ ID NO 504
<211> LENGTH: 17
<212> TYPE: DNA
<213> ORGANISM: Homo sapiens

<400> SEQUENCE: 504
ggtataactg gaactac                                                          17

<210> SEQ ID NO 505
<211> LENGTH: 28
<212> TYPE: DNA
<213> ORGANISM: Homo sapiens

<400> SEQUENCE: 505
agcatattgt ggtggtgatt gctattcc                                              28

<210> SEQ ID NO 506
<211> LENGTH: 28
<212> TYPE: DNA
<213> ORGANISM: Homo sapiens

<400> SEQUENCE: 506
```
agcatattgt ggtggtgact gctattcc                28

<210> SEQ ID NO 507
<211> LENGTH: 31
<212> TYPE: DNA
<213> ORGANISM: Homo sapiens

<400> SEQUENCE: 507
aggatattgt actaatggtg tatgctatac c            31

<210> SEQ ID NO 508
<211> LENGTH: 37
<212> TYPE: DNA
<213> ORGANISM: Homo sapiens

<400> SEQUENCE: 508
gtattatgat tacgtttggg ggagttatgc ttatacc      37

<210> SEQ ID NO 509
<211> LENGTH: 31
<212> TYPE: DNA
<213> ORGANISM: Homo sapiens

<400> SEQUENCE: 509
gtattacgat attttgactg gttattataa c            31

<210> SEQ ID NO 510
<211> LENGTH: 19
<212> TYPE: DNA
<213> ORGANISM: Homo sapiens

<400> SEQUENCE: 510
tgactacggt ggtaactcc                          19

<210> SEQ ID NO 511
<211> LENGTH: 16
<212> TYPE: DNA
<213> ORGANISM: Homo sapiens

<400> SEQUENCE: 511
tgactacagt aactac                             16

<210> SEQ ID NO 512
<211> LENGTH: 23
<212> TYPE: DNA
<213> ORGANISM: Homo sapiens

<400> SEQUENCE: 512
gtggatatag tggctacgat tac                     23

<210> SEQ ID NO 513
<211> LENGTH: 20
<212> TYPE: DNA
<213> ORGANISM: Homo sapiens

<400> SEQUENCE: 513
gtagagatgg ctacaattac                         20

<210> SEQ ID NO 514
<211> LENGTH: 18
<212> TYPE: DNA
<213> ORGANISM: Homo sapiens

```
<400> SEQUENCE: 514
gggtatagca gcggctac                                                    18

<210> SEQ ID NO 515
<211> LENGTH: 18
<212> TYPE: DNA
<213> ORGANISM: Homo sapiens

<400> SEQUENCE: 515
gagtatagca gctcgtcc                                                    18

<210> SEQ ID NO 516
<211> LENGTH: 11
<212> TYPE: DNA
<213> ORGANISM: Homo sapiens

<400> SEQUENCE: 516
ctaactgggg a                                                           11

<210> SEQ ID NO 517
<211> LENGTH: 5
<212> TYPE: PRT
<213> ORGANISM: Homo sapiens

<400> SEQUENCE: 517

Gly Thr Thr Gly Thr
1               5

<210> SEQ ID NO 518
<211> LENGTH: 5
<212> TYPE: PRT
<213> ORGANISM: Homo sapiens

<400> SEQUENCE: 518

Val Gln Leu Glu Arg
1               5

<210> SEQ ID NO 519
<211> LENGTH: 5
<212> TYPE: PRT
<213> ORGANISM: Homo sapiens

<400> SEQUENCE: 519

Tyr Asn Trp Asn Asp
1               5

<210> SEQ ID NO 520
<211> LENGTH: 5
<212> TYPE: PRT
<213> ORGANISM: Homo sapiens

<400> SEQUENCE: 520

Val Val Pro Val Val
1               5

<210> SEQ ID NO 521
<211> LENGTH: 5
<212> TYPE: PRT
<213> ORGANISM: Homo sapiens

<400> SEQUENCE: 521

Ser Phe Gln Leu Tyr
1               5
```

```
<210> SEQ ID NO 522
<211> LENGTH: 5
<212> TYPE: PRT
<213> ORGANISM: Homo sapiens

<400> SEQUENCE: 522

Arg Ser Ser Cys Thr
1               5

<210> SEQ ID NO 523
<211> LENGTH: 30
<212> TYPE: PRT
<213> ORGANISM: Homo sapiens

<400> SEQUENCE: 523

Ala Lys Gly Pro Ser Val Pro Ala Ala Arg Ala Glu Tyr Phe Gln His
1               5                   10                  15

Gly Pro Ser Val Pro Ala Ala Arg Ala Glu Tyr Phe Gln His
            20                  25                  30

<210> SEQ ID NO 524
<211> LENGTH: 32
<212> TYPE: PRT
<213> ORGANISM: Homo sapiens

<400> SEQUENCE: 524

Ala Arg Glu Gly Gly Leu Gly Tyr Tyr Tyr Arg Glu Trp Tyr Phe Asp
1               5                   10                  15

Leu Glu Gly Gly Leu Gly Tyr Tyr Tyr Arg Glu Trp Tyr Phe Asp Leu
            20                  25                  30

<210> SEQ ID NO 525
<211> LENGTH: 22
<212> TYPE: PRT
<213> ORGANISM: Homo sapiens

<400> SEQUENCE: 525

Ala Lys Pro Asp Tyr Gly Ala Glu Tyr Phe Gln His Pro Asp Tyr Gly
1               5                   10                  15

Ala Glu Tyr Phe Gln His
            20

<210> SEQ ID NO 526
<211> LENGTH: 26
<212> TYPE: PRT
<213> ORGANISM: Homo sapiens

<400> SEQUENCE: 526

Ala Lys Glu Ile Val Val Pro Ser Ala Glu Tyr Phe Gln His Glu Ile
1               5                   10                  15

Val Val Pro Ser Ala Glu Tyr Phe Gln His
            20                  25

<210> SEQ ID NO 527
<211> LENGTH: 16
<212> TYPE: PRT
<213> ORGANISM: Homo sapiens

<400> SEQUENCE: 527

Tyr Tyr Cys Gln Glu Ser Phe His Ile Pro Tyr Thr Phe Gly Gly Gly
1               5                   10                  15
```

-continued

```
<210> SEQ ID NO 528
<211> LENGTH: 11
<212> TYPE: PRT
<213> ORGANISM: Homo sapiens

<400> SEQUENCE: 528

Thr Phe Gly Gln Gly Thr Lys Val Glu Ile Lys
1               5                   10

<210> SEQ ID NO 529
<211> LENGTH: 6
<212> TYPE: PRT
<213> ORGANISM: Homo sapiens

<400> SEQUENCE: 529

Thr Phe Gly Gly Gly Thr
1               5

<210> SEQ ID NO 530
<211> LENGTH: 4
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Ser, Val, Leu, or Tyr

<400> SEQUENCE: 530

Asp Xaa Trp Gly
1

<210> SEQ ID NO 531
<211> LENGTH: 99
<212> TYPE: PRT
<213> ORGANISM: Homo sapiens

<400> SEQUENCE: 531

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly

<210> SEQ ID NO 532
<211> LENGTH: 98
<212> TYPE: PRT
<213> ORGANISM: Homo sapiens

<400> SEQUENCE: 532

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
```

-continued

```
                 35                  40                  45
Ile Tyr Ser Asn Asn Gln Arg Pro Ser Val Pro Asp Arg Phe Ser
 50                  55                  60
Gly Ser Lys Ser Gly Thr Ser Ala Ser Leu Ala Ile Ser Gly Leu Gln
 65                  70                  75                  80
Ser Glu Asp Glu Ala Asp Tyr Tyr Cys Ala Ala Trp Asp Asp Ser Leu
                 85                  90                  95
Asn Gly
```

<210> SEQ ID NO 533
<211> LENGTH: 98
<212> TYPE: PRT
<213> ORGANISM: Homo sapiens

<400> SEQUENCE: 533

```
Gln Ser Val Leu Thr Gln Pro Pro Ser Val Ser Ala Ala Pro Gly Gln
 1               5                  10                  15
Lys Val Thr Ile Ser Cys Ser Gly Ser Ser Ser Asn Ile Gly Asn Asn
                 20                  25                  30
Tyr Val Ser Trp Tyr Gln Gln Leu Pro Gly Thr Ala Pro Lys Leu Leu
                 35                  40                  45
Ile Tyr Asp Asn Asn Lys Arg Pro Ser Gly Ile Pro Asp Arg Phe Ser
 50                  55                  60
Gly Ser Lys Ser Gly Thr Ser Ala Thr Leu Gly Ile Thr Gly Leu Gln
 65                  70                  75                  80
Thr Gly Asp Glu Ala Asp Tyr Tyr Cys Gly Thr Trp Asp Ser Ser Leu
                 85                  90                  95
Ser Ala
```

<210> SEQ ID NO 534
<211> LENGTH: 99
<212> TYPE: PRT
<213> ORGANISM: Homo sapiens

<400> SEQUENCE: 534

```
Gln Ser Ala Leu Thr Gln Pro Ala Ser Val Ser Gly Ser Pro Gly Gln
 1               5                  10                  15
Ser Ile Thr Ile Ser Cys Thr Gly Thr Ser Ser Asp Val Gly Gly Tyr
                 20                  25                  30
Asn Tyr Val Ser Trp Tyr Gln Gln His Pro Gly Lys Ala Pro Lys Leu
                 35                  40                  45
Met Ile Tyr Glu Val Ser Asn Arg Pro Ser Gly Val Ser Asn Arg Phe
 50                  55                  60
Ser Gly Ser Lys Ser Gly Asn Thr Ala Ser Leu Thr Ile Ser Gly Leu
 65                  70                  75                  80
Gln Ala Glu Asp Glu Ala Asp Tyr Tyr Cys Ser Ser Tyr Thr Ser Ser
                 85                  90                  95
Ser Thr Leu
```

<210> SEQ ID NO 535
<211> LENGTH: 95
<212> TYPE: PRT
<213> ORGANISM: Homo sapiens

<400> SEQUENCE: 535

```
Ser Tyr Glu Leu Thr Gln Pro Ser Val Ser Val Ser Pro Gly Gln
 1               5                  10                  15
```

```
Thr Ala Ser Ile Thr Cys Ser Gly Asp Lys Leu Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Ala
                85                  90                  95
```

<210> SEQ ID NO 536
<211> LENGTH: 96
<212> TYPE: PRT
<213> ORGANISM: Homo sapiens

<400> SEQUENCE: 536

```
Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                85                  90                  95
```

<210> SEQ ID NO 537
<211> LENGTH: 96
<212> TYPE: PRT
<213> ORGANISM: Homo sapiens

<400> SEQUENCE: 537

```
Ser Tyr Val Leu Thr Gln Pro Pro Ser Val Ser Val Ala Pro Gly Lys
 1               5                  10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                85                  90                  95
```

<210> SEQ ID NO 538
<211> LENGTH: 99
<212> TYPE: PRT
<213> ORGANISM: Homo sapiens

<400> SEQUENCE: 538

```
Gln Leu Val Leu Thr Gln Ser Pro Ser Ala Ser Ala Ser Leu Gly Ala
 1               5                  10                  15
```

```
Ser Val Lys Leu Thr Cys Thr Leu Ser Ser Gly His Ser Ser Tyr Ala
            20                  25                  30

Ile Ala Trp His Gln Gln Pro Glu Lys Gly Pro Arg Tyr Leu Met
        35                  40                  45

Lys Leu Asn Ser Asp Gly Ser His Ser Lys Gly Asp Gly Ile Pro Asp
 50                  55                  60

Arg Phe Ser Gly Ser Ser Gly Ala Glu Arg Tyr Leu Thr Ile Ser
 65                  70                  75                  80

Ser Leu Gln Ser Glu Asp Glu Ala Asp Tyr Tyr Cys Gln Thr Trp Gly
                85                  90                  95

Thr Gly Ile
```

<210> SEQ ID NO 539
<211> LENGTH: 98
<212> TYPE: PRT
<213> ORGANISM: Homo sapiens

<400> SEQUENCE: 539

```
Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                85                  90                  95

Ser Asn
```

<210> SEQ ID NO 540
<211> LENGTH: 104
<212> TYPE: PRT
<213> ORGANISM: Homo sapiens

<400> SEQUENCE: 540

```
Gln Ala Val Leu Thr Gln Pro Ala Ser Leu Ser Ala Ser Pro Gly Ala
 1               5                  10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
 50                  55                  60

Pro Ser Arg Phe Ser Gly Ser Lys Asp Ala Ser Ala Asn Ala Gly Ile
 65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Ser
            100
```

<210> SEQ ID NO 541
<211> LENGTH: 98
<212> TYPE: PRT
<213> ORGANISM: Homo sapiens -continued

<400> SEQUENCE: 541

Gln Thr Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Tyr Tyr Pro Asn Trp Phe Gln Gln Lys Pro Gly Gln Ala Pro Arg Ala
        35                  40                  45

Leu Ile Tyr Ser Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Tyr Tyr Gly Gly
                85                  90                  95

Ala Gln

<210> SEQ ID NO 542
<211> LENGTH: 6
<212> TYPE: PRT
<213> ORGANISM: Homo sapiens

<400> SEQUENCE: 542

Gly Tyr Tyr Tyr Asp Val
1               5

<210> SEQ ID NO 543
<211> LENGTH: 16
<212> TYPE: PRT
<213> ORGANISM: Homo sapiens

<400> SEQUENCE: 543

Asp Gly Gly Tyr Cys Ser Gly Ser Cys Tyr Ser Tyr Phe Gln His
1               5                   10                  15

<210> SEQ ID NO 544
<211> LENGTH: 14
<212> TYPE: PRT
<213> ORGANISM: Homo sapiens

<400> SEQUENCE: 544

Glu Arg Ile Thr Ile Phe Gly Val Gly Gly Tyr Phe Asp Tyr
1               5                   10

<210> SEQ ID NO 545
<211> LENGTH: 14
<212> TYPE: PRT
<213> ORGANISM: Homo sapiens

<400> SEQUENCE: 545

Pro Pro Val Leu Leu Trp Phe Gly Glu Leu Leu Asp Asp Leu
1               5                   10

<210> SEQ ID NO 546
<211> LENGTH: 21
<212> TYPE: PRT
<213> ORGANISM: Homo sapiens

<400> SEQUENCE: 546

Gly Gly Ser Gly Tyr Tyr Tyr Gly Ser Gly Ser Tyr Tyr Asn Pro Ala
1               5                   10                  15

Glu Tyr Phe Gln His

<210> SEQ ID NO 547
<211> LENGTH: 16
<212> TYPE: PRT
<213> ORGANISM: Homo sapiens

<400> SEQUENCE: 547

Asp Arg Gly Val Ile Ile Met Tyr Tyr Tyr Tyr Gly Met Asp Val
1               5                   10                  15

<210> SEQ ID NO 548
<211> LENGTH: 21
<212> TYPE: PRT
<213> ORGANISM: Homo sapiens

<400> SEQUENCE: 548

Glu Ser Gly Tyr Tyr Tyr Asp Ser Ser Gly Tyr Tyr Thr Gly Leu
1               5                   10                  15

Trp Tyr Phe Asp Leu
            20

<210> SEQ ID NO 549
<211> LENGTH: 11
<212> TYPE: PRT
<213> ORGANISM: Homo sapiens

<400> SEQUENCE: 549

Ser Asp Tyr Gly Asp Tyr Ser Ile Phe Asp Ile
1               5                   10

<210> SEQ ID NO 550
<211> LENGTH: 13
<212> TYPE: PRT
<213> ORGANISM: Homo sapiens

<400> SEQUENCE: 550

Pro Gly Trp Phe Gly Pro Ser Tyr Tyr Gly Met Asp Val
1               5                   10

<210> SEQ ID NO 551
<211> LENGTH: 13
<212> TYPE: PRT
<213> ORGANISM: Homo sapiens

<400> SEQUENCE: 551

Cys Ser Gly Gly Ser Cys Ala Tyr Asn Trp Phe Asp Pro
1               5                   10

<210> SEQ ID NO 552
<211> LENGTH: 12
<212> TYPE: PRT
<213> ORGANISM: Homo sapiens

<400> SEQUENCE: 552

Trp Thr Phe Gly Gln Gly Thr Lys Val Glu Ile Lys
1               5                   10

<210> SEQ ID NO 553
<211> LENGTH: 12
<212> TYPE: PRT
<213> ORGANISM: Homo sapiens

<400> SEQUENCE: 553

Tyr Thr Phe Gly Gln Gly Thr Lys Leu Glu Ile Lys
1               5                   10

<210> SEQ ID NO 554
<211> LENGTH: 12
<212> TYPE: PRT
<213> ORGANISM: Homo sapiens

<400> SEQUENCE: 554

Phe Thr Phe Gly Pro Gly Thr Lys Val Asp Ile Lys
1               5                   10

<210> SEQ ID NO 555
<211> LENGTH: 12
<212> TYPE: PRT
<213> ORGANISM: Homo sapiens

<400> SEQUENCE: 555

Leu Thr Phe Gly Gly Gly Thr Lys Val Glu Ile Lys
1               5                   10

<210> SEQ ID NO 556
<211> LENGTH: 12
<212> TYPE: PRT
<213> ORGANISM: Homo sapiens

<400> SEQUENCE: 556

Ile Thr Phe Gly Gln Gly Thr Arg Leu Glu Ile Lys
1               5                   10

<210> SEQ ID NO 557
<211> LENGTH: 12
<212> TYPE: PRT
<213> ORGANISM: Homo sapiens

<400> SEQUENCE: 557

Tyr Val Phe Gly Thr Gly Thr Lys Val Thr Val Leu
1               5                   10

<210> SEQ ID NO 558
<211> LENGTH: 12
<212> TYPE: PRT
<213> ORGANISM: Homo sapiens

<400> SEQUENCE: 558

Val Val Phe Gly Gly Gly Thr Lys Leu Thr Val Leu
1               5                   10

<210> SEQ ID NO 559
<211> LENGTH: 12
<212> TYPE: PRT
<213> ORGANISM: Homo sapiens

<400> SEQUENCE: 559

Trp Val Phe Gly Gly Gly Thr Lys Leu Thr Val Leu
1               5                   10

<210> SEQ ID NO 560
<211> LENGTH: 12
<212> TYPE: PRT
<213> ORGANISM: Homo sapiens

<400> SEQUENCE: 560

Val Val Phe Gly Gly Gly Thr Lys Leu Thr Val Leu
1               5                   10

-continued

<210> SEQ ID NO 561
<211> LENGTH: 12
<212> TYPE: PRT
<213> ORGANISM: Homo sapiens

<400> SEQUENCE: 561

Asn Val Phe Gly Ser Gly Thr Lys Val Thr Val Leu
1               5                   10

<210> SEQ ID NO 562
<211> LENGTH: 12
<212> TYPE: PRT
<213> ORGANISM: Homo sapiens

<400> SEQUENCE: 562

Ala Val Phe Gly Gly Gly Thr Gln Leu Thr Val Leu
1               5                   10

<210> SEQ ID NO 563
<211> LENGTH: 12
<212> TYPE: PRT
<213> ORGANISM: Homo sapiens

<400> SEQUENCE: 563

Ala Val Phe Gly Gly Gly Thr Gln Leu Thr Ala Leu
1               5                   10

<210> SEQ ID NO 564
<211> LENGTH: 100
<212> TYPE: PRT
<213> ORGANISM: Homo sapiens

<400> SEQUENCE: 564

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser
            100

<210> SEQ ID NO 565
<211> LENGTH: 97
<212> TYPE: PRT
<213> ORGANISM: Homo sapiens
<220> FEATURE:
<221> NAME/KEY: misc_feature
<222> LOCATION: (97)..(97)
<223> OTHER INFORMATION: His or Gln

<400> SEQUENCE: 565

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala

```
            20                  25                  30

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Xaa

<210> SEQ ID NO 566
<211> LENGTH: 97
<212> TYPE: PRT
<213> ORGANISM: Homo sapiens

<400> SEQUENCE: 566

Ser Tyr Val Leu Thr Gln Pro Pro Ser Val Ser Val Ala Pro Gly Lys
  1               5                  10                  15

Thr Ala Arg Ile Thr Cys Gly Gly Asn Asn Ile Gly Ser Lys Ser Val
             20                  25                  30

His Trp Tyr Gln Gln Lys Pro Gly Gln Ala Pro Val Leu Val Ile Tyr
         35                  40                  45

Tyr Asp Ser Asp Arg Pro Ser Gly Ile Pro Glu Arg Phe Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Pro

<210> SEQ ID NO 567
<211> LENGTH: 99
<212> TYPE: PRT
<213> ORGANISM: Homo sapiens
<220> FEATURE:
<221> NAME/KEY: misc_feature
<222> LOCATION: (99)..(99)
<223> OTHER INFORMATION: His or Gln

<400> SEQUENCE: 567

Asn Phe Met Leu Thr Gln Pro His Ser Val Ser Glu Ser Pro Gly Lys
  1               5                  10                  15

Thr Val Thr Ile Ser Cys Thr Arg Ser Ser Gly Ser Ile Ala Ser Asn
             20                  25                  30

Tyr Val Gln Trp Tyr Gln Gln Arg Pro Gly Ser Ser Pro Thr Thr Val
         35                  40                  45

Ile Tyr Glu Asp Asn Gln Arg Pro Ser Gly Val Pro Asp Arg Phe Ser
     50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Ser Asn Xaa

<210> SEQ ID NO 568
<211> LENGTH: 12
```

```
<212> TYPE: PRT
<213> ORGANISM: Homo sapiens

<400> SEQUENCE: 568

Tyr Val Phe Gly Gly Gly Thr Lys Leu Thr Val Leu
1               5                   10

<210> SEQ ID NO 569
<211> LENGTH: 12
<212> TYPE: PRT
<213> ORGANISM: Homo sapiens

<400> SEQUENCE: 569

Ala Val Phe Gly Gly Gly Thr Lys Leu Thr Val Leu
1               5                   10

<210> SEQ ID NO 570
<211> LENGTH: 188
<212> TYPE: DNA
<213> ORGANISM: Homo sapiens

<400> SEQUENCE: 570
gctattagtg gtagtggtgg tagcacatac tacgcagact ccgtgaaggg ccggttcacc      60
atctccagag acaattccaa gaacacgctg tatctgcaaa tgaacagcct gagagccgag     120
gacacggcgg tgtactactg cgccaaggac cattgcgctt agcctaggtt atattcccca     180
gaacatca                                                              188

<210> SEQ ID NO 571
<211> LENGTH: 894
<212> TYPE: DNA
<213> ORGANISM: Homo sapiens

<400> SEQUENCE: 571
gacacggcgg tgtactactg cgccagagac cattgcgctt agcctaggtt atattcccca      60
gaacatcagg ttaatggcgt ttttgatgtc attttcgcgg tggctgagat cagccacttc     120
ttccccgata acggaaaccg gcacactggc catatcggtg gtcatcatgc gccagctttc     180
atccccgata tgcaccaccg ggtaaagttc acgggagact ttatctgaca gcagacgtgc     240
actggccagg gggatcacca tccgtcgccc gggcgtgtca ataatatcac tctgtacatc     300
cacaaacaga cgataacggc tctctctttt ataggtgtaa accttaaact gcatttcacc     360
agcccctgtt ctcgtcagca aaagagccgt tcatttcaat aaaccgggcg acctcagcca     420
tcccttcctg attttccgct ttccagcgtt cggcacgcag acgacgggct tcattctgca     480
tggttgtgct taccagaccg gagatattga catcatatat gccttgagca actgatagct     540
gtcgctgtca actgtcactg taatacgctg cttcatagca tacctctttt tgacatactt     600
cgggtataca tatcagtata tattcttata ccgcaaaaat cagcgcgcaa atatgcatac     660
tgttatctgg ctttttagtaa gccgcctagg tcatcagaag acaactcagc tagcaccaag     720
ggcccatcgg tctttcccct ggcaccctcc tccaagagca cctctggggg cacagcggcc     780
ctgggctgcc tggtcaagga ctacttcccc gaaccggtga cggtgtcgtg gaactcaggc     840
gccctgacca gcggcgtgca caccttcccg gctgtcctac agtcctcagg actc           894

<210> SEQ ID NO 572
<211> LENGTH: 489
<212> TYPE: DNA
<213> ORGANISM: Homo sapiens
```

<400> SEQUENCE: 572
gctattagtg gtagtggtgg tagcacatac tacgcagact ccgtgaaggg ccggttcacc    60
atctccagag acaattccaa gaacacgctg tatctgcaaa tgaacagcct gagagccgag   120
gacacggcgg tgtactactg cgccaaggac gccggaggat attattatgg gtcaggaagc   180
tattacaacg ctgcggctta ctactactat tatggcatgg acgtgtgggg acaaggtaca   240
acagtcaccg tctcctcagc tagcaccaag ggcccatcgg tctttcccct ggcaccctcc   300
tccaagagca cctctggggg cacagcggcc ctgggctgcc tggtcaagga ctacttcccc   360
gaaccggtga cggtgtcgtg gaactcaggc gccctgacca gcggcgtgca caccttcccg   420
gctgtcctac agtcctcagg actctactcc ctcagcagcg tggtgaccgt gccctccagc   480
agcttgggc                                                          489

<210> SEQ ID NO 573
<211> LENGTH: 240
<212> TYPE: DNA
<213> ORGANISM: Homo sapiens

<400> SEQUENCE: 573
ctctgtgaag ggccgattca ccatctccag agacaatgcc aagaactcac tgtatctgca    60
aatgaacagc ctgagagctg aggacacggc ggtgtactac tgcgccagag gccaataggg   120
ccaactataa caggggtacc ccggccaata aggccgtcac cgtctcctca gctagcacca   180
agggcccatc ggtcttcccc ctggcaccct cctccaagag cacctctggg ggcacagcgg   240

<210> SEQ ID NO 574
<211> LENGTH: 55
<212> TYPE: DNA
<213> ORGANISM: Homo sapiens

<400> SEQUENCE: 574
tctgcaaatg aacagcctga gagctgagga cacggcggtg tactactgcg ccaga          55

<210> SEQ ID NO 575
<211> LENGTH: 55
<212> TYPE: DNA
<213> ORGANISM: Homo sapiens

<400> SEQUENCE: 575
tctgcaaatg aacagcctga gagccgagga cacggcggtg tactactgcg ccaga          55

<210> SEQ ID NO 576
<211> LENGTH: 55
<212> TYPE: DNA
<213> ORGANISM: Homo sapiens

<400> SEQUENCE: 576
tctgcaaatg aacagcctga gagccgagga cacggcggtg tactactgcg ccaga          55

<210> SEQ ID NO 577
<211> LENGTH: 55
<212> TYPE: DNA
<213> ORGANISM: Homo sapiens

<400> SEQUENCE: 577
tctgcaaatg aacagcctga gagccgagga cacggcggtg tactactgcg ccaag          55

<210> SEQ ID NO 578
<211> LENGTH: 9

```
<212> TYPE: PRT
<213> ORGANISM: Homo sapiens

<400> SEQUENCE: 578

Asp Thr Ala Val Tyr Tyr Cys Ala Lys
1               5

<210> SEQ ID NO 579
<211> LENGTH: 9
<212> TYPE: PRT
<213> ORGANISM: Homo sapiens

<400> SEQUENCE: 579

Asp Thr Ala Val Tyr Tyr Cys Ala Arg
1               5

<210> SEQ ID NO 580
<211> LENGTH: 6
<212> TYPE: PRT
<213> ORGANISM: Homo sapiens

<400> SEQUENCE: 580

Ser Ser Ala Ser Thr Lys
1               5

<210> SEQ ID NO 581
<211> LENGTH: 633
<212> TYPE: DNA
<213> ORGANISM: Homo sapiens

<400> SEQUENCE: 581
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggcggtgt actactgcgc caaggagggc     300
ggacctgggt attgcagttc aacttcttgt tataccagg aggctacta ctattactac       360
ggcatggacg tgtggggaca aggtacaaca gtcaccgtct cctcagctag caccaagggc     420
ccatcggtct tccccctggc accctcctcc aagagcacct ctgggggcac agcggccctg     480
ggctgcctgg tcaaggacta cttccccgaa ccggtgacgg tgtcgtggaa ctcaggcgcc     540
ctgaccagcg gcgtgcacac cttcccggct gtcctacagt cctcaggact ctactccctc     600
agcagcgtgg tgaccgtgcc ctccagcagc ttg                                  633

<210> SEQ ID NO 582
<211> LENGTH: 830
<212> TYPE: DNA
<213> ORGANISM: Homo sapiens

<400> SEQUENCE: 582
aatgcgcttt ccgagcattt ttaccgcagt tctgtttgcg gcgagcagcg cgctggcggc      60
gccggcgaac accaccaccg aagatgaaac cgcgcagatt ccggcggaag cggtgattga     120
ttatagcgat ctggaaggcg attttgatgc ggcggcgctg ccgctgagca acagcaccaa     180
caacggcctg agcagcacca acaccaccat tgcgagcatt gcggcgaaag aagaaggcgt     240
gcagctggat aaacgcgaca tccagatgac ccagtctcca tcctccctgt ctgcatctgt     300
aggagacaga gtcaccatca cttgccgggc aagtcagagc attagcagct atttaaattg     360
```

```
gtatcagcag aaaccaggga aagcccctaa gctcctgatc tatgctgcat ccagtttgca    420
aagtggggtc ccatcaaggt tcagtggcag tggatctggg acagatttca ctctcaccat    480
cagcagtctg caacctgaag attttgcaac ttactactgt caacagagtt acagtacccc    540
tctcactttt ggcggaggga ccaaggttga gatcaaacgt acggtggccg ctccttccgt    600
gttcatcttc cctccctccg acgagcagct gaagtccggc accgccagcg tggtgtgcct    660
gctgaacaac ttctaccctc gggaggccaa ggtgcagtgg aaggtggaca acgccctgca    720
gagcggcaac tcccaggagt ccgtcaccga gcaggactcc aaggacagca cctactccct    780
gtcctccacc ctgaccctgt ttcaaccggg gcgagtgcta ggcggccgca               830
```

<210> SEQ ID NO 583
<211> LENGTH: 5
<212> TYPE: PRT
<213> ORGANISM: Homo sapiens

<400> SEQUENCE: 583

Glu Tyr Phe Gln His
1               5

<210> SEQ ID NO 584
<211> LENGTH: 4
<212> TYPE: PRT
<213> ORGANISM: Homo sapiens

<400> SEQUENCE: 584

Tyr Phe Gln His
1

<210> SEQ ID NO 585
<211> LENGTH: 5
<212> TYPE: PRT
<213> ORGANISM: Homo sapiens

<400> SEQUENCE: 585

Trp Tyr Phe Asp Leu
1               5

<210> SEQ ID NO 586
<211> LENGTH: 4
<212> TYPE: PRT
<213> ORGANISM: Homo sapiens

<400> SEQUENCE: 586

Tyr Phe Asp Leu
1

<210> SEQ ID NO 587
<211> LENGTH: 4
<212> TYPE: PRT
<213> ORGANISM: Homo sapiens

<400> SEQUENCE: 587

Trp Phe Asp Ser
1

<210> SEQ ID NO 588
<211> LENGTH: 8
<212> TYPE: PRT
<213> ORGANISM: Homo sapiens

<400> SEQUENCE: 588

```
Tyr Tyr Tyr Tyr Gly Met Asp Val
1               5

<210> SEQ ID NO 589
<211> LENGTH: 7
<212> TYPE: PRT
<213> ORGANISM: Homo sapiens

<400> SEQUENCE: 589

Tyr Tyr Tyr Gly Met Asp Val
1               5

<210> SEQ ID NO 590
<211> LENGTH: 6
<212> TYPE: PRT
<213> ORGANISM: Homo sapiens

<400> SEQUENCE: 590

Tyr Tyr Gly Met Asp Val
1               5

<210> SEQ ID NO 591
<211> LENGTH: 5
<212> TYPE: PRT
<213> ORGANISM: Homo sapiens

<400> SEQUENCE: 591

Tyr Gly Met Asp Val
1               5

<210> SEQ ID NO 592
<211> LENGTH: 4
<212> TYPE: PRT
<213> ORGANISM: Homo sapiens

<400> SEQUENCE: 592

Gly Met Asp Val
1

<210> SEQ ID NO 593
<211> LENGTH: 8
<212> TYPE: PRT
<213> ORGANISM: Homo sapiens

<400> SEQUENCE: 593

Val Leu Leu Trp Phe Gly Glu Leu
1               5

<210> SEQ ID NO 594
<211> LENGTH: 7
<212> TYPE: PRT
<213> ORGANISM: Homo sapiens

<400> SEQUENCE: 594

Val Leu Leu Trp Phe Gly Glu
1               5

<210> SEQ ID NO 595
<211> LENGTH: 7
<212> TYPE: PRT
<213> ORGANISM: Homo sapiens

<400> SEQUENCE: 595

Val Leu Leu Leu Trp Phe Gly
```

```
1               5

<210> SEQ ID NO 596
<211> LENGTH: 5
<212> TYPE: PRT
<213> ORGANISM: Homo sapiens

<400> SEQUENCE: 596

Val Leu Leu Trp Phe
1               5

<210> SEQ ID NO 597
<211> LENGTH: 4
<212> TYPE: PRT
<213> ORGANISM: Homo sapiens

<400> SEQUENCE: 597

Val Leu Leu Trp
1

<210> SEQ ID NO 598
<211> LENGTH: 8
<212> TYPE: PRT
<213> ORGANISM: Homo sapiens

<400> SEQUENCE: 598

Leu Leu Trp Phe Gly Glu Leu Leu
1               5

<210> SEQ ID NO 599
<211> LENGTH: 7
<212> TYPE: PRT
<213> ORGANISM: Homo sapiens

<400> SEQUENCE: 599

Leu Leu Trp Phe Gly Glu Leu
1               5

<210> SEQ ID NO 600
<211> LENGTH: 6
<212> TYPE: PRT
<213> ORGANISM: Homo sapiens

<400> SEQUENCE: 600

Leu Leu Trp Phe Gly Glu
1               5

<210> SEQ ID NO 601
<211> LENGTH: 5
<212> TYPE: PRT
<213> ORGANISM: Homo sapiens

<400> SEQUENCE: 601

Leu Leu Trp Phe Gly
1               5

<210> SEQ ID NO 602
<211> LENGTH: 4
<212> TYPE: PRT
<213> ORGANISM: Homo sapiens

<400> SEQUENCE: 602

Leu Leu Trp Phe
1
```

```
<210> SEQ ID NO 603
<211> LENGTH: 7
<212> TYPE: PRT
<213> ORGANISM: Homo sapiens

<400> SEQUENCE: 603

Leu Trp Phe Gly Glu Leu Leu
1               5

<210> SEQ ID NO 604
<211> LENGTH: 6
<212> TYPE: PRT
<213> ORGANISM: Homo sapiens

<400> SEQUENCE: 604

Leu Trp Phe Gly Glu Leu
1               5

<210> SEQ ID NO 605
<211> LENGTH: 5
<212> TYPE: PRT
<213> ORGANISM: Homo sapiens

<400> SEQUENCE: 605

Leu Trp Phe Gly Glu
1               5

<210> SEQ ID NO 606
<211> LENGTH: 4
<212> TYPE: PRT
<213> ORGANISM: Homo sapiens

<400> SEQUENCE: 606

Leu Trp Phe Gly
1

<210> SEQ ID NO 607
<211> LENGTH: 6
<212> TYPE: PRT
<213> ORGANISM: Homo sapiens

<400> SEQUENCE: 607

Trp Phe Gly Glu Leu Leu
1               5

<210> SEQ ID NO 608
<211> LENGTH: 5
<212> TYPE: PRT
<213> ORGANISM: Homo sapiens

<400> SEQUENCE: 608

Trp Phe Gly Glu Leu
1               5

<210> SEQ ID NO 609
<211> LENGTH: 4
<212> TYPE: PRT
<213> ORGANISM: Homo sapiens

<400> SEQUENCE: 609

Trp Phe Gly Glu
1

<210> SEQ ID NO 610
```

```
<211> LENGTH: 5
<212> TYPE: PRT
<213> ORGANISM: Homo sapiens

<400> SEQUENCE: 610

Phe Gly Glu Leu Leu
1               5

<210> SEQ ID NO 611
<211> LENGTH: 4
<212> TYPE: PRT
<213> ORGANISM: Homo sapiens

<400> SEQUENCE: 611

Phe Gly Glu Leu
1

<210> SEQ ID NO 612
<211> LENGTH: 4
<212> TYPE: PRT
<213> ORGANISM: Homo sapiens

<400> SEQUENCE: 612

Gly Glu Leu Leu
1

<210> SEQ ID NO 613
<211> LENGTH: 4
<212> TYPE: PRT
<213> ORGANISM: Homo sapiens

<400> SEQUENCE: 613

Asp Tyr Gly Asp
1

<210> SEQ ID NO 614
<211> LENGTH: 4
<212> TYPE: PRT
<213> ORGANISM: Homo sapiens

<400> SEQUENCE: 614

Tyr Gly Asp Tyr
1

<210> SEQ ID NO 615
<211> LENGTH: 9
<212> TYPE: PRT
<213> ORGANISM: Homo sapiens

<400> SEQUENCE: 615

Gly Tyr Cys Ser Ser Thr Ser Cys Tyr
1               5

<210> SEQ ID NO 616
<211> LENGTH: 9
<212> TYPE: PRT
<213> ORGANISM: Homo sapiens

<400> SEQUENCE: 616

Tyr Cys Ser Ser Thr Ser Cys Tyr Thr
1               5

<210> SEQ ID NO 617
<211> LENGTH: 8
<212> TYPE: PRT
```

<213> ORGANISM: Homo sapiens

<400> SEQUENCE: 617

Cys Ser Ser Thr Ser Cys Tyr Thr
1               5

<210> SEQ ID NO 618
<211> LENGTH: 8
<212> TYPE: PRT
<213> ORGANISM: Homo sapiens

<400> SEQUENCE: 618

Gly Tyr Cys Ser Ser Thr Ser Cys
1               5

<210> SEQ ID NO 619
<211> LENGTH: 8
<212> TYPE: PRT
<213> ORGANISM: Homo sapiens

<400> SEQUENCE: 619

Tyr Cys Ser Ser Thr Ser Cys Tyr
1               5

<210> SEQ ID NO 620
<211> LENGTH: 7
<212> TYPE: PRT
<213> ORGANISM: Homo sapiens

<400> SEQUENCE: 620

Cys Ser Ser Thr Ser Cys Tyr
1               5

<210> SEQ ID NO 621
<211> LENGTH: 7
<212> TYPE: PRT
<213> ORGANISM: Homo sapiens

<400> SEQUENCE: 621

Tyr Cys Ser Ser Thr Ser Cys
1               5

<210> SEQ ID NO 622
<211> LENGTH: 6
<212> TYPE: PRT
<213> ORGANISM: Homo sapiens

<400> SEQUENCE: 622

Cys Ser Ser Thr Ser Cys
1               5

<210> SEQ ID NO 623
<211> LENGTH: 4
<212> TYPE: PRT
<213> ORGANISM: Homo sapiens

<400> SEQUENCE: 623

Gly Ala Thr Thr
1

<210> SEQ ID NO 624
<211> LENGTH: 4
<212> TYPE: PRT
<213> ORGANISM: Homo sapiens

```
<400> SEQUENCE: 624

Gly Ile Val Gly
1

<210> SEQ ID NO 625
<211> LENGTH: 4
<212> TYPE: PRT
<213> ORGANISM: Homo sapiens

<400> SEQUENCE: 625

Ile Val Gly Ala
1

<210> SEQ ID NO 626
<211> LENGTH: 4
<212> TYPE: PRT
<213> ORGANISM: Homo sapiens

<400> SEQUENCE: 626

Val Gly Ala Thr
1

<210> SEQ ID NO 627
<211> LENGTH: 5
<212> TYPE: PRT
<213> ORGANISM: Homo sapiens

<400> SEQUENCE: 627

Gly Ile Val Gly Ala
1               5

<210> SEQ ID NO 628
<211> LENGTH: 5
<212> TYPE: PRT
<213> ORGANISM: Homo sapiens

<400> SEQUENCE: 628

Ile Val Gly Ala Thr
1               5

<210> SEQ ID NO 629
<211> LENGTH: 5
<212> TYPE: PRT
<213> ORGANISM: Homo sapiens

<400> SEQUENCE: 629

Val Gly Ala Thr Thr
1               5

<210> SEQ ID NO 630
<211> LENGTH: 6
<212> TYPE: PRT
<213> ORGANISM: Homo sapiens

<400> SEQUENCE: 630

Gly Ile Val Gly Ala Thr
1               5

<210> SEQ ID NO 631
<211> LENGTH: 6
<212> TYPE: PRT
<213> ORGANISM: Homo sapiens

<400> SEQUENCE: 631
```

```
Ile Val Gly Ala Thr Thr
1               5

<210> SEQ ID NO 632
<211> LENGTH: 4
<212> TYPE: PRT
<213> ORGANISM: Homo sapiens

<400> SEQUENCE: 632

Tyr Ser Gly Ser
1

<210> SEQ ID NO 633
<211> LENGTH: 5
<212> TYPE: PRT
<213> ORGANISM: Homo sapiens

<400> SEQUENCE: 633

Tyr Ser Gly Ser Tyr
1               5

<210> SEQ ID NO 634
<211> LENGTH: 4
<212> TYPE: PRT
<213> ORGANISM: Homo sapiens

<400> SEQUENCE: 634

Asp Ile Val Val
1

<210> SEQ ID NO 635
<211> LENGTH: 4
<212> TYPE: PRT
<213> ORGANISM: Homo sapiens

<400> SEQUENCE: 635

Ile Val Val Val
1

<210> SEQ ID NO 636
<211> LENGTH: 4
<212> TYPE: PRT
<213> ORGANISM: Homo sapiens

<400> SEQUENCE: 636

Pro Ala Ala Met
1

<210> SEQ ID NO 637
<211> LENGTH: 4
<212> TYPE: PRT
<213> ORGANISM: Homo sapiens

<400> SEQUENCE: 637

Val Pro Ala Ala
1

<210> SEQ ID NO 638
<211> LENGTH: 4
<212> TYPE: PRT
<213> ORGANISM: Homo sapiens

<400> SEQUENCE: 638

Val Val Pro Ala
1
```

```
<210> SEQ ID NO 639
<211> LENGTH: 4
<212> TYPE: PRT
<213> ORGANISM: Homo sapiens

<400> SEQUENCE: 639

Val Val Val Pro
1

<210> SEQ ID NO 640
<211> LENGTH: 5
<212> TYPE: PRT
<213> ORGANISM: Homo sapiens

<400> SEQUENCE: 640

Asp Ile Val Val Val
1               5

<210> SEQ ID NO 641
<211> LENGTH: 5
<212> TYPE: PRT
<213> ORGANISM: Homo sapiens

<400> SEQUENCE: 641

Ile Val Val Val Pro
1               5

<210> SEQ ID NO 642
<211> LENGTH: 5
<212> TYPE: PRT
<213> ORGANISM: Homo sapiens

<400> SEQUENCE: 642

Val Pro Ala Ala Met
1               5

<210> SEQ ID NO 643
<211> LENGTH: 5
<212> TYPE: PRT
<213> ORGANISM: Homo sapiens

<400> SEQUENCE: 643

Val Val Pro Ala Ala
1               5

<210> SEQ ID NO 644
<211> LENGTH: 5
<212> TYPE: PRT
<213> ORGANISM: Homo sapiens

<400> SEQUENCE: 644

Val Val Val Pro Ala
1               5

<210> SEQ ID NO 645
<211> LENGTH: 6
<212> TYPE: PRT
<213> ORGANISM: Homo sapiens

<400> SEQUENCE: 645

Asp Ile Val Val Val Pro
1               5
```

```
<210> SEQ ID NO 646
<211> LENGTH: 6
<212> TYPE: PRT
<213> ORGANISM: Homo sapiens

<400> SEQUENCE: 646

Ile Val Val Val Pro Ala
1               5

<210> SEQ ID NO 647
<211> LENGTH: 6
<212> TYPE: PRT
<213> ORGANISM: Homo sapiens

<400> SEQUENCE: 647

Val Val Pro Ala Ala Met
1               5

<210> SEQ ID NO 648
<211> LENGTH: 6
<212> TYPE: PRT
<213> ORGANISM: Homo sapiens

<400> SEQUENCE: 648

Val Val Val Pro Ala Ala
1               5

<210> SEQ ID NO 649
<211> LENGTH: 7
<212> TYPE: PRT
<213> ORGANISM: Homo sapiens

<400> SEQUENCE: 649

Asp Ile Val Val Val Pro Ala
1               5

<210> SEQ ID NO 650
<211> LENGTH: 7
<212> TYPE: PRT
<213> ORGANISM: Homo sapiens

<400> SEQUENCE: 650

Ile Val Val Val Pro Ala Ala
1               5

<210> SEQ ID NO 651
<211> LENGTH: 7
<212> TYPE: PRT
<213> ORGANISM: Homo sapiens

<400> SEQUENCE: 651

Val Val Val Pro Ala Ala Met
1               5

<210> SEQ ID NO 652
<211> LENGTH: 8
<212> TYPE: PRT
<213> ORGANISM: Homo sapiens

<400> SEQUENCE: 652

Asp Ile Val Val Val Pro Ala Ala
1               5

<210> SEQ ID NO 653
<211> LENGTH: 8
```

```
<212> TYPE: PRT
<213> ORGANISM: Homo sapiens

<400> SEQUENCE: 653

Ile Val Val Val Pro Ala Ala Met
1               5

<210> SEQ ID NO 654
<211> LENGTH: 6
<212> TYPE: PRT
<213> ORGANISM: Homo sapiens

<400> SEQUENCE: 654

Cys Ser Gly Gly Ser Cys
1               5

<210> SEQ ID NO 655
<211> LENGTH: 7
<212> TYPE: PRT
<213> ORGANISM: Homo sapiens

<400> SEQUENCE: 655

Cys Ser Gly Gly Ser Cys Tyr
1               5

<210> SEQ ID NO 656
<211> LENGTH: 7
<212> TYPE: PRT
<213> ORGANISM: Homo sapiens

<400> SEQUENCE: 656

Tyr Cys Ser Gly Gly Ser Cys
1               5

<210> SEQ ID NO 657
<211> LENGTH: 8
<212> TYPE: PRT
<213> ORGANISM: Homo sapiens

<400> SEQUENCE: 657

Cys Ser Gly Gly Ser Cys Tyr Ser
1               5

<210> SEQ ID NO 658
<211> LENGTH: 8
<212> TYPE: PRT
<213> ORGANISM: Homo sapiens

<400> SEQUENCE: 658

Gly Tyr Cys Ser Gly Gly Ser Cys
1               5

<210> SEQ ID NO 659
<211> LENGTH: 8
<212> TYPE: PRT
<213> ORGANISM: Homo sapiens

<400> SEQUENCE: 659

Tyr Cys Ser Gly Gly Ser Cys Tyr
1               5

<210> SEQ ID NO 660
<211> LENGTH: 9
<212> TYPE: PRT
<213> ORGANISM: Homo sapiens
```

```
<400> SEQUENCE: 660

Gly Tyr Cys Ser Gly Gly Ser Cys Tyr
1               5

<210> SEQ ID NO 661
<211> LENGTH: 9
<212> TYPE: PRT
<213> ORGANISM: Homo sapiens

<400> SEQUENCE: 661

Tyr Cys Ser Gly Gly Ser Cys Tyr Ser
1               5

<210> SEQ ID NO 662
<211> LENGTH: 4
<212> TYPE: PRT
<213> ORGANISM: Homo sapiens

<400> SEQUENCE: 662

Phe Gly Val Val
1

<210> SEQ ID NO 663
<211> LENGTH: 4
<212> TYPE: PRT
<213> ORGANISM: Homo sapiens

<400> SEQUENCE: 663

Gly Val Val Ile
1

<210> SEQ ID NO 664
<211> LENGTH: 4
<212> TYPE: PRT
<213> ORGANISM: Homo sapiens

<400> SEQUENCE: 664

Ile Phe Gly Val
1

<210> SEQ ID NO 665
<211> LENGTH: 4
<212> TYPE: PRT
<213> ORGANISM: Homo sapiens

<400> SEQUENCE: 665

Ile Thr Ile Phe
1

<210> SEQ ID NO 666
<211> LENGTH: 4
<212> TYPE: PRT
<213> ORGANISM: Homo sapiens

<400> SEQUENCE: 666

Thr Ile Phe Gly
1

<210> SEQ ID NO 667
<211> LENGTH: 4
<212> TYPE: PRT
<213> ORGANISM: Homo sapiens

<400> SEQUENCE: 667
```

Val Val Ile Ile
1

<210> SEQ ID NO 668
<211> LENGTH: 5
<212> TYPE: PRT
<213> ORGANISM: Homo sapiens

<400> SEQUENCE: 668

Phe Gly Val Val Ile
1               5

<210> SEQ ID NO 669
<211> LENGTH: 5
<212> TYPE: PRT
<213> ORGANISM: Homo sapiens

<400> SEQUENCE: 669

Gly Val Val Ile Ile
1               5

<210> SEQ ID NO 670
<211> LENGTH: 5
<212> TYPE: PRT
<213> ORGANISM: Homo sapiens

<400> SEQUENCE: 670

Ile Phe Gly Val Val
1               5

<210> SEQ ID NO 671
<211> LENGTH: 5
<212> TYPE: PRT
<213> ORGANISM: Homo sapiens

<400> SEQUENCE: 671

Ile Phe Gly Val Val
1               5

<210> SEQ ID NO 672
<211> LENGTH: 5
<212> TYPE: PRT
<213> ORGANISM: Homo sapiens

<400> SEQUENCE: 672

Thr Ile Phe Gly Val
1               5

<210> SEQ ID NO 673
<211> LENGTH: 6
<212> TYPE: PRT
<213> ORGANISM: Homo sapiens

<400> SEQUENCE: 673

Phe Gly Val Val Ile Ile
1               5

<210> SEQ ID NO 674
<211> LENGTH: 6
<212> TYPE: PRT
<213> ORGANISM: Homo sapiens

<400> SEQUENCE: 674

Ile Phe Gly Val Val Ile

```
1               5

<210> SEQ ID NO 675
<211> LENGTH: 6
<212> TYPE: PRT
<213> ORGANISM: Homo sapiens

<400> SEQUENCE: 675

Ile Thr Ile Phe Gly Val
1               5

<210> SEQ ID NO 676
<211> LENGTH: 6
<212> TYPE: PRT
<213> ORGANISM: Homo sapiens

<400> SEQUENCE: 676

Thr Ile Phe Gly Val Val
1               5

<210> SEQ ID NO 677
<211> LENGTH: 7
<212> TYPE: PRT
<213> ORGANISM: Homo sapiens

<400> SEQUENCE: 677

Ile Phe Gly Val Val Ile Ile
1               5

<210> SEQ ID NO 678
<211> LENGTH: 7
<212> TYPE: PRT
<213> ORGANISM: Homo sapiens

<400> SEQUENCE: 678

Ile Thr Ile Phe Gly Val Val
1               5

<210> SEQ ID NO 679
<211> LENGTH: 7
<212> TYPE: PRT
<213> ORGANISM: Homo sapiens

<400> SEQUENCE: 679

Thr Ile Phe Gly Val Val Ile
1               5

<210> SEQ ID NO 680
<211> LENGTH: 8
<212> TYPE: PRT
<213> ORGANISM: Homo sapiens

<400> SEQUENCE: 680

Ile Thr Ile Phe Gly Val Val Ile
1               5

<210> SEQ ID NO 681
<211> LENGTH: 8
<212> TYPE: PRT
<213> ORGANISM: Homo sapiens

<400> SEQUENCE: 681

Thr Ile Phe Gly Val Val Ile Ile
1               5
```

```
<210> SEQ ID NO 682
<211> LENGTH: 4
<212> TYPE: PRT
<213> ORGANISM: Homo sapiens

<400> SEQUENCE: 682

Phe Gly Glu Leu
 1

<210> SEQ ID NO 683
<211> LENGTH: 4
<212> TYPE: PRT
<213> ORGANISM: Homo sapiens

<400> SEQUENCE: 683

Gly Glu Leu Leu
 1

<210> SEQ ID NO 684
<211> LENGTH: 4
<212> TYPE: PRT
<213> ORGANISM: Homo sapiens

<400> SEQUENCE: 684

Leu Leu Trp Phe
 1

<210> SEQ ID NO 685
<211> LENGTH: 4
<212> TYPE: PRT
<213> ORGANISM: Homo sapiens

<400> SEQUENCE: 685

Leu Trp Phe Gly
 1

<210> SEQ ID NO 686
<211> LENGTH: 4
<212> TYPE: PRT
<213> ORGANISM: Homo sapiens

<400> SEQUENCE: 686

Val Leu Leu Trp
 1

<210> SEQ ID NO 687
<211> LENGTH: 4
<212> TYPE: PRT
<213> ORGANISM: Homo sapiens

<400> SEQUENCE: 687

Trp Phe Gly Glu
 1

<210> SEQ ID NO 688
<211> LENGTH: 5
<212> TYPE: PRT
<213> ORGANISM: Homo sapiens

<400> SEQUENCE: 688

Phe Gly Glu Leu Leu
 1               5

<210> SEQ ID NO 689
```

```
<211> LENGTH: 5
<212> TYPE: PRT
<213> ORGANISM: Homo sapiens

<400> SEQUENCE: 689

Leu Leu Trp Phe Gly
1               5

<210> SEQ ID NO 690
<211> LENGTH: 5
<212> TYPE: PRT
<213> ORGANISM: Homo sapiens

<400> SEQUENCE: 690

Leu Trp Phe Gly Glu
1               5

<210> SEQ ID NO 691
<211> LENGTH: 5
<212> TYPE: PRT
<213> ORGANISM: Homo sapiens

<400> SEQUENCE: 691

Val Leu Leu Trp Phe
1               5

<210> SEQ ID NO 692
<211> LENGTH: 5
<212> TYPE: PRT
<213> ORGANISM: Homo sapiens

<400> SEQUENCE: 692

Trp Phe Gly Glu Leu
1               5

<210> SEQ ID NO 693
<211> LENGTH: 6
<212> TYPE: PRT
<213> ORGANISM: Homo sapiens

<400> SEQUENCE: 693

Leu Leu Trp Phe Gly Glu
1               5

<210> SEQ ID NO 694
<211> LENGTH: 6
<212> TYPE: PRT
<213> ORGANISM: Homo sapiens

<400> SEQUENCE: 694

Leu Trp Phe Gly Glu Leu
1               5

<210> SEQ ID NO 695
<211> LENGTH: 6
<212> TYPE: PRT
<213> ORGANISM: Homo sapiens

<400> SEQUENCE: 695

Val Leu Leu Trp Phe Gly
1               5

<210> SEQ ID NO 696
<211> LENGTH: 6
<212> TYPE: PRT
```

-continued

```
<213> ORGANISM: Homo sapiens

<400> SEQUENCE: 696

Trp Phe Gly Glu Leu Leu
1               5

<210> SEQ ID NO 697
<211> LENGTH: 7
<212> TYPE: PRT
<213> ORGANISM: Homo sapiens

<400> SEQUENCE: 697

Leu Leu Trp Phe Gly Glu Leu
1               5

<210> SEQ ID NO 698
<211> LENGTH: 7
<212> TYPE: PRT
<213> ORGANISM: Homo sapiens

<400> SEQUENCE: 698

Leu Trp Phe Gly Glu Leu Leu
1               5

<210> SEQ ID NO 699
<211> LENGTH: 7
<212> TYPE: PRT
<213> ORGANISM: Homo sapiens

<400> SEQUENCE: 699

Val Leu Leu Trp Phe Gly Glu
1               5

<210> SEQ ID NO 700
<211> LENGTH: 8
<212> TYPE: PRT
<213> ORGANISM: Homo sapiens

<400> SEQUENCE: 700

Leu Leu Trp Phe Gly Glu Leu Leu
1               5

<210> SEQ ID NO 701
<211> LENGTH: 8
<212> TYPE: PRT
<213> ORGANISM: Homo sapiens

<400> SEQUENCE: 701

Val Leu Leu Trp Phe Gly Glu Leu
1               5

<210> SEQ ID NO 702
<211> LENGTH: 4
<212> TYPE: PRT
<213> ORGANISM: Homo sapiens

<400> SEQUENCE: 702

Gly Ser Gly Ser
1

<210> SEQ ID NO 703
<211> LENGTH: 4
<212> TYPE: PRT
<213> ORGANISM: Homo sapiens
```

```
<400> SEQUENCE: 703

Gly Ser Tyr Tyr
1

<210> SEQ ID NO 704
<211> LENGTH: 4
<212> TYPE: PRT
<213> ORGANISM: Homo sapiens

<400> SEQUENCE: 704

Ser Gly Ser Tyr
1

<210> SEQ ID NO 705
<211> LENGTH: 4
<212> TYPE: PRT
<213> ORGANISM: Homo sapiens

<400> SEQUENCE: 705

Ser Tyr Tyr Asn
1

<210> SEQ ID NO 706
<211> LENGTH: 4
<212> TYPE: PRT
<213> ORGANISM: Homo sapiens

<400> SEQUENCE: 706

Tyr Gly Ser Gly
1

<210> SEQ ID NO 707
<211> LENGTH: 4
<212> TYPE: PRT
<213> ORGANISM: Homo sapiens

<400> SEQUENCE: 707

Tyr Tyr Gly Ser
1

<210> SEQ ID NO 708
<211> LENGTH: 4
<212> TYPE: PRT
<213> ORGANISM: Homo sapiens

<400> SEQUENCE: 708

Tyr Tyr Tyr Gly
1

<210> SEQ ID NO 709
<211> LENGTH: 5
<212> TYPE: PRT
<213> ORGANISM: Homo sapiens

<400> SEQUENCE: 709

Gly Ser Gly Ser Tyr
1               5

<210> SEQ ID NO 710
<211> LENGTH: 5
<212> TYPE: PRT
<213> ORGANISM: Homo sapiens

<400> SEQUENCE: 710
```

Gly Ser Tyr Tyr Asn
1               5

<210> SEQ ID NO 711
<211> LENGTH: 5
<212> TYPE: PRT
<213> ORGANISM: Homo sapiens

<400> SEQUENCE: 711

Ser Gly Ser Tyr Tyr
1               5

<210> SEQ ID NO 712
<211> LENGTH: 5
<212> TYPE: PRT
<213> ORGANISM: Homo sapiens

<400> SEQUENCE: 712

Tyr Gly Ser Gly Ser
1               5

<210> SEQ ID NO 713
<211> LENGTH: 5
<212> TYPE: PRT
<213> ORGANISM: Homo sapiens

<400> SEQUENCE: 713

Tyr Tyr Gly Ser Gly
1               5

<210> SEQ ID NO 714
<211> LENGTH: 5
<212> TYPE: PRT
<213> ORGANISM: Homo sapiens

<400> SEQUENCE: 714

Tyr Tyr Tyr Gly Ser
1               5

<210> SEQ ID NO 715
<211> LENGTH: 6
<212> TYPE: PRT
<213> ORGANISM: Homo sapiens

<400> SEQUENCE: 715

Gly Ser Gly Ser Tyr Tyr
1               5

<210> SEQ ID NO 716
<211> LENGTH: 6
<212> TYPE: PRT
<213> ORGANISM: Homo sapiens

<400> SEQUENCE: 716

Ser Gly Ser Tyr Tyr Asn
1               5

<210> SEQ ID NO 717
<211> LENGTH: 6
<212> TYPE: PRT
<213> ORGANISM: Homo sapiens

<400> SEQUENCE: 717

Tyr Gly Ser Gly Ser Tyr
1               5

```
<210> SEQ ID NO 718
<211> LENGTH: 6
<212> TYPE: PRT
<213> ORGANISM: Homo sapiens

<400> SEQUENCE: 718

Tyr Tyr Gly Ser Gly Ser
1               5

<210> SEQ ID NO 719
<211> LENGTH: 6
<212> TYPE: PRT
<213> ORGANISM: Homo sapiens

<400> SEQUENCE: 719

Tyr Tyr Tyr Gly Ser Gly
1               5

<210> SEQ ID NO 720
<211> LENGTH: 7
<212> TYPE: PRT
<213> ORGANISM: Homo sapiens

<400> SEQUENCE: 720

Gly Ser Gly Ser Tyr Tyr Asn
1               5

<210> SEQ ID NO 721
<211> LENGTH: 7
<212> TYPE: PRT
<213> ORGANISM: Homo sapiens

<400> SEQUENCE: 721

Tyr Gly Ser Gly Ser Tyr Tyr
1               5

<210> SEQ ID NO 722
<211> LENGTH: 7
<212> TYPE: PRT
<213> ORGANISM: Homo sapiens

<400> SEQUENCE: 722

Tyr Tyr Gly Ser Gly Ser Tyr
1               5

<210> SEQ ID NO 723
<211> LENGTH: 7
<212> TYPE: PRT
<213> ORGANISM: Homo sapiens

<400> SEQUENCE: 723

Tyr Tyr Tyr Gly Ser Gly Ser
1               5

<210> SEQ ID NO 724
<211> LENGTH: 8
<212> TYPE: PRT
<213> ORGANISM: Homo sapiens

<400> SEQUENCE: 724

Tyr Gly Ser Gly Ser Tyr Tyr Asn
1               5
```

```
<210> SEQ ID NO 725
<211> LENGTH: 8
<212> TYPE: PRT
<213> ORGANISM: Homo sapiens

<400> SEQUENCE: 725

Tyr Tyr Gly Ser Gly Ser Tyr Tyr
1               5

<210> SEQ ID NO 726
<211> LENGTH: 8
<212> TYPE: PRT
<213> ORGANISM: Homo sapiens

<400> SEQUENCE: 726

Tyr Tyr Tyr Gly Ser Gly Ser Tyr
1               5

<210> SEQ ID NO 727
<211> LENGTH: 9
<212> TYPE: PRT
<213> ORGANISM: Homo sapiens

<400> SEQUENCE: 727

Tyr Tyr Gly Ser Gly Ser Tyr Tyr Asn
1               5

<210> SEQ ID NO 728
<211> LENGTH: 9
<212> TYPE: PRT
<213> ORGANISM: Homo sapiens

<400> SEQUENCE: 728

Tyr Tyr Tyr Gly Ser Gly Ser Tyr Tyr
1               5

<210> SEQ ID NO 729
<211> LENGTH: 4
<212> TYPE: PRT
<213> ORGANISM: Homo sapiens

<400> SEQUENCE: 729

Gly Val Ile Ile
1

<210> SEQ ID NO 730
<211> LENGTH: 4
<212> TYPE: PRT
<213> ORGANISM: Homo sapiens

<400> SEQUENCE: 730

Ile Thr Met Val
1

<210> SEQ ID NO 731
<211> LENGTH: 4
<212> TYPE: PRT
<213> ORGANISM: Homo sapiens

<400> SEQUENCE: 731

Met Val Arg Gly
1

<210> SEQ ID NO 732
<211> LENGTH: 4
```

```
<212> TYPE: PRT
<213> ORGANISM: Homo sapiens

<400> SEQUENCE: 732

Arg Gly Val Ile
1

<210> SEQ ID NO 733
<211> LENGTH: 4
<212> TYPE: PRT
<213> ORGANISM: Homo sapiens

<400> SEQUENCE: 733

Thr Met Val Arg
1

<210> SEQ ID NO 734
<211> LENGTH: 4
<212> TYPE: PRT
<213> ORGANISM: Homo sapiens

<400> SEQUENCE: 734

Val Arg Gly Val
1

<210> SEQ ID NO 735
<211> LENGTH: 5
<212> TYPE: PRT
<213> ORGANISM: Homo sapiens

<400> SEQUENCE: 735

Ile Thr Met Val Arg
1               5

<210> SEQ ID NO 736
<211> LENGTH: 5
<212> TYPE: PRT
<213> ORGANISM: Homo sapiens

<400> SEQUENCE: 736

Met Val Arg Gly Val
1               5

<210> SEQ ID NO 737
<211> LENGTH: 5
<212> TYPE: PRT
<213> ORGANISM: Homo sapiens

<400> SEQUENCE: 737

Arg Gly Val Ile Ile
1               5

<210> SEQ ID NO 738
<211> LENGTH: 5
<212> TYPE: PRT
<213> ORGANISM: Homo sapiens

<400> SEQUENCE: 738

Thr Met Val Arg Gly
1               5

<210> SEQ ID NO 739
<211> LENGTH: 5
<212> TYPE: PRT
<213> ORGANISM: Homo sapiens
```

<400> SEQUENCE: 739

Val Arg Gly Val Ile
1               5

<210> SEQ ID NO 740
<211> LENGTH: 6
<212> TYPE: PRT
<213> ORGANISM: Homo sapiens

<400> SEQUENCE: 740

Ile Thr Met Val Arg Gly
1               5

<210> SEQ ID NO 741
<211> LENGTH: 6
<212> TYPE: PRT
<213> ORGANISM: Homo sapiens

<400> SEQUENCE: 741

Met Val Arg Gly Val Ile
1               5

<210> SEQ ID NO 742
<211> LENGTH: 6
<212> TYPE: PRT
<213> ORGANISM: Homo sapiens

<400> SEQUENCE: 742

Thr Met Val Arg Gly Val
1               5

<210> SEQ ID NO 743
<211> LENGTH: 6
<212> TYPE: PRT
<213> ORGANISM: Homo sapiens

<400> SEQUENCE: 743

Val Arg Gly Val Ile Ile
1               5

<210> SEQ ID NO 744
<211> LENGTH: 7
<212> TYPE: PRT
<213> ORGANISM: Homo sapiens

<400> SEQUENCE: 744

Ile Thr Met Val Arg Gly Val
1               5

<210> SEQ ID NO 745
<211> LENGTH: 7
<212> TYPE: PRT
<213> ORGANISM: Homo sapiens

<400> SEQUENCE: 745

Met Val Arg Gly Val Ile Ile
1               5

<210> SEQ ID NO 746
<211> LENGTH: 7
<212> TYPE: PRT
<213> ORGANISM: Homo sapiens

<400> SEQUENCE: 746

```
Thr Met Val Arg Gly Val Ile
1               5

<210> SEQ ID NO 747
<211> LENGTH: 8
<212> TYPE: PRT
<213> ORGANISM: Homo sapiens

<400> SEQUENCE: 747

Ile Thr Met Val Arg Gly Val Ile
1               5

<210> SEQ ID NO 748
<211> LENGTH: 8
<212> TYPE: PRT
<213> ORGANISM: Homo sapiens

<400> SEQUENCE: 748

Thr Met Val Arg Gly Val Ile Ile
1               5

<210> SEQ ID NO 749
<211> LENGTH: 4
<212> TYPE: PRT
<213> ORGANISM: Homo sapiens

<400> SEQUENCE: 749

Asp Ser Ser Gly
1

<210> SEQ ID NO 750
<211> LENGTH: 4
<212> TYPE: PRT
<213> ORGANISM: Homo sapiens

<400> SEQUENCE: 750

Gly Tyr Tyr Tyr
1

<210> SEQ ID NO 751
<211> LENGTH: 4
<212> TYPE: PRT
<213> ORGANISM: Homo sapiens

<400> SEQUENCE: 751

Ser Gly Tyr Tyr
1

<210> SEQ ID NO 752
<211> LENGTH: 4
<212> TYPE: PRT
<213> ORGANISM: Homo sapiens

<400> SEQUENCE: 752

Ser Ser Gly Tyr
1

<210> SEQ ID NO 753
<211> LENGTH: 4
<212> TYPE: PRT
<213> ORGANISM: Homo sapiens

<400> SEQUENCE: 753

Tyr Asp Ser Ser
```

<210> SEQ ID NO 754
<211> LENGTH: 4
<212> TYPE: PRT
<213> ORGANISM: Homo sapiens

<400> SEQUENCE: 754

Tyr Tyr Asp Ser
1

<210> SEQ ID NO 755
<211> LENGTH: 4
<212> TYPE: PRT
<213> ORGANISM: Homo sapiens

<400> SEQUENCE: 755

Tyr Tyr Tyr Asp
1

<210> SEQ ID NO 756
<211> LENGTH: 5
<212> TYPE: PRT
<213> ORGANISM: Homo sapiens

<400> SEQUENCE: 756

Asp Ser Ser Gly Tyr
1               5

<210> SEQ ID NO 757
<211> LENGTH: 5
<212> TYPE: PRT
<213> ORGANISM: Homo sapiens

<400> SEQUENCE: 757

Ser Gly Tyr Tyr Tyr
1               5

<210> SEQ ID NO 758
<211> LENGTH: 5
<212> TYPE: PRT
<213> ORGANISM: Homo sapiens

<400> SEQUENCE: 758

Ser Ser Gly Tyr Tyr
1               5

<210> SEQ ID NO 759
<211> LENGTH: 5
<212> TYPE: PRT
<213> ORGANISM: Homo sapiens

<400> SEQUENCE: 759

Tyr Asp Ser Ser Gly
1               5

<210> SEQ ID NO 760
<211> LENGTH: 5
<212> TYPE: PRT
<213> ORGANISM: Homo sapiens

<400> SEQUENCE: 760

Tyr Tyr Asp Ser Ser
1               5

```
<210> SEQ ID NO 761
<211> LENGTH: 5
<212> TYPE: PRT
<213> ORGANISM: Homo sapiens

<400> SEQUENCE: 761

Tyr Tyr Tyr Asp Ser
1               5

<210> SEQ ID NO 762
<211> LENGTH: 6
<212> TYPE: PRT
<213> ORGANISM: Homo sapiens

<400> SEQUENCE: 762

Asp Ser Ser Gly Tyr Tyr
1               5

<210> SEQ ID NO 763
<211> LENGTH: 6
<212> TYPE: PRT
<213> ORGANISM: Homo sapiens

<400> SEQUENCE: 763

Ser Ser Gly Tyr Tyr Tyr
1               5

<210> SEQ ID NO 764
<211> LENGTH: 6
<212> TYPE: PRT
<213> ORGANISM: Homo sapiens

<400> SEQUENCE: 764

Tyr Asp Ser Ser Gly Tyr
1               5

<210> SEQ ID NO 765
<211> LENGTH: 6
<212> TYPE: PRT
<213> ORGANISM: Homo sapiens

<400> SEQUENCE: 765

Tyr Tyr Asp Ser Ser Gly
1               5

<210> SEQ ID NO 766
<211> LENGTH: 6
<212> TYPE: PRT
<213> ORGANISM: Homo sapiens

<400> SEQUENCE: 766

Tyr Tyr Tyr Asp Ser Ser
1               5

<210> SEQ ID NO 767
<211> LENGTH: 7
<212> TYPE: PRT
<213> ORGANISM: Homo sapiens

<400> SEQUENCE: 767

Asp Ser Ser Gly Tyr Tyr Tyr
1               5

<210> SEQ ID NO 768
```

```
<211> LENGTH: 7
<212> TYPE: PRT
<213> ORGANISM: Homo sapiens

<400> SEQUENCE: 768

Tyr Asp Ser Ser Gly Tyr Tyr
1               5

<210> SEQ ID NO 769
<211> LENGTH: 7
<212> TYPE: PRT
<213> ORGANISM: Homo sapiens

<400> SEQUENCE: 769

Tyr Tyr Asp Ser Ser Gly Tyr
1               5

<210> SEQ ID NO 770
<211> LENGTH: 7
<212> TYPE: PRT
<213> ORGANISM: Homo sapiens

<400> SEQUENCE: 770

Tyr Tyr Tyr Asp Ser Ser Gly
1               5

<210> SEQ ID NO 771
<211> LENGTH: 8
<212> TYPE: PRT
<213> ORGANISM: Homo sapiens

<400> SEQUENCE: 771

Tyr Asp Ser Ser Gly Tyr Tyr Tyr
1               5

<210> SEQ ID NO 772
<211> LENGTH: 8
<212> TYPE: PRT
<213> ORGANISM: Homo sapiens

<400> SEQUENCE: 772

Tyr Tyr Asp Ser Ser Gly Tyr Tyr
1               5

<210> SEQ ID NO 773
<211> LENGTH: 8
<212> TYPE: PRT
<213> ORGANISM: Homo sapiens

<400> SEQUENCE: 773

Tyr Tyr Tyr Asp Ser Ser Gly Tyr
1               5

<210> SEQ ID NO 774
<211> LENGTH: 9
<212> TYPE: PRT
<213> ORGANISM: Homo sapiens

<400> SEQUENCE: 774

Tyr Tyr Asp Ser Ser Gly Tyr Tyr Tyr
1               5

<210> SEQ ID NO 775
<211> LENGTH: 9
<212> TYPE: PRT
```

<213> ORGANISM: Homo sapiens

<400> SEQUENCE: 775

Tyr Tyr Tyr Asp Ser Ser Gly Tyr Tyr
1               5

<210> SEQ ID NO 776
<211> LENGTH: 4
<212> TYPE: PRT
<213> ORGANISM: Homo sapiens

<400> SEQUENCE: 776

Gly Tyr Ser Tyr
1

<210> SEQ ID NO 777
<211> LENGTH: 4
<212> TYPE: PRT
<213> ORGANISM: Homo sapiens

<400> SEQUENCE: 777

Ser Tyr Gly Tyr
1

<210> SEQ ID NO 778
<211> LENGTH: 4
<212> TYPE: PRT
<213> ORGANISM: Homo sapiens

<400> SEQUENCE: 778

Tyr Ser Tyr Gly
1

<210> SEQ ID NO 779
<211> LENGTH: 5
<212> TYPE: PRT
<213> ORGANISM: Homo sapiens

<400> SEQUENCE: 779

Gly Tyr Ser Tyr Gly
1               5

<210> SEQ ID NO 780
<211> LENGTH: 5
<212> TYPE: PRT
<213> ORGANISM: Homo sapiens

<400> SEQUENCE: 780

Tyr Ser Tyr Gly Tyr
1               5

<210> SEQ ID NO 781
<211> LENGTH: 4
<212> TYPE: PRT
<213> ORGANISM: Homo sapiens

<400> SEQUENCE: 781

Ser Ser Ser Trp
1

<210> SEQ ID NO 782
<211> LENGTH: 4
<212> TYPE: PRT
<213> ORGANISM: Homo sapiens

```
<400> SEQUENCE: 782

Ser Ser Trp Tyr
1

<210> SEQ ID NO 783
<211> LENGTH: 4
<212> TYPE: PRT
<213> ORGANISM: Homo sapiens

<400> SEQUENCE: 783

Tyr Ser Ser Ser
1

<210> SEQ ID NO 784
<211> LENGTH: 5
<212> TYPE: PRT
<213> ORGANISM: Homo sapiens

<400> SEQUENCE: 784

Gly Tyr Ser Ser Ser
1               5

<210> SEQ ID NO 785
<211> LENGTH: 5
<212> TYPE: PRT
<213> ORGANISM: Homo sapiens

<400> SEQUENCE: 785

Ser Ser Ser Trp Tyr
1               5

<210> SEQ ID NO 786
<211> LENGTH: 5
<212> TYPE: PRT
<213> ORGANISM: Homo sapiens

<400> SEQUENCE: 786

Tyr Ser Ser Ser Trp
1               5

<210> SEQ ID NO 787
<211> LENGTH: 6
<212> TYPE: PRT
<213> ORGANISM: Homo sapiens

<400> SEQUENCE: 787

Gly Tyr Ser Ser Ser Trp
1               5

<210> SEQ ID NO 788
<211> LENGTH: 6
<212> TYPE: PRT
<213> ORGANISM: Homo sapiens

<400> SEQUENCE: 788

Tyr Ser Ser Ser Trp Tyr
1               5

<210> SEQ ID NO 789
<211> LENGTH: 4
<212> TYPE: PRT
<213> ORGANISM: Homo sapiens

<400> SEQUENCE: 789
```

Gly Tyr Ser Ser
1

<210> SEQ ID NO 790
<211> LENGTH: 4
<212> TYPE: PRT
<213> ORGANISM: Homo sapiens

<400> SEQUENCE: 790

Ser Gly Trp Tyr
1

<210> SEQ ID NO 791
<211> LENGTH: 4
<212> TYPE: PRT
<213> ORGANISM: Homo sapiens

<400> SEQUENCE: 791

Ser Ser Gly Trp
1

<210> SEQ ID NO 792
<211> LENGTH: 4
<212> TYPE: PRT
<213> ORGANISM: Homo sapiens

<400> SEQUENCE: 792

Tyr Ser Ser Gly
1

<210> SEQ ID NO 793
<211> LENGTH: 5
<212> TYPE: PRT
<213> ORGANISM: Homo sapiens

<400> SEQUENCE: 793

Gly Tyr Ser Ser Gly
1               5

<210> SEQ ID NO 794
<211> LENGTH: 5
<212> TYPE: PRT
<213> ORGANISM: Homo sapiens

<400> SEQUENCE: 794

Ser Ser Gly Trp Tyr
1               5

<210> SEQ ID NO 795
<211> LENGTH: 5
<212> TYPE: PRT
<213> ORGANISM: Homo sapiens

<400> SEQUENCE: 795

Tyr Ser Ser Gly Trp
1               5

<210> SEQ ID NO 796
<211> LENGTH: 6
<212> TYPE: PRT
<213> ORGANISM: Homo sapiens

<400> SEQUENCE: 796

Gly Tyr Ser Ser Gly Trp
1               5

```
<210> SEQ ID NO 797
<211> LENGTH: 6
<212> TYPE: PRT
<213> ORGANISM: Homo sapiens

<400> SEQUENCE: 797

Tyr Ser Ser Gly Trp Tyr
1               5

<210> SEQ ID NO 798
<211> LENGTH: 4
<212> TYPE: PRT
<213> ORGANISM: Homo sapiens

<400> SEQUENCE: 798

Ala Val Ala Gly
1

<210> SEQ ID NO 799
<211> LENGTH: 4
<212> TYPE: PRT
<213> ORGANISM: Homo sapiens

<400> SEQUENCE: 799

Gly Ile Ala Val
1

<210> SEQ ID NO 800
<211> LENGTH: 4
<212> TYPE: PRT
<213> ORGANISM: Homo sapiens

<400> SEQUENCE: 800

Ile Ala Val Ala
1

<210> SEQ ID NO 801
<211> LENGTH: 5
<212> TYPE: PRT
<213> ORGANISM: Homo sapiens

<400> SEQUENCE: 801

Gly Ile Ala Val Ala
1               5

<210> SEQ ID NO 802
<211> LENGTH: 5
<212> TYPE: PRT
<213> ORGANISM: Homo sapiens

<400> SEQUENCE: 802

Ile Ala Val Ala Gly
1               5

<210> SEQ ID NO 803
<211> LENGTH: 4
<212> TYPE: PRT
<213> ORGANISM: Homo sapiens

<400> SEQUENCE: 803

Ala Ala Ala Gly
1
```

-continued

```
<210> SEQ ID NO 804
<211> LENGTH: 4
<212> TYPE: PRT
<213> ORGANISM: Homo sapiens

<400> SEQUENCE: 804

Gly Ile Ala Ala
1

<210> SEQ ID NO 805
<211> LENGTH: 4
<212> TYPE: PRT
<213> ORGANISM: Homo sapiens

<400> SEQUENCE: 805

Ile Ala Ala Ala
1

<210> SEQ ID NO 806
<211> LENGTH: 5
<212> TYPE: PRT
<213> ORGANISM: Homo sapiens

<400> SEQUENCE: 806

Gly Ile Ala Ala Ala
1               5

<210> SEQ ID NO 807
<211> LENGTH: 5
<212> TYPE: PRT
<213> ORGANISM: Homo sapiens

<400> SEQUENCE: 807

Ile Ala Ala Ala Gly
1               5

<210> SEQ ID NO 808
<211> LENGTH: 16
<212> TYPE: PRT
<213> ORGANISM: Homo sapiens

<400> SEQUENCE: 808

Glu Tyr Phe Gln His Trp Gly Gln Gly Thr Leu Val Thr Val Ser Ser
1               5                   10                  15

<210> SEQ ID NO 809
<211> LENGTH: 15
<212> TYPE: PRT
<213> ORGANISM: Homo sapiens

<400> SEQUENCE: 809

Tyr Phe Gln His Trp Gly Gln Gly Thr Leu Val Thr Val Ser Ser
1               5                   10                  15

<210> SEQ ID NO 810
<211> LENGTH: 14
<212> TYPE: PRT
<213> ORGANISM: Homo sapiens

<400> SEQUENCE: 810

Phe Gln His Trp Gly Gln Gly Thr Leu Val Thr Val Ser Ser
1               5                   10

<210> SEQ ID NO 811
<211> LENGTH: 13
```

```
<212> TYPE: PRT
<213> ORGANISM: Homo sapiens

<400> SEQUENCE: 811

Gln His Trp Gly Gln Gly Thr Leu Val Thr Val Ser Ser
1               5                   10

<210> SEQ ID NO 812
<211> LENGTH: 16
<212> TYPE: PRT
<213> ORGANISM: Homo sapiens

<400> SEQUENCE: 812

Trp Tyr Phe Asp Leu Trp Gly Arg Gly Thr Leu Val Thr Val Ser Ser
1               5                   10                  15

<210> SEQ ID NO 813
<211> LENGTH: 15
<212> TYPE: PRT
<213> ORGANISM: Homo sapiens

<400> SEQUENCE: 813

Tyr Phe Asp Leu Trp Gly Arg Gly Thr Leu Val Thr Val Ser Ser
1               5                   10                  15

<210> SEQ ID NO 814
<211> LENGTH: 14
<212> TYPE: PRT
<213> ORGANISM: Homo sapiens

<400> SEQUENCE: 814

Phe Asp Leu Trp Gly Arg Gly Thr Leu Val Thr Val Ser Ser
1               5                   10

<210> SEQ ID NO 815
<211> LENGTH: 13
<212> TYPE: PRT
<213> ORGANISM: Homo sapiens

<400> SEQUENCE: 815

Asp Leu Trp Gly Arg Gly Thr Leu Val Thr Val Ser Ser
1               5                   10

<210> SEQ ID NO 816
<211> LENGTH: 14
<212> TYPE: PRT
<213> ORGANISM: Homo sapiens

<400> SEQUENCE: 816

Phe Asp Val Trp Gly Gln Gly Thr Met Val Thr Val Ser Ser
1               5                   10

<210> SEQ ID NO 817
<211> LENGTH: 13
<212> TYPE: PRT
<213> ORGANISM: Homo sapiens

<400> SEQUENCE: 817

Asp Val Trp Gly Gln Gly Thr Met Val Thr Val Ser Ser
1               5                   10

<210> SEQ ID NO 818
<211> LENGTH: 14
<212> TYPE: PRT
<213> ORGANISM: Homo sapiens
```

```
<400> SEQUENCE: 818

Phe Asp Tyr Trp Gly Gln Gly Thr Leu Val Thr Val Ser Ser
1               5                   10

<210> SEQ ID NO 819
<211> LENGTH: 13
<212> TYPE: PRT
<213> ORGANISM: Homo sapiens

<400> SEQUENCE: 819

Asp Tyr Trp Gly Gln Gly Thr Leu Val Thr Val Ser Ser
1               5                   10

<210> SEQ ID NO 820
<211> LENGTH: 15
<212> TYPE: PRT
<213> ORGANISM: Homo sapiens

<400> SEQUENCE: 820

Trp Phe Asp Ser Trp Gly Gln Gly Thr Leu Val Thr Val Ser Ser
1               5                   10                  15

<210> SEQ ID NO 821
<211> LENGTH: 14
<212> TYPE: PRT
<213> ORGANISM: Homo sapiens

<400> SEQUENCE: 821

Phe Asp Ser Trp Gly Gln Gly Thr Leu Val Thr Val Ser Ser
1               5                   10

<210> SEQ ID NO 822
<211> LENGTH: 13
<212> TYPE: PRT
<213> ORGANISM: Homo sapiens

<400> SEQUENCE: 822

Asp Ser Trp Gly Gln Gly Thr Leu Val Thr Val Ser Ser
1               5                   10

<210> SEQ ID NO 823
<211> LENGTH: 19
<212> TYPE: PRT
<213> ORGANISM: Homo sapiens

<400> SEQUENCE: 823

Tyr Tyr Tyr Tyr Gly Met Asp Val Trp Gly Gln Gly Thr Thr Val Thr
1               5                   10                  15

Val Ser Ser

<210> SEQ ID NO 824
<211> LENGTH: 18
<212> TYPE: PRT
<213> ORGANISM: Homo sapiens

<400> SEQUENCE: 824

Tyr Tyr Tyr Gly Met Asp Val Trp Gly Gln Gly Thr Thr Val Thr Val
1               5                   10                  15

Ser Ser

<210> SEQ ID NO 825
<211> LENGTH: 17
```

```
<212> TYPE: PRT
<213> ORGANISM: Homo sapiens

<400> SEQUENCE: 825

Tyr Tyr Gly Met Asp Val Trp Gly Gln Gly Thr Thr Val Thr Val Ser
1               5                   10                  15

Ser

<210> SEQ ID NO 826
<211> LENGTH: 16
<212> TYPE: PRT
<213> ORGANISM: Homo sapiens

<400> SEQUENCE: 826

Tyr Gly Met Asp Val Trp Gly Gln Gly Thr Thr Val Thr Val Ser Ser
1               5                   10                  15

<210> SEQ ID NO 827
<211> LENGTH: 15
<212> TYPE: PRT
<213> ORGANISM: Homo sapiens

<400> SEQUENCE: 827

Gly Met Asp Val Trp Gly Gln Gly Thr Thr Val Thr Val Ser Ser
1               5                   10                  15

<210> SEQ ID NO 828
<211> LENGTH: 14
<212> TYPE: PRT
<213> ORGANISM: Homo sapiens

<400> SEQUENCE: 828

Met Asp Val Trp Gly Gln Gly Thr Thr Val Thr Val Ser Ser
1               5                   10

<210> SEQ ID NO 829
<211> LENGTH: 13
<212> TYPE: PRT
<213> ORGANISM: Homo sapiens

<400> SEQUENCE: 829

Asp Val Trp Gly Gln Gly Thr Thr Val Thr Val Ser Ser
1               5                   10

<210> SEQ ID NO 830
<211> LENGTH: 5
<212> TYPE: PRT
<213> ORGANISM: Homo sapiens

<400> SEQUENCE: 830

Glu Tyr Phe Gln His
1               5

<210> SEQ ID NO 831
<211> LENGTH: 4
<212> TYPE: PRT
<213> ORGANISM: Homo sapiens

<400> SEQUENCE: 831

Tyr Phe Gln His
1

<210> SEQ ID NO 832
<211> LENGTH: 5
```

```
<212> TYPE: PRT
<213> ORGANISM: Homo sapiens

<400> SEQUENCE: 832

Trp Tyr Phe Asp Leu
1               5

<210> SEQ ID NO 833
<211> LENGTH: 4
<212> TYPE: PRT
<213> ORGANISM: Homo sapiens

<400> SEQUENCE: 833

Tyr Phe Asp Leu
1

<210> SEQ ID NO 834
<211> LENGTH: 4
<212> TYPE: PRT
<213> ORGANISM: Homo sapiens

<400> SEQUENCE: 834

Trp Phe Asp Ser
1

<210> SEQ ID NO 835
<211> LENGTH: 8
<212> TYPE: PRT
<213> ORGANISM: Homo sapiens

<400> SEQUENCE: 835

Tyr Tyr Tyr Tyr Gly Met Asp Val
1               5

<210> SEQ ID NO 836
<211> LENGTH: 7
<212> TYPE: PRT
<213> ORGANISM: Homo sapiens

<400> SEQUENCE: 836

Tyr Tyr Tyr Gly Met Asp Val
1               5

<210> SEQ ID NO 837
<211> LENGTH: 6
<212> TYPE: PRT
<213> ORGANISM: Homo sapiens

<400> SEQUENCE: 837

Tyr Tyr Gly Met Asp Val
1               5

<210> SEQ ID NO 838
<211> LENGTH: 5
<212> TYPE: PRT
<213> ORGANISM: Homo sapiens

<400> SEQUENCE: 838

Tyr Gly Met Asp Val
1               5

<210> SEQ ID NO 839
<211> LENGTH: 4
<212> TYPE: PRT
<213> ORGANISM: Homo sapiens
```

```
<400> SEQUENCE: 839

Gly Met Asp Val
1

<210> SEQ ID NO 840
<211> LENGTH: 4
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 840

Cys Ala Arg Xaa
1

<210> SEQ ID NO 841
<211> LENGTH: 11
<212> TYPE: PRT
<213> ORGANISM: Homo sapiens

<400> SEQUENCE: 841

Thr Phe Gly Gly Gly Thr Lys Val Glu Ile Lys
1               5                   10

<210> SEQ ID NO 842
<211> LENGTH: 11
<212> TYPE: PRT
<213> ORGANISM: Homo sapiens

<400> SEQUENCE: 842

Thr Phe Gly Gln Gly Thr Lys Leu Glu Ile Lys
1               5                   10

<210> SEQ ID NO 843
<211> LENGTH: 11
<212> TYPE: PRT
<213> ORGANISM: Homo sapiens

<400> SEQUENCE: 843

Thr Phe Gly Pro Gly Thr Lys Val Asp Ile Lys
1               5                   10

<210> SEQ ID NO 844
<211> LENGTH: 11
<212> TYPE: PRT
<213> ORGANISM: Homo sapiens

<400> SEQUENCE: 844

Thr Phe Gly Gln Gly Thr Arg Leu Glu Ile Lys
1               5                   10

<210> SEQ ID NO 845
<211> LENGTH: 633
<212> TYPE: DNA
<213> ORGANISM: Homo sapiens

<400> SEQUENCE: 845
ctccacgtcg acaacctcag accccctccg aaccatgtcg acccccag ggactctgag      60 aggacacgtc ggagacctaa gtggaaatcg tcgatacggt actcgaccca ggcggtccga     120
ggtcccttcc ccgacctcac ccagagtcga taatcaccat caccaccatc gtgtatgatg     180
```

```
cgtctgaggc acttcccggc caagtggtag aggtctctgt taaggttctt gtgcgacata      240
gacgtttact tgtcggactc tcggctcctg tgccgccaca tgatgacgcg gttcctcccg      300
cctggaccca taacgtcaag ttgaagaaca atatgtggtc ctccgatgat gataatgatg      360
ccgtacctgc acaccctgt tccatgttgt cagtggcaga ggagtcgatc gtggttcccg       420
ggtagccaga aggggaccg tgggaggagg ttctcgtgga gaccccgtg tcgccgggac        480 ccgacggacc agttcctgat gaaggggctt ggccactgcc acagcacctt gagtccgcgg      540
gactggtcgc cgcacgtgtg aagggccga caggatgtca ggagtcctga gatgagggag       600
tcgtcgcacc actggcacgg gaggtcgtcg aac                                   633
```

<210> SEQ ID NO 846
<211> LENGTH: 910
<212> TYPE: DNA
<213> ORGANISM: Homo sapiens

<400> SEQUENCE: 846

```
ttacgcgaaa ggctcgtaaa aatggcgtca agacaaacgc cgctcgtcgc gcgaccgccg       60
cggccgcttg tggtggtggc ttctactttg gcgcgtctaa ggccgccttc gccactaact      120
aatatcgcta gaccttccgc taaaactacg ccgccgcgac ggcgactcgt tgtcgtggtt      180
gttgccggac tcgtcgtggt tgtggtggta acgctcgtaa cgccgctttc ttcttccgca      240
cgtcgaccta tttgcgctgt aggtctactg ggtcagaggt aggagggaca gacgtagaca      300
tcctctgtct cagtggtagt gaacggcccg ttcagtctcg taatcgtcga taaatttaac      360
catagtcgtc tttggtccct ttcggggatt cgaggactag atacgacgta ggtcaaacgt      420
ttcaccccag ggtagttcca agtcaccgtc acctagaccc tgtctaaagt gagagtggta      480
gtcgtcagac gttggacttc taaaacgttg aatgatgaca gttgtctcaa tgtcatgggg      540
agagtgaaaa ccgcctccct ggttccaact ctagtttgca tgccaccggc gaggaaggca      600
caagtagaag ggagggaggc tgctcgtcga cttcaggccg tggcggtcgc accacacgga      660
cgacttgttg aagatgggag ccctccggtt ccacgtcacc ttccacctgt tgcgggacgt      720
ctcgccgttg agggtcctca ggcagtggct cgtcctgagg ttcctgtcgt ggatgaggga      780
caggaggtgg gactgggaca ggttccggct gatgctcttc gtattccaca tgcggacgct      840
ccactgggtg gtcccggaca ggtcgggaca ctggttcagg aagttggccc cgctcacgat      900
ccgccggcgt                                                             910
```

<210> SEQ ID NO 847
<211> LENGTH: 211
<212> TYPE: PRT
<213> ORGANISM: Homo sapiens

<400> SEQUENCE: 847

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Glu Gly Gly Pro Gly Tyr Cys Ser Ser Thr Ser Cys Tyr Thr
            100                 105                 110

Pro Gly Gly Tyr Tyr Tyr Tyr Gly Met Asp Val Trp Gly Gln Gly
            115                 120                 125

Thr Thr Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu
    210

<210> SEQ ID NO 848
<211> LENGTH: 299
<212> TYPE: PRT
<213> ORGANISM: Homo Sapiens

<400> SEQUENCE: 848

Met Arg Phe Pro Ser Ile Phe Thr Ala Val Leu Phe Ala Ala Ser Ser
1               5                   10                  15

Ala Leu Ala Ala Pro Ala Asn Thr Thr Thr Glu Asp Glu Thr Ala Gln
            20                  25                  30

Ile Pro Ala Glu Ala Val Ile Asp Tyr Ser Asp Leu Glu Gly Asp Phe
        35                  40                  45

Asp Ala Ala Ala Leu Pro Leu Ser Asn Ser Thr Asn Asn Gly Leu Ser
    50                  55                  60

Ser Thr Asn Thr Thr Ile Ala Ser Ile Ala Ala Lys Glu Glu Gly Val
65                  70                  75                  80

Gln Leu Asp Lys Arg Asp Ile Gln Met Thr Gln Ser Pro Ser Ser Leu
                85                  90                  95

Ser Ala Ser Val Gly Asp Arg Val Thr Ile Thr Cys Arg Ala Ser Gln
            100                 105                 110

Ser Ile Ser Ser Tyr Leu Asn Trp Tyr Gln Gln Lys Pro Gly Lys Ala
        115                 120                 125

Pro Lys Leu Leu Ile Tyr Ala Ala Ser Ser Leu Gln Ser Gly Val Pro
    130                 135                 140

Ser Arg Phe Ser Gly Ser Gly Ser Gly Thr Asp Phe Thr Leu Thr Ile
145                 150                 155                 160

Ser Ser Leu Gln Pro Glu Asp Phe Ala Thr Tyr Tyr Cys Gln Gln Ser
                165                 170                 175

Tyr Ser Thr Pro Leu Thr Phe Gly Gly Gly Thr Lys Val Glu Ile Lys
            180                 185                 190

Arg Thr Val Ala Ala Pro Ser Val Phe Ile Phe Pro Pro Ser Asp Glu
        195                 200                 205

Gln Leu Lys Ser Gly Thr Ala Ser Val Val Cys Leu Leu Asn Asn Phe
    210                 215                 220

Tyr Pro Arg Glu Ala Lys Val Gln Trp Lys Val Asp Asn Ala Leu Gln
225                 230                 235                 240
```

```
Ser Gly Asn Ser Gln Glu Ser Val Thr Glu Gln Asp Ser Lys Asp Ser
            245                 250                 255

Thr Tyr Ser Leu Ser Ser Thr Leu Thr Leu Ser Lys Ala Asp Tyr Glu
            260                 265                 270

Lys His Lys Val Tyr Ala Cys Glu Val Thr His Gln Gly Leu Ser Ser
        275                 280                 285

Pro Val Thr Lys Ser Phe Asn Arg Gly Glu Cys
    290                 295

<210> SEQ ID NO 849
<211> LENGTH: 15
<212> TYPE: PRT
<213> ORGANISM: Homo sapiens

<400> SEQUENCE: 849

Ala Phe Asp Ile Trp Gly Gln Gly Thr Met Val Thr Val Ser Ser
1               5                   10                  15

<210> SEQ ID NO 850
<211> LENGTH: 14
<212> TYPE: PRT
<213> ORGANISM: Homo sapiens

<400> SEQUENCE: 850

Phe Asp Ile Trp Gly Gln Gly Thr Met Val Thr Val Ser Ser
1               5                   10

<210> SEQ ID NO 851
<211> LENGTH: 13
<212> TYPE: PRT
<213> ORGANISM: Homo sapiens

<400> SEQUENCE: 851

Asp Ile Trp Gly Gln Gly Thr Met Val Thr Val Ser Ser
1               5                   10

<210> SEQ ID NO 852
<211> LENGTH: 4
<212> TYPE: PRT
<213> ORGANISM: Homo sapiens

<400> SEQUENCE: 852

Ala Phe Asp Ile
1

<210> SEQ ID NO 853
<211> LENGTH: 16
<212> TYPE: PRT
<213> ORGANISM: Homo sapiens

<400> SEQUENCE: 853

Asn Trp Phe Asp Pro Trp Gly Gln Gly Thr Leu Val Thr Val Ser Ser
1               5                   10                  15

<210> SEQ ID NO 854
<211> LENGTH: 15
<212> TYPE: PRT
<213> ORGANISM: Homo sapiens

<400> SEQUENCE: 854

Trp Phe Asp Pro Trp Gly Gln Gly Thr Leu Val Thr Val Ser Ser
1               5                   10                  15
```

```
<210> SEQ ID NO 855
<211> LENGTH: 14
<212> TYPE: PRT
<213> ORGANISM: Homo sapiens

<400> SEQUENCE: 855

Phe Asp Pro Trp Gly Gln Gly Thr Leu Val Thr Val Ser Ser
1               5                  10

<210> SEQ ID NO 856
<211> LENGTH: 13
<212> TYPE: PRT
<213> ORGANISM: Homo sapiens

<400> SEQUENCE: 856

Asp Pro Trp Gly Gln Gly Thr Leu Val Thr Val Ser Ser
1               5                  10

<210> SEQ ID NO 857
<211> LENGTH: 5
<212> TYPE: PRT
<213> ORGANISM: Homo sapiens

<400> SEQUENCE: 857

Asn Trp Phe Asp Pro
1               5

<210> SEQ ID NO 858
<211> LENGTH: 4
<212> TYPE: PRT
<213> ORGANISM: Homo sapiens

<400> SEQUENCE: 858

Trp Phe Asp Pro
1
```